United States Patent
Soni

(10) Patent No.: US 11,986,452 B2
(45) Date of Patent: May 21, 2024

(54) METHODS OF REDUCING THE RISK OF HEART FAILURE

(71) Applicant: Amarin Pharmaceuticals Ireland Limited, Dublin (IE)

(72) Inventor: Paresh Soni, Mystic, CT (US)

(73) Assignee: AMARIN PHARMACEUTICALS IRELAND LIMITED, Dublin (IE)

(*) Notice: Subject to any disclaimer, the term of this patent is extended or adjusted under 35 U.S.C. 154(b) by 0 days.

(21) Appl. No.: 17/723,598

(22) Filed: Apr. 19, 2022

(65) Prior Publication Data

US 2022/0347148 A1    Nov. 3, 2022

Related U.S. Application Data

(60) Provisional application No. 63/177,723, filed on Apr. 21, 2021.

(51) Int. Cl.
- *A61K 31/232* (2006.01)
- *A61P 9/10* (2006.01)

(52) U.S. Cl.
CPC .............. *A61K 31/232* (2013.01); *A61P 9/10* (2018.01)

(58) Field of Classification Search
CPC .................................................. A61K 31/232
See application file for complete search history.

(56) References Cited

U.S. PATENT DOCUMENTS

| | | | |
|---|---|---|---|
| 3,598,858 A | 8/1971 | Bergstrom et al. |
| 4,377,526 A | 3/1983 | Fujita et al. |
| 4,526,902 A | 7/1985 | Rubin |
| 4,920,098 A | 4/1990 | Cotter et al. |
| 4,935,243 A | 6/1990 | Borkan et al. |
| 5,013,443 A | 5/1991 | Higashidate et al. |
| 5,116,871 A | 5/1992 | Horrobin et al. |
| 5,178,873 A | 1/1993 | Horrobin et al. |
| 5,198,468 A | 3/1993 | Horrobin |
| 5,215,630 A | 6/1993 | Hata et al. |
| 5,252,333 A | 10/1993 | Horrobin |
| 5,262,168 A | 11/1993 | Lenk et al. |
| 5,262,437 A | 11/1993 | Chan |
| 5,343,389 A | 8/1994 | Otvos |
| 5,385,929 A | 1/1995 | Bjorge et al. |
| 5,457,130 A | 10/1995 | Tisdale et al. |
| 5,502,077 A | 3/1996 | Breivik et al. |
| 5,567,730 A | 10/1996 | Miyashita et al. |
| 5,589,508 A | 12/1996 | Schlotzer et al. |
| 5,603,959 A | 2/1997 | Horrobin et al. |
| 5,604,119 A | 2/1997 | Haraldsson et al. |
| 5,618,558 A | 4/1997 | Horrobin et al. |
| 5,656,667 A | 8/1997 | Breivik et al. |
| 5,674,488 A | 10/1997 | Reich |
| 5,698,594 A | 12/1997 | Breivik et al. |
| 5,760,081 A | 6/1998 | Leaf et al. |
| 5,763,496 A | 6/1998 | Holland |
| 5,776,978 A | 7/1998 | Bruzzese |
| 5,792,795 A | 8/1998 | Buser et al. |
| 5,837,731 A | 11/1998 | Vaddadi |
| 5,840,944 A | 11/1998 | Furihata et al. |
| 5,886,037 A | 3/1999 | Klor et al. |
| 5,888,541 A | 3/1999 | Horrobin et al. |
| 5,948,818 A | 9/1999 | Buser et al. |
| 6,011,049 A | 1/2000 | Whitcomb |
| 6,025,008 A | 2/2000 | Akahoshi |
| 6,069,168 A | 5/2000 | Horrobin et al. |
| 6,077,525 A | 6/2000 | Vanderhoek |
| 6,193,999 B1 | 2/2001 | Gennadios |
| 6,207,699 B1 | 3/2001 | Rothman |
| 6,234,464 B1 | 5/2001 | Krumbholz et al. |
| 6,284,268 B1 | 9/2001 | Mishra et al. |
| 6,313,330 B1 | 11/2001 | Kiyohara et al. |
| 6,326,031 B1 | 12/2001 | Hsia et al. |
| 6,326,355 B1 | 12/2001 | Abbruzzese et al. |
| 6,331,568 B1 | 12/2001 | Horrobin |
| 6,362,236 B1 | 3/2002 | Aviram |
| 6,368,621 B1 | 4/2002 | Engel et al. |
| 6,383,482 B1 | 5/2002 | Gorsek |
| 6,384,077 B1 | 5/2002 | Peet et al. |
| 6,440,961 B1 | 8/2002 | Lohray et al. |
| 6,479,544 B1 | 11/2002 | Horrobin |
| 6,482,421 B2 | 11/2002 | Weidner |
| 6,531,150 B1 | 3/2003 | Sunohara et al. |
| 6,555,700 B1 | 4/2003 | Horrobin et al. |
| 6,596,766 B1 | 7/2003 | Igarashi et al. |
| 6,620,821 B2 | 9/2003 | Robl |

(Continued)

FOREIGN PATENT DOCUMENTS

| | | |
|---|---|---|
| AU | 2008/272135 | 1/2009 |
| CA | 2628305 | 5/2007 |

(Continued)

OTHER PUBLICATIONS

Brook et al., Inhalation of fine particulate air pollution and ozone causes acute arterial vasoconstriction in healthy adults, Circulation, 2002: 105:1534-1536.

Budoff et al., Effect of icosapent ethyl on progression of coronary atherosclerosis in patients with elevated triglycerides on statin therapy: final results of the Evaporate trial, Euro Heat J. (2020) 41:3925-3932.

Cherng et al., Mechanisms of diesel-induced endothelial nitric oxide synthasedysfunction in coronary arterioles, Environmental Health Perspectives, Jan. 2011, vol. 119, No. 1, p. 98-106.

Courtois et al., Impairment of No. dependent relaxation in intralobar pulmonary arteries: comparison of urban particulate matter and manufactured nanoparticles, Environmental Health Perspectives, Oct. 2008, vol. 116, No. 10.

(Continued)

*Primary Examiner* — Paul V Ward
(74) *Attorney, Agent, or Firm* — Perkins Coie LLP

(57) ABSTRACT

In various embodiments, the present disclosure provides methods reducing the risk of heart failure in a subject on statin therapy by administering to the subject a pharmaceutical composition comprising about 1 g to about 4 g of eicosapentaenoic acid ethyl ester or a derivative thereof.

18 Claims, 55 Drawing Sheets

(56) References Cited

U.S. PATENT DOCUMENTS

| | | |
|---|---|---|
| 6,689,812 B2 | 2/2004 | Peet |
| 6,846,942 B2 | 1/2005 | Rubin |
| 7,022,713 B2 | 4/2006 | Aoki et al. |
| 7,112,609 B2 | 9/2006 | Hermelin et al. |
| 7,119,118 B2 | 10/2006 | Peet |
| 7,179,491 B1 | 2/2007 | Mag |
| 7,205,329 B2 | 4/2007 | Chien et al. |
| 7,405,302 B2 | 7/2008 | Hutchinson et al. |
| 7,498,359 B2 | 3/2009 | Yokoyama et al. |
| 7,511,131 B2 | 3/2009 | Crooke et al. |
| 7,598,227 B2 | 10/2009 | Crooke et al. |
| 7,642,287 B2 | 1/2010 | Guzman |
| 7,776,881 B2 | 8/2010 | Aoki et al. |
| 8,188,146 B2 | 5/2012 | Peet et al. |
| 8,293,727 B2 | 10/2012 | Manku et al. |
| 8,293,728 B2 | 10/2012 | Manku et al. |
| 8,298,554 B2 | 10/2012 | Manku |
| 8,314,086 B2 | 11/2012 | Manku et al. |
| 8,318,715 B2 | 11/2012 | Manku et al. |
| 8,324,195 B2 | 12/2012 | Manku et al. |
| 8,357,677 B1 | 1/2013 | Manku et al. |
| 8,367,652 B2 | 2/2013 | Manku et al. |
| 8,377,920 B2 | 2/2013 | Manku et al. |
| 8,410,086 B2 | 4/2013 | Osterloh et al. |
| 8,431,560 B1 | 4/2013 | Manku et al. |
| 8,440,650 B1 | 5/2013 | Manku et al. |
| 8,455,472 B2 | 6/2013 | Osterloh et al. |
| 8,518,929 B2 | 8/2013 | Manku et al. |
| 8,524,698 B2 | 9/2013 | Manku et al. |
| 8,546,372 B2 | 10/2013 | Manku et al. |
| 8,551,521 B2 | 10/2013 | Manku et al. |
| 8,563,608 B2 | 10/2013 | Manku et al. |
| 8,617,593 B2 | 12/2013 | Manku et al. |
| 8,617,594 B2 | 12/2013 | Manku et al. |
| 8,618,166 B2 | 12/2013 | Osterloh et al. |
| 8,618,168 B2 | 12/2013 | Fujii et al. |
| 8,623,406 B2 | 1/2014 | Manku et al. |
| 8,642,077 B2 | 2/2014 | Manku et al. |
| 8,660,662 B2 | 2/2014 | Li et al. |
| 8,669,245 B2 | 3/2014 | Osterloh et al. |
| 8,680,144 B2 | 3/2014 | Osterloh et al. |
| 8,691,871 B2 | 4/2014 | Osterloh et al. |
| 8,703,185 B2 | 4/2014 | Manku et al. |
| 8,703,188 B1 | 4/2014 | Dumbre |
| 8,709,475 B2 | 4/2014 | Manku et al. |
| 8,802,718 B2 | 8/2014 | Yokoyama et al. |
| 8,846,321 B2 | 9/2014 | Sacks et al. |
| 8,853,256 B2 | 10/2014 | Yokoyama et al. |
| 8,906,964 B2 | 12/2014 | Bobotas et al. |
| 9,006,285 B2 | 4/2015 | Ohnishi |
| 9,060,981 B2 | 6/2015 | Sato et al. |
| 9,138,415 B2 | 9/2015 | Manku et al. |
| 9,452,121 B2 | 9/2016 | Manku et al. |
| 9,452,150 B2 | 9/2016 | Ueshima et al. |
| 9,452,151 B2 | 9/2016 | Manku et al. |
| 9,585,859 B2 | 3/2017 | Osterloh et al. |
| 9,603,826 B2 | 3/2017 | Soni |
| 9,610,272 B2 * | 4/2017 | Soni .................. A61P 9/00 |
| 9,623,001 B2 | 4/2017 | Soni |
| 9,624,492 B2 | 4/2017 | Zakrzewski |
| 9,693,984 B2 | 7/2017 | Soni |
| 9,693,985 B2 | 7/2017 | Soni |
| 9,693,986 B2 | 7/2017 | Soni |
| 9,700,537 B2 | 7/2017 | Yokoyama et al. |
| 9,855,237 B2 | 1/2018 | Osterloh et al. |
| 9,918,954 B2 | 3/2018 | Soni |
| 10,058,521 B2 | 8/2018 | Bobotas et al. |
| 10,166,209 B2 | 1/2019 | Manku et al. |
| 10,220,013 B2 | 3/2019 | Osterloh et al. |
| 10,265,290 B2 | 4/2019 | Manku et al. |
| 10,278,935 B2 | 5/2019 | Soni |
| 10,278,936 B2 | 5/2019 | Soni |
| 10,292,959 B2 | 5/2019 | Osterloh et al. |
| 10,441,593 B2 | 10/2019 | Loumaye et al. |
| 10,555,925 B1 | 2/2020 | Soni |
| 10,557,856 B2 | 2/2020 | Singbartl et al. |
| 10,561,631 B2 | 2/2020 | Osterloh et al. |
| 10,568,861 B1 | 2/2020 | Soni |
| 10,576,054 B1 | 3/2020 | Soni |
| 10,610,508 B2 | 4/2020 | Manku |
| 10,722,485 B2 | 7/2020 | Osterloh et al. |
| 10,786,478 B2 * | 9/2020 | Soni .................... A61K 31/232 |
| 10,792,267 B2 | 10/2020 | Osterloh et al. |
| 10,842,762 B2 | 11/2020 | Nidorf |
| 10,842,766 B2 | 11/2020 | Manku |
| 10,851,374 B2 | 12/2020 | Zakrzewski |
| 10,966,968 B2 | 4/2021 | Braeckman et al. |
| 10,973,797 B2 | 4/2021 | Manku et al. |
| 11,033,523 B2 | 6/2021 | Manku et al. |
| 11,116,743 B2 | 9/2021 | Soni |
| 11,154,526 B2 | 10/2021 | Osterloh et al. |
| 11,179,362 B2 | 11/2021 | Osterloh et al. |
| 11,185,525 B2 | 11/2021 | Manku et al. |
| 11,213,504 B2 | 1/2022 | Manku et al. |
| 11,285,127 B2 | 3/2022 | Osterloh et al. |
| 2001/0035125 A1 | 11/2001 | Talieh et al. |
| 2002/0016312 A1 | 2/2002 | Seed et al. |
| 2002/0025983 A1 | 2/2002 | Horrobin |
| 2002/0035125 A1 | 3/2002 | Shear |
| 2002/0052394 A1 | 5/2002 | Mason |
| 2002/0054871 A1 | 5/2002 | Huang |
| 2002/0055529 A1 | 5/2002 | Bisgaier et al. |
| 2002/0055539 A1 | 5/2002 | Bockow et al. |
| 2002/0077361 A1 | 6/2002 | Peet et al. |
| 2002/0137082 A1 | 9/2002 | Lewandrowski et al. |
| 2002/0169209 A1 | 11/2002 | Horrobin |
| 2002/0177602 A1 | 11/2002 | Piper |
| 2002/0183389 A1 | 12/2002 | Peet |
| 2002/0193439 A1 | 12/2002 | Peet et al. |
| 2002/0198177 A1 | 12/2002 | Horrobin et al. |
| 2003/0100610 A1 | 5/2003 | Shibuya |
| 2003/0104048 A1 | 6/2003 | Patel et al. |
| 2003/0161918 A1 | 8/2003 | Kendrick et al. |
| 2003/0166614 A1 | 9/2003 | Harrison |
| 2003/0232385 A1 | 12/2003 | Breit et al. |
| 2004/0009208 A1 | 1/2004 | Edson |
| 2004/0018248 A1 | 1/2004 | Bendich |
| 2004/0048919 A1 | 3/2004 | Dreon et al. |
| 2004/0062847 A1 | 4/2004 | Koiki et al. |
| 2004/0077723 A1 | 4/2004 | Granata |
| 2004/0106591 A1 | 6/2004 | Pacioretty et al. |
| 2004/0121000 A1 | 6/2004 | Bowe et al. |
| 2004/0162348 A1 | 8/2004 | Peet et al. |
| 2004/0204356 A1 | 10/2004 | Guenzler-Pukall |
| 2004/0258645 A1 | 12/2004 | Trejo et al. |
| 2005/0042214 A1 | 2/2005 | Gershwin et al. |
| 2005/0137253 A1 | 6/2005 | Phinney et al. |
| 2005/0147665 A1 | 7/2005 | Horrobin et al. |
| 2005/0187292 A1 | 8/2005 | Aoki et al. |
| 2005/0215625 A9 | 9/2005 | Nesselroad |
| 2005/0244367 A1 | 11/2005 | Hui et al. |
| 2005/0272095 A1 | 12/2005 | Wang |
| 2006/0034815 A1 | 2/2006 | Guzman et al. |
| 2006/0051418 A1 | 3/2006 | Cowen et al. |
| 2006/0088502 A1 | 4/2006 | Sata et al. |
| 2006/0111437 A1 | 5/2006 | Aoki et al. |
| 2006/0134178 A1 | 6/2006 | Doisaki et al. |
| 2006/0134206 A1 | 6/2006 | Iyer et al. |
| 2006/0135607 A1 | 6/2006 | Kobayashi et al. |
| 2006/0135610 A1 | 6/2006 | Bortz et al. |
| 2006/0141022 A1 | 6/2006 | Kawamura et al. |
| 2006/0142390 A1 | 6/2006 | Manku et al. |
| 2006/0172012 A1 | 8/2006 | Finley et al. |
| 2006/0189682 A1 | 8/2006 | Payne et al. |
| 2006/0211749 A1 | 9/2006 | Bobotas et al. |
| 2006/0211761 A1 | 9/2006 | Kumar et al. |
| 2006/0211762 A1 | 9/2006 | Rongen |
| 2006/0211763 A1 | 9/2006 | Fawzy et al. |
| 2006/0217356 A1 | 9/2006 | Wright et al. |
| 2006/0223838 A1 | 10/2006 | Jiang et al. |
| 2006/0241088 A1 | 10/2006 | Arterburn et al. |
| 2006/0252833 A1 | 11/2006 | Peet et al. |
| 2007/0021504 A1 | 1/2007 | Yokoyama et al. |
| 2007/0060532 A1 | 3/2007 | Junien et al. |

(56) References Cited

U.S. PATENT DOCUMENTS

| | | |
|---|---|---|
| 2007/0098787 A1 | 5/2007 | Kakiuchi |
| 2007/0104779 A1 | 5/2007 | Rongen et al. |
| 2007/0105793 A1 | 5/2007 | Hendrix |
| 2007/0105954 A1 | 5/2007 | Puri |
| 2007/0141138 A1 | 6/2007 | Feuerstein et al. |
| 2007/0167520 A1 | 7/2007 | Bruzzese |
| 2007/0185198 A1 | 8/2007 | Yokoyama et al. |
| 2007/0191467 A1 | 8/2007 | Rongen et al. |
| 2007/0202159 A1 | 8/2007 | Mathur et al. |
| 2007/0212411 A1 | 9/2007 | Fawzy et al. |
| 2007/0219271 A1 | 9/2007 | Mittmann et al. |
| 2007/0248586 A1 | 10/2007 | Arterburn et al. |
| 2007/0265340 A1 | 11/2007 | Shalwitz et al. |
| 2007/0269507 A1 | 11/2007 | Sachetto et al. |
| 2007/0292501 A1 | 12/2007 | Udell |
| 2008/0020018 A1 | 1/2008 | Moodley et al. |
| 2008/0057115 A1 | 3/2008 | Okamoto |
| 2008/0085911 A1 | 4/2008 | Rongen et al. |
| 2008/0089876 A1 | 4/2008 | Cavazza |
| 2008/0113046 A1 | 5/2008 | Gardette |
| 2008/0125490 A1 | 5/2008 | Svensson et al. |
| 2008/0139604 A1 | 6/2008 | Fitzpatrick et al. |
| 2008/0185198 A1 | 8/2008 | Jones |
| 2008/0200453 A1 | 8/2008 | Cincotta |
| 2008/0200547 A1 | 8/2008 | Peet et al. |
| 2008/0200707 A1 | 8/2008 | Shimano et al. |
| 2008/0214531 A1 | 9/2008 | Saxena et al. |
| 2008/0299187 A1 | 12/2008 | Opheim et al. |
| 2008/0306154 A1 | 12/2008 | Svensson et al. |
| 2008/0319077 A1 | 12/2008 | Suzuki et al. |
| 2009/0012167 A1 | 1/2009 | Rongen et al. |
| 2009/0018125 A1 | 1/2009 | Mittmann et al. |
| 2009/0042979 A1 | 2/2009 | Guzman et al. |
| 2009/0054329 A1 | 2/2009 | Willemsen et al. |
| 2009/0105340 A1 | 4/2009 | Yokoyama |
| 2009/0148543 A1 | 6/2009 | Theoharides |
| 2009/0156675 A1 | 6/2009 | Yokoyama et al. |
| 2009/0182049 A1 | 7/2009 | Opheim |
| 2009/0202668 A1 | 8/2009 | Hugenholtz |
| 2009/0227602 A1 | 9/2009 | Griffin et al. |
| 2009/0233843 A1 | 9/2009 | Marin |
| 2009/0239927 A1 | 9/2009 | Bobotas et al. |
| 2009/0304784 A1 | 12/2009 | Mane et al. |
| 2009/0311322 A1 | 12/2009 | Dlugatch et al. |
| 2010/0021555 A1 | 1/2010 | Geiringer et al. |
| 2010/0063018 A1 | 3/2010 | Pellicciari et al. |
| 2010/0069492 A1 | 3/2010 | Geiringen et al. |
| 2010/0112066 A1 | 5/2010 | Kamiya et al. |
| 2010/0113506 A1 | 5/2010 | Kawano et al. |
| 2010/0113811 A1 | 5/2010 | Yadav et al. |
| 2010/0119598 A1 | 5/2010 | Yoshinari et al. |
| 2010/0130608 A1 | 5/2010 | Ryan et al. |
| 2010/0160261 A1 | 6/2010 | Fortin |
| 2010/0233280 A1 | 9/2010 | Driscoll |
| 2010/0254951 A1 | 10/2010 | Shido et al. |
| 2010/0278879 A1 | 11/2010 | Manku |
| 2010/0285121 A1 | 11/2010 | Uchiyama et al. |
| 2010/0298379 A1 | 11/2010 | Jacobsen |
| 2010/0305205 A1 | 12/2010 | Yokoyama et al. |
| 2010/0311834 A1 | 12/2010 | Manku et al. |
| 2011/0034555 A1 | 2/2011 | Osterloh et al. |
| 2011/0065793 A1 | 3/2011 | Peet et al. |
| 2011/0071176 A1 | 3/2011 | Rowe |
| 2011/0082119 A1 | 4/2011 | Yano |
| 2011/0092592 A1 | 4/2011 | Yano |
| 2011/0105510 A1 | 5/2011 | Ishikawa |
| 2011/0130458 A1 | 6/2011 | Breivik et al. |
| 2011/0158932 A1 | 6/2011 | Jiang et al. |
| 2011/0178105 A1 | 7/2011 | Gillies et al. |
| 2011/0195061 A1 | 8/2011 | Minatelli |
| 2011/0218243 A1 | 9/2011 | Rowe |
| 2011/0223158 A1 | 9/2011 | Sacks et al. |
| 2011/0236476 A1 | 9/2011 | Manku |
| 2011/0268811 A1 | 11/2011 | Minatelli et al. |
| 2011/0288171 A1 | 11/2011 | Manku et al. |
| 2011/0294841 A1 | 12/2011 | Guzman et al. |
| 2012/0035105 A1 | 2/2012 | Geho et al. |
| 2012/0035262 A1 | 2/2012 | Osterloh et al. |
| 2012/0039997 A1 | 2/2012 | Manku et al. |
| 2012/0046251 A1 | 2/2012 | Schaefer et al. |
| 2012/0093922 A1 | 4/2012 | Manku et al. |
| 2012/0093924 A1 | 4/2012 | Manku et al. |
| 2012/0100208 A1 | 4/2012 | Manku |
| 2012/0108659 A1 | 5/2012 | Manku et al. |
| 2012/0108660 A1 | 5/2012 | Manku et al. |
| 2012/0108663 A1 | 5/2012 | Manku et al. |
| 2012/0121698 A1 | 5/2012 | Manku et al. |
| 2012/0156285 A1 | 6/2012 | Manku et al. |
| 2012/0157530 A1 | 6/2012 | Manku et al. |
| 2012/0157531 A1 | 6/2012 | Osterloh et al. |
| 2012/0172432 A1 | 7/2012 | Manku et al. |
| 2012/0184595 A1 | 7/2012 | Macdonald et al. |
| 2012/0195963 A1 | 8/2012 | Peet et al. |
| 2012/0207800 A1 | 8/2012 | Abu-Baker |
| 2012/0214771 A1 | 8/2012 | Sampalis |
| 2012/0225120 A1 | 9/2012 | Manku et al. |
| 2012/0232145 A1 | 9/2012 | Osterloh et al. |
| 2012/0237594 A1 | 9/2012 | Manku et al. |
| 2012/0245121 A1 | 9/2012 | Lopez Pedrosa et al. |
| 2012/0264824 A1 | 10/2012 | Mizuguchi et al. |
| 2012/0295976 A1 | 11/2012 | Yokoyama |
| 2012/0302589 A1 | 11/2012 | Manku et al. |
| 2012/0329852 A1 | 12/2012 | Yokoyama et al. |
| 2013/0004566 A1 | 1/2013 | Manku et al. |
| 2013/0004567 A1 | 1/2013 | Manku et al. |
| 2013/0004568 A1 | 1/2013 | Manku et al. |
| 2013/0004572 A1 | 1/2013 | Manku et al. |
| 2013/0005757 A1 | 1/2013 | Osterloh et al. |
| 2013/0005809 A1 | 1/2013 | Manku et al. |
| 2013/0011471 A1 | 1/2013 | Manku et al. |
| 2013/0011472 A1 | 1/2013 | Manku et al. |
| 2013/0012580 A1 | 1/2013 | Osterloh et al. |
| 2013/0017256 A1 | 1/2013 | Manku et al. |
| 2013/0065956 A1 | 3/2013 | Yokoyama |
| 2013/0079409 A1 | 3/2013 | Manku et al. |
| 2013/0090383 A1 | 4/2013 | Manku et al. |
| 2013/0095178 A1 | 4/2013 | Manku |
| 2013/0095179 A1 | 4/2013 | Davidson et al. |
| 2013/0096197 A1 | 4/2013 | Manku |
| 2013/0102674 A1 | 4/2013 | Manku |
| 2013/0115284 A1 | 5/2013 | Fujii et al. |
| 2013/0131170 A1 | 5/2013 | Manku |
| 2013/0156852 A1 | 6/2013 | Manku et al. |
| 2013/0158120 A1 | 6/2013 | Manku et al. |
| 2013/0164375 A1 | 6/2013 | Manku et al. |
| 2013/0165513 A1 | 6/2013 | Manku et al. |
| 2013/0171249 A1 | 7/2013 | Manku et al. |
| 2013/0171250 A1 | 7/2013 | Manku et al. |
| 2013/0171251 A1 | 7/2013 | Manku et al. |
| 2013/0172413 A1 | 7/2013 | Manku |
| 2013/0189355 A1 | 7/2013 | Manku et al. |
| 2013/0190275 A1 | 7/2013 | Mendlovic et al. |
| 2013/0195972 A1 | 8/2013 | Manku et al. |
| 2013/0252989 A1 | 9/2013 | Manku et al. |
| 2013/0252990 A1 | 9/2013 | Manku et al. |
| 2013/0253030 A1 | 9/2013 | Osterloh et al. |
| 2013/0253031 A1 | 9/2013 | Osterloh et al. |
| 2013/0260403 A1 | 10/2013 | Button et al. |
| 2013/0261180 A1 | 10/2013 | Gillies et al. |
| 2013/0281534 A1 | 10/2013 | Osterloh et al. |
| 2013/0295173 A1 | 11/2013 | Machielse et al. |
| 2013/0303614 A1 | 11/2013 | Kanehiro et al. |
| 2013/0324607 A1 | 12/2013 | Mason |
| 2013/0331447 A1 | 12/2013 | Manku et al. |
| 2014/0004183 A1 | 1/2014 | Soni et al. |
| 2014/0005264 A1 | 1/2014 | Soni et al. |
| 2014/0005265 A1 | 1/2014 | Soni et al. |
| 2014/0017306 A1 | 1/2014 | Manku |
| 2014/0057981 A1 | 2/2014 | Fujii |
| 2014/0073692 A1 | 3/2014 | Peet |
| 2014/0080850 A1 | 3/2014 | Mason |
| 2014/0080909 A1 | 3/2014 | Manku |
| 2014/0088194 A1 | 3/2014 | Manku |
| 2014/0094520 A1 | 4/2014 | Bobotas et al. |

(56) References Cited

U.S. PATENT DOCUMENTS

| | | |
|---|---|---|
| 2014/0107199 A1 | 4/2014 | Fawzy et al. |
| 2014/0127289 A1 | 5/2014 | Osterloh et al. |
| 2014/0128453 A1 | 5/2014 | Mullick et al. |
| 2014/0128464 A1 | 5/2014 | Rowe |
| 2014/0142127 A1 | 5/2014 | Almarsson |
| 2014/0154310 A1 | 6/2014 | Osterloh et al. |
| 2014/0155455 A1 | 6/2014 | Osterloh et al. |
| 2014/0155481 A1 | 6/2014 | Osterloh et al. |
| 2014/0186438 A1 | 7/2014 | Manku et al. |
| 2014/0187633 A1 | 7/2014 | Manku et al. |
| 2014/0213648 A1 | 7/2014 | Manku et al. |
| 2014/0221358 A1 | 8/2014 | Zakrzewski |
| 2014/0221452 A1 | 8/2014 | Zakrzewski |
| 2014/0221486 A1 | 8/2014 | Manku et al. |
| 2014/0221676 A1 | 8/2014 | Braeckman et al. |
| 2014/0234410 A1 | 8/2014 | Moodley et al. |
| 2014/0235716 A1 | 8/2014 | Manku et al. |
| 2014/0243389 A1 | 8/2014 | Zakrzewski |
| 2014/0249200 A1 | 9/2014 | Braeckman et al. |
| 2014/0249214 A1 | 9/2014 | Braeckman et al. |
| 2014/0249220 A1 | 9/2014 | Braeckman et al. |
| 2014/0249225 A1 | 9/2014 | Mason |
| 2014/0256809 A1 | 9/2014 | Zakrzewski |
| 2014/0271841 A1 | 9/2014 | Grandolfi |
| 2014/0271907 A1 | 9/2014 | Zakrzewski |
| 2014/0275252 A1 | 9/2014 | Zakrzewski |
| 2014/0275253 A1 | 9/2014 | Zakrzewski |
| 2014/0322314 A1 | 10/2014 | Fawzy et al. |
| 2014/0357717 A1 | 12/2014 | Braeckman et al. |
| 2014/0364459 A1 | 12/2014 | Zakrzewski |
| 2015/0045431 A1 | 2/2015 | Zakrzewski |
| 2015/0051143 A1 | 2/2015 | Harada et al. |
| 2015/0051282 A1 | 2/2015 | Zakrzewski |
| 2015/0065572 A1 | 3/2015 | Zakrzewski |
| 2015/0073050 A1 | 3/2015 | Zakrzewski |
| 2015/0141510 A1 | 5/2015 | Kiyohara et al. |
| 2015/0147276 A1 | 5/2015 | Ingber et al. |
| 2015/0157592 A1 | 6/2015 | Soni |
| 2015/0157593 A1 | 6/2015 | Braeckman et al. |
| 2015/0164850 A1 | 6/2015 | Osterloh et al. |
| 2015/0190361 A1 | 7/2015 | Osterloh et al. |
| 2015/0216831 A1 | 8/2015 | Manku et al. |
| 2015/0250754 A1 | 9/2015 | Ohta |
| 2015/0250756 A1 | 9/2015 | Mason |
| 2015/0250757 A1 | 9/2015 | Soni |
| 2015/0258051 A1 | 9/2015 | Manku et al. |
| 2015/0265566 A1 | 9/2015 | Osterloh et al. |
| 2015/0265574 A1 | 9/2015 | Rowe |
| 2015/0272917 A1 | 10/2015 | Manku et al. |
| 2015/0283074 A1 | 10/2015 | Fujii |
| 2015/0284473 A1 | 10/2015 | Bessac et al. |
| 2015/0290154 A1 | 10/2015 | Roberts et al. |
| 2015/0335607 A1 | 11/2015 | Rowe |
| 2015/0359775 A1 | 12/2015 | Osterloh et al. |
| 2016/0045444 A1 | 2/2016 | Kim et al. |
| 2016/0058729 A1 | 3/2016 | Manku et al. |
| 2016/0120837 A1 | 5/2016 | Manku et al. |
| 2016/0143875 A1 | 5/2016 | Zakrzewski |
| 2016/0151319 A1 | 6/2016 | Kimura |
| 2016/0158184 A1 | 6/2016 | Ito |
| 2016/0213636 A1 | 7/2016 | Manku et al. |
| 2016/0213639 A1 | 7/2016 | Suzuki et al. |
| 2016/0220522 A1 | 8/2016 | Osterloh et al. |
| 2016/0287546 A1 | 10/2016 | Osterloh et al. |
| 2017/0014366 A1 | 1/2017 | Osterloh et al. |
| 2017/0035722 A1 | 2/2017 | Soni |
| 2017/0056361 A1 | 3/2017 | Soni |
| 2017/0079946 A1 | 3/2017 | Ohta |
| 2017/0087111 A1 | 3/2017 | Mason |
| 2017/0100363 A9 | 4/2017 | Zakrzewski |
| 2017/0119721 A1 | 5/2017 | Zakrzewski |
| 2017/0119722 A1 | 5/2017 | Manku et al. |
| 2017/0119723 A1 | 5/2017 | Soni |
| 2017/0119724 A1 | 5/2017 | Fujii |
| 2017/0128402 A1 | 5/2017 | Manku et al. |
| 2017/0128405 A1 | 5/2017 | Osterloh et al. |
| 2017/0128406 A1 | 5/2017 | Rowe |
| 2017/0136055 A1 | 5/2017 | Zakrzewski |
| 2017/0143656 A1 | 5/2017 | Soni |
| 2017/0143657 A1 | 5/2017 | Braeckman et al. |
| 2017/0143658 A1 | 5/2017 | Soni |
| 2017/0151202 A1 | 6/2017 | Mason |
| 2017/0151206 A1 | 6/2017 | Yokoyama |
| 2017/0217943 A1 | 8/2017 | Lairson et al. |
| 2017/0258753 A1 | 9/2017 | Soni |
| 2017/0258754 A1 | 9/2017 | Soni |
| 2017/0258755 A1 | 9/2017 | Soni |
| 2017/0273928 A1 | 9/2017 | Yokoyama et al. |
| 2017/0304249 A1 | 10/2017 | Abu-Baker |
| 2017/0333377 A1 | 11/2017 | Mason |
| 2017/0348268 A1 | 12/2017 | Kimura |
| 2017/0348273 A1 | 12/2017 | Ito |
| 2017/0368184 A1 | 12/2017 | Ito |
| 2018/0015038 A1 | 1/2018 | Ito |
| 2018/0015071 A1 | 1/2018 | Braeckman et al. |
| 2018/0028480 A1 | 2/2018 | Mason |
| 2018/0028505 A1 | 2/2018 | Oshima |
| 2018/0042880 A1 | 2/2018 | Osterloh et al. |
| 2018/0042883 A1 | 2/2018 | Manku et al. |
| 2018/0064676 A1 | 3/2018 | Zakrzewski |
| 2018/0085334 A1 | 3/2018 | Soni |
| 2018/0125862 A1 | 5/2018 | Hayardeny-Nissimov et al. |
| 2018/0153846 A1 | 6/2018 | Soni |
| 2018/0185320 A1 | 7/2018 | Manku et al. |
| 2018/0280334 A1 | 10/2018 | Manku |
| 2018/0289657 A1 | 10/2018 | Soni |
| 2018/0289658 A1 | 10/2018 | Soni |
| 2018/0289659 A1 | 10/2018 | Soni |
| 2018/0333383 A1 | 11/2018 | Philip |
| 2019/0038590 A1 | 2/2019 | Manku |
| 2019/0054054 A1 | 2/2019 | Mason |
| 2019/0054058 A1 | 2/2019 | Thero |
| 2019/0060308 A1 | 2/2019 | Mason |
| 2019/0070141 A1 | 3/2019 | Osterloh |
| 2019/0076388 A1 | 3/2019 | Soni |
| 2019/0076389 A1 | 3/2019 | Soni |
| 2019/0076390 A1 | 3/2019 | Manku |
| 2019/0083444 A1 | 3/2019 | Manku |
| 2019/0083445 A1 | 3/2019 | Soni |
| 2019/0099422 A1 | 4/2019 | Grandolfi |
| 2019/0175535 A1 | 6/2019 | Mason |
| 2019/0175537 A1 | 6/2019 | Osterloh |
| 2019/0175538 A1 | 6/2019 | Osterloh |
| 2019/0183829 A1 | 6/2019 | Osterloh |
| 2019/0183831 A1 | 6/2019 | Osterloh |
| 2019/0183840 A1 | 6/2019 | Braeckman |
| 2019/0192472 A1 | 6/2019 | Soni |
| 2019/0201364 A1 | 7/2019 | Manku |
| 2019/0209506 A1 | 7/2019 | Mason |
| 2019/0240182 A1 | 8/2019 | Osterloh |
| 2019/0240183 A1 | 8/2019 | Manku |
| 2019/0269642 A1 | 9/2019 | Philip |
| 2019/0274991 A1 | 9/2019 | Osterloh |
| 2019/0275057 A1 | 9/2019 | Philip |
| 2019/0282533 A1 | 9/2019 | Osterloh |
| 2019/0316122 A1 | 10/2019 | Zakrzewski |
| 2019/0321323 A1 | 10/2019 | Soni |
| 2019/0343788 A1 | 11/2019 | Soni |
| 2019/0358185 A1 | 11/2019 | Mason |
| 2020/0000759 A1 | 1/2020 | Manku |
| 2020/0061011 A1 | 2/2020 | Mason |
| 2020/0061012 A1 | 2/2020 | Manku et al. |
| 2020/0069632 A1 | 3/2020 | Soni |
| 2020/0078329 A1 | 3/2020 | Soni |
| 2020/0093777 A1 | 3/2020 | Soni |
| 2020/0093778 A1 | 3/2020 | Soni |
| 2020/0093790 A1 | 3/2020 | Rowe |
| 2020/0108041 A1 | 4/2020 | Braeckman et al. |
| 2020/0113862 A1 | 4/2020 | Manku et al. |
| 2020/0113864 A1 | 4/2020 | Soni |
| 2020/0121628 A1 | 4/2020 | Osterloh et al. |
| 2020/0121630 A1 | 4/2020 | Osterloh et al. |
| 2020/0138768 A1 | 5/2020 | Soni |
| 2020/0163925 A1 | 5/2020 | Soni |

(56) References Cited

U.S. PATENT DOCUMENTS

| | | |
|---|---|---|
| 2020/0188343 A1 | 6/2020 | Osterloh |
| 2020/0188344 A1 | 6/2020 | Osterloh |
| 2020/0197350 A1 | 6/2020 | Manku |
| 2020/0215017 A1 | 7/2020 | Manku |
| 2020/0237699 A1 | 7/2020 | Mason |
| 2020/0237700 A1 | 7/2020 | Mason |
| 2020/0246300 A1 | 8/2020 | Manku et al. |
| 2020/0261391 A1 | 8/2020 | Soni |
| 2020/0268702 A1 | 8/2020 | Braeckman et al. |
| 2020/0289450 A1 | 9/2020 | Mason |
| 2020/0297681 A1 | 9/2020 | Rowe |
| 2020/0297682 A1 | 9/2020 | Osterloh |
| 2020/0297683 A1 | 9/2020 | Manku |
| 2020/0316006 A1 | 10/2020 | Manku |
| 2020/0338035 A1 | 10/2020 | Soni |
| 2020/0360330 A1 | 11/2020 | Rowe |
| 2020/0397735 A1 | 12/2020 | Osterloh et al. |
| 2020/0405675 A1 | 12/2020 | Manku et al. |
| 2020/0405677 A1 | 12/2020 | Osterloh et al. |
| 2021/0000779 A1 | 1/2021 | Osterloh et al. |
| 2021/0046036 A1 | 2/2021 | Manku |
| 2021/0046037 A1 | 2/2021 | Osterloh et al. |
| 2021/0069142 A1 | 3/2021 | Manku et al. |
| 2021/0069145 A1 | 3/2021 | Braeckman et al. |
| 2021/0085629 A1 | 3/2021 | Mason |
| 2021/0100764 A1 | 4/2021 | Osterloh et al. |
| 2021/0100765 A1 | 4/2021 | Osterloh et al. |
| 2021/0100768 A1 | 4/2021 | Soni |
| 2021/0108202 A1 | 4/2021 | Zakrzewski |
| 2021/0113509 A1 | 4/2021 | Osterloh et al. |
| 2021/0113510 A1 | 4/2021 | Manku et al. |
| 2021/0113513 A1 | 4/2021 | Osterloh et al. |
| 2021/0128582 A1 | 5/2021 | Manku et al. |
| 2021/0137872 A1 | 5/2021 | Philip |
| 2021/0137873 A1 | 5/2021 | Soni |
| 2021/0137879 A1 | 5/2021 | Soni |
| 2021/0145786 A1 | 5/2021 | Zakrzewski |
| 2021/0145787 A1 | 5/2021 | Manku et al. |
| 2021/0154164 A1 | 5/2021 | Soni |
| 2021/0205255 A1 | 7/2021 | Osterloh et al. |
| 2021/0206710 A1 | 7/2021 | Osterloh et al. |
| 2021/0212974 A1 | 7/2021 | Osterloh et al. |
| 2021/0212975 A1 | 7/2021 | Manku et al. |
| 2021/0251941 A1 | 8/2021 | Manku et al. |
| 2021/0260016 A1 | 8/2021 | Rowe |
| 2021/0330624 A1 | 10/2021 | Granowitz |
| 2021/0379002 A1 | 12/2021 | Osterloh |
| 2021/0386701 A1 | 12/2021 | Rowe |
| 2022/0000829 A1 | 1/2022 | Soni |

FOREIGN PATENT DOCUMENTS

| | | |
|---|---|---|
| CA | 2653787 | 12/2007 |
| CA | 2675836 | 7/2008 |
| CA | 2724983 | 11/2009 |
| CA | 2772378 | 12/2010 |
| CN | 101252837 | 8/2008 |
| EP | 0273708 | 7/1988 |
| EP | 0277747 | 8/1988 |
| EP | 0302482 | 2/1989 |
| EP | 0347509 | 12/1989 |
| EP | 0460917 | 12/1991 |
| EP | 0606012 | 7/1994 |
| EP | 0610506 | 8/1994 |
| EP | 0641562 A1 | 3/1995 |
| EP | 0843972 | 5/1998 |
| EP | 0610506 B1 | 6/1999 |
| EP | 1125914 | 8/2001 |
| EP | 1157692 | 11/2001 |
| EP | 1296670 | 4/2003 |
| EP | 1314424 | 5/2003 |
| EP | 1549299 | 12/2003 |
| EP | 1743644 | 1/2007 |
| EP | 1782801 | 5/2007 |
| EP | 1790339 A1 | 5/2007 |
| EP | 1803440 | 7/2007 |
| EP | 1834639 A1 | 9/2007 |
| EP | 1946755 | 7/2008 |
| EP | 1982710 A1 | 10/2008 |
| EP | 2022495 | 2/2009 |
| EP | 2395991 | 8/2010 |
| EP | 2308493 A1 | 4/2011 |
| EP | 2343066 A1 | 7/2011 |
| EP | 2433630 | 3/2012 |
| EP | 2719382 A1 | 4/2014 |
| EP | 2792746 | 10/2014 |
| EP | 3275438 | 1/2018 |
| FR | 2635263 | 2/1990 |
| GB | 2148713 | 6/1985 |
| GB | 2221843 | 2/1990 |
| GB | 2229363 | 9/1990 |
| GB | 9901809.5 | 1/1999 |
| GB | 2480146 | 11/2011 |
| IL | 55227 | 12/1982 |
| JP | 61035356 | 2/1986 |
| JP | 04182426 | 6/1992 |
| JP | H0692847 | 4/1994 |
| JP | 08040981 | 2/1996 |
| JP | 09059206 | 3/1997 |
| JP | H10139662 | 5/1998 |
| JP | H1180083 A | 3/1999 |
| JP | 2001139981 | 5/2001 |
| JP | 2003306690 | 10/2003 |
| JP | 2007238594 | 9/2007 |
| JP | 2007238598 | 9/2007 |
| JP | 2008050367 | 3/2008 |
| JP | 2009-544701 T | 12/2009 |
| JP | 2015-522029 T | 8/2015 |
| KR | 10-2006-0109988 | 10/2006 |
| KR | 10-2007-0058460 | 6/2007 |
| RU | 2281764 C2 | 8/2006 |
| RU | 2290185 | 12/2006 |
| RU | 2005128993 | 3/2007 |
| RU | 2302248 C2 | 7/2007 |
| RU | 2402326 C1 | 10/2010 |
| WO | WO1990/004391 | 5/1990 |
| WO | WO1992/021335 | 12/1992 |
| WO | WO1994/010125 | 5/1994 |
| WO | WO1994/028891 | 12/1994 |
| WO | WO1995/024459 | 9/1995 |
| WO | WO1996/036329 | 11/1996 |
| WO | WO1997/039759 | 10/1997 |
| WO | WO1998/016216 | 4/1998 |
| WO | WO1999/026583 | 6/1999 |
| WO | WO1999/029316 | 6/1999 |
| WO | WO2000/044361 | 8/2000 |
| WO | WO2000/051573 | 9/2000 |
| WO | WO2001/015552 | 3/2001 |
| WO | WO2002/002105 | 1/2002 |
| WO | WO2002/058793 | 8/2002 |
| WO | WO2002/089787 | 11/2002 |
| WO | WO2002/096408 | 12/2002 |
| WO | WO2003/068216 | 8/2003 |
| WO | WO2003/092673 | 11/2003 |
| WO | WO2004/047835 | 6/2004 |
| WO | WO2004/050913 | 6/2004 |
| WO | WO2004/064716 | 8/2004 |
| WO | WO2004/078166 | 9/2004 |
| WO | WO2004/082402 | 9/2004 |
| WO | WO2005/038037 | 4/2005 |
| WO | WO2005/060954 | 7/2005 |
| WO | WO2005/065652 | 7/2005 |
| WO | WO2005063231 | 7/2005 |
| WO | WO2005/079797 | 9/2005 |
| WO | WO2005/079853 | 9/2005 |
| WO | WO2005/102301 | 11/2005 |
| WO | WO2005/123060 | 12/2005 |
| WO | WO2005/123061 | 12/2005 |
| WO | WO2006/017627 | 2/2006 |
| WO | WO2006/017698 | 2/2006 |
| WO | WO2006/029577 | 3/2006 |
| WO | WO2006/045865 | 5/2006 |
| WO | WO2006/062748 | 6/2006 |
| WO | WO2006/096806 | 9/2006 |

(56) References Cited

FOREIGN PATENT DOCUMENTS

| | | |
|---|---|---|
| WO | WO2007/011886 | 1/2007 |
| WO | WO2007/016256 | 2/2007 |
| WO | WO2007/017240 | 2/2007 |
| WO | WO2007/073176 | 6/2007 |
| WO | WO2007/075841 | 7/2007 |
| WO | WO2007/091338 | 8/2007 |
| WO | WO2007/103160 | 9/2007 |
| WO | WO2007/103557 | 9/2007 |
| WO | W02007/130714 | 11/2007 |
| WO | WO2007/128801 | 11/2007 |
| WO | WO2007/130713 | 11/2007 |
| WO | WO2007/142118 | 12/2007 |
| WO | WO2008/004900 | 1/2008 |
| WO | WO2008012329 A2 | 1/2008 |
| WO | WO2008/045465 | 4/2008 |
| WO | 2008/063323 A1 | 5/2008 |
| WO | WO2008/088415 | 7/2008 |
| WO | WO2008/106787 | 9/2008 |
| WO | WO2008/115529 | 9/2008 |
| WO | WO2008/145170 | 12/2008 |
| WO | WO2009/004999 | 1/2009 |
| WO | WO2006117668 | 2/2009 |
| WO | WO2009/085386 | 7/2009 |
| WO | WO2009/085388 | 7/2009 |
| WO | WO2010/028067 | 3/2010 |
| WO | WO2010/093634 | 8/2010 |
| WO | WO2010/103402 | 9/2010 |
| WO | WO2010/119319 | 10/2010 |
| WO | WO2010/127099 | 11/2010 |
| WO | WO2010/127103 | 11/2010 |
| WO | WO2010/134614 | 11/2010 |
| WO | WO2010/147994 | 12/2010 |
| WO | WO2011/028689 | 3/2011 |
| WO | WO2011/038122 | 3/2011 |
| WO | WO2011/047259 | 4/2011 |
| WO | WO2011/085211 | 7/2011 |
| WO | WO2011/109724 | 9/2011 |
| WO | WO2012/032414 | 3/2012 |
| WO | WO2012/074930 | 6/2012 |
| WO | WO2012/128587 | 9/2012 |
| WO | WO2013/070735 | 5/2013 |
| WO | WO2013/103958 | 7/2013 |
| WO | WO2013/136277 | 9/2013 |
| WO | WO2013/148136 | 10/2013 |
| WO | WO2014/004861 | 1/2014 |
| WO | WO2014/004993 | 1/2014 |
| WO | WO2014/005013 | 1/2014 |
| WO | WO2014/057522 | 4/2014 |
| WO | WO2014/074552 | 5/2014 |
| WO | WO2014/130200 | 8/2014 |
| WO | WO2014/134466 | 9/2014 |
| WO | WO2014/142364 | 9/2014 |
| WO | WO2014/143469 | 9/2014 |
| WO | WO2014/143523 | 9/2014 |
| WO | WO2014/205310 | 12/2014 |
| WO | WO2015/021141 | 2/2015 |
| WO | WO2015/066512 | 5/2015 |
| WO | WO2015/195662 | 12/2015 |
| WO | WO2016/140949 | 9/2016 |
| WO | WO2017077528 | 5/2017 |
| WO | WO2018/213663 | 11/2018 |
| WO | WO2020/037153 | 2/2020 |
| WO | WO2020/065402 | 4/2020 |
| WO | WO2020/068163 | 4/2020 |
| WO | WO2020/168251 | 8/2020 |
| WO | W02021/019037 | 2/2021 |
| WO | WO2021/097120 | 5/2021 |

OTHER PUBLICATIONS

Duan et al., Effect of w-3 polyunsaturated fatty acids-derived bioactive lipids on metabolic disorders, Frontiers in Physiology, May 25, 2021, 12:646491.

Förstermann et al., Nitric oxide synthases: regulation and function, Euro Heart J. (2011) 33:829-837.

Franklin et al., Air pollution and cardiovascular disease, Curr Probl Cardiol, May 2015, p. 207-238.

Gabbs et al., Advances in our understanding of oxylipins derived from dietary PUFAs, ADV. Nutr (2015) 6:513-40.

Gill et al., Bacterial lipopolysaccharide induces endothelial cells to sythesize a degrantulating factor for neutrophils, FASEB J, 1998, 12, p. 673-684.

Hansen et al., diesel exhaust particles induce endothelial dysfunction in apoE mice, Toxicology and Applied Pharmacology, 2006, vol. 219, p. 24-32.

Hoenderdos et al., Hypoxia upregulates neutrophil degranulation and potential for tissue injury, Thorax, 2016, 71:1030-1038.

Ito, Matthew K., A comparative overview of prescription omega-3 fatty acid products, P&T, Dec. 2015, vol. 40, No. 12, pp. 826-857.

Lacy, Mechanisms of degranulation in neutrophils, Allergy, Asthma, and Clinical Immunology, 2006, vol. 2, No. 3, p. 98-108.

Li et al., Production of structured phosphatidylcholine with high content of DHA/EPA byimmobilized phospholipase A1-catalyzed transesterification, Int. J. Mol. Sci. (2014) 15:15244-15258.

Mason et al., Eicosapentaenoic acid improves endothelial function and nitric oxidebioavailability in a manner that is enhanced in combination with a statin, Biomed Pharmacother. (2018) 103:1231-1237.

Mason RP et al., Emerging mechanisms of cardiovascular protection for the omega-3 fatty acid eicosapentaenoic acid, Arteriosclerosis, Thrombosis, and Vascular Biology, 2020, 40:1135-1147.

Mason RP et al., Rationale for different formulations of omega-3 fatty acids leading todifferences in residual cardiovascular risk reduction, Metabolism, 2022, vol. 130, 155161, p. 1-4.

Mori T, et al., Efficacy and safety of self-emulsifying formulation of highly purified eicosapentaenoic acid ethyl ester (MND-2119) versus highly purified eicosapentaenoic acid ethyl ester in patients with hypertriglyceridemia: results from a 12-week randomized, doubleblind, active-controlled, phase 3 study, Journal of Clinical Lipidology (2022), vol. 16, Issue 5 pp. 704-714, Sep.-Oct. 2022, doi: https://doi.org/10.1016/j.jacl.2022.06.007.

Mori T, et al., Pharmacokinetics of single and multiple oral administration of a self- emulsifying formulation of highly purified eicosapentaenoic acid ethy ester (MND-2119)comparted with the nonself-emulsifying formulation in healthy male subjects, Clinical Pharmacology in Drug Development 2022, 0(0), pp. 1-9, The American College of Clinical Pharmacology, DOI: 10.1002/cpdd. 1177.

Newman et al., Effect of Omega-3 fatty acid ethyl esters on the oxylipin composition oflipoproteins in hypertriglyceridemic, statin-treated subjects, PLoS ONE Nov. 13, 2014, 9(11):e111471.

Nurkiewicz et al., Particulate matter exposure impairs systemic microvascularendothelium-dependent dilation, Environmental Health Perspectives, Sep. 2004, vol. 112, No. 13, p. 1299-1306.

Ochoa-Flores et al., Optimization of the synthesis of structured phosphatidylcholine with medium chain fatty acid, J. Oleo Sci. (2017) 66(11):1207-1215.

Pope III et al., Exposure to fine particulate air pollution is associated with endothelialinjury and systemic inflammation, Circulation Research, Nov. 11, 2016, 119(11):1204-1214.

Rajagopalan et al., Air pollution and cardiovascular disease, Journal of American College of Cardiology, 2018, Vo. 72, No. 17, p. 2054-2070.

Sherratt et al., EPA and DHA containing phospholipids have contrasting effects on membrane structure, J Lipid Res. (2021) 62, 100106.

Sherratt et al., Omega-3 and omega-6 fatty acids have distinct effects on endothelialfatty acid content and nitric oxide bioavailability, Prostaglandins Leukot Essent Fatty Acids. (2021) 173.

Amarin Corporation, Eicosapentaenoic acid (EPA) levels from VASCEPA (Icosapent Ethyl) in Reduce-It strongly correlated with cardiovascular outcomes, Press Release, Mar. 30, 2020, 4 pages.

Amarin Reduce-It heart failure analyses by Vascepa (Icosapent Ethyl)-driven serum eicosapentaenoic acid (EPA) levels suggest potential benefit in New Hear Failure, Press Release, May 15, 2021.

Amarin VASCEPA (Icosapent Ethyl) Reported to Impact Vulnerable Coronary Plaque Features in New Analyses of EVAPORATE Study

(56) References Cited

OTHER PUBLICATIONS

Presented as Late-Breaking Science at ESC Preventive Cardiology 2021, Press release, Apr. 17, 2021, 3 pages.
Amarin VASCEPA (Icosapent Ethyl) Reported to Significantly Reduce Coronary Plaque in EVAPORATE Study Final Results Presented at ESC Congress 2020, Press release, Aug. 29, 2020, 4 pages.
Bays et al., Icosapent ethyl: Eicosapentaenoic acid concentration and triglyceride-lowering effects across clinical studies, Prostaglandins and other Lipid Mediators, Sep. 2016, vol. 125, pp. 57-64.
Bays et al., MARINE ESCO Oral Presentation Slides published Aug. 17, 2011; (Year: 2011), 18 slides.
Brunton et al., Differentiating prescription omega-3-acid ethyl esters (P-OM3) fromdietary-supplement omega-3 fatty acids, Curr Med Res Opin, May 2007, 23(5):1139-45.
Di Spirito et al., Effect of omega-3-acid ethyl esters on steady-state plasma pharmacokinetics of atorvastatin in healthy adults, Expert Opinion on Pharmacotherapy 2008 (9), pp. 2939-2945, 9 pages.
Joensen et al., Dietary intake of total marine n-3 polyunsaturated fatty acids, eicosapentaenoic acid, docosahexaenoic acid and docosapentaenoic acid and the riskof acute coronary syndrome—a cohort study. Br J Nutr. Feb. 2010;103(4):602-7. doi: 10.1017/S0007114509992170. published online: Oct. 14, 2009, PMID: 19825219, 6 pages.
Mason RP et al., Eicosapentaenoic acid reduces small dense low density lipoprotein oxidation and improves endothelial function in vitro as compared to other triglyceride-lowering agents, JACC, Mar. 17, 2015, vol. 65, Issue 10S, 1 page.
Reduction in heart failure with icosapent ethyl: insights from reduce-it hf, abstract, American College of Cardiology, 1043-07, May 16, 2021, 1 page.
Van Dam et al., Efficacy of Concentrated n-3 Fatty Acids in Hypertriglyceridaemia, A Comparison with Gemfibrozil; Clinical Drug Investigation, 2001, vol. 21, No. 3, pp. 175-181.
Von Schacky, Clemens, Omega-3 fatty acids and cardiovascular disease/ Current Opinion in Clinical Nutrition and Metabolic Care, 2007, vol. 10, pp. 129-135.
Alderman et al., Comparison of coronary bypass surgery with angioplasty in patientswith multivessel disease, New England Journal of Medicine, Jul. 25, 1996, vol. 335 No. 4, pp. 217-225.
Anonymous, Assessment report Vazkepa, Jan. 28, 2021 (Jan. 28, 2021), pp. 1-129, XP093085997, Retrieved fr Internet: URL:https://www.ema.europa.eu/en/documents/assessment-report/vazkepa-epar-public-assessment-report_en.pdf.
Anonymous, Maltitol—EPA—European Association of Polyol Producers, Jan. 1, 2021 (Jan. 1, 2021), pp. 1-2, XP093086013, Retrieved fr Internet: URL:https://polyols-eu. org/polyols/maltitol/.
Baczek et al: "Predictors of warfarin use in atrial fibrillation in the United States: asystematic review and meta-analysis", BMC Family Practice, Biomed Central, London, GB, vol. 13, No. 1, Feb. 3, 2012.
Bays, H. et al., "Pharmacotherapy of dyslipidemia-current therapies and futureagents", Expert Opinion on Pharmacotherapy, vol. 4, u No. 11, pp. 1901-1938 (2003).
Bhatt et al., Supplementary Appendix, Cardiovascular risk reduction with icosapent ethyl for hypertriglyceridemia, N Engl J Med 2019; 380:11-22, DOI: 10.1056/NEJMoa1812792.
Bhatt et al: "Effects of Icosapent Ethyl on Total Ischemic Events", Journal of the American College of Cardiology, vol. 73, No. 22, Jun. 1, 2019.
Bhatt et al: "Reduce-It USA : Results From the 3146 Patients Randomized in the United States", Circulation, vol. 141, No. 5, Nov. 11, 2019 (Nov. 11, 2019), pp. 367-375.
Bhatt et al: "Supplemental Material to Reduce-It USA", Circulation, vol. 141, No. 511 Nov. 2019 (Nov. 11, 2019), pp. 1-44.
Bhatt, Deepak L, "Cardiovascular Risk Reduction with Icosapent Ethyl for Hypertriglyceridemia",Jan. 3, 2019.
Boriani et al: "Pharmacological treatment of atrial fibrillation: a review onprevention of recurrences and control of ventricular response", Archives of Gerontology and Geriatrics, vol. 27, No. 2, Oct. 1, 1998, pp. 127-139.

Clinical Trials Arena, AMR101-Omega-3-based treatment for hypertriglyceridaemia, Apr. 7, 2010, 7 pages.
Devassy, "Effect of dietary soy protein and oils containing omega-3 fatty acids on disease and renal oxylipins in polycystic kidney disease"; Thesis for partial fulfillment of the requirement for the degree of doctor of philosophy in the University of Manitoba; 2016, p. i-xxiii and 1-276 (p. i; p. 13, para 2; p. 39; p. 43; tables 2.5 and 2.7).
Epadel S series Product Label, Nov. 2005, cited in opposition as D14.
Epadel S Series Product Sheet Jan. 2007, cited in opposition as D19.
Ferdouse, "Effects of dietary n-3 and n-6 fatty acids and sex on the heart and brain oxylipin profiles in healthy rals"; Thes1s for partial fulfillment of the requirement for lhe degree of master of science in the University of Manitoba; 2018, p. i-xvii and 1-176 (p. i; p. 83, para 2).
Handbook of pharmaceutical excipients; Sixth edition, "Glycerin" pp. 283-286 and "Sorbitol" pp. 679-682, 1986.
Innes et al., The differential effects of eicosapentaenoic acid and docosahexaenoic acid on cardiometabolic risk factors: a systemic review, International Journal of Molecular Sciences, Feb. 9, 2018, vol. 19, 532, 22 pages.
Itakura et al., Relationships between plasma fatty acid coposition and coronary artery disease, Journal of Atherosclerosis and Thrombosis, 2011, vol. 18, No. 2, pp. 99-107.
Jue-Min Clinic, Why you should take deep-sea fish oil, WayBack Machine, Aug. 9, 2017.
Lazich et al., Effects of combining simvastatin with rosiglitazone on inflammation, oxidant stress and ambulatory blood pressure in patients with the metabolic syndrome: siroco study, Diabetes, Obesity and Metabolism, Feb. 2012, 14(2):181-186, abstract.
Li et al., Protection against fine particle-induced pulmonary and systemicinflammation by omega-3 polyunsaturated fatty acids, Biochim Biophys Acta Gen Subj. Mar. 2017; 1861(3): 577-584. Epub Dec. 21, 2016.
Lovaza (omega-3-acid ethyl esters) Capsules, Prescribing information, revised Jun. 2013, 27 pages.
Newby et al., Unstable angina: the first 48 hours and later in-hospital management, British Medical Bulletin, Oct. 2001, vol. 59, No. 1, pp. 69-87.
NHS, Coronary angioplasty and stent insertion, website: www.nhs.uk/ page last reviewed Oct. 4, 2022, 4 pages.
Origasa et al, Clinical importance of adherence to treatment with Eicosapentaenoic Acid by patients with hypercholesterolemia, Circulation Journal, Mar. 2010, vol. 74, doi: 10.1253/circj.cj-09-0746. Epub Feb. 9, 2010.
Peter et al., Nutritional solutions to reduce risks of negative health impacts of air pollution, Nutrients, Dec. 10, 2015, vol. 7, pp. 10398-10416.
Press Release, Amarin's AMR101 Phase 3 Anchor Trial meets all Primary and secondary endpoints with statistically significant reductions in triglycerides at both 4 gram and 2 gram doses and statistically significant decrease in ldl-c, Apr. 18, 2011, 8 pages.
Reddy et al,. Improving lipids with prescription icosapent ethyl after previous use of fish oil dietary supplements. Future Cardiology. May 2016; 12(3): 261-268.
RGD, "Ontology Browser, [10(S), 17(S)-dihydroxy-omega 6-docosapentaenoic acid]"; Rat Genome Database (RGD); online database, date created: Nov. 2019, p. 1-4 (p. 1, para 2) URL: https://rgd.mcw.edu/rgdweb/ontology/view.html?acc _id= CHEBI:13867 4&offset=154.
Trilipix Package Insert (Sep. 2011) 59 pages.
Zhulenko et al., Pharmacology, Textbooks and study guides for students of higher education institutions, 2008, Moscow, KolosS with translation.
Zimmerman JJ, et al., Evaluation of a potential tigecycline-warfarin drug interaction. Pharmacotherapy Jul. 28, 2008 (7): 895-905; https://accpjournals.onlinelibrary.wiley.com/doi/abs/10.1592/phco.28.7.895, Manuscript received Aug. 2, 2007. Accepted for publication in final form Jan. 23, 2008, Issue online: Jan. 6, 2012.
A study of AMR101 to evaluate its ability to reduce cardiovascular events in high risk patients with hypertriglyceridemia and on statin

(56) References Cited

OTHER PUBLICATIONS (REDUCE-IT). Available at: http://clinicaltrials.gov/show/NCT01492361, First Posted Dec. 15, 2011; Last Update Posted Jun. 6, 2019 (3 pages).
Aarsetoey H, Gurndt H, Nygaard O. The Role of Long-Chained Marine N-3 Polyunsaturated Fatty Acids in Cardiovascular Disease. Cardiol Res Pract. 2012. Epub Dec. 13, 2012.
Aarsland, et al., "On the Effect of Peroximsomal beta-Oxidation and Carnitine Palmitoyltransferase Activity by Eicosapentaenoic Aid in Live and Heart of Rats." Lipids, 25:546-548, (Sep. 1990); https://link.springer.com/article/10.1007/BF02537162, Received Mar. 6, 1990, Accepted Jun. 6, 1990, Issue Date Sep. 1990.
Aas, V., et al., "Eicosapentaenoic acid (20:5 n-3) increases fatty acid and glucose uptake in cultured human skeletal muscle cells." Journal of Lipid Research, 47:366-374 (Feb. 2006); https://www.jlr.org/content/47/2/366.abstract , First published JLR Papers in Press, Nov. 21, 2005.
Abbey, M., et al., "Effect of fish oil on lipoproteins, lecithin:cholesterol acyltransferase, and lipid transfer protein activity in humans." Arterioscler. Thromb. Vasc. Biol. 10:85-94 (Jan./Feb. 1990); https://www.ahajournals.org/doi/10.1161/01.ATV.10.1.85 Originally published Jan. 1, 1990.
Abela GS, Aziz K. "Cholesterol crystals cause mechanical damage to biological membranes: a proposed mechanism of plaque rupture and erosion leading to arterial thrombosis." Clin. Cardiol. (Sep. 2005);28(9):413-420; https://onlinelibrary.wiley.com/doi/abs/10.1002/clc.4960280906, First published Dec. 5, 2006.
Abelo A, Andersson TB, Antonsson M, et al. "Stereoselective metabolism of omeprazole by human cytochrome P450 enzymes." Drug Metab. Dispos. Aug. 28, 2000 (8): 966-72.
Ackman et al., "The 'Basic' Fatty Acid Composition of Atlantic Fish Oils: Potential Similarties Useful for Enrichment of Polyunsaturated Fatty Acids by Urea Complexation," JAOCS, vol. 65, 1:136-138 (Jan. 1988); https://aocs.onlinelibrary.wiley.com/doi/abs/10.1007/BF02542565, First published Jan. 1, 1988.
Adan, Y, et al., "Effects of docosahexaenoic and eicosapentaenoic acid on lipid metabolism, eicosanoid production, platelet aggregation and atherosclerosis." Biosci. Biotechnol. Biochem. 63(1), 111-119 (Jan. 1999); https://www.jstage.jst.go.jp/article/bbb/63/1/63_1_111/_article/-char/ja/.
Adan, Y., et al., "Concentration of serum lipids and aortic lesion size in female and male apo E-deficient mice fed docosahexaenoic acid." Biosci. Biotechnol. Biochem. 63(2):309-313 (Feb. 1999); https://www.tandfonline.com/doi/abs/10.1271/bbb.63.309 , Received Aug. 25, 1988, Accepted Oct. 22, 1998, published online May 22, 2014.
Adorini et al., "Farnesoid X receptor targeting to treat nonalcoholic steatohepatitis," Drug Discover Today, 14(17-18):988-997 (Sep. 2012)(available online May 28, 2012)
Agren JJ, Vaisanen S, Hanninen O, et al. "Hemostatic factors and platelet aggregation after a fish-enriched diet or fish oil or docosahexaenoic acid supplementation." Prostaglandins Leukot Essent Fatty Acids (Oct. 1997) 57 (4-5): 419-21; https://www.sciencedirect.com/science/article/abs/pii/3095232789790421X, Available online Jun. 18, 2004.
Agren, J.J., et al., "Fatty acid composition of erythrocyte, platelet, and serum lipids in strict vegans." Lipids 30:365-369 (Apr. 1995); https://aocs.oniinelibrary.wiley.com/doi/abs/10.1007/BF02536047, First published—Apr 1, 1995.
Agren, J.J., et al., "Fish diet, fish oil and docosahexaenoic acid rich oil lower fasting and postprandial plasma lipid levels." Eur J Clin Nutr., 50:765-771. (Nov. 1996); https://europepmc.org/article/med/8933125, Oct. 31, 1996.
Aguilar-Salinas et al., "High Prevalence of Low HDL Cholesterol Concentrations and Mixed Hyperlipldemia in a Mexican Nationwide Survey," J Lipid Res., (Aug. 2001), 42:1298-1307; https://www.jlr.org/content/42/8/1298.short , Received Jan. 5, 2001. Revision received Mar. 20, 2001.
Ai M, Otokozawa S, et al., "Small dense LDL cholesterol and coronary heart disease: results from the Framingham Offspring Study." Clin. Chem. (Jun. 2010);56(6):967-976; https://academic.oup.com/clinchem/article/56/6/967/5622464 , Published Jun. 1, 2010.
Ait-Said, et al., "Inhibition by eicosapentaenoic acid of IL-1β-induced PGHS-2 expression in human microvascular endothelial cells: involvement of lipoxygenase-derived metabolites and p38 MAPK pathway." Biohimicia et Biophysica Acta, 1631:66-85 (Feb. 2003); https://www.sciencedirect.com/science/article/abs/pii/S138819810200358X, Accepted Nov. 14, 2002, Available online Dec. 4, 2002.
Akil et al., Relationships between obesity and cardiovascular diseases in four southern states and colorado, J Health Care Poor Underserved, 2011, 22(4 Suppl):61-72.
Albert CM, et al., Blood Levels of Long-Chain n-3 Fatty Acids and the Risk of Sudden Death. N Engl J Med 346(15):1113-1138, Apr. 2002; https://www.nejm.org/doi/full/10.1056/NEJMoa012918, Apr. 11, 2002.
Alberti K, et. al. Harmonizing the Metabolic Syndrome: A Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity. Circulation. 120:1640-1645; Oct. 20, 2009.
Alderman, J.D., et al., "Effect of a modified, well-tolerated niacin regimen on serum total cholesterol, high density lipoprotein cholesterol and the cholesterol to high density lipoprotein ratio," Am. J. Cardio, 64: 725-729.A (Oct. 1989); https://www.ajconline.org/article/0002-9149(89)90754-6/fulltext, Oct. 1, 1989.
Alessandri, J-M., et al., "Estradiol favors the formation of eicosapentaenoic acid (20:5n-3) and n-3 docosapentaenoic acid (22:5n-3) from alpha-linolenic acid (18:3n-3) in SH-SY5Y neuroblastoma cells." Lipids 43:19-28 (Jan. 2008); https://link.springer.com/article/10.1007/s11745-007-3117-6, Published Oct. 3, 2007.
Allard et al. "Nutritional assessment and hepatic fatty acid composition in non-alcoholic fatty liver disease (NAFLD): a cross-sectional study." J Hepatol. Feb. 2008;48(2):300-7; https://www.sciencedirect.com/science/article/abs/pii/S0168827807005855, Available online Nov. 20, 2007.
Allred, C., et al., "PPARγ1 as a molecular target of eicosapentaenolc acid in human colon cancer (HT-29) cells." J. Nutr. 138:250-256 (Feb. 2008); https://academic.oup.com/jn/article/138/2/250/4664979, Published Feb. 1, 2008.
Almeida et al., "Effect of nebicapone on the pharmacokinetics and pharmacodynamics of warfarin in healthy subjects." Eur J Clin Pharmacol. (Oct. 2008);64(10):961-6; https://link.springer.com/article/10.1007/s00228-008-0534-2, Published Aug. 6, 2008.
Amarin Appoints Medpace as CRO for Two Phase 3 Cardiovascular Trials, published Oct. 19, 2009 (2 pages).
Amarin Corporation Announces First Patients Enrolled in Two Phase 3 Clinical Trials Assessing AMR101 for the Treatment of Cardiovascular Disease [online], Amarin Corporation, Jan. 11, 2010 [retrieved Apr. 27, 2011], Retrieved from Internet: <http://inestor.amarincorp.com/releasedetail.cfm?ReleaseID=504380> (2 pages).
Amarin Corporation, Annual Report, Jun. 24, 2010,submitted in 3 parts: Part I: Cover and pp. 1-39 (81 pages); Part II: pp. 40 through F-10 (81 pages); Part III: pp. F11-F51 (83 pages)) 245 pages total).
Amarin Corporation, Executive Informational Overview, "Neurological Disease-Focused Biopharmaceutical Opportunity," SEC filing dated Oct. 11, 2005 (99 pages).
Amarin Corporation, Globe Newswire press release, "Reduce-It™ Cardiovascular Outcomes Study of Vascepa® (icosapent ethyl) Capsules Met Primary Endpoint," Sep. 24, 2018 (4 pages).
Amarin Corporation, press release (Jan. 18, 2008)(1 page).
Amarin Presentation "Next Generation Lipid Modification in Cardiovascular Disease," (Aug. 2011)(27 pages).
Amarin Presentation "Next Generation Lipid Modification in Cardiovascular Disease," (Mar. 2010)(25 pages).
Amarin Proceeding to Phase 3 with AMR101 for Hypertriglyceridemia, published Jul. 23, 2008 (1 page).
Amarin, Next Generation Lipid Modification in Cardiovascular Disease, Investor Meetings, Nov. 2010, (http://files.shareholder.com/downloads/AMRN/0x0x417754/AA72705F-1D67-4E1D-A989-

(56) References Cited

OTHER PUBLICATIONS

5805E5CF0244/Investor_Presentation_2010_Nov_10.pdf, accessed Jan. 6, 2015; (http://files.shareholder.com/downloads/AMRN/0x0x417754/AA72705F-1D67-4E1D-A989-5805E5CF0244/Investor_Presentation_2010_Nov_10.pdf.

Amarin's Vascepa® Briefing Document for the Endocrinologic and Metabolic Drugs Advisory Committee Meeting dated Oct. 16, 2013, (117 pages).

American Heart Association. Heart Disease and Stroke Statistics—2010 Update. Dallas, Texas: American Heart Association; 2010; Lloyd-Jones, D., Adams, R. J., Brown, T. M., Carnethon, M., Dai, S., De Simone, G., Go, A. (2010), American Heart Association Statistics Committee and Stroke Statistics Subcommittee. Executive summary: heart disease and stroke statistics—2010 update: a report from the American Heart Association. Circulation, 121(7), 948-954, https://www.ncbi.nlm.nih.gov/pubmed/20019324 , Feb. 23, 2010; Epub Dec. 17, 2009.

Anand RG, Alkadri M, Lavie CJ, Milani RV. The Role of Fish Oil in Arrhythmia Prevention. J Cardioplin Rehabil Preven., Mar./Apr. 2008; 28:92-98; https://journals.lww.com/jcrjournal/Abstract/2008/03000/The_Role_of_Fish_Oil_in_Arrhythmia_Prevention.3.aspx , Originally published Mar. 1, 2008.

Anber V, Griffin BA, McConnell M, Packard CJ, Shepherd J. Influence of plasma lipid and LDL-subfraction profile on the interaction between low density lipoprotein with human arterial wall proteoglycans. *Atherosclerosis*. Aug. 1996;124(2):261-271; https://www.sciencedirect.com/science/article/abs/pii/002191509605842X, Aug. 2, 1996.

Anderson JL, et al., ACC/AHA 2007 guidelines for the management of patients with unstable angina/non-ST-elevation myocardial infarction—executive summary. A report of the American College of Cardiology/American Heart Association Task Force on Practice Guidelines (Writing Committee to Revise the 2002 Guidelines for the Management of Patients With Unstable Angina/Non-ST-Elevation Myocardial Infarction) developed in Collaboration with the American College of Emergency Physicians, the Society for Cardiovascular Angiography and Interventions, and the Society of Thoracic Surgeons Endorsed by the American Association of Cardiovascular and Pulmonary Rehabilitation and the Society for Academic Emergency Medicine. J Am Coll Cardiol 50:652-726, Aug. 14, 2007.

Anderson TJ, et al., 2012 update of the Canadian Cardiovascular Society guidelines for the diagnosis and treatment of dyslipidemia for the prevention of cardiovascular disease in the adult. Can. J. Cardiol. Feb. 2013;29:151-167; https://www.sciencedirect.com/soience/article/abs/pii/S0828282X12015103 Feb. 2013, Available online Jan. 23, 2013.

Anderson TJ, et al., The effect of cholesterol-lowering and antioxidant therapy on endothelium-dependent coronary vasomotion. N. Engl. J. Med. Feb. 1995;332:488-493; https://www.nejm.org/doi/full/10.1056/NEJM199502233320802, Feb. 23, 1995.

Anderson, "Lipoprotein-Associated Phospholipase A2: An Independent Predictor of Coronary Artery Disease Events in Primary and Secondary Prevention," 101 Am. J. Cardiology 23F-33F, Jun. 2008; https://www.sciencedirect.com/science/article/abs/pii/S0002914908006863, Jun. 16, 2008; Available online Jun. 10, 2008.

Ando, M., et al., "Eicosapentanoic acid reduces plasma levels of remnant lipoproteins and prevents in vivo peroxidation of LDL in dialysis patients." J. Am. Soc. Nephrol., 10:2177-2184, Oct. 1999; https://jasn.asnjournals.org/content/10/10/2177.short , Published online Oct. 1, 1999.

Ando, Y., et al., "Positional distribution of highly unsaturated fatty acids in triacyl-sn-glycerols of Artemia Nauplii enriched with docosahexaenoic acid ethyl ester." Lipids 36:733-740, Jul. 2001; https://aocs.onlinelibrary.wiley.com/doi/abs/10.1007/s11745-001-0779-4, First published Jul. 1, 2001.

Andrade, SE et al., "Discontinuation of antihyperlipidaemic drugs, do rates reported in clinical trials reflect rates in primary care settings?" New Eng. J. Med. 332: 1125-1131. (Apr. 1995); https://www.nejm.org/doi/full/10.1056/nejm199504273321703, Apr. 27, 1995.

Andrews HE, et al., Low-density lipoproteins inhibit endotheliumdependent relaxation rabbit aorta. Nature. May 1987;327:237-239; https://www.nature.com/articles/327237a0, Published May 21, 1987.

Angerer et al., "n-3 Polyunsaturated Fatty Acids and the Cardiovascular System", Current Opinion in Lipidology, 11(1):57-63 (Feb. 2000); https://journals.lww.com/co-lipidology/Abstract/2000/02000/n_3_Polyunsaturated_fatty_acids_and_the.9.aspx.

Anil, Eliz, "The Impact of EPA and DHA on Blood Lipids and Lipoprotein Metabolism: Influence of ApoE Genotype", Proceedings of the Nutrition Society, 66:60-68, (Feb. 2007); https://www.cambridge.org/core/journals/proceedings-of-the-nutrition- society/article/impact-of-epa-and-dha-on-blood-lipids-and-lipoprotein-metabolism-influence-of-apoe-genotype/D0D744A2217FED07F04ABB43AC5F8FA0, Published online Feb. 28, 2007.

Annex to Rule 161 Response dated Apr. 16, 2012 (4 pages).

Antman E, Anbe D, Armstrong P, et al. ACC/AHA guidelines for the management of patients with ST-elevation myocardial infarction—executive summary. A report of the American College of Cardiology/American Heart Association Task Force on Practice Guidelines (Writing Committee to revise the 1999 guidelines for the management of patients with acute myocardial infarction). J Am Coll Cardiol 44:671-719, Aug. 4, 2004.

Aoki T et al. "Experience of the use of ethyl eicosapentaenoic acid preparation (Epadel) in patients with arteriosclerosis obliterans complicated with diabetes mellitus. A study of the long-term effects on glycemic control and blood lipids," Rinsho to Kenkyu; 70:625-631. (1993) (with English translation).

Appendix A to Defendants' Invalidity Contentions, 3:14-CV-02550-MLC-DEA (D.N.J.), 478 pages (Dec. 5, 2014).

Appleton, Katherine M., et al., "Effects of n-3 long-chain polyunsaturated fatty acids on depressed mood: systematic review of published trials", Am. J. Clin. Nutr., 84(6):1308-1316, (Dec. 2006); https://academic.oup.com/ajcn/article/84/6/1308/4649114, Published Dec. 1, 2006.

Arca et al., "Treating statin-intolerant patients," Diabetes, Metabolic Syndrome and Obesity: Targets and Therapy, 4:155-156 (Apr. 28, 2011).

Armaganijan L, et al., Do Omega-3 fatty acids prevent atrial fibrillation after open heart surgery? A meta-analysis of randomized controlled trials. Clinics. 2011(accepted for publication Jul. 19, 2011); 66(11):1923-1928.

Arrol, S. et al., "The effects of fatty acids on apolipoprotein B secretion by human hepatoma cells (HEP G2)," Atherosclerosis 150:255-264. (Jun. 2000); https://www.sciencedirect.com/science/article/abs/pii/S0021915099003743, Available online Jun. 8, 2000.

Arshad, A., et al., "Sudden cardiac death and the role of medical therapy." Progress in Cardiovascular Diseases, vol. 50, No. 6, 420-438, (May/Jun. 2008); https://www.sciencedirect.com/science/article/abs/pii/S0033062007001314, Available online May 9, 2008.

Arterburn, L., et al., "Distribution, interconversion, and dose response of n-3 fatty acids in humans." Am J Clin Nutr., 83:1467S-76S (Jun. 2006); https://academic.oup.com/ajcn/article/83/6/1467S/4633217, Published: Jun. 1, 2006.

Asahara, EPA Products What is the Clinical Significance of Epadel? Obesity and Diabetes 10(6):903-905 (2011) (with English translation).

Asano, M., et al., "Eicosapentaenoic acid inhibits vasopressin-activated Ca2q influx and cell proliferation in rat aortic smooth muscle cell lines." European Journal of Pharmacology 379:199-209 (Aug. 1999); https://www.sciencedirect.com/science/article/abs/pii/S0014299999004768, Available online Jan. 10, 2000.

Asano, M., et al., "Inhibitory effects of ω-3 polyunsaturated fatty acids on receptor-mediated non-selective cation currents in rat A7r5 vascular smooth muscle cells." British Journal of Pharmacology 120:1367-1375, (Apr. 1997); https://bpspubs.onlinelibrary.wiley.com/doi/full/10.1038/sj.bjp.0701047, First published: Feb. 17, 2009.

ASCEND Study Collaborative Group. Effects of n-3 fatty acid supplements in diabetes mellitus. N Engl J Med, 379(16):1540-1550 (publication date Oct. 18, 2018; epublication date Aug. 26, 2018).

Ascenta Health "Fish Oil as Triglycerides vs. Ethyl Esters: Why this Matters." (2015)(14 pages); Not found.

(56) References Cited

OTHER PUBLICATIONS

Astarita et al., "Targeted lipidomics strategies for oxygenated metabolites of polyunsaturated fatty acids," Biochim Biophys Acta, 1851(4):456-468 (Apr. 2015); https://www.sciencedirect.com/science/article/abs/pii/S1388198114002510, Available online Dec. 5, 2014.

At-a-Glance: Coronary Heart Disease; National Heart, Lung and Blood Institute, NIH Publication, Aug. 2009.

Atorvastatin Package Leaflet, Reg. No. LSR-005205/08, Sep. 30, 2016 [retrieved Sep. 30, 2016] retrieved from Internet: academ-clinic.ru/drugs/atorvastatin (6 pages).

ATP III guidelines, NIH publication No. 01-3305 (2001).(6 pages).

Attie AD, et al., "Relationship between stearoyl-CoA desaturase activity and plasma trigylcerides in human and mouse hypertriglyceridemia," J. Lipid Res. 2002;43:1899-907; https://www.jlr.org/content/43/11/1899.short, First Published on Aug. 16, 2002.

Ault, "Prescription omega-3 fatty acid formulation approved," OB.GYN.NEWS, (Jan. 15, 2005).

Aung T, et al., Associations of omega-3 fatty acid supplement use with cardiovascular disease risks: Meta-analysis of 10 trials involving 77917 individuals. JAMA Cardiol 3:225-34 (publication date Mar. 1, 2018; epublication date Jan. 31, 2018).

Avandia [package insert]. Research Triangle Park, NC: GlaxoSmithKline; 2011.(45 pages).

Avery et al., "Upper Gastrointestinal System," Integrating Therapeutic and Complementary Nutrition, Edited by Mary Marian, CRC Press (2006)(14 pages); https://www.routledge.com/Integrating-Therapeutic-and-Complementary-Nutrition-1st-Edition/Marian-Williams-Mullen-Bowers/p/book/9780849316128, This is a book chapter.

Aviram M, et al., Atorvastatin and gemfibrozil metabolites, but not the parent drugs, are potent antioxidants against lipoprotein oxidation. Atherosclerosis. Jun. 1998; 138(2):271-280; https://www.sciencedirect.com/science/article/abs/pii/S002191509800032X, Available online Jun. 24, 1998.

Ayton, et al., "A pilot open case series of Ethyl-EPA supplementation in the treatment of anorexia nervosa," Prostaglandins, Leukotrienes and Essential Fatty Acids 71, pp. 205-209. (Oct. 2004); https://www.sciencedirect.com/science/article/abs/pii/S0952327804000584, Available online May 18, 2004.

Ayton, et al., "Rapid improvement of severe anorexia nervosa during treatment with ethyl-eicosapentaenoate and micronutrients," European Psychiatry 19, pp. 317-319. (Aug. 2004); https://s3.amazonaws.com/academia.edu.documents/45835056/ayton_case.pdf?response-content-disposition=inline%3B%20filename%3DRapid_improvement_of_severe_anorexia_ner.pdf&X-Amz-Algorithm=AWS4-HMAC-SHA256&X-Amz-Credential=AKIAIWOWYYGZ2Y53UL3A%2F20200317%2Fus-east-1%2Fs3%2Faws4_request&X-Amz-Date=20200317T203439Z&X-Amz-Expires=3600&X-Amz-SignedHeaders=host&X-Amz-Signature=03e3af4b62a77d3e420dcefd567640b3b3549fd24910ce283bbde2b41fc5edd0, No publication date available, other versions available here: https://scholar.google.com/scholar?cluster=4862195463092004751&hl=en&as_sdt=1, 14.

Baigent, C., et al., "Efficacy and safety of cholesterol-lowering treatment: prospective meta-analysis of data from 90,056 participants in 14 randomised trials of statins." Lancet; 366:1267-1278. (Oct. 2005); https://www.thelancet.com/journals/lancet/article/PIIS0140673605673941/fulltext, Published: Sep. 27, 2005.

Baldwin RM, et al., Increased omeprazole metabolism in carriers of the CYP2C19*17 allele; a pharmacokinetic study in healthy volunteers. Br. J. Clin. Pharmacol. May 2008 65 (5): 767-74; https://bpspubs.onlinelibrary.wiley.com/doi/full/10.1111/j.1365-2125.2008.03104.x, First published:Feb. 20, 2008.

Baldwin SJ, Clarke SE, Chenery RJ. Characterization of the cytochrome P450 enzymes involved in the in vitro metabolism of rosiglitazone. Br. J. Clin. Pharmacol. Sep. 1999;48:424-432; https://www.ncbi.nlm.nih.gov/pmc/articles/PMC2014317/.

Balfour et al., "Rosiglitazone," Drugs, 57(6):921-930 (Jun. 1999); https://link.springer.com/article/10.2165/00003495-199957060-00007, published Oct. 10, 2012.

Balk, E.M., et al., "Effects of omega-3 fatty acids on serum markers of cardiovascular disease risk: a systematic review. Atherosclerosis." 189:19-30. (Nov. 2006); https://www.sciencedirect.com/science/article/abs/pii/S0021915006000694, Available online Mar. 10, 2006.

Ballantyne CM, et al., Efficacy and safety of eicosapentaenoic acid ethyl ester (AMR 101) therapy in statin-treated patients with persistent high triglycerides (from the ANCHOR study). Am J Cardiol Oct. 2012 110 (7): 984-992; https://www.sciencedirect.com/science/article/abs/pii/S0002914912014324, Available online Jul. 20, 2012.

Ballantyne et al., "Abstract 15071: AMR101 Lowers Triglycerides, Atherogenic Lipoprotein, Phospholipase $A_2$, and High-sensitivity C-reactive Protein Levels in Patients with High Triglycerides and on Background Statin Therapy (the ANCHOR Study)," Circulation, Lippincott Williams and Wilkins, vol. 124, No. 21, Suppl., Nov. 22, 2011.

Ballantyne et al., Effects of icosapent ethyl on lipoprotein particle concentration and the fatty acid desaturation index in statiotreated patients with persistent high triglycerides (the ANCHOR study), Journ. Clin. Lipidology, 2013, 7(3):270-271; https://www.sciencedirect.com/science/article/pii/S1933287414004085, Available online Nov. 29, 2014.

Ballantyne et al., Icosapent ethyl (eicosapentaenoic acid ethyl ester): effects on remnant-like particle cholesterol from the marine and anchor studies; Atherosclerosis, Aug. 20, 2016, pp. 81-87.

Ballantyne et al., Influence of low-high density lipoprotein cholesterol and elevated triglyceride on coronary heart disease events and response to simvastatin therapy in 4S, Circulation, 104:3046-3051 (Dec. 2001); https://www.ahajournals.org/doi/full/10.1161/h05001.100624, Originally published Dec. 18, 2001.

Bang Ho, Dyerberg J. "Plasma lipids and Lipoproteins in Greenlandic west coast Eskimos" Acta Med Scand, 192:85-94. (Jul./Aug. 1972); https://onlinelibrary.wiley.com/doi/abs/10.1111/j.0954-6820.1972.tb04782.x, First published: Jan./Dec. 1972.

Banga, A., et al., "Adiponectin translation is increased by the PPARγ agonists pioglitazone and ω-3 fatty acids." Am J Physiol Endocrinol Metab 296:480-489 (Mar. 2009); https://journals.physiology.org/doi/full/10.1152/ajpendo.90892.2008, Mar. 1, 2009.

Bangham et al., "Diffusion of univalent ions across the lamellae of swolloen phospholipids." J. Mol. Biol. (Aug. 1965) 13(1):238-252; https://www.sciencedirect.com/science/article/abs/pii/S0022283665800936, Available online May 7, 2009.

Bansal S, et al., "Fasting Compared With Nonfasting Triglycerides and Risk of Cardiovascular Events in Women," JAMA, 298:309-316 (Jul. 2007); https://jamanetwork.com/journals/jarna/article-abstract/208018, Jul. 18, 2007.

Barter et al., "Effectiveness of Combined Statin Plus Omega-3 Fatty Acid Therapy for Mixed Dyslipidemia." Am. J. Cardiol. 102(8):1040-1045 (Oct. 15, 2008).

Basu, A., et al., "Dietary Factors That Promote or Retard Inflammation." Arterioscler. Thromb. Vasc. Biol. 26:995-1001 (May 2006); https://www.ahajournals.org/doi/full/10.1161/01.atv.0000214295.86079.d1, Originally published Feb. 16, 2006.

Baynes JW, Role of oxidative stress in development of complications in diabetes. Diabetes. Apr. 1991;40(4):405-412; https://diabetes.diabetesjournals.org/content/40/4/405.short, Published in print Apr. 1, 1991.

Bays H.E. et al., Comparison of once-daily, niacin extended-release/lovastatin with standard dosdes of atorvastatin and simvastatin (the advisor versus other cholesterol-modulating agents trial evaluation [Advocate], Am J. Cardiol, Mar. 15, 2003, vol. 91, pp. 667-672.

Bays HE et al., "Prescription omega 3 fatty acids and their lipid effects: physiologic mechanisms of action and clinical implications," Expert Rev Cardiovasc Ther., 6:391-409. (Mar. 2008); https://www.tandfonline.com/doi/full/10.1586/14779072.6.3.391, Published online: Jan. 10, 2014.

Bays HE et al., "AMR101, a Pure Ethyl Eicosapentaenoic Acid Omega-3 Fatty Acid: Effects on Inflammation-Associated End POInts from the Marine and Anchor Studies," Journ. Clin. Lipid., vol. 6 No. 3, p. 279 (May 30, 2012), abstract #150.

(56) References Cited

OTHER PUBLICATIONS

Bays HE et al., Effects of prescription omega-3-acid ethyl esters on non-high-density lipoprotein cholesterol when coadministered with escalating doses of atorvastatin; Mayo Clinic Proc. 85(2):122-128 (Feb. 2010).

Bays HE et al., Icosapent ethyl, a pure ethyl ester of eicosapentaenoic acid: effects on circulating markers of inflammation from the MARINE and ANCHOR studies. Am. J. Cardiovasc. Drugs. Feb. 2013;13(1):37-46; https://link.springer.com/article/10.1007/s40256-012-0002-3, Published Jan. 17, 2013.

Bays HE, Braeckman RA, Ballantyne CM, et al. Icosapent ethyl, a pure EPA omega-3 fatty acid: Effects on lipoprotein particle concentration and size in patients with very high triglyceride levels (the MARINE study). J. Clin. Lipidol. Nove/Dec. 2012;6:565-572; https://www.sciencedirect.com/science/article/abs/pii/S1933287412002735, Available online Jul. 24, 2012.

Bays HE, Safety considerations with omega-3 fatty acid therapy. Am. J. Cardiol. Mar. 2007 99 (6A): 35C-43C; https://www.sciencedirect.com/science/article/abs/pii/S0002914906022387, Available online Nov. 28, 2006.

Bays, H., Clinical Overview of Omacor: A Concentrated Formulation of Omega-3 Polyunsaturated Fatty Acids, Am J Cardiol.; 98[suppl]:71i-76i (Aug. 2006); https://www.sciencedirect.com/science/article/abs/pii/S0002914905021922, Available online May 30, 2006.

Bays, H., "Rationale for Prescription Omega-3-Acid Ethyl Ester Therapy for Hypertriglyceridemia: A Primer for Clinicians," Drugs of Today, 44(3); 205-246. (Mar. 2008); https://journals.prous.com/journals/servlet/xmlxsl/pk_journals.xml_summary_pr?p_JournalId=4&p_RefId=1166387&p_IsPs=N.

Bays, H.E., Eicosapentaenoic Acid Ethyl Ester (AMR101) Therapy in Patients With Very High Triglyceride Levels (from the Multicenter, plAcebo-controlled, Randomized, double-blINd, 12-week study with an open-label Extension [MARINE] Trial) Am J Cardiol;108:682-690. (Sep. 2011); https://www.sciencedirect.com/science/article/abs/pii/S0002914911015992, Available online Jun. 16, June 2011.

Bays, H.E., et al., "Long-term up to 24-month efficacy and safety of concomitant prescription omega-3-acid ethyl esters and simvastatin in hypertriglyceridemic patients." Curr Med Res Opin.; 26:907-915. (Apr. 2010); https://www.tandfonline.com/doi/abs/10.1185/03007991003645318, Published online: Feb. 15, 2010.

Beal, M.F., Annals of Neurology, vol. 38, No. 3, "Aging, Energy, and Oxidative Stress in Neurodegenerative Diseases", pp. 357-366, (Sep. 1995); https://onlinelibrary.wiley.com/doi/abs/10.1002/ana.410380304, First published: Sep. 1995.

Beaumont et al., Design of Ester Prodrugs to Enhance Oral Absorption of Poorly Permeable Compounds: Challenges to the Discovery Scientist, Current Drug and Metabolism. (Dec. 2003) 4:461-485; https://www.ingentaconnect.com/content/ben/cdm/2003/00000004/00000006/art00001, Publication date: Dec. 1, 2003.

Becker LB, et al., AHA Consensus Statement: Primary Outcomes for Resuscitation Science Studies: A Consensus Statement From the American Heart Association. Circulation 2011; CIR. 0b013e3182340239 published online before print Oct. 3, 2011, doi:10.1161/CIR.0b013e3182340239.

Belarbi et al., "A process for high yield and scaleable recovery of high purity eicosapentaenoic acid esters from microalgae and fish oil," Enzyme and Microbail Technology 26:516-529 (Apr. 2000); https://www.sciencedirect.com/science/article/pii/S0032959200001266, Available online Jun. 23, 2000, website says article is retracted.

Belger et al., "Assessment of prefrontal activation by infrequent visual targets and non-target noval stimuli in schisophrenia: a function MRI study," Presented at the 9th Biennial winter workshop on schizophrenia, Davos, Switzerland, Feb. 7-13, 1998, Abstract in Schizophrenia Research. vol. 29. No. 1/02, Jan. 1998.

Belikov, Pharmaceutical Chemistry in Two Parts, 1/General Pharmaceutical Chemistry 43-47 (1993) (with English translation)(9 pages); Book: https://www.biblio.com/book/belikov-vg-pharmaceutical-chemistry-volume-1/d/1262927120, Published in 1993.

Belmaker et al., "Addition of Omega-3 Fatty Acid to Maintenance Medication Treatment for Recurrent Unipolar Depressive Disorder," Am. J. Psychiatry, 159:477-479 (Mar. 2002); https://ajp.psychiatryonline.org/doi/full/10.1176/appi.ajp.159.3.477, Published Online:Mar. 1, 2002.

Belmaker, et al., "Omega-3 Eicosapentaenoic Acid in Bipolar Depression: Report of a Small Open-Label Study," J Clin Psychiatry; 66:726-729. (Jun. 2005); https://europepmc.org/article/med/15960565, May 31, 2005.

Bender NK, et al., Effects of marine fish oils on the anticoagulation status of patients receiving chronic warfarin therapy. J. Thromb. Thrombolysis Jul. 5, 1998 (3): 257-61.

Bénistant, C., et al., "Docosapentaenoic acid (22:5, n-3): metabolism and effect on prostacyclin production in endothelial cells." Prostaglandins, Leukotrienes and Essential Fatty Acids, 55(4):287-292, (Oct. 1996); https://www.sciencedirect.com/science/article/abs/pii/S0952327896900101, Accepted Oct. 3, 1996. Available online Jun. 21, 2004.

Benn et al., Improving Prediction of Ischemic Cardiovascular Disease in the General Population Using Apolipoprotein B: The Copenhagen City Heart Study, 27 Arteriosclerosis, Thrombosis, & Ascular Biology 661 (Mar. 2007); https://www.ahajournals.org/doi/full/10.1161/01.ATV.0000255580.73689.8e, Originally published Dec. 14, 2006.

Bennett et al., "Treatment of IgA nephropathy with eicosapentanoic acid (EPA): a two-year prospective trial [Abstract Only]." Clin. Nephrol. 31(3):128-131 (Mar. 1989); https://www.ahajournals.org/doi/full/10.1161/01.ATV.0000255580.73689.8e, Originally Qublished Dec. 14, 2006.

Berge, R.K., et al., "In contrast with docosahexaenoic acid, eicosapentaenoic acid and hypolipidaemic derivatives decrease hepatic synthesis and secretion of triacylglycerol by decreased diacylglycerol acyltransferase activity and stimulation of fatty acid oxidation." Biochem J.; 343(Pt 1):191-197. (Oct. 1999); https://www.ncbi.nlm.nih.gov/pubmed/10493929, Oct. 1, 1999.

Berglund L, Brunzell JD, Goldberg AC, et al. Evaluation and treatment of hypertriglyceridemia: an endocrine society clinical practice guideline. J. Clin. Endocrinol. Metab. Sep. 2012 97 (9): 2969-89; https://academic.oup.com/jcem/article/97/9/2969/2536709, Published: Sep. 1, 2012.

Berliner JA, Watson AD. A role for oxidized phospholipids in atherosclerosis. N. Engl. J. Med. Jul. 2005;353(1):9-11; https://www.nejm.org/doi/pdf/10.1056/nejmp058118, Jul. 7, 2005.

Bertelsen M, Anggard EE, Carrier MJ. Oxidative stress impairs insulin internalization in endothelial cells in vitro. Diabetologia. May 2001;44(5):605-613; https://link.sgringer.com/article/10.1007/s001250051667, Published: Apr. 2001.

Betteridge, D.J., "Diabetic dyslipidemia: past, present and future." Practical Diabetes Int, 21(2): 78-85. (Mar. 2004); https://onlinelibrary.wiley.com/doi/full/10.1002/pdi.593, First published:Mar. 26, 2004.

Bhatt DL, Eagle KA, Ohman EM, et al. Comparative determinants of 4-year cardiovascular event rates in stable outpatients at risk of or with atherothrombosis. JAMA 304(12):1350-7 (publication date Sep. 22, 2010; epublication date Aug. 30, 2010).

Bhatt DL, et al. Rationale and design of REDUCE-IT: Reduction of Cardiovascular Events with Icosapent Ethyl-Intervention Trial. Clin Cardiol 40:138-48 (publication date Mar. 2017; epublication date Mar. 15, 2017).

Bhatt DL, et al., Antiplatelet and anticoagulation therapy for acute coronary syndromes. Circ Res 114(12):1929-43 (publication date Jun. 6, 2014).

Bhatt DL, et al., CHARISMA Investigators. Clopidogrel and aspirin versus aspirin alone for the prevention of atherothrombotic events. N Engl J Med. 354(16):1706-1717 (publication date Apr. 20, 2006; epublication date Mar. 12, 2006).

Bhatt DL, et al.; REACH Registry Investigators. International prevalence, recognition and treatment of cardiovascular risk factors in outpatients with atherothrombosis. *JAMA*. 295(2):180-189 (publication date Jan. 11, 2006).

Bhatt et al., "Cardiovascular Risk Reduction with Icosapent Ethyl for Hypertiglyceridemia," N. Eng. J. Med., Nov. 10, 2018, vol. 380,

(56) References Cited

OTHER PUBLICATIONS pp. 11-22, (epub ahead of print)(12 pages)(downloaded from nejm.org on Nov. 13, 2018 at https://www.nejm.org/doi/full/10.1056/NEJMoa1812792).
Bild et at., "Multi-Ethnic Study of Atherosclerosis: objectives and design," Am J Epidemiol 156(9):871-81 (Nov. 1, 2002).
Billman et al., "Effects of dietary omega-3 fatty acids on ventricular function in dogs with healed myocardial infarctions: in vivo and in vitro studies." Am. J. Physiol Heart Circ. Physiol., 298:H1219-H1228 (Jan. 22, 2010).
Black et al., "Effect of intravenous eicosapentaenoic acid on cerebral blood flow, edema, and brain prostaglandins in ischemic gerbils", Prostaglandins, 28(4), pp. 545-546. cited by other. (Oct. 1984); https://www.sciencedirect.com/science/article/pii/0090698084902430, Accepted Sep. 4, 1984, Available online Dec. 1, 2003.
Blankenhorn D.H. et al., "Beneficial effects of combined colestipol-niacin therapy on coronary atherosclerosis and coronary venous bypass grafts." JAMA 257: 3233-3240. (Jun. 1987); https://jamanetwork.com/journals/jama/article-abstract/366621 , Jun. 19, 1987.
Block, R.C., et al., "EPA and DHA in blood cell membranes from acute coronary syndrome patients and controls." Atherosclerosis, 197(2):821-828 (Apr. 2008); https://www.sciencedirect.com/science/article/abs/pii/S0021915007004765, Available online Sep. 17, 2007.
Blumenthal, RS, Overview of the Adult Treatment Panel (ATP III) Guidelines, Advanced Studies in Medicine, 2:148-157 (Mar. 2002); https://pdfs.semanticscholar.org/0c7c/7efd16d0297283b5d6a083616dc76c3af837.pdf.
Boden WE, et al., "Niacin in patients with low hdl cholesterol levels receiving intensive statin therapy," N. Engl. J. Med. Dec. 2011;365:2255-2267; https://www.nejm.org/doi/pdf/10.1056/NEJMoa1107579, Dec. 15, 2011 (PDF of grint article).
Bonaa, KH et al., Docosahexaenoic and Eicosapentaenoic acids in plasma phospholipids are divergently associated with high density lipoprotein in humans, Arterioscler. Thromb. Vasc. Biol.;12;675-681 (Jun. 1992); https://www.ahajournals.org/doi/abs/10.1161/01.ATV.12.6.675, Originally published Jun. 1, 1992.
Bonnet et al., "Comparative Effects of 10-mg Versus 80-mg Atorvastatin on High-Sensitivity C-Reactive Protein in Patients with Stable Coronary Artery Disease: Results of the CAP (Comparative Atorvastatin Pleiotropic Effects) Study," Clinical Therapeutics. 30(12):2298-2313 (Dec. 2008); https://www.sciencedirect.com/science/article/abs/pii/S014929180800458X, Available online Jan. 22, 2009.
Borchman D, et al., The dual effect of oxidation on lipid bilayer structure. Lipids. Apr. 1992;27(4):261-265; https://link.springer.com/article/10.1007/BF02536472, Published Apr. 1992.
Bordin et al., "Effects of fish oil supplementation on apolipoprotein B100 production and lipoprotein metabolism in normolipidaemic males," Eur. J. Clin. Nutr. 52: 104-9 (Feb. 1998); https://www.nature.com/articles/1600522, Published Mar. 23, 1998.
Borow et al., "Biologic plausibility, cellular effects, and molecular mechanisms of eicosapentaenoic acid (EPA) in atherosclerosis," Atherosclerosis, 242(1):357-66 (Sep. 2015); https://www.sciencedirect.com/science/article/pii/S0021915015300551, Available online Jul. 22, 2015.
Borthwick et al., "The effects of an omega-3 ethyl ester concentrate on blood lipid concentrations in pateitns with hyperlipidemia," Clin. Drug Investig. (1998) 15(5): 397-404; https://link.springer.com/article/10.2165/00044011-199815050-00004, Published: Aug. 28, 2012.
Bossaller C, et al., Impaired muscarinic endothelium-dependent relaxation and cyclic guanosine 5'-monophosphate formation in atherosclerotic human coronary artery and rabbit aorta. J. Clin. Invest. Jan. 1987;79:170-174; https://www.jci.org/articles/view/112779, First published Jan. 1, 1987.
Bousserouel, S., et al., "Different effects of n-6 and n-3 polyunsaturated fatty acids on the activation of rat smooth muscle cells by interleukin-1beta." J. Lipid Res. 44:601-611 (Mar. 2003); https://www.jlr.org/content/44/3/601.short, First published on Jan. 1, 2003.
Bousserouel, S., et al., "Modulation of cyclin D1 and early growth response factor-1 gene expression in interleukin-1beta-treated rat smooth muscle cells by n-6 and n-3 polyunsaturated fatty acids." Eur. J. Biochem. 271:4462-4473 (Nov. 2004); https://febs.onlinelibrary.wiley.com/doi/full/10.1111/j.1432-1033.2004.04385.x, First published:Nov. 19, 2004.
Brady, L., et al., Increased n-6 polyunsaturated fatty acids do not attenuate the effects of long-chain n-3 polyunsaturated fatty acids on insulin sensitivity or triacylglycerol reduction in Indian Asians. Am J Clin Nutr 79:983-91 (Jun. 2004); https://academic.oup.com/ajcn/article/79/6/983/4690259, Published: Jun. 1, 2004.
Braeckman et al., "Abstract 18549: Effects of AMR101, a Pure Eicosapentaenoic Omega-3 Fatty Acid, on the Fatty Acid Profile in Plasma and Red Blood Cells in Statin-Treated Patients with Persistent High Triglycerides—Results from the ANCHOR study," Circulation 126(21S):A15071 (Nov. 20, 2012)(2 pages).
Braeckman et al., "Effect of Concomitant lcosapent Ethyl (Eicosapentaenoic Acid Ethyl Ester) on Pharmacokinetics of Atorvastatin," Clinical Drug Investigation. (Jan. 2015) (3)45-51; https://link.springer.com/article/10.1007/S40261-014-0252-8, Published: Dec. 4, 2014.
Braeckman RA, et al., Icosapent ethyl, a pure EPA omega-3 fatty acid: effects on plasma and red blood cell fatty acids in patients with very high triglyceride levels (results from the MARINE study). Prostaglandins Leukot Essent Fatty Acids. Sep. 2013;89(4):195-201; https://www.sciencedirect.com/science/article/abs/pii/S0952327813001555, Available online Jul. 31, 2013.
Braeckman RA, Stirtan WG, Soni PN. Pharmacokinetics of eicosapentaenoic acid in plasma and red blood cells after multiple oral dosing with AMR101 (ethyleicosapentaenoic acid) in healthy subjects [abstract]. Presented at: Congress of the International Society for the Study of Fatty Acids and Lipids, Vancouver, Canada, May 26-30, 2012.
Braeckman RA, Stirtan WG, Soni PN. Pharmacokinetics of eicosapentaenoic acid in plasma and red blood cells after multiple oral dosing with icosapent ethyl in healthy subjects. Clin. Pharmacol. Drug Dev. Mar. 2014 (epub Oct. 22, 2013); 3:101-108.
Braunersreuther V, et al., A novel rantes antagonist prevents progression of established atherosclerotic lesions in mice. Arterioscler. Thromb. Vasc. Biol. Jun. 2008;28:1090-1096; https://www.ahajournals.org/doi/full/10.1161/ATVBAHA.108.165423, Originally published Apr. 3, 2008.
Breslow, J., "n-3 Fatty acids and cardiovascular disease." Am J Clin Nutr., 83:1477S-82S (Jun. 2006); https://academic.oup.com/ajcn/article/83/6/1477S/4633237, Published: Jun. 1, 2006.
Brinton EA, et al., Effects of AMR101 on lipid and inflammatory parameters in patients with diabetes mellitus-2 and residual elevated triglycerides (200-500 mg/dl) on statin therapy at LDL-C goal: the ANCHOR study.[abstract 629-P] Diabetes. 2012;61 (suppl 1):A159-A160; see also European Heart Journal (vol. 33, pp. 280-280). Great Clarendon St, Oxford OX2 GDP, England: Oxford Univ Press.
Brinton et al., "Effects of icosapent ethyl on lipid and inflammatory parameters in patients with diabetes mellitus-2, residual elevated triglycerides (200-500 mg/dL), and on statin therapy at LDL-C goal: the ANCHOR study," Cardiovasc. Diabetol. Jul. 9, 2013;12:100. doi: 10.1186/1475-2840-12-100.
Brinton et al., Prescription omega-3 fatty acid products containing highly purified eicosapentaenoic acid (epa); Lipids in Health and Disease, 2017, 16:23, DOI 10.1186/x12944-017-0415-8.
Brossard, N., et al., "Retroconversion and metabolism of [13C]22:6n-3 in humans and rats after intake of a single dose of [13C]22:6n-3—3-triacyylglycerols." Am. J. Clin. Nutr. 64:577-86 (Oct. 1996).
Brouwer, I.A., et al., "Effect of fish oil on ventricular tachyarrhythmia and death in patients with implantable cardioverter defibrillators." JAMA. 295(22):2613-2619 (Jun. 2006); https://jamanetwork.com/journals/jama/article-abstract/202999, Jun. 14, 2006.
Brovkovych V, et al., Nitric oxide release from normal and dysfunctional endothelium. J. Physiol. Pharmacol. Dec. 1999;50:575-586; https://europepmc.org/article/med/10639008, Nov. 30, 1999.
Brown et al., Simvastatin and Niacin, Antioxidant Vitamins, or the Combination for the Prevention of Coronary Disease, N Engl J Med, vol. 345, No. 22, 1583-1592 (Nov. 29, 2001).

(56) References Cited

OTHER PUBLICATIONS

Brown, A. J., et al., "Administration of n-3 Fatty Acids in the Diets of Rats or Directly to Hepatocyte Cultures Results in Different Effects on Hepatocellular ApoB Metabolism and Secretion." Arterioscler. Thromb. Vasc. Biol. 19:106-114 (Jan. 1999); https://www.ahajournals.org/doi/full/10.1161/01.ATV.19.1.106, Originally published Jan. 1, 1999.

Brown, A. J., et al., "Persistent changes in the fatty acid composition of erythrocyte membranes after moderate intake of n-3 polyunsaturated fatty acids: study design and implications." Am.J. Ciin. Nutri. 54:668-73(Oct. 1991); https://academic.oup.com/ajcn/article-abstract/54/4/668/4694264, Published: Oct. 1, 1991.

Brown, G., et al., "Regression of coronary artery-disease as a result of intensive lipid-lowering therapy in men with high levels of apolipoprotein," B., N. Engl. J. Med. 323:1289-1298. (Nov. 1990); https://www.nejm.org/doi/full/10.1056/nejm199011083231901, Nov. 8, 1990 (PDF of rint article).

Brownlee M. Biochemistry and molecular cell biology of diabetic complications. Nature. Dec. 2001 ; 414(6865):813-820; https://www.nature.com/articles/414813a, Published: Dec. 13, 2001.

Bryhn, M., et al., "The bioavailability and pharmacodynamics of different concentrations of omega-3 acid ethyl esters." Prostagiandins, Leukotrienes and Essential Fatty Acids 75:19-24 (Jul. 2006); https://www.sciencedirect.com/science/article/abs/pii/S0952327806000536, Available online Jun. 27, 2006.

Budavari, S., Editor, "The Merck Index", Merck & Co., Inc., p. 725 item 4511 and p. 279 and item 2417 (1989); https://www.amazon.com/Merck-Index-Eleventh-Susan-Budavari/dg/B0036FBD2K, no specific date.

Budoff, "Triglycerides and Triglyceride-Rich Lipoproteins in the Causal Pathway of Cardiovascular Disease," Am. J. Cardiol., 118(1):138-45 (Jul. 1, 2016).

Bunting et al. "Depression in Parkinson's Disease". J Neurosci Nurs.; 23(3):158-164. (Abstract Only) (Jun. 1991); https://europepmc.org/article/med/1831480 , May 31, 1991.

Burdge, G.C., et al., "Eicosapentaenoic and docosapentaenoic acids are the principal products of a-linolenic acid metabolism in young men." British Journal of Nutrition 88:355-363 (Oct. 2002); https://www.cambridge.org/core/journals/british-journal-of-nutrition/article/eicosapentaenoic-and-docosapentaenoic-acids-are-the-principal-products-of-linolenic-acid-metabolism-in-young-men/602A731B990E9FE14F22F0ADD63E77D4 , Oct. 2002, Published online Mar. 9, 2007.

Burdge, G.C., et al., "Lack of effect of meal fatty acid composition on postprandial lipid, glucose and insulin responses in men and women aged 50-65 years consuming their habitual diets." British Journal of Nutrition, 96:489-500 (Sep. 2006); https://www.cambridge.org/core/journals/british-journal-of-nutrition/article/lack-of-effect-of-meal-fatty-acid-composition-on-postprandial-lipid-glucose-and-insulin-responses-in-men-and-women-aged-5065-years-consuming-their-habitual-diets/1031BE7402ED8256F1E355907E2AE159, Sep. 2006, Published online Feb. 19, 2008.

Burdge, G.C., et al., "The effect of altering the 20:5n-3 and 22:6n-3 content of a meal on the postprandial incorporation of n-3 polyunsaturated fatty acids into plasma triacylglycerol and non-esterified fatty acids in humans." Prostaglandins, Leukotrienes and Essential Fatty Acids 77:59-65 (Jul. 2007); https://www.cambridge.org/core/journals/british-journal-of-nutrition/article/lack-of-effect-of-meal-fatty-acid-composition-on-postprandial-lipid-glucose-and-insulin-responses-in-men-and-women-aged-5065-years-consuming-their-habitual-diets/1031BE7402ED8256F1E355907E2AE159, Sep. 2006. Published online Feb. 19, 2008.

Burr ML, Sweetham PM, Fehily AM. Diet and reinfarction. Eur Heart J 15:1152-1153, Aug. 1994; https://www.ncbi.nlm.nih.gov/pubmed/7988613.

Burr, M. L., et al., "Effects of changes in fat, fish and fibre intakes on death and myocardial reinfarction: Diet and reinfarction trial." The Lancet, 2(8666):757-61 (Sep. 1989); https://www.sciencedirect.com/science/article/pii/S0140673689908283 , Sep. 30, 1989. Available online Sep. 24, 2003.

Buse JB, et al. Primary prevention of cardiovascular diseases in people with diabetes mellitus: a scientific statement from the American Heart Association and the American Diabetes Association. Diabetes Care. 2007;30: 162-172; https://www.ahajournals.org/doi/full/10.1161/circulationaha.106.179294, Originally published Dec. 27, 2006.

Calabresi, L., et al., "Omacor in familial combined hyperlipidemia: effects on lipids and low density lipoprotein subclasses." Atherosclerosis 148:387-396 (Feb. 2000); https://www.sciencedirect.com/science/article/abs/pii/S0021915099002671, Available online Feb. 2, 2000.

Calder PC, Omega-3 Fatty Acids and Inflammatory Processes. Nutrients 2(3):355-374: Mar. 2010 (epub Mar. 18, 2010); thttps://onlinelibrary.wiley.com/doi/full/10.1002/mnfr.201100710, First published: Jul. 4, 2012.

Calder PC, The role of marine omega-3 (n-3) fatty acids in inflammatory processes, atherosclerosis and plaque stability. Mol. Nutr. Food Res. Jul. 2012;56(7):1073-1080.

Calo et al., N-3 fatty acids for the prevention of atrial fibrillation after coronary artery bygass surgery, J. Amer. Coll. Cardiology, May 17 2005, vol. 45, No. 10; pp. 1723-8.

Campos, H. et al., "Lowdensity lipoprotein size, pravastatin treatment, and coronary events." JAMA, 286:1468-1474 (Sep. 2001); https://jamanetwork.com/journals/jama/article-abstract/194223, Sep. 26, 2001.

Canner P.L. et al., "Fifteen year mortality in Coronary Drug Project patients: long-term benefit with niacin," J. Am. Coll. Cardiol. 8. 1245-1255. (Dec. 1986); http://www.onlinejacc.org/content/8/6/1245. abstract, Accepted Jun. 6, 1986.

Cannon CP. et al. Intensive versus moderate lipid lowering with statins after acute coronary syndromes. N Engl J Med 350(15):1495-1504 (publication date Apr. 8, 2004; epublication date Mar. 8, 2004).

Cannon CP, et al; IMPROVE-IT Investigators. "Ezetimibe added to statin therapy after acute coronary syndromes." *N Engl J Med*. 372:2387-2397. (Jun. 18, 2015/epub Jun. 3, 2015).

Cao H, et al., Omega-3 Fatty Acids in the Prevention of Atrial Fibrillation Recurrences after Cardioversion: A Meta-analysis of Randomized Controlled Trials. Intern. Med. 2012 (epub Sep. 15, 2012); 51:2503-2508.

Cao, et al., "Cloning, Expression, and Chromosomal Locatlization . . . ", Genomics, 49:327-331, (Apr. 15, 1998).

Cao, J., et al., "Incorporation and Clearance of Omega-3 Fatty Acids in Erythrocyte Membranes and Plasma Phospholipids." Clinical Chemistry 52(12):2265-2272 (Dec. 2006); https://academic.oup.com/clinchem/article/52/12/2265/5626765, Published: Dec. 1, 2006.

Capuzzi, DM et al., "Efficacy and safety of an extended-release niacin (Niaspan): a long-term study." Am. J. Cardiol. 82: 74U-81U. (Dec. 17, 1998).

Carlson, L.A. & Rosenhamer G., "Reduction of mortality in the Stockholm Ischaemic Heart Disease Secondary Prevention Study by combined treatment with clofibrate and nicotinic acid." Acta Med. Scand. 223, 405-418 (1988); https://pubmed.ncbi.nlm.nih.gov/3287837/.

Carlson, L.A., "Nicotinic acid: the broad spectrum lipid drug. A 50th Anniversary review", J. Int. Med., 258:94-114, (Aug. 2005); https://onlinelibrary.wiley.com/doi/full/10.1111/j.1365-2796.2005.01528.x, First published: Jul. 14, 2005.

Carrero et al., "Intake of Fish Oil, Oleic Acid, Folic Acid, and Vitamins B-6 and E for 1 Year Decreases Plasma C-Reactive Protein and Reduces Coronary Heart Disease Risk Factors in Male Patients in a Cardiac Rehabilitation Program", pp. 384-390 (Feb. 2007); https://academic.oup.com/jn/article/137/2/384/4664551, Published: Feb. 1, 2007.

Carrero, J.J. et al. "Efectos cardiovasculares de los acidos grasos omega-3 y alternativas para incrementar su ingesta," Nutricion Hospitalaria. (2005) (1) 63-69 [with English abstract]; http://scielo.isciii.es/pdf/nh/v20n1/alimentos1.pdf (PDF of print article), Aceptado: 7-VI-2004.

Carroll, D.N., et al., "Evidence for the Cardioprotective Effects of Omega-3 Fatty Acids." Ann Pharmacother., 36:1950-6 (Dec. 2002); https://journals.sagepub.com/doi/abs/10.1345/aph.1A314, First Published Dec. 1, 2002.

(56) References Cited

OTHER PUBLICATIONS

Carulli et al., "Chenodeoxycholic acid and ursodeoxycholic acid effects in endogenous hypertriglyceridemias. A controlled double-blind trial." J. Clin. Pharmacol., 21(10):436-42 (Oct. 1981); https://accp1.onlinelibrary.wiley.com/doi/abs/10.1002/j.1552-4604.1981.tb01746.x, First published: Oct. 1981.

Caughey GE, et al., The effect on human tumor necrosis factor α and interleukin 1β production of diets enriched in n-3 fatty acids from vegetable oil or fish oil. Am J Clin Nutr. Jan. 1996;63:116-122.

Cavender MA, et al; REACH Registry Investigators. Impact of diabetes mellitus on hospitalization for heart failure, cardiovascular events, and death: outcomes at 4 years from the reduction of atherothrombosis for continued health (REACH) registry. Circulation. 132(10):923-931 (publication date Sep. 8, 2015; epublication date Jul. 7, 2015.

Cawood AL, Ding R, Napper FL, et al. Eicosapentaenoic acid (EPA) from highly concentrated n-3 fatty acid ethyl esters is incorporated into advanced atherosclerotic plaques and higher plaque EPA is associated with decreased plaque inflammation and increased stability. Atherosclerosis. Sep. 2010 (epub May 20, 2010); 212:252-259.

Cazzola, R., et al., "Age- and dose-dependent effects of an eicosapentaenoic acid-rich oil on cardiovascular risk factors in healthy male subjects." Atherosclerosis 193:159-167 (Jul. 2007); https://www.sciencedirect.com/science/article/abs/pii/S0021915006003455, Available online Aug. 1, 2006.

Ceci et al., "The effects of oral 5-hydroxytryptophan administration on feeding behavior in obese adult female subjects," J Neural. Transm (1989) 76(2):109-117; https://link.springer.com/article/10.1007/BF01578751, Published: Jun. 1989.

Cefali, E.A., et al., "Aspirin reduces cutaneous flushing after administration of an optimised extended-release niacin formulation", Int. J. Clin. Pharmacol. & Ther., 45(2):78-88, (Feb. 2007); https://europepmc.org/article/med/17323787, Jan. 31, 2007.

Center for Drug Evaluation and Research. Application No. 21-853, 21654s016, (Omacor). Statistical Review and Evaluation: Clinical Studies, Omacor (omega-3 acid ethyl ester) Capsules, 4 grams/day; 2007. Available at: http://www.accessdata.fda.gov/drugsatfda_docs/nda/2007/021853s000;%20021654s016_StatR.pdf. (Accessed Jan. 26, 2012) (156 pages).

Center for Drug Evaluation and Research. Approval Package for Application No. 202057Orig1s000. Review—Vascepa (formerly AMR101), 373 pages (Jul. 26, 2012)(in two parts).

Center for Drug Evaluation and Research. Approval Package for: 21-654 (Omacor/Lovaza). Statistical Review; 2004. Available at: http://www.accessdata.fda.gov/drugsatfda_docs/nda/2004/21-654_Omacor_AdminCorres_P1.pdf. Accessed Jan. 26, 2012. (54 pages).

Ceriello A, Motz E. Is oxidative stress the pathogenic mechanism underlying insulin resistance, diabetes, and cardiovascular disease? The common soil hypothesis revisited. Arterioscler. Thromb. Vasc. Biol. (May 2004);24(5):816-823; https://www.ahajournals.org/doi/full/10.1161/01.atv.0000122852.22604.78, Originally published Feb. 19, 2004.

Chait A, et al., Susceptibility of small, dense, low-density lipoproteins to oxidative modification in subjects with the atherogenic lipoprotein phenotype, pattern B. Am. J. Med. (Apr. 1993);94(4):350-356; https://www.sciencedirect.com/science/article/abs/pii/000293439390144E, Accepted Jul. 21, 1992, Available online Mar. 21, 2004.

Chan et al., "Effect of Atorvastatin and Fish Oil on Plasma High-Sensitivity C-Reactive Protein Concentrations in Individuals with Visceral Obesity", Clin. Chem., vol. 48, pp. 877-883 (2002); https://academic.oup.com/clinchem/article/48/6/877/5641698, Published: Jun. 1, 2002.

Chan et al., Factorial Study of the Effects of Atorvastatin and Fish Oil on Dyslipidaemia in Visceral Obesity, 32 Euro. J. Clinical Investigation. 32(6):429-36 (Jun. 2002); https://onlinelibrary.wiley.com/doi/abs/10.1046/j.1365-2362.2002.01001.x, First published Jun. 13, 2002.

Chan, D.C., et al., "Randomized controlled trial of the effect of n-3 fatty acid supplementation on the metabolism of apolipoprotein B-100 and chylomicron remnants in men with visceral obesity." Am J Clin Nutr 77:300-7 (2003); https://academic.oup.com/ajcn/article/77/2/300/4689666, Published: Feb. 1, 2003.

Chang CL, et al.,. n-3 Faity Acids Decrease Arterial Low-Density Lipoprotein Cholesterol Delivery and Lipoprotein Lipase Levels in Insulin-Resistant Mice. Arterioscler Thromb Vasc Biol. Dec. 2010 (epub Oct. 7, 2010); 30(12):2510-2517.

Chapman, M.J., et al., "Cholesteryl ester transfer protein: at the heart of the action of lipid-modulating therapy with statins, fibrates, niacin, and cholesteryl ester transfer protein inhibitors." Eur Heart J., 31(2):149-164 (Jan. 2010); https://academic.oup.com/eurheartj/article/31/2/149/718394, Published: Oct. 12, 2009.

Chatterjee SN, Agarwal S. Liposomes as membrane model for study of lipid peroxidation. Free Radic. Biol. Med. 1988;4(1):51-72; https://www.sciencedirect.com/science/article/abs/pii/0891584988900111, Accepted May 5, 1987, Available online Jan. 10, 2003.

Chemical Book, Eicosapentaenoic acid ethyl ester, copyright 2010, printed Jun. 16, 2011 from www.chemicalbook.com. (2010).

Chen, H., et al., "Eicosapentanoic acid inhibits hypoxia-reoxygenation-induced injury by attenuating upregulation of MMP-1 in adult rat myocytes." Cardiovascular Research 59:7-13 (Jul. 2003); https://academic.oup.com/cardiovascres/article/59/1/7/283704, Published: Jul. 1, 2003.

Chen, H., et al., "EPA and DHA attenuate ox-LDL-induced expression of adhesion molecules in human coronary artery endothelial cells via protein kinase B pathway." Journal of Molecular and Cellular Cardiology 35:769-775 (Jul. 2003); https://www.sciencedirect.com/science/article/pii/S0022282803001202, Available online Apr. 17, 2003.

Chen, I.S., et al., "In vitro clearance of chylomicron triglycerides containing (ω-3) eicosapentaenoate." Atherosclerosis, 65:193-198 (1987); https://www.sciencedirect.com/science/article/abs/pii/0021915087900347, Date: Jun. 1987.

Cheng et al., "Antagonism of the prostaglandin D2 receptor 1 suppresses nicotinic acid-induces vasodilation in mice and humans," PNAS 103(17):6682-7 (Apr. 25, 2006).

Childs, M.T., et al., "Divergent lipoprotein Responses to Fish Oils With Various Ratios of Eicosapentaenoic Acid and Docasahexaenoic Acid", American Society for Clinical Nutrition, 52:632-9, (Oct. 1990); https://academic.oup.com/ajcn/article-abstract/52/4/632/4650895, Published: Oct. 1, 1990.

Christensen, J. H., et al., "Effect of fish oil on heart rate variability in survivors of myocardial infarction: a double blind randomised controlled trial." BMJ, 312:677-678 (Mar. 16, 1996).

Christensen, M.S., et al., "Intestinal absorption and lymphatic transport of eicosapentaenoic (EPA), docosahexaenoic (DHA), and decanoic acids: dependence on intramolecular triacyiglycerol structure." Am J Clin Nutr 61:56-61 (Jan. 1995); https://academic.oup.com/ajcn/article-abstract/G1/1/56/4651581, Published: Jan. 1, 1995.

Citizen Petition; Pronova BioPharma Norge AS, (Aug. 4, 2009), at ii (Appendix), available at www.regulations.gov.

Classification of Hyperlipidaemias and Hyperlipoproteinaemias, Bulletin of the World Health Organization, 43(6): 891-915 (1970).

Claudel et al., The Farnesoid x receptor, a molecular link between bile acid and lipid and glucose metabolism; Arterioscler Thromb Vasc Biol; Oct. 1, 2005; 25:2020-2031.

Cleland, L.G., et al., "A Biomarker of n-3 compliance in patients taking fish oil for rheumatoid arthritis." Lipids 38:419-424 (Apr. 2003); https://link.springer.com/article/10.1007/s511745-003-1078-9, Published: Apr. 2003.

Clinical Trial NCT01047501, Effect of AMR101 (Ethyl Icosapentate) on Triglyceride (Tg) Levels in Patients on Statins With High Tg Levels (>200 and <500 mg/dL) (ANCHOR), ClinicalTrials.gov [database online], U.S. National Institute of Health, Jan. 2010 [retrieved Apr. 27, 2011], Retrieved from Internet: <http://clinicaltrials.gov/ct2/show/NCT01047501> (3 pages).

Cohen AW, et al., Role of caveolin and caveolae in insulin signaling and diabetes. American journal of physiology. Endocrinology and metabolism. (Dec. 2003);285(6):E1151-1160; https://journals.physiology.org/doi/full/10.1152/ajpendo.00324.2003, Dec. 1, 2003.

(56) References Cited

OTHER PUBLICATIONS

Cohen, J.D., et al., "30-year trends in serum lipids among United States adults: results from the National Health and Nutrition Examination Surveys II, III, and 1999-2006." Am J Cardiol., 106:969-975, (Dec. 15, 2010).
Cole et al., "Challenges and opportunities in the encapsulation of liquid and semi-solid formulations into capsules for oral administration," Advanced Drug Delivery Reviews, vol. 60, No. 6, pp. 747-756. (Mar. 17, 2007).
Colhoun, H. M., et al., "Primary prevention of cardiovascular disease with atorvastatin in type 2 diabetes in the Collaborative Atorvastatin Diabetes Study (CARDS): multicentre randomised placebo-controlled trial." Lancet 364: 685-9 (Aug. 21-24, 2004).
Colihan, Statins lower blood pressure; WebMD, Apr. 11, 2008.
Collins, N., et al., "Differences between Dietary Supplement and Prescription Drug Omega-3 Fatty Acid Formulations: A Legislative and Regulatory Perspective." Journal of the American College of Nutrition, 27 (6):659-666 (Dec. 2008); https://www.tandfonline.com/doi/abs/10.1080/07315724.2008.10719743, Received Aug. 20, 2007, Accepted Dec. 18, 2007, Published online: Jun. 14, 2013.
Committee Roster for the Oct. 16, 2013 Meeting of the Endocrinologic and Metabolic Drugs Advisor Committee, 2 pages. (2013); not online.
Conklin, S. M., et al., "Serum ω-3 fatty acids are associated with variation in mood, personality and behavior in hypercholesterolemic community volunteers." Psychiatry Research 152: 1-10 (Jul. 30, 2007).
Connor et al, "Are Fish Oils Beneficial in the Prevention and Treatment of Coronary Artery Disease?", Am J Clin Nutr vol. 66, No. 4, Jan. 1, 1997, pp. 1020S-1031S, XP002502041.
Connor et al., "Seminars in thrombosis and hemostasis," 14:271-284. (1988).
Connor, W.E., "Importance of n-3 Fatty Acids in Health and Disease", Am. J. Clin. Nutr., 71(1(S)):171S-175S, (Jan. 2000); https://academic.oup.com/ajcn/article/71/1/171S/4729333, Published: Jan. 1, 2000.
Conquer, J.A., et al., "Effect of supplementation with different doses of DHA on the levels of circulating DHA as non-esterified fatty acid in subjects of Asian Indian background. J Lipid Res." 39:286-292. (Feb. 1998); https://www.jlr.org/content/39/2/286.short, Received May 12, 1997. Revision received Oct. 9, 1997.
Conquer, J.A., et al., "Supplementation with an algae source of docosahexaenoic acid increases (n-3) fatty acid status and alters selected risk factors for heart disease in vegetarlan subjectst.". j Nutr., 126: 3032-3039. (Dec. 1996); https://academic.oup.com/jn/article/126/12/3032/4724655, Published: Dec. 1, 1996.
Contacos et al. Effect of pravastatin and omega-3 fatty acids on plasma lipids and lipoproteins in patients with combined hyperlipidemia, pp. 1755-1762 (Dec. 1993); https://www.ahajournals.org/doi/abs/10.1161/01.ATV.13.12.1755, Originally published Dec. 1, 1993.
Coronary Artery Bypass Grafting, NIH, published online Feb. 23, 2012 (12 pages).
Costanzo S, di Niro V, Castelnuovo AD, et al. Prevention of postoperative atrial fibrillation in open heart surgery patients by preoperative supplementation with n-3 polyunsaturated fatty acids: An updated meta-analysis. Periop Manga. 2013; Apr. 12 epub; https://www.sciencedirect.com/science/article/pii/S0022522313003176, Oct. 2013.
Coumadin [package insert], Princeton, NJ: Bristol-Myers Squibb; 2011. (10 pages).
Cox PJ, Ryan DA, Hollis FJ, et al. Absorption, disposition, and metabolism of rosiglitazone, a potent thiazoiidinedione insulin sensitizer, in humans. Drug Metab. Dispos. Jul. 2000;28:772-780; http://dmd.aspetjournais.org/content/28/7/772.short, Received Jul. 27, 1999, Accepted Apr. 10, 2000, Published online Jul. 1, 2000.
Creager MA, Gallagher SJ, Girerd XJ, Coleman SM, Dzau VJ, Cooke JP. L-arginine improves endothelium-dependent vasodilation in hypercholesterolemic humans. J. Clin. Invest. Oct. 1992;90:1248-1253; https://www.jci.org/articles/view/115987, First published Oct. 1, 1992.

Crevel et al., "Allergenicity of Refined Vegetable Oils," Food and Chemical Toxicology, 38, pp. 385-393 (Apr. 2000); https://www.sciencedirect.com/science/article/pii/S0278691599001581, Accepted Sep. 20, 1999, Available online Sep. 13, 2000.
Criqui, M., "Triglycerides and Coronary Heart Disease Revisited (Again)," vol. 147 No. 6, pp. 425-427 (Sep. 18, 2007).
Cromwell et al., "LDL particle number and risk of future cardiovascular disease in the Framingham Offspring Study—Implications for LDL Management," Journal of Lipidololgy (Dec. 2007) 1, 583-592; https://www.sciencedirect.com/science/article/abs/pii/S1933287407002838, Received Jun. 19, 2007, Accepted Oct. 11, 2007, Available online Oct. 18, 2007.
Crowe, F.L., et al., "Serum phospholipid n-3 long-chain polyunsaturated fatty acids and physical and mental health in a population-based survey of New Zealand adolescents and adults." Am J Clin Nutr 86:1278-85 (Nov. 2007); https://academic.oup.com/ajcn/article/86/5/1278/4650617, Published: Nov. 1, 2007, Received Dec. 22, 2006, Accepted Jun. 11, 2007.
Cruz et al., "The metabolic syndrome in children and adolescents," Curr. Diab. Rep., vol. 4(1):53-62 (Feb. 2004); https://link.springer.com/article/10.1007%2Fs11892-004-0012-x, Published: Feb. 2004.
Culhane et al., "Rosuvastatin for the treatment of hypercholesterolemia," Pharmacotherapy, 25(7):990-1000 (Jul. 2005); https://accpjournals.onlinelibrary.wiley.com/doi/abs/10.1592/phco.2005.25.7.990, First published: Jan. 16, 2012.
Daggy, B., et al., Dietary fish oil decreases VLDL production rates. Biochimica et Biophysics Acta 920: 293-300 (Aug. 15, 1987).
Dall et al., "Clinical utility of low-density lipoprotein particle measurement in management of cardiovascular disease: a case report," Research Reports in Clin. Cardiol., vol. 2, pp. 57-62 (2011); http://www.taradall.com/resources/LowDensityParticleMeasurement.pdf, Published Apr. 26, 2011.
Daniel et al., "The Effect of Elevated Triglycerides on the Onset and Progressron of Coronary Artery Disease: a Retrospective Chart Review," Cholesterol, vol. 2015, Article ID 292935, 5 pages (epub Nov. 4, 2015).
Das, U.N., Essential fatty acids as possible mediators of the actions of statins. Prostaglandins, Leukotrienes and Essential FattyAcids 65(1):37-40, (Jul. 2001); https://www.sciencedirect.com/science/article/abs/pii/S0952327801902856, Received Jan. 16, 2001, Accepted Feb. 7, 2001, Available online May 25, 2002.
Davidson MH, Ballantyne CM, Jacobson TA, et al. Clinical utility of inflammatory markers and advanced lipoprotein testing: advice from an expert panel of lipid specialists. J. Clin. Lipidol. Sep./Oct. 2011;5:338-367; https://www.sciencedirect.com/science/article/abs/pii/S1933287411006726 Received Jul. 28, 2011, Accepted Jul. 29, 2011, Available online Oct. 5, 2011.
Davidson MH, et al., Effects of prescription omega-3-acid ethyl esters on lipo protein particle concentrations, apoiipoproteins AI and CIII, and lipoprotein-associated phosphoiipase $A_2$ mass in statin-treated subjects with hypertrigylceridemia, J.Ciin. Lipid., vol. 3(5), pp. 332-40 (Oct. 2009); https://www.sciencedirect.com/science/article/abs/pii/S1933287409003249 Received May 15, 2009, Accepted Aug. 27, 2009, Available online Aug. 31, 2009.
Davidson MH, Rosenson RS, Maki KC, Nicholls SJ, Ballantyne CM, Mazzone T, Carlson DM, Williams LA, Kelly MT, Camp HS, Lele A, Stolzenbach JC. Effects of fenofibric acid on carotid intima-media thickness in patients with mixed dyslipidemia on atorvastatin therapy: Randomized, placebo-controlled study (first). Arterioscler. Thromb. Vasc. Biol. Jun. 2014;34:1298-1306; https://www.ahajournalsorg/doi/full/10.1161/atvbaha.113.302926, Originally published Apr. 17, 2014.
Davidson MH, Stein EA, Bays HE et al. "Efficacy and tolerability of adding prescription omega-3 fatty acids 4 g/d to simvastatin 40 mg/d in hypertriglyceridemic patients: an 8-week, randomized, double-blind, placebo-controlled study," Clin Ther., 29:1354-1367. (Jul. 26, 2007).
Davidson MH., "Mechanisms for the hypotriglyceridemic effect of marine omega 3 my acids." Am J Cardiol 98(4A):27i-33i. (Aug. 21, 2006).
Davidson, M.H., et al., "Effects of docosahexaenoic acid on serum lipoproteins in patients with combined hyperlipidemia: a randomized, doubieblind, piacebo-controlled trial." J Am Coll Nutr., 16:236-

(56) References Cited

OTHER PUBLICATIONS 243. (Jun. 1997); https://www.tandfonline.com/doi/abs/10.1080/07315724.1997.10718680, Published online Sep. 4, 2013.

Davies et al., "Rapid separation of LDL subclasses by iodixanol gradient ultracentrifugation," Clin. Chem, 49(11):1865-72. (Nov. 2003); https://academic.oup.com/clinchem/article/49/11/1865/5642057, Published: Nov. 1, 2003.

Davies-Tuck et al., "Total cholesterol and triglycerides are associated with development of new bone marrow lesions in asymptomatic middle-aged women—a prospective cohort study," Arthritis Research & Therapy. (published online Dec. 4, 2009) pp. 1-7.

De Caterina, R, et al., "Control of Endothelial Leukocyte Adhesion Molecules by Fatty Acids." Lipids, vol. 31:857-863 (1996); https://aocs.onlinelibrary.wiley.com/doi/abs/10.1007/BF02637052, First published: Jan. 1996.

De Caterina, R., et al., "The Omega-3 fatty acid docosahexaenoate reduces cytokine-induced expression of proatherogenic and proinflammatory proteins in human endothelial cells." Arterioscler. Thromb. Vasc. Biol. 14:1829-1836 (1994); https://www.ahajournals.org/doi/abs/10.1161/01.ATV.14.11.1829, Originally published Nov. 1, 1994.

De Graaf J, Hak-Lemmers HL, Hectors MP, Demacker PN, Hendriks JC, Stalenhoef AF. Enhanced V susceptibility to in vitro oxidation of the dense low density lipoprotein subtraction in healthy subjects. Arterioscler. Thromb. 1991;11(2):298-306; https://www.ahajournals.org/doi/abs/10.1161/01.ATV.11.2.298, Originally published Mar. 1, 1991.

de Morais et al., "Evaluation of lipid extraction and fatty acid composition of human plasma," Rev. Bras. Hematoi. Hemoter. 32(6):439-443 (2010); https://www.scielo.br/scielo.php?pid=S1516-84842010000600006&script=sci_arttext, Received: Jun. 14, 2010. Accepted: Aug. 2, 2010.

Deckelbaum,, R. J., et al., "Conclusions and recommendations from the symposium, Beyond Cholesterol: Prevention and Treatment of Coronary Heart Disease with n-3 Fatty Acids." Am J Clin Nutr 87:2010S-12S (2008); https://academic.oug.com/ajcn/article/87/6/2010S/4633491, Published Jun. 1, 2008.

Defendants' Invalidity Contentions, 3:14-CV-02550-MLC-DEA (D.N.J.), 520 pages (Dec. 5, 2014).

Defendants' Joint Invalidity Contentions, 3:14-CV-02550-MLC-TJB (D.N.J.), 901 pages (Dec. 5, 2014).

DeMets DL, Lan KK. Interim Analysis: the Alpha Spending Function Approach. Stat Med., Jul. 15-30, 1994; 13(13-14):1341-52.

Denster et al., Dietary Supplements and Military Divers, A synopsis for Undersea Medical Officers, Jan. 2004.

Dewailly, E., et al., "n-3 Fatty acids and cardiovascular disease risk factors among the Inuit of Nunavik." Am J Clin Nutr 74:464-73 (2001); https://academic.oup.com/ajcn/article/74/4/464/4737394, Received Nov. 22, 2000. Accepted: Apr. 16, 2001. Published: Oct. 1, 2001.

Dewey FE, Gusarova V, O'Dushlaine C, et al. Supplement to: Inactivating variants in ANGPTL4 and risk of coronary artery disease. N Engl J Med. DOI: 10.1056/NEJMoa1510926; Mar. 24, 2016 (epub Mar. 2, 2016).

Di Spirito, M., Morelli, G., Doyle, R.T., Johnson, J. & McKenney, J. Effect of omega-3-acid ethyl esters on steady-state plasma pharmacokinetics of atorvastatin in healthy adults. Expert Opin. Pharmacother. 9, 2939-2945 (2008); https://www.tandfonllne.com/doi/abs/10.1517/14656560802233827, Published onlIne Nov. 12, 2008.

Diagnostic and Statistical Manual of Mental Disorders, 4.Ed. Text revision, published by the American Psychiatric Assoc, 99. 154-163 and 369-381 (2000).

Diagnostic and Statistical Manual of Mental Disorders, 4.sup.th Ed., published by the American Psychiatric Assoc, 99. 285-286, (1994).

Dijan, P., et al., Proc. Natl. Acad. Sci., vol. 93, "Codon repeats in genes associated with human diseases: Fewer repeats in the genes of nonhuman primates and nucleotide substitutions concentrated at the sites of reiteration," pp. 417-421, (Jan. 9, 1996).

Dijk, J. M., et al., "Carotid intima-media thickness and the risk of new vascular events in patients with manifest atherosclerotic disease: the SMART study." European Heart Journal 27:1971-1978 (2006); https://academic.oup.com/eurheartj/article/27/16/1971/2887202, Received Jan. 11, 2006, Revision received May 22, 2006, Accepted Jun. 15, 2006, Published Jul. 11, 2006.

Din et al., "Omega 3 fatty acids and cardiovascular disease—fishing for a natural treatment," BMJ, vol. 327, No. 7430, pp. 30-5 (Jan. 3, 2004).

Djousse L, Akinkuolie AO, Wu JHY, Ding EL, Gaziano JM. Fish consumption, omega-3 fatty acids and risk of heart failure: A meta-analysis. Clin Nutr. Dec. 2012 (epub Jun. 6, 2012); 31:846-853.

Do R, Stitziel NO, Won HH, et. al. Exome sequencing identifies rare LDLR and APOA5 alleles conferring risk for myocardial infarction. Nature. Feb. 5, 2015 (epub Dec. 10, 2014); 518(7537):102-106.

Do R, Willer CJ, Schmidt EM, et al. Common variants associated with plasma triglycerides and risk for coronary artery disease. Nat Genet Nov. 2013 (Oct. 6, 2013);45(11):1345-52.

Dodin, S., et al., "Flaxseed on cardiovascular disease markers in healthy menopausal women: a randomized, double-blind, placebo-controlled trial." Nutrition 24:23-30 (2008); https://www.sciencedirect.com/science/article/abs/pii/S0899900707003024, Received Jun. 13, 2007, Revised Sep. 26, 2007, Available online Nov. 5, 2007.

Doi M, Nosaka K, Miyoshi T, et al. Early eicosapentaenoic acid treatment after percutaneous coronary intervention reduced acute inflammatory responses and ventricular arrhythmias in patients with acute myocardial infarction: A randomized controlled study. Int J Cardiol., 176(3):577-82 (publication date Oct. 20, 2014; epublication date Aug. 19, 2014).

Dolecek, "Epidemiological Evidence of Relationships Between Dietary Polyunsaturated Farry Acids and Morality in the Multiple Risk Factor intervention Trial", Society of Experimental Biology and Medicine, 200(2):177-182, (1991); https://journals.sagepub.com/doi/abs/10.3181/00379727-200-43413, First Published Jun. 1, 1992.

Draft Agenda for the Oct. 16, 2013 Meeting of the Endocrinologic and Metabolic Drugs Advisory Committee, 2 pages.

Draft Meeting Roster for the Oct. 16, 2013 Meeting of the Endocrinologic and Metabolic Drugs Advisor Committee, 2 pages.

Draft Questions for the Oct. 16, 2013 Meeting of the Endocrinologic and Metabolic Drugs Advisor Committee, 1 page.

Drexler H, Zeiher AM, Meinzer K, Just H. Correction of endothelial dysfunction in coronary microcirculation of hypercholesterolaemic patients by l-arginine. Lancet. 1991;338:1546-1550; https://www.sciencedirect.com/science/article/abs/pii/0140673691923729, Available online Nov. 10, 2003.

Dullenmeijer, C., et al., "n-3 Fatty acid proportions in plasma and cognitive performance in older adults." Am J Clin Nutr 86:1479-85 (2007); https://academic.oup.com/ajcn/article/86/5/1479/4650849, Received Mar. 7, 2007, Accepted Jun. 1, 2007, Published Nov. 1, 2007.

Duncan, R. E., et al., "Regulation of HMG-CoA reductase in MCF-7 cells by genistein, EPA, and DHA, alone and in combination with mevastatin." Cancer Letters 224:221-228 (2005); https://www.sciencedirect.com/science/article/abs/pii/S0304383504008900, Received Sep. 2, 2004, Revised Oct. 11, 2004, Accepted Nov. 1, 2004, Available online Dec. 16, 2004.

Durrington PN et al. "An omega 3 poly unsaturated fatty acid concentrate administered for one year decreased triglycerides in simvastatin treated patients with coronary heart disease and persistent Hypertriglyceridemia," Heart, 85:544-48 (2001); http://heart.bmj.com/content/85/5/544.short, May 1, 2001.

Dwyer, J. H., et al., "Arachidonate 5-Lipoxygenase Promoter Genotype, Dietgry Arachidonic Acid, and Atherosclerosis." N. Engl. J. Med., 350:1 (2004); https://www.nejm.org/doi/full/10.1056/nejmoa025079, Jan. 1, 2004.

Dyerberg, J., et al., "Marine Oils and Thrombogenesis." Prog. Lipid Res. 21:255-269 (1982); https://www.sciencedirect.com/science/article/abs/pii/016378278290011X, Available online Jan. 16, 2003.

Egert, S., et al., "Dietary alpha-linolenic acid, EPA, and DHA have differential effects on LDL fatty acid composition but similar effects on serum lipid profiles in normolipidemic humans." J Nutr., 139:861-868 (2009); https://academic.oup.com/jn/article/139/5/861/

(56) References Cited

OTHER PUBLICATIONS

4670359, Received: Dec. 22, 2008. Revision received Jan. 19, 2009, Accepted Feb. 4, 2009. Published Mar. 4, 2009.

Ehara S, et al., Elevated levels of oxidized low density lipoprotein show a positive relationship with the severity of acute coronary syndromes. Circulation. 2001;103(15):1955-1960; https://www.ahajournals.org/doi/full/10.1161/01.CIR.103.15.1955, Originally published Apr. 17, 2001.

Eilat-Adar et al. "Association of Intentional Changes in Body Weight with Coronary Heart Disease Event Rates in Overweight Subjects who have an Additional Coronary Risk Factor," Amer. Journ. Epidemiol.161(4)pp. 352-358 (Sep. 9, 2004).

Eisenberg S, Bilheimer DW, Levy RI, Lindgren FT. "On the metabolic conversion of human plasma very low density lipoprotein to low density lipoprotein," Biochim Biophys Acta, 326:361-77 (1973); https://www.sciencedirect.com/science/article/abs/pii/0005276073901380, Dec. 20, 1973, Received Jul. 23, 1973, Available online Dec. 13, 2002.

Eisenberg S, Rachmilewitz D. "Metabolism of rat plasma very low density lipoprotein. I. Fate in circulation of the whole lipoprotein," Biochim Biophys Acta, 326:378-90 (1973); https://www.sciencedirect.com/science/article/abs/pii/0005276073901392, Received May 21, 1973, Revised Aug. 7, 1973, Available online Dec. 13, 2002.

El-Serag HB, Graham DY, Satia JA, et al. Obesity is an independent risk factor for GERD symptoms and erosive esophagitis. Am. J. Gastroenterol. Jun. 2005 100 (6):1243-50; https://journals.lww.com/ajg/Abstract/2005/06000/Obesity_Is_an_Independent_Risk_Factor_for_GERD.7.aspx, Jun. 2005.

Elam, M.B., et al., "Effect of niacin on lipid and lipoprotein levels and glycemic control in patients with diabetes and peripheral arterial disease study: a randomized trial", The ADMIT [Arterial Disease Multiple Intervention Trial] JAMA, 284:1263-1270, (2000); https://jamanetwork.com/journals/jama/article-abstract/193064, Sep. 13, 2000.

El-Saadani M, et al., A spectrophotometric assay for lipid peroxides in serum lipoproteins using commercially available reagent. J. Lipid Res. 1989;30:627-630; https://www.jlr.org/content/30/4/627.short, Apr. 1989.

El-Sohemy, A., et. al., "Regulation of Mevalonate Synthesis in Low Density Lipoprotein Receptor Knockout Mice Fed n-3 or n-6 Polyunsaturated Fatty Acids." Lipids, 34 (10):1037-43 (1999); https://link.springer.com/article/10.1007/s11745-999-0455-8, Published Oct. 1999, Received Mar. 15, 1999, Revised Jun. 9, 1999, Accepted Jun. 22, 1999.

Emsley et al., "Randomized, Placebo-Controlled Study of Ethyl-Eicosapentaenoic Acid as Supplemental Treatment in Schizophrenia," Am. J. Psychiatry, 159:1596-1598 (2002); https://ajp.psychiatryonline.org/doi/full/10.1176/appi.ajp.159.9.1596, Published Online: Sep. 1, 2002.

Endo et al., "The Effects of Dietary Fatty Acids on Serum Lipids and Plasma Prostaglandin Levels in the Treatment of Obesity," Japanese Journal of Pediatric Gastroenterology and Nutrition 7(1):67-72 (Apr. 15, 1993) (with English translation)(22 pages).

eNews—JAX, "Cholesterol Crystals Induce Atherosclerosis-Associated Inflammation in Mice," 1-4 (Jun. 14, 2010)(4 pages).

Engler, et al., "Docosahexaenoic acid restores endothelial function in children with hyperlipidemia: results from the EARLY Study." International Journal of Clinical Pharmacology and Therapeutics, vol. 42—No. 12-2004 (672-679). (2004); https://www.researchgate.net/profile/Marguerite_Engler/publication/8107212_Docosahexaenoic_acid_restores_endothelial_function_in_children_with_hyperlipidemia_Results_from_the_EARLY_Study/links/0046351743e39201a8000000/Docosahexaenoic-acid-restores-endothelial-function-in-children-with-hyperlipidemia-Results-from-the-EARLY-Study.pdf, Dec. 2004, Received Jul. 17, 2003. Accepted Jul. 24, 2004.

Engler, M.B., et al., "Mechanisms of vasorelaxation induced by eicosapentaenoic acid (20:5n-3) in WKY rat aorta." British Journal of Pharmacology 131:1793-1799 (2000); https://www.ncbi.nlm.nih.gov/pmc/articles/PMC1572512/, Dec. 2000, Received Jun. 16, 2000, Accepted Oct. 2, 2000.

Engler, M.M., et al., "The effects of a diet rich in docosahexaenoic acid on organ and vascular fatty acid composition in spontaneously hypertensive rats." Prostaglandins, Leukotrienes and Essential Fatty Acids 61(5):289-295 (1999); https://www.sciencedirect.com/science/article/abs/pii/S0952327899901023, Received Jun. 24, 1999, Accepted Aug. 16, 1999, Available online May 25, 2002.

Ennis JL, Cromwell WC, Clinical utility of low-density lipoprotein particles and apolipoprotein B in patients with cardiovascular risk. J. Fam. Pract. 2013;62:1-8; https://europepmc.org/article/med/23957035, Jun. 30, 2013.

Epadel—PubChem CID 9831415, Retrieved on Apr. 9, 2014 [Retrieved from Internet] <URL:http://pubchem.ncbi.nlm.nih.gov/compound/9831415> (19 pages).

Epadel 1990 and JELIS Study (4 pages).

Epadel Capsules 300, Japan Pharmaceutical Reference 369-371 (2nd ed.) (1991). (5 pages).

Egadel drug information brochure (2000), certified English translation (36 pages).

Egadel Package Insert 2007 (with Translation)(6 pages).

Epadel Summary of Product Characteristics (SPC), Mochida Pharmaceutical Co., Ltd. Tokyo, Japan, Oct. 2013.

Epadel® [Complete prescribing information]. Update (Version 5). Tokyo, Japan: Mochida Pharmaceutical; Jan. 2007 (9 pages).

Epanova® (omega-3-carboxylic acids) capsules, for oral use, Prescribing information, 5 pgs., AstraZeneca Pharmaceuticals LP, (Revised: Mar. 2017)(5 pages).

Eritsland J, Arnesen H, Gronseth K, et al. Effect of dietary supplementation with n-3 fatty acids on coronary artery bypass graft patency. Am. J. Cardiol. Jan. 1996 77 (1):31-6; https://www.sciencedirect.com/science/article/abs/pii/S0002914997891308, Received May 18, 1995, Accepted Sep. 18, 1995, Available online Nov. 30, 1999.

Eritsland J, Arnesen H, Seljeflot I, et al. Long-term effects of n-3 polyunsaturated fatty acids on haemostatic variables and bleeding episodes in patients with coronary artery disease. Blood Coagul. Fibrinolysis Feb. 1995 6 (1): 17-22; https://journals.lww.com/bloodcoagulation/Abstract/1995/02000/Long_term_effects_of_n_3_polyunsaturated_fatty.3.aspx, https://europepmc.org/article/med/7795149, Jan. 31, 1995.

Errata to the FDA Briefing Document Endocrinologic and Metabolic Drug Advisory Committee Meeting Oct. 16, 2013, 1 page.

Esposito, "Effect of a Mediterranean-Style Diet on Endothelial Dysfunction and Markers ofVascular Inflammation in the Metabolic Syndrome: A Randomized Trial," Journal of the American Medical Association, 2004, 292(12), 1440- 1446; https://jamanetwork.com/journals/jama/article-abstract/199488, Sep. 22-29, 2004.

Essentialis Inc. press release, "Essentialis Meets Primary Endpoint in Phase 2b Trial of DCCR for Treatement of Hypertriglyceridemia and is Granted Extensive Patent Coverage in the US," PR Newswire (May 17, 2009)(2 pages).

Exhibit A to Defendants' Joint Invalidity Contentions, 3:14-CV-02550-MLC-TJB (D.N.J.), 48 pages (Dec. 5, 2014).

Exhibit B to Defendants' Joint Invalidity Contentions, 3:14-CV-02550-MLC-TJB (D.N.J.), 6 pages (Dec. 5, 2014).

Exhibit C to Defendants' Joint Invalidity Contentions, 3:14-CV-02550-MLC-TJB (D.N.J.), 14 pages (Dec. 5, 2014).

Exhibit D to Defendants' Joint Invalidity Contentibns, 3:14-CV-02550-MLC-TJB (D.N.J.), 19 pages (Dec. 5, 2014).

Exhibit E to Defendants' Joint Invalidity Contentions, 3:14-CV-02550-MLC-TJB (D.N.J.), 6 pages (Dec. 5, 2014).

Exhibit F to Defendants' Joint Invalidity Contentions, 3:14-CV-02550-MLC-TJB (D.N.J.), 10 pages (Dec 5, 2014).

Exhibit G to Defendants' Joint Invalidity Contentions, 3:14-CV-02550-MLC-TJB (D.N.J.), 21 pages (Dec. 5, 2014).

Exhibit H to Defendants' Joint Invalidity Contentions, 3:14-CV-02550-MLC-TJB (D.N.J.), 10 pages (Dec. 5, 2014).

Exhibit I to Defendants' Joint Invalidity Contentions, 3:14-CV-02550-MLC-TJB (D.N.J.), 14 pages (Dec. 5, 2014).

Exhibit J to Defendants' Joint Invalidity Contentions, 3:14-CV-02550-MLC-TJB (D.N.J.), 13 pages (Dec. 5, 2014).

Exhibit K to Defendants' Joint Invalidity Contentions, 3:14-CV-02550-MLC-TJB (D.N.J.), 5 pages (Dec. 5, 2014).

(56) References Cited

OTHER PUBLICATIONS

Exhibit L in Defendants' Joint Invalidity Contentions, 3:14-CV-02550-MLC-TJB (D.N.J.), 5 pages (Dec. 5, 2014).
Exhibit M to Defendants' Joint Invalidity Contentions, 3:14-CV-02550-MLC-TJB (D.N.J.), 7 pages (Dec. 5, 2014).
Exhibit N to Defendants' Joint Invalidity Contentions, 3:14-CV-02550-MLC-TJB (D.N.J.), 15 pages (Dec. 5, 2014).
Exhibit O to Defendants' Joint Invalidity Contentions, 3:14-CV-02550-MLC-TJB (D.N.J.), 6 pages (Dec. 5, 2014).
Exhibit P to Defendants' Joint Invalidity Contentions, 3:14-CV-02550-MLC-TJB (D.N.J.), 17 pages (Dec. 5, 2014).
Exhibit Q to Defendants' Joint Invalidity Contentions, 3:14-CV-02550-MLC-TJB (D.N.J.), 64 pages (Dec. 5, 2014).
Faggin, E., et al., "Fish Oil Supplementation Prevents Neointima Formation in Nonhypercholesterolemic Balloon-Injured Rabbit Carotid Artery by Reducing Medial and Adventitial Cell Activation." Arterioscler. Thromb. Vasc. Biol., 20:152-163 (2000); https://www.ahajournals.org/doi/full/10.1161/01.ATV.20.1.152, Originally published Jan. 1, 2000.
FDA Briefing Document, Endocrinologic and Metaboloic Drugs Advisory Committee Meeting, dated Oct. 16, 2013, available publicly at least as of Oct. 16, 2013, 115 pages.
FDA News Release, "FDA approves new orphan drug Kynamro to treat inherited cholesterol disorder," U.S. Food and Drug Administration, Protecting and Promoting Your Health (Jan. 29, 2013)(2 pages).
Fer, M., et al., "Metabolism of eicosapentaenoic and docosahexaenoic acids by recombinant human cytochromes P450." Archives of Biochemistry and Biophysics 471:116-125 (2008); https://www.sciencedirect.com/science/article/abs/pii/S0003986108000040, Mar. 15, 2008, Received Sep. 21, 2007, Revised Dec. 26, 2007, Available online Jan. 11, 2008.
Ferns, G., et al., "Investigation and management of hypertriglyceridaemia." J. Clin. Pathol. 61:1174-1183 (2008); https://jcp.bmj.com/content/61/11/1174.short Oct. 2008.
Feron O, et al., Hydroxy-methylgluataryl-coenzyme a reductase inhibition promotes endothelial nitric oxide synthase activation through a decrease in caveolin abundance. Circulation. 2001;103:113-118; https://www.ahajournals.org/doi/full/10.1161/01.cir.103.1.113, Originally published Jan. 2, 2001.
Final Agenda for the Oct. 16, 2013 Meeting of the Endocrinologic and Metabolic Drugs Advisory Committee, 2 pages.
Final Meeting Roster for the Oct. 16, 2013 Meeting of the Endocrinologic and Metabolic Drugs Advisory Committee, 2 pages.
Final Questions for the Oct. 16, 2013 Meeting of the Endocrinologic and Metabolic Drugs Advisory Committee, 1 page.
Finnen et al., Purification and characterisation of phospholipase A2 from human epidermis, Biochemical Society Trans,19(2):91S, 1991; https://europepmc.org/article/med/1889683, Mar. 31, 1991, http://pubmed.ncbi.nlm.nih.gov/1889683/, Apr. 1991.
Fischer, R., et al., "Dietary n-3 polyunsaturated fatty acids and direct renin inhibition improve electrical remodeling in a model of high human renin hypertension." Hypertension 51 :540-546 (2008); https://www.ahajournals.org/doi/full/10.1161/hypertensionaha.107.103143, Originally published Dec. 24, 2007.
Fisher et al., Journal of Biological Chemistry (2001) 276(3) 27855-27863; https://www.jbc.org/content/276/30/27855.short, First Published on Apr. 2, 2001.
Flaten, H., et al., "Fish-oil concentrate: effects on variables related to cardiovascular disease." Am. J. Clin. Nutr. 52:300-306 (1990); https://academic.oup.com/ajcn/article-abstract/52/2/300/4651469 Published: Aug. 1, 1990.
Fontela et al., Estimated glomerular filtration rate in patients with type 2 diabetes mellitus; Rev Assoc Med Bras 2014; 60(6):531-537.
Food and Drug Administration (FDA), (2005) *Niaspan niacin extended release tablets*.
Food and Drug Administration (FDA), (2005) *Tablets Zocor® (Simvastatin)*.
Ford, ES et al., "Hypertriglyceridemia and Its Pharmacologic Treatment Among US Adults." Arch. Intern. Med., 169(6): 572-78 (2009); https://jamanetwork.com/journals/jamainternalmedicine/article-abstract/414870, Mar. 23, 2009, Accepted for Publication: Oct. 12, 2008.
Förstermann et al., "Roles of Vascular Oxidative Stress and Nitric Oxide in the Pathogenesis of Atherosclerosis," Circ. Res. Feb. 17, 2017; 120(4):713-735 (Received Nov. 2, 2016; Accepted Dec. 26, 2016).
Fraker TD, Fihn SD. Writing on behalf of the 2002 Chronic Stable Angina Writing Committee. 2007 chronic angina focused update of the ACC/AHA guidelines for the management of patients with chronic stable angina. A Report of the ACC/AHA Task Force on Practice Guidelines. Circulation 50:2264-2274, Dec. 4, 2007.
Frangou et al., "Efficacy of ethyl-eicosapentaenoic acid in bipolar depression: randomised double-blind placebo-controlled study," British Journ. Psychiatry, 188, 46-50 (2006); https://www.cambridge.org/core/journals/the-british-journal-of-psychiatry/article/efficacy-of-ethyleicosapentaenoic-acid-in-bipolar-depression-randomised-doubleblind-placebocontrolled-study/28477138E1C9F99F07EE1099F5C73E64, Jan. 2006, presented at the 3rd European Stanley Foundation Conference on Bipolar Disorder, Freiburg, Germany, Sep. 12-14, 2002, Published online by Cambridge University Press: Jan. 2, 2018.
Frey R, et al., Riociguat (BAY 63-2521) and warfarin: a pharmacodynamic and pharmacokinetic interaction study. J. Clin. Pharmacol. Jul. 2011 51 (7): 1051-60; https://accp1.onlinelibrary.wiley.com/doi/abs/10.1177/0091270010378119, First published: Mar. 7, 2013.
Frick, MH, et al., "Helsinki Heart Study. Primary prevention trial with gemfibrozil in middle-aged men with dyslipidaemia. Safety of treatment, changes in risk factors and incidence of coronary heart disease," N. Eng. J. Med., 317:1237-1245, (1987); https://www.nejm.org/doi/full/10.1056/NEJM198711123172001 Nov. 12, 1987.
Friedewald, WT et al., "Estimation of the concentration of low-density lipoprotein cholesterol in plasma, without use of the preparative ultracentrifuge." Clin Chem.,18:499-502 (1972); https://academic.oup.com/clinchem/article-abstract/18/6/499/5676160, Received: Feb. 29, 1972. Accepted: Mar. 13, 1972. Published: Jun. 1, 1972.
Friedman, A.N., et al., "Fish Consumption and Omega-3 Fatty Acid Status and Determinants in Long-Term Hemodiaiysis." Amer. J. Kidney Diseases, 47(6):1064-1071 (2006); https://www.sciencedirect.com/science/article/abs/pii/S0272638606005282, Received Jan. 17, 2006, Accepted Mar. 8, 2006, Available online Feb. 21, 2008.
Frøyland et al., "Chronic administration of eicosapentaenoic acid and docosahexaenoic acid as ethyl esters reduced plasma cholesterol and changed the fatty acid composition in rat blood and organs." Lipids 31(2):169-78 (Feb. 1996); https://link.sgringer.com/article/10.1007/BF02522617, Published: Feb. 1996.
Frøyland, L., et al., "Hypotriacylglycerolemic component of fish oil." Prostaglandins, Leukotrienes and Essential Fatty Acids 57 (4 & 5):387-388 (1997); https://pascal-francis.inist.fr/vibad/index.php?action=getRecordDetail&idt=2121851, Conference: ETRO/ISSFAL symposium on Lipids, Membranes and Thrombosis (Maastricht Jul. 10, 1996).
Furuta T, et al. Influence of CYP2C19 pharmacogenetic polymorphism on proton pump inhibitor-based therapies. Drug Metab. Pharmacokinet Jan. 2005 20 (3): 153-67; https://www.jstage.jst.go.jp/article/dmpk/20/3/20_3_153/_article/-char/ja/.
Futata et al., "Effect of Eicosapentaenoic Acid (EPA) Formulation on Glucose Metabolism in Non-Insulin Dependent Diabetic Patients," Journal of Clinical and Experimental Medicine 169(8):889-890 (May 21, 1994)(English translation, 4 pages).
Galan P, Kesse-Guyot E, Czernichow S, et al. Effects of B vitamins and omega 3 fatty acids on cardiovascular diseases: a randomised placebo controlled trial. Br Med J. Nov. 29, 2010;341:c6273.
Galeano NF, et al., Small dense low density lipoprotein has increased affinity for LDL receptor-independent cell surface binding sites: a potential mechanism for increased atherogenicity. J. Lipid Res. 1998;39(6):1263-1273; https://www.jlr.org/content/39/6/1263.short, Jun. 1998. Preliminary reports of this study were presented in abstract form at the Annual Meetings of the American Heart Association, Nov. 1993.

(56) References Cited

OTHER PUBLICATIONS

Gallagher et al., "Germline BRCA Mutations Denote a Clinicopathalogic Subset of Prostate Cancer," Amer. Assoc. Cancer Res. Clin Cancer Res., 16(7):2115-21 (Apr. 1, 2010).
Ganda OP, Bhatt DL, Mason RP, Miler M, Boden WE. Unmet need for adjunctive dyslipidemia therapy in hypertriglyceridemia management. J Am Coll Cardiol 72(3):330-43 (publication date Jul. 17, 2018).
Garber AJ, Abrahamson MJ, Barzilay JI, et al. American Association of Clinical Endocrinologists' comprehensive diabetes management algorithm 2013 consensus statement. Endocr. Pract. 2013;19(suppl 2):1-48; https://journals.aace.com/doi/pdf/10.4158/EP13176.CSUPPL, May/Jun. 2013.
Gardner CD, Fortmann SP, Krauss RM. Association of small low-density lipoprotein particles with the incidence of coronary artery disease in men and women. JAMA. 1996;276(11):875-881; https://jamanetwork.com/journals/jama/article-abstract/407945, Sep. 18, 1996.
Garg, R., et al., "Niacin treatment increases plasma homocyst(e)ine levels", Am. Heart. J., 138:1082-1087, (1999); https://www.sciencedirect.com/science/article/abs/pii/S0002870399700736, Received Aug. 10, 1998, Accepted Dec. 16, 1998, Available online Nov. 4, 2005.
Garnett, "Interactions with Hydroxymethylglutaryl-coenzyme A reductase inhibitors," Am J Health—Sys Pharm vol. 52, 1639-1645, (Aug. 1, 1995).
Geleijnse JM, et al., Blood pressure response to fish oil supplementation: V metaregression analysis of randomized trials. J Hypertens. Aug. 2002;20(8):1493-1499; https://journals.lww.com/jhypertension/Abstract/2002/08000/Blood_pressure_response_to_fish_oil.10.aspx.
Genest, JJ, et al., "Familial lipoproteinidisorders in patients with premature coronary artery disease", 85:2025-2033, (1992); https://www.ahajournals.org/doi/abs/10.1161/01.cir.85.6.2025, Originally published Jun. 1, 1992.
Geppert, et al. "Microalgal docosahexaenoic acid decreases plasma triacylglycerol in normolipidaemic vegetarians: a randomized trial." British Journal of Nutrition, 95, 779-786. (2006); https://vwvw.cambridge.org/core/journals/british-journal-of-nutrition/article/microalgal-docosahexaenoic-acid-decreases-plasma-triacylglycerol-in-normolipidaemic-vegetarians-a-randomised-trial/95911131A8FB8584F7566A0CDSBDBEB7, Apr. 2006, Published online by Cambridge University Press: Mar. 8, 2007.
Gillet L, Roger S, Bougnoux P, Le Guennec JY, Besson P. Beneficial effects of omega-3 long-chain fatty acids in breast cancer and cardiovascular diseases: voltage-gated sodium channels as a common feature? Biochimi. Jan. 2011 (epub Feb. 16, 2010); 93:4-6.
Gillies, et al. "Effect of a Novel Eicosaientaenoic Acid-Rich Oil on Serum Cholesterol in Man," DuPont 2010.
Ginsberg et al., Regulation of plasma triglycerides in insulin resistance and diabetes, Archives of Medical Research, Vo. 36, Issue 3, May-Jun. 2005, pp. 232-240.
Ginsberg HN, et al., Effects of combination lipid therapy in type 2 diabetes mellitus. N. Engl. J. Med. Apr. 29, 2010;362:1563-1574; https://gubmed.ncbi.nlm.nih.gov/20228404/, Epub Mar. 14, 2010.
Ginsberg HN. "Hypertriglyceridemia: new insights and new approaches to pharmacologic therapy," Am J Cardiol, 87:1174-1180 (2001); https://www.ajconline.org/article/S0002-9149(01)01489-8/fulltext, May 15, 2001, Accepted: Dec. 21, 2000. Received in revised form: Dec. 21, 2000, Received Sep. 4, 2000.
Girotti A W. Lipid hydroperoxide generation, turnover, and effector action in biological systems. J. Lipid Res. 1998;39(8):1529-1542; https://www.jlr.org/content/39/8/1529.short, Aug. 1998. Received Mar. 18, 1998, Revision received Apr. 16, 1998.
GISSI-HF Investigators. Effect of n-3 polyunsaturated fatty acids in patients with chronic heart failure (the GISSI-HF trial): a randomised, double-blind, placebo-controlled trial. Lancet. Oct. 4, 2008 (epub Aug. 29, 2008); 372(9645):1223-1230.

GISSI-Prevenzione Investigators, "Dietary Supplementation with his Polyunsaturated Fatty Acids and Vitamin E after Myocardial Infarction: Results of the GISSI-Prevenzione Trial," The Lancet, 354:447-455, (Aug. 7, 1999).
Glod, "Recent Advances in the Pharmacotherapy of Major Depression", Arch. Psychiatr. Nurs., 10(6):355-364 (Dec. 1996); https://www.sciencedirect.com/science/article/abs/pii/S0883941796800495, Available online Dec. 10, 2004.
Goff DC, et al., ACC/AHA Prevention Guideline: 2013 ACC/AHA Guideline on the Assessment of Cardiovascular Risk: A Report of the American College of Cardiology/American Heart Association Task Force on Practice Guidelines. Circulation. Jun. 24, 2014 (epub Nov. 12, 2013); 129:S74-S75.
Goldberg, AC, "Combination therapy of dyslipidemia," Current Treatment Options in Cardiovascular Medicine 200708 GB, vol. 9, No. 4, pp. 249-258 (2007); https://link.springer.com/article/10.1007%2Fs11936-007-0020-7, Published: Jul. 9, 2007.
Goodman & Gilman (Robert W. Mahley & Thomas P. Bersot) Drug Therapy for Hypercholesterolemia and Dyslipidemia, in Goodman & Gilman's The Pharmacological Basis fo Therapeutics 971 (Hardman et al., eds 10th ed. 2001)(32 pages).
Gordon, DJ. et al., High density lipoprotein cholesterol and cardiovascular disease: four prospective American studies. Circulation. 79: 8-15. (1989); https://www.ahajournals.org/doi/abs/10.1161/01.cir.79.1.8, Originally published Jan. 1, 1989.
Gorriz JL et al., "Rhabdomyolysis and Acute Renal Failure Associated with Gemfibrozil Therapy," Nephron 74(2): 437-438 (1996); https://www.karger.com/article/Abstract/189355, Published online: Dec. 24, 2008, Issue release date: 1996.
Gorriz, JL, "Rhabdomyolysis and Acute Renal Failure Associated with Bezafibrate Treatment," Nephrol Dial Transplant 10(12):2371-2372 (1995); https://academic.oup.com/ndt/article-abstract/10/12/2371/1804883?redirectedFrom=fulltext, Published: Dec. 1, 1995.
Gosai, P, et al. Effect of omega-3-acid ethyl esters on the steady-state plasma pharmacokinetics of rosuvastatin in healthy adults. Expert Opin. Pharmacother. 9, 2947-2953 (2008); https://www.tandfonline.com/doi/abs/10.1517/14656560802532640, Published online: Nov. 12, 2008.
Goto, Y, et al., "Clinical Pharmacological Trial of Ethyl Icosapentate (MND-21)—Dose Finding Study." Journal of Clinical Therageutic & Medicines 8:1293-309 (1992).
Gould, AL, et al., "Cholesterol reduction yields clinical benefit: impact of statin trials." Circulation, 97:946-952 (1998); https://www.ahajournals.org/doi/full/10.1161/01.CIR.97.10.946, Manuscript received Aug. 15, 1997. Manuscript accepted Nov. 18, 1997, Originally published Mar. 17, 1998.
Greenblatt DJ, et al., Interaction of warfarin with drugs, natural substances, and foods. J. Clin. Pharmacoi. Feb. 2005 45 (2): 127-32; https://accp1.onlinelibrary.wiley.com/doi/abs/10.1177/0091270004271404, First published: Mar. 7, 2013. Version of Record online: Mar. 7, 2013, Submitted for publication Aug. 5, 2004; revised version accepted Sep. 23, 2004.
Grenyer, Brin, et al., "Fish Oil Supplementation in the Treatment of Major Depression: A Randomised Double-Blind Placebo-Controlled Trial", Progress in Neuro-Psychopharmacology & Biological Psychiatry, 31:1393-1396, (2007); https://www.sciencedirect.com/science/article/abs/pii/S0278584607001960, Received Sep. 4, 2006, Revised Apr. 25, 2007, Accepted Jun. 12, 2007, Available online Jun. 19, 2007.
Griffin, MD, et al., "Effects of altering the ratio of dietary n-6 to n-3 fatty acids on insulin sensitivity, lipoprotein size, and postprandial lipemia in men and postmenopausal women aged 45-70 y: the OPTILIP Study." Am J Clin Nutr 84:1290-8 (2006); https://academic.oup.com/ajcn/article/84/6/1290/4649077, Received Sep. 26, 2005, Accepted Jul. 17, 2006, Published: Dec. 1, 2006.
Grimsgaard et al., "Effects of Highly Purified Eicosapentaenoic Acid and Docosahexaenoic Acid on Hemodynamics in Humans" American Society for Clinical Nutrition, 68:52-9, (1998); https://academic.oup.com/ajcn/article/68/1/52/4666036, Published: Jul. 1, 1998.
Grimsgaard S, et al., "Highly purified eicosapentaenoic acid and docosahexaenoic acid in humans have similar triacylglycerol-lowering effects but divergent effects on serum fatty acids" Am J

(56) References Cited

OTHER PUBLICATIONS

Clin Nutr, 66:649-659. (1997); https://academic.oup.com/ajcn/article/66/3/649/4655798, Published: Sep. 1, 1997.

Gromova, O.A. et al, published Jan. 2009, [found online Dec. 11, 2019] (found from Internet: t-patient.ru/articles/6417/) with English Machine Translation, и др. Систематический анализ биохимических эффектов эйкозапентаеновой и докозагексаеновой omera 3 ПНЖК на физиологию беременности и развитие развитие Трудный пациент Январь 2009.

Grundy SM, et al. Implications of Recent Clinical Trials for the National Cholesterol Education Prgram Adult Treatment Panel III Guidelines, Circulation. 2004; 110:227-39; https://www.onlinejacc.org/content/44/3/720.abstract, Aug. 2004. Published online Aug. 4, 2004.

Grundy SM, et al., Efficacy, safety, and tolerability of once-daily niacin for the treatment of dyslipidemia associated with type 2 diabetes: results of the Assessment of Diabetes Control and Evaluation of the Efficacy of Niaspan Trial. Arch. Intern. Med. 162: 1568-1576 (2002); https://jamanetwork.com/journals/jamainternalmedicine/article-abstract/212257, Jul. 22, 2002, Accegted for publication Dec. 3, 2001.

Grundy, Scott M, "Low-Density Lipoprotein, Non-High-Density Lipoprotein, and Apolipoprotein B as Targets of Lipid-Lowering Therapy" Circulation. 106:2526-2529 (2002); https://www.ahajournals.org/doi/full/10.1161/01.cir.0000038419.53000.d6, Originally published Nov. 12, 2002.

Guallar, E, et al., "Omega-3 fatty acids in adipose tissue and risk of myocardial infarction—The EURAMIC study." Arterioscler. Thromb. Vasc. Biol., 19:1111-1118 (1999); https://www.ahajournals.org/doi/full/10.1161/01.atv.19.4.1111, Manuscript received Feb. 9, 1998. Manuscript accepted Oct. 28, 1998, Originally published Apr. 1, 1999.

Guillot et al., "Increasing intakes of the long-chain omega-3 docosahexaenoic acid: effects on platelet functions and redox status in healthy men," The FASEV Journal, vol. 23, pp. 2909-2916 (2009); https://faseb.onlinelibrary.wiley.com/doi/abs/10.1096/fj.09-133421, First published May 14, 2009. Version of Record online May 14, 2009, Manuscript accepted: Apr. 30, 2009. Manuscript received Mar. 24, 2009.

Guise, Bone loss and fracture risk assocated wrth cancer therapy, The Oncologist, 2006; 11:1121-1131, available online at www.theoncologist.com.

Guizy, M, et al., "ω-3 and ω-6 Polyunsaturated fatty acids block HERG channels." Am J Physiol Cell Physiol 289:C1251-C1260 (2005); hnps://journals.physiology.org/doi/full/10.1152/ajpcell.00036.2005 , Received Jan. 27, 2005. Accepted Jan. 28, 2005, Published online Nov. 1, 2005. Published in print Nov. 1, 2005.

Gyarmathy, M., "Selection from the industrial manufacturing. 5th part: Geiatine capsules. 5/2 part: Soft gelatine capsules," Gyogyszereszet, vol. 38, No. 2, 1994, pp. 105-109, (w/Engiish summary).

Hakonarson, H., et al., "Effects of a 5-lipoxygenase-activating protein inhibitor on biomarkers associated with risk of myocardial infarction—a randomized trial." JAMA, 293(8):2245-56 (May 11, 2005).

Hall, WL, et al., "A high-fat meal enriched with eicosapentaenoic acid reduces postprandial arterial stiffness measured by digital volume pulse analysis in healthy men." J. Nutr. 138: 287-291 (Feb. 2008); https://academic.oup.com/jn/article/138/2/287/4664997, Received: Sep. 3, 2007. Revision received: Sep. 26, 2007, Accepted: Nov. 14, 2007. Published: Feb. 1, 2008.

Hamazaki et al., "Docosahexaenoic Acid-Rich Fish Oil Does Not Affect Serum Lipid Concentrations of Normolipidemic Young Adults," American Institute of Nutrition, 126(11):2784-2789, Nov. (1996); https://academic.oup.com/jn/article/126/11/2784/4724665 , Received Jan. 8, 1996. Accepted Jul. 9, 1996. Published Nov. 1, 1996.

Hamazaki et al., "Effects of fish oil rich in eicosapentaenoic acid on serum lipid in hyperlipidemic hemodialysis patients," Kidney Int'l., 26:81-84 (Jul. 1984); https://www.sciencedirect.com/science/article/pii/S0085253815332464 , Received May 13, 1983, Revised Jan. 27, 1984, Available online Dec. 18, 2015.

Hamazaki et al., "Effects of Orally Administered Ethyl Ester of Eicosapentaenoic Acid (EPA: C20:5, omega-3) On PGI2-Like Substance Production by Rat Aorta" Prostaglandins, vol. 23 No. 4, pp. 557-567 (Apr. 1982); https://www.sciencedirect.com/science/article/abs/pii/0090698082901162, Received Sep. 9, 1981, Accepted Jan. 3, 1982, Available online Dec. 1, 2003.

Hamazaki T, et al., "Reduction of microalbuminuria in diabetics by Eicosapentaenoic acid ethyl ester" Lipids. 25 (9):542-5 (Sep. 1990); https://link.springer.com/article/10.1007/BF02537161, Published: Sep. 1990, Received Aug. 24, 1989. Accepted May 29, 1990.

Hampel H, et al., Meta-analysis: obesity and the risk for gastroesophageal reflux disease and its complications. Ann. Intern. Med. Aug. 2005 143 (3): 199-211; https://www.acpjournals.org/doi/full/10.7326/0003-4819-143-3-200508020-00006, ePublished Aug. 2, 2005, Issue Published Aug. 2, 2005.

Han, JJ, et al., "Enhancement of both reaction yield and rate of synthesis of structured triacylglycerol containing eicosapentaenoic acid under vacuum with water activity control." Lipids 34:989-995 (Sep. 1999); https://link.springer.com/article/10.1007/511745-999-0449-6, Received Apr. 8, 1999. Revised Aug. 11, 1999, Accepted Aug. 20, 1999, Issue dated Sep. 1999.

Hanasaki, K., et al., "Potent modification of low density lipoprotein by group X secretory phospholipase A2 is linked to macrophage foam cell formation." J. Biol. Chem. 277(32):29116-24 (Aug. 9, 2002).

Haney, EM, et al., "Screening for lipid disorders in children and adolescents; Systematic evidence review for the U.S. Preventive Services Task Force (evidence synthesis)." No. 47. Rockville, MD: Agency for Healthcare Research and Quality, US Department of Health and Human Services; AHRQ Publication No. 07-0598-EF-1; Jul. 2007. Available at: http://www.uspreventiveservicestaskforce.org/uspstf07/chlipid/chlipidsyn.pdf. (Accessed Mar. 23, 2011)(573 gages).

Hannah, J, et al., "Effect of dietary fatty acids on LDL binding." Ann N Y Acad Sci., 683:178-182 (Jun. 14, 1993).

Hansen et al., "Comparative effects of prolonged intake of highly purified fish oils as ethyl ester or triglyceride on lipids, haemostasis and platelet function in normolipaemic men." Eur. J. Clin. Nutr. 47(7):497-507 (Jul. 1993); https://europepmc.org/article/med/8404785 , Jun. 30, 1993.

Hansen, JB, et al., "Effects of highly purified eicosapentaenoic acid and docosahexaenoic acid on fatty acid absorption, incorporation into serum phospholipids and postprandial triglyeridemia." Lipids 33:131-38 (Feb. 1998); https://aocs.onlinelibrary.wiley.com/doi/abs/10.1007/511745-998-0188-8, Version of Record online Feb. 1, 1998, Manuscript accepted Dec. 15, 1997, Manuscript revised Dec. 15, 1997, Manuscript received Mar. 31, 1997.

Harada-Shiba et al., Journal of Clinical and Experimental Medicine, Jun. 30, 2007, vol. 221, No. 13, pp. 1068-1073 (with English translation).

Harris WS, "n-3 Fatty acids and lipoproteins: a comparison of results from human and animal studies," Lipids 31, 243-252 (Mar. 1996); https://aocs.onlinelibrary.wiley.com/doi/abs/10.1007/BF02529870 , Issue Online: Mar. 1, 1996. Version of Record online: Mar. 1, 1996, Manuscript accepted: Feb. 9, 1996. Manuscript revised: Feb. 6, 1996, Manuscript received: Sep. 19, 1995.

Harris WS, International recommendations for consumption of long-chain omega-3 fatty acids. J Cardiovasc Med (Hagerstown) 8(suppl 1):S50-S52, Sep. 2007; https://journals.lww.com/jcardiovascularmedicine/Abstract/2007/09001/International_recommendations_for_consumption_of.13.aspx.

Harris, W.S., et al., "Stearidonic acid increases the red blood cell and heart eicosapentaenoic acid content in dogs." Lipids 42:325-333 (Apr. 2007)(epub Mar. 9, 2007).

Harris, W.S., et al., "Tissue n-3 and n-6 fatty acids and risk for coronary heart disease events." Atherosclerosis 193:1-10 (Jul 2007)(epub May 15, 2007).

Harris, WS, "Expert opinion: omega-3 fatty acids and bleeding-cause for concern?" The American Journal of Cardiolo 99(6A): 45C-46C (Mar. 19, 2007).

(56) References Cited

OTHER PUBLICATIONS

Harris, WS, "Fish oils and plasma lipid and lipoprotein metabolism in humans: a critical review." J Lipid Res. 30:785-807 (Jun. 1989); https://www.jlr.org/content/30/6/785.short.

Harris, WS, "n-3 Fatty acids and human lipoprotein metabolism: an update." Lipids 34:S257-S258 (1999); https://search.proquest.com/openview/c23a45284d9ebd10947fb9974f83fdc3/1 ?pq-origsite=gscholar&cbl=35263 Jan. 1999.

Harris, WS, "n-3 Fatty acids and serum lipoproteins: human studies." Am J Clin Nutr 65:1645S-548 (1997); https://academic.oup.com/ajcn/article/65/5/1645S/4655609, Published: May 1, 1997

Harris, WS, "Omega-3 fatty acids in cardiac biopsies from heart transplantation patients." Circulation 110;1645-1649 (Sep. 21, 2004).

Harris, WS, "The omega-3 index as a risk factor for coronary heart disease." Am J Clin Nutr 87:1997S-2002S (Jun. 2008); https://academic.oup.com/ajcn/article/87/6/1997S/4633363, Published: Jun. 1, 2008.

Harris, WS, et al. "Safety and efficacy of Omacor in severe hypertriglyceridemia," Journal of Cardiovascular Risk, 4:385-391 (Oct.-Dec. 1997); https://journals.sagepub.com/doi/abs/10.1177/174182679700400511 , First Published Jan. 1, 1997.

Harris, WS, et al., "Comparison of the effects of fish and fish-oil capsules on the n-3 fatty acid content of blood cells and plasma phospholipids." Am J Clin Nutr 86:1621-5 (Dec. 2007); https://academic.oup.com/ajcn/article/86/6/1621/4649678, Received Mar. 18, 2007, Accepted Aug. 7, 2007, Published Dec. 1, 2007.

Harris, WS, et al., "n-3 Fatty acids and urinary excretion of nitric oxide metabolites in humans." Am. J. Clin. Nutr., 65:459-64 (Feb. 1997); http://academic.oup.com/ajcn/article/65/2/459/4655355, Published: Feb. 1, 1997.

Harris, WS, et al., "Omega-3 fatty acids and coronary heart disease risk: Clinical and mechanistic perspectives." Atherosclerosis 197:12-24 (Mar. 2008)(epub Dec. 26, 2007).

Harris, WS, et al., "Influence of n-3 fatty acid supplementation on the endogenous lactivities of plasma lipases." Am. J. Clin. Nutr. 66:254-60 (Aug. 1997); https://academic.oup.com/ajcn/article/66/2/254/4655660, Published: Aug. 1, 1997.

Hartweg, J, et al., "Potential impact of omega-3 treatment on cardiovascular disease in type 2 diabetes." Curr Opin Lipidol., 20:30-38 (Feb. 2009); https://journals.lww.com/co-lipidology/Abstract/2009/02000/Potential_impact_of_omega_3_treatment_on.7.aspx , Feb. 2009.

Hata et al, Geriatric Medicine, 30 (5), 799-852, 1992 (with English introduction).

Hawthorne, et al., "High dose eicosapentaenoic acid ethyl ester: effects on lipids and neutrophil leukotriene production in normal volunteers." Br. J. Clin. Pharmac., vol. 30, 187-194 (Aug. 1990); https://bpspubs.onlinelibrary.wiley.com/doi/abs/10.1111/j.1365-2125.1990.tb03764.x First published Aug. 1990, Issue Online Jul. 26, 2012, Version of Record online Jul. 26, 2012.

Hayashi et al, Decreases in Plasma Lipid Content and Thrombotic Activity by Ethyl Icosapentate Purified from Fish Oiles, Current Therapeutic Research, vol 56, No. 1, pp. 24-31 (1995); https://www.sciencedirect.com/science/articie/pii/0011393x95850163, Jan. 1995. Received Sep. 3, 1994, Available online Oct. 10, 2001.

Herbette L, et al., A direct analysis of lamellar x-ray diffraction from hydrated oriented multilayers of fully functional sarcoplasmic reticulum. Biophys. J. Nov. 1977;20(2):245-272; https://www.sciencedirect.com/science/articie/pii/S0006349577855471 , Available online Jan. 6, 2009.

Hibbeln, JR, et al., "Healthy intakes of n-3 and n-6 fatty acids: estimations considering worldwide diversity." Am J Clin Nutr. 83:1483S-93S (Jun. 2006); https://academic.oup.com/ajcn/article/83/6/1483S/4633242, Published: Jun. 1, 2006.

Higashihara et al. "Effects of Eicosapentaenoic Acid on Biochemical Failure after Radical Prostatectomy for Prostate Cancer," in vivo 24:561-566 (Jul./Aug. 2010); http://iv.iiarjournals.org/content/24/4/561.short.

Hilpert, KF, et al., "Postprandial effect of n-3 polyunsaturated fatty acids on apolipoprotein B-containing lipoproteins and vascular reactivity in type 2 diabetes." Am J Clin Nutr 85:369-76 (Feb. 2007); https://academic.oup.com/ajcn/article/85/2/369/4649471, Received Nov. 21, 2005, Accepted Sep. 12, 2006, Published Feb. 1, 2007.

Hirafuji, M., et al., "Docosahexaenoic acid potentiates interleukin-1beta induction of nitric oxide synthase through mechanism involving p44/42 MAPK activation in rat vascular smooth muscle cells." British Journal of Pharmacology 136:613-619 (Jun. 2002).

Hirai, A., et al., "The effects of the oral administration of fish oil concentrate on the release and the metabolism of [14C] arachidonic acid and [14C] eicosapentaenoic acid by human glatelets", Thromb. Res., 28:285-298, (Nov. 1, 1982).

Hirano T, et al., Clinical significance of small dense low-density lipoprotein cholesterol levels determined by the simple precipitation method. Arterioscler. Thromb. Vase. Biol. Mar. 2004;24(3):558-563.(epub Jan. 15, 2004).

Hirano, R, et al., "Regulation by long-chain fatty acids of the expression of cholesteryl ester transfer protein in HepG2 cells." Lipids, 36:401-406 (Apr. 2001); https://link.springer.com/article/10.1007/s11745-001-0735-3 Received Nov. 6, 2000, Revised Mar. 9, 2001, Accepted Mar. 12, 2001, Published Apr. 2001.

Hofacer R, et al., Omega-3 fatty acid deficiency increases stearoyl-CoA desaturase expression and activity indices in rat liver: Positive association with non-fasting plasma triglyceride levels, Prostaglandins Leukot. Essent. Fatty Acids. Jan./Feb. 2012;86:71-7. (epub Nov. 1, 2011).

Hoffman, "Atherosclerosis: Prevention through the Ages," WebMD, https://www.webmed.com/heart/features/atherosclerosis-prevention-through-ages#1 , (Dec. 4, 2007).

Hohenester, "Primary Biliary Cirrhosis," Semin Immunopathol. 31L:283-307, 285 (Sep. 2009)(epub Jul. 15, 2009).

Holmeide, AK, et al., "Oxidative degradation of eicosapentaenoic acid into polyunsaturated aldehydes," Tetrahedron 59:7157-7162 (2003); https://www.sciencedirect.com/science/article/abs/pii/S0040402003010962 Received Feb. 11, 2003, Revised Jun. 6, 2003, Accepted Jul. 10, 2003, Available online Aug. 2, 2003.

Holub, B.J., PhD, "Fish Oils and Cardiovascular Disease", Canadian Medical Association Journal, 141(10):1063 (Nov. 15, 1989).

Holvoet P, et al., The metabolic syndrome, circulating oxidized LDL, and risk of myocardial infarction in wellfunctioning elderly people in the health, aging, and body composition cohort. Diabetes. Apr. 2004;53(4):1068-1073; https://diabetes.diabetesjournals.org/content/53/4/1068.short, Received Jun. 23, 2003. Accepted Jan. 9, 2004.

Horn et al., "Soft Gelatin Capsules II: Oxygen Permeability Study of Capsule Shells," J Pharm Sci. (May 1975) 64(5):851-857; https://onlinelibrary.wiley.com/doi/abs/10.1002/jps.2600640528 , First published May 1975, Manuscript received Jul. 15, 1974. Manuscript accepted Oct. 24, 1974, Version of Record online Sep. 18, 2006.

Hombeck, M, et al., "Biosynthesis of the algal pheromone fucoserratene by the freshwater diatom Asterionella formosa (Bacillariophyceae)." Tetrahedron 54:11033-11042 (1998); https://www.sciencedirect.com/science/article/abs/pii/S0040402098006607 , Received Jun. 8, 1998, Accepted Jul. 2, 1998, Available online Oct. 21, 1998.

Hong KN, Fuster V, Rosenson RS, Rosendorff C, Bhatt DL. How low to go with glucose, cholesterol, and blood pressure in primary prevention of CVD. J Am Coll Cardiol 70(17):2171-85 (publication date Oct. 24, 2017; epublication date Oct. 16, 2017).

Hong, Coronary artery calcification and risk factors for atherosclerosis in patients with venous thromboembolism, Atherosclerosis, 2005, vol. 183, pp. 169-174.

Hoogeveen EK, et al., No effect of n-3 fatty acids supplementation on NT-proBNP after myocardial infarction: the Alpha Omega Trial. Eur J Prev Cardiol. May 2015;22:648-55; https://journals.sagepub.com/doi/abs/10.1177/2047487314536694, Article first published online May 30, 2014, Issue published May 1, 2015.

Horrobin, DF, The Phospholipid Concept of Psychiatric Disorders and its Relationship to the Neurodevelopmental Concept of Schizophrenia. In M. Peet (ed.) Phospholipid Spectrum Disorder in Psychiatry pp. 1-19 (1999).

Hoskins et al., "Combination use of statins and omega-3 fatty acids: an emerging therapy for combined hyperlipidemia," Abstract, 1(5):

(56) References Cited

OTHER PUBLICATIONS 579-591(13) (2006); https://www.tandfonline.com/doi/abs/10.2217/17460875.1.5579, Published online: Jan. 18, 2017.

Howe, PR, et al., "Equal antithrombotic and triglyceride-lowering effectiveness of eicosapentaenoic acid-rich and docosahexaenoic acid-rich fish oil supplements." Lipids 34:S307-S308 (1999); https://search.proquest.com/openview/ee10d66c9b25bf249c00afcdf89e5e60/1?pq-origsite=gscholar&cbl=35263 , Jan. 1999.

HPs2-thrive Collaborative Group, "randomized placebo-controlled trial in 25 673 high-risk patients of er niacin/laroprant: Trial design, pre-specified muscle and liver outcomes, and reasons for stopping study treatment." Eur. Heart J. May 2013;34:1279-1291; https://academic.oup.com/eurheartj/article/34/17/1279/444301, Received Nov. 9, 2012, Revision received Jan. 18, 2013, Accepted Jan. 30, 2013, Published Feb. 26, 2013.

HPS2-THRIVE Collaborative Group, Landray MJ, Haynes R, et al. Effects of extended-release niacin with laropiprant in high-risk patients. N Engl J Med. Jul. 17, 2014; 371(3):203-12.

Hruska MW, et al., The effect of trimethoprim on CYP2C8 mediated rosiglitazone metabolism in human liver microsomes and healthy subjects. Br. J. Clin. Pharmacol. Jan. 2005;59:70-79; https://bpspubs.onlinelibrary.wiley.com/doi/full/10.1111/j.1365-2125.2005.02263.x , First published: Dec. 16, 2004. Version of Record online: Dec. 16, 2004 Editorial history: Received Apr. 15, 2004 Accepted Jul. 20, 2004.

Hughes et al., "Fish oil produces an atherogenic lipid profile in hypertensive men," Atherosclerosis, 84, pp. 229-237 (Oct. 1990); https://www.sciencedirect.com/science/article/abs/pii/002191509090095Z , Received Jan. 24, 1990, Revised Apr. 3, 1990, Revised Jun. 18, 1990, Accepted Jun. 26, 1990, Available online Apr. 14, 2005.

Hulthe J, et al., Low adipocyte-derived plasma protein adiponectin CJ concentrations are associated with the metabolic syndrome and small dense low-density lipoprotein particles: atherosclerosis and insulin resistance study. Metab. Clin. Exp. Dec. 2003;52(12):1612-1614; https://www.sciencedirect.com/scienoe/article/abs/pii/S0026049503003135, Received Mar. 13, 2003, Accepted Jun. 11, 2003, Available online Nov. 27, 2003.

Huntington's Diesase Drug Works—The DHA Dilemma, http://hddrugworks.org/index2.php?option=com_content&task=view&id=185&pop=1&pa . . . Printed on Aug. 22, 2008.(2 pages).

Ignarro LJ, et al., Endothelium-derived relaxing factor produced and released from artery and vein is nitric oxide. Proc. Natl. Acad. Sci. USA. Dec. 1987;84:9265-9269; https://www.pnas.org/content/84/24/9265.short Dec. 1, 1987.

Illingworth, DR, et al., "Comparative effects of lovastatin and niacin in primary hypercholesterolemia: A prospective trial," Arch. Int. Med., 154:1586-1595, (Jul. 25, 1994).

Inoue, I, et al., "Expression of peroxisome proliferator-activated recerptor α (PPARα) in primary cultures of human vascular endothelial cells." Biochem. Biophys. Res. Comm., 246, 370-374 (May 19, 1998).

Inzucchi et al., "Diagnosis of Diabetes," New Engl. Journ of Med., 367(6):541-550 (Aug. 9, 2012).

Ishida, Y, et al., "α-Lipoic Acid and Insulin Autoimmune Syndrome." Diabeters Care, 30(9): 2240-41 (Sep. 2007); https://care.diabetesjournals.org/content/30/9/2240.short, Published in print Aug. 28, 2007, Published online ahead of print Jun. 22, 2007.

Isley, et al., "Pilot study of combined therapy with ω-3 fatty acids and niacin in atherogenic dyslipidemia," Journal of Clinical Lipidology, 1, 211-217 (Jul. 2007); https://www.sciencedirect.com/science/article/abs/pii/S1933287407001389 , Received Feb. 2, 2007, Revised May 1, 2007, Accepted May 13, 2007, Available online May 18, 2007.

Itoh et al., "Increased adiponectln secretion by highly purified eicosapentaenoic acid in rodent models of obesity and human obses subjects," Arterioscler. Thromb. Vasc. Biol, pp. 1918-1925 (together with online Supplements 1-15) (Sep. 2007)(epub Jun. 14, 2007).

Ivanova et al., "Small Dense Low-Density Lipoprotein as Biomarker for Atherosclerotic Diseases," May 9, 2017, Oxidative Medicine and Cellular Longevity (2017), 10 pp.

Jacob RF, et al., Atorvastatin active metabolite inhibits oxidative modification of small dense low-density lipoprotein. J. Cardiovasc. Pharmacol. Aug. 2013;62(2):160-166; https://journals.lww.com/cardiovascularpharm/Abstract/2013/08000/Atorvastatin_Active_Metabolite_Inhibits_Oxidative.7.aspx.

Jacob RF, Mason RP. Lipid peroxidation induces cholesterol domain formation in model membranes. J. Biol. Chem. Nov. 25, 2005;280(47):39380-39387.(epub Sep. 28, 2005).

Jacobson et al. "Hypertrigiyceridemia and Cardiovascuiar Risk Reduction", Clinical Therapeutics, vol. 29 pp. 763-777 (May 2007); https://www.sciencedirect.com/science/articie/abs/pii/S0149291807001208, Available online Aug. 11, 2007.

Jacobson TA, Opening a new lipid "apo-thecary": incorporating apolipoproteins as potential risk factors and treatment targets to reduce cardiovascular risk. Mayo Clin. Proc. Aug. 2011;86:762-780; https://www.sciencedirect.com/science/article/abs/pii/S0025619611651781 , Available online Dec. 23, 2011.

Jacobson, T. Secondary Prevention of Coronary Artery Disease with Omega-3 Fatty Acids. Am J Cardiol; 98 [suppl]: 61i-70i (Aug. 21, 2006).

Jacobson, T.A., "Role of n—3 fatty acids in the treatment of hypertriglyceridemia and cardiovascular disease." Am J Clin Nutr 87:19818-908 (Jun. 2008); https://academic.oup.com/ajcn/article/87/6/1981S/4633487 Published: Jun. 1, 2008.

Jacobson, T.A., et al., "Effects of eicosapentaenoic acid and docosahexaenoic acid on low-density lipoprotein cholesterol and other lipids: A review." J. Clin. Lipidology, vol. 6, pp. 5-18 (Jan./Feb. 2012); https://www.sciencedirect.com/science/article/abs/pii/S1933287411007458, Received Apr. 4, 2011, Accepted Oct. 23, 2011, Available online Nov. 3, 2011.

Jakus V, et al., Advanced glycation end-products and the progress of diabetic vascular complications. Physiol. Res. 2004;53(2): 131-142; https://www.researchgate.net/profiie/Vladimir_Jakus/publication/8653397_Advanced_Glycation_End-Products_and_the_Progress_of_Diabetic_Vascular_Complications/links/0a85e533c07988653b000000.pdf , Received Jan. 17, 2003. Accepted Jun. 9, 2003.

Jenner, "Presymptomatic Detection of Parkinson's Disease". J Neural Transm Suppl., 40:23-36. (Abstract only) (1993); https://europepmc.org/article/med/8294898, Dec. 31, 1992.

Jialal I, et al., Antioxidants and atherosclerosis: Don't throw out the baby with the bath water. Circulation. Feb. 25, 2003;107:926-928.

Jialal, I, "Editorial: Remnant lipoproteins: measurement and clinical significance." Clinical Chemistry 48(2):217-219 (Feb. 2002); https://academic.oup.com/clinchem/article/48/2/217/5641526, Feb. 1, 2002.

Jinno Y, Nakakuki M, Kawano H, Notsu T, Mizuguchi K, Imada K. Eicosapentaenoic acid administration attenuates the pro-inflammatory properties of VLDL by decreasing its susceptibility to lipoprotein lipase in macrophages. Atheroscler.Dec. 2011;219:566-572.(epub Oct. 4, 2011).

Jong et al., "Role of ApoCs in Lipoprotein Metabolism: Function Differences Between ApoC1, ApoC2, and ApoC3," Arteriosclerosis, Thrombosis and Vascular Biology. (Mar. 1999) 19(3):472-484; https://www.ahajournals.org/doi/full/10.1161/01.atv.19.3.472, Manuscript received Jun. 3, 1998, Manuscript accepted Jul. 10, 1998, Originally published Mar. 1, 1999.

Jørgensen AB, Frikke-Schmidt R, Nordestgaard BG, Tybjærg-Hansen A. Loss-of-function mutations in APOC3 and risk of ischemic vascular disease. N Engl J Med. Jul. 3, 2014; 371(1):32-41 (epub Jun. 18, 2014).

Journal of Practical Pharmacy, "Hyperlipidemia Drug," 58(4):1303-1324 (2007) (with English abstract); not online.

Journal of the Japan Diabetes Society, "The Relationship Between Postprandial ApoB48 Increase and Insulin Resistance in Type-2 Diabetes," 55(Suppl. 1):S310 (Apr. 2012) (with English Translation), 2 pages.

Journal of the Japanese Diabetes Society, "A Case of Familial Combined Hyperlipidemia Associated with Obesity, Type 2 Diabetes Mellitus and Severe Hypertriglyceridemia," 51(3), pp. 233-237 (Mar. 30, 2008) (with English abstract).

(56) References Cited

OTHER PUBLICATIONS

Jun M, et al., Effects of fibrates cardiovascular outcomes: a systematic review and meta-analysis. Lancet 375 (9729):1875-1884, May 29, 2010 (epub May 10, 2010).
Jung, UJ, et al., "n-3 Fatty acids and cardiovascular disease: mechanisms underlying beneficial effects." Am J Clin Nutr 87: 2003S-9S (Jun. 2008); https://academic.oup.com/ajcn/article/87/6/2003S/4633490, Published: Jun. 1, 2008.
Kamanna et al., "Mechanism of Action of Niacin," The American Journal of Cardiology (Apr. 17, 2008), 101(8), S20-S26.
Kamido et al., Lipid Composition of Platelets from Patients with Atherosclerosis:Effect of Purified Eicosapentaenoic Acid Ethyl Ester Administration, Oct. 1988, Lipids, 23, pp. 917-923 [Abstract only], 7 pp.; https://link.springer.com/article/10.1007/BF02536337, Received Sep. 2, 1987, Accepted May 10, 1988, Issue Date Oct. 1988.
Kaminski WE, Jendraschak E, Kiefl R, et al. Dietary omega-3 fatty acids lower levels of platelet-derived growth factor mRNA in human mononuclear cells. Blood Apr. 1993, 81(7): 1871-9; not online.
Kanayasu, T, et al., "Eicosapentaenoic acid inhibits tube formation of vascular endothelial cells in vitro." Lipids 26:271-276 (Apr. 1991); https://aocs.onlinelibrary.wiley.com/doi/abs/10.1007/BF02537136 Issue Online: Apr. 1, 1991. Version of Record online: Apr. 1, 1991, Manuscript accepted Jan. 19, 1991, Manuscript received Feb. 19, 1990.
Kastelein et al., Omega-3 Free Fatty Acids for the Treatment of Severe Hypertriglyceridemia: The EpanoVa for Lowering Very High Triglycerides (EVOLVE) Trial, J. Clin. Ligidoi. (JACL 597) Jan./Feb. 2014 (epub Oct. 14, 2013).
Katan, MB, et al., "Kinetics of the incorporation of dietary fatty acids into serum cholesteryl esters, erythrocyte membranes, and adipose tissue: an 18-month controlled study." J. Lipid Res. 38: 2012-2022 (Oct. 1997); https://www.jlr.org/content/38/10/2012.short.
Katayama et al., Effect of long-term administration of ethyl eicosapentate (EPA-E) on local cerebral blood flow and glucose utilization in stroke-prone spontaneously hypertensive rats (SHRSP), Brain Research, vol. 761, pp. 300-305 (Dec. 31, 1997).
Katayama et al., "Efficacy and Safety of Ethyl Icosapentate (Epadel) Given for a Long Term Against Hyperlipidemia," Prog. Med., 21:457-467 (2001) (with English translation).
Kato, T, et al., "Palmitate impairs and eicosapentaenoate restores insulin secretion through regulation of SREBP-1c in pancreatic islets." Diabetes, 57(9):2382-2392 (2008) (published online May 5, 2008).
Kawamura et al., "Effects of 4 weeks' intake of polyunsaturated fatty acid ethylester rich in eicosapentaenoic acid (ethylester) on plasma lipids, plasma and platelet phsopholipid fatty acid composition and platelet aggregation; a double blind study," Nihon Naika Gakkai Zasshi 72(1):18-24 (Jan. 10, 1983).
Kawano, H, et al., "Changes in aspects such as the collagenous fiber density and foam cell size of atherosclerotic lesions composed of foam cells, smooth muscle cells and fibrous components in rabbits caused by all-cis 5, 8, 11, 14, 17-icosapentaenoic acid," J. Atheroscler. Thromb., 9:170-177, (2002); https://www.jstage.jst.go.jp/article/jat/9/4/9_4_170/_article/-char/ja/ , Sep. 4, 2002.
Kawashima, H., et al., "Oral Administration of Dihomo-γ-Linolenic Acids Prevents Development of Atopic Dermatitis in NC/Nga Mice." Lipids 43:37-43 (Jan. 2008)(epub Nov. 6, 2007).
Keech A, Simes RJ, Barter P, Best J, Scott R, Taskinen MR, Forder P, Pillai A, Davis T, Glasziou P, Drury P, Kesaniemi Y A, Sullivan D, Hunt D, Colman P, d'Emden M, Whiting M, Ehnholm C, Laakso M. Effects of long-term fenofibrate therapy on cardiovascular events in 9795 people with type 2 diabetes mellitus (the FIELD study): Randomised controlled trial. Lancet. Nov. 26, 2005;366:1849-1861.
Kelley, DS, et al., "Docosahexaenoic Acid Supplementation Decreases Remnant-Like Particle-Cholesterol and Increases the (n-3) Index in Hypertriglyceridemic Men." J. Nutr. 138: 30-35 (Jan. 2008); https://academic.oup.com/jn/article/138/1/30/4665053, Received: Sep. 6, 2007. Revision received: Sep. 18, 2007, Accepted: Oct. 10, 2007. Published: Jan. 1, 2008.
Kelley, et al., "Docosahexaenoic acid supplementation improves fasting and postprandial lip profiles in hypertriglyceridemic men." The American Journal of Clinical Nutrition, 86: 324-333 (Aug. 2007); https://academic.oup.com/ajcn/article/86/2/324/4754058, Received Oct. 4, 2006, Accepted Apr. 5, 2007, Published Aug. 1, 2007.
Kellner-Weibel G, et al., Crystallization of free cholesterol in model macrophage foam cells. Arterioscler. Thromb. Vasc. Biol. Aug. 1999;19(8):1891-1898; https://www.ahajournals.org/doi/full/10.1161/01.ATV.19.8.1891, Manuscript received Oct. 28, 1998, Manuscript accepted Jan. 22, 1999, Originally published Aug. 1, 1999.
Kendall BJ, et al., The risk of Barrett's esophagus associated with abdominal obesity in males and females. Int. J. Cancer May 2013 132 (9): 2192-9; https://onlinelibrary.wiley.com/doi/full/10.1002/ijc.27887 , Issue Online: Feb. 18, 2013. Version of Record online Oct. 30, 2012, Accepted manuscript online Oct. 3, 2012, Manuscript accepted Sep. 7, 2012, Manuscript received Jun. 3, 2012.
Kerr, S, et al., Dominiczak AF, Hamilton CA. Superoxide anion production is increased in a model of genetic hypertension role of the endothelium. Hypertension. Jun. 1999;33:1353-1358; https://www.ahajournals.org/doi/full/10.1161/01.hyp.33.6.1353, Manuscript received Dec. 29, 1998, Manuscript accepted Feb. 15, 1999, Originally published Jun. 1, 1999.
Kew, S, et al., "Effects of oils rich in eicosapentaenoic and docosahexaenoic acids on immune cell composition and function in healthy humans." Am J Clin Nutr 79:674-81 (Apr. 2004); https://academic.oup.com/ajcn/article/79/4/674/4690168, Received May 7, 2003, Accepted Sep. 8, 2003, Published Apr. 1, 2004.
Kholodov et al., "Clinical Pharmacokinetics," M. Medicine. (1985) pp. 89-98, 134-138, 160, 378-380 [with English Summary](27 pages).
Khoueiry G, et al., Do omega-3 polyunsaturated fatty acids reduce risk of sudden cardiac death and ventricular arrhythmias? A meta-analysis of randomized trials, Heart and Lung. Jul./Aug. 2013;42:251-256. (epub May 25, 2013); https://www.sciencedirect.com/science/article/abs/pii/S0147956313000800 Received Jul. 15, 2012, Revised Mar. 15, 2013, Accepted Mar. 19, 2013, Available online May 25, 2013.
Kim F, et al., Activation of IKKbeta by glucose is necessary and sufficient to impair insulin signaling and nitric oxide production in endothelial cells. J. Mol. Cell. Cardiol. Aug. 2005;39(2):327-334; https://www.sciencedirect.com/science/article/pii/S0022282805001641 , Received Dec. 22 2004, Revised Apr. 13, 2005, Accepted May 16, 2005, Available online Jun. 22, 2005.
Kim KA, et al., Effect of quercetin on the pharmacokinetics of rosiglitazone, a CYP2C8 substrate, in healthy subjects. J. Clin. Pharmacol. Aug. 2005;45:941-946; https://accp1.onlinelibrary.wiley.com/doi/abs/10.1177/0091270005278407, Issue Online: Mar. 19, 2013. Version of Record online: Mar. 19, 2013, Editorial history: Revised version accepted May 5, 2005.
Kimura, F., et al., "Long-term supplementation of docosahexaenoic acid-rich, eicosapentaenoic acid-free microalgal oil in n-3 fatty acid-deficient rat pups." Biosci. Biotechnol. Biochem., 72(2):608-610 (Feb. 2008); https://www.jstage.jst.go.jp/article/bbb/72/2/72_70692/_article/-char/ja/, 2008-72-2.
Kinoshita, "Anti-hyperlipidemic agents," Nihon Rinsho, 60(5):968-74 (May 2002) (w/English Abstract)(11 pages); https://europepmc.org/article/med/12030001, Apr. 30, 2002.
Kinsella, JE, et al., "Dietary n-3 polyunsaturated fatty acids and amelioration of cardiovascular disease: possible mechanisms." Am J Clin Nutr 52:1-28 (Jul. 1990); https://academic.oup.com/ajcn/arlicle-abstract/52/1/1/4695376, Published: Jul. 1, 1990.
Kitada, 9th Diabetes Drug and Drug Related Seminar Diabetes Q&A, Kanazawa Medical University, Diabetes and Endocrine Internal Medicine (http://plaza.umin.ac.jp/iby/etcdata/yakuyaku110410.pdf)(Apr. 10, 2011) (w/English translation)(105 pages).
Klempfner R, et al., Elevated triglyceride level is independently associated with increased all-cause mortality in patients with established coronary heart disease: Twenty-two-year follow-up of the

(56) References Cited

OTHER PUBLICATIONS

Bezafibrate Infarction Prevention Study and Registry. Circ Cardiovasc Qual Outcomes 9(2):100-8 (publication date Mar. 8, 2016).
Knapp HR, Dietary fatty acids in human thrombosis and hemostasis. Am. J. Clin. Nutr. May 1997 65 (5 Suppl): 1687S-98S; https://academic.oup.com/ajcn/article/65/5/1687S/4655644, Published: May 1, 1997.
Knopp, RH, et al., Contrasting effects of unmodified and time-release forms of niacin on lipoproteins in hyperlipidemic subjects: clues to mechanism of action of niacin, Metabolism, 34:642-650, (Jul. 1985); https://www.sciencedirect.com/science/article/abs/pii/0026049585900927, Available online Apr. 2, 2004.
Koba S, et al., Significance of small dense low-density lipoprotein-cholesterol concentrations in relation to the severity of coronary heart diseases. Atherosclerosis. Nov. 2006;189(1):206-214. (epub Jan. 18, 2006).
Kohno, M, et al., "Inhibition by Eicosapentaenoic Acid of Oxidized-LDL- and Lysophosphatidylcholine-Induced Human Coronary Artery Smooth Muscle Cell Production of Endothelin." J. Vasc. Res. 38:379-388 (Jul./Aug. 2001); https://www.karger.com/Article/Abstract/51069.
Kojda G, Harrison DG. Interactions between no and reactive oxygen species: Pathophysiological importance in atherosclerosis, hypertension, diabetes and heart failure. Cardiovasc. Res. Aug. 15, 1999;43:562-571.
Kojima, T, et al., "Long-term administration of highly purified eicosapentaenoic acid provides improvement of psoriasis." Dermatologica, 182:225-230 (1991); https://www.karger.com/Article/Abstract/247800.
Koroshetz, WJ, Huntington's Disease, In Samuels, M. (ed.) Office Practice of Neurology, pp. 654-661 (1996); https://books.google.com/books?id=bbZrAAAAMAAJ&source=gbs_book_other_versions.
Kosonen, O., et al., "Inhibition by nitric oxide-releasing compounds of E-selectin expression in and neutrophil adhesion to human endothelial cells." European Journal of Pharmacology 394:149-156 (Apr. 7, 2000).
Koyama et al., Plaque Reduction and Stabilization Observed in Borderline Diabetes Using Coronary CT Angiogram During Administration of Purified Eicosapentaenoic Acid (EPA) Ther. Res. 31(2):219-225 (Feb. 2010) (with English translation)(20 pages).
Krauss RM, Heterogeneity of plasma low-density lipoproteins and atherosclerosis risk. Curr. Opin. Lipidol. Oct. 1994;5(5):339-349; https://europepmc.org/article/med/7858908, Sep. 30, 1994.
Kris-Etherton, et al., "Fish Consumption, Fish Oil, Omega-3 Fatty Acids, and Cardiovascular Disease" Circulation, 106:2747-2757 (Nov. 19, 2002)(epub Jan. 28, 2003).
Kris-Etherton, PM, et al., "Omega-3 Fatty acids and Cardiovascular Disease—New Recommendations From the American Heart Association." Arterioscler Thromb Vasc Biol. 23:151-152 (Feb. 1, 2003).
Krzynowek et al., "Purification of Omega-3 Fatty Acids from Fish Oils Using HPLC: An Overview," National Marine Fisheries—Proceedings of the first joint conference of the Tropical and Subtropical Fisheries Technological Soceity of the Americas with the Atlantic Fisheries Technological Society, pp. 74-77 (1988).
Ku, K., et al., "Beneficial Effects of to-3 Fatty Acid Treatment on the Recovery of Cardiac Function After Cold Storage of Hyperlipidemic Rats." Metabolism, 48(10):123-1209 (Oct. 1999).
Kunimoto M, et al., Effect of ferrous ion and ascorbate-induced lipid peroxidation on liposomal membranes. Biochem. Bioghys. Acta. Aug. 6, 1981;646(1):169-178.
Kurabayashi, T, et al., "Eicosapentaenoic acid effect on hyperlipidemia in menopausal Japanese women. The Niigata Epadel Study Group" Obstet Gynecol 96:521-8 (Oct. 2000); https://www.sciencedirect.com/science/article/abs/pii/S0029784400009881, Received Jan. 10, 2000, Revised Apr. 21, 2000, Accepted May 3, 2000, Available online Sep. 20, 2000.

Labor Diagnostik Karisruhe, "Target Values of Lipid Metabolism [Recommendation for lipid plasma levels in Germany]," (exact publication date unknown; circa 2006) (with English abstract)(4 pages).
Lada et al., "Associations of Low Density Lipoprotein Particle Compositions with Atherogenicity," Curr. Opin. Lipidol. (Feb. 2004) 15(1):19-24; https://journals.lww.com/co-lipidology/Abstract/2004/02000/Associations_of_low_density_lipoprotein_particle.5.aspx.
Lai, E, et al., "Suppression of niacin-induced vasodilation with an antagonist to prostaglandin D2 receptor subtype 1", Clin. Pharm. & Ther., 81:849-857, (Jun. 2007/epub Mar. 28, 2007).
Laidlaw, M, et al., "Effects of supplementation with fish oil-derived n-3 fatty acids and γ-linolenic acid on circulating plasma lipids and fatty acid profiles in women." Am J Clin Nutr 77:37-42 (Jan. 2003); https://academic.oup.com/ajcn/article/77/1/37/4689631, Received Nov. 27, 2001, Accepted Feb. 14, 2002, Published Jan. 1, 2003.
Laird et al., "Relationship of early hyperglcemia to mortality in trauma patients," J. Trauma, 56(5):1058-1062 (May 2004); https://journals.lww.com/jtrauma/Fulltext/2004/05000/Association_of_Hyperglycemia_with_Increased.19.aspx.
Lamb RE, Goldstein BJ. Modulating an Oxidative-Inflammatory Cascade: Potential New Treatment Strategy for Improving Glucose Metabolism, Insulin Resistance, and Vascular Function. Int. J. Clin. Pract. Jul. 2008(epub May 16, 2008); 62(7): 1087-1095.
Lamharzi N, et al., Hyperlipidemia in concert with hyperglycemia stimulates the proliferation of macrophages in atherosclerotic lesions: potential role of glucose-oxidized LDL. Diabetes. Dec. 2004;53(12):3217-3225; https://diabetes.diabetesjournals.org/content/53/12/3217.short, History Aug. 20, 2004, Dec. 1, 2003, Published in print Nov. 23, 2004.
Landmesser U, et al., Oxidation of tetrahydrobiopterin leads to uncoupling of endothelial cell nitric oxide synthase in hypertension. J. Clin. Invest, Apr. 2003;111:1201-1209; https://www.jci.org/articles/view/14172, First published Apr. 15, 2003—Version history, Received: Sep. 7, 2001; Accepted: Feb. 18, 2003.
LaRosa JC. Understanding risk in hypercholesterolemia. Clin Cardiol 26(Suppl 1):3-6, Jan. 2003; https://onlinelibrary.wiley.com/doi/abs/10.1002/clc.4960261303, First published: Jul. 5, 2007, Issue Online: Jul. 5, 2007, Version of Record online: Jul. 5, 2007.
Larsen, LN, et al., "Heneicosapentaenoate (21:5n-3): Its incorporation into lipids and its effects on arachidonic acid and eicosanoid Synthesis." Lipids 32:707-714 (Jul. 1997); https://aocs.onlinelibrary.wiley.com/doi/abs/10.1007/s11745-997-0090-4, Issue Online: Jul. 1, 1997. Version of Record online: Jul. 1, 1997, Manuscript accepted: May 5, 1997, Manuscript revised: May 5, 1997, Manuscript received: Aug. 6, 1996.
Laufs et al., "Upregulation of endothelial nitric oxide synthase by hmg coa reductase inhibitors," Circulation (Mar. 31, 1998) 97:1129-1135.
Law TK, et al., Primary prevention of cardiovascular disease: global cardiovascular risk assessment and management in clinical practice. *Eur Heart J Qual Care Clin Outcomes.* 1(1):31-36 (publication date Jul. 2, 2015; epublication date Jul. 1, 2015).
Law, M.R., et al., "Quantifying effect of statins on low density lipoprotein cholesterol, ischaemic heart disease, and stroke: systematic review and meta-analysis." Br Med J., 326:1423-1427 (Jun. 28, 2003).
Lawrence MJ, Polyoxyethylene Sorbitan Fatty Acid Esters, Handbook of Pharmaceutical Excipients Fifth Edition by Rowe et al., 2006, Pharmaceutical Press, London/Chicago, XP002765740, ISBN: 0853696187, pp. 580-584 (table VIII).
Lawson et al., "Human absorption of fish oil fatty acids as triacylglycerols, free acids or ethyl esters," Biochemical and Biophysical Research Communications 152(1):328-335 (Apr. 15, 1988).
Leaf A, et al. for the Fatty Acid Antiarrhythmia Trial Investigators. Prevention of Fatal Arrhythmias in High-Risk Subjects by Fish Oil n-3 Fatty Acid Intake. Circ. Nov. 1, 2005;112:2762-2768.
Leaf A, Kang JX, Prevention of cardiac sudden death by N-3 fatty acids: a review of the evidence. J Intern Med 240:5-12, Jul. 1996; https://onlinelibrary.wiley.com/doi/abs/10.1046/j.1365-2796.1996.449803000.x, First published: Jul. 1996, Issue Online: Oct. 31, 2003. Version of Record online: Oct. 31, 2003.

(56) References Cited

OTHER PUBLICATIONS

Leaf, "Hypertriglyceridemia: A Guide to Assessment and Treatment," Hospital Physician 17-23 (Sep. 2008).
Leaf, A., "Historical overview of n3 fatty acids and coronary heart disease." Am J Clin Nutr 87:1978S-80S. (Jun. 2008); https://academic.oup.com/ajcn/article/87/6/19788/4633486 Published: Jun. 1, 2008.
Lee C, et al., All ApoB-containing lipoproteins induce monocyte chemotaxis and adhesion when minimally modified. Modulation of lipoprotein bioactivity by platelet-activating factor acetylhydrolase. Arterioscler. Thromb. Vasc. Biol, Jun. 1999; 19(6):1437-1446; https://vwvw.ahajournals.org/doi/full/10.1161/01.ATV.19.6.1437, Manuscript received Jul. 21, 1998. Manuscript accepted Dec. 2, 1998, Originally published Jun. 1, 1999.
Lee et al., "The Role of Omega-3 Fatty Acids in the Secondary Prevention of Cardiovascular Disease", Q J Med, 96:465-480, (Jul. 2003); https://academic.oup.com/gjmed/article/96/7/465/1627745, Published: Jul. 1, 2003.
Lee, JH, et al., "Omega-3 fatty acids for cardioprotection." Mayo Clin Proc., 83(3):324-332 (Mar. 2008); https://www.sciencedirect.com/science/article/abs/pii/S0025619611608665, Available online Oct. 20, 2011.
Leigh-Firbank et al., "Eicosapentaenoic acid and docosahexanoic acid from fish oils: differential associations with lipid responses," Br. J. Nutr. 87:435-445 (May 2002); https://www.cambridge.org/core/journals/british-journal-of-nutrition/article/eicosapentaenoic-acid-and-docosahexaenoic-acid-from-fish-oils-differential-associations-with-lipid-responses/E6EF955A85B6C8BC5F94F76CE9E7087A, Published online by Cambridge University Press: Mar. 9, 2007.
Lemaitre, RN, et al., "n-3 Polyunsaturated fatty acids, fatal ischemic heart disease, and nonfatal myocardial infarction in older adults: the Cardiovascular Health Study." Am J Clin Nutr 77:319-25 (Feb. 2003); https://academic.oup.com/ajcn/article/77/2/319/4689669, Received: May 22, 2002. Accepted: Aug. 5, 2002. Published: Feb. 1, 2003.
Leonard, Brian E., "Neurological Aspects," Fundamentals of Psychopharmacology,186-187, (1997).
Leucht, S., et al., Schizophrenia Research, vol. 35, "Efficacy and extrapyramidal side-effects of the new antipsychotics olanzapine, quetiapine, risperidone, and sertindole compared to conventional antipsychotics and placebo. A meta-analysis of randomized controlled trials," pp. 51-68, (Jan. 4, 1999).
Levey A, at. al. A New Equation to Estimate Glomerular Filtration Rate. Ann Intern Med. 150:604-612; May 5, 2009.
Li et al, Lipid profile and incidence of atrial fibrillation: a prospective cohort study in China; Wiley Clinical Cardiology, Mar. 2018, vol. 41, No. 3, pp. 314-320.
Li, D, et al., "Effect of dietary a-linoienic acid on thrombotic risk factors in vegetarian men." Am J Clin Nutr 69:872-82 (May 1999); https://academic.oup.com/ajcn/article/69/5/872/4714829, Received: Jun. 3, 1998. Accepted: Oct. 20, 1998. Published: May 1, 1999.
Li, H, et al., "EPA and DHA reduce LPS-induced inflammation responses in HK-2 cells: Evidence for a PPAR-γ-dependent mechanism." Kidney Int'l. 67:867-74 (Mar. 2005); https://www.sciencedirect.com/science/article/pii/80085253815505322, Received Feb. 25, 2004, Revised Aug. 16, 2004, Accepted Sep. 22, 2004, Available online Dec. 16, 2015.
Li, Q, et al., Eicosapentaenoic acid modifies lipid composition in caveolae and induces translocation of endothelial nitric oxide synthase, Biochimie 89 (2007) pp. 169-177 (publ online Nov. 7, 2006).
Li, X, et al., "Protection against fine particle-induced pulmonary and systemic inflammation by omega-3 polyunsaturated fatty acids." vol. 1861, No. 3, pp. 577-584 (Dec. 21, 2016).
Libby P. Triglycerides on the rise: should we swap seats on the seesaw? *Eur Heart J*. 36(13):774-776 (publication date Apr. 1, 2015; epublication date Dec. 29, 2014).
Libby, "Inflammation and atherosclerosis," Nature (Dec. 2002) 420(6917):868-874.
Lichtman et al., "Depression and Coronary Heart Disease, Recommendations for Screening, Referral and Treatment," AHA Science Advisory, Circulation 118:1768-1775 (Sep. 29, 2008).
Lien, EL, "Toxicology and safety of DHA." Prostaglandins Leukot Essent Fatty Acids., 81:125-132 (2009); https://www.sciencedirect.com/science/article/abs/pii/S0952327809000945, Issue date: Aug.-Sep. 2009, Available online Jun. 8, 2009.
Lin, Pao-Yen, et al., "A Meta-Analytic Review of Double-Blind, Placebo-Controlled Trials of Antidepressant Efficacy of Omega-3 Fatty Acids", Psychiatry, 1056-1061 (Jul. 2007); https://brainnutrient.securearea.eu/Files/2/42000/42087/PageHomeDownloadDocs/8867_nl.pdf Journal not online. Received Apr. 17, 2006. Accepted Dec. 7, 2006.
Lin, Y., et al., "Differential effects of eicosapentaenoic acid on glycerolipid and apolipoprotein B metabolism in primary human hepatocytes compared to HepG2 cells and primary rat hepatocytes." Biochimica et Biophysica Acta 1256:88-96 (Apr. 28, 1995).
Lin, Z., et al., "Cardiovascular Benefits of Fish-Oil Supplementation Against Fine Particulate Air Pollution in China." Apr. 30, 2019; 73(16):2076-2085.
Lindsey, S, et al., "Low density lipoprotein from humans supplemented with n-3 fatty acids depresses both LDL receptor activity and LDLr mRNA abundance in HepG2 cells." J Lipid Res., 33:647-658 (Mar. 1992); https://www.jlr.org/content/33/5/647.short, May 1992.
Lins et al., "Pharmacokinetics of Atorvastatin and its Metabolites After Single and Multiple Dosing in Hypercholesterolaemic Haemodialysis Patients," Nephrol. Dial. Transplant, May 2003; 18(5):967-76 (Received for publication Apr. 2, 2002; Accepted in Revised Form May 12, 2002).
Ligitor [package insert]. New York, NY: Parke-Davis (2012). (22 pages).
Lipitor [product information] Dublin, Ireland: Pfizer Inc. (2007).(18 pages).
Liu et al., "Effects of stable fish oil and simvastatin on plasma lipoproteins in patients gwith hyperlipidemia," Nutrion Res. , vol. 23, pp. 1027-1034 (Aug. 2003); https://www.sciencedirect.com/science/article/pii/S0271531703001027 , Received Sep. 24, 2002, Revised Apr. 24, 2003, Accepted Apr. 25, 2003, Available online Jul. 10, 2003.
Liu X, et al., Stearoyl CoA Desaturase 1: Role in Celluiar Inflammation and Stress, Adv. Nutr. Jan. 2011 (Jan. 10, 2011); 2:15-22.
Lohmussaar, E., et al., "ALOX5AP Gene and the PDE4D Gene in a Central European Population of Stroke Patients." Stroke, 36:731-736 (Apr. 2005)(epub Feb. 24, 2005).
Lovaza (omega-3-acid ethyl esters) Capsules, Prescribing information, GlaxoSmithKline (Nov. 2008).(9 pages).
Lovaza [package insert]. Research Triangle Park, NC: GlaxoSmithKline (2012). (14 pages).
Lovaza Side Effects, web archived webpage, archived from Drugs.com website on (Jul. 31, 2010), Retrieved from URL <https://web.archive.org/web/20100731021902/https://www.drugs.com/sfx/lovaza-side-effects.html> (4 pages)(Jul. 2010).
Lovaza TM (omega-3-acid ethyl esters) Capsules, Aug. 2007 (Aug. 1, 2007)m oaget 1-2, XP055589332.
Lovaza United States Prescribing Information, GlaxoSmithKline. Research Triangle Park, USA, May 2014.
Lovaza, (omega-3-acid ethyl esters) Capsules, Prescribing information Smith Kline Beechum (Jul. 2009).(17 pages).
Lovaza, GlaxoSmithKline, Lovaza Prescribing Information, Jun. 2008 [retrieved from Internet Jun. 6, 2012 <https://web.archive.org/web/20090206170311/http://us.gsk.com/products/assets/us_lovaza.pdf>]; Table 3, p. 1, section entitled 'Description;' p. 3, section entitled 'Very High Triglycerides: Monotherapy;' p. 4 section entitled 'Indications and Usage' and 'Information for Patients.' (12 pages).
Lovaza® (omega-3-acid ethyl esters) Capsules, Prescribing information, GlaxoSmithKline, (Dec. 2010)(12 pages).
Lovaza®, Physicians' Desk Reference 2699-2701 (62d ed., 2008). (4 pages).
Lovegrove et al., "Moderate fish-oil supplementation reverses low-platelet, long chain n-3 polyunsaturated fatty acid status and reduced plasma triacylglycerol concentrations in British Indo-Asians," Am. J. Clin. Nutr., 79:974-982 (Jun. 2004); https://academic.oup.com/ajcn/article/79/6/974/4690258, Received: Jun. 30, 2003. Accepted: Nov. 20, 2003. Published: Jun. 1, 2004.

(56) References Cited

OTHER PUBLICATIONS

Lu, G., et al., "Omega-3 fatty acids alter lipoprotein subtraction distributions and the in vitro conversion of very low density lipoproteins to lowdensity lipoproteins." J Nutr Biochem., 10:151-158 (Mar. 1999); https://www.sciencedirect.com/science/article/abs/pii/S0955286398000941 , Received Jul. 16, 1998, Accepted Nov. 11, 1998, Available online Mar. 4, 1999.

Lucas, M., et al., "Ethyl-eicosapentaenoic acid for the treatment of psychological distress and depressive symptoms in middle-aged women: a double-blind, placebo-controlled, randomized clinical trial." Am J Clin Nutr 89:641-51 (Feb. 2009)(epub Dec. 30, 2008).

Luo et al., The emerging role of apolipoprotein C-III: beyond effects on triglyceride metabolism; Lipids in Health and Disease, 2016, 15:184, 7 pages.

Luria, MH, "Effect of low-dose niacin on high-density lipoprotein cholesterol and total cholesterol/high density lipoprotein cholesterol ratio," Arch. Int. Med., 148:2493-2495, (Nov. 1998); https://jamanetwork.com/journals/jamainternalmedicine/article-abstract/610768.

Lvovich V, Scheeline A. Amperometric sensors for simultaneous superoxide and hydrogen peroxide detection. Anal. Chern. Feb. 1, 1997;69:454-462.

Madhavi et al., "Effect of n -6 and n -3 fatty acids on the survival of vincristine sensitive and resistant human cervical carcinoma cells in vitro," Cancer Letters, vol. 84. No. 1, pp. 31-41 (Aug. 29, 1994).

Madsen, L, et al., "Eicosapentaenoic and Docosahexaenoic Acid Affect Mitochondrial and Peroxisomal Fatty Acid Oxidation in Relation to Substrate Preference." Lipids 34:951-963 (Sep. 1999); https://link.springer.com/article/10.1007/511745-999-0445-x, Received Jan. 25, 1999. Revised Jul. 23, 1999. Accepted Aug. 17, 1999, Issue date Sep. 1999.

Mak IT, et al., Antioxidant properties of calcium channel blocking drugs. Methods Enzymol. 1994;234:620-630; https://www.sciencedirect.com/science/article/pii/0076687994341338, Available online Jan. 7, 2004 (book chapter).

Maki et al., "Effects of Adding Prescription Omega-3 Acid Ethyl Esters to Simvastatin (20 mg/day) on Lipids and Lipoprotein Particles in Men and Women with Mixed Dyssipidemia," Am. J. Cardiol., 102:429-433 (Aug. 15, 2008)(Epub May 22, 2008).

Maki, KC, et al., "Baseline lipoprotein lipids and low-density lipoprotein cholesterol response to prescription omega-3 acid ethyl ester added to simvastatin therapy." Am J Cardiol., 105:1409-1412 (May 15, 2010)(epub Mar. 30, 2010).

Maki, PhD, et al., "Lipid Responses to a Dietary Docosahexaenoic Acid Supplement in Men and Women with Below Average Levels of High Density Lipoprotein Cholesterol." Journal of the American College of Nutrition, vol. 24, No. 3, 189-199 (Jun. 2005); https://www.tandfonline.com/doi/abs/10.1080/07315724.2005.10719465 Received Apr. 23, 2004, Accepted Jan. 19, 2005, Published online: Jun. 18, 2013.

Malinowski et al., "Elevation of Low-Density Lipoprotein Cholesterol Concentration with Over-the-Counter Fish Oil Supplementation." Annals of Pharmacotherapy 41:1296-1300 (Jul./Aug. 2007); https://journals.sagepub.com/doi/abs/10.1345/aph.1H695, First Published Jul. 1, 2007.

Malinski T, Taha Z. Nitric oxide release from a single cell measured in situ by a porphyrinic-based microsensor. Nature. Aug. 20, 1992;358:676-678.

Mallat, Z, et al., "Apoptosis in the vasculature: mechanisms and functional importance." British Journal of Pharmacology 130:947-962 (Jul. 2000); https://bpspubs.onlinelibrary.wiley.com/doi/full/10.1038/sj.bjp.0703407 Received Jan. 14, 2000, Revised Mar. 30, 2000, Accepted Apr. 3, 2000, First Pubiished online: Jan. 29, 2009.

Mallat, Z., et al., "Protective role of interleukin-10 in atherosclerosis." Circ. Res. 85:e17-e24 (Oct. 15, 1999).

Manninen V, et al., Joint effects of serum triglyceride and LDL cholesterol and HDL cholesterol concentrations on coronary heart disease risk in the Helsinki Heart Study. Implications for treatment. Circulation 85:37-45, Jan. 1992; https://www.ahajournals.org/doi/abs/10.1161/01.cir.85.1.37, Originally published Jan. 1, 1992.

Marangell, Lauren B., et al., "A Double-Blind, Placebo-Controlled Stury of the Omega-3 Fatty Acid Docosahexaenoic Acid in the Treatment of Major Depression", Am. J. Psychiatry, 160(5):996-998, (May 2003); https://ajp.psychiatryonline.org/doi/full/10.1176/appi.ajp.160.5.996, Published Online: May 1, 2003.

Marchioli R, et al, GISSI-Prevenzione Investigators. Early protection against sudden death by n-3 polyunsaturated fatty acids after myocardial infarction: time-course analysis of the results of the Gruppo Italiano per lo Studio della Sopravvivenza nell'Infarto Miocardico (GISSI)-Prevenzione. Circulation. 105(16):1897-1903, Apr. 23, 2002.

Marckmann, P, "Fishing for heart protection." Am J Clin Nutr, 7811-2 (Jul. 2003); https://academic.oup.com/ajcn/article/78/1/1/4689890, Published: Jul. 1, 2003.

Marcoux et al., "Plasma remnant-like particle lipid and apolipoprotein levels in normolipidemic and hyperlipidemic subjects," Atherosclerosis, vol. 139, pp. 161-171 (Jul. 1998); https://www.sciencedirect.com/science/article/abs/pii/S0021915098000422 , Received Sep. 16, 1997, Revised Jan. 5, 1998, Accepted Jan. 21, 1998, Available online Dec. 21, 1998.

Marder, "An Approach to Treatment Resistance in Schizophrenia," British Journ. Psychiatry, 37:19-22 (1999); https://www.cambridge.org/core/journals/the-british-journal-of-psychiatry/article/an-approach-to-treatment-resistance-in-schizophrenia/A1560127B71799F95FBDE2350B239323, Feb. 1999, Published online by Cambridge University Press: Aug. 6, 2018.

Margolis, Simeon "What is Hyperlipidemia?" (http:www.healthcommunities.com/highcholesterol/whatishyperlipidemia.shtml, accessed Oct. 20, 2015, published Aug. 25, 2011)(4 pages).

Martin SS, Biaha MJ, Elshazly MB, et al. Comparison of a novel method vs the Friedewald equation for estimating low-density lipoprotein cholesterol levels from the standard lipid profile. JAMA. Nov. 20, 2013;310:2061-8.

Martinez et al., "Serum level changes of long chain-polyunsaturated fatty acids in patients undergoing periodontal therapy combined with one year of omega-3 supplementation: a pilot randomized clinical trial;" Journal of Periodontal & Implant Science, Aug. 28, 2014, vol. 44, pp. 169-177.

Martinez-Gonzalez J, et al., 3-hydroxy-3-methylglutaryl coenzyme a reductase inhibition prevents endothelial no synthase downregulation by atherogenic levels of native ldls: Balance between transcriptional and posttranscriptional regulation. Arterioscler. Thromb. Vasc. Biol. May 2001;21:804-809; https://www.ahajournals.org/doi/full/10.1161/01.atv.21.5.804 , Manuscript received Nov. 27, 2000. Manuscript accepted Dec. 22, 2000 Originally published May 1, 2001.

Martinez-Gonzalez, Jose, et al., "Estatinas y acidos grasos omega-3. Disminucion de la mortalidad cardiovascular dependiente e independiente de la reduccion de la colesterolemia," (2006) Rev Esp Cardiol Suppl., 6(D):20D-30D [with English abstract]; https://www.sciencedirect.com/science/article/abs/pii/S1131358706748233, Available online Jan. 6, 2009.

Martin-Jadraque, R. et al., Effectiveness of low dose crystalline nicotinic acid in men with low density lipoprotein cholesterol levels. Arch. Int. Med. 156: 1081-1088. (May 27, 1996).

Martz, "Moving Upstream in Huntington's," Science-Business eXchange, 2 pgs., Oct. 2008; https://link.springer.com/article/10.1038/scibx.2008.841, Issue Date Oct. 2, 2008.

Mason et al., "Comparative lipid antioxidant effects of omega-3 fatty acids in combination with HMG-CoA reductase inhibitors," Journ. Clin. Lipidology (May/Jun. 2011) 5(3):201; https://www.lipidjournal.com/article/S1933-2874(11)00091-2/abstract.

Mason et al., "Direct evidence for cholesterol crystalline domains in biological membranes: role in human pathobiology," Biochimica et Biophysica Acta 198-207 (Mar. 10, 2003).

Mason et al., "Eicosapentaenoic Acid (EPA) inhibits the formation of membrane cholesterol crystalline domains by a potent antioxidant mechanism," Journ. Clin. Lipid., 7(3): 272-273 (May/Jun. 2013) [Abstract only]; https://www.lipidjournal.com/article/S1933-2874(13)00135-9/abstract, May 1, 2013 https://www.sciencedirect.com/science/article/abs/pii/S1933287413001359, Available online May 30, 2013.

(56) References Cited

OTHER PUBLICATIONS

Mason et al., "Eicosapentaenoic acid inhibits glucose-induced membrane cholesterol crystalline domain formation through a potent antioxidant mechanism," Biochim. Biophy. Acta., 1848(2):502-9, (Feb. 2015); https://www.sciencedirect.com/science/article/pii/S0005273614003514, Received Jul. 18, 2014, Revised Oct. 2, 2014, Accepted Oct. 14, 2014, Available online Oct. 22, 2014.

Mason et al., "Eicosapentaenoic Acid Inhibits Oxidation of ApoB-containing Lipoprotein Particles of Different Size In Vitro When Administered Alone or in Combination With Atorvastatin Active Metabolite Compared With Other Triglyceride-lowering Agents," J. Cardiovasc. Pharmacol, 68(1):33-40 (Jul. 2016); https://www.ncbi.nlm.nih.gov/pmc/articles/PMC4936437/, Published online Mar. 3, 2016.

Mason et al., "Eicosapentaenoic acid reduces membrane fluidity, inhibits cholesterol domain formation, and normalizes bilayer width in atherosclerotic-like model membranes," Biochim. Biophy. Acta., 1858(12):3131-3140 (Dec. 2016); https://www.sciencedirect.com/science/article/pii/S0005273616303297, Received May 17, 2016, Revised Sep. 1, 2016, Accepted Oct. 3, 2016, Available online Oct. 5, 2016.

Mason RP, et al., Effect of enhanced glycemic control with saxagliptin on endothelial nitric oxide release and CD40 levels in obese rats. J. Atheroscler. Thromb. Epub June 13, 2011;18:774-783.

Mason RP, et al., Partitioning and location of Bay K 8644, 1,4-dihydropyridine calcium channel agonist, in model and biological membranes. Biophys. J. April 1989;55(4):769-778; https://www.ncbi.nlm.nih.gov/pmc/articles/PMC1330560/.

Mason RP, Jacob RF. Membrane microdomains and vascular biology: Emerging role in atherogenesis. Circulation. May 6, 2003; 107:2270-2273.

Mason RP, Kalinowski L, Jacob RF, Jacoby AM, Malinski T. Nebivolol reduces nitroxidative stress and restores nitric oxide bioavaiiability in endothelium of black americans. Circulation. Dec. 13, 2005 (epub Dec. 5, 2005); (epub Dec. 5, 2005); 112:3795-3801.

Mason RP, Kubant R, Heeba G, Jacob RF, Day CA, Mediin YS, Funovics P, Malinski T. Synergistic effect of amlodipine and atorvastatin in reversing ldl-induced endothelial dysfunction. Pharm. Res. Aug. 2008 (epub 2007 Dec. 2018); 25:1798-1806.

Mason RP, Walter MF, Day CA, Jacob RF. Active metabolite of atorvastatin inhibits membrane cholesterol domain formation by an antioxidant mechanism. J. Biol. Chem. Apr. 7, 2006 (epub Feb. 7, 2006) ;281(14):9337-9345.

Mason RP, Walter MF, Day CA, Jacob RF. Intermolecular differences for HMG-CoA reductase inhibitors contribute to distinct pharmacologic and pleiotropic actions. Am. J Cardiol. Sep. 5, 2005;96(5A):11F-23F.

Mason RP, Walter MF, Jacob RF. Effects of hmg-coa reductase inhibitors on endothelial function: Role of microdomains and oxidative stress. Circulation. Jun. 1, 2004;109:II34-II41.

Mason RP, Walter MF, Mason PE. Effect of oxidative stress on membrane structure: Small angle x-ray diffraction analysis. Free Radic. Biol. Med. 1997;23(3):419-425; https://www.ncbi.nlm.nih.gov/pmc/articles/PMC1330560/.

Mason RP. Molecular basis of differences among statins and a comparison with antioxidant vitamins. Am. J. Cardiol. Dec. 4, 2006 (epub Oct. 10, 2006); 98:34P-41P.

Mataki et al., "Effect of Eicosapentaenoic Acid in Combination with HMG-CoA Reductase Inhibitor on Lipid Metabolism," Int. Med. J. 5(1):35-36 (Mar. 1998); https://www.sciencedirect.com/science/articie/abs/pii/S0021915097886984, Oct. 1997, Available online May 27, 1999.

Mater, MK, et al., "Arachidonic acid inhibits lipogenic gene expression in 3T3-L1 adipocytes through a prostanoid pathway." J. Lipid Res. 39:1327-1334 (Jul. 1998); https://www.jlr.org/content/39/7/1327.short , Received Nov. 21, 1997. Revision received Feb. 2, 1998. Revision received Mar. 9, 1998.

Matsumoto, M, et al., "Orally administered eicosapentaenoic acid reduces and stabilizes atherosclerotic lesions in ApoE-deficient mice." Atherosclerosis, 197(2):524-533 (Apr. 2008/epub Sep. 4, 2007).

Matsuzaki et al., "Incremental Effects of Eicosapentaenoic Acid on Cardiovascular Events in Statin-Treated Patients with Coronary Artery Disease," Circulation Journal, vol. 73, pp. 1283-1290 (Jul. 2009/epub May 8, 2009).

Matsuzawa, Y., et al., "Effect of Long-Term Administration of Ethyl Icosapentate (MND-21) in Hyperlipaemic Patients," J. Clin Therapeutic & Medicines, 7: 1801-16 (1991).

Mattson MP, Modification of ion homeostasis by lipid peroxidation: roles in neuronal degeneration and adaptive plasticity. Trends Neurosci. Feb. 1998;21(2):53-57; https://www.sciencedirect.com/science/article/abs/pii/S0166223697011880, Available online Jul. 6, 1998.

Mayatepek, E., et al., The Lancet, vol. 352, Leukotriene C4-synthesis deficiency: a new inborn error of metabolism linked to a fatal developmental syndrome, pp. 1514-1517 (Nov. 7, 1998).

Mayo Clinic at http://www.mayoclinic.org.diseases-conditions/high-blood-cholesterol/in-depth/cholesterol (2014)(5 pages).

Mayo Clinic, Diabetes Diagnosis and Treatment, 1998, http://www.mayoclinic.org/diseases-conditions/diabetes/diagnosis-treatment/drc-20371451 (1998-2018).

McCabe, John B. "Literature of Resuscitation", Resuscitation, Elsevier, IE, vol. 19, No. 3 (Jun. 1, 1990), vol. 19, pp. 303-319, DOI: 10.1016/0300-9572 (90)90109-R.

McElroy, SL, et al., "Clozapine in the Treatment of Psychotic Mood Disorders, Schizoaffective Disorder, and Schizophrenia", Journal of Clinical Psychiatry, vol. 52, No. 10, pp. 411-414 (Oct. 1991); https://psycnet.apa.org/record/1992-13950-001, Manuscript received Jun. 12, 1997. Manuscript accepted Jun. 16, 1997, Originally published Dec. 1, 1997.

McIntyre M, et al., Sex differences in the abundance of endotheiial nitric oxide in a model of genetic hypertension. Hypertension. Dec. 1997;30:1517-1524; https://www.ahajournals.org/doi/full/10.1161/01.hyp.30.6.1517.

McKenney et al., "Prescription omega-3 fatty acids for the treatment of hypertriglyceridemia," Am. J. Health Syst. Pharm., 64(6):595-605 (Mar. 15, 2007).

McKenney et al., CMRO, "Comparison of the efficacy of rosuvastatin versus atorvastatin, simvastatin and pravastatin in achieving lipid goals: results from the STELLAR trial," 689-98 (2003); https://www.tandfonline.com/doi/abs/10.1185/030079903125002405, Accepted Sep. 5, 2003, Published online: Sep. 22, 2008.

McKenney, J., "Niacin for dyslipidemia: considerations in product selection," Am. J. Health Syst. Pharm, 60:995-1005, (May 15, 2003).

McKenney, James et al., "Role of prescription omega-3 fatty acids in the treatment of Hypertriglyceridemia," Pharmacotherapy, LNKD—Pubmed: 17461707, vol. 27, No. 5, pp. 715-728 (May 2007); https://accpjournals.onlinelibrary.wiley.com/doi/abs/10.1592/phco.27.5.715, Issue Online: Jan. 6, 2012, Version of Record online: Jan. 6, 2012.

McKenney, JM, et al. Study of the pharmacokinetic interaction between simvastatin and prescription omega-3-acid ethyl esters. J. Clin. Pharmacol. 46, 785-791 (Jul. 2006); https://accp1.onlinelibrary.wiley.com/doi/abs/10.1177/0091270006289849 , Issue Online: Mar. 8, 2013. Version of Record online: Mar. 8, 2013, Editorial history: Submitted for publication Jan. 13, 2006, revised version accepted Apr. 11, 2006.

McKeone et al., "Alterations in serum phosphatidylcholine fatty acyl species by eicosapentaenoic and docosahexaenoic ethyl esters in patients with severe hypertriglyceridemia." J. Lipid Res. 38:429-436 (Mar. 1997); https://www.jlr.org/content/38/3/429.short.

McMurchie, E.J., et al., "Incorporation and effects of dietary eicosapentaenoate (20 : 5(n - 3)) on plasma and erythrocyte lipids of the marmoset following dietary supplementation with differing levels of linoleic acid." Biochimica et Biophysics Acta, 1045:164-173 (Jul. 16, 1990).

McNamara JR, et al., Remnant-like particle (RLP) Cholesterol is an independent cardiovascular disease risk factor in women: results from the Framingham Heart Study, Atherosclerosis, vol. 154(1), pp. 229-36 (Jan. 2001); https://www.sciencedirect.com/science/article/

(56) References Cited

OTHER PUBLICATIONS abs/pii/S0021915000004846 , Received Dec. 9, 1999, Revised Mar. 16, 2000, Accepted Mar. 23, 2000, Available online Dec. 21, 2000.
MedlinePlus. "Coronary heart disease," Available at: https://medlineplus.gov/ency/article/007115.htm (review date Jul. 14, 2015)(accessed Sep. 2, 2016)(5 pages).
Menuet, R, et al., "Importance and management of dyslipidemia in the metabolic syndrome," American Journal of the Medical Sciences 200512 US, vol. 33, No. 6, pp. 295-302 (2005); https://www.sciencedirect.com/science/article/abs/pii/S0002962915328809, Dec. 2005, Available online Dec. 16, 2015.
Merched, AJ, et al., "Atherosclerosis: evidence for impairment of resolution of vascular inflammation governed by specific lipid mediators." FASEB J. 22:3595-3606 (Oct. 2008/epub Jun. 17, 2008).
Merkl et al., "Antisense Oligonucleotide Directed to Human Apolipoprotein B-100 Reduces Lipoprotein(a) Levels and Oxidized Phospholipids on Human Apolipoprotein B-100 Particles in Lipoprotein(a) Transgenic Mice," Circulation, vol. 118, pp. 743-753 (epub Jul. 28, 2008).
Mesa, M, "Effects of oils rich in Eicosapentaenoic and docosahexaenoic acids on the oxidizability and thrombogenicity of low-density lipoprotein," Artheroscierosis 175, pp. 333-343 (Aug. 2004); https://www.sciencedirect.com/science/article/abs/pii/S0021915004002151 , Received Jan. 14, 2004, Revised Mar. 22, 2004, Accepted Apr. 20, 2004, Available online Jun. 15, 2004.
Metcalf, RG et al., "Effects of fish-oil supplementation on myocardial fatty acids in humans." Am J Clin Nutr 85:1222-28 (May 2007); https://academic.oup.com/ajcn/article/85/5/1222/4633062, Received Aug. 24, 2006, Accepted Dec. 11, 2006, Published: May 1, 2007.
Metcalf, RG et al., "Effect of dietary n-3 polyunsaturated fatty acids on the inducibility of ventricular tachycardia in patients with ischemic cardiomyopathy." Am J Cardiol 101:758-761 (Mar. 15, 2008/epub Jan. 14, 2008).
Meyer et al., "Comparison of Seal Oil to Tuna Oil on Plasma Lipid Levels and Blood Pressure in Hypertriglyceridaemic Subjects," Lipids, 44:827-835 (Sep. 2009); https://link.springer.com/article/10.1007/s11745-009-3333-3, Received Apr. 15, 2009. Accepted Jul. 20, 2009. Published Aug. 29, 2009, Issue date Sep. 2009.
Meyer et al., "Dose-Dependent Effects of Docosahexaenoic Acid Supplementation on Blood Lipids in Statin-Treated Hyperlipidaemic Subjects." Lipids, 42:109-115 (Mar. 2007/epub Feb. 8, 2007).
Meyers, et at., "Nicotinic acid induces secretion of prostaglandin D2 in human macrophages: An in vitro model of the niacin-flush," Atherosclerosis, 192:253-258, (Jun. 2007/ epub Sep. 1, 2006).
Micheletta F, Natoli S, Misuraca M, Sbarigia E, Diczfalusy U, Iuliano L. Vitamin E supplementation in patients with carotid atherosclerosis: Reversal of altered oxidative stress in plasma but not in plaque. Arterioscler. Thromb. Vasc. Biol. Jan. 2004 (epub Dec. 16, 2006); 24:136-140.
Michos et al., "Niacin and Statin Combination Therapy for Atherosclerosis Regression and Prevention of Cardiovascular Disease Events," Journ. Amer. Coll. Cardiol., vol. 59, No. 23:2058-2064 (Jun. 5, 2012)(epub Apr. 18, 2012).
Mii, S, et al., "Perioperative use of eicosapentaenoic acid and patency of infrainguinal vein bypass: a retrospective chart review." Curr Ther Res Clin Exp. 68:161-174 (May 2007); https://www.sciencedirect.com/science/article/pii/S0011393X07000525, Accepted Apr. 11, 2007, Available online Aug. 22, 2007.
Miles, et al., "Effect of orlistat in overweight and obese patients with type 2 diabetes treated with metformin," Diabetes Care, 25(7):1123-1128 (2002); https://care.diabetesjournals.org/content/25/7/1123.short.
Miller AK, DiCicco RA, Freed MI. The effect of ranltidine on the pharmacokinetics of rosiglitazone in healthy adult male volunteers. Clin. Ther. Jul. 2002;24:1062-1071; https://www.tandfonline.com/doi/abs/10.1185/03007990802205985, Accepted May 16, 2008, Published online: Jun. 25, 2008.
Miller AK, Inglis AM, et al., The effect of acarbose on the pharmacokinetics of rosiglitazone. Eur. J. Clin. Pharmacol. May 2001;57:105-109; https://link.springer.com/article/10.1007/s002280100275 Received Jul. 18, 2000. Published Feb. 7, 2014. Issue date May 2001.
Miller M, Cannon CP, et al. Impact of triglyceride levels beyond low-density lipoprotein cholesterol after acute coronary syndrome in the PROVE IT-TIMI 22 trial. J Am Coll Cardiol 51:724-730, Feb. 19, 2008.
Miller M, Stone NJ, et al. Triglycerides and cardiovascular disease: a scientific statement from the American Heart Association. Circulation. May 24, 2011 (epub Apr. 18, 2011); 123:2292-2333.
Miller, M, Current perspectives on the management of hypertrigtyceridemia. Am Heart J 140:232-40, 2000; https://www.sciencedirect.com/science/article/abs/pii/S0002870300784870 , Received May 27, 1999, Accepted Mar. 27, 2000, Available online May 25, 2002.
Miller, M, et al., "Impact of lowering triglycerides on raising HDL-C in hypertriglyceridemic and non-hypertriglyceridemic subjects." International Journal of Cardiology 119:192-195 (Jul. 10, 2007) (epub Oct. 18, 2006).
Minihane, AM, et al., "ApoE polymorphism and fish oil supplementation in subjects with an atherogenic lipoprotein phenotype." Arterioscler. Thromb. Vasc. Biol. 20:1990-1997 (Aug. 2000); https://www.ahajournals.org/doi/full/10.1161/01.ATV.20.8.1990, Originally published Aug. 1, 2000.
Mishra, A., et al., "Oxidized omega-3 fatty acids inhibit NF-κB activation via a PPARα-Dependent Pathway." Arterioscler Thromb Vasc Biol. 24:1621-1627 (Sep. 2004)(epub Jul. 1, 2004).
Missouri DUReport, Statin Therapy (Oct./Nov. 2003) Drug Use Review Newsletter 8(6):1-9.
Mita, T. et al., Eicosapentaenoic acid reduces the progression of carotid intima-media thickness in patients with type 2 diabetes, Atherosclerosis 191:162-167 (Mar. 2007)(epub Apr. 17, 2006).
Mizota M, et al. "Pharmacological studies of eicosapentaenoic acid ethylester (EPA E) on high cholesterol diet-fed rabbits," Nippon Yakurigaku Zasshi, 91:255-66 (Apr. 1988) (with English abstract); https://europepmc.org/article/med/2839398, Mar. 31, 1988.
Mizota M, et al., "The effects of eicosapentaenoic acid ethylester (EPA E) on arterial thrombosis in rabbits and vascular lesions in rats," Nippon Yakurigaku Zasshi, 91:81-9 (Feb. 1988)(with English abstract); https://europepmc.org/article/med/2836280, Jan. 31, 1988.
Mizuguchi K, Yano T, et al., "Hypolipidemic effect of ethyl all-cis-5,8,11,14,17-eicosapentaenoate (EPA-E) in rats," Jpn J Pharmacol., 59(3):307-12 (Jul. 1992); https://www.jstage.jst.go.jp/article/jphs1951/59/3/59_3_307/_article/-char/ja/.
Mizuguchi, K., et al., "Ethyl all-cis-5,8,11,14,17-icosapentaenoate modifies the biochemical properties of rat very low-density lipoprotein." European Journal of Pharmacology, 231:221-227 (Apr. 28, 1993).
Mizuguchi, K., et al., "Mechanism of the lipid-lowering effect of ethyl all-cis-5,8,11,14,17-icosapentaenoate." European Journal of Pharmacology, 231:121-127 (Jan. 1993); https://www.sciencedirect.com/science/article/abs/pii/001429999390692B , Received May 25, 1992, Revised Oct. 12, 1992, Accepted Nov. 3, 1993, Available online Nov. 26, 2002.
Mochida Press Release, Pharmaceutical Col., Ltd.: Conclusion of Distributorship Agreement Concerning Switch-OTC Drug for Hyperlipidemia Treatment, Epadel, (Apr. 30, 2009)(1 page).
Mochida, Announcement, Mochida Announces Completion of "JELIS" Major Clinical Trial for "Egadel," Mar. 22, 2005 (2 pages).
Mochida's Epadel Reduces Risk of Stroke Recurrence—New Results of JELIS Major Clinical Trial, JCNNetwork Newswire Nov. 13, 2006 (2 pages).
Mora, S, et al., "LDL particle subclasses, LDL particle size, and carotid atherosclerosis in the Multi-Ethnic Study of Atherosclerosis (MESA)." Atherosclerosis. ;192:211-217 (May 2007); https://www.sciencedirect.com/science/article/abs/pii/S0021915006002590, Received Jan. 26, 2006, Revised May 2, 2006, Accepted May 4, 2006, Available online Jun. 12, 2006.
Mori et al., "Differential Effects of Eicosapentaenoic Acid and Docosahexaenoic Acid on Vascular Reactivity of the Forearm Microcirculation in Hyperlipidemic, Overweight Men," Circulation, 102:1264-1269 (Sep. 12, 2000).

(56) References Cited

OTHER PUBLICATIONS

Mori TA, Woodman RJ. "The independent effects of eicosapentaenoic acid and docosahexaenoic acid on cardiovascular risk factors in humans," Curr Opin Clin Nutr Metab Care 2006; 9:95-104 (Mar. 2006); https://journals.lww.com/co-clinicalnutrition/Abstract/2006/03000/The_independent_effects_of_eicosapentaenoic_acid.6.aspx, Originally published: Mar. 2006.

Mori TA. Omega-3 fatty acids and blood pressure. Cell Mol Biol. Feb. 25, 2010;56(1):83-92; https://europepmc.org/article/med/20196972, Feb. 24, 2010.

Mori, et al., "Purified Eicosapentaenoic and docosahexaenoic acids have differential effects on serum lipids and lipoproteins, LDL particle size, glucose, and insulin in mildly hyperlipidemic men," Am J Clin Nutr 71:1085-1094 (May 2000); https://academic.oup.com/ajcn/article/71/5/1085/4729166, Received: Aug. 10, 1999, Accepted: Oct. 20, 1999, Published: May 1, 2000.

Mori, T. et al., Effect of Eicosapentaenoic acid and docosahexaenoic acid on oxidative stress and inflammatory markers in treated-hypertensive type 2 diabetic subjects, Free Radical Biology & Medicine, vol. 35, No. 7, pp. 772-781 (Oct. 1, 2003).

Mori, Trevor, et al., "Docosahexaenoic Acid but Not Eicosapentaenoic Acid Lowers Ambulatory Blood Pressure and Heart Rate in Humans", Hypertension, 34(2):253-60 (Aug. 1999); https://www.ahajournals.org/doi/full/10.1161/01.hyp.34.2.253 Manuscript received Feb. 22, 1999. Manuscript accepted Apr. 6, 1999 Originally published Aug. 1, 1999.

Morin et al., "Anti-proliferative effects of a new docosapentaenoic acid monoacylglyceride in colorectal carcinoma cells;" Prostaglandins, Leukotrienes and Essential Fatty Acids, Aug. 7, 2013, vol. 89, pp. 203-213.

Morita, I, et al., "Effects of purified eicosapentaenoic acid on arachidonic acid metabolism in cultured murine aortic smooth muscle cells, vessel walls and platelets." Lipids 18:42-490 (Jan. 1983); https://aocs.onlinelibrary.wiley.com/doi/abs/10.1007/BF02534689, Manuscript received: Aug. 9, 1982. Issue Online: Jan. 1, 1983, Version of Record online: Jan. 1, 1983.

Molds M, et al., Does fish oil lower blood pressure? A meta-analysis of controlled trials. Circ., Aug. 1993;88:523-533; https://www.ahajournals.org/doi/abs/10.1161/01.cir.88.2.523, Originally published Aug. 1, 1993.

Morrow JD, "Release of markedly increased quantities of prostaglandin D2 in vivo in humans following the administration of nicotinic acid", Prostaglandins, 38:268-274, (Aug. 1989); https://www.sciencedirect.com/science/article/abs/pii/0090698089900889, Received Jun. 26, 1989, Accepted Jul. 24, 1989, Available online Dec. 1, 2003.

Morton RE, "Specificity of lipid transfer protein for molecular species of cholesteryl ester." J Lipid Res., 27:523-529 (May 1986); https://www.jlr.org/content/27/5/523.short, May 1, 1986.

Mosher LR, et al., "Nicotinic Acid Side Effects and Toxicity: A review," Am J Psychiat., 126: 1290-1296 (Mar. 1970); https://ajp.psychiatryonline.org/doi/abs/10.1176/ajp.126.9.129, Published Online: Apr. 1, 2006. Published in print Mar. 1, 1970.

Mostad et al., "Effects of Marine N-3 Fatty Acid Supplementation on Lipoprotein Subclasses Measured by Nuclear Magnetic Resonance in Subjects with Type II Diabetes," European Journ. Clin. Nutr., 62(3):419-429 (Mar. 2008/epub Feb. 27, 2007).

Mostad, I.L., et al., "Effects of n-3 fatty acids in subjects with type 2 diabetes: reduction of insulin sensitivity and time-dependent alteration from carbohydrate to fat oxidation." Am J Clin Nutr 84:540-50 (Sep. 2006); https://academic.oup.com/ajcn/articie/84/3/540/4648766, Received: Sep. 5, 2005. Accepted: Apr. 20, 2006. Published: Dec. 1, 2006.

Mozaffarian D, Benjamin EJ, et al., on behalf of the American Heart Association Statistics Committee and Stroke Statistics Subcommittee. Heart disease and stroke statistics—2016 update: a report from the American Heart Association [published online ahead of print Dec. 16, 2015]. Circulation. doi: 10.1161/CIR.0000000000000350.

Mozaffarian D, et al., Effect of Fish Oil on Heart Rate in Humans a Meta-Analysis of Randomized Controlled Trials. Circ.Sep. 27, 2005/ epub Sep. 19, 2005; 112:1945-1952; https://academic.oup.com/ajcn/article/87/6/1991S/4633489, Published: Jun. 1, 2008.

Mozaffarian D, Marchioli R, et al. Fish Oil and Postoperative Atrial Fibrillation The Omega-3 Fatty Acids for Prevention of Postoperative Atrial Fibrillation (OPERA) Randomized Trial. JAMA. Nov. 21, 2012;308(19):2001-11.

Mozaffarian D, Psaty B, et al., Fish intake and Risk of Incident Atrial Fibrillation. Circ., Jul. 27, 2004/epub Jul. 19, 2004; 110:368-373.

Mozaffarian et al., Omega-3 fatty acids and cardiovascular disease: effects on risk factors, molecular pathways and clinical events, J. Am. Coll. Cardiol. (Nov. 8, 2011) 58(20): 2047-2067.

Mozaffarian, "JELIS, fish oil, and cardiac events," www.thelancet.com vol. 369, pp. 1062-1063 (Mar. 31, 2007).

Mozaffarian, D, "Fish and n-3 fatty acids for the prevention of fatal coronary heart disease and sudden cardiac death." Am J Clin Nutr, 87:1991S-6S (Jun. 2008); https://academic.oup.com/ajcn/article/87/6/1991S/4633489 , Published: Jun. 1, 2008.

Mozaffarian, D, et al., "Dietary fish and ω-3 fatty acid consumption and heart rate variability in US adults." Circulation, 117:1130-1137 (Mar. 4, 2008/ epub Feb. 19, 2008).

Murck et al., "Ethyl-EPA in Huntington disease—Potentially relevant mechanism of action," Brain Research Bulletin, 72:159-164 (2007) (available online Nov. 15, 2006).

Murphy SA, Cannon CP, Blazing MA, et al. Reduction in total cardiovascular events with ezetimibe/simvastatin post-acute coronary syndrome. J Am Coll Cardiol. 67(4):353-361 (epublication date Feb. 2, 2016; epublication date Jan. 25, 2016).

Naba, H, et al., "Improving effect of ethyl eicosapentanoate on statin-induced rhabdomyolysis in Eisai hyperbilirubinemic rats." Biochemical and Biophysical Research Communications, 340:215-220 (Feb. 2006/epub Dec. 9, 2005).

Nagakawa et al., Effect of [EPA] on the Platelet Aggregation and Composition of Fatty Acid in Man: A Double Blind Study, Atherosclerosis 47(1):71-75 (Apr. 1983); https://www.sciencedirect.com/science/article/abs/pii/0021915083900734 , Received Oct. 7, 1982, Revised Nov. 16, 1982, Accepted Nov. 18, 1982, Available online Apr. 14, 2005.

Naik H, Wu JT, Palmer R, McLean L. The effects of febuxostat on the pharmacokinetic parameters of rosiglitazone, a CYP2C8 substrate. Br. J. Clin. Pharmacol. Jan. 13, 2012;74:327-335.

Nakamura et al., Remnant lipoproteinemia is a risk factorifor endothelial vasomotor dysfuction and coronary artery disease in metabolic syndrome, Atherosclerosis, vol. 181(2), pp. 321-327 (Aug. 2005/epub Feb. 16, 2005).

Nakamura, et al., "Effects of Eicosapentaenoic Acids on Remnant-like Particles, Cholesterol Concentrations and Plasma Fatty Acid Composition in Patients with Diabetes Mellitus." in vivo 12: 311-314 (May/Jun. 1998); https://europepmc.org/article/med/9706476 Apr. 30, 1998.

Nakamura, H, et al., "Evaluation of ethyl icosapentate in the treatment of hypercholesterolemia in kidney transplant recipients." Transplantation Proceedings, 30:3047-3048 (Nov. 1998); https://pascal-francis.inist.fr/vibad/index.php?action=getRecordDetail&idt=1650649 , Congress of the Asian Society for Transplantation (5; Manila Dec. 4, 1997).

Nakamura, N, et al., "Joint effects of HMG-CoA reductase inhibitors and eicosapentaenoic acids on serum lipid profile and plasma fatty acid concentrations in patients with hyperlipidemia," International Journal of Clinical and Laboratory Research, Springer, Berlin, DE LNKD-DOI: 10.1007/S005990050057, vol. 29, No. 1, pp. 22-25 (1999); https://link.springer.com/article/10.1007/s005990050057 , Received Oct. 26, 1998, Accepted Jan. 12, 1988, Issue Date Mar. 1999.

Nambi V, Bhatt DL. Primary prevention of atherosclerosis: Time to take a selfie? J Am Coll Cardiol 2017;70(24):2992-4 (publication date Dec. 19, 2017; epublication date Dec. 11, 2017).

Nambi, V., et al., "Combination therapy with statins and omega-3 fatty acids." Am J Cardiol 98:34i-38i (Aug. 21, 2006/epub May 30, 2006).

Nasa et al., "Long-Term Supplementation With Eicosapentaenoic Acid Salvages Cardiomyocytes From Hypoxia/Reoxygenation-Induced injury in Rats Fed With Fish-Oil-Deprived Diet," Jpn. J.

(56) References Cited

OTHER PUBLICATIONS

Pharmacol. 77, 137-146 (Jun. 1998); https://www.jstate.jst.go.jp/article/jjp/77/2/77_2_137/_article/-char/ja/.

National Kidney Foundation, "Glomerular Filtration Rate (GFR)," Jan. 30, 2017 (Jan. 30, 2017), retrieved on Jul. 30, 2018 from https://web.archive.org/web/20170130183218/https://www.kidney.org/atoz/content/gfr; entire document, especially p. 1 paragragh 1 and p. 3, paragragh 2.

National Kidney Foundation, "The Heart and Kidney Connection," Apr. 17, 2017 (Apr. 17, 2017), retrieved on Jul. 30, 2018 from https://web.archive.org/web/20170417004l6/https://www.kidney.org/atoz/content/heart-and-kidney-connection; entire document, especially p. 2, paragragh 1.

National Kidney Foundation, Clinical Practice Guidelines for Chronic Kidney Disease: Evaluation, Classification and Stratification; Cogyright 2002, 356 pages.

Natsuno et al., "Clinical Effects of Eicosapentaenoic Acid on Type-2 Diabetes Effects on Serum Lipids, Pulse Wave Speed, and Ankle-Brachial Blood Pressure Index," Diagnosis and Treatment 93(12):133-137 (2005)(16 pages).

Nattel S, et al., "Atrial remodeling and atrial fibrillation: Mechanisms and implications." Circ Arrhythmia Electrophysiol, 1:62-73 (Apr. 2008); https://www.ahajournals.org/doi/full/10.1161/CIRCEP.107.754564 Originally Qublished Apr. 1, 2008.

NCBI, Table 6-1 "Factors for Converting International Units of Vitamin E$^a$ to α-Tocopherol$^b$(mg) to Meet Recommended Intake," taken from Dietary Reference Intakes for Vitamin C, Vitamin E, Selenium and Carotenoids, Institute of Medicine (US) Panel on Dietary Antioxidants and Related Compounds, Washington DC, National Academies Press (US) 2000.

Needleman P, et al., Triene prostaglandins: prostacyclin and thromboxane biosynthesis and unique biological properties. Proc Natl Acad Sci USA. Feb. 1979;76:944-948; https://www.pnas.org/content/76/2/944.short?_cf_chl_jschi_tk_=ac2fd629e3183e15c541f712df7a9f121128e4bd-1593527565-0-AaVshpn8aqJ65Lwi4-CdjCnbRDi7KbxHebgijR1uxqtVRVw6oCucSKnLOREHMPhmpjbNbNiY4sHOc7MjgbNNpaMDfS-qHpGrPmP6oC7-3Xh-Ns5k-wL5RvxdJR6_SaRvSRgVCM6_ud-XzblOjXQKl2oiP9ocNekcqgPcoj-rbPli4vpEUaeTCydRySjvoUCTVsOjDydfU947TSTsloosVEYwFoC0NLpClWrR0Dp-sDs8iQ6lij_2AteaKUQiNoNIK0QreRzmzX6yHENk7s8lqlZmXSNaX8wyjW-mSiEQ-orR0A-Arv-tEL0nhhdX3Y4-Xw, Feb. 1, 1979.

Negre-Salvayre, A., et al., "Advanced lipid peroxidation end products in oxidative damage to proteins. Potential role in diseases and therapeutic prospects for the inhibitors." British Journal of Pharmacology 153:6-20 (Jan. 2008/epub Jul. 23, 2007).

Nelson et al., "Icosapent Ethyl for Treatment of Elevated Triglyceide Levels," Annals of Pharmacotheraphy,47(11):1517-1523 (Nov. 2013/epub Nov. 5, 2013).

Nelson JR, et al., Potential benefits of eicosapentaenoic acid on atherosclerotic plaques. Vascul Pharmacol. 91:1-9 (publication date Apr. 2017; epublication date Mar. 2, 2017).

Nelson, G.J., et al., "The Effect of Dietary Docosahexaenoic Acid on Plasma Lipoproteins and Tissue Fatty Acid Composition in Humans", Lipids, 32(11):1137-1146, (Nov. 1997); https://aocs.onlinelibrary.wiley.com/doi/abs/10.1007/s11745-997-0146-5, First published Nov. 1, 1997. Version of Record online Nov. 1, 1997, Manuscript accepted Oct. 6, 1997. Manuscript revised Sep. 23, 1997, Manuscript received Jul. 14, 1997.

Nemets, Boris, "Addition of Omega-3 Fatty Acid to Maintenance Medication Treatment for Recurrent Unipolar Depressive Disorder", Am. J. Psychiatry, 159(3):477-479, (Mar. 2002); https://ajp.psychiatryonline.org/doi/full/10.1176/appi.ajp.159.3.477, Published Oniine Mar. 1, 2002.

Nemoto et al., "Ethyl-eicosapentaenoic Acid Reduces Liver Lipids and Lowers Plasma Levels of Lipids in Mice Fed a High-Fat Diet, in vivo," 23:685-690 (Sep./Oct. 2009); http://iv.iiarjournals.org/content/23/5/685.short, Received Mar. 6, 2009. Revision received Jun. 4, 2009, Accepted Jun. 26, 2009.

Nenseter, MS et al., "Effect of dietary supplementation with n-3 polyunsaturated fatty acids on physical properties and metabolism of low density lipoprotein in humans," Arterioscler. Thromb. Vasc. Biol., 12;369-379 (Mar. 1992); https://www.ahajournalsorg/doi/abs/10.1161/01.atv.12.3.369 Originally published Mar. 1, 1992.

Nestel et al., "The n—3 fatty acids eicosapentaenoic acid and docosahexaenoic acid increase systemic arterial compliance in humans," Am J Clin Nutr., 76:326-30 (Aug. 2002); https://academic.oup.com/ajcn/article/76/2/326/4689508, Received Jan. 16, 2001, Accepted Aug. 2, 2001, Published Aug. 1, 2002.

Nestel, PJ, "Effects of N-3 fatty acids on lipid metabolism." Ann Rev Nutr., 10:149-167 (1990); https://www.annualreviews.org/doi/pdf/10.1146/annurev.nu.10.070190.001053.

Nichols GA, et al., Increased cardiovascular risk in hypertriglyceridemic patients with statin-controlled LDL cholesterol. J Clin Endocrinol Metab 103(8):3019-27 (publication date Aug. 1, 2018; epublication date May 29, 2018).

Nichols GA, et al., Increased residual cardiovascular risk in patients with diabetes and high vs. normal triglycerides despite statin-controlled LDL Cholesterol. Diabetes Obes Metab (publication date Sep. 17, 2018; epublication date Sep. 17, 2018).

Niemi M, Backman JT, Grantors M, et al., Gemfibrozil considerably increases the plasma concentrations of rosiglitazone. Diabetoiogia. Oct. 2003/Jul. 29, 2003); 46: 1319-1323; https://ascpt.onlinelibrary.wiley.com/doi/abs/10.1016/j.clpt.2004.05.001, First published Sep. 4, 2004, Version of Record online Sep. 4, 2004, Manuscript accepted May 3, 2004, Manuscript received Feb. 10, 2004.

Niemi M, Backman JT, Neurvonen PJ, Effects of trimethoprim and rifampin on the pharmacokinetics of the cytochrome P450 2C8 substrate rosiglitazone. Clin. Pharmacol. Ther., Sep. 2004;76:239-249.

Nigon F, et al., Discrete subspecies of human low density lipoproteins are heterogeneous in their interaction with the cellular LDL receptor. J. Lipid Res., Nov. 1991;32(11):1741-1753; https://www.jlr.org/content/32/11/1741.short.

Nippon Rinsho, Metabolic Syndrome 2nd Edition—Basics and New Clinical Findings, Jan. 20, 2011, Special Issue 1 (vol. 69), pp. 503-506 (with English translation).

Nishikawa M, et al., "Effects of Eicosapentaenoic acid (EPA) on prostacyciin production in diabetics. GC/MS analysis of PG12 and PG13 levels" Methods Find Exp Clin Pharmacol. 19(6):429-33 (Jul./Aug. 1997); https://europepmc.org/article/med/9385592, Jun. 30, 1997.

Nobukata, H, et al., "Age-related changes in coagulation, fibrinolysis, and platelet aggregation in male WBN/Kob rats." Thrombosis Research 98: 507-516 (Jun. 15, 2000).

Nobukata, H, et al., "Long-term administration of highly purified eicosapentaenoic acid ethyl ester improves the dysfunction of vascular endotheiiai and smooth muscle cells in male WBN/Kob rats." Metabolism, 49(12): 1588-1591 (Dec. 2000); https://www.sciencedirect.com/science/article/abs/pii/S0026049500435912, Available online May 25, 2002.

Nobukata, H, et al., "Long-term administration of highly purified eicosapentaenoic acid ethyl ester prevents diabetes and abnormalities of blood coagulation in male WBN/Kob rats." Metabolism, 49(12): 912-919 (Jul. 2000); https://www.sciencedirect.com/science/article/abs/pii/S0026049500131701, Available online May 25, 2002.

Noguchi et al., Chemopreventien of DMBA-induced mammary carcinogenesis in rats by low-dose EPA and DHA, Br. J. Cancer 75(3): 348-353 (1997); https://www.nature.com/articles/bjc199757, Feb. 1, 1997.

Nomura et al., "The effects of pitavastatin, eicosapentaenoic acid and combined therapy on platelet-derived microparticles and adiponectin in hyperlipidemic, diabetic patients." Platelets, 20(1):16-22 (Feb. 2009); https://www.tandfonline.com/doi/abs/10.1080/09537100802409921, Received Apr. 26, 2008, Accepted Aug. 14, 2008, Published online: Jul. 7, 2009.

Nomura S, et al., Effects of eicosapentaenoic acid on endothelial cell-derived microparticles, angiopoietins and adiponectin in patients with type 2 diabetes. J Atheroscler Throm., Apr. 2009;16:83-90; https://www.jstage.jst.go.jp/articie/jat/advpub/0/advpub_E091/_article/-char/ja/.

(56) References Cited

OTHER PUBLICATIONS

Nourooz-Zadeh J, et al., "Urinary 8-epi-PGF2α and its endogenous β-oxidation products (2,3-dinor and 2,3-dinor-5,6-dihydro) as biomarkers of total body oxidative stress." Biochemical and Biophysical Research Communications 330:731-736 (May 13, 2005).
Nozaki S, et al., "Effects of purified Eicosapentaenoic acid ethyl ester on plasma lipoproteins in primary hypercholesterolemia" Int J Vitam Nutr Res. 62(3):256-260 (1992); https://europepmc.org/article/med/1473909 Dec. 31, 1991.
Obata et al., Eicosapentaenoic acid inhibits prostaglandin D2 generation by inhibiting 3 cyclo-oxygenase in cultured human mast cells, Clin. & Experimental Allergy, 29:1129-1135, (Aug. 1999); https://europepmc.org/article/med/10457118, Jul. 31, 1999.
O'Donnell CJ, et al., "Leukocyte telomere length and carotid artery intimal medial thickness—the Framingham heart study." Arteriosclerosis, Thrombosis, and Vascular Biology.28:1165-1171 ( Jun. 2008/epub Apr. 3, 2008).
Oemar BS, et al., Reduced endotheiial nitrioioxide synthase expression and production in human atherosclerosis. Circulation., Jun. 30, 1998;97:2494-2498.
Oh, Robert C et al., Management of Hypertriglyceridemia, American Family Physician, LNKD-PUBMED: 17508532, vol. 75, No. 9, pp. 1365-1371 (May 1, 2007).
Ohara Y, et al., Hypercholesterolemia increases endothelial superoxide anion production. J. Clin. Invest. Jun. 1993;91:2546-2551; https://www.jci.org/articles/view/116491, First published Jun. 1, 1993.
Ohashi, Journal of Clinical and Experimental Medicine, Feb. 14, 2009, vol. 228, No. 7, pp. 795-805 (with English translation).
Okuda Y, et al., Eicosapentaenoic acid enhances nitric oxide production by cultured human endothelial cells. Biochem. Biophys. Res. Commun. 232: 487-491 (Mar. 17, 1997).
Okuda Y, et al., Long-term effects of eicosapentaenoic acid on diabetic peripheral neuropathy and serum lipids in patients with type II diabetes mellitus, Journal of Diabetes and Its Complications 10:280-287 (Sep./Oct. 1996); https://www.sciencedirect.com/science/article/abs/pii/105687279500081X, Available online Mar. 19, 1999.
Okumura T, et al., "Eicosapentaenoic acid improves endothelial function in hypertriglyceridemic subjects despite increased lipid oxidizability." Am J Med Sci 324(5):247-253 (Nov. 2002); https://www.sciencedirect.com/science/article/abs/pii/S000296291534369X, Received Apr. 23, 2002, Accepted Jun. 17, 2002, Available online Dec. 16, 2015.
Oliw EH, et al., "Biosynthesis of prostaglandins from 17(18)epoxyeicosatetraenoic acid, a cytochrome P-450 metabolite of eicosapentaenoic acid." Biochimica el Biophysica Acta, 1126, 261-268 (Jun. 26, 1992).
Olofsson et al., "Apolipoprotein B: a clinically important apolipoprotein which assembles atherogenic lipoproteins and promotes the development of atherosclerosis" Journal of Internal Medicine, 258: 395-410 (Nov. 2005); https://onlinelibrary.wiley.com/doi/full/10.1111/j.1365-2796.2005.01556.x, First published: Sep. 22, 2005. Version of Record online: Sep. 22, 2005.
Omacor Summary of Product Characteristics, Pronova BioPharma Norge AS. Lysaker, Norway, Mar. 2015.
Omacor® Prescribing Information (Omega-3-acid ethyl esters, capsules) (2004). (9 pages).
Omacor®, Physicians' Desk Reference 2735 (60th ed. 2006)(3 pages).
Ona Vo, et al., Nature, vol. 399, Inhibition of caspase-1 slows disease progression in a mouse model of Huntington's disease, pp. 263-267 (May 20, 1999).
Ooi EM, "Apolipoprotein C-III: Understanding an emerging cardiovascular risk factor", Clin.Sci. (London), vol. 114, pp. 611-624 (May 2008); https://portlandpress.com/clinsci/article-abstract/114/10/611/68347 Apr. 14, 2008. Received Sep. 3, 2007, Revision Received Nov. 19, 2007, Accepted Dec. 12, 2007.
Opalinska et al., "Increasing Level of Prostate-Specific Antigen and Prostate Cancer Risk Factors Among 193 Men Examined in Screening Procedure," Ann. Univ. Curie Sklowoska Med., 58(2):57-63 (Abstract Only)(2003)(2 pages); https://europepmc.org/article/med/15323167, Dec. 31, 2002.
Origin Trial Investigators (The). n-3 fatty acids and cardiovascular outcomes in patients with dysglycemia. N Engl J Med Jul. 6, 2012/epub Jun. 11, 2012; 367:309-318.
O'Riordan, DHA and EPA have differential effects on LDL-cholsterol, May 24, 2011 [online][Retrieved on Aug. 21, 2015] Retrieved from website: http://www.medscape.com/viewarticle/743305 (2 pages).
Osher et al., Omega-3 Eicosapentaenoic Acid in Bipolar Depression: Report of a Small Open-Label Study, J. Clin. Psych. 66:726-729 (Jun. 2005); https://www.psychiatrist.com/jcp/article/pages/2005/v66n06/v66n0608.aspx.
Otvos et al., "Clinical Implications of Discordance Between LDL Cholesterol and LDL Particle Number," J. Clin. Lipidol, 5(2):105-113 (Mar.-Apr. 2011)(available online Mar. 1, 2011).
Ou Z, et al., L-4f, an apolipoprotein a-1 mimetic, restores nitric oxide and superoxide anion balance in low-density lipoprotein-treated endothelial cells. Circulation. Mar. 25, 2003;107:1520-1524.
Ozaki M, et al., Overexpression of endothelial nitric oxide synthase accelerates atherosclerotic lesion formation in apoe-deficient mice. J. Clin. Invest. Aug. 2002; 110:331-340; https://www.jci.org/articles/view/15215 , Received: Feb. 6, 2002, Accepted Jun. 3, 2002, First published Aug. 1, 2002.
Ozawa et al., Determination of higher fatty acids in various lipid fractions of human plasma, platelets, and erythrocyte membrane using thin layer chromatography and gas chromatography, Bunseki Kagaku, 32:174-8 (1982) (with English abstract).
Padgett et al., Phylogenetic and immunological definition of four lipoylated proteins from *Novosphingobium aromaticivorans*, implications for primary biliary cirrhosis, Journ. Autoimmunity 24:209-219 (May 2005); https://www.sciencedirect.com/science/article/abs/pii/S0896841105000156, Received Nov. 24, 2004, Available online Feb. 24, 2005.
Park JH, et al., Metabolic syndrome is associated with erosive esophagitis. World J. Gastroenterol. Sep. 2008 14 (35): 5442-7; https://www.ncbi.nlm.nih.gov/pmc/articles/PMC2744163/ Published online Sep. 21, 2008.
Park JY, et al., Effect of rifampin on the pharmacokinetics of rosiglitazone in healthy subjects. Clin. Pharmacol. Ther., Mar. 2004;75:157-162; https://ascpt.onlinelibrary.wiley.com/doi/abs/10.1016/j.clpt.2003.10.003 , First published Mar. 9, 2004. Version of Record online Mar. 9, 2004, Manuscript accepted Oct. 8, 2003. Manuscript received Aug. 5, 2003.
Park Y, et al., "Omega-3 fatty acid supplementation accelerates chylomicron triglyceride clearance." J. Lipid Res. 44:455-463 (Mar. 2003); httgs://www.jlr.org/content/44/3/455.short, First Published on Dec. 1, 2002.
Pase M, et al., Do long-chain n-3 fatty acids reduce arterial stiffness? A meta-analysis of randomized controlled trials.Br J Nutr., Oct. 2011; 106:974-980; https://www.cambridge.org/core/journals/british-journal-of-nutrition/article/do-longchain-n3-fatty-acids-reduce-arterial-stiffness-a-metaanalysis-of-randomised-controlled-trials/3D293E4E535EFAA111C080914EE2143F, Oct. 14, 2011. Published online by Cambridge University Press: Jul. 6, 2011.
Patel et al., Rosiglitazone monotherapy improves glycaemic control in patients with type 2 diabetes: a twelve-week, randomized, placebo-controlled study, Diabetes, Obesity and Metabolism, vol. 1, pp. 165-172 (May 1999); https://dom-pubs.onlinelibrary.wiley.com/doi/abs/10.1046/j.1463-1326.1999.00020.x Received Jan. 8, 1999, returned for revision Feb. 25, 1999, revised version accepted Mar. 28, 1999, First published Dec. 25, 2001.
Paton, CM, Ntambi, JM., Biochemical and physiological function of stearoyl-CoA desaturase, AM. J. Physiol. Endocrinol. Metab. Jul. 2009/epub Dec. 9, 2008; 297:E28-E37.
PCT/GB00/00164 International Search Report dated Oct. 20, 2000 (8 pages).
PCT/US2011/062247 Internrational Search Report and Written Opinion dated Jun. 14, 2012 (12 pages).
PCT/US2013/020526 International Search Report dated Mar. 29, 2013 (2 pages).

(56) References Cited

OTHER PUBLICATIONS

PCT/US2013/048241 International Search Report dated Dec. 13, 2013 (3 pages).
PCT/US2013/048516 International Search Report dated Dec. 20, 2013 (3 gages).
PCT/US2013/048559 International Search Regort dated Dec. 13, 2013 (3 pages).
PCT/US2013/068647 International Search Report and Written Opinion dated May 13, 2014 (18 pages).
PCT/US2014/019454 International Search Report and Written Opinion dated Jun. 3, 2014 (12 pages).
Pedersen RS, Damkier P, Brosen K. The effects of human CYPZC8 genotype and fluvoxamine on the pharmacokinetics of rosiglitazone in healthy subjects. Br. J. Clin. Pharmacol. Dec. 2006/epub Jul. 12, 2006; 62:682-689.
Pedersen, T., et al., "Randomised trial of cholesterol lowering in 4444 patients with coronary heart disease: the Scandinavian Simvastation Survival Study (4S)," The Lancet, No. 19, vol. 344, 8934, p. 1383-1389 (Nov. 19, 1994).
Peet et al., "A Dose-Ranging Study of the Effects of Ethyl-Eicosapentaenoate in Patients with Ongoing Depression Despite Apparently Adequate Treatment with Standard Drugs", Arch. Gen. Psychiatry, 59:913-919, (Oct. 2002); https://jamanetwork.com/journals/jamapsychiatry/article-abstract/206794 , Submitted for publication Apr. 27, 2001 ; final revision received Oct. 19, 2001 ; accepted Nov. 1, 2001, presented as a poster at the Society of Biological Psychiatry Meeting in New Orleans, LA, May 2001, at the Fourth International Conference on Bipolar Disorder in Pittsburgh, PA, Jun. 2001, and at the British Association of Psychopharmacology Meeting, Harrogate, England, Jul. 2001.
Peet, M., et al., Phospholipid Spectrum Disorder in Psychiatry pp. 1-19, (1999).
Pejic et al., "Hypertriglyceridimia", Journ. Amer. Board Fam. Med., vol. 19(3):310-316 (May/Jun. 2006); https://www.jabfm.org/content/19/3/310.short, May 2006.
Pennathur S, et al., Mechanisms for oxidative stress in diabetic cardiovascular disease. Antioxid. Redox Signal. Jul. 2007;9(7):955-969; https://www.liebertpub.com/doi/abs/10.1089/ars.2007.1595, Published Online: May 17, 2007.
Pepys, MB, et al, C-reactive protein: a critical update, Journal of Clinical Investigation, e-pub Jun. 15, 2003; Jul. 2003, vol. 111(12), pp. 1805-1812; https://www.jci.org/articles/view/18921, First published Jun. 15, 2003.
Piccini M, et al., FACL4, a new gene encoding long-chain acyl-CoA synthetase 4, is deleted in a family with Alport syndrome, elliptocytosis, and mental retardation, Genomics, vol. 47, pp. 350-358 (Feb. 1998); https://www.sciencedirect.com/science/article/pii/S0888754397951041, Received Jun. 20, 1997 Accepted Oct. 24, 1997, Available online May 25, 2002.
Piche ME, et al., Relation of High-Sensitivity C-Reactive Protein, Interleukin-6 Tumor Necrosis Factor-Alpha, and Fibrlnogen to Abdominal Adipose Tissue, Blood Pressure, and Cholesterol and Triglyceride Levels in Healthy Postmenopausal Women, American Journal of Cardiology, 2005, 96(1), 92-97; https://www.sciencedirect.com/science/article/abs/pii/S0002914905005874, Received Oct. 25, 2004, Accepted Feb. 28, 2005, Available online May 10, 2005.
Pike NB, Flushing out the role of GPR109A (HM74V) in the clinical efficacy of nicotinic acid, J. Clin. Invest, 115:3400-3403, (Dec. 2005); https://www.jci.org/articles/view/27160, First published Dec. 1, 2005.
Plusepa® Product brochure "Super Critically" Different from Other Omega-3 Fish Oil Supplements for Depression and ADHD, by Minami Nutrition (Apr. 2009, pp. 1-6).
Pocock et al., A Score for predicting risk otdeath from cardiovascular disease in adults with raised blood pressure, based on individual patent data from randomised controlled trials, British Medical Journal, Jul. 14, 2001, vol. 3223, pp. 75-81.
Poirier, "Obesity and Cardiovascular Disease: Pathophysiology, Evaluation, and Effect of Weight Loss," Circulation, Feb. 14, 2006;113(6):898-918. Epub Dec. 27, 2005.

Pollin TI, Damcott CM, Shen H, et al. A null mutation in human APOC3 confers a favorable plasma lipid profile and apparent cardioprotection. Science. Dec. 12, 2008;322(5908):1702-1705.
Pownall HJ, et al., Correlation of serum triglyceride and its reduction by ω-3 fatty acids with lipid transfer activity and the neutral lipid compositions of high-density and low-density lipoproteins, Atherosclerosis 143:285-297 (Apr. 1999); https://www.sciencedirect.com/science/article/abs/pii/S0021915098003013, Received Feb. 9, 1998, Revised Sep. 8, 1998, Accepted Nov. 6, 1998, Available online Mar. 18, 1999.
Press Release: Amarin Corporation Says Huntington's Diease Drug Failed in Trials, http://www.fiercebiotech.com/node/6607/print (Apr. 24, 2007) (Printed on Aug. 22, 2008)(12 pages).
Pritchard KA, Ackerman AW, et al., Native low-density lipoprotein induces endothelial nitric oxide synthase dysfunction: Role of heat shock protein 90 and caveolin-1. Free Radic. Biol. Med. Jul. 2002;33:52-62; https://www.sciencedirect.com/science/article/abs/pii/S0891584902008511, Received Jan. 28, 2002, Accepted Mar. 20, 2002 Available online Jun. 19, 2002.
Pritchard KA, Groszek L, et al., Native low-density lipoprotein increases endothelial cell nitric oxide synthase generation of superoxide anion. Circ. Res. Sep. 1995;77:510-518; https://www.ahajournals.org/doi/full/10.1161/01.res.77.3.510, Manuscript received Sep. 26, 1994, Manuscript accepted May 8, 1995, Originally published Sep. 1, 1995.
Puri B, et al., "Sustained remission of positive and negative symptoms of schizophrenia following treatment with eicosapentaenoic acid," Archives of General Psychiatry, No. 55, pp. 188-189, (Feb. 1998); https://jamanetwork.com/journals/jamapsychiatry/article-abstract/190490.
Puri B, et al., "Eicosapentaenoic Acid in Treatment-Resistant Depression Associated with Symptom Remission, Structural Brain Changes and Reduced Neuronal Phospholipid Turnover," Int J Clinical Practice, 55:560-563 (Oct. 2001); https://europepmc.org/article/med/11695079/reload=0 Sep. 30, 2001.
Puri et al., "Reduction in Cerebral Atrophy/fitssociated with Ethyl-eicosapentaenoic Acid Treatment in Patients with Huntington's Disease," Journ. Int'l. Med. Research, 36:896-905 (Oct. 1, 2008).
Puri, BK, et al., "Ethyl-EPA in Huntington Disease: A Double-Blind, Randomized, Placebo-Controlled Trial," Neurology, 65:286-292, (Jul. 26, 2005).
Qi K, et al., Omega-3 fatty acid containing diets decrease plasma triglyceride concentrations in mice by reducing endogenous triglyceride synthesis and enhancing the blood clearance of triglyceride-rich particles, Clinical Nutrition 27(8):424-430 (Jun. 2008/epub Mar. 24, 2008).
Rader, Lipid Disorders, in Eric J. Topol (ed.)Textbook of Cardiovascular Medicine pp. 55-75 (2007) [chapter of book].
Rahimy M, et al., Effect of tolterodine on the anticoagulant actions and pharmacokinetics of single-dose warfarin in healthy volunteers. Arzneimittelforschung 2002 52 (12): 890-5; https://www.thieme-connect.com/products/ejournals/abstract/10.1055/s-0031-1299986, Publication date: Dec. 26, 2011 (online).
Raitt MH, et al., "Fish oil supplementation and risk of ventricular tachycardia and ventricular fibrillation in patients with implantable defibrillators—a randomized controlled trial." JAMA. 29(23):2884-2891 (Jun. 15, 2005).
Rambjor GS, et al., "Elcosapentaenoic Acid is Primarily Responsible for Hypotrigylceridemic Effect of Fish Oil in Humans", Fatty Acids and Lipids from Cell Biology to Human Disease: Proceedings of the 2nd international Congress of the ISSFAL (International Society for the Study of Fatty Acids and Lipids, AOCS Press, 31:S-45-S-49, (Mar. 1, 1996).
Randomised trial of cholesterol lowering in 4444 patients with coronary heart disease, The Scandinavian Simvastatin Survival Study, Lancet. 344: 1383-1389 (1994); https://www.sciencedirect.com/science/article/abs/pii/S0140673694905665, Nov. 19, 1994. Available online Sep. 22, 2003.
Rao MN, et al., Lack of effect of sucralfate on the absorption and pharmacokinetics of rosiglitazone. J. Clin. Pharmacol. Jun. 2002;42:670-675; https://accp1.onlinelibrary.wiley.com/doi/abs/10.1177/

(56) References Cited

OTHER PUBLICATIONS

00970002042006010, Revised version accepted Feb. 18, 2002. Version of Record online: Mar. 8, 2013 First published: Mar. 8, 2013.

Rauch B, et al., OMEGA, a randomized, placebo-controlled trial to test the effect of highly purified omega-3 fatty acids on top of modern guideline-adjusted therapy after myocardial infarction, Circulation. Nov. 23, 2010 (epub Nov. 8, 2010); 122:2152-2159.

Rees DD, et al., The role of endothelium-derived nitric oxide in the regulation of blood pressure. Proc. Natl. Acad. Sci. USA. May 1989;86:3375-3378; https://www.ahajournalsorg/dol/full/10.1161/01.res.87.12.1108, Manuscript received Oct. 3, 2000. Manuscript accepted Oct. 19, 2000, Originally published Dec. 8, 2000.

Reich, "Formulation and physical properties of soft capsules," Pharmaceutical capsules; (2004) Chapter 11:201-212; http://www.pharmpress.com/files/docs/Chap%20t1.pdf, Book chapter from Pharmaceutical Capsules, Pharmaceutical Press, London (2004).

Reiffel JA, et al., "Antiarrhythmic effects of omega-3 fatty acids." Am J Cardiol 98:50i-60i (Aug. 21, 2006/epub May 26, 2006).

Reiner Z, et al., ESC/EAS Guidelines for the management of dyslipidaemias: the Task Force for the management of dyslipidaemias of the European Society of Cardiology (ESC) and the European Atherosclerosis Society (EAS). Eur. Heart J. Jul. 2011(epub Jun. 28, 2011); 32:1769-1818.

Richter WO, "Hypertriglyceridamie: Ein klinischer-Leitfaden," Wissenschaftliche Verlagsgesellschaft mbH Stuttgart, front page to p. V, pp. 2 to 55, 64 to 85, 90 to 97 (2008) (with English Summary).

Ridker PM, et al., Antiinflammatory Therapy with canakinumab for atherosclerotic disease, N Engl J Med 377(12):1119-31 (publication date Sep. 21, 2017; epublication date Aug. 27, 2017).

Ridker, "C-Reactive Protein : A Simple Test to Help Predict Risk of Heart Attack and Stroke", Circulation: Journal of the American Heart Association, Sep. 23, 2003, 108, e81-e85.

Riediger ND, et al., "A systemic review of the roles of n-3 fatty acids in health and disease." J Am Diet Assoc. 109:668-679. (Apr. 2009); https://www.sciencedirect.com/science/article/abs/pii/S0002822308023353, Accepted Oct. 3, 2008, Available online Mar. 26, 2009.

Rifai, High-Sensitivity C-Reactive Protein: A Novel and Promising Marker of Coronary Heart Diseas, Clinical Chemistry, Mar. 2001, 47(3), 403-411; https://academic.oup.com/clinchem/article/47/3/403/5639279, Published: Mar. 1, 2001.

Risé P, et al., Effects of simvastatin on the metabolism of polyunsaturated fatty acids and on glycerolipid, cholesterol, and de novo lipid synthesis in THP-1 cells, J. Lipid Res. 38:1299-1307 (Jul. 1997); https://www.jlr.org/content/38/7/1299.short.

Risk and Prevention Study Collaborative Group, Roncaglioni MC, Tombesi M, et al. n-3 fatty acids in patients with multiple cardiovascular risk factors. N Engl J Med., May 9, 2013;368(19):1800-8.

Rissanen et al., "Fish Oil-Derived Fatty Acids, Docosahexaenoic Acid and Docosapentaenoic Acid, and the Risk of Acute Coronary Events The Kuopio Ischaemic Heart Disease Risk Factor Study," Circulation. (Nov. 28, 2000)(102):2677-2679 doi:10.1161/01.CIR.102.22.2677.

Rizzo M, et al., Low-density lipoprotein size and cardiovascular risk assessment. Q. J. Med. Jan. 2006; 99(1): 1-14; https://academic.oup.com/gjmed/article/99/1/1/1523832, Published Jan. 1, 2006.

Roach PD, et al., "The effects of dietary fish oil on hepatic high density and low density lipoprotein receptor activities in the rat." FEBS Lett., 222: 159-162 (Sep. 28, 1987).

Robinson JG, et al., "Meta-analysis of the relationship between non-high-density lipoprotein cholesterol reduction and coronary heart risk." J Am Coll Cardiol., 53: 316-322 (Jan. 27, 2009).

Roche HM, et al., "Effect of long-chain n-3 polyunsaturated fatty acids on fasting and postprandial triacylglycerol metabolism." Am J Clin Nutr 71:232S-7S (Jan. 2000); https://academic.oup.com/ajcn/artlcle/71/1/232s/4729393, Published: Jan. 1, 2000.

Roche HM, et al., "Long-chain n-3 polyunsaturated fatty acids and triacylglycerol metabolism in the postprandial state." Lipids 34: S259-S265 (1999); https://link.springer.com/article/10.1007/BF02562313, Published Jan. 1999.

Rodriguez Y, et al., Long-chain ω6 polyunsaturated fatty acids in erythrocyte phospholipids are associated with insulin resistance in non-obese type 2 diabetics, Clinica Chimica Acta 354:195-199 (Apr. 2005); https://www.sciencedirect.com/science/article/abs/pii/s0009898104005571, Received Sep. 17, 2004, Revised Nov. 12, 2004, Accepted Nov. 12, 2004, Available online Jan. 11, 2005.

Roe MT, et al., Prasugrel versus clopidogrel for acute coronary syndromes without revascularization, Trilogy ACS Investigators, N Engl J Med. 367(14):1297-1309 (publication date Oct. 4, 2012; epublication Aug. 25, 2012).

Rogers PJ, "No effect of n-3 long-chain polyunsaturated fatty acid (EPA and DHA) supplementation on depressed mood and cognitive function: a randomised controlled trial" British Journal of Nutrition, 99:421-431, (Feb. 2008/epub Oct. 24, 2007).

Rost KL, et al., Nonlinear kinetics after high-dose omeprazole caused by saturation of genetically variable CYP2C19. Hepatology Jun. 1996 23 (6): 1491-7; https://aasldpubs.onlinelibrary.wiley.com/doi/abs/10.1002/hep.510230628. First published: Jun. 1996.

Rubins HB, et al., "Distribution of lipids in 8,500 men with coronary artery disease: Department of Veterans Affairs HDL intervention Trial Study Group," Am. J. Cardiol, 75:1196-1201, (Jun. 15, 1995).

Rubins HB, et al., "Gemfibrozil for the secondary prevention of coronary heart disease in men with low levels of high-density lipoprotein cholesterol: Veterans Affairs HDL-C Intervention Trial Stud Group," N. Eng. J. Med., 341:410-418, (Aug. 5, 1999).

Ruiz-Narváez EA, et al., Abdominal obesity and hyperglycemia mask the effect of a common APOC3 haplotype on the risk of myocardial infarction, Am J Clin Nutr 87:1932-8 (Jun. 2008); https://academic.oup.com/ajcn/article/87/6/1932/4633423, Received: Nov. 2, 2007. Accepted: Jan. 20, 2008. Published: Jun. 1, 2008.

Ruocco MJ, et al., Interaction of cholesterol with galactocerebroside and galactocerebroside phosphatidylcholine bilayer membranes. Biophys. J. Dec. 1984; 46:695-707; https://www.ncbi.nlm.nih.gov/pmc/articles/PMC1435096/.

Rupp, "Omega-3-Fettsauren in der Sekundarpravention nach Myokardinfarkt," Clin. Res. Cardiol., vol. 95:Suppl. 6, Vi/12/-V1-16 (2006)(with English summary); https://link.springer.com/article/10.1007/s00392-006-1803-7, Published Sep. 2006.

Rustan AC, et al., Eicosapentaenoic acid inhibits cholesterol esterification in cultured parenchymal cells and isolated microsomes from rat liver, J. Bio. Chem. 263(17):8126-32 (Jun. 15, 1988).

Rustan AC, et al., Eicosapentaenoic acid reduces hepatic synthesis and secretion of triacylglycerol by decreasing the activity of acyl-coenzyme A:1,2-diacylglycerol acyltransferase, J. Lipid Res. 29:1417-1426 (Nov. 1988); https://www.jlr.org/content/29/11/1417.short, Nov. 1988.

Rustan AC, et al., Postprandial decrease in plasma unesterified fatty acids during n-3 fatty acid feeding is not caused by accumulation of fatty acids in adipose tissue, Biochimica et Bioghysica Acta 1390. 245-25 (Feb. 23, 1998).

Ryan, AM, et al., "Enteral nutrition enriched with eicosapentaenoic acid (EPA) preserves lean body mass following esophageal cancer surgery: results of a double-blinded randomized controlled trial." Ann Surg 249:355-363 (Mar. 2009); https://journals.lww.com/annalsofsurgery/Abstract/2009/03000/Enteral_Nutrition_Enriched_With_Eicosapentaenoic.1.aspx, Originally published Mar. 2009.

Ryan, AS, et al., "Clinical overview of algal-docosahexaenoic acid: effects on triglyceride levels and other cardiovascular risk factors." Am J Ther., 16:183-192 (Mar./Apr. 2009); https://journals.lww.com/americantherapeutics/Abstract/2009/03000/Clinical_Overview_of_Algal_Docosahexaenoic_Acid_.13.aspx.

Sacks, Frank M, The apolipoprotein story, Atherosclerosis Supplements, 23-27 (Aug. 2006/epub Jul. 5, 2006).

Saito et al., "Effects of Ethyl Eicosapentaenoate (EPA-E), Clopidogrel, and Their Combination on Platelet Aggregation and Bleeding Time;" Japanese Pharmacology & Therapeutics, Feb. 20, 2007 (epub Jan. 2007), vol. 35, No. 2, pp. 179-185 (English abstract only).

Saito et al., "Effects of EPA on coronary artery disease in hypercholesterolemic patients with multiple risk factors: Sub-

(56) References Cited

OTHER PUBLICATIONS analysis of primary prevention cases from the Japan EPA Lipid intervention Study (JELIS)," Atherosclerosis, 200:135-140 (Sep. 2008/epub Jun. 19, 2008).
Saito et al., "Results of Clinical Usage of Improved Formulation (MND-21S) Epadel Capsule 300 with Respect to Hyperlipidemia," 26(12) Jpn. Pharmacol. Ther. 2047-62 (1998) (with English abstract).
Saito, J, et al., "Mechanisms of enhanced production of PGI2 in cultured rat vascular smooth muscle cells enriched with eicosapentaenoic acid." Atherosclerosis 131: 219-228 (Jun. 1997); https://www.sciencedirect.com/science/article/abs/pii/S0021915097000488 , Received Jul. 24, 1996, Revised Feb. 12, 1997, Accepted Feb. 27, 1997, Available online Sep. 9, 1997.
Sampath H, et al., Role of stearoyl-CoA desaturasieiin human metabolic disease, Future Lipidol. 2008;3:2,163-73; https://www.tandfonline.com/doi/abs/10.2217/17460875.3.2.163, Published online Jan. 18, 2017.
Sampath H, et al., The Role of stearoyl-CoA desaturase in obesity, insulin resistance, and inflammation, Ann. NY. Acad. Sci. Dec. 2011 ; 1243:4 7-53; https://nyaspubs.onlinelibrary.wiley.com/doi/full/10.1111/j.1749-6632.2011.06303.x, First published: Dec. 23, 2011.
Samuels, Martin A, et al., Huntington's Disease, Office Practice of Neurology, (122):654-655, (1996); Published by Churchill Livingstone, Edinburgh.
Sanders T.A., et al., "Influence of an algal triacylglycerol containing docosahexaenoic acid (22:6n-3) and docosapentaenoic acid (22:5n-6) on cardiovascular risk factors in healthy men and women," British Journal of Nutrition, 95, 525-531 (Mar. 2006); https://www.cambridge.org/core/journals/british-journal-of-nutrition/article/influence-of-an-algal-triacylglycerol-containing-docosahexaenoic-acid-226n3-and-docosapentaenoic-acid-225n6-on-cardiovascular-risk-factors-in-healthy-men-and-women/8206943D80EE8C7EA5E61FAFF6C13270, Published online by Cambridge University Press Mar. 8, 2007.
Sanders, A, et al., Influence of n-3 fatty acids on blood lipids in normal subjects, Journal of Internal Medicine. 225:99-104,(1989); https://onlinelibrary.wiley.com/doi/abs/10.1111/j.1365-2796.1989.tb01442.x, First published Dec. 1989: Version of Record online: Feb. 13, 2014.
Sanders, T.A., et al., "Effect of varying the ratio of n-6 to n-3 fatty acids by increasing the dietary intake of α-linolenic acid, eicosapentaenoic and docosahexaenoic acid, or both on fibrinogen and clotting factors VII and XII in persons aged 45-70 y: the OPTILIP Study." Am J Clin Nutr 84:513-22 (Sep. 2006).
Sanders, T.A., et al., "Triglyceride-lowering effect of marine polyunsaturates in patients with hypertriglyceridemia." Arterioscler. Thromb. Vasc. Biol. 5:459-465 (Sep./Oct. 1985); https://academic.oup.com/ajcn/article/84/3/513/4648804, Received Nov. 14, 2005, Accepted May 11, 2006, Published Dec. 1, 2006.
Sarwar N, et al., Triglycerides and the risk of coronary heafdisease: 10,158 incident cases among 262,525 participants in 29 Western prospective studies. Circulation 115:450-458, Jan. 30, 2007/epub Dec. 26, 2006.
Sasaki J, et al., Administration of highly purified eicosapentaenoic acid to stain-treated diabetic patients further improves vascular function. Endocrine J. Jan. 27, 2012; 59(4):297-304.
Sasaki J, et al., Relationship between coronary artery disease and non-HDL-C, and effect of highly purified EPA on the risk of coronary artery disease in hypercholesteroiemic patients treated with statins: sub-analysis of the Japan EPA Lipid Intervention Study (JELIS). J. Atheroscler. Thromb. Dec. 17, 2012;19:194-204.
Sasaki YF, et al., Bio-anticlastogenic effects of unsaturated fatty acids included in fish oil—docosahexaenoic acid, docosapentaenoic acid, and eicosapentaenoic acid—in cultured Chinese hamster cells, Mutation Research, 320: 9-22 (Jan. 1994); https://www.sciencedirect.com/science/article/abs/pii/0165121894900558, Received Mar. 9, 1993, Revised Jun. 22, 1993, Accepted Jun. 29, 1993, Available online Nov. 18, 2002.
Sato et al., General Pharmacological Studies on 5 8 11 14 17 Eicosapentaenoic Acid Ethyl Ester EPA-E, Folia Pharmacol JPN, 94 (1), 35-47. cited by other (Jul. 1989) (with English abstract); htttgs://europepmc.org/articie/med/2551801, Jun. 30, 1989.
Sato, Effects of Highly Purified Ethyl All-cis-5,8,11,14,17-icosapentaenoate (EPA-E) on Rabbit Platelets, Biol. Pharm. Bull., 16(4)362-367 (Apr. 1993); https://www.jstage.jst.go.jp/article/bpb1993/16/4/16_4_362/_article/-char/ja/.
Satoh et al., "Highly purified eicosapentaenoic acid reduces cardio-ankle vascular index in association with decreased serum amyloid A-LDL in metabolic syndrome," Hypertension Research (Nov. 2009/epub Sep. 18, 2009) (32):1004-1008.
Satoh, N., et al., "Purified eicosapentaenoic acid reduces small dense LDL, remnant lipoprotein particles, and C-reactive protein in metabolic syndrome." Diabetes Care, 30(1): 144-146 (Jan. 2007); https://care.diabetesjournals.org/content/30/1/144.short.
Satoh-Asahara N, et al., Highly purified eicosapentaenoic acid increases interieukia-10 levels of peripheral blood monocytes in obese patients with dyslipidemia, Diabetes Care. Dec. 2012/epub Aug. 21, 2012; 35(12):2631-2639.
Schaefer EJ, et al., "Effects of eicosapentaenoic acid, docosahexaenoic acid, and olive oil on cardiovascular disease risk factors [abstract 20007]." Circulation, 122:A20007 (2010) (Abstract only); https://www.ahajournals.org/doi/abs/10.1161/circ.122.suppl_21.a20007, Originally published Mar. 23, Mar 2018.
Schectman G, et al., "Dietary fish oil decreases low-density-lipoprotein clearance in nonhuman primates." Am J Clin Nutr., 64:215-221 (Aug. 1996); htttgs://academic.oup.com/ajcn/article/64/2/215/4650420, Published: Aug. 1, 1996.
Schectman G, et al., "Heterogeneity of Low Density Lipoprotein Responses to Fish-Oil Supplementation in Hypertriglyceridemic Subjects." Arterioscler. Thromb. Vasc. Biol. 9:345-354 (May/Jun. 1989); https://www.ahajournals.org/doi/abs/10.1161/01.ATV.9.3.345, Originally published May 1, 1989.
Schectman G, et al., Drug therapy for hypercholesterolemia in patients with cardiovascular disease: factors limiting achievement of lipid goals, Am. J. Med., 100:197-204, (Feb. 1996); https://www.sciencedirect.com/science/article/abs/pii/S0002934397894594 , Received Feb. 2, 1995, Accepted Jul. 21, 1995, Available online Apr. 3, 2001.
Schmidt EB, et al., Lipoprotein-associated phospholipase A2 concentrations in plasma are associated with the extent of coronary artery disease and correlate to adipose tissue levels of marine n-3 fatty acids, Atherosclerosis 196: 420-424 (Jan. 2008); https://www.sciencedirect.com/science/article/abs/pii/S0021915006007015 , Received Aug. 21, 2006, Revised Nov. 15, 2006, Accepted Nov. 17, 2006, Available online Dec. 8, 2006.
Schmitz PG, et al., Prophylaxis of hemodialysis graft thrombosis with fish oil: double-blind, randomized, prospective trial. J. Am. Soc. Nephrol. Jan. 2002 13 (1): 184-90; https://jasn.asnjournals.org/content/13/1/184.short.
Schmitz, G, et al., "The opposing effects of n-3 and n-6 fatty acids." Progress in Lipid Research, 47:147-155 (Mar. 2008/epub Dec. 27, 2007).
Schreiner et al., Lipoprotein[a] as a Risk Factor for Preclinical Atherosclerosis, 13 Atherosclerosis, Thrombosis & Vascular Biology 6: 826-833 (1993); https://www.ahajournals.org/doi/abs/10.1161/01.ATV.13.6.826; Originally published Jun. 1, 1993.
Schuirmann, DJ, A comparison of the two one-sided tests procedure and the power approach for assessing the equivalence of average bioavailability, J. Pharmacokinet. Biopharm. 15(6), 657-680 (Dec. 1987); https://link.springer.com/article/10.1007%2FBF01068419, Received Mar. 2, 1987, Revised Sep. 22, 1987, Published Dec. 1, 1987.
Schunkert H, König IR, Kathiresan S, et al. Large-scale association analysis identifies 13 new susceptibility loci for coronary artery disease. Nat Genet. Mar. 6, 2011;43(4):333-8.
Schwartz GG, Bessac L, Berdan LG, et al. Effect of alirocumab, a monoclonal antibody to PCSK9, on long-term cardiovascular outcomes following acute coronary syndromes: rationale and design of the Odyssey outcomes trial. Am Heart J 168(5):682-9 (publication date Nov. 2014, epublication date Aug. 7, 2017).
Schwarz S., et al., "Lycopene inhibits disease progression in patients with benign prostate hyperplasia." J. Nutr. 138: 49-53 (Jan. 2008);

(56) References Cited

OTHER PUBLICATIONS https://academic.oup.com/jn/article/138/1/49/4665062, Received Apr. 12, 2007, Revision received May 19, 2007, Accepted Oct. 22, 2007, Published Jan. 1, 2008.

Schwellenbach et al., The Triglyceride-Lowering Effects of a Modest Dose of Docosahexaenoic Acid Alone Versus in Combination with Low Dose Eicosapentaenoic Acid in Patients with Coronary Artery Disease and Elevated Triglycerides, J. Am. Coll. Nutr. 25(6):480-485 (Dec. 2006); https://www.tandfonline.com/doi/abs/10.1080/07315724.2006.10719562, Received Jan. 4, 2006, Accepted Apr. 18, 2006, Published online: Jun. 18, 2013.

Segrest et al., Structure of Apolipoprotein B-100 in Low Density Lipoproteins, J. Lipid Res. 42(9):1346-1367 (Sep. 2001); https://www.jlr.org/content/42/9/1346.short.

Self-Medlin Y, Byun J, Jacob RF, Mizuno Y, Mason RP. Glucose promotes membrane cholesterol crystalline domain formation by lipid peroxidation. Biochim. Biophys. Acta. Jun. 2009/epub Apr. 17, 2009; 1788(6): 1398-1403.

Serhan C, et al., Resolving inflammation: dual anti-inflammatory and pro-resolution lipid mediators. Nat Rev Immunol. May 2008; 8:3449-361; https://www.nature.com/articles/nri2294/, Published May 2008.

Serhan CN, et al., Resolvins: A family of bioactive products of omega-3 fatty acid transformation circuits initiated by aspirin treatment that counter proinflammation signals, J. Exp. Med. 196:1025-1037 (Oct. 21, 2002).

Sevanian A, et al., Lipid peroxidation in membranes and low-density lipoproteins: similarities and differences. Free Radic. Biol. Med, Aug. 2000;29(3-4):306-311; https://www.sciencedirect.com/science/article/abs/pii/SO891584900003427, Received May 10, 2000, Accepted May 18, 2000, Available online Sep. 25, 2000.

Shah S, et al., "Eicosapentaenoic Acid (EPA) as an Adjunct in the Treatment of Schizophrenia", Schizophrenia Research, vol. 29, No. 1/02 (1998); https://www.infona.pl/resource/bwmeta1.element.elsevier-554c669f-0994-3a2f-b34d-0a00044944be.

Shan Z, et al., "A combination study of spin-trapping, LC/ESR and LC/MS on carbon-centred radicals formed from lipoxygenase-catalysed peroxidation of eicosapentaenoic acid." Free Radical Research, 43(1):13-27 (Jan. 2009); https://www.tandfonline.com/doi/abs/10.1080/10715760802567606, Received Apr. 14, 2008, Published online Aug. 6, 2009.

Shearer et al., "Red Blood Cell Fatty Acid Patters and Acute Coronary Syndrome," PLoS One 4(5): e5444, publ. May 6, 2009 (doi:10.1371/journal/pone.0005444).

Shen, W., et al., "Influence of Omega-3 Fatty Acids Intake on Human Responsiveness to Ambient Air Pollution Exposure", Apr. 1, 2017, The FASEB Journal; retrieved from Internet: URL://https://www.fasebj.org/doi/abs/10.1096/fasebj.31.1_supplement.971.2; [retrieved on Jan. 7, 2020].

Sherratt SCR, Mason RP. Eioosapentaenoic acid and docosahexaenoic acid have distinct membrane locations and lipid interactions as determined by X-ray diffraction. Chem Phys Lipids 212:73-9 (publication date May 2018, epublication date Jan. 31, 2018).

Shimizu et al., "Effects of Highly Purified Eicosapentaenoic Acid on Erythrocyte Fatty Acid Composition and Leukocyte and Colonic Mucosa Leukotriene B4 Production in Children with Ulcerative Colitis," J. Pediatr. Gastroenterol. Nutr., vol. 37, No. 5, pp. 581-585 (Nov. 2003); https://journals.lww.com/jpgn/fulltext/2003/11000/effects_of_highiy_purified_eicosapentaenoic_acid.15.aspx.

Shimizu H, et al., "Long-term effect of eicosapentaenoic acid ethyl (EPA-E) on albuminuria of non-insulin dependent diabetic patients." Diabetes Research and Clinical Practice 28: 35-40 (Apr. 1995); https://www.sciencedirect.com/science/article/abs/pii/016882279501056J, Received Nov. 29, 1994, Revised Mar. 6, 1995, Accepted Apr. 5, 1995, Available online Feb. 4, 2000.

Shimokawa H, et al., Loss of endothelial pertussis toxin-sensitive g protein function in atherosclerotic porcine coronary arteries. Circulation. Feb. 1991;83:652-660; https://www.ahajournals.org/doi/abs/10.1161/01.CIR.83.2.652, Originally published Feb. 1, 1991.

Shinozaki K, et al., The long-term effect of Eicosapentaenoic acid on serum levels of lipoprotein (a) and lipids in patients with vascular disease, J Atheroscler Thromb. 2(2):207-9 (1996); https://www.jstage.jst.go.jp/article/jat1994/2/2/2_2_107/_article/-char/ja/.

Shishehbor MH, et al., Statins promote potect systemic antioxidant effects through sgecific inflammatory pathways. Circulation. Jul. 29, 2003;108(4):426-431.

Sicherer et al., "Prevalence of seafood allergy in the United States determined by a random telephone survey," J. Allergy Clin. Immunol., 114(1):159-165 (Jul. 2004); https://www.sciencedirect.com/science/article/abs/pii/S0091674904013296, Received Feb. 27, 2004, Revised Apr. 2, 2004, Accepted Apr. 2, 2004, Available online Jul. 2, 2004.

Sierra S, et al., "Dietary eicosapentaenoic acid and docosahexaenoic acid equally incorporate as decosahexaenoic acid but differ in inflammatory effects." Nutrition 24:245-254 (Mar. 2008); https://www.sciencedirect.com/science/article/abs/pii/S0899900707003504, Received May 8, 2007, Accepted Nov. 27, 2007, Available online Feb. 5, 2008.

Signori S, et al., "Administration of omega-3 fatty acids and Raloxifene to women at high risk of breast cancer: interim feasibility and biomarkers analysis from a clinical trial," European Journ of Clin. Nutr., 66, 878-884 (gublished online Jun. 6, 2012).

Silvers Karen M, et al., "Randomised double-blind placebo-controlled trial of fish oil in the treatment of depression", Prostagandins, Leukotrienes and Essential Fatty Acids, 72:211-218, (Mar. 2005); https://www.sciencedirect.com/science/article/abs/pii/S0952327804001905, Received Jul. 23, 2004, Accepted Nov. 21, 2004, Available online Jan. 1, 2005.

Simoens CM, et al., Inclusion of 10% fish oil in mixed medium-chain triacylglycerol-long chain triacylglycerol emulsions increases plasma triacylglycerol clearance and induces rapid eicosapentaenoic acid (20:5n-3) incorporation into blood cell phospholipids, Am J Clin Nutr 88: 282-8 (Aug. 2008); https://academic.oup.com/ajcn/article/88/2/282/4649896, Received Dec. 10, 2007, Accepted Apr. 30, 2008, Published Aug. 1, 2008.

Simon Joel A, et al., "Serum Fatty Acids and the Risk of Coronary Heart Disease", American Journal of Epidemiology, 142(5):469-476, (Sep. 1, 1995).

Simopolous, The Importance of the Omega-6/Omega-3 Fatty Acid Ratio in Cardiovascular Disease and Other Chronic Diseases, Exp. Biol. Med, 233:674-688 (Jun. 1, 2008)(availabie online Jun. 1, 2008); https://academic.oup.com/ajcn/article-abstract/54/3/438/4694393, Received Feb. 27, 1991, Accepted Mar. 20, 1991, Published Sep. 1, 1991.

Simopoulos, Omega-3 fatty acids in health and disease and in growth and development, Am. J. Clin. Nutr. 54:438-63 (Sep. 1991); https://academic.oup.com/ajcn/article-abstract/54/3/438/4694393, Received Feb. 27, 1991, Accepted Mar. 20, 1991, Published: Sep. 1, 1991.

Singer Peter, "Fluvastatin plus fish oil are more effective on cardiovascular risk factors than fluvastatin alone," Letter to the Editor, Prostaglandinis, Leukotrienes and Essential Fatty Acids, vol. 72, pp. 379-380 (May 2005).

Singh RB, et al., Randomized, double-blind, placebo-controlled trial of fish oil and mustard oil in patients with suspected acute myocardial infarction: the Indian experiment of infarct survival—4, Cardiovascular Drugs and Therapy 11:485-491 (Jul. 1997); https://link.springer.com/article/10.1023/A:1007757724505, Published Jul. 1997.

Sirtori CR, et al., One-year treatment with ethyl esters of n-3 fatty acids in patients with hypertriglyceridemia and glucose intolerance—Reduced triglyceridemia, total cholesterol and increased HDL-C, Atherosclerosis 137: 419-427 (Apr. 1998); https://www.sciencedirect.com/science/article/abs/pii/S0021915097002980, Received Jun. 17, 1997, Revised Nov. 21, 1997, Accepted Nov. 27, 1997, Available online Jun. 15, 1998.

Siscovick et al., "Dietary Intake and Cell Membrane levels of Long-chain N-3 Polyunsaturated Fatty Acids and the Risk of Primary Cardiac Arrest", JAMA, vol. 274, No. 17, Nov. 1, 1995, pp. 1363-1367, XP008041164.

Skinner JS, et al., on behalf of the Guideline Development Group, Secondary prevention for patients following a myocardial infarc-

(56) References Cited

OTHER PUBLICATIONS tion; summary of NICE guidance. Heart, 93:862-864 (Jul. 2007); https://heart.bmj.com/content/93/7/862.short, Published Online First: Jun. 14, 2007.

Slides for the Oct. 16, 2013 Meeting of the Endocrinologic and Metabolic Drugs Advisory Committee, (158 pages).

Smith et al., Pharmacokinetics and Pharmacodynamics of Epoetin Delta in Two Studies in Health Volunteers and Two Studies in Patients with Chronic Kidney Disease, Clinical Therapeutics/vol. 29, pp. 1368-1380 (Jul. 2007); https://www.sciencedirect.com/science/article/abs/pii/S0149291807002068, Received May 16, 2007, Available online Sep. 4, 2007.

Sniderman A, et al., Update on the detection and treatment of atherogenic low-density lipoproteins. Curr. Opin. Endocrinol. Diabetes Obes. Apr. 20, 2013;20:140-147.

Sohma R, et al., Protective effect of n-3 polyunsaturated fatty acid on primary culture of rat hepatocytes without glycemic alterations, Journal of Gastroenterology and Hepatology 22: 1965-1970 (Nov. 2007); https://onlinelibrary.wiley.com/doi/abs/10.1111/j.1440-1746.2006.04684.x , First published: Oct. 2, 2007.

Spector AA, Arachidonic acid cytochrome P450 epoxygenase pathway, Journal of Lipid Research, 50: S52-S56 (2009) (published online on Oct. 23, 2008).

Spector AA, et al., Epoxyeicosatrienoic acids (EETs): metabolism and biochemical function, Progress in Lipid Research 43: 55-90 (Jan. 2004); https://www.sciencedirect.com/science/article/abs/pii/S0163782703000493, Available online Aug. 27, 2003.

Springer TA, Traffic signals for lymphocyte recirculation and leukocyte emigration: The multistep paradigm, Cell, 76: 301-314 (Jan. 28, 1994).

Squires RW, et al., "Low-dose, time release nicotinic acid: effects in selected patients with low concentrations of high density lipoprotein cholesterol", Mayo Clinic Proc., 67:855-860, (Sep. 1992); https://www.sciencedirect.com/science/article/abs/pii/S0025619612608246, Available online Dec. 13, 2012.

Srinivas et al., Controlled release of lysozyme from succinylated gelatin microspheres, J. Biomater. Sci., Polymer Ed., vol. 12(2):137-148 (2001); https://www.tandfonline.com/doi/abs/10.1163/156856201750180870, Published online: Apr. 2, 2012.

Stalenhoef AF, et al., "The effect of concentrated n-3 fatty acids versus gemfibrozil on plasma lipoproteins, low density lipoprotein heterogeneity and oxidizability in patients with hypertriglyceridemia." Atherosclerosis 153: 129-138 (Nov. 2000); https://www.sciencedirect.com/science/article/abs/pii/S0021915000003816 , Received Apr. 23, 1999, Revised Dec. 6, 1999, Accepted Jan. 7, 2000, Available online Oct. 27, 2000.

Stampfer MJ, et al., A prospective study of triglyceride level, lowdensity lipoprotein particle diameter, and risk of myocardial infarction. JAMA. Sep. 1996;276:882-888; https://jamanetwork.com/journals/jama/article-abstract/407965, Sep. 18, 1996.

Stancu et al., Statins: Mechanism of Action and Effects, *Journal of Cellular and Molecular Medicine* (Oct.-Dec. 2001), 5(4), 378-387; https://onlinelibrary.wiley.com/doi/abs/10.1111/j.1582-4934.2001.tb00172.x , Received Nov. 12, 2001, Accepted Dec. 5, 2001, Issue online May 1, 2007, First published: May 1, 2007.

Stark KB, "The percentage of n-3 highly unsaturated fatty acids in total HUFA as a biomarker for omega-3 fatty acid status in tissues." Lipids 43:45-53 (Jan. 2008/epub Nov. 6, 2007).

Stark KD, et al., "Effect of a fish-oil concentrate on serum lipids in postmenopausal women receiving and not receiving hormone replacement therapy in a placebo-controlled, double-blind trial." Am J Clin Nutr 72:389-94 (Aug. 2000); https://academic.oup.com/ajcn/article/72/2/389/4729436, Received Jul. 2, 1999, Accepted Jan. 31, 2000, Published Aug. 1, 2000.

Stark KD, Holub, B.J., Differential eicosapentaenoic acid elevations and altered cardiovascular disease risk factor responses after supplementation with docosahexaenoic acid in postmenopausal women receiving and not receiving hormone replacement therapy, Am. J. Clin. Nutr., vol. 79, pp. 765-73 (May 2004); https://academic.oup.com/ajcn/article/79/5/765/4690185, Received May 1, 2003, Accepted Oct. 8, 2003, Published May 1, 2004.

Steg PG, et al; REACH Registry Investigators. One-year cardiovascular event rates in outpatients with atherothrombosis. JAMA. 297(11):1197-1206 (publication date May 21, 2007).

Stein et al., "Effect of Statin Therapy on Remnant Lipoprotein Cholesterol Levels in Patients with Combined Hyperlipidemia," Arteriosclerosis, Thrombosis and Vascular Biology, vol. 21, pp. 2026-2031(Dec. 1, 2001).

Steinberg D, Lewis A, Conner Memorial Lecture: Oxidative modification of LDL and atherogenesis. Circulation. Feb. 18, 1997;95(4):1062-1071.

Steinberg D, Witztum JL. Is the oxidative modification hypothesis relevant to human atherosclerosis? Do the antioxidant trials conducted to date refute the hypothesis? Circulation. Apr. 30, 2002;105:2107-2111.

Stepp DW, et al., Native ldl and minimally oxidized ldl differentially regulate superoxide anion in vascular endothelium in situ. Am. J. Physiol. Aug. 2002;283:H750-H759; https://journals.physiology.org/doi/full/10.1152/ajpheart.00029.2002, Received Jan. 15, 2002, Accepted Mar. 18, 2002, Published online Aug. 1, 2002, Published in print Aug. 1, 2002.

Sternbach, "The Glasgow Coma Scale." The Journal of Emergency Medicine, 19(1):67-71 (Feb. 8, 2000).

Stielow et al., "Novel Nox Inhibitor of oxLDL-Induced Reactive Oxygen Species Formation in Human Endothelial Cells," Biochem. Biophys. Res. Comm, 344:200-205 (May 26, 2006/epub Mar. 26, 2006).

Stiles, FDA approves EPA-only omega-3 PUFA capsule for high TG, Jul. 26, 2012, http://www.medscape.com/viewarticle/791268, accessed Dec. 17, 2014 (1 page).

Stitziel N, Stirrups K, Masca N, et al. Supplement to: Coding variation in ANGPTL4, LPL, and SVEP1 and the risk of coronary disease. N Engl J Med. DOI: 10.1056/NEJMoa1507652; Mar. 24, 2016/epub Mar. 2, 2016.

Stojancevic et al., "The impact of farnesoid X receptor activation on intestinal permeability in inflammatory bowel disease," Can. J Gastroenterol. 26(9):631-637 (Sep. 2012); https://www.hindawi.com/journals/cjgh/2012/538452/, Received Jul. 25, 2011. Accepted Dec. 30, 2011.

Stoll Andrew L, et al., "Omega 3 Fatty Acids in Bipolar Disorder", Arch. Gen. Psychiatry, 56:407-412, (May 1999); https://jamanetwork.com/journals/jamapsychiatry/article-abstract/204999 , Accepted for publication Oct. 2, 1998. Presented in part at the 36th Annual Meeting of the American College of Neuropsychopharmacology, Waikoloa, Hawaii, Dec. 10, 1997.

Stone NJ, et al. ACC/AHA Prevention Guideline: 2013 ACC/AHA Guideline on the Treatment of Blood Cholesterol to Reduce Atherosclerotic Cardiovascular Risk in Adults: A Report of the American College of Cardiology/American Heart Association Task Force on Practice Guidelines. erratum in Circulation. Jun. 24, 2014;129:S46-S48.

Su KP, et al., "Omega-3 Fatty Acids in Major Depressive Disorder a Preliminary Double-Blind, Placebo-Controlled Trial", European Neuropsychopharmacology, 13:267-271, (Aug. 2003); https://www.sciencedirect.com/science/article/abs/pii/S0924977X03000324 , Received Oct. 8, 2002, Revised Jan. 28, 2003, Accepted Jan. 28, 2003, Available online Apr. 18, 2003.

Sugiyama et al., A Comparison of the Hypotensive Effects of Eicosapentaenoic Acid Ethyl (EPA) on Three Diseases (Occluded Arteriosclerosis, Hyperlipidemia, and These Two Diseases Combined) P2-504 Abstract, Annual Meeting of the Japanese Society of Pharmaceutical Health Care and Sciences 20:473 (Nov. 2010) (with English translation)(3 pages).

Sugiyama, E., et al., "Eicosapentaenoic acid lowers plasma and liver cholesterol levels in the presence of peroxisome proliferators-activated receptor alpha," Life Sciences, 83:19-28 (Jul. 4, 2008/epub May 1, 2008).

Superko et al., "Lipid Management to Reduce Cardiovascular Risk: A New Strategy is Reguired," Circulation, 117:560-568 (Jan. 29, 2008).

Surette ME, et al., "Dependence on dietary cholesterol for n-3 polyunsaturated fatty acid induced changes in plasma cholesterol in

(56) References Cited

OTHER PUBLICATIONS the Syrian hamster," J Lipid Res., 33:263-271 (Feb. 1992); https://www.jlr.org/content/33/2/263.short.

Surette ME, et al., "Evidence for mechanisms of the hypotriglyceridemic effect of n - 3 polyunsaturated fatty, acids." Biochimica et Biophysic Acta, 1126: 199-205 (Jun. 22, 1992).

Tagawa H, et al., Long-term treatment with eicosapentaenoic acid augments both nitric oxide-mediated and non-nitric oxide-mediated endothelium-dependent forearm vasodilatation in patients with coronary artery disease. J Cardiovasc Pharmacol 33(4):633-40, Apr. 1999; https://journals.lww.com/cardiovascularpharm/Fulltext/1999/04000/Short_Term_Estrogen_Augments_Both_Nitric.17.aspx.

Takaki A, et al., Add-on therapy of epa reduces oxidative stress and inhibits the progression of aortic stiffness in patients with coronary artery disease and statin therapy: A randomized controlled study. J. Atheroscler. Thromb. Jun. 23, 2011;18:857-866.

Takaku et al., Study on the Efficacy and Safety of Ethyl Icosapentate (MND-21) in Treatment of Hyperlipidemia Based on a Long-Term Administration Test, 7 J. Clin. Ther. Med. 191 (1991) (w/English Translation)(27 pages).

Talayero BG, et al., The role of triglycerides in atherosclerosis, Curr. Cardiol. Rep. 2011;13:544-552; https://link.springer.com/article/10.1007%2Fs11886-011-0220-3, Published Oct. 4, 2011.

Tamura et al., Study of the Clinical Usefulness of Ethyl Icosapentate (MND-21) in Long-Term Treatment of Hyperlipaemic Patients, J Clin Thera & Medicines, 7:1817-1834 (1991).

Tanaka et al., "Administration of high dose eicosapentaenoic acid enhances anti-inflammatory properties of high-density lipoprotein in Japanese patients with dyslipidemia," Atherosclerosis, 237(2):577-83 (Dec. 2014); https://www.sciencedirect.com/science/article/abs/pii/S0021915014014440 , Received Jun. 19, 2014, Revised Sep. 22, 2014, Accepted Oct. 14, 2014, Available online Oct. 18, 2014.

Tanaka et al., "Eicosapentaenoic Acid-Enriched High-Density Lipoproteins Exhibit Anti-Atherogenic Properties," Circ. J., doi: 10.1253/circj.CJ-17-0294. [Epub ahead of print] (Jun. 23, 2017)(6 pages).

Tanaka et al., Genome-Wide Association Study of Plasma Polyunsaturated Fatty Acids in the InCHIANTI Study, PLoS Genetics 5(1):1-8 (Jan. 2009); https://journals.plos.org/plosgenetics/article?id=10.1371/journal.pgen.1000338 , Published: Jan. 16, 2009.

Tanaka et al., Suppression of prostaglandin synthesis by arachidonic acid or eicosapentaenoic acid in a macrophage-like cell line, RAW 264.7, treated with LPS, Biol. Pharm. Bull, 22(10):1052-7 (Oct. 1999); https://www.jstage.jst.go.jp/article/bpb1993/22/10/22_10_1052/_article/-char/ja/.

Tanaka, KT, et al., "Reduction in the recurrence of stroke by eicosapentaenoicracid for hypercholesterolemic patients—Subanalysis of the JELIS trial." Stroke, 39(7):2052-8 (Jul. 2008/epub May 1, 2008).

Tatarczyk et al., "Analysis of long-chain ω-3 fatty acid content in fish-oil supplements," Wien Klin Wochenschr, 119/13-14: 417-422 (2007); https://link.springer.com/article/10.1007/s00508-007-0820-5 Received Nov. 21 2006, Accepted Apr. 16, 2007, Issue Date Jul. 2007.

Tatsuno et al., Efficacy and safety of TAK-085 compared with eicosapentaenoic acid in Japanese subjects with hypertrigiyceridemia undergoing lifestyle modification: The omega-3 fatty acids randomized double-blind (ORL) study, J. Clin. Lipid; vol. 7(6), pp. 615-625 (Sep. 12, 2013).

Taylor et al., "Fish allergy: fish and products thereof," Journal Food Science (2004) 69.8 R175-R180; https://onlinelibrary.wiley.com/doi/abs/10.1111/j.1750-3841.2004.tb18022.x#:~:text=All%20species%20of%20fish%20are,occurring%20muscle%20protein%20called%20parvalbumin , Received Feb. 16, 2004, Accepted May 31, 2004, Version of Record Online May 9, 2011.

Taylor, AJ, et al., Arterial Biology for the Investigation of the Treatment Effects of Reducing Cholesterol (ARBITER) 2: a double-blind, placebo-controlled study of extended-release niacin on atherosclerosis progression in secondary prevention patients treated with statins, Circulation, 110:3512-3517, (Dec. 7, 2004/epub Nov. 10, 2004).

Tedgui A, et al., "Anti-inflammatory mechanisms in the vascular wall." Circ. Res. 88:877-887 (May 11, 2001).

Teissier E, et al., Peroxisome proliferator-activated receptor alpha induces NADPH oxidase activity in macrophages, leading to the generation of LDL with PPAR-aipha activation properties. Circ. Res. Dec. 10, 2004/epub Nov. 11, 2004;95(12):1174-1182.

Teramoto T, et al., Diagnosis of atherosclerosis. Executive Summary of the Japan Atherosclerosis Society (JAS) Guidelines for the Diagnosis and Prevention of Atherosclerotic Cardiovascular Diseases in Japan—2012 Version. J Atheroscler Thromb. 2014;21(4):296-8. Electronic publication Dec. 10, 2013.

Terano et al., "Effect of Oral Administration of Highly Purified Eicosapentaenoic Acid on Platelet Function, Blood Viscosity and Red Cell Deformability in Healthy Human Subjects," Atherosclerosis, 46, 321-331 (Mar. 1983); https://www.sciencedirect.com/science/article/abs/pii/0021915083901818, Received Jul. 26, 1982, Revised Oct. 15, 1982, Accepted Oct. 25, 1982, Available online Apr. 14, 2005.

The Lipid, 2003, vol. 14, No. 1, pp. 68-75, in Japanese.

The TG and HDL Working Group of the Exome Sequencing Project, National Heart, Lung, and Blood Institute. Loss-of-function mutations in APOC3, triglycerides, and coronary disease. N Engl J Med. Jul. 3, 2014/epub Jun. 18, 2014; 371(1):222-31.

Theilla M, et al., "A diet enriched in eicosapentaenoic acid, gamma-linolenic acid and antioxidants in the prevention of new pressure ulcer formation in critically ill patients with acute lung injury: A randomized, prospective, controlled study." Clinical Nutrition 26: 752-757 (Dec. 2007/epub Oct. 22, 2007).

Theobald et al., LDL Cholesterol-Raising Effect of Low-Dose Docosahexaenoic Acid in Middle-Aged Men and Women, Am. J. Clin. Nutr. 79:558-63 (Apr. 2004); https://academic.oup.com/ajcn/article/79/4/558/4690135, Received Mar. 7, 2003, Accepted Sep. 22, 2003, Published Apr. 1, 2004.

Thies F, et al., "Association of n-3 polyunsaturated fatty acids with stability of atherosclerotic plaques: a randomised controlled trial." Lancet 361: 477-85 (Feb. 8, 2003).

Thies F, et al., "Dietary supplementation with eicosapentaenoic acid, but not with other long-chain n-3 or n-6 polyunsaturated fatty acids, decreases natural killer cell activity in healthy subjects aged >55 y." Am J Clin Nutr 73:539-48 (Mar. 2001); https://academic.oup.com/ajcn/article/73/3/539/4737356, Received: Mar. 31, 2000. Accepted: Jul. 28, 2000. Published: Mar. 1, 2001.

Third Report of the National Cholesterol Education Program (NCEPP) Expert Panel on Detection, Evaluation, and Treatment of High blood Cholesterol in Adults (Adult Treatment Panel III) May 2001, National Institutes of Health, Publication No. 01-3670.

Third Report of the NCEP Expert Panel on Detection, Evaluation, and Treatment of High Blood Cholesterol in Adults (Adult Treatment Panel III) Final Report, NIH Publication No. 02-5215 Sep. 2002 (220 pages in three parts).

Thomas et al., "Renal Failure—Measuring the Glomeruiar Filtration Rate," Dtsch Arztebl Int., Dec. 18, 2009, 106(51-52); 849-54.

Thomas II et al., "Prostate Cancer Risk in Men with Baseline History of Coronary Artery Disease: Results from the REDUCE Study," Cancer Epidemiology, Biomarkers and Prevention, 21 (4) published online Feb. 7, 2012.

Thorwest M, et al., Dietary fish oil reduces microvascular thrombosis in a porcine experimental model. Thromb. Res. Jul. 2000, 99(2): 203-8; https://www.sciencedirect.com/science/article/abs/pii/S0049384800002334, Received Dec. 13, 1999, Revised Mar. 9, 2000, Accepted Mar. 9, 2000, Available online Aug. 15, 2000.

Thygesen K, et al., Third Universal Definition of Myocardial Infarction. J Am Coll Cardiol.,Oct. 16, 2012/epub Sep. 5, 2012; 60(16):1581-1598.

Tilg H, et al., Inflammatory Mechanisms in the Regulation of Insulin Resistance. Mol. Med., Mar./Apr. 2008;14(3-4):222-231; https://link.springer.com/article/10.2119/2007-00119.Tilg, Received Nov. 14, 2007. Accepted Jan. 18, 2008. Published Mar. 1, 2008.

Tirosh et al., "Changes in Triglyceride Levels and Risk for Coronary Heart Disease in Young Men," American College of Physicians, pp. 377-385 (Sep. 18, 2007).

Tong H, et al., "Omega-3 fatty acid supplementation appears to attenuate particulate air pollution-induced cardiac effects and lipid

(56) References Cited

OTHER PUBLICATIONS changes in healthy middle-aged adults." Eniron. Health Perspect, Jul. 2012, epub Apr. 19, 2012; 120(7):952-7.
Torrejon C, et al., "n-3 Fatty acids and cardiovascular disease: Actions and molecular mechanisms," Prostaglandins Leukotrienes & Essent. Fatty Acids, 77(5-6):319-26 Nov./Dec. 2007/epub Dec. 3, 2007. doi:10.1016/j.plefa.2007.10.014 (2007).
Toth PP, et al., High Triglycerides are associated with increased cardiovascular events, medical costs, and resource use: A real-world administrative claims analysis of statin-treated patients with high residual cardiovascular risk. Journal of the American Heart Association, 7(15):e008740 (publication date Jul. 25, 2018; epublication Aug. 7, 2018).
Toyoda, Pharmacotherapy for the Secondary Prevention of Stroke, Drugs, 69(6) pp. 633-647 (2009).
Transcript from Oct. 16, 2013 Meeting of the Endocrinologic and Metabolic Drugs Advisory Committee, 76 pages.
TREND-HD Investigators, Randomized controlled trial of ethyl-eicosapentaenoic acid in Huntington disease: the TREND-HD study, Arch Neurol., vol. 65(12): 1582-9 (Dec. 2008); https://jamanetwork.com/journals/jamaneurology/fullarticle/1107464, Accepted for Publication: May 9, 2008.
Tribble DL, et al., Enhanced oxidative susceptibility and reduced antioxidant content of metabolic precursors of small, dense low-density lipoproteins. Am. J. Med. Feb. 1, 2001;110(2):103-110.
Tribble DL, et al., Variations in oxidative susceptibility among six low density lipoprotein subfractions of differing density and particle size. Atherosclerosis. Apr. 1992;93(3):189-199; https://www.sciencedirect.com/science/article/abs/pii/002191509290255F, Received Nov. 15, 1991, Accepted Jan. 9, 1992, Available online Apr. 14, 2005.
Triglyceride vs. Ethyl Ester Forms of Fish Oil Omega-3S, ScienceBased Health, Apr. 18, 2012; URL:https://web.archive.org/web/20120420022941/https://www.sciencebasedhealth.com/Fish-Oil-EE-vs-TGomega-3s-which-is-better-W119.aspx.
Trilipix Package Insert (Sep. 2010)(10 pages).
Tsimikas S, et al., High-dose atorvastatin reduces total plasma levels of oxidized phospholipids and immune complexes present on apolipoprotein B-100 in patients with acute coronary syndromes in the MIRACL trial. Circulation, Sep. 14, 2004/epub Sep. 7, 2004; 110(11):1406-1412.
Tsuruta K, et al., Effects of purified eicosapentaenoate ethyl ester on fibrioiytic capacity in patients with stable coronary artery disease and lower extremity ischaemia, Coron Artery Dis. 7(11):837-42 (Nov. 1996); https://europepmc.org/article/med/8993942, Oct. 31, 1996.
Tulenko TN, et al., Physical effects of cholesterol on arterial smooth muscle membranes: Evidence of immiscible cholesterol domains and alterations in bilayer width C during atherogenesis. J. Lipid Res. May 1998;39:947-956; https://www.jlr.org/content/39/5/947.short.
Tungsiripat et al., "Dyslipidemia in HIV patients," Cleveland Clinic Journal of Medicine, v. 72, No. 12 (Dec. 2005); https://mdedge-files-live.s3.us-east-2.amazonaws.com/files/s3fs-public/issues/articles/content_72_1113.pdf.
Turini et al., Short-term fish oil supplementation improved innate immunity, but increased ex vivo oxidation of LDL in man—a pilot study, Eur. J. Nutr. 40:56-65 (Apr. 2001); https://link.springer.com/article/10.1007%2Fs003940170016, Published Apr. 2001.
U.S. Appl. No. 14/245,499, filed Apr. 4, 2014 (now abandoned) (43 pages).
U.S. District Court of Nevada, judginent dated Mar. 30, 2020 in *Amarin Pharma, Inc. et al.* v. *Hikma Pharmaceuticals USA Inc. et al.*, Case 2:16-cv-02525-MMC-NJK Document 381 Filed Mar. 30, 2020 (70 pages).
U.S. Food and Drug Administration and Dept of Health and Human Services. Substances affirmed as generally recognized as safe: Menhaden Oil. Fed Register, 62:30751-30757 (Jun. 5, 1997).
Ullian ME, "Fatty acid inhibition of angiotensin II-stimulated inositol phosphates in smooth muscle cells." Am J Physiol Heart Circ Physiol., 264 (2 Pt 2):H595-603 (Feb. 1998); https://journals.physiology.org/doi/abs/10.1152/ajpheart.1993.264.2.H595, Published online Feb. 1, 1993. Published in print Feb. 1, 1993.
Urakaze M, et al., "Infusion of emulsified trieicosapentaenoylglycerol into rabbits—The effects on platelet aggregation, polymorphonuclear leukocyte adhesion, and fatty acid composition in plasma and platelet phospholipids", Thromb. Res., 44(5):673-682 (Dec. 1986); https://www.sciencedirect.com/science/article/abs/pii/0049384886901684, Received Jun. 3, 1986, Accepted Aug. 11, 1986, Available online Apr. 2, 2004.
Urquhart et al., Profile of eicosanoids produced by human saphenous vein endothelial cells and the effect of dietary fatty acids, Prostagiandins Leukot. Essent. Fatty Acid, 65(1):15-22 (Jul. 2001); https://www.sciencedirect.com/science/article/abs/pii/S0952327801902820, Received Feb. 22, 2001, Accepted Jun. 1, 2001, Available online May 25, 2002.
Vaagenes et al., "The Hypolipidaemic Effect of EPA is Potentiated by 2- and 3-Methylation." In P. Quant & S. Eaton (eds.) Current Views of Fatty Acid Oxidation and Ketogenesis from Organelles to Point Mutations; Advances in Experimental Medicine and Biology, vol. 466, pp. 221-226 (1999); book chapter.
Vaddadi KS, et al., "A Randomised, Placebo-Controlled, Double-Blind Study of Treatment of Huntington's Disease with Unsaturated Fatty Acids", Clinical Neuroscience and Neuropathology, 13(1):29-33, (Jan. 2002); https://journals.lww.com/neuroreport/Abstract/2002/01210/A_randomised,_placebo_controlled, double blind.11.aspx, Jan. 21, 2002.
Vaduganathan M, et al., Moving toward global primordial prevention in cardiovascular disease: The heart of the matter. J Am Coll Cardiol Oct. 6, 2015;66(14):1535-7.
Van der Steeg WA, at al., "High-density lipoprotein cholesterol, high-density lipoprotein particle size, and apolipoprotein A-I: Significance for cardiovascular risk—the IDEAL and EPIC-Norfolk studies." J. Am. Coll. Cardiol. 51;634-642 (Feb. 12, 2008).
Van Do at al., "Allergy to fish parvalbumins: Studies on the cross-reactivity of allergens from 9 commonly consumed fish," Journ. Allergy & Clin. Immunol., 16(6):1314-1320 (Dec. 1, 2005).
Van Wijk et al., Rosiglitazone improves postprandial triglyceride and free fatty acid metabolism in type 2 diabetes. Diabetes Care, vol. 28, No. 4, (Apr. 2005) pp. 844-849; https://care.diabetesjournals.org/content/28/4/844.short, Received Aug. 6, 2004. Accepted Dec. 21, 2004.
Varbo A, et al., Reply to letters regarding article, "Elevated remnant cholesterol causes both low-grade inflammation and ischemic heart disease, whereas elevated low-density lipoprotein Cholesterol causes ischemic heart disease without inflammation." Circulation. Jun. 17, 2014; 129(24):e656.
Varbo et al., Remnant Chelesterol as a Causal Risk Factor for Ischemic Heart Disease, J. Am. Coll. Cardiol., vol. 61 (4), pp. 427-36 (Jan. 29, 2013/epub Dec. 19, 2012).
Varbo et al., Remnant cholesterol as a cause of ischemic heart disease: Evidence, definition, measurement, atherogenicity, high risk patients, and present and future treatment, Pharmacol. Ther., vol. 141 (3), pp. 358-67 (Mar. 2014/epub Nov. 26, 2013).
Vascepa [package insert], Bedminster, NJ: Amarin Pharma Inc.; Jul. 2012. (12 gages).
Vascepa [package insert]. Bedminster, NJ: Amarin Pharma Inc.; Nov. 2013. (11 pages).
Vasudevan et al., "Effective Use of Combination Lipid Therapy", Curr. Atheroscl. Rep., vol. 8, pp. 76-84 (Jan. 2006); https://link.springer.com/article/10.1007%2Fs11883-006-0068-y, Published Jan. 2006.
Vedin I, et al., Effects of docosahexaenoic acid—rich n-3 fatty acid supplementation on cytokine release from blood mononuclear leukocytes: the OmegAD study, Am J Clin Nutr 87:1616-22 (Jun. 2008); https://academic.oup.com/ajcn/article/87/6/1616/4633436, Received Nov. 8, 2007, Accepted Jan. 18, 2008, Published Jun. 1 2008.
Vega et al., Hypercholesterolemia with Cholesterol-Enriched LDL and Normal Levels of LDL-Apolipoprotein B; Arteriosclerosis, Thrombosis and Vascular Biology, Apr. 1996; 16(4):517-22 (Accepted Jan. 3, 1996; Received Aug. 9, 1995).
Velliquette et al., "Regulation of human stearoyl-CoA desaturase by omega-3 and omega-6 fatty acids: Implications for the dietary

(56) References Cited

OTHER PUBLICATIONS management of elevated serum triglycerides," Journal of Clinical Lipdology, (Aug. 2009/epub Jun. 21, 2009) 3:281-288.

Vergnani L, et al., Effect of native and oxidized low-density lipoprotein on endothelial nitric oxide and superoxide production: Key role of l-arginine availability, Circulation, Mar. 21, 2000; 101:1261-1266.

Verma S, et al., CANTOS ushers in a new calculus of inflammasome targeting for vascular protection—and maybe more. Cell Metab 26(5):703-5 (publication date Nov. 7, 2017; epublication date Oct. 19, 2017).

Vidal F, et al., Atherogenic concentrations of native low density lipoproteins down-regulate nitric-oxide-synthase mma and protein levels in endothelial cells. Eur. J. Biochem. Mar. 15, 1998; 252:378-384.

Vidgren HM, et al., Incorporation of n-3 fatty acids into plasma lipid fractions, and erythrocyte membranes and platelets during dietary supplementation with fish, fish oil, and docosahexaenoic acid-rich oil among healthy young men, Lipids 32: 697-705 (Jul. 1997); https://link.springer.com/article/10.1007/s11745-997-0089-x, Received Nov. 26, 1996, Revised Apr. 29, 1996, Accepted Apr. 30, 1997, Published Jul. 1997.

Virani et al., "The Role of Lipoprotein-associated Phospholipase A2 as a marker for atherosclerosis", Curr. Atheroscler. Rep. 9[2]: 97-103 (Aug. 2007); https://link.springer.com/article/10.1007%2Fs11883-007-0004-9, Published Apr. 26, 2007.

Volcik KA, et al., "Peroxisome proliferator-activated receptor agenetic variation interacts with n-6 and long-chain n-3 fatty acid intake to affect total cholesterol and LDL-cholesterol concentrations in the Atherosclerosis Risk in Communities Study." Am J Clin Nutr 87:1926-31 (Jun. 2008); https://academic.oup.com/ajcn/article/87/6/1926/4633499, Received Dec. 7, 2007, Accepted Jan. 16, 2008, Published Jun. 1, 2008.

Von Schacky C, "A review of omega-3 ethyl esters for cardiovascular prevention and treatment of increased blood triglyceride levels." Vascular Health and Risk Management 2(3): 251-262 (Sep. 2006); https://www.ncbi.nlm.nih.gov/pmc/articles/PMC1993981/, Published online Sep. 2006.

Von Schacky C, et al., The effect of n-3 fatty acids on coronary atherosclerosis: results from SCIMO, an angiographic study, background and implications. Lipids 2001 36 Suppl: S99-102; https://link.springer.com/article/10.1007/s11745-001-0689-5, Received Apr. 26, 2001, Accepted Nov. 17, 2001, Issue Date Jan. 2001.

Von Schacky, C, et al., "The Effect of Dietary ω-3 Fatty Acids on Cornoray Atherosclerosis: A Randomized, Double-Blind, Placebo-Controlled Trial," American College of Physicians-American Society of internal Medicine, 130(7):554-562, (Apr. 6, 1999).

Wada M, et al., "Enzymes and receptors of prostaglandin pathways with arachidonic acid-derived versus eicosapentaenoic acid-derived substrates and products." J. Biol. Chem. 282(31): 22254-22266 (Aug. 3, 2007/egub May 22, 2007).

Wagner AH, et al., Improvement of nitric oxide-dependent vasodilation by hmg-coa reductase inhibitors through attenuation of endothelial superoxide anion formation. Arterioscler. Thromb. Vasc. Biol, Jan. 2000;20:61-69; https://www.ahajournals.org/doi/full/10.1161/01.ATV.20.1.61, Originally published Jan. 1, 2000.

Walker G, Mandagere A, Button C, et al. The pharmacokinetics and pharmacodynamics of warfarin in combination with ambrisentan in healthy volunteers. Br. J. Clin. Pharmacol. May 2009/epub Feb. 4, 2009; 67 (5): 527-34.

Wall R, et al: Fatty acids from fish: the anti-inflammatory potential of long-chain 1 omega-3 fatty acids. Nutr Rev. May 2010; 68:280-289; https://academic.oup.com/nutritionreviews/article/68/5/280/1829259 , Published: May 1, 2010.

Walldius G, et al., "Editorial: Rationale for using apoiipoprotein B and apolipoprotein A-I as indicators of cardiac risk and as targets for lipid-lowering therapy." European Heart Journal 26, 210-212 (Feb. 2005/epub Dec. 15, 2004).

Walter MF, et al., Circulating lipid hydroperoxides predict cardiovascular events in patients with stable coronary artery disease: the PREVENT study. J. Am. Coll. Cardiol., Mar. 25, 2008;51(12):1196-1202.

Walter MF, et al., Serum levels of thiobarbituric acid reactive substances predict cardiovascular events in patients with stable coronary artery disease: A longitudinal analysis of the PREVENT study. J. Am. Coll. Cardiol. Nov. 16, 2004; 44(10):1996-2002.

Wander RC, et al., "Influence of long.chain polyunsaturated fatty acids on oxidation of low density lipoprotein." Prostaglandins, Leukotrienes and Essential Fatty Acids 59(2):143-151 (Aug. 1998); https://www.sciencedirect.com/science/article/abs/pii/S095232789890093X , Received Jun. 1, 1998, Accepted Jul. 2, 1998, Available online Jun. 18, 2004.

Wang C, et al., "n-3 Fatty acids from fish or fish-oil supplements, but not α-linolenic acid, benefit cardiovascular disease outcomes in primary- and secondary-prevention studies: a systematic review." Am J Clin Nutr 845-17 (Jan. 2006); https://academic.oup.com/ajcn/article/84/1/5/4633070 , Received Nov. 18, 2005, Accepted Jan. 22, 2006, Published Jun. 1, 2006.

Wang L, et al., "Triglyceride-rich lipoprotein iipolysis releases neutral and oxidized FFAs that induce endothelial cell inflammation." J. Lipid Res. 50:204-213 (Feb. 2009/epub Sep. 23, 2008).

Wang Q, Liang X, Wang L, Lu X, Huang J, Cao J, Li H, Gu D. Effect of omega-3 fatty acids supplementation on endothelial function: A meta-analysis of randomized controlled trials. Atherosc. Apr. 2012/epub Jan. 20, 2012; 221:563-543.

Warren, Stephen T, "The Expanding World of Trinucleotide Repeats," Science, 271:1374-1375, (Mar. 8, 1996).

Wassmann S, et al., Cellular antioxidant effects of atorvastatin in vitro and in vivo. Arterioscler. Thromb. Vasc. Biol. Feb. 1, 2002; 22:300-305.

Watanabe et al., "Bile acids lower triglyceride levels via a pathway involving FXR, SHP, and SREBP-1c," J Clin Invest. 113(10): 1408-1418 (May 2004); https://www.jci.org/articles/view/21025 Received Jan. 9, 2004. Accepted Mar. 23, 2004. First published May 15, 2004.

Watanabe T, et al., A randomized controlled trial of eicosapentaenoic acid in patients with coronary heart disease on statins. J Cardiol 70(6):537-44 (publication date Dec. 2017; epublication date Aug. 31, 2017).

Watanabe, Ikuyoshi, et al., "Usefulness of EPA-E (eicosapentaenoic acid ethyl ester) in preventing neointimal formation after vascular injury," Kokyu to Junkan, 42(7):673-677 (1994) (with English summary).

Weaver, KL, et al., "Effect of Dietary Fatty Acids on Inflammaiery Gene Expression in Heaithy Humans." J. Biol. Chem, 284(23): 15400-15407 (2009) (published online Apr. 9, 2009).

Webcast Information for the Oct. 16, 2013 Meeting of the Endocrinoiogic and Metabolic Drugs Advisory Committee, (1 page).

Weber P, Triglyceride-lowering effect of n-3 long chain polyunsaturated fatty acid: eicosapentaenoic acid vs. docosahexaenoic acid, Lipids 34: S269 (1999); https://search.proquest.com/openview/c450f60b01bd53d0c43c78e8a12e39e8/1?pq-origsite=gscholar&cbl=35263, (ProQuest db) Jan. 1999.

Wei et al., Effects of [EPA] Versus [DHA] on Serum Lipids: A Systematic Review and Meta-Analysis, 13 Current Atherosclerosis Rep. 13(6):474-483 (Dec. 2011); https://www.researchgate.net/profile/Melissa_Wei/publication/278649556_EPA_DHA_meta/links/558192c708ae1b14a0a0fc1a/EPA-DHA-meta.pdf, Published online Oct. 6, 2011.

Wei LJ, et al., Regression analysis of multivariate incomplete failure time data by modeling marginal distributions. *J Am Stat Assoc.* 84(408):1065-1073 (publication date Dec. 1989); https://amstat.tandfonline.com/doi/abs/10.1080/01621459.1989.10478873, Received Nov. 1, 1987 Published online: Mar. 12, 2012.

Westerveld HT, et al., "Effects of low-dose EPA-Eon glycemic control, lipid profile, lipoprotein(a), platelet aggretation, viscosity, and platelet and vessel wall interaction in NIDDM" Diabetes Care 16(5):683-8 (May 1993); https://care.diabetesjournals.org/content/16/5/683.short.

Westphal S, et al., "Postprandial chylomicrons and VLDLs in severe hypertriacylglycerolemia are lowered more effectively than are

(56) References Cited

OTHER PUBLICATIONS chylomicron remnants after treatment with n23 fatty acids." Am J Clin Nutr 71:914-20 (Apr. 2000); https://academic.oup.com/ajcn/article/71/4/914/4729124, Received Feb. 26, 1999, Accepted Sep. 14, 1999, Published Apr. 1, 2000.

Whelan J, et al., "Evidence that dietary arachidonic acid increases circulating triglycerides." Lipids 30, 425-429 (May 1995); https://link.springer.com/article/10.1007/BF02536300, Received Oct. 18, 1994, Revised Mar. 15, 1995, Accepted Mar. 15, 1995, Issue Date May 1995.

Wierzbicki, AS, "Editorial: Newer, lower, better? Lipid drugs and cardiovascular disease—the continuing story." Int J Clin Pract, 61(7):1064-1067 (Jul. 2007); https://onlinelibrary.wiley.com/doi/abs/10.1111/j.1742-1241.2007.01375.x, First published: Jun. 15, 2007.

Wierzbicki, AS, "Editorial: Raising HDL-C: back to the future?" Int J Clin Pract, 61(7):1069-1071 (Jul. 2007); https://onlinelibrary.wiley.com/doi/abs/10.1111/j.1742-1241.2007.01412.x, First published: Jun. 15, 2007.

Wikipedia, "Diabetes mellitus," Dec. 12, 2016 (Dec. 12, 2016), retrieved on Jul. 30, 2018 from https://en.wikipedia.org/w/index.php?title=Diabetes_mellitus&oldid=754431573; entire document, especially p. 1, paragragh 1.

Wikipedia, "Ethyl eicosapentaenoic acid," Apr. 1, 2016 (Apr. 1, 2016); retrieved on Jul. 27, 2018 from https://en.wikipedia.org/w/index.php?title=Ehtyl_eicosapentaenoic_acid&oldid=713086755; entire document, especially p. 1, col. 2 and p. 3, paragragh 2.

Williams et al., "NADPH Oxidase Inhibitors New Antihypertensive Agents?" J. Cardiovasc Pharmacol 50(1):9-16 (Jul. 1, 2007).

Willumsen N, et al., "On the effect of 2-deuterium- and 2-methyl-eicosapentaenoic acid derivatives on triglycerides, peroxisomal beta-oxidation and platelet aggregation in rats," Biochimica et Biophysica Acta, vol. 1369,pp. 193-203, (Mar. 2, 1998); https://aocs.onlinelibrary.wiley.com/doi/abs/10.1007/BF02523828, First published: Jun. 1, 1996.

Willumsen, N., et al., "Eicosapentaenoic acid, but not docdsahexaenoic acid, increased, mitochondrial fatty acid oxidation and upregulates 2,3-dienoyl-CoA reductase gene exgression in rats." Lipids, 31:579-592 (Jun. 1996).

Wilson Omega 3 fish oil: EPA versus DHA (Dietivity.com, 1-16) (2006).

Wilt VM, Gumm, JG, "Isolated low high-density lipoprotein cholesterol", Ann. Pharmacol., 31:89-97, (Jan. 1997); https://journals.sagepub.com/doi/abs/10.1177/106002809703100115, First Published Jan. 1, 1997.

Wink J, et al., Effect of very-low-dose niacin on high-density lipoprotein in patients undergoing iong-term statin therapy, Am. Heart J., 143:514-518, (Mar. 2002); https://www.sciencedirect.com/science/article/abs/pii/S0002870302935040, Received Nov. 15, 2000, Accepted Sep. 7, 2001, Available online May 25, 2002.

Wittrup HH, et al., Lipoprotein lipase mutations, plasma lipids and lipoproteins, and risk of ischemic heart disease: a meta-analysis. Circulation, Jun. 8, 1999; 99:2901-2907.

Witztum JL, The oxidation hypothesis of atherosclerosis. Lancet, Sep. 17, 1994;344(8925):793-795.

Wojczynski et al., "High-fat meal effect on LDL, HDL and VLDL particle size and number in the Genetics of Lipid-Lowering Drugs and Diet Network (GOLDN): an interventional study," Lipids in Health and Disease 10:181, pp. 1-11 (Oct. 18, 2011).

Wojenski CM, et al., "Eicosapentaenoic acid ethyl ester as an antithrombotic agent: comparison to an extract of fish oil." Biochimica et Biophysica Acta. 1081:33-38 (Jan. 4, 1991).

Wong SH, et al., "Effects of eicosapentaenoic and docosahexaenoic acids on Apoprotein B mRNA and secretion of very low density lipoprotein in HepG2 cells." Arterioscler. Thromb. Vasc. Biol. 9;836-841 (Nov./Dec. 1989); https://www.ahajournals.org/doi/abs/10.1161/01.ATV.9.6.836, Originally published Nov. 1, 1989.

Wood et al., "Carbohydrate Restriction Alters Lipoprotein Metabolism by Modifying VLDL, LDL and HDL Subraction Distribution and Size in Overweight Men," Journ. of Nutrition, 136(2):384-9 (Feb. 2006); https://academic.oup.com/jn/article/136/2/384/4664306, Received: Sep. 30, 2005. Revision received: Oct. 26, 2005, Accepted: Nov. 1, 2005. Published: Feb. 1, 2006.

Woodman et al., Effects of Purified Eicosapentaenoic and Docosahexaenoic Acids on Glycemic Control, Blood Pressure, and Serum Lipids in Type 2 Diabetic Patients with Treated Hypertension, The American Journal of Clinical Nutrition: Official Journal of the American Society for Clinical Nutrition, Inc., 76(5):1007-1015 (Nov. 1, 2002).

Woodman, RJ, et al., "Effects of purified eicosapentaenoic acid and docosahexaenoic acid on platelet, fibrinolytic and vascular function in hypertensive type 2 diabetic patients." Atherosclerosis 166: 85-93 (Jan. 2003); https://www.sciencedirect.com/science/article/abs/pii/S0021915002003076 , Received Apr. 25, 2002, Revised Jul. 8, 2002, Accepted Jul. 17, 2002, Available online Oct. 4, 2002.

Wu et al., "Diabetic dyslipidemia," Metabolism Clinical and Experimental, 63:1469-1479 (Dec. 2014)(available online Aug. 29, 2014); https://www.nature.com/articles/1602328, Received Oct. 27, 2004. Revised Aug. 16, 2005, Accepted Sep. 14, 2005, Published Nov. 9, 2005, Issue Date Mar. 1, 2006.

Wu WH, et al., "Effects of docosahexaenoic acid supplementation on blood lipids, estrogen metabolism, and in vivo oxidative stress in postmenopausal vegetarian women." Eur J Clin Nutr., 60:386-392 (Mar. 2006).

Xiao, YF, et al., "Blocking effects of polyhnsaturated fatty acids on Na+ channels of neonatal rat ventricular myocytes." Proc. Natl. Acad. Sci. 92: 11000-11004 (Nov. 21, 1995).

Xiao, YF, et al., "Fatty acids suppress voltage-gated Na+ currents in HEK293t cells transfected with the a-subunit of the human cardiac Na+ channel." Proc. Natl. Acad. Sci. 95: 2680-2685 (Mar. 3, 1998).

Xiao, YF, et al., "Inhibitory effect of n-3 fish oil fatty acids on cardiac Na+/Ca2+ exchange currents in HEK293t cells." Biochemical and Biophysical Research Communications 321: 116-123 (Aug. 13, 2004).

Xydakis AM, et al., "Combination therapy for combined dyslipidemia," American Journal of Cardiology, Nov. 20, 2002 US, vol. 90, No. 10 Suppl. 2, p. 21 K-29K (Nov. 20, 2002).

Yacyshyn BR, Thomson AB. The clinical importance of proton pump inhibitor pharmacokinetics. Digestion 2002 66 (2): 67-78; https://www.karger.com/Article/Abstract/65588.

Yadav D, et al., Issues in Hyperlipidemic Pancreatitis. J Clin Gastroenterol 236(1):54-62, Jan. 2003; https://journals.lww.com/jcge/Fulltext/2003/01000/Issues_in_Hyperlipidemic_Pancreatitis.16.aspx.

Yagi K, Assay for blood plasma or serum, Methods Enzymol 1984;105:328-331 ; https://www.sciencedirect.com/science/article/pii/S0076687984050424, Available online Jan. 7, 2004.

Yamagishi K, et al., Plasma fatty acid composition and incident heart failure in middle-aged adults: The Atherosclerosis Risk in Communities (ARIC) Study. Am Heart J., Nov. 2008/epub Aug. 29, 2008; 156:965-974.

Yamakawa K, et al., Eicosapentaenoic Acid Supplementation Changes Fatty Acid Composition and Corrects Endothelial Dysfunction in Hyperlipidemic Patients. Cardiol Res Practice. Dec. 26, 2012; epub Article ID 754181.

Yamamoto H, et al., Improvement of coronary vasomotion with Eicosapentaenoic acid does not inhibit acetylcholine-induced coronary vasospasm in patients with variant angina: Jpn Cir J. 59(9):608-16 (Sep. 1995); https://www.jstage.jst.go.jp/article/circj1960/59/9/59_9_608/_article/-char/ja/.

Yamamoto K, et al., "4-Hydroxydocosahexaenoic acid, a potent Peroxisome Proliferator-Activated Receptor C agonist alleviates the symptoms of DSS-induced colitis." Biochemical and Biophysical Research Communications 367: 566-572 (Mar. 14, 2008/epub Jan. 10, 2008).

Yamano T, et al. Impact of eicosapentaenoic acid treatment on the fibrous cap thickness in patients with coronary atherosclerotic plaque: an optical coherence tomography study. J Atheroscler Thromb. 2015/epub Aug. 15, 2014;22:52-61.

Yamashita et al., J. Biochem, vol. 122, No. 1, "Acyl-transferases and Transaclyases Involved in Fatty Acid Remodeling of Phospholipids and Metabolism of Bioactive Lipids in Mammalian Cells," pp. 1-16

(56) References Cited

OTHER PUBLICATIONS (Jul. 1997); https://academic.oup.com/jb/article/122/1/1/764052, Received Apr. 1, 1997, Published Jul. 1, 1997.

Yamashita N, et al., "Inhibition of natural killer cell activity of human lymphocytes by eicosapentaenoic acid." Biochem. Biophys. Res. Comm. 138(3): 1058-1067 (Aug. 25, 1986).

Yamazaki et al., "Changes in fatty acid composition in rat blood and organs after infusion of eicosapentaenoic acid ethyl ester," Biochim. Biophys. ACTA, 1128(1):35-43, (Sep. 22, 1992).

Yamazaki et. al., "Dissolution tests by RDC method for soft gelatin capsules containing ethyl icosapentate," Pharm. Tech. Japan, vol. 15, No. 4, pp. 595-603 Abstract (Apr. 1999) (with English abstract).

Yang SP, et al., "Eicosapentaenoic acid attenuates vascular endothelial growth factor-induced proliferation via inhibiting Flk-1 receptor expression in bovine carotid artery endothelial cells." J. Cell. Physio. 176:342-349 (Aug. 1998); https://onlinelibrary.wiley.com/doi/abs/10.1002/(SICI)1097-4652(199808)176:2%3C342::AID-JCP12%3E3.0.CO;2-5, First published Dec. 6, 1998.

Yano T, et al., "Effects of ethyl-all-cis-5,8,11,14,17-icosapentaenoate (EPA-E), pravastatin and their combination on serum lipids and intimal thickening of cuff-sheathed carotid artery in rabbits", Life Sciences, 61(20):2007-2015 (Oct. 10, 1997); https://www.sciencedirect.com/science/article/abs/pii/S002432059700859X, Revised Aug. 11, 1997, Available online Jan. 21, 1998.

Yano T, et al., Effects of ethyl all-cis-5,8,11,14,17-icosapentaenoate on low density lipoprotein in rabbits, Yakugaku Zasshi, 115:843-51 (Oct. 1995); https://europepmc.org/article/med/8531063, Sep. 30, 1995.

Yao et al., "Oxidized high density lipoprotein induces macrophage apoptosie via toll-like receptor 4-dependent CHOIP pathway," Journ. Lipid Res., 58:164-177 (Jan. 2017) (First Published Nov. 28, 2016).

Yates RA, et al., The effect of anastrozole on the single-dose pharmacokinetics and anticoagulant activity of warfarin in healthy volunteers. Br. J. Clin. Pharmacol. May 2001 51(5): 429-35; https://bpspubs.onlinelibrary.wiley.com/doi/full/10.1046/j.1365-2125.2001.01358.x, Received Jan. 19, 2000, accepted Dec. 18, 2000, Issue Online: Jan. 12, 2002.

Yerram NR, et al., "Eicosapentaenoic acid metabolism in brain microvessel endothelium: effect on prostaglandin formation." J. Lipid Res.30:1747-1757 (Nov. 1989); https://www.jlr.org/content/30/11/1747.short.

Yokoyama et al., "Effects of eicosapentaenoic acid on cardiovascular events in Japanese patients with hypercholesterolemia: Rationale, design, and baseline characteristics of the Japan EPA Lipid Intervention Study (JELIS)," Amer. Heart Journal 146(4):613-620 (Oct. 2003); https://www.sciencedirect.com/science/article/abs/pii/S0002870303003673, Received May 27, 2002, Accepted Mar. 11, 2003, Available online Oct. 8, 2003.

Yokoyama et al., "Effects of eicosapentaenoic acid on major coronary events in hypercholesterolaemic patients (JELIS): a randomized open-label, blinded endpoint analysis," Lancet, vol. 369, pp. 1090-1098 (Mar. 31, 2007).

Yorioka N, "Lipid-lowering therapy and coagulation/fibrinolysis parameters in patients on peritoneal dialysis," The International Journal of Artificial Organs, vol. 23(1):27-32 (Jan. 2000); https://journals.sagepub.com/doi/abs/10.1177/039139880002300105, Issue published Jan. 1, 2000.

Yoshimura et al., "Effects of highly purified eicosapentaenoic acid on plasma beta thromboglobulin level and vascular reactivity to angiotensin II," Artery, 14(5):295-303 (1987); https://pubmed.ncbi.nlm.nih.gov/2821970/.

Zaima N., et al., "Trans geometric isomers of EPA decrease LXRa-induced cellular triacylglycerol via suppression of SREBP-1c and PGC-1β," J. Lipid Res. 47: 2712-2717 (Dec. 2006); https://www.jlr.org/content/47/12/2712.short, First Published on Sep. 27, 2006.

Zalewski et al., Role of Lipoprotein-Associated Phospholipase A2 in Atherosclerosis: Biology, Epidemiology, and Possible Therapeutic Target, Arteriosclerosis, Thrombosis, & Vascular Biology 25(5):923-931 (May 2005/epub Feb. 24, 2005).

Zanarini et al., "Omega-3 Fatty Acid Treatment of Women with Borderline Personality Disorder: A Double-Blind, Placebo-Controlled Pilot Study," Am J Psychiatry, 160:167-169 (Jan. 2003); https://ajp.psychiatryonline.org/doi/full/10.1176/appi.ajp.160.1.167, Published Online Jan. 1, 2003.

Zhan S, et. al. "Meta-analysis of the effects of soy protein containing isofiavones on the lipid profile," Am. J. Ciin. Nutr. (Feb. 2005), 81, p. 397-408; https://academic.oup.com/ajcn/article/81/2/397/4607461 Received: Jul. 5, 2004. Accepted: Oct. 4, 2004. Published: Feb. 1, 2005.

Zhang M, et al., "Effects of eicosapentaenoic acid on the early stage of type 2 diabetic nephropathy in KKAy/Ta mice: involvement of anti-inflammation and antioxidative stress." Metabolism Clinical and Experimental 55:1590-1598 (Dec. 2006); https://www.sciencedirect.com/science/article/abs/pii/S002604950600268X, Received Mar. 17, 2006, Accepted Jul. 20, 2006, Available online Dec. 2, 2006.

Zhang YW, et al., "Inhibitory effects of eicosapentaenoic acid (EPA) on the hypoxia/reoxygenation-induced tyrosine kinase activation in cultured human umbilical vein endothelial cells." Prostaglandins, Leukotrienes and Essential Fatty Acids 67(4):253-261 (Oct. 2002); https://www.sciencedirect.com/science/article/abs/pii/S0952327802904278, Received Feb. 11, 2002, Accepted Jun. 11, 2002, Available online Oct. 20, 2002.

Zhang YW, et al., "Pretreatment with eicosapentaenoic acid prevented hypoxia/reoxygenation-induced abnormality in endothelial gap junctional intercellular communication through inhibiting the tyrosine kinase activity." Prostaglandins, Leukotrienes and Essential Fatty Acids 61(1): 33-40 (Jul. 1999); https://www.sciencedirect.com/science/article/abs/pii/S0952327899900704, Received Mar. 15, 1999, Accepted Apr. 13, 1999, Available online May 25, 2002.

Zhao et al., "Polyunsaturated Fatty Acids are FXR Ligands and Differentially Regulate Expression of FXR Targets," DNA and Cell Biology, 23(8):519-526 (Aug. 25, 2004).

Zhao G, et al., "Dietary α-linolenic acid inhibits proinflammatory cytokine production by peripheral blood mononuclear cells in hypercholesterolemic subjects." Am J Clin Nutr 85:385-91 (Feb. 2007); https://academic.oup.com/ajcn/article/85/2/385/4649479, Received Jan. 30, 2006. Accepted Sep. 11, 2006, Published Feb. 1, 2007.

Zhao G, et al., "Dietary α-linolenic acid reduces inflammatory and lipid cardiovascular risk factors in hypercholesterolemic men and women." J. Nutr. 134: 2991-2997 (Nov. 2004); https://academic.oup.com/jn/article/134/11/2991/4688439, Received May 21, 2004, Revision received Jun. 28, 2004, Accepted Aug. 9, 2004, Published Nov 1, 2004.

Zheng et al., "Function of ω-3 long chain unsaturated fatty acid in metabolic syndrome," Chinese Journal of Endocrinology and Metabolism, vol. 27, No. 9, pp. 787-790 (Sep. 30, 2011)(with English translation).

Ziegler D, et al., "Treatment of symptomatic diabetic polyneuropathy with the antioxidant α-lipoic acid: A 7-month multicenter randomized controlled trial (ALADIN III Study)." Diabetes Care 22:1296-1301 (Aug. 1999); https://care.diabetesjournals.org/content/22/8/1296.short.

Zimmer et al., "Danger signaling in Atherosclerosis," Circulation Research. Jan. 16, 2015, vol. 116, pp. 323-340.

Zimmerman JJ, et al., Evaluation of a potential tigecycline-warfarin drug interaction. Pharmacotherapy Jul. 2008 28 (7): 895-905; https://accpjournals.onlinelibrary.wiley.com/doi/abs/10.1592/phco.28.7.895, Manuscript received Aug. 2, 2007. Accepted for publication in final form Jan. 23, 2008, Issue online: Jan. 6, 2012.

Zuijdgeest-van Leeuwen et al., "N-3 Fatty Acids Administered as Triacylglycerols or as Ethyl Esters Have Different Effects on Serum Lipid Concentrations in Healthy Subjects," N-3 Fatty Acids, Lipid Metabolism and Cancer, Chapter 8,pp. 89-100 (2000).

Zuijdgeest-van Leeuwen, SD, et ai., "Eicosapentaenoic acid inhibits lipoiysis in weight-losing cancer patients as well as in healthy volunteers," Eur J Gastroenterol & Hepatol., 10(12):A67 (1998); https://journals.lww.com/eurojgh/Citation/i998/12000/Eicosapentaenoic_acid_inhibits_lipolysis_in.217.aspx, Dec. 1998.

Zuijdgeest-van Leeuwen, SD, et al., Incorporation and washout of orally administered n-3 fatty acid ethyl esters in different plasma lipid fractions, British Journal of Nutrition 82:481-488 (1999);

(56) References Cited

OTHER PUBLICATIONS https://www.cambridge.org/core/journals/british-journal-of-nutrition/article/incorporation-and-washout-of-orally-administered-n3-fatty-acid-ethyl-esters-in-different-plasma-lipid-fractions/0385A1191F944083C729D7F158CDFA6D, Dec. 1999 Published online by Cambridge University Press Mar. 9, 2007.

Zvyaga T, et al., Evaluation of six proton pump inhibitors as inhibitors of various human cytochromes P450: focus on cytochrome P450 2C19. Drug Metab. Dispos. Sep. 2012 40(9): 1698-711; http://dmd.aspetjournals.org/content/40/9/1698.short, Sep. 2012.

Brunzell, John, Hypertriglyceridemia, New England Journal of Medicine, 2007, 357:1009-17.

\* cited by examiner

Prespecified exploratory analysis with no adjustment for multiple comparisons. Repeated-measurements analysis of change from baseline blood pressure over time by mixed-effects model. ITT population. Icosapent ethyl n=4089, Placebo n=4091. Maximum number of observations per patient = 6.

METHODS OF REDUCING THE RISK OF HEART FAILURE

CROSS-REFERENCE TO RELATED APPLICATIONS

This application is a continuation of provisional Application No. 63/177,723 filed Apr. 21, 2021, the content of which is herein incorporated in its entirety.

BACKGROUND

Cardiovascular disease is one of the leading causes of death in the United States and most European countries. It is estimated that over 70 million people in the United States alone suffer from a cardiovascular disease or disorder including but not limited to high blood pressure, coronary heart disease, dyslipidemia, congestive heart failure and stroke.

Lovaza®, a lipid regulating agent, is indicated as an adjunct to diet to reduce triglyceride levels in adult patients with very high triglyceride levels. Unfortunately, Lovaza® can significantly increase LDL-C and/or non-HDL-C levels in some patients. A need exists for improved treatments for cardiovascular diseases and disorders.

SUMMARY

In various embodiments, the present disclosure provides methods of treating and preventing cardiovascular diseases and disorders.

In one aspect, the present disclosure provides methods of reducing risk of heart failure in a subject, the methods comprising administering to said subject about 4 g of ethyl icosapentate per day for a period effective to reduce the risk of heart failure.

In some embodiments, after administration of ethyl icosapentate, the subject has a fasting baseline serum and/or plasma eicosapentaenoic acid (EPA) level of at least about 104 µg/mL. In another embodiment, after administration of ethyl icosapentate, the subject has a baseline serum and/or plasma EPA level of about 104 µg/mL to about 175 µg/mL. In yet another embodiment, after administration of ethyl icosapentate, the subject has a baseline serum and/or plasma EPA level of at least about 175 µg/mL.

In another aspect, the present disclosure provides methods of reducing risk of heart failure in a subject, the methods comprising administering to said subject about 4 g of ethyl icosapentate per day for a period effective to increase said subject's baseline serum and/or plasma EPA level to at least about 104 µg/mL.

In yet another aspect, the present disclosure provides methods of reducing risk of heart failure in a subject having a baseline serum and/or plasma EPA level of about 26 µg/mL, the method comprising administering to said subject about 4 g of ethyl icosapentate per day for a period effective to increase said subject's baseline serum and/or plasma EPA level to at least about 104 µg/mL.

In some embodiments, the subject is administered ethyl icosapentate for a period of time effective to increase said subject's baseline serum and/or plasma EPA level to about 104 µg/mL to about 175 µg/mL. In another embodiment, the subject is administered ethyl icosapentate for a period of time effective to increase said subject's baseline serum and/or plasma EPA level to at least about 175 µg/mL.

In some embodiments, the subject has a baseline serum and/or plasma EPA level of about 26 µg/mL. In some embodiments, the subject has a baseline triglyceride level of at least 135 mg/dL. In some embodiments, the subject is in statin therapy.

In some embodiments, the heart failure is new heart failure. In some embodiments, the heart failure is new heart failure requiring hospitalization.

In some embodiments, the methods further comprise reducing a risk of one or more of cardiovascular death, myocardial infarction, stroke, coronary revascularization, and unstable angina.

In some embodiments, the ethyl icosapentate is present in a pharmaceutical composition and the ethyl icosapentate comprises at least about 90 wt. % of all omega-3 fatty acids in the pharmaceutical composition. In another embodiment, the ethyl icosapentate is present in a pharmaceutical composition and the ethyl icosapentate comprises at least about 96 wt. % of all omega-3 fatty acids in the pharmaceutical composition. In yet another embodiment, about 1 g of the pharmaceutical composition is present in each of 4 capsules.

In some embodiments, the subject has established cardiovascular disease. In another embodiment, the subject has a high risk for cardiovascular disease and at least one risk factor for cardiovascular disease.

BRIEF DESCRIPTION OF THE DRAWINGS

FIGS. 3A and 3B indicate a 25% relative risk reduction for the primary composite endpoint over the course of 5 years.

FIGS. 5A and 5B indicate that there was a 26% RRR for the key secondary composite endpoint over the course of 5 years.

FIGS. 6 and 7 indicate that a subject's baseline triglyceride levels (e.g., ≥150 vs. <150 mg/dL or ≥200 or <200 mg/dL) did not influence the primary endpoint outcomes.

FIGS. 8 and 9 indicate that a subject's baseline triglyceride levels (e.g., ≥150 vs. <150 mg/dL or ≥200 or <200 mg/dL) did not influence the key secondary endpoint outcomes.

FIGS. 10A and 10B indicate that patient's triglyceride levels had no influence on the efficacy of icosapent ethyl as compared with placebo with respect to the primary or key secondary efficacy endpoint outcomes.

FIG. 13 indicates that the first, second, and recurrent ischemic events were reduced in patients randomized to icosapent ethyl (IPE) compared to placebo.

FIG. 17 indicates that the times to first, second, third, or fourth occurrences of the primary composite endpoint were consistently reduced in the icosapent ethyl group as compared to placebo.

FIG. 20 indicates that the total events for each component of the primary endpoint events were significantly reduced.

FIG. 33 indicates that there was a 30% relative risk reduction in total events for the primary composition endpoint in patients randomized to icosapent ethyl.

FIGS. 34A and 34B indicate that both primary and key secondary endpoints were significantly reduced in patients randomized to icosapent ethyl compare to placebo.

FIG. 47 indicates that total primary composite endpoints were reduced in all patients across the entire triglyceride range and within each of the defined triglyceride tertiles.

FIG. 48 demonstrates that the time to first event of the primary composite endpoint was reduced across the entire triglyceride range.

DETAILED DESCRIPTION

Figure 1:
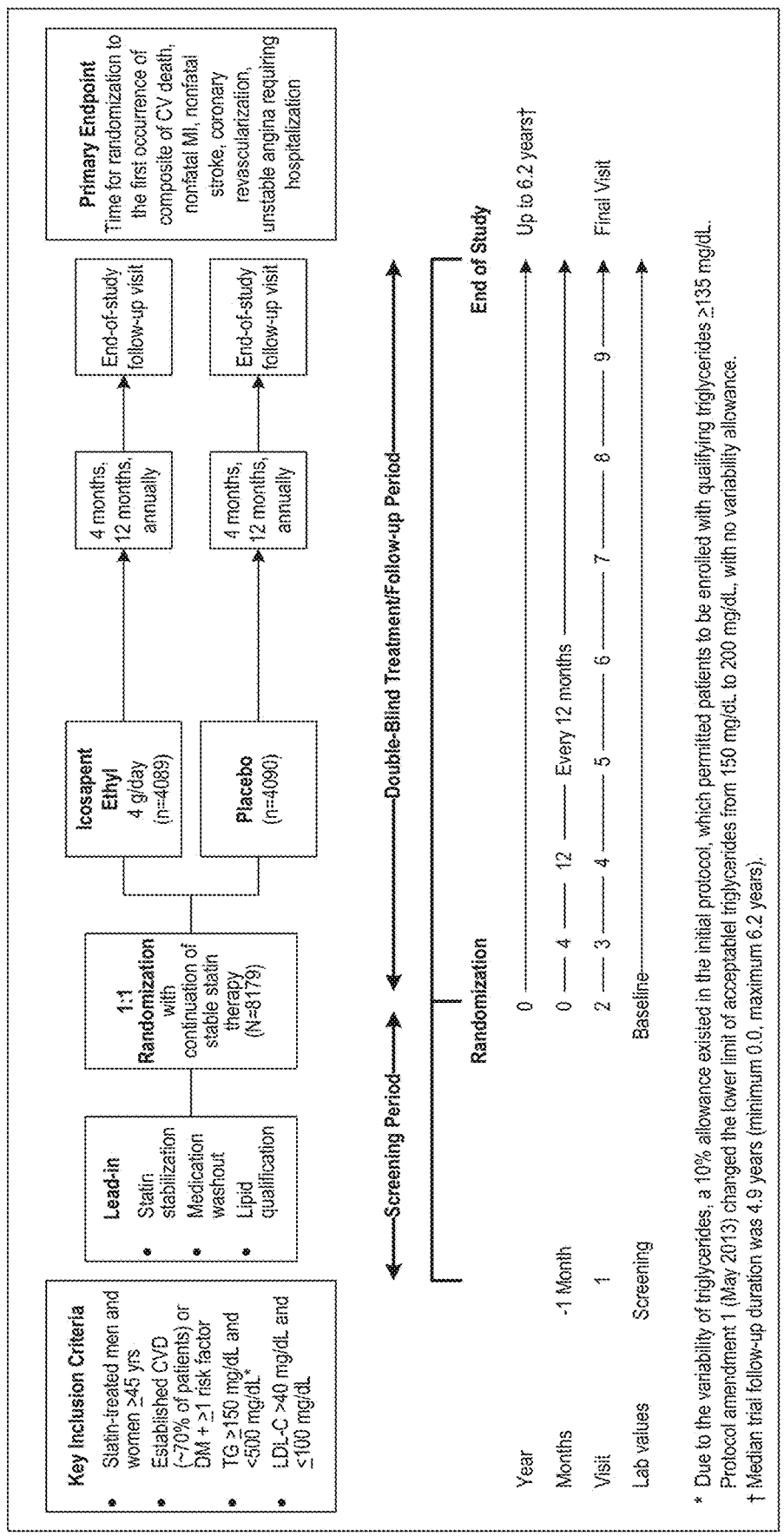
FIG. 1 is a schematic of the study design according to an embodiment of the present disclosure.

While the present disclosure is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading may be combined with embodiments illustrated under any other heading.

The use of numerical values in the various quantitative values specified in this application, unless expressly indicated otherwise, are stated as approximations as though the minimum and maximum values within the stated ranges were both preceded by the word "about." It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

The term "about," as used herein when referring to a measurable value such as an amount or concentration and the like, is meant to encompass variations of 20%, 10%, 5%, 1%, 0.5%, or even 0.1% of the specified amount.

The term "derivative," as used herein when referring to a fatty acid, is meant to encompass any modified form of the fatty acid that was derived for example, by a chemical reaction from the fatty acid in free acid form (i.e., terminal carboxylic acid functional group). Non-limiting examples of fatty acid derivatives as used herein include alkyl esters such as methyl esters, propyl esters, butyl esters, or ethyl esters, a salt of the fatty acid such as a lithium, sodium, or potassium salt, or glyceride form of the fatty acid such as a mono-, di-, or triglyceride fatty acid.

In one embodiment, the free fatty acid of eicosapentaenoic acid is administered to the subject and the amount administered is the gram weight sufficient to substantially match the pharmacokinetic profile produced by administration of 4 g of E-EPA per day to a human subject. In another embodiment, a derivative of eicosapentaenoic acid is administered to the subject and the amount administered is the gram weight sufficient to substantially match the pharmacokinetic profile produced by administration of 4 g of E-EPA per day to a human subject. With respect to a dose of 3.7 g per day of eicosapentaenoic acid, a dose-equivalent amount of E-EPA is about 4 g of E-EPA per day.

The phrase "control subject," as used herein refers to any subject used as a basis for comparison to the test subject. A control subject includes, but is not limited to, any subject who has not been administered the composition, administered a composition other than the test composition (e.g., Lovaza® comprised of 365 mg of E-EPA and 375 mg of E-DHA), or administered a placebo.

The phrase "cardiovascular risk category 1," as used herein refers to subjects categorized as having an established cardiovascular disease. Patients from cardiovascular risk category 1 were stratified to the secondary prevention cohort. The designations for patients defined by cardiovascular risk category 1 are collectively referred to as: secondary prevention stratum, secondary prevention cohort, and the primary risk category.

The phrase "cardiovascular risk category 2," as used herein refers to a subject categorized as having diabetes (which itself is a risk factor for cardiovascular disease) and at least one additional risk factor for cardiovascular disease but who does not have an established cardiovascular disease. Patients from cardiovascular risk category 2 were stratified to the primary prevention cohort. The designations for patients defined by cardiovascular risk category 2 are collectively referred to as: primary prevention stratum, primary prevention cohort, and secondary risk category.

Also, the disclosure of ranges is intended as a continuous range including every value between the minimum and maximum values recited as well as any ranges that can be formed by such values. Also disclosed herein are any and all ratios (and ranges of any such ratios) that can be formed by dividing a disclosed numeric value into any other disclosed numeric value. Accordingly, the skilled person will appreciate that many such ratios, ranges, and ranges of ratios can be unambiguously derived from the numerical values presented herein and in all instances such ratios, ranges, and ranges of ratios represent various embodiments of the present disclosure.

The phrase "statistical significance," as used herein refers to a result from data generated by testing or experimentation is not likely to occur randomly or by chance, but is instead likely to be attributable to a specific cause. Statistical significance is evaluated from a calculated probability (p-value), where the p-value is a function of the means and standard deviations of the data samples and indicates the probability under which a statistical result occurred by chance or by sampling error. A result is considered statistically significant if the p-value is 0.05 or less, corresponding to a confidence level of 95%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

List of abbreviations: ANOVA, analysis of variance; ASCVD, atherosclerotic cardiovascular disease; CI, confidence interval; RRR, relative risk reduction; HR, hazard ratio; CV, cardiovascular; DM, diabetes mellitus; HDL-C, high-density lipoprotein cholesterol; HIV/AIDS, human immunodeficiency virus/acquired immune deficiency syndrome; ICD-9, International Classification of Diseases, Ninth Revision; TG, triglyceride; TO, total cholesterol; VLDL-C very low dense lipoprotein cholesterol, apo B, apolipoprotein B; hsCRP, high sensitivity-C reactive protein; hsTnT, high-sensitivity troponin; RLP-C, remnant like particle cholesterol; LDL-C, low-density lipoprotein cholesterol; MI, myocardial infarction; non-HDL-C, non-high density lipoprotein cholesterol; PAD, peripheral artery disease; REDUCE-IT, Reduction of Cardiovascular Events with Icosapent Ethyl-Intervention Trial; SD, standard deviation; TG, triglycerides; and HLB; hydrophilic lipophilic balance.

Compositions

In one embodiment, a composition of the disclosure is administered to a subject in an amount sufficient to provide a daily dose of eicosapentaenoic acid of about 1 mg to about 10,000 mg, 25 about 5000 mg, about 50 to about 3000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, about 5000 mg, about 5025 mg, about 5050 mg, about 5075 mg, about 5100 mg, about 5125 mg, about 5150 mg, about 5175 mg, about 5200 mg, about 5225 mg, about 5250 mg, about 5275 mg, about 5300 mg, about 5325 mg, about 5350 mg, about 5375 mg, about 5400 mg, about 5425 mg, about 5450 mg, about 5475 mg, about 5500 mg, about 5525 mg, about 5550 mg, about 5575 mg, about 5600 mg, about 5625 mg, about 5650 mg, about 5675 mg, about 5700 mg, about 5725 mg, about 5750 mg, about 5775 mg, about 5800 mg, about 5825 mg, about 5850 mg, about 5875 mg, about 5900 mg, about 5925 mg, about 5950 mg, about 5975 mg, about 6000 mg, about 6025 mg, about 6050 mg, about 6075 mg, about 6100 mg, about 6125 mg, about 6150 mg, about 6175 mg, about 6200 mg, about 6225 mg, about 6250 mg, about 6275 mg, about 6300 mg, about 6325 mg, about 6350 mg, about 6375 mg, about 6400 mg, about 6425 mg, about 6450 mg, about 6475 mg, about 6500 mg, about 6525 mg, about 6550 mg, about 6575 mg, about 6600 mg, about 6625 mg, about 6650 mg, about 6675 mg, about 6700 mg, about 6725 mg, about 6750 mg, about 6775 mg, about 6800 mg, about 6825 mg, about 6850 mg, about 6875 mg, about 6900 mg, about 6925 mg, about 6950 mg, about 6975 mg, about 7000 mg, about 7025 mg, about 7050 mg, about 7075 mg, about 7100 mg, about 7125 mg, about 7150 mg, about 7175 mg, about 7200 mg, about 7225 mg, about 7250 mg, about 7275 mg, about 7300 mg, about 7325 mg, about 7350 mg, about 7375 mg, about 7400 mg, about 7425 mg, about 7450 mg, about 7475 mg, about 7500 mg, about 7525 mg, about 7550 mg, about 7575 mg, about 7600 mg, about 7625 mg, about 7650 mg, about 7675 mg, about 7700 mg, about 7725 mg, about 7750 mg, about 7775 mg, about 7800 mg, about 7825 mg, about 7850 mg, about 7875 mg, about 7900 mg, about 7925 mg, about 7950 mg, about 7975 mg, about 8000 mg, about 8025 mg, about 8050 mg, about 8075 mg, about 8100 mg, about 8125 mg, about 8150 mg, about 8175 mg, about 8200 mg, about 8225 mg, about 8250 mg, about 8275 mg, about 8300 mg, about 8325 mg, about 8350 mg, about 8375 mg, about 8400 mg, about 8425 mg, about 8450 mg, about 8475 mg, about 8500 mg, about 8525 mg, about 8550 mg, about 8575 mg, about 8600 mg, about 8625 mg, about 8650 mg, about 8675 mg, about 8700 mg, about 8725 mg, about 8750 mg, about 8775 mg, about 8800 mg, about 8825 mg, about 8850 mg, about 8875 mg, about 8900 mg, about 8925 mg, about 8950 mg, about 8975 mg, about 9000 mg, about 9025 mg, about 9050 mg, about 9075 mg, about 9100 mg, about 9125 mg, about 9150 mg, about 9175 mg, about 9200 mg, about 9225 mg, about 9250 mg, about 9275 mg, about 9300 mg, about 9325 mg, about 9350 mg, about 9375 mg, about 9400 mg, about 9425 mg, about 9450 mg, about 9475 mg, about 9500 mg, about 9525 mg, about 9550 mg, about 9575 mg, about 9600 mg, about 9625 mg, about 9650 mg, about 9675 mg, about 9700 mg, about 9725 mg, about 9750 mg, about 9775 mg, about 9800 mg, about 9825 mg, about 9850 mg, about 9875 mg, about 9900 mg, about 9925 mg, about 9950 mg, about 9975 mg, or about 10,000 mg.

In one embodiment, a composition for use in methods of the disclosure comprises eicosapentaenoic acid, or a pharmaceutically acceptable ester, derivative, conjugate or salt thereof, or mixtures of any of the foregoing, collectively referred to herein as "EPA." The term "pharmaceutically acceptable" in the present context means that the substance in question does not produce unacceptable toxicity to the subject or interaction with other components of the composition. In one embodiment, derivatives of EPA include, but are not limited to, methyl or other alkyl esters, re-esterified monoglycerides, re-esterified diglycerides and re-esterified triglycerides or mixtures thereof. In one embodiment, such derivatives of EPA are administered daily in amounts containing the same number of moles of EPA contained in 4 grams of ethyl icosapentate.

In another embodiment, the EPA comprises an eicosapentaenoic acid ester. In another embodiment, the EPA comprises a $C_1$-$C_5$ alkyl ester of eicosapentaenoic acid. In another embodiment, the EPA comprises eicosapentaenoic acid ethyl ester (E-EPA), eicosapentaenoic acid methyl ester, eicosapentaenoic acid propyl ester, or eicosapentaenoic acid butyl ester.

In another embodiment, the EPA is in the form of ethyl-EPA, methyl-EPA, lithium EPA, mono-, di- or triglyceride EPA or any other ester or salt of EPA, or the free acid form of EPA. The EPA may also be in the form of a 2-substituted derivative or other derivative which slows down its rate of oxidation but does not otherwise change its biological action to any substantial degree. Where any particular form of EPA (e.g. eicosapentaenoic acid ethyl ester, icosapent ethyl or E-EPA) is referred to throughout this application, any pharmaceutically acceptable derivative of EPA can be substituted in its place including icosapent methyl or eicosapentaenoic acid in free acid form. Eicosapentaenoic acid ethyl ester, icosapent ethyl, and E-EPA are referenced interchangeably.

In another embodiment, EPA is present in a composition useful in accordance with methods of the disclosure in an amount of about 50 mg to about 5000 mg, about 75 mg to about 2500 mg, or about 100 mg to about 1000 mg, for example about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 525 mg, about 550 mg, about 575 mg, about 600 mg, about 625 mg, about 650 mg, about 675 mg, about 700 mg, about 725 mg, about 750 mg, about 775 mg, about 800 mg, about 825 mg, about 850 mg, about 875 mg, about 900 mg, about 925 mg, about 950 mg, about 975 mg, about 1000 mg, about 1025 mg, about 1050 mg, about 1075 mg, about 1100 mg, about 1025 mg, about 1050 mg, about 1075 mg, about 1200 mg, about 1225 mg, about 1250 mg, about 1275 mg, about 1300 mg, about 1325 mg, about 1350 mg, about 1375 mg, about 1400 mg, about 1425 mg, about 1450 mg, about 1475 mg, about 1500 mg, about 1525 mg, about 1550 mg, about 1575 mg, about 1600 mg, about 1625 mg, about 1650 mg, about 1675 mg, about 1700 mg, about 1725 mg, about 1750 mg, about 1775 mg, about 1800 mg, about 1825 mg, about 1850 mg, about 1875 mg, about 1900 mg, about 1925 mg, about 1950 mg, about 1975 mg, about 2000 mg, about 2025 mg, about 2050 mg, about 2075 mg, about 2100 mg, about 2125 mg, about 2150 mg, about 2175 mg, about 2200 mg, about 2225 mg, about 2250 mg, about 2275 mg, about 2300 mg, about 2325 mg, about 2350 mg, about 2375 mg, about 2400 mg, about 2425 mg, about 2450 mg, about 2475 mg, about 2500 mg, about 2525 mg, about 2550 mg, about 2575 mg, about 2600 mg, about 2625 mg, about 2650 mg, about 2675 mg, about 2700 mg, about 2725 mg, about 2750 mg, about 2775 mg, about 2800 mg, about 2825 mg, about 2850 mg, about 2875 mg, about 2900 mg, about 2925 mg, about 2950 mg, about 2975 mg, about 3000 mg, about 3025 mg, about 3050 mg, about 3075 mg, about 3100 mg, about 3125 mg, about 3150 mg, about 3175 mg, about 3200 mg, about 3225 mg, about 3250 mg, about 3275 mg, about 3300 mg, about 3325 mg, about 3350 mg, about 3375 mg, about 3400 mg, about 3425 mg, about 3450 mg, about 3475 mg, about 3500 mg, about 3525 mg, about 3550 mg, about 3575 mg, about 3600 mg, about 3625 mg, about 3650 mg, about 3675 mg, about 3700 mg, about 3725 mg, about 3750 mg, about 3775 mg, about 3800 mg, about 3825 mg, about 3850 mg, about 3875 mg, about 3900 mg, about 3925 mg, about 3950 mg, about 3975 mg, about 4000 mg, about 4025 mg, about 4050 mg, about 4075 mg, about 4100 mg, about 4125 mg, about 4150 mg, about 4175 mg, about 4200 mg, about 4225 mg, about 4250 mg, about 4275 mg, about 4300 mg, about 4325 mg, about 4350 mg, about 4375 mg, about 4400 mg, about 4425 mg, about 4450 mg, about 4475 mg, about 4500 mg, about 4525 mg, about 4550 mg, about 4575 mg, about 4600 mg, about 4625 mg, about 4650 mg, about 4675 mg, about 4700 mg, about 4725 mg, about 4750 mg, about 4775 mg, about 4800 mg, about 4825 mg, about 4850 mg, about 4875 mg, about 4900 mg, about 4925 mg, about 4950 mg, about 4975 mg, or about 5000 mg.

In another embodiment, a composition useful in accordance with the disclosure contains not more than about 10%, not more than about 9%, not more than about 8%, not more than about 7%, not more than about 6%, not more than about 5%, not more than about 4%, not more than about 3%, not more than about 2%, not more than about 1%, or not more than about 0.5%, by weight, docosahexaenoic acid (DHA), if any. In another embodiment, a composition of the disclosure contains substantially no DHA. In still another embodiment, a composition useful in the present disclosure contains no DHA and/or derivative thereof. In one embodiment, derivatives of DHA include, but are not limited to, methyl or other alkyl esters, re-esterified monoglycerides, re-esterified diglycerides and re-esterified triglycerides or mixtures thereof.

In another embodiment, EPA comprises at least about 70%, at least about 80%, at least about 90%, at least about 95%, at least about 96%, at least about 97%, at least about 98%, at least about 99%, or 1 about 100%, by weight, of all fatty acids present in a composition that is useful in methods of the present disclosure.

In some embodiments, the composition comprises at least 96% by weight of eicosapentaenoic acid ethyl ester and less than about 2% by weight of a preservative. In some embodiments, the preservative is a tocopherol such as all-racemic α-tocopherol.

In another embodiment, a composition useful in accordance with methods of the disclosure contains less than about 10%, less than about 9%, less than about 8%, less than about 7%, less than about 6%, less than about 5%, less than about 4%, less than about 3%, less than about 2%, less than about 1%, less than about 0.5% or less than about 0.25%, by weight of the total composition or by weight of the total fatty acid content, of any fatty acid other than EPA. Illustrative examples of a "fatty acid other than EPA" include linolenic acid (LA), arachidonic acid (AA), docosahexaenoic acid (DHA), alpha-linolenic acid (ALA), stearidonic acid (STA), eicosatrienoic acid (ETA) and/or docosapentaenoic acid (DPA). In another embodiment, a composition useful in accordance with methods of the disclosure contains about 0.1% to about 4%, about 0.5% to about 3%, or about 1% to about 2%, by weight, of total fatty acids other than EPA and/or DHA. In one embodiment, fatty acids other than EPA include derivatives of those fatty acids. Derivatives of the fatty acids include, but are not limited to, methyl or other alkyl esters, re-esterified monoglycerides, re-esterified diglycerides and re-esterified triglycerides or mixtures thereof of the fatty acids.

In another embodiment, a composition useful in accordance with the disclosure has one or more of the following features: (a) eicosapentaenoic acid ethyl ester represents at least about 96%, at least about 97%, or at least about 98%, by weight, of all fatty acids present in the composition; (b) the composition contains not more than about 4%, not more than about 3%, or not more than about 2%, by weight, of total fatty acids other than eicosapentaenoic acid ethyl ester; (c) the composition contains not more than about 0.6%, not more than about 0.5%, or not more than about 0.4% of any individual fatty acid other than eicosapentaenoic acid ethyl ester; (d) the composition has a refractive index (20° C.) of about 1 to about 2, about 1.2 to about 1.8 or about 1.4 to about 1.5; (e) the composition has a specific gravity (20° C.) of about 0.8 to about 1.0, about 0.85 to about 0.95 or about 0.9 to about 0.92; (e) the composition contains not more than about 20 ppm, not more than about 15 ppm or not more than about 10 ppm heavy metals, (f) the composition contains not more than about 5 ppm, not more than about 4 ppm, not more than about 3 ppm, or not more than about 2 ppm arsenic, and/or (g) the composition has a peroxide value of not more than about 5 meq/kg, not more than about 4 meq/kg, not more than about 3 meq/kg, or not more than about 2 meq/kg.

In some embodiments, a composition for use in accordance with the disclosure is a self-emulsifying composition. In some embodiments, the self-emulsifying composition comprises at least one compound selected from the group consisting of an omega-3 fatty acid and derivative thereof (e.g., pharmaceutically acceptable salt and/or ester). In another embodiment, the composition comprises an emulsifier. In some embodiments, the emulsifier has a hydrophilic lipophilic balance (HLB) of at least about 10. Non-limiting examples of emulsifiers include polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin. In another embodiment, the omega-3 fatty acids or derivative thereof are present in an amount of about 50% to about 95% by weight of the total weight of the composition or by weight of the total fatty acids of the total composition. In some embodiments, the omega-3 fatty acid is EPA and/or DHA. In some embodiments, the EPA is present in amount at least about 95%, by weight, of all fatty acids present in the self-emulsifying composition. In another embodiment, the composition contains substantially no DHA. In yet another embodiment, the composition contains substantially no ethanol.

In another embodiment, the composition is a self-emulsifying composition comprising about 50% to about 95% by weight of the total weight of the composition at least one compound selected from the group consisting of omega-3 polyunsaturated fatty acids and derivative thereof (e.g., pharmaceutically acceptable salt and/or ester). In another embodiment, the composition comprises about 1% to about 20% by weight of the total weight of the composition, a sucrose fatty acid ester as an emulsifier having a hydrophilic lipophilic balance of at least about 10. In another embodiment, the composition comprises glycerin. In another embodiment, the composition comprises about 0% to about 5% by weight of the total composition, ethanol. In another embodiment, the self-emulsifying composition comprises about 50% to about 95% by weight of the total weight of the composition, at least one compound selected from the group consisting of omega-3 polyunsaturated fatty acids and derivative thereof; about 1% to about 20%, by weight of the total weight of the composition, a sucrose fatty acid ester as an emulsifier having a HLB of at least about 10; glycerin; and about 0% to about 4% by weight of the total weight of the composition, ethanol. In another embodiment, the sucrose fatty acid ester is one or more of: sucrose laurate, sucrose myristate, sucrose palmitate, sucrose stearate, or sucrose oleate. In another embodiment, the omega-3 polyunsaturated fatty acid is one or more of EPA, DHA, or derivative thereof. In yet another embodiment, the omega-3 polyunsaturated fatty acid is ethyl-EPA and/or ethyl-DHA.

In another embodiment, the composition is a self-emulsifying composition comprising about 50% to about 95% by weight of the total weight of the composition, at least one compound selected from the group consisting of omega-3 polyunsaturated fatty acids and derivative thereof (e.g., pharmaceutically acceptable salt and ester); and about 5% to about 50%, by weight, of the total weight of the composition an emulsifier having a HLB of at least about 10; wherein ethanol content is up to about 4% by weight of the total weight of the composition. In some embodiments, the omega-3 polyunsaturated fatty acid is EPA and/or DHA. In another embodiment, the composition does not contain ethanol. In another embodiment, the emulsifier is at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin. In another embodiment, the emulsifier is at least one member selected from the group consisting of polyoxyethylene hydrogenated castor oil, polyoxyethylene sorbitan fatty acid ester, polyoxyethylene castor oil, and sucrose fatty acid ester.

In another embodiment, the hydrogenated castor oil is at least one member selected from the group consisting of include polyoxyethylene (20) hydrogenated castor oil, polyoxyethylene (40) hydrogenated castor oil, polyoxyethylene (50) hydrogenated castor oil, polyoxyethylene (60) hydrogenated castor oil, or polyoxyethylene (100) hydrogenated castor oil. In another embodiment, the polyoxyethylene sorbitan fatty acid ester is at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate. In another embodiment, the sucrose fatty acid ester is at least one member selected from the group consisting of sucrose laurate, sucrose myristate, sucrose palmitate, sucrose stearate, and sucrose oleate.

In some embodiments, the composition contains a lecithin selected from the group consisting of soybean lecithin, enzymatically decomposed soybean lecithin, hydrogenated soybean lecithin, and egg yolk lecithin. In another embodiment, the composition contains a polyhydric alcohol, wherein the polyhydric alcohol is propylene glycol or glycerin. In another embodiment, the composition contains at least one member selected from the group consisting of EPA, DHA, and/or derivative thereof (e.g., their pharmaceutically acceptable salt and ester), wherein the composition contains ethyl-EPA and/or ethyl-DHA. In another embodiment, the composition comprises an emulsifier having a HLB of at least about 10 and is about 10 to about 100 parts by weight in relation to 100 parts by weight of the at least one compound selected from the group consisting of omega-3 polyunsaturated fatty acids and/or derivative thereof (e.g., pharmaceutically acceptable salt and/or ester).

In another embodiment, the self-emulsifying composition comprises about 70% to about 90%, by weight, eicosapentaenoic acid ethyl ester as a first medicinal component. In some embodiments, the composition further comprises about 0.5 to about 0.6%, by weight, water. In some embodiments, the composition comprises about 1% to about 29%, by weight, polyoxyethylene sorbitan fatty acid ester as an emulsifier. In another embodiment, the composition comprises about 1 to about 25 parts, by weight, lecithin in relation to about 100 parts, by weight, eicosapentaenoic acid ethyl ester. In yet another embodiment, the composition comprises pitavastatin, rosuvastatin, or a salt thereof as a second medicinal component. In another embodiment, ethanol and/or polyhydric alcohol constitutes up to about 4% by weight of the total weight of the composition. In another embodiment, the composition comprises about 0.01 to about 1 part, by weight, of pitavastatin or its salt in relation to about 100 parts, by weight, of the eicosapentaenoic acid ethyl ester, or about 0.03 to about 5 parts, by weight, rosuvastatin or its salt in relation to about 100 parts, by weight, eicosapentaenoic acid ethyl ester as a second medicinal component. In some embodiments, the composition is encapsulated in a hard capsule and/or a soft capsule, wherein a capsule film of the soft capsule may contain gelatin. In another embodiment, the self-emulsifying composition further comprises polyoxyethylene hydrogenated castor oil and/or polyoxyethylene castor oil. In another embodiment, the emulsifier comprises polyoxyethylene sorbitan fatty acid ester and polyoxyethylene castor oil. In some embodiments, the pitavastatin, rosuvastatin, or a salt thereof is pitavastatin calcium or rosuvastatin calcium. In another embodiment, the lechtin is soybean lechtin. In another embodiment, the polyoxyethylene sorbitan fatty acid ester is polyoxyethylene (20) sorbitan monooleate.

In some embodiments, the self-emulsifying composition comprising E-EPA has improved bioavailability compared as compared to a standard E-EPA formulation. A standard E-EPA formulation is a formulation that is not self-emulsifying. In some embodiments, a self-emulsifying composition comprising about 1.8 to about 3.8 g of E-EPA has substantially equivalent bioavailability to about 4 g E-EPA that is not formulated as a self-emulsifying composition. In some embodiments, the self-emulsifying comprising E-EPA is assessed for a bioequivalence to about 4 g E-EPA that is not formulated as a self-emulsifying using for example, U.S. Food and Drug Administration (FDA) guidelines.

In another embodiment, compositions useful in accordance with methods of the disclosure are orally deliverable. The terms "orally deliverable" or "oral administration" herein include any form of delivery of a therapeutic agent or a composition thereof to a subject wherein the agent or composition is placed in the mouth of the subject, whether or not the agent or composition is swallowed. Thus "oral administration" includes buccal and sublingual as well as esophageal administration. In one embodiment, the composition is present in a capsule, for example a soft gelatin capsule.

A composition for use in accordance with the disclosure can be formulated as one or more dosage units. The terms "dose unit" and "dosage unit" herein refer to a portion of a pharmaceutical composition that contains an amount of a therapeutic agent suitable for a single administration to provide a therapeutic effect. Such dosage units may be administered one to a plurality (i.e. 1 to about 10, 1 to 8, 1 to 6, 1 to 4 or 1 to 2) of times per day, or as many times as needed to elicit a therapeutic response.

In one embodiment, compositions of the disclosure, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, exhibit at least about 90%, at least about 95%, at least about 97.5%, or at least about 99% of the active ingredient(s) originally present therein.

Therapeutic Methods

In one embodiment, the disclosure provides a method for treatment and/or prevention of cardiovascular-related disease and disorders. The term "cardiovascular-related disease and disorders" herein refers to any disease or disorder of the heart or blood vessels (i.e. arteries and veins) or any symptom thereof. Non-limiting examples of cardiovascular-related disease and disorders include hypertriglyceridemia, hypercholesterolemia, mixed dyslipidemia, coronary heart disease, vascular disease, stroke, atherosclerosis, arrhythmia, hypertension, myocardial infarction, and other cardiovascular events.

The term "treatment" in relation a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development if already present.

In various embodiments, the present disclosure provides methods of reducing a risk of a cardiovascular event in a subject on statin therapy. In some embodiments, the methods comprise (a) identifying a subject on statin therapy and having a fasting baseline triglyceride level of about 135 mg/dL to about 500 mg/dL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day. The terms "composition" and "pharmaceutical composition" as provided herein are referenced interchangeably.

In some embodiments, the present disclosure provides methods of reducing a risk of heart failure in a subject. In some embodiments, the methods comprise (a) identifying a subject on statin therapy and having a fasting baseline triglyceride level of about 135 mg/dL to about 500 mg/dL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day.

In some embodiments, the methods of reducing a risk of heart failure in a subject comprise administering to said subject ethyl icosapentate daily for a period effective to reduce the risk of heart failure. In some embodiments, the subject is administered about 4 g of ethyl icosapentate per day for a period effective to reduce the risk of heart failure In some embodiments, the present disclosure provides methods of reducing a risk of heart failure in a subject. In some embodiments, the methods comprise (a) identifying a subject on statin therapy and having a baseline serum and/or plasma EPA level of about 26 µg/mL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day.

In some embodiments, the methods of reducing a risk of heart failure in a subject having a baseline serum and/or plasma EPA level of about 26 µg/mL comprise administering to said subject ethyl icosapentate daily for a period effective to reduce the risk of heart failure. In some embodiments, the subject is administered about 4 g of ethyl icosapentate per day for a period effective to reduce the risk of heart failure In some embodiments, the present disclosure provides methods of reducing a risk of heart failure in a subject on statin therapy. In some embodiments, the methods comprise (a) identifying a subject on statin therapy and having a fasting baseline triglyceride level of about 135 mg/dL to about 500 mg/dL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day.

In some embodiments, the methods of reducing a risk of heart failure in a subject on statin therapy comprise administering to said subject ethyl icosapentate daily for a period effective to reduce the risk of heart failure. In some embodiments, the subject is administered about 4 g of ethyl icosapentate per day for a period effective to reduce the risk of heart failure In some embodiments, the present disclosure provides methods of reducing a risk of heart failure in a subject on statin therapy. In some embodiments, the methods comprise (a) identifying a subject on statin therapy and having a baseline serum and/or plasma EPA level of about 26 µg/mL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day.

In some embodiments, the methods of reducing a risk of heart failure in a subject having a baseline serum and/or plasma EPA level of about 26 µg/mL and on statin therapy comprise administering to said subject ethyl icosapentate daily for a period effective to reduce the risk of heart failure. In some embodiments, the subject is administered about 4 g of ethyl icosapentate per day for a period effective to reduce the risk of heart failure.

In some embodiments, the present disclosure provides methods of reducing a risk of heart failure in a subject by administration of ethyl icosapentate daily for a period effective to increase said subject's baseline serum and/or plasma EPA level to at least about 104 µg/mL. In some embodiments, the subject has a baseline serum and/or plasma EPA level of about 26 µg/mL. In some embodiments, the subject is administered ethyl icosapentate daily for a period effective to increase said subject's baseline serum and/or plasma EPA level to about 104 µg/mL to about 175 µg/mL. In some embodiments, the subject is administered ethyl icosapentate daily for a period effective to increase said subject's baseline serum and/or plasma EPA level to at least about 175 µg/mL. In some embodiments, the subject is administered about 4 g of ethyl icosapentate per day.

In some embodiments, after administration of ethyl icosapentate, the subject has a baseline serum and/or plasma EPA level of at least about 100 µg/mL, at least about 110 µg/mL, at least about 120 µg/mL, at least about 130 µg/mL, at least about 140 µg/mL, at least about 150 µg/mL, at least about 160 µg/mL, at least about 170 µg/mL, at least about 180 µg/mL, at least about 190 µg/mL, at least about 200 µg/mL, at least about 210 µg/mL, at least about 220 µg/mL, at least about 230 µg/mL, at least about 240 µg/mL, at least about 250 µg/mL, at least about 260 µg/mL, at least about 270 µg/mL, at least about 280 µg/mL, at least about 290 µg/mL, or at least about 300 µg/mL.

In another embodiment, the present disclosure provides methods of reducing risk of heart failure in a subject having a baseline serum and/or plasma EPA level of about 26 µg/mL, the method comprising administering to said subject ethyl icosapentate daily for a period effective to increase said subject's baseline serum and/or plasma EPA level to at least about 104 µg/mL. In some embodiments, the subject is administered ethyl icosapentate daily for a period effective to increase said subject's baseline serum and/or plasma EPA level to about 104 µg/mL to about 175 µg/mL. In some embodiments, the subject is administered ethyl icosapentate daily for a period effective to increase said subject's baseline serum and/or plasma EPA level to at least about 175 µg/mL. In some embodiments, the subject is administered about 4 g of ethyl icosapentate per day.

In some embodiments, the present disclosure provides methods of reducing a risk of heart failure, wherein the subject further exhibits a reduction in risk of one or more of cardiovascular death, myocardial infarction, stroke, coronary revascularization, and unstable angina.

In some embodiments, the heart failure is new heat failure. In some embodiments, the heart failure is new heart failure requiring hospitalization.

In some embodiments, the present disclosure provides methods of reducing a risk of a heart failure in a subject on low, medium, or high statin therapy. In some embodiments, the methods comprise administering to the subject a composition comprising eicosapentaenoic acid or derivative thereof per day and a low, medium, or high intensity statin therapy. In some embodiments, the low intensity statin therapy includes about 5 mg to about 10 mg of simvastatin. In some embodiments, the medium intensity statin therapy includes about 5 mg to about 10 mg of rosuvastatin, about 10 mg to about 20 mg of atorvastatin, about 20 mg to 40 mg of simvastatin, or about 10 mg to about 20 mg of simvastatin plus about 5 mg to about 10 mg of ezetimibe. In some embodiments, the high intensity statin therapy includes about 20 mg to about 40 mg rosuvastatin, about 40 mg to about 80 mg of atorvastatin, about 80 mg of simvastatin, or about 40 mg to about 80 mg of simvastatin plus about 5 mg to about 10 mg of ezetimibe. In some embodiments, the subject administered the high statin therapy a greater reduction in a cardiovascular event as compared to a subject in either a low or medium statin therapy. In some embodiments, the subject on a medium statin therapy exhibits a greater reduction in a cardiovascular event as compared to a subject on either a high or low statin therapy. In some embodiments, the subject on a low statin therapy exhibits a greater reduction in a cardiovascular evet as compared to a subject of a high or a medium statin therapy. In some embodiments, the greater reduction is a reduction of at least about 5%, at least about 10%, at least about 20%, at least about 30%, at least about 50%, at least about 60%, at least about 70%, at least about 80%, at least about 90%, at least about 100%, or more.

In some embodiments, the present disclosure provides methods of reducing heart failure in a subject having a baseline serum and/or plasma EPA level of at least about 104 µg/mL after administration ethyl icosapentate as compared to a second subject having a baseline serum and/or plasma EPA level of less than about 104 µg/mL after administration of ethyl icosapentate. In some embodiments, the subject having a baseline serum and/or plasma EPA level of less than about 104 µg/mL after administration of ethyl icosapentate exhibits no statistically significant reduction in risk of heart failure.

In various embodiments, the present disclosure provides methods of reducing a risk of a heart failure in a subject on statin therapy. In some embodiments, the methods comprise (a) identifying a subject on statin therapy and having a fasting baseline triglyceride level of about 80 mg/dL to about 1500 mg/dL, wherein said subject has established cardiovascular disease or has a high risk of developing cardiovascular disease; and (b) administering to the subject a composition comprising about 1 g to about 4 g of eicosapentaenoic acid (free acid) or derivative thereof (ethyl or methyl ester) per day. In some embodiments, the reduction in a risk of a cardiovascular event is not correlated to a reduction in the subject's triglyceride levels.

In some embodiments, the present disclosure provides methods of reducing a risk of a cardiovascular event in a subject on statin therapy with or without an associated in reduction a baseline triglyceride level of the subject. As such, a reduction of cardiovascular events is not correlated to a reduction in the subject's triglyceride levels. Accordingly, regardless of whether the subject exhibits a reduction in triglyceride levels, the subject experiences a reduction in a risk of a cardiovascular event. In some embodiments, the methods comprise administering to the subject a composition comprising eicosapentaenoic acid or derivative thereof, wherein the subject does not exhibit a statistically significant change in fasting triglyceride levels for a period of time after administration of the composition. In some embodiments, the period of time is about 1 year to about 5 years, about 1 year to about 6 years, about 1 year to about 7 years, about 1 year to about 8 years, or about 1 year to about 9 years. In another embodiment, the subject exhibits a reduction in fasting triglycerides at a period time of greater than about 5 years, greater than about 6 years, greater than about 7 years, greater than about 8 years, greater than about 9 years, or greater than about 10 years.

In some embodiments, the present disclosure provides methods of reducing a risk of total cardiovascular events in a subject on statin therapy. In some embodiments, the methods comprise administering to the subject a composition comprising eicosapentaenoic acid or derivative thereof. Total cardiovascular events include a first, second, third, fourth, fifth, sixth, eight, ninth, tenth or more cardiovascular event. In some embodiments, the subject has not experienced a cardiovascular event, but is at a high risk for experiencing a cardiovascular event. In some embodiments, the subject has experienced multiple cardiovascular events (i.e., a second, third, fourth, or more) and a reduction in a risk of any subsequent cardiovascular event. In some embodiments, the total cardiovascular events are reduced by at least about 20%, at least about 25%, at least about 30%, at least about 35%, at least about 40%, at least about 45%, or at least about 50%. In some embodiments, the total cardiovascular events are reduced regardless of the subject's fasting baseline triglyceride level. For example, total cardiovascular events are reduced in a subject having a fasting baseline triglyceride level in a low, medium, or high tertile. Subjects in the low baseline fasting triglyceride tertile have triglyceride levels between about 80 mg/dL to about 190 mg/dL (median triglyceride level of 160 mg/dL), subjects in the medium baseline fasting triglyceride tertile have triglyceride levels between about 191 mg/dL to about 250 mg/dL (median triglyceride level of 215 mg/dL), and lastly, subjects in the high baseline fasting triglyceride tertile have triglyceride levels between about 251 mg/dL to about 1400 mg/dL (median triglyceride level of 304 mg/dL).

In some embodiments, the present disclosure provides methods of reducing a cardiovascular event in a subject on statin therapy, the methods comprising instructing or having instructed a caregiver of the subject to inquire if the subject has or previously has had atrial fibrillation and/or flutter, assessing or having assessed whether the subject has or has previously had symptoms of atrial fibrillation and/or flutter, monitoring or having monitored the subject for symptoms of atrial fibrillation and/or flutter, and/or providing or having provided guidance to a caregiver of the subject to monitor the subject for symptoms of atrial fibrillation and/or flutter. In some embodiments, the methods further comprise administering or having administered to the subject a composition comprising of eicosapentaenoic acid or derivative thereof per day.

In some embodiments, the present disclosure provides methods of reducing an incidence of a cardiovascular event in a subject on statin therapy. In some embodiments, the methods comprise administering to the subject a composition comprising eicosapentaenoic acid or derivative thereof per day, wherein the subject experiences atrial fibrillation and/or flutter and a reduction in or no cardiovascular event. For example, administration of the composition shifts the cardiovascular event to a less medically severe outcome of atrial fibrillation and/or flutter. As such, in some embodiments, the subject experiences atrial fibrillation and/or flutter instead of a cardiovascular event. In another embodiment, the subject exhibits an increase in the symptoms of atrial fibrillation and/or flutter and a reduction in a cardiovascular event as compared to baseline or a placebo control. In some embodiments, the increase in the symptoms of atrial fibrillation and/or flutter are statistically significant as compared to baseline or a placebo control. For example, the symptoms of atrial fibrillation and/or flutter increase by at least about 1%, at least about 2%, at least about 3%, at least about 4%, or at least about 5%. In yet another embodiment, an incidence of atrial fibrillation and/or flutter requiring hospitalization is greater in the subject as compared to baseline or a placebo control. In some embodiments, the subject experiences a reduction in heart rate.

In some embodiments, the present disclosure provides methods of reducing a risk of a cardiovascular event in a subject on low, medium, or high statin therapy. In some embodiments, the methods comprise administering to the subject a composition comprising eicosapentaenoic acid or derivative thereof per day and a low, medium, or high intensity statin therapy. In some embodiments, the low intensity statin therapy includes about 5 mg to about 10 mg of simvastatin. In some embodiments, the medium intensity statin therapy includes about 5 mg to about 10 mg of rosuvastatin, about 10 mg to about 20 mg of atorvastatin, about 20 mg to 40 mg of simvastatin, or about 10 mg to about 20 mg of simvastatin plus about 5 mg to about 10 mg of ezetimibe. In some embodiments, the high intensity statin therapy includes about 20 mg to about 40 mg rosuvastatin, about 40 mg to about 80 mg of atorvastatin, about 80 mg of simvastatin, or about 40 mg to about 80 mg of simvastatin plus about 5 mg to about 10 mg of ezetimibe. In some embodiments, the subject administered the high statin therapy a greater reduction in a cardiovascular event as compared to a subject in either a low or medium statin therapy. In some embodiments, the subject on a medium statin therapy exhibits a greater reduction in a cardiovascular event as compared to a subject on either a high or low statin therapy. In some embodiments, the subject on a low statin therapy exhibits a greater reduction in a cardiovascular evet as compared to a subject of a high or a medium statin therapy. In some embodiments, the greater reduction is a reduction of at least about 5%, at least about 10%, at least about 20%, at least about 30%, at least about 50%, at least about 60%, at least about 70%, at least about 80%, at least about 90%, at least about 100%, or more.

In some embodiments, the present disclosure provides methods of delaying an onset of: (a) non-fatal myocardial infarction; (b) fatal or non-fatal stroke; (c) cardiovascular death; (d) unstable angina; (e) coronary revascularization; (f) hospitalization for unstable angina; (g) composite of cardiovascular death or nonfatal myocardial infarction; (h) fatal or nonfatal myocardial infarction; (i) non-elective coronary revascularization represented the composite of emergent or urgent classifications; (j) cardiovascular death; (k) unstable angina determined to be caused by myocardial ischemia by invasive or non-invasive testing and requiring emergent hospitalization; and/or (l) a composite of total mortality, nonfatal myocardial infarction, and/or nonfatal stroke. An onset of a disease and/or cardiovascular event refers to a first appearance of a sign and/or symptom of the cardiovascular event. In some embodiments, delaying an onset of a cardiovascular event prevents the subject from experiencing the cardiovascular event and/or developing any further symptoms of the cardiovascular event. In some embodiments, the methods comprise administering a composition comprising eicosapentaenoic acid or derivative thereof per day.

In yet another embodiment, the present disclosure provides methods of reducing risk of occurrence of one or more components of a 3-point composite endpoint composed of cardiovascular death, non-fatal myocardial infarction, or non-fatal stroke in a subject on statin therapy or reducing risk occurrence of one or more components of a 5-point composite endpoint composed of cardiovascular death, non-fatal stroke, non-fatal myocardial infarction, coronary revascularization, or unstable angina requiring hospitalization in a subject on statin therapy. In some embodiments, each of the individual components of 3-point composite and 5-point composite endpoints is reduced. For example, each of cardiovascular death, non-fatal myocardial infarction, and non-fatal stroke are reduced within the combination. In some embodiments, the methods comprise administering a composition comprising eicosapentaenoic acid or derivative thereof per day. In some embodiments, the 3-point composite endpoint or the 5-point composite endpoint is reduced by at least about 20%, at least about 30%, at least about 40%, or at least about 50%. In some embodiments, each of the individual components of the 3-point composite endpoint or the 5-point composite endpoint is reduced by at least about 20%, at least about 30%, at least about 40%, or at least about 50%.

In another embodiment, the present disclosure provides methods of reducing a cardiovascular event, the methods comprising administering a composition comprises EPA or derivative thereof that is formulated such that when administered to the subject, the composition provides an amount of EPA or derivative thereof effective to achieve an efficacy equivalent dose to about a 4 g dose of EPA or derivative thereof but at a lower daily dose of EPA or derivative thereof. In some embodiments, the lower daily dose of the EPA or derivative thereof of is not more than about 3.8 g, not more than about 3.6 g, not more than about 3.4 g, not more than about 3.2 g, not more than about 3 g, not more than about 2.8 g, not more than about 2.6 g, or not more than about 2.5 g. In some embodiments, the lower daily dose of the EPA or derivative thereof is reduced by at least about 10%, at least about 20%, at least about 30%, at least about 40% in the subject as compared to a baseline or placebo control. In one embodiment, administering the composition to the subject results in an improved pharmacokinetic profile in the subject as compared a control subject, wherein the subject and control subject are in either or fed or fasting state, and wherein the pharmacokinetic profile is defined by maximum serum concentration ($C_{max}$) and area under the curve (AUC). In some embodiments, the control subject is on a statin therapy and administered a placebo or other fatty acid composition such as Lovaza comprised of 365 mg of E-EPA and 375 mg of E-DHA.

In some embodiments, the present disclosure provides methods of reducing a cardiovascular event in a subject on a statin therapy, the methods comprising administering a composition comprising EPA or derivative thereof, wherein the subject does not experience an adverse event. Non-limiting examples of adverse events include back pain, nasopharyngitis, arthralgia, bronchitis, oedema peripheral, dyspnea, osteoarthritis, cataract, fatigue, constipation, musculoskeletal pain, gout, fall, type 2 diabetes mellitus, gastroesophageal reflux disease, insomnia, acute kidney injury, hepatic disorders, bleeding related disorders (e.g., gastrointestinal or central nervous system bleeding), newly diagnosed diabetes, newly diagnosed neoplasms (e.g., benign or malignant neoplasms), upper respiratory tract infection, chest pain, peripheral edema, pneumonia, influenza, urinary tract infection, cough, dizziness, pain in an extremity, angina pectoris, and anemia.

In yet another embodiment, the present disclosure provides methods of reducing a cardiovascular event in a subject on a statin therapy and less than about 65 years of age or greater than about 65 years of age, the method comprising administering to the subject a composition comprising EPA or derivative thereof. In some embodiments, the degree by which the cardiovascular event is reduced is dependent upon the age of the subject. For example, in some embodiments, the subject less than about 65 years of age exhibits a statistically significant reduction in a cardiovascular event as compared to a subject greater than about 65 years of age. Conversely, in some embodiments, the subject greater than about 65 years of age exhibits a statistically significant reduction in a cardiovascular event as compared to a subject less than about 65 years of age. As such, in some embodiments, the methods for reducing a cardiovascular event are correlated to the age of the subject.

In some embodiments, the present disclosure provides methods of reducing a cardiovascular event in a subject on a statin therapy, the methods comprising administering to the subject a self-emulsifying composition. In some embodiments, the self-emulsifying composition comprises at least one compound selected from the group consisting of an omega-3 fatty acid and derivative thereof (e.g., pharmaceutically acceptable salt and/or ester). In another embodiment, the composition comprises an emulsifier. In some embodiments, the emulsifier has a hydrophilic lipophilic balance (HLB) of at least about 10. Non-limiting examples of emulsifiers include polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin. In another embodiment, the omega-3 fatty acids or derivative thereof are present in an amount of about 50% to about 95% by weight of the total weight of the composition or by weight of the total fatty acids of the total composition. In some embodiments, the omega-3 fatty acid is EPA and/or DHA. In some embodiments, the EPA is present in amount at least about 95%, by weight, of all fatty acids present in the self-emulsifying composition. In another embodiment, the composition contains substantially no DHA. In yet another embodiment, the composition contains substantially no ethanol.

In some embodiments, the subject has symptoms of atrial fibrillation and/or flutter. Non-limiting examples of symptoms of atrial fibrillation and/or flutter include heart rate greater than about 100 beats per minute (bpm); heart palpitations; shortness of breath; pain, pressure, tightness or discomfort in chest; dizziness; lightheadedness; or fainting. In some embodiments the subject has a risk factor for atrial fibrillation and/or flutter including (a) heart failure; (b) previous heart attack; (c) heat valve abnormalities; (d) high blood pressure; (e) thyroid dysfunction; (f) chronic lung disease; (g) diabetes; (h) obesity; and (i) congenital heart disease.

In some embodiments, the methods further comprising monitoring a subject for atrial fibrillation and/or flutter or for symptoms of atrial fibrillation and/or flutter. Non-limiting examples for methods to monitor atrial fibrillation and/or flutter include electrocardiograms (ECGs), implantable pacemakers, implantable cardioverter defibrillators, and/or subcutaneous implantable cardiac monitors.

In some embodiments, the subject has atrial fibrillation and/or flutter or has symptoms of atrial fibrillation and/or flutter and has been determined to have a heart rate of about 80 bpm, about 85, bpm, about 90 bpm, about 95 bpm, about 100 bpm, about 105 bpm, about 110 bpm, about 115 bpm, about 120 bpm, about 125 bpm, about 130 bpm, about 135 bmp, about 140 bmp, about 145 bmp, about 150 bpm, about 155 bpm, about 160 bpm, about 165 bpm, about 170 bpm, about 175 bpm, about 180 bpm, about 185, bpm, about 190 bpm or a heart rate between about 80 bpm to about 100 bpm, about 90 bpm to about 200 bpm, about 100 bpm to about 175 bpm, about 120 bpm to about 180 bpm, or about 85 bpm to about 200 bpm.

In some embodiments, the present disclosure provides methods of reducing blood pressure in a subject. In one embodiment, administration of 4 g per day of comprising EPA or derivative thereof (E-EPA) for a period at least 1, 2, 3 or 4 year reduces systolic blood pressure by at least about 1 mm Hg and reduces diastolic blood pressure aby at least about 0.5 mm Hg, compared to baseline or a placebo control subject.

In some embodiments, the subject has a fasting baseline triglyceride level of about 135 mg/dL to about 500 mg/dL, for example about 135 mg/dL to about 500 mg/dL, about 150 mg/dL to about 500 mg/dL, about 200 mg/dL to about 499 mg/dL or about 200 mg/dL to <500 mg/dL. In some embodiments, the subject has a fasting baseline triglyceride level of about 50 mg/dL to about 1500 mg/dL, for example about 50 mg/dL to about 1500 mg/dL, about 80 mg/dL to about 1500 mg/dL, about 50 mg/dL to about 190 mg/dl, about 80 mg/dL to about 190 mg/dl, about 190 mg/dL to about 250 mg/dL, about 250 mg/dL to about 1400 mg/dL. In one embodiment, the subject has a fasting baseline triglyceride level of about 80 mg/dL to about 1400 mg/dL. In some embodiments, the subject or subject group has a baseline triglyceride level (or median baseline triglyceride level in the case of a subject group), fed or fasting, of about 50 mg/dL, about 55 mg/dL, about 60 mg/dL, about 65 mg/dL, about 70 mg/dL, about 75 mg/dL, about 80 mg/dL, about 85 mg/dL, about 90 mg/dL, about 95 mg/dL, about 100 mg/dL, about 105 mg/dL, about 110 mg/dL, about 115 mg/dL, about 120 mg/dL, about 125 mg/dL, about 130 mg/dL, about 135 mg/dL, about 140 mg/dL, about 145 mg/dL, about 150 mg/dL, about 155 mg/dL, about 160 mg/dL, about 165 mg/dL, about 170 mg/dL, about 175 mg/dL, about 180 mg/dL, about 185 mg/dL, about 190 mg/dL, about 195 mg/dL, about 200 mg/dL, about 205 mg/dL, about 210 mg/dL, about 215 mg/dL, about 220 mg/dL, about 225 mg/dL, about 230 mg/dL, about 235 mg/dL, about 240 mg/dL, about 245 mg/dL, about 250 mg/dL, about 255 mg/dL, about 260 mg/dL, about 265 mg/dL, about 270 mg/dL, about 275 mg/dL, about 280 mg/dL, about 285 mg/dL, about 290 mg/dL, about 295 mg/dL, about 300 mg/dL, about 305 mg/dL, about 310 mg/dL, about 315 mg/dL, about 320 mg/dL, about 325 mg/dL, about 330 mg/dL, about 335 mg/dL, about 340 mg/dL, about 345 mg/dL, about 350 mg/dL, about 355 mg/dL, about 360 mg/dL, about 365 mg/dL, about 370 mg/dL, about 375 mg/dL, about 380 mg/dL, about 385 mg/dL, about 390 mg/dL, about 395 mg/dL, about 400 mg/dL, about 405 mg/dL, about 410 mg/dL, about 415 mg/dL, about 420 mg/dL, about 425 mg/dL, about 430 mg/dL, about 435 mg/dL, about 440 mg/dL, about 445 mg/dL, about 450 mg/dL, about 455 mg/dL, about 460 mg/dL, about 465 mg/dL, about 470 mg/dL, about 475 mg/dL, about 480 mg/dL, about 485 mg/dL, about 490 mg/dL, about 495 mg/dL, about 500 mg/dL, about 1000 mg/dL, about 1100 mg/dL, about 1200 mg/dL, about 1300 mg/dL, about 1400 mg/dL, about 1500 mg/dL, about 2000 mg/dL, about 2500 mg/dL, about 3000 mg/dL, about 3500 mg/dL, about 4000 mg/dL, about 4500 mg/dL, about 5000 mg/dL, or greater than about 5000 mg/dL. In some embodiments, the subject or subject group has a baseline triglyceride level (or median baseline triglyceride level in the case of a subject group), fed or fasting, greater than or equal to about 80 mg/dL, greater than or equal to about 100 mg/dL, greater than or equal to about 120 mg/dL greater than or equal to about 150 mg/dL, greater than or equal to about 175 mg/dL, greater than or equal to about 250 mg/dL, or greater than equal to about 500 mg/dL, for example about 190 mg/dL to about 250 mg/dL, about 80 mg/dL to about 190 mg/dL, about 250 mg/dL to about 1400 mg/dL, about 200 mg/dL to about 500 mg/dL, about 300 mg/dL to about 1800 mg/dL, about 500 mg/dL to about 1500 mg/dL, or about 80 mg/dL to about 1500 mg/dL.

In some embodiments, the subject or subject group is also on stable therapy with a statin (with or without ezetimibe). In some embodiments, the subject or subject group also has established cardiovascular disease, or is at high risk for establishing cardiovascular disease. In some embodiments, the subject's statin therapy includes administration of one or more statins. For example, and without limitation, the subject's statin therapy may include one or more of: atorvastatin, fluvastatin, lovastatin, pitavastatin, pravastatin, rosuvastatin, and simvastatin. In some embodiments, the subject is additionally administered one or more of: amlodipine, ezetimibe, niacin, and sitagliptin. In some embodiments, the subject's statin therapy includes administration of a statin and ezetimibe. In some embodiments, the subject's statin therapy includes administration of a statin without ezetimibe.

In some embodiments, the statin therapy is classified as monotherapies, combinations, and or 3-hydroxy-3-methyl-glutaryl-coenzyme A (HMG CoA) reductase inhibitor combinations. In some embodiments, the monotherapies include simvastatin, lovastatin, pravastatin, fluvastatin, atorvastatin, cerivastatin, rosuvastatin, or pitavastatin. In some embodiments, the combinations include lovastatin and nicotinic acid, simvastatin and ezetimibe, pravastatin and fenofibrate, simvastatin and fenofibrate, atorvastatin and ezetimibe, or rosuvastatin and ezetimibe. In some embodiments, the HMG CoA inhibitor combinations include simvastatin and acetylsalicylic acid; pravastatin and acetylsalicylic acid; atorvastatin and amlodipine; simvastatin, acetylsalicylic acid, and ramipril; rosuvastatin and acetylsalicylic acid; atorvastatin, acetylsalicylic acid, and ramipril; rosuvastatin, amlodipine, and lisinopril; atorvastatin and acetylsalicylic acid; rosuvastatin and amlodipine; rosuvastatin and valsartan; atorvastatin, amlodipine, and perindopril; atorvastatin, acetylsalicylic acid, and perindopril; rosuvastatin, perindopril, and indapamide; rosuvastatin, amlodipine, and perindopril; or atorvastatin and perindopril.

In some embodiments, the statin therapy is a low, medium (i.e., moderate), or high intensity statin therapy. In some embodiments, the low intensity statin therapy includes about 5 mg to about 10 mg of simvastatin. In some embodiments, the medium intensity statin therapy includes about 5 mg to about 10 mg of rosuvastatin, about 10 mg to about 20 mg of atorvastatin, about 20 mg to about 40 mg of simvastatin, or about 10 mg to about 20 mg of simvastatin plus about 5 mg to about 10 mg of ezetimibe. In some embodiments, the high intensity statin therapy includes about 20 mg to about 40 mg rosuvastatin, about 40 mg to about 80 mg of atorvastatin, about 80 mg of simvastatin, or about 40 mg to about 80 mg of simvastatin plus about 5 mg to about 10 mg of ezetimibe.

In some embodiments, the subject's statin therapy does not include administration of 200 mg or more per day of niacin and/or fibrates. In some embodiments, the subject is not on concomitant omega-3 fatty acid therapy (e.g., is not being administered or co-administered a prescription and/or over-the-counter composition comprising an omega-3 fatty acid active agent). In some embodiments, the subject is not administered or does not ingest a dietary supplement comprising an omega-3 fatty acid.

In some embodiments, the subject has established cardiovascular (CV) disease ("CV disease" or "CVD"). The status of a subject as having CV disease can be determined by any suitable method known to those skilled in the art. In some embodiments, a subject is identified as having established CV disease by the presence of any one of: documented coronary artery disease, documented cerebrovascular disease, documented carotid disease, documented peripheral arterial disease, or combinations thereof. In some embodiments, a subject is identified as having CV disease if the subject is at least 45 years old and: (a) has one or more stenosis of greater than 50% in two major epicardial coronary arteries; (b) has had a documented prior MI; (c) has been hospitalized for high-risk NSTE ACS with objective evidence of ischemia (e.g., ST-segment deviation and/or biomarker positivity); (d) has a documented prior ischemic stroke; (e) has symptomatic artery disease with at least 50% carotid arterial stenosis; (f) has asymptomatic carotid artery disease with at least 70% carotid arterial stenosis per angiography or duplex ultrasound; (g) has an ankle-brachial index ("ABI") of less than 0.9 with symptoms of intermittent claudication; and/or (h) has a history of aorto-iliac or peripheral arterial intervention (catheter-based or surgical).

In some embodiments, the subject or subject group being treated in accordance with methods of the disclosure has a high risk for developing CV disease. For example and without limitation, a subject or subject group has a high risk for developing CV disease if the subject or subject in a subject group is age about 50 or older, has diabetes mellitus (Type 1 or Type 2), and at least one of: (a) is a male age about 55 or older or a female age about 65 or older; (b) is a cigarette smoker or was a cigarette smoker who stopped less than about 3 months prior; (c) has hypertension (e.g., a blood pressure of about 140 mmHg systolic or higher, or greater than about 90 mmHg diastolic); (d) has an HDL-C level of ≤about 40 mg/dL for men or ≤about 50 mg/dL for women; (e) has an hsCRP level of >about 3.0 mg/L; (f) has renal dysfunction (e.g., a creatinine clearance ("CrCL") of greater than about 30 mL/min and less than about 60 mL/min); (g) has retinopathy (e.g., defined as any of: non-proliferative retinopathy, preproliferative retinopathy, proliferative retinopathy, maculopathy, advanced diabetic eye disease, or history of photocoagulation); (h) has microalbuminuria (e.g., a positive micral or other strip test, an albumin/creatinine ratio of ≥about 2.5 mg/mmol, or an albumin excretion rate on timed collection of ≥about 20 mg/min all on at least two successive occasions); (i) has macroalbuminuria (e.g., Albustix or other dip stick evidence of gross proteinuria, an albumin/creatinine ratio of ≥about 25 mg/mmol, or an albumin excretion rate on timed collection of ≥about 200 mg/min all on at least two successive occasions); and/or (j) has an ankle-brachial index of <about 0.9 without symptoms of intermittent claudication.

In some embodiments, the subject's baseline lipid profile is measured or determined prior to administering the composition to the subject. Lipid profile characteristics can be determined by any suitable method known to those skilled in the art including, for example, by testing a fasting or non-fasting blood sample obtained from the subject using standard blood lipid profile assays. In some embodiments, the subject has one or more of: a baseline non-HDL-C value of about 200 mg/dL to about 300 mg/dL; a baseline total cholesterol value of about 250 mg/dL to about 300 mg/dL; a baseline VLDL-C value of about 140 mg/dL to about 200 mg/dL; a baseline HDL-C value of about 10 mg/dL to about 30 mg/dL; a baseline LDL-C value of about 40 mg/dL to about 100 mg/dL; and/or a baseline hsCRP level of about 2 mg/dL or less.

In some embodiments, the cardiovascular event for which risk is reduced is one or more of: cardiovascular death; nonfatal myocardial infarction; nonfatal stroke; coronary revascularization; unstable angina (e.g., unstable angina determined to be caused by myocardial ischemia by, for example, invasive or non-invasive testing, and requiring hospitalization); cardiac arrest; peripheral cardiovascular disease requiring intervention, angioplasty, bypass surgery or aneurysm repair; death; sudden cardiac death, sudden death, and onset of new congestive heart failure. In some embodiments, the cardiovascular event is a first, second, third, fourth, or more cardiovascular event experienced by the subject.

In some embodiments, the subject is administered about 1 g to about 4 g of the composition per day for about 4 months, about 1 year, about 1.25 years, about 1.5 years, about 1.75 years, about 2 years, about 2.25 years, about 2.5 years, about 2.75 years, about 3 years, about 3.25 years, about 3.5 years, about 3.75 years, about 4 years, about 4.25 years, about 4.5 years, about 4.75 years, about 5 years, or more than about 5 years. Thereafter, in some embodiments the subject exhibits one or more of (a) a reduction in triglyceride levels compared to baseline or control;
(b) a reduction in Apo B levels compared to baseline or control;
(c) an increase in HDL-C levels compared to baseline or control;
(d) no increase or increase in LDL-C levels compared to baseline or control;
(e) a reduction in LDL-C levels compared to baseline;
(f) a reduction in non-HDL-C levels compared to baseline or control;
(g an increase in non-HDL-C levels compared to baseline or control;
(h) a reduction in VLDL-C levels compared to baseline or control;
(i) a reduction in total cholesterol levels compared to baseline or control;
(j) a reduction in high sensitivity C-reactive protein (hsCRP) levels compared to baseline or control;
(k) a reduction in high sensitivity troponin (hsTnT) levels compared to baseline or control;
(l) a reduction in a risk of cardiovascular death, coronary revascularization, unstable angina, myocardial infarction, and/or stroke as compared to baseline or control;
(m) a reduction in a risk of cardiac arrest as compared to baseline or control;
(n) a reduction in a risk of sudden death as compared to baseline or control;
(o) a reduction in a first, second, third, fourth, or more cardiovascular event as compared to baseline or placebo control;
(p) a reduction in total cardiovascular events as compared to baseline or control;
(q) a reduction in a 3-point composite endpoint of cardiovascular death, non-fatal myocardial infarction, or non-fatal stroke as compared to baseline or control;
(r) a reduction in a 5-point composite endpoint of cardiovascular death, non-fatal stroke, non-fatal myocardial infarction, coronary revascularization, or unstable angina as compared to baseline or control;
(s) an increase in atrial fibrillation and/or flutter as compared to baseline or control;
(t) an increase in symptoms of atrial fibrillation and/or flutter as compared to baseline or control;
(u) a reduction of total mortality (i.e., death from any cause) as compared to baseline or control;
(v) a reduction in a composite of total mortality, non-fatal myocardial infarction, and stroke as compared to baseline or placebo control;
(w) a reduction in new congestive heart failure (CHF) or new CHF as the primary cause of hospitalization as compared to baseline or control;
(x) a reduction in transient ischemic attack as compared to baseline or control;
(y) a reduction in a risk of amputation for peripheral vascular disease (PVD) as compared to baseline or control;
(z) a reduction in a risk of carotid revascularization as compared to baseline or control;
(aa) a reduction in cardiac arrhythmias as compared to baseline or control;
(bb) a reduction in hypertension as compared to baseline or control;
(cc) a reduction in type 1 or type 2 diabetes as compared to baseline or control;
(dd) a reduction in body weight and/or weight circumference as compared to baseline or control; and/or
(ee) an increase in fasting baseline serum and/or plasma EPA levels as compared to baseline or control.

In one embodiment, methods of the present disclosure comprise measuring baseline levels of one or more markers set forth in (a)-(ee) above prior to dosing the subject or subject group. In another embodiment, the methods comprise administering a composition as disclosed herein to the subject after baseline levels of one or more markers set forth in (a)-(ee) are determined, and subsequently taking an additional measurement of said one or more markers.

In another embodiment, upon treatment with a composition of the present disclosure, the subject exhibits one or more of:

(a) a reduction in triglyceride levels of at least about 5%, at least about 10%, at least about 15%, at least about 20%, at least about 25%, at least about 30%, at least about 35%, at least about 40%, at least about 45%, at least about 50%, or at least about 55% as compared to baseline or control;
(b) a reduction in Apo B levels of at least about 5%, at least about 10%, at least about 15%, at least about 20%, at least about 25%, at least about 30%, at least about 35%, at least about 40%, at least about 45%, at least about 50%, at least about 55% or at least about 75% as compared to baseline or control;
(c) an increase in HDL-C levels of at least about 5%, at least about 10%, at least about 15%, at least about 20%, at least about 25%, at least about 30%, at least about 35%, at least about 40%, at least about 45%, at least about 50%, at least about 55% or at least about 75% as compared to baseline or control;
(d) no increase or an increase in LDL-C levels of less than 30%, less than 20%, less than 10%, less than 5% as compared to baseline or control; and/or
(e) a reduction in LDL-C levels of at least about 5%, at least about 10%, at least about 15%, at least about 20%, at least about 25%, at least about 30%, at least about 35%, at least about 40%, at least about 45%, at least about 50%, or at least about 55% as compared to baseline or control.
(f) a reduction in non-HDL-C levels of at least about 1%, at least about 3%, at least about 5%, at least about 10%, at least about 15%, at least about 20%, at least about 25%, at least about 30%, at least about 35%, at least about 40%, at least about 45%, or at least about 50% as compared to baseline or control;

(g) an increase in non-HDL-C levels of less than 30%, less than 20%, less than 10%, less than 5% (actual % change or median % change), or no increase in non-HDL-C levels as compared to baseline or control;

(h) a reduction in VLDL-C levels of at least about 5%, at least about 10%, at least about 15%, at least about 20%, at least about 25%, at least about 30%, at least about 35%, at least about 40%, at least about 45%, at least about 50%, or at least about 100% compared to baseline or control;

(i) a reduction in total cholesterol levels of at least about 5%, at least about 10%, at least about 15%, at least about 20%, at least about 25%, at least about 30%, at least about 35%, at least about 40%, at least about 45%, at least about 50%, at least about 55% or at least about 75% as compared to baseline or control; and/or (j) a reduction in hsCRP levels of at least about 5%, at least about 10%, at least about 15%, at least about 20%, at least about 25%, at least about 30%, at least about 35%, at least about 40%, at least about 45%, at least about 50%, or at least about 100% as compared to baseline or control;

(k) a reduction in high sensitivity troponin (hsTnT) levels of at least about 5%, at least about 10%, at least about 15%, at least about 20%, at least about 25%, at least about 30%, at least about 35%, at least about 40%, at least about 45%, at least about 50%, or at least about 100% as compared to baseline or control;

(l) a reduction in a risk of cardiovascular death, coronary revascularization, unstable angina, myocardial infarction, and/or stroke of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(m) a reduction in a risk of cardiac arrest of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(n) a reduction in a risk of sudden cardiac death and/or sudden death of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(o) a reduction in a first, second, third, fourth, or more cardiovascular event experienced by the subject of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(p) a reduction in total cardiovascular events of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(q) a reduction in a 3-point composite endpoint of cardiovascular death, non-fatal myocardial infarction, or non-fatal stroke of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(r) a reduction in a 5-point composite endpoint of cardiovascular death, non-fatal stroke, non-fatal myocardial infarction, coronary revascularization, or unstable angina of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(s) an increase in atrial fibrillation and/or flutter of at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, or at least about 10% as compared to baseline or control;

(t) an increase in symptoms of atrial fibrillation and/or flutter of at least about 1%, at least about 1.5%, at least about 2%, at least about 2.5%, at least about 3%, at least about 3.5%, at least about 4%, at least about 4.5%, at least about 5%, at least about 5.5%, at least about 6%, at least about 6.5%, at least about 7%, at least about 7.5%, at least about 8%, at least about 8.5%, at least about 9%, at least about 9.5%, or at least about 10% as compared to baseline or control;

(u) a reduction of total mortality (i.e., death from any cause) of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(v) a reduction in a composite of total mortality, non-fatal myocardial infarction, and stroke of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(w) a reduction in new CHF or new CHF as the primary cause of hospitalization of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(x) a reduction in transient ischemic attack of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(y) a reduction in a risk of amputation for PVD of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(z) a reduction in a risk of carotid revascularization of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(aa) a reduction in cardiac arrhythmias of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(bb) a reduction in hypertension of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(cc) a reduction in type 1 or type 2 diabetes of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control;

(dd) a reduction in body weight and/or weight circumference of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control; and/or (ee) an increase in fasting baseline serum and/or plasma EPA levels of at least about 5%, at least about 10%, at least about 15%, at least about 20%, at least about 25%, at least about 30%, at least about 35%, at least about 40%, at least about 45%, at least about 50%, at least about 55%, at least about 75%, at least about 80%, at least about 85%, at least about 90%, at least about 95%, or at least about 100% as compared to baseline or control.

In one embodiment, the subject or subject group being treated has a baseline EPA blood level on a (mol %) basis of less than 2.6, less than 2.5, less than 2.4, less than 2.3, less than 2.2, less than 2.1, less than 2, less than 1.9, less than 1.8, less than 1.7, less than 1.6, less than 1.5, less than 1.4, less than 1.3, less than 1.2, less than 1.1 or less than 1.

In another embodiment, the subject or subject group being treated has a baseline triglyceride level (or median baseline triglyceride level in the case of a subject group), fed or fasting, of about 135 mg/dL to about 500 mg/dL. In some embodiments, the subject or subject group being treated has a baseline triglyceride level (or median baseline triglyceride level in the case of a subject group), fed or fasting, of about 80 mg/dL to about 1500 mg/dL. In some embodiments, the subject or subject group being treated in accordance with methods of the disclosure is on stable therapy with a statin (with or without ezetimibe). As used herein, the phrase "on stable therapy with a statin" means that the subject or subject group has been on the same daily dose of the same statin for at least 28 days and, if applicable, the same daily dose of ezetimibe for at least 28 days. In some embodiments, the subject or subject group on stable statin therapy has an LDL-C level of about 40 mg/dL to about 100 mg/dL.

In some embodiments, safety laboratory tests of subject blood samples include one or more of: hematology with complete blood count ("CBC"), including RBC, hemoglobin (Hgb), hematocrit (Hct), white cell blood count (WBC), white cell differential, and platelet count; and biochemistry panel including total protein, albumin, alkaline phosphatase, alanine aminotransferase (ALT/SGPT), aspartate aminotransferase (AST/SGOT), total bilirubin, glucose, calcium, electrolytes, (sodium, potassium, chloride), blood urea nitrogen (BUN), serum creatinine, uric acid, creatine kinase, and $HbA_{1c}$.

In some embodiments, a fasting lipid panel associated with a subject includes TG, TC, LDL-C, HDL-C, non-HDL-C, and VLDL-C. In some embodiments, LDL-C is calculated using the Friedewald equation, or is measured by preparative ultracentrifugation (Beta Quant) if the subject's triglyceride level is greater than 400 mg/dL. In some embodiments, LDL-C is measured by ultracentrifugation (Beta Quant) at randomization and again after about one year after randomization.

In some embodiments, a biomarker assay associated with blood obtained from a subject includes hsCRP, Apo B and hsTnT.

In some embodiments, a medical history associated with a subject includes family history, details regarding all illnesses and allergies including, for example, date(s) of onset, current status of condition(s), and smoking and alcohol use.

In some embodiments, demographic information associated with a subject includes day, month and year of birth, race, and gender.

In some embodiments, vital signs associated with a subject include systolic and diastolic blood pressure, heart rate, respiratory rate, and body temperature (e.g., oral body temperature).

In some embodiments, a physical examination of a subject includes assessments of the subject's general appearance, skin, head, neck, heart, lung, abdomen, extremities, and neuromusculature.

In some embodiments, the subject's height and weight are measured. In some embodiments, the subject's weight is recorded with the subject wearing indoor clothing, with shoes removed, and with the subject's bladder empty.

In some embodiments, a waist measurement associated with the subject is measured. In some embodiments, the waist measurement is determined with a tape measure at the top of the subject's hip bone.

In some embodiments, an electrocardiogram associated with the subject is obtained. In some embodiments, an ECG is obtained every year during the treatment/follow-up portion of the study. In some embodiments, the ECG is a 12-lead ECG. In some embodiments, the ECG is analyzed for detection of silent MI.

In some embodiments, subjects randomly assigned to the treatment group receive 4 g per day of a composition comprising at least 96% by weight of eicosapentaenoic acid ethyl ester. In some embodiments, the composition is encapsulated in a gelatin capsule. In some embodiments, subjects in this treatment group continue to take 4 g per day of the composition for about 1 year, about 2 years, about 3 years, about 4 years, about 4.75 years, about 5 years, about 6 years, about 7 years, about 8 years, about 9 years, about 10 years, or more than about 10 years. In some embodiments, a median treatment duration is planned to be about 4 years.

In some embodiments, the present disclosure provides a method of reducing a risk of cardiovascular events in a subject. In some embodiments, the method comprises administering to the subject a composition comprising at least 96% by weight of eicosapentaenoic acid ethyl ester. In some embodiments, the subject is administered about 1 g to about 4 g of the composition per day.

In some embodiments, the reduced risk of CV events is indicated or determined by comparing an amount of time (e.g., an average amount of time) associated with a subject or subject group from first dosing to a first CV event selected from the group consisting of: CV death, nonfatal MI, nonfatal stroke, coronary revascularization, and hospitalization (e.g., emergent hospitalization) for unstable angina determined to be caused by myocardial ischemia (e.g., by invasive or non-invasive testing), to an amount of time (e.g., an average amount of time) associated with a placebo or untreated subject or group of subjects from first dosing with a placebo to a first CV event selected from the group consisting of: CV death, nonfatal MI, nonfatal stroke, coronary revascularization, and hospitalization (e.g., emergent hospitalization) for unstable angina determined to be caused by myocardial ischemia (e.g., by invasive or non-invasive testing), wherein said placebo does not include eicosapentaenoic acid ethyl ester. In some embodiments, the amount of time associated with the subject or group of subjects are compared to the amount of time associated with the placebo or untreated subject or group of subjects are compared using a log-rank test. In some embodiments, the log-rank test includes one or more stratification factors such as CV Risk Category, use of ezetimibe, and/or geographical region.

In some embodiments, the present disclosure provides a method of reducing risk of CV death in a subject on stable statin therapy and having CV disease or at high risk for developing CV disease, comprising administering to the subject a composition as disclosed herein.

In another embodiment, the present disclosure provides a method of reducing risk of recurrent nonfatal myocardial infarction (including silent MI) in a subject on stable statin therapy and having CV disease or at high risk for developing CV disease, comprising administering to the patient one or more compositions as disclosed herein.

In some embodiments, the present disclosure provides a method of reducing risk of nonfatal stroke in a subject on stable statin therapy and having CV disease or at high risk for developing CV disease, comprising administering to the subject a composition as disclosed herein.

In some embodiments, the present disclosure provides a method of reducing risk of coronary revascularization in a subject on stable statin therapy and having CV disease or at high risk for developing CV disease, comprising administering to the subject a composition as disclosed herein.

In some embodiments, the present disclosure provides a method of reducing risk of developing unstable angina caused by myocardial ischemia in a subject on stable statin therapy and having CV disease or at high risk for developing CV disease, comprising administering to the subject a composition as disclosed herein.

In some embodiments, the present disclosure provides a method of reducing risk of cardiac arrest in a subject on stable statin therapy and having CV disease or at high risk for developing CV disease, comprising administering to the subject a composition as disclosed herein.

In some embodiments, the present disclosure provides a method of reducing risk of heart failure in a subject on stable statin therapy and having CV disease or at high risk for developing CV disease, comprising administering to the subject a composition as disclosed herein.

In some embodiments, the present disclosure provides a method of reducing risk of sudden cardiac death and/or sudden death in a subject on stable statin therapy and having CV disease or at high risk for developing CV disease, comprising administering to the subject a composition as disclosed herein.

In some embodiments, the present disclosure provides a method of reducing risk of first, second, third, fourth, or more cardiovascular event in a subject on stable statin therapy and having CV disease or at high risk for developing CV disease, comprising administering to the subject a composition as disclosed herein In another embodiment, any of the methods disclosed herein are used in treatment or prevention of a subject or subjects that consume a traditional Western diet. In one embodiment, the methods of the disclosure include a step of identifying a subject as a Western diet consumer or prudent diet consumer and then treating the subject if the subject is deemed a Western diet consumer. The term "Western diet" herein refers generally to a typical diet consisting of, by percentage of total calories, about 45% to about 50% carbohydrate, about 35% to about 40% fat, and about 10% to about 15% protein. A Western diet may alternately or additionally be characterized by relatively high intakes of red and processed meats, sweets, refined grains, and desserts, for example more than 50%, more than 60% or more or 70% of total calories come from these sources.

In another embodiment, a composition as described herein is administered to a subject once or twice per day. In another embodiment, 1, 2, 3 or 4 capsules, each containing about 1 g of a composition as described herein, are administered to a subject daily. In another embodiment, 1 or 2 capsules, each containing about 1 g of a composition as described herein, are administered to the subject in the morning, for example between about 5 am and about 11 am, and 1 or 2 capsules, each containing about 1 g of a composition as described herein, are administered to the subject in the evening, for example between about 5 μm and about 11 pm.

In some embodiments, the risk of a cardiovascular event in a subject is reduced compared to a control population. In some embodiments, a plurality of control subjects to a control population, wherein each control subject is on stable statin therapy, has a fasting baseline triglyceride level of about 135 mg/dL to about 500 mg/dL, and has established cardiovascular disease or a high risk of developing cardiovascular disease, and wherein the control subjects are not administered the composition comprising about 1 g to about 4 g of eicosapentaenoic acid ethyl ester per day.

In some embodiments, the risk of a cardiovascular event in a subject is reduced compared to a control population. In some embodiments, a plurality of control subjects to a control population, wherein each control subject is on stable statin therapy, has a fasting baseline triglyceride level of about 80 mg/dL to about 1500 mg/dL, and has established cardiovascular disease or a high risk of developing cardiovascular disease, and wherein the control subjects are not administered the composition comprising about 1 g to about 4 g of eicosapentaenoic acid ethyl ester per day.

In some embodiments, a first time interval beginning at (a) an initial administration of a composition as disclosed herein to the subject to (b) a first cardiovascular event of the subject is greater than or substantially greater than a first control time interval beginning at (a') initial administration of a placebo to the control subjects to (b') a first cardiovascular event in the control subjects. In some embodiments, the first cardiovascular event of the subject is a major cardiovascular event selected from the group consisting of: cardiovascular death, nonfatal myocardial infarction, nonfatal stroke, coronary revascularization, and unstable angina caused by myocardial ischemia. In some embodiments, the first cardiovascular event of the control subjects is a major cardiovascular event selected from the group consisting of: cardiovascular death, nonfatal myocardial infarction, nonfatal stroke, coronary revascularization, and unstable angina caused by myocardial ischemia. In some embodiments, the first cardiovascular event of the subject and the first cardiovascular event of the control subjects is any of: death (from any cause), nonfatal myocardial infarction, or nonfatal stroke. In some embodiments, the first cardiovascular event of the subject and the first cardiovascular event of the control subjects is any of: death from a cardiovascular cause, nonfatal myocardial infarction, coronary revascularization, unstable angina, peripheral cardiovascular disease, or cardiac arrhythmia requiring hospitalization. In some embodiments, the first cardiovascular event of the subject and the first cardiovascular event of the control subjects is any of: death from a cardiovascular cause, nonfatal myocardial infarction, and coronary revascularization, unstable angina. In some embodiments, the first cardiovascular event of the subject and the first cardiovascular event of the control subjects is any of: death from a cardiovascular cause and nonfatal myocardial infarction. In some embodiments, the first cardiovascular event of the subject and the first cardiovascular event of the control subjects is death (from any cause). In some embodiments, the first cardiovascular event of the subject and the first cardiovascular event of the control subjects is any of: fatal myocardial infarction and nonfatal myocardial infarction (optionally including silent MI). In some embodiments, the first cardiovascular event of the subject and the first cardiovascular event of the control subjects is coronary revascularization. In some embodiments, the first cardiovascular event of the subject and the first cardiovascular event of the control subjects is hospitalization (e.g. emergent hospitalization) for unstable angina (optionally unstable angina caused by myocardial ischemia). In some embodiments, the first cardiovascular event of the subject and the first cardiovascular event of the control subjects is any one of: fatal stroke or nonfatal stroke. In some embodiments, the first cardiovascular event of the subject and the first cardiovascular event of the control subjects is any one of: new coronary heart failure, new coronary heart failure leading to hospitalization, transient ischemic attack, amputation for coronary vascular disease, and carotid revascularization. In some embodiments, the first cardiovascular event of the subject and the first cardiovascular event of the control subjects is any one of: elective coronary revascularization and emergent coronary revascularization. In some embodiments, the first cardiovascular event of the subject and the first cardiovascular event of the control subjects is an onset of diabetes. In some embodiments, the first cardiovascular event of the subject and the first cardiovascular event of the control subjects is cardiac arrhythmia requiring hospitalization. In some embodiments, the first cardiovascular event of the subject and the first cardiovascular event of the control subjects is cardiac arrest. In some embodiments, the first cardiovascular event of the subject and the first cardiovascular event of the control subjects is sudden cardiac death and/or sudden death.

In some embodiments, a second time interval beginning at (a) an initial administration of the composition to the subject to (c) a second cardiovascular event of the subject is greater than or substantially greater than a second control time interval beginning at (a') initial administration of a placebo to the control subjects to (c') a second cardiovascular event in the control subjects. In some embodiments, the second cardiovascular event of the subject and the second cardiovascular event of the control subjects is a major cardiovascular event selected from the group consisting of: cardiovascular death, nonfatal myocardial infarction, nonfatal stroke, coronary revascularization, and unstable angina caused by myocardial ischemia. In some embodiments, the major cardiovascular event(s) is further selected from the group consisting of: cardiac arrest, sudden cardiac death, and/or sudden death.

In some embodiments, the subject has diabetes mellitus and the control subjects each have diabetes mellitus. In some embodiments, the subject has metabolic syndrome and the control subjects each have metabolic syndrome.

In some embodiments, the subject exhibits one or more of (a) reduced triglyceride levels compared to the control population; (b) reduced Apo B levels compared to the control population; (c) increased HDL-C levels compared to the control population; (d) no increase in LDL-C levels compared to the control population; (e) a reduction in LDL-C levels compared to the control population; (f) a reduction in non-HDL-C levels compared to the control population; (g) a reduction in VLDL levels compared to the control population; (h) a reduction in total cholesterol levels compared to the control population; (i) a reduction in high sensitivity C-reactive protein (hsCRP) levels compared to the control population; and/or (j) a reduction in high sensitivity troponin (hsTnT) levels compared to the control population.

In some embodiments, the subject's weight after administration of the composition is less than a baseline weight determined before administration of the composition. In some embodiments, the subject's waist circumference after administration of the composition is less than a baseline waist circumference determined before administration of the composition.

In methods of the present disclosure in which a time interval is determined or assessed, the time interval may be for example an average, a median, or a mean time interval. For example, in embodiments wherein a first control time interval is associated with a plurality of control subjects, the first control time interval is an average, a median, or a mean of a plurality of first control time intervals associated with each control subject. Similarly, in embodiments wherein a second control time interval is associated with a plurality of control subjects, the second control time interval is an average, a median, or a mean of a plurality of second control time intervals associated with each control subject.

In some embodiments, the reduced risk of cardiovascular events is expressed as a difference in incident rates between a study group and a control population. In some embodiments, the subjects in the study group experience a first major cardiovascular event after an initial administration of a composition as disclosed herein at a first incidence rate which is less than a second incidence rate, wherein the second incidence rate is associated with the rate of cardiovascular events in the subjects in the control population. In some embodiments, the first major cardiovascular event is any one of: cardiovascular death, nonfatal myocardial infarction, nonfatal stroke, coronary revascularization, and hospitalization for unstable angina (optionally determined to be caused by myocardial ischemia). In some embodiments, the first and second incidence rates are determined for a time period beginning on the date of the initial administration and ending about 4 months, about 1 year, about 2 years, about 3 years, about 4 years, or about 5 years after the date of initial administration.

In another embodiment, the disclosure provides use of any composition described herein for treating hypertriglyceridemia in a subject in need thereof, comprising: providing a subject having a fasting baseline triglyceride level of about 135 mg/dL to about 500 mg/dL and administering to the subject a composition as described herein. In one embodiment, the composition comprises about 1 g to about 4 g of eicosapentaenoic acid ethyl ester, wherein the composition contains substantially no docosahexaenoic acid.

In yet another embodiment, the disclosure provides use of any composition described herein for treating hypertriglyceridemia in a subject in need thereof, comprising: providing a subject having a fasting baseline triglyceride level of about 80 mg/dL to about 1500 mg/dL and administering to the subject a composition as described herein. In one embodiment, the composition comprises about 1 g to about 4 g of eicosapentaenoic acid ethyl ester, wherein the composition contains substantially no docosahexaenoic acid.

EXAMPLES

Example 1: Impact of Icosapent Ethyl on Reducing Cardiovascular Events in High Risk Statin-Treated Patients Among patients with cardiovascular risk factors who are receiving treatment for secondary or primary prevention, the rates of cardiovascular events remain high. Even in patients receiving appropriate treatment with statins, a substantial residual cardiovascular risk remains. In such patients, an elevated triglyceride level serves as an independent marker for increased ischemic risk, as shown in epidemiological and mendelian randomization studies. In randomized trials, medications that reduce triglycerides, such as extended-release niacin and fibrates, have not reduced the rates of cardiovascular events when administered in addition to appropriate medical therapy, including statins. Further, contemporary trials and recent meta-analyses of omega-3 fatty acid products have not shown benefit in patients receiving statin therapy. Accordingly, the objective of the present study was to determine if and how icosapent ethyl (referenced interchangeably with AMR101 or VASCEPA®) reduced cardiovascular events in patients with elevated triglyceride levels on a statin therapy.

The following study, also referred to as the REDUCE-IT clinical trial, was a large cardiovascular (CV) outcome trial designed to assess CV risk reduction benefit of AMR101 treatment (commercially known as VASCEPA®) versus placebo on the 5-point primary composite endpoint: CV death, non-fatal stroke, non-fatal myocardial infarction (MI), coronary revascularizations, or unstable angina requiring hospitalization.

A multi-center, prospective, randomized, double-blind, placebo-controlled, parallel-group study was performed to evaluate the effect of AMR101 (4 g per day) on cardiovascular health and mortality in hypertriglyceridemic patients with cardiovascular disease or at high risk for cardiovascular disease. The intended expanded indication of the study was treatment with AMR101 as an add-on to statin therapy to reduce the risk of cardiovascular events in patients with clinical cardiovascular disease or with multiple risk factors for cardiovascular disease.

The primary objective of this study was, in patients at LDL-C goal while on statin therapy, with established cardiovascular disease (CVD) or at high risk for CVD, and hypertriglyceridemia (e.g., fasting triglycerides (TG) 200 mg/dL and <500 mg/dL), to evaluate the effect of AMR101 4 g daily on time from randomization to first occurrence of any component of the composite of the following major CV events: CV death; nonfatal MI; (including silent MI; electrocardiograms (ECGs) were performed annually for the detection of silent MIs); nonfatal stroke; coronary revascularization; and unstable angina determined to be caused by myocardial ischemia by invasive/non-invasive testing and requiring emergent hospitalization.

The key secondary objective of this study was to evaluate the effect of AMR101 4 g daily on the time from randomization to the first occurrence of the composite of following major CV events: CV death, nonfatal MI (including silent MI), and nonfatal stroke.

Other secondary objectives for this study were to evaluate the effect of therapy on time from randomization to the first occurrence of the following individual or composite endpoints: composite of CV death or nonfatal MI (including silent MI); fatal or nonfatal MI (including silent MI); non-elective coronary revascularization represented as the composite of emergent or urgent classifications; CV death; unstable angina determined to be caused by myocardial ischemia by invasive/non-invasive testing and requiring emergent hospitalization; fatal or nonfatal stroke; composite of total mortality, nonfatal MI (including silent MI), or nonfatal stroke; and total mortality.

The key tertiary objectives for this study were to evaluate the effect of AMR101 4 g daily from baseline and percent change from baseline in fasting triglycerides and LDL-C. Other tertiary objectives for this study were to evaluate the effect of therapy on the following in addition to supporting efficacy and safety analyses:

Total CV events analysis defined as the time from randomization to occurrence of the first and all recurrent major CV events defined as CV death, nonfatal MI (including silent MI), nonfatal stroke, coronary revascularization, or unstable angina determined to be caused by myocardial ischemia by invasive/non-invasive testing and requiring emergent hospitalization;

Primary composite endpoint in the subset of patients with diabetes mellitus at baseline;

Primary composite endpoint in the subset of patients with metabolic syndrome at baseline as defined with waist circumference of 35 inches (88 cm) for all women and Asian, Hispanic, or Latino men, and 40 inches (102 cm) for all other men;

Primary composite endpoint in the subset of patients with impaired glucose metabolism at baseline (Visit 2 fasting blood glucose (FBG) of 100-125 mg/dL);

Key secondary composite endpoint in the subset of patients with impaired glucose metabolism at baseline (Visit 2 FBG 100-125 mg/dL);

Composite of CV death, nonfatal MI (including silent MI), nonfatal stroke, cardiac arrhythmia requiring hospitalization of 24 hours, or cardiac arrest;

Composite of CV death, nonfatal MI (including silent MI), non-elective coronary revascularizations (defined as emergent or urgent classifications), or unstable angina determined to be caused by myocardial ischemia by invasive/non-invasive testing and requiring emergent hospitalization;

Composite of CV death, nonfatal MI (including silent MI), non-elective coronary revascularizations (defined as emergent or urgent classifications), unstable angina determined to be caused by myocardial ischemia by invasive/non-invasive testing and requiring emergent hospitalization, nonfatal stroke, or peripheral vascular disease (PVD) requiring intervention, such as angioplasty, bypass surgery, or aneurism repair;

Composite of CV death, nonfatal MI (including silent MI), non-elective coronary revascularizations (defined as emergent or urgent classifications), unstable angina determined to be caused by myocardial ischemia by invasive/non-invasive testing and requiring emergent hospitalization, PVD requiring intervention, or cardiac arrhythmia requiring hospitalization of 24 hours;

New congestive heart failure (CHF);

New CHF as the primary cause of hospitalization;

Transient ischemic attack (TIA);

Amputation for PVD;

Carotid revascularization;

All coronary revascularizations defined as the composite of emergent, urgent, elective, or salvage;

Emergent coronary revascularizations;

Urgent coronary revascularizations;

Elective coronary revascularizations;

Salvage coronary revascularizations;

Cardiac arrhythmias requiring hospitalization of 24 hours;

Cardiac arrest;

Ischemic stroke;

Hemorrhagic stroke;

Fatal or nonfatal stroke in the subset of patients with a history of stroke prior to baseline;

New onset diabetes, defined as Type 2 diabetes newly diagnosed during the treatment/follow-up period;

New onset hypertension, defined as blood pressure ≥140 mmHg systolic or ≥90 mmHg diastolic newly diagnosed during the treatment/follow-up period;

Fasting triglycerides (TG), total cholesterol (TC), low dense lipoprotein cholesterol (LDL-C), high dense lipoprotein cholesterol (HDL-C), non-dense lipoprotein cholesterol (non-HDL-C), very low dense lipoprotein cholesterol (VLDL-C), apolipoprotein B (apo B), high sensitivity-C reactive protein (hsCRP and log [hsCRP]), high-sensitivity troponin (hsTnT), and remnant like particle cholesterol (RLP-C; were estimated from standard lipid panel, RLP-C=TC−HDL-C−LDL-C [Varbo 2014]), (based on ITT estimands):

Assessment of the relationship between baseline biomarker values and treatment effects within the primary and key secondary endpoints;

Assessment of the effect of AMR101 on each marker; and

Assessment of the relationship between post-baseline biomarker values and treatment effects within the primary and key secondary composite endpoints by including post-baseline biomarker values (for example, at 4 months, or at 1 year) as a covariate.

Change from baseline and percent change from baseline in fasting TG, TC, LDL-C, HDL-C, non-HDL-C, VLDL-C, apo B, hsCRP, hsTnT, and RLP-C;

Change in body weight; and

Change in waist circumference.

Study Population

The population for this study were men and women 45 years of age with established CVD, or men and women 50 years of age with diabetes in combination with one additional risk factor for CVD. In addition, all patients had atherogenic dyslipidemia defined as on treatment for hypercholesterolemia (but at treatment goal for LDL-C, by treatment with a statin) and hypertriglyceridemia. More details regarding the patient population are listed in the inclusion criteria below. The patients needed to provide consent to participate in the study and were willing and able to comply with the protocol and the study procedures.

Study Periods

This study consisted of the following study periods:

Screening Period: During the screening period, patients were evaluated for inclusion and exclusion criteria.

At the first visit to the Research Unit (Visit 1), study procedures were performed for evaluation of patient's eligibility in the study. At this screening visit, patients signed an informed consent form before any study procedure was performed; the informed consent form covered the treatment/follow-up period. Based on the evaluation from Visit 1, the following situations occurred:

Patients who were eligible for participation based on the study procedures on Visit 1 returned to the Research Unit for Visit 2 (randomization visit) to start the treatment/follow-up period. This case included, for example, patients at Visit 1 who were on a stable dose of a statin, were planning to stay on the same statin and the same dose of the statin, and who did not need to wash out any non-statin lipid-altering medications.

Patients who were not eligible for participation based on the study procedures on Visit 1 and were unlikely to become eligible in the next 28 days (for example: unlikely to stabilize statin dose, unable to wash out non-statin lipid-altering medications, etc.): these patients were screen failed after Visit 1.

Patients that were not eligible for participation in the study based on the study procedures on Visit 1 could become eligible in the next 28 days: To become eligible, patients returned at the discretion of the investigator for a second optional screening visit (Visit 1.1) at which time the procedures needed for re-evaluation of the previously failed inclusion/exclusion criteria were repeated. This case included, for example, patients who were started on a statin at Visit 1, whose statin dose was changed at Visit 1, and/or needed to wash out non-statin lipid-altering medications. The following applied for these patients:

Patients with a change in the statin or statin dose on Visit 1 needed to be on a stable statin dose for at least 28 days before the lipid qualifying measurements at Visit 1.1. Other concomitant medications (antidiabetic therapy, for example) could have been optimized or stabilized during this period.

Patients starting a washout at Visit 1 had a washout period of at least 28 days (only 7 days for bile acid sequestrants) before the lipid qualifying measurements at Visit 1.1.

Patients at Visit 1 who were on a stable dose of a statin, were planning to stay on the same statin at the same dose, and who did not need any medication washout, but were asked to return for Visit 1.1 to repeat one or more of the other study procedures not related to concomitant medications.

Patients who became eligible for participation based on the additional study procedures at Visit 1.1 returned to the Research Unit for Visit 2 (randomization visit) to start the treatment/follow-up period.

At the end of the screening period, patients needed to meet all inclusion and exclusion criteria before they were randomized. Patients who were not eligible for participation after the screening period (based on study procedures at Visit 1 and/or Visit 1.1) could return at a later date for rescreening. These patients needed to re-start with all procedures starting with Visit 1. This included patients who need more time to stabilize one or more conditions or therapies (for example: statin, antidiabetic, antihypertensive, thyroid hormone, HIV-protease inhibitor therapy).

Treatment/Follow-Up Period: Within 42 days after the first screening visit (Visit 1) or within 60 days after the first screening visit (Visit 1) for those patients that had a second screening visit (Visit 1.1), eligible patients entered the treatment/follow-up period. During this period, the patients received study drug during the planned visits at the Research Site and took the study drug while away from the Research Site.

During the visits, study procedures were performed for evaluation of efficacy and safety. A detailed schedule of the procedures is provided below in Table 1.

TABLE 1

Schedule of Procedures

| Study Day | Screening Up to 42 days before Day 0 | If a Visit 1.1 takes place, Visit 1 may occur up to 60 days before Day 0[2] | Follow-Up (FU)[13] | | | | | | | | Last Visit (LV)[15] |
|---|---|---|---|---|---|---|---|---|---|---|---|
| | | | 0 | 120 ± 10 | 360 ± 10 | 720 ± 10 | 1080 ± 10 | 1440 ± 10 | 1800 + 30 | 2160 ± 10 | |
| Months of FU | | | 0 | 4 | 12 | 24 | 36 | 48 | 60 | 72 | Varies |
| Years of FU | | | 0 | 0.33 | 1 | 2 | 3 | 4 | 5 | 6 | Varies |
| Visit # | 1 | 1.1 | 2 | 3 | 4 | 5 | 6 | 7 | 8 | 9[14] | LV |
| Study Procedures: | | | | | | | | | | | |
| Informed Consent | X | | | | | | | | | | |
| Medical, Surgical & Family History | X | | | | | | | | | | |
| Demographics | X | | | | | | | | | | |
| Evaluate inclusion/exclusion criteria | X[1] | X[3] | X | | | | | | | | |
| Physical Examination | | | X | X | X | X | X | X | X | X | X |
| Weight, Height[4] | X | | X | X | X | X | X | X | X | X | X |
| Vital Signs[5] | X | X | X | X | X | X | X | X | X | X | X |
| Waist Circumference | | | X | | | X | | | | | X |
| 12-Lead ECG | X | | X | | X | X | X | X | X | X | X |
| Urine pregnancy test[6] | X | | X | | | | | | | | |
| Concomitant Meds | X | X | X | X | X | X | X | X | X | X | X |
| Randomization | | | X | | | | | | | | |
| Dosing at the Research Site[7] | | | X | X | X | X | X | X | X | X | |
| Efficacy events | | | | X | X | X | X | X | X | X | X |
| AE Evaluations | | | X | X | X | X | X | X | X | X | X |
| Compliance Check[8] | | | | X | X | X | X | X | X | X | X |
| Chemistry and hematology[9] | X | X[3] | X | X | X | X | X | X | X | X | X |

TABLE 1-continued

Schedule of Procedures

| Study Day | Screening Up to 42 days before Day 0 | If a Visit 1.1 takes place, Visit 1 may occur up to 60 days before Day 0[2] | 0 | 120 ± 10 | 360 ± 10 | 720 ± 10 | Follow-Up (FU)[13] 1080 ± 10 | 1440 ± 10 | 1800 + 30 | 2160 ± 10 | Last Visit (LV)[15] |
|---|---|---|---|---|---|---|---|---|---|---|---|
| Fasting lipid profile[10] | X | X[3] | X | X | X | X | X | X | X | X | X |
| Genetic testing[11] | | X | | | | | | | | | |
| Biomarkers: hsCRP, apo B, hsTNT | | | X | | | X | | | | | X |
| Fasting blood sample for archiving [12] | | | X | | X | X | X | X | X | X | X |

[1]Includes procedures and (fasting) blood samples (for example, hsCRP, calculated creatinine clearance) as needed to determine the CV risk category (see inclusion criteria).
[2]Screening visit to re-evaluate inclusion/exclusion criteria for patients who were not eligible for participation based on data from Visit 1.
[3]Inclusion/exclusion criteria were re-evaluated for selected study procedures that were performed on Visit 1.1 because patients failed to meet them at Visit 1.
[4]Height at first screening visit only.
[5]Vital signs, including systolic and diastolic blood pressure (mmHg), heart rate, respiratory rate and body temperature. Participants were seated for at least 5 minutes before assessments of vital signs.
[6]For women of childbearing potential.
[7]The patients fasted at least 10 hours before arriving at the Research Site, when all fasting blood samples were obtained. After blood samples were obtained, patients were given drug with food.
[8]Review study drug compliance by unused capsule count, discussed with and counseled patients about compliance if needed; final study compliance at last visit.
[9]Safety Laboratories - Complete Blood Count: Included RBC, Hgb, Hct, WBC and differential, and platelet count. Biochemistry includes total protein, albumin, alkaline phosphatase, ALT, AST, total bilirubin, glucose, calcium, electrolytes (sodium, potassium, chloride), blood urea nitrogen (BUN), serum creatinine, uric acid, creatine kinase, HbA1c. Safety labs were repeated as deemed necessary by the Investigator.
[10]TG, TC, HDL-C, LDL-C, non-HDL-C, and VLDL-C.
[11]Fasting blood sample were stored for future genetic testing at the discretion of the Sponsor. This sample was optional as local regulations may prohibit genetic samples to be collected or shipped outside the country, or patients may not have consented.
[12]Used at the Sponsor's discretion to perform repeat analyses described in the protocol or to perform other tests related to cardiovascular health.
[13]Site personnel contacted each patient by telephone in-between Visit 2 and Visit 3 and between Visit 3 and Visit 4. After Visit 4 contact was made every 3 months. The purpose of the contact was to collect information about efficacy events, adverse events, concomitant medications, confirm patient's current address and contact information and remind patients about taking their study medication and logistics for the next visit.
[14]Office visits continued at 360-day intervals and phone visits at 90-day intervals until study end date was determined.
[15]The last visit (LV) could have occurred within 30 days after the study end date as determined by the DMC; the study end date is tentatively schedule for Day 2160 but the actual date was determined by the DMC may be different.

Study Duration

Patients were randomized at different times during the enrollment period but all ended the study at approximately the same date (i.e., at the study end date) and, therefore, the duration of follow-up differed based on date of randomization. It was planned that all randomized patients received study medication and were followed-up until the study end date. It was expected that a minimum of approximately 1612 primary endpoint events were required during the study. 8179 patients were randomized at multiple Research Sites worldwide over a period of approximately 4.2 years. After randomization, patients were treated and followed up to an estimated maximum of 6.5 years. The study end date was determined to be when approximately 1612 primary efficacy events had been adjudicated. Table 2 shows the study milestones from the first patient screened to the last patient visit and subsequent database lock.

TABLE 2

Study Milestones

| Study Milestones | Date |
|---|---|
| First Patient Screened | 21 Nov. 2011 |
| First Patient Randomized | 28 Nov. 2011 |
| Last Patient Randomized | 4 Aug. 2016 |
| SAP Finalization | 8 Jul. 2016 |
| First DMC Interim Efficacy Review | 9 Sep. 2016 |
| Second DMC Interim Efficacy Review | 11 Aug. 2017 |
| First Patient Last Visit | 1 Mar. 2018 |
| Last Patient Last Visit | 31 May 2018 |
| Database Lock | 6 Sep. 2018 |

Study Groups

At Visit 2 (Day 0), eligible study patients were randomly assigned to the following treatment groups:
Group 1: AMR101 (>96% E-EPA) 4 g daily (four 1000 mg capsules daily)
Group 2: placebo (four capsules daily)
The four AMR101 or placebo capsules daily were taken as two capsules in the morning and two capsules in the evening (twice-per-day dosing regimen).

Number of Patients

This was an event-driven trial and it was expected that a minimum of 1612 primary efficacy endpoint events were required during the study. A total of approximately 8179 patients entered into the study to either receive AMR101 or placebo (approximately 4089 patients per treatment group)

in order to observe an estimated 1612 events that made up the primary composite endpoint for efficacy.

Randomization

On Day 0, eligible patients were randomized to one of the 2 study groups using a computer-generated randomization schema. Randomized treatment assignment to either AMR101 or placebo in a 1:1 ratio was provided using the internet (IWR).

Blinding

This was a double-blind study. Patients, investigators, pharmacists and other supporting staff at the Research Sites, personnel and designees of the Sponsor, study administrators and personnel at the organization(s) and vendors supporting the study were unaware of the randomization code (i.e., they did not know which study participants were receiving the experimental drug and which were receiving the placebo drug). The study medication AMR101 and placebo capsules were similar in size and appearance to maintain blinding.

During the double-blind treatment/follow-up period, everyone (patients, investigators, pharmacists and other supporting staff at the Research Sites, personnel and designees of the Sponsor, study administrators and personnel at the organization(s) and vendors managing/supporting the study), with the exception of the laboratory personnel performing the analysis, were blinded to individual results of the efficacy laboratory measurements (including lipid values). Individual results from the lipid profile could be unblinded in the event of an emergency for a patient.

Stratification

Participants were assigned to treatment groups stratified by CV risk category, use of ezetimibe and by geographical region (e.g., Westernized, Eastern European, and Asia Pacific countries). There were two CV risk categories:

- CV Risk Category 1: patients with established CVD defined in the inclusion criteria. Patients with diabetes and established CVD were included in this category. These patients are defined as the secondary prevention stratum, primary risk category, and/or secondary prevention cohort.
- CV Risk Category 2: patients with diabetes and at least one additional risk factor for CVD, but no established CVD. These patients are defined as the primary prevention stratum, secondary risk category, and/or primary prevention cohort.

Stratification was recorded in the IWR at the time of enrollment. Approximately 70% of randomized patients were in the CV Risk Category 1 and approximately 30% of randomized patients were in the CV Risk Category 2. Enrollment with patients of a CV risk category was stopped when the planned number of patients in that risk category was reached.

Study Population

Inclusion Criteria. A detailed list of the inclusion criteria for this study is provided in Tables 3-5. Specifically, Table 3 outlines the inclusion criteria for patients in this study whereas Tables 4 and 5 further outline the inclusion criteria based on whether that patient is part of the primary prevention risk category or the secondary prevention risk category of patients, respectively.

TABLE 3

Patient Inclusion Criteria for this Study
Study Inclusion Criteria

1 Men or women ≥45 years of age with established CVD (i.e., Primary Prevention Risk Category; see Table 4) or ≥50 years of age with diabetes in combination with one additional risk factor for CVD (i.e., Secondary Prevention Risk Category; see Table 5).
2 Fasting TG levels ≥150 mg/dL (2.26 mmol/L) and <500 mg/dL (5.64 mmol/L). Due to the variability of triglycerides, a 10% allowance existed in the initial protocol, which permitted patients to be enrolled with qualifying triglyceride levels ≥135 mg/dL. Protocol amendment made in May of 2013 changed the lower limit of acceptable triglyceride levels from 150 mg/dL to 200 mg/dL, with no variability allowance.
3 LDL-C >40 mg/dL and ≤100 mg/dL and on stable statin therapy (±ezetimibe) for ≥4 weeks prior to the LDL-C and TG qualifying measurements for randomization.
4 Women who are not pregnant, not planning on becoming pregnant, and using an acceptable form of birth control during the study (if of child-bearing potential), unless their sexual partner(s) were surgically sterile or the woman was abstinent. Women of child bearing potential needed a negative urine pregnancy test prior to randomization.
5 Able to provide informed consent and adhere to study schedules.
6 Agree to follow and maintain a physician-recommended diet during the study.

Stable therapy was defined as the same daily dose of the same statin for at least 28 days before the lipid qualification measurements (TG and LDL-C) and, if applicable, the same daily dose of ezetimibe for at least 28 days before the lipid qualification measurements (TG and LDL-C). Patients who had their statin therapy or use of ezetimibe initiated at Visit 1, or had their statin, statin dose and/or ezetimibe dose changed at Visit 1, needed to go through a stabilization period of at least 28 days since initiation/change and had their qualifying lipid measurements measured (TG and LDL-C) after the washout period (at Visit 1.1). Statins may have been administered with or without ezetimibe.

If patients qualified at the first qualification visit (Visit 1) for TG and LDL-C, and met all other inclusion/exclusion criteria, they were randomized at Visit 2. If patients did not qualify at the first qualifying visit (Visit 1), a second re-qualifying visit (Visit 1.1) was allowed. For some patients, because they needed to stabilize medications and/or needed to washout medications, the second re-qualifying visit (Visit 1.1) was needed after the stabilization/washout period.

Women were not considered to be of childbearing potential if they met one of the following criteria as documented by the investigator: they had a hysterectomy, tubal ligation or bilateral oophorectomy prior to signing the informed consent form; and/or they were post-menopausal, defined as ≥1 year since their last menstrual period or have a follicle-stimulating hormone (FSH) level in a menopausal range.

Patients having established CVD (in CV Risk Category 1) were defined as detailed in Table 4.

TABLE 4

Inclusion Criteria for the Primary Prevention Risk Category (i.e., CV Risk Category 1)
Primary Prevention Risk Category (i.e., Secondary Prevention Cohort)
Defined as men and women ≥45 years of age with one or more of the following:

1. Documented coronary artery disease (CAD; one or more of the following primary criteria must be satisfied):
    a. Documented multi vessel CAD (≥50% stenosis in at least two major epicardial coronary arteries - with or without antecedent revascularization).
    b. Documented prior MI.
    c. Hospitalization for high-risk non-ST-segment elevation acute coronary syndrome (NSTE-ACS) (with objective evidence of ischemia: ST-segment deviation or biomarker positivity).
2. Documented cerebrovascular or carotid disease (one of the following primary criteria must be satisfied):
    a. Documented prior ischemic stroke.
    b. Symptomatic carotid artery disease with ≥50% carotid arterial stenosis.
    c. Asymptomatic carotid artery disease with ≥70% carotid arterial stenosis per angiography or duplex ultrasound.
    d. History of carotid revascularization (catheter-based or surgical).
3. Documented peripheral arterial disease (PAD; one or more of the following primary criteria must be satisfied):
    a. Ankle-brachial index (ABI) <0.9 with symptoms of intermittent claudication.
    b. History of aorto-iliac or peripheral arterial intervention (catheter-based or surgical).

Patients at high risk for CVD (in CV Risk Category 2) were defined as detailed in Table 5.

TABLE 5

Inclusion Criteria for the Secondary Prevention Risk Category (i.e., CV Risk Category 2)
Secondary Prevention Risk Category (i.e., Primary Prevention Cohort)
Defined as having each of the following:

1. Diabetes mellitus (Type 1 or Type 2) requiring treatment with medication.
2. Men and women ≥50 years of age.
3. One of the following at Visit 1 (additional risk factor for CVD):
    a. Men ≥55 years of age and Women ≥65 years of age.
    b. Cigarette smoker or stopped smoking within 3 months before Visit 1.
    c. Hypertension (blood pressure ≥140 mmHg systolic OR ≥90 mmHg diastolic) or on antihypertensive medication.
    d. HDL-C ≤40 mg/dL for men or ≤50 mg/dL for women.
    e. HsCRP >3.00 mg/L (0.3 mg/dL).
    f. Renal dysfunction: Creatinine clearance (CrCL) >30 and <60 mL/min.
    g. Retinopathy, defined as any of the following: non-proliferative retinopathy, pre-proliferative retinopathy, proliferative retinopathy, maculopathy, advanced diabetic eye disease or a history of photocoagulation.
    h. Micro- or macroalbuminuria. Microalbuminuria is defined as either a positive micral or other strip test (may be obtained from medical records), an albumin/creatinine ratio ≥2.5 mg/mmol or an albumin excretion rate on timed collection ≥20 mg/min all on at least two successive occasions; macroalbuminuria, defined as Albustix or other dipstick evidence of gross proteinuria, an albumin/creatinine ratio ≥25 mg/mmol or an albumin excretion rate on timed collection ≥200 mg/min all on at least two successive occasions.
    i. ABI <0.9 without symptoms of intermittent claudication (patients with ABI <0.9 with symptoms of intermittent claudication are counted under Secondary Prevention Risk Category).

Patients with diabetes and CVD as defined above are eligible based on the CVD requirements and will be counted under CV Risk Stratum 1. Only patients with diabetes and no documented CVD as defined above needed at least one additional risk factor as listed, and were counted under Primary Prevention Risk Category.

Exclusion Criteria: Patients meeting the following exclusion criteria enumerated in Table 6 were not eligible for the study.

TABLE 6

Patient Exclusion Criteria for this Study
Study Exclusion Criteria

1. Severe (New York Heart Association [NYHA] class IV) heart failure.
2. Any life-threatening disease expected to result in death within the next 2 years (other than CVD).
3. Diagnosis or laboratory evidence of active severe liver disease.
4. Hemoglobin A1c >10.0% (or 86 mmol/mol IFCC units) at screening (Visit 1). If patients failed this criterion (HbA1c >10.0% or 86 mmol/mol IFCC units) at Visit 1, they could have had their antidiabetic therapy optimized and be retested at Visit 1.1.
5. Poorly controlled hypertension: systolic blood pressure (SBP) ≥200 mmHg or diastolic blood pressure (DBP) ≥100 mmHg (despite antihypertensive therapy).
6. Planned coronary intervention or any non-cardiac major surgical procedure.
7. Known familial lipoprotein lipase deficiency (Fredrickson Type I), apolipoprotein C-II deficiency, or familial dysbetalipoproteinemia (Fredrickson Type III).

TABLE 6-continued

Patient Exclusion Criteria for this Study
Study Exclusion Criteria

8. Participation in another clinical trial involving an investigational agent within 90 days prior to screening (Visit 1). Patients could not participate in any other investigational medication or medical device trial while participating in this study (participation in a registry or observational study without an additional therapeutic intervention was allowed).
9. Intolerance or hypersensitivity to statin therapy.
10. Known hypersensitivity to fish and/or shellfish, or ingredients of the study product or placebo.
11. History of acute or chronic pancreatitis.
12. Malabsorption syndrome and/or chronic diarrhea. (Note: patients who had undergone gastric/intestinal bypass surgery were considered to have malabsorption, hence were excluded; patients who had undergone gastric banding were allowed to enter the trial).
13. Use of non-study drug-related, non-statin, lipid-altering medications, dietary supplements, or foods during the screening period (after Visit 1) and/or plans for use during the treatment/follow-up period including:
    a. niacin >200 mg/day or fibrates during the screening period (after Visit 1) and/or planned to use during the study; patients who were taking niacin >200 mg/day or fibrates during the last 28 days before Visit 1 needed to go through washout of at least 28 days after their last use and have their qualifying lipids measured (TG and LDL-C) after the washout period (Visit 1.1).
    b. any omega-3 fatty acid medications (prescription medicines containing EPA and/or DHA) during the screening period (after Visit 1) and/or planned to use during the treatment/follow-up period of the study. To be eligible for participation in the study, patients who were taking omega-3 fatty acid medications during the last 28 days before Visit 1 (except patients in The Netherlands), needed to go through a washout period of at least 28 days after their last use and have their qualifying lipids measured (TG and LDL-C) after the washout period (at Visit 1.1). However, for patients in the Netherlands only being treated with omega-3 fatty acid medications containing EPA and/or DHA were excluded and no washout was allowed.
    c. dietary supplements containing omega-3 fatty acids (e.g., flaxseed, fish, krill, or algal oils) during the screening period (after Visit 1) and/or planned to use during the treatment/follow-up period of the study. To be eligible for participation in the study, patients who were taking >300 mg/day omega-3 fatty acids (combined amount of EPA and DHA) within 28 days before Visit 1 (except patients in The Netherlands), needed to go through a washout period of at least 28 days since their last use and have their qualifying lipid measurements measured (TG and LDL-C) after the washout period (at Visit 1.1). However, for patients in the Netherlands only being treated with dietary supplements containing omega-3 fatty acids of >300 mg/day EPA and/or DHA were excluded and no washout was allowed.
    d. bile acid sequestrants during the screening period (after Visit 1) and/or planned to use during the treatment/follow-up period of the study. To be eligible for participation in the study, patients who were taking bile acid sequestrants within 7 days before Visit 1, needed to go through a washout period of at least 7 days since their last use and have their qualifying lipid measurements measured (TG and LDL-C) after the washout period (at Visit 1.1).
    e. proprotein convertase subtilisin kexin 9 (PCSK9) inhibitors during the screening period (after Visit 1) and/or planned to use during the treatment/follow-up period of the study. To be eligible for participation in the study, patients could not have taken a PCSK9 inhibitor within 90 days prior to their screening visit.
14. Other medications (not indicated for lipid alteration):
    a. Tamoxifen, estrogens, progestins, thyroid hormone therapy, systemic corticosteroids (local, topical, inhalation, or nasal corticosteroids are allowed), HIV-protease inhibitors that have not been stable for ≥28 days prior to the qualifying lipid measurements (TG and LDL-C) during screening. To be eligible for participation in the study, patients who were not taking a stable dose of these medications within 28 days before Visit 1, needed to go through a stabilization period of at least 28 days since their last dose change and have their qualifying lipid measurements measured (TG and LDL-C) after the washout period (at Visit 1.1).
    b. Cyclophosphamide or systemic retinoids during the screening period (unless ≥28 day washout) and/or plans for use during the treatment/follow-up period. To be eligible for participation in the study, patients who were taking these medications within 28 days before Visit 1, needed to go through a washout period of at least 28 days since their last use and have their qualifying lipid measurements measured (TG and LDL-C) after the washout period (at Visit 1.1).
15. Known AIDS (HIV-positive patients without AIDS are allowed).
16. Requirement for peritoneal dialysis or hemodialysis for renal insufficiency or creatinine clearance <30 mL/min (0.50 mL/sec).
17. Unexplained elevated creatine kinase concentration >5 × ULN or elevation due to known muscle disease (e.g., polymyositis, mitochondrial dysfunction) at Visit 1.
18. Any condition or therapy which, in the opinion of the investigator, might pose a risk to the patient or make participation in the study not in the patient's best interest.
19. Drug or alcohol abuse within the past 6 months, and inability/unwillingness to abstain from drug abuse and excessive alcohol consumption during the study or drinking 5 units or more for men or 4 units or more for women in any one hour (episodic excessive drinking or binge drinking). Excessive alcohol consumption was on average >2 units of alcohol per day. A unit of alcohol was defined as a 12-ounce (350 mL) beer, 5-ounce (150 mL) wine, or 1.5-ounce (45 mL) of 80-proof alcohol for drinks.
20. Mental/psychological impairment or any other reason to expect patient difficulty in complying with the requirements of the study or understanding the goal and potential risks of participating in the study (evaluated at Visit 1).

Study Procedures

The Screening Period for this study included two visits, Visit 1 and Visit 1.1.

Screening Visit (Visit 1): During Visit 1, patients came to the Research Site for and were instructed to fast for at least 10 hours before their visit. If patients qualified for randomization based on the procedures at Visit 1, they needed to be randomized within 42 days after Visit 1. The following procedures were performed at the screening Visit 1:

- Obtained signed informed consent;
- Assigned the patient a patient number;
- Obtained medical, surgical and family history;
- Recorded demographics;
- Obtained height, weight, and body mass index;
- Obtained vital signs (systolic and diastolic blood pressure, heart rate, respiratory rate, and body temperature);
- Obtained a 12-lead electrocardiogram;
- Evaluated inclusion/exclusion criteria;
- This included procedures and (fasting) blood samples (for example, hsCRP, calculated creatinine clearance) as needed to determine the CV risk category (See inclusion criteria);
- Obtained fasting blood samples for chemistry and hematology testing;
- Obtained a fasting blood sample for the lipid profile (TG, TC, HDL-C, LDL-C, non-HDL-C, VLDL-C);
- Performed a urine pregnancy test on women of childbearing potential;
- Recorded concomitant medication(s); and
- Instructed patient to fast for at least 10 hours prior to the next visit.

Screening Visit (Visit 1.1): Patients who qualified for study participation after Visit 1 because they meet all inclusion criterion and none of the exclusion criteria, skipped Visit 1.1 and returned to the Research Site for Visit 2 to be randomized and to start the treatment/follow-up period of the study. For these patients, Visit 2 occurred soon after Visit 1. Patients, who did not qualify at Visit 1, returned to the Research Site for a second qualifying visit (Visit 1.1) at the discretion of the investigator. At Visit 1.1, procedures that caused failure of eligibility at Visit 1 were repeated. Patients were eligible for randomization after Visit 1.1 if they meet all inclusion criteria and if they no longer failed the exclusion criteria. If patients were evaluated at Visit 1.1 and qualified for randomization based on the repeated procedures at Visit 1.1, they needed to be randomized within 60 days after Visit 1. For some patients, Visit 1.1 was mandatory at least 28 days after Visit 1 in order to check eligibility. These were patients who at Visit 1 started treatment with a statin, changed their statin, changed the daily dose of their statin, started to washout prohibited medications or started a stabilization period with certain medications (See inclusion/exclusion criteria above for details). Any of these changes at Visit 1 may have affected the qualifying lipid levels and therefore, patients needed to have Visit 1.1 to determine whether they qualified based on lipid level requirements (TG and LDL-C) determined at Visit 1. Other procedures that caused failure of eligibility at Visit 1 were also repeated at Visit 1.1. The following procedures were performed at the screening Visit 1.1:

- Obtained vital signs (systolic and diastolic blood pressure, heart rate, respiratory rate, and body temperature);
- Evaluated inclusion/exclusion criteria; only those evaluations were repeated that deemed the patient not eligible on Visit 1;
- Obtained fasting blood samples for chemistry and hematology testing. Only those samples were obtained that deemed the patient not eligible on Visit 1;
- Obtained a fasting blood sample for the lipid profile (TG, TC, HDL-C, LDL-C, non-HDL-C, VLDL-C) if the patient was deemed not eligible on Visit 1. This included patients who at Visit 1 started treatment with a statin, changed their statin, changed the daily dose of their statin, started to washout prohibited medications or started a stabilization period with certain medications (See inclusion/exclusion criteria for details). These patients had a fasting blood sample collected at Visit 1.1 for the qualifying lipid values (TG and LDL-C), and the TG and LDL-C inclusion criteria were evaluated and
- Recorded concomitant medication(s).

The treatment/follow-up period for this study included Visit 2, Visit 3, and Visits 4-9. Every attempt was made to complete the follow-up visits during the defined window periods.

Randomization visit (Visit 2; Day 0): Qualified patients returned to the Research Site for Visit 2. The following procedures were performed at Visit 2:

- Performed physical examination;
- Obtained weight;
- Obtained vital signs (systolic and diastolic blood pressure, heart rate, respiratory rate, and body temperature);
- Measured waist circumference (one of the factors to diagnose metabolic syndrome);
- Obtained a 12-lead electrocardiogram;
- Evaluated inclusion/exclusion criteria;
- Obtained fasting blood samples for:
  - Chemistry and hematology testing;
  - Lipid profile (baseline);
  - Biomarker assays (baseline);
  - Genetic testing (optional blood sample); and
  - Archived (in countries and at sites approved by IRB/IEC and dependent on country regulations).
- Performed a urine pregnancy test on women of childbearing potential (must be negative for randomization);
- Dispensed study drug and record randomization number;
- Instructed patient on how to take study drug;
- Administered study drug—Note: Study drug was taken orally with food following the collection of all fasting blood samples;
- Assessed for and recorded adverse events;
- Recorded concomitant medication(s); and
- Instructed patient:
  - To bring all study supplies with them to the next visit;
  - Not to take study drug on the morning of their next visit; and
  - To fast for 10 hours prior to the next visit.

Visit 3 (Day 120; ~4 Months): Patients returned to the Research Site for Visit 3 on Day 120±10 days. The following procedures were performed:

- Physical examination;
- Obtained weight;
- Obtained vital signs (systolic and diastolic blood pressure, heart rate, respiratory rate, and body temperature);
- Obtained fasting blood samples for:
  - Chemistry and hematology testing; and
  - Lipid profile.
- Reviewed study drug compliance by unused capsule count; discuss with and counsel patients about compliance if needed;

Administered study drug—Note: Study drug should be taken orally with food following the collection of all fasting blood samples;
Assessed and record efficacy events;
Assessed for and record adverse events;
Recorded concomitant medication(s);
Instructed patient:
To bring all study supplies with them to the next visit;
Not to take study drug on the morning of their next visit; and
To fast for 0 hours prior to the next visit.

Visits 4, 5, 6, 7, 8, and 9: At Visit 4: Day 360±10; Visit 5: Day 720±10; Visit 6: Day 1080±10; and Visit 7: Day 1440±10: Visit 8: Day 1800±10, Visit 9: Day 2160±10, the following procedures were performed:
Physical examination;
Obtained weight;
Obtained vital signs (systolic and diastolic blood pressure, heart rate, respiratory rate, and body temperature);
Measured waist circumference (collected at Visit 5 only);
Obtained a 12-lead electrocardiogram;
Obtained fasting blood samples for:
Chemistry and hematology testing;
Lipid profile;
Biomarker assays (collected at Visit 5 only); and
Archived (in countries and at sites approved by international review board (IRB)/independent ethics committee (IEC) and dependent on country regulations);
Reviewed study drug compliance by unused capsule count; discussed with and counseled patients about compliance if needed;
Administered study drug—Note: Study drug should be taken orally with food following the collection of all fasting blood samples;
Assessed and record efficacy events;
Assessed for and record adverse events;
Recorded concomitant medication(s); and
Instructed patient:
To bring all study supplies with them to the next visit;
Not to take study drug on the morning of their next visit; and
To fast for 0 hours prior to the next visit.

Additional Visits: The end date of the study was expected for Day 2160 but the actual end date was dependent on the determination of the study end date by the DMC and when approximately 1612 primary efficacy events had occurred. If the actual study end date was later than the expected end date, additional visits were planned between Visit 7 and the Last Visit with a maximum of 360±10 days between visits. If the actual study end date was sooner than the expected end date, fewer visits occurred, and the last visit (See below, section titled Last Visit—End of Study) occurred sooner. On additional visits the same procedures were performed. Irrespective of the number of additional visits, after the DMC had established the end of the study date, there was a last visit with procedures as listed below in section titled Last Visit—End of Study.

Last Visit—End of Study: All patients completed the study at the same time (within a 30-day window after the study end date), irrespective of the date that they were randomized. The end date of the study was planned for Day 2160 but the actual end date was dependent on the determination of the study end date by the DMC when approximately 1612 primary efficacy events had occurred (event-driven trial). For each patient, the last visit may have occurred within 30 days after the actual study end date as determined by the DMC. However, for the efficacy endpoints based on CV events, only events occurring up to and including the scheduled actual study end date were included in the efficacy analyses. A final follow-up visit was required for all patients. In a rare case that a final follow-up visit did not occur within the 30-day timeframe following the study end date, any attempt to contact the patient was recorded on a special contact form, until/unless appropriate information was obtained. At the Last Visit, the following procedures were performed:
Physical examination;
Obtained weight;
Obtained vital signs (systolic and diastolic blood pressure, heart rate, respiratory rate, and body temperature);
Measured waist circumference;
Obtained a 12-lead electrocardiogram;
Obtained fasting blood samples for:
Chemistry and hematology testing;
Lipid profile;
Biomarker assays; and
Archived (in countries and at sites approved by IRB/IEC and dependent on country regulations).
Determined study drug compliance by unused capsule count;
Assessed and record efficacy events;
Assessed for and record adverse events; and
Recorded concomitant medication(s).

Telephoned Follow-up Contact: Site personnel contacted each patient by telephone on the following study days: Day 60±3 days; Day 180±5 days; Day 270±5 days; Day 450±5 days; Day 540±5 days; Day 630±5 days; Day 810±5 days; Day 900±5 days; Day 990±5 days; Day 1170±5 days; Day 1260±5 days; Day 1350±5 days; Day 1530±5 days; Day 1620±5 days; Day 1710±5 days; Day 1890±5 days; Day 1980±5 days; and Day 2070±5 days.

If the treatment/follow-up period of the study was extended beyond the expected end date (Day 2160), additional follow-up phone calls were made every 3 months in-between additional visits±5 days. If the treatment/follow period of the study was shorter than the expected end date, less follow-up phone calls were needed. Every attempt was made to talk to each patient within this timeframe. The following information was collected from the patient:
Possible efficacy endpoints related to CV events. Patients were asked to return to the Research Site to assess for any endpoints or events identified;
Adverse events;
Concomitant medications; and
Current address and contact information.
Patients were reminded about the following items:
To take the study medication according to the dosing schedule assigned, with food;
When to return to the Research Center for the next visit;
To bring the unused study medication to the next visit;
To not take study drug on the morning of their next visit; and
To fast for at least 10 hours prior to the next visit.

Laboratory Procedures

Clinical Laboratory Procedures and Evaluations: All clinical laboratory determinations for screening and safety were performed by a certified clinical laboratory under the supervision of the Sponsor or its designee. Whenever possible and appropriate, samples for the clinical laboratory procedures were collected after fasting for at least 10 hours. For the purposes of this study, fasting was defined as nothing by mouth except water (and any essential medications). The investigator reviewed and signed all laboratory test reports.

At screening, patients who had laboratory values that are outside the exclusionary limits specified in the exclusion criteria were not enrolled in the study (patients would have been considered for the study if values were classified as not clinically significant by the investigator). After randomization, the investigator was notified if laboratory values were outside of their normal range. In this case, the investigator was required to conduct clinically appropriate follow-up procedures.

Safety Laboratory Tests: The safety parameters were analyzed by a certified clinical laboratory at screening (Visit 1 or Visit 1.1), Randomization visit (Visit 2; Day 0), Visit 3 (Day 120; ~4 Months) and all other follow-up visits including the Last Visit. The safety laboratory tests included:

- Hematology with complete blood count (CBC), including RBC, hemoglobin (Hgb), hematocrit (Hct), white cell blood count (WBC), white cell differential, and platelet count; and
- Biochemistry panel including total protein, albumin, alkaline phosphatase, alanine aminotransferase (ALT/SGPT), aspartate aminotransferase (AST/SGOT), total bilirubin, glucose, calcium, electrolytes (sodium, potassium, chloride), blood urea nitrogen (BUN), serum creatinine, uric acid, creatine kinase, and HbA1c.

Each laboratory result was classified as low (L), normal (N), and high (H) at each visit according to the laboratory-supplied normal range. The shift from baseline was presented for each post-baseline visit and overall post-baseline visits. If multiple measurements for a test parameter were available for a post-baseline patient-visit, the most extreme value was included in the shift table. For shift from baseline to overall post-baseline visits, values from all visits (including unscheduled measurements) were included. The chemistry shift table included fasting lipid parameters. The continuous lipid values were presented as part of the efficacy analysis.

Fasting Lipid Profile: The fasting lipid panel included: TG, TC, LDL-C, HDL-C, non-HDL-C, and VLDL-C. At all visits, LDL-C was calculated using the Friedewald equation. At Visit 1 and Visit 1.1 direct LDL-C were used if at the same visit TG>400 mg/dL (4.52 mmol/L). These LDL-C values were used for the evaluation of the LDL-C inclusion criterion (LDL-C qualifying measurements for randomization) and for the assessment of changes in the statin therapy when LDL-C was not at goal. At all remaining visits (except Visit 2 and Visit 4) LDL-C was measured by direct LDL cholesterol or by preparative ultracentrifugation if at the same visit TG>400 mg/dL (4.52 mmol/L). In addition, irrespective of the TG levels, at Visit 2 (0 Months of Follow-up, baseline) and at Visit 4 (12 Months of Follow-up), LDL-C were measured by preparative ultracentrifugation. These preparative ultracentrifugation LDL-C measurements were used in the statistical analysis including the calculation of the percent change from baseline (1 year versus baseline). Hopkins LDL-C was calculated for each visit.

Genetic Testing: A fasting blood sample was stored for future genetic testing at the discretion of the Sponsor. The specifics of this test were determined at a later date. This sample was optional as local regulations may prohibit genetic samples to be collected or shipped outside the country, or patients may not have consented. Research on genetic testing looked for links between genes and certain diseases, including their treatment(s) such as medicines and medical care. The blood samples were collected in the study center with the regular protocol-required labs. Each patient tube with a sample for genetic testing were labeled with patient number only. The site maintained a Subject Code Identification List for cross-reference. The patient number did not contain any identifiable information (i.e., patient initials, date of birth, etc.). Un-analyzed samples were stored frozen by the Sponsor for a period of up to 2 years following the end of the study, at which time they were destroyed. If samples were tested, results were not reported to the patient, parents, relatives, or attending physician and were not recorded in the patient's medical records. There was no follow-up contact with the sites or patients regarding this sample. The subject could withdraw their consent for genetic testing at any time up to analysis, even after the sample had been obtained. The subject could notify the site in writing that they withdraw their consent for the genetic testing portion of the study, and it was documented by the site in the subject chart, as well as captured in the CRF. The lab was notified to pull the sample and destroy it. Potential genetic bioassays may have been performed and may have been as broad as a genome-wide association study (GWAS) or as limited as a single gene-target approach; potential target genes include, but are not limited to the genes encoding: Apo C3, Apo A5, CETP, LPL, PCSK9, TNFα, TNFβ, ALOX5, COX2, FABP genes, haptoglobin 1 and haptoglobin 2.

Biomarkers Assays: The biomarker assays included: hsCRP, Apo B and hsTnT.

Additional laboratory tests: Additional laboratory tests were performed and included:

- A urine pregnancy test was administered to women of childbearing potential at certain visits as listed in schedule of procedures (Table 1). The urine pregnancy tests was performed at the Research Site utilizing marketed test kits, or at a certified clinical laboratory;
- A fasting blood sample (10 mL) for archiving. This sample was collected only at sites in countries where allowed by local regulations and at sites for which approved by the IRB or IEC. The plasma from the archiving sample was stored frozen in 2 separate equal aliquots, and was used at the Sponsor's discretion to perform repeat analyses described in the protocol or to perform other tests related to cardiovascular health; and
- Potential non-genetic bioassays were performed, including but not limited to: Apo A1, Apo C3, Apo E, NMR lipid profile (particle size and number), oxidized LDL, Lp(a), Lp-PLA$_2$, serum fatty-acids concentrations, and gamma-glutamyltransferase (GGT).

Blinding of Laboratory Results: All efficacy laboratory results during the double-blind period of the trial were blinded (values not provided) to patients, investigators, pharmacists and other supporting staff at the Research Sites, personnel and designees of the Sponsor, study administrators and personnel at the organization(s) and vendors managing and/or supporting the study, with the exception of the laboratory personnel conducting the assays. To ensure patient safety, hsTnT values were reported to the site.

Flagging of Critical Lab Values: Critical lab values are values that may have warranted medical intervention to avoid possible harm to a patient. Critical lab values were defined in the Laboratory Manual for the study, and the Research Site was notified of the occurrence of a critical lab value (critical high or critical low) by a special annotation (flag) in the laboratory reports provided to the Research Sites. Although laboratory values that were part of the efficacy endpoints during the double-blind period of the study were not provided to the Research Site, the sites were notified when the TG value of a patient sample was >1000 mg/dL (11.29 mmol/L) (critical high TG value) or if the LDL-C values of a patient sample was >130 mg/dL (3.37 mmol/L) (critical high LDL-C value). These critical high values were confirmed by a repeat measurement (new fasting blood sample) within 7 days. TG value of >2000 mg/dL (22.58 mmol/L) were also flagged, so that appropriate medical action could be taken by the investigator as soon as possible.

If TG values were confirmed critically high, patients could be discontinued from study drug with the option to remain on study. The investigator used the best clinical judgment for each patient which included the use of approved TG-lowering medications after patients had discontinued from study drug. If LDL-C values were confirmed

TABLE 7A

Vital Signs Value Categories

| Vital Sign | Low | Normal | High |
|---|---|---|---|
| Systolic Blood Pressure | ≤90 mmHg | >90 mmHg to <160 mmHg | ≥160 mmHg |
| Diastolic Blood Pressure | ≤50 mmHg | >50 mmHg to <100 mmHg | ≥100 mmHg |
| Pulse | ≤50 beats/min | >50 beats/min to <90 beats/min | ≥90 beats/min |

TABLE 7B

Potentially Clinically Significant Vial Signs Value Definitions

| Vital Sign | PCS Low | PCS High |
|---|---|---|
| Systolic Blood Pressure | ≤90 mmHg AND decrease of ≥20 mmHg; ≤90 mmHg; decrease of ≥20 mmHg | ≥160 mmHg AND increase of ≥20 mmHg; ≥160 mmHg; increase of ≥20 mmHg |
| Diastolic Blood Pressure | ≤50 mmHg AND decrease of ≥10 mmHg; ≤50 mmHg; decrease of >10 mmHg | ≥100 mmHg AND increase of >10 mmHg; ≥100 mmHg; increase of 10 mmHg |
| Pulse | ≤50 beats/min AND decrease of ≥15 beats/min; ≤50 beats/min; decrease of ≥15 beats/min | ≥90 beats/min AND increase of ≥15 beats/min; ≥90 beats/min; increase of ≥15 beats/min | critically high, the investigator needed to take appropriate medical action which included: reinforcing/intensifying therapeutic lifestyle changes (including diet and physical activity), increasing the dose of the present statin therapy, adding ezetimibe, or prescribing a more potent statin to lower LDL-C. The investigator used the best clinical judgment for each patient.

Medical Procedures

Medical, Surgical and Family History: Medical history, including family history and details regarding all illnesses and allergies, date(s) of onset, status of current condition, and smoking and alcohol use were collected on all patients.

Demographics: Demographic information including day, month, and year of birth, race, and gender were collected for all patients.

Vital Signs and Patient Measurements: Vital signs included systolic and diastolic blood pressure, heart rate, respiratory rate, and body temperature. Blood pressure was measured using a standardized process:

Patient sat for 5 minutes with feet flat on the floor and measurement arm supported so that the midpoint of the manometer cuff was at heart level; and Used a mercury sphygmomanometer or automatic blood pressure device with an appropriately sized cuff with the bladder centered over the brachial artery.

Blood pressure was recorded to the nearest 2 mmHg mark on the manometer or to the nearest whole number on an automatic device. A blood pressure reading was repeated 1 to 2 minutes later, and the second reading recorded to the nearest 2 mmHg mark.

The baseline value categories and post-baseline endpoint value categories shown in Table 6 were measured and presented. Definitions for potentially clinically significant (PCS) vital signs treatment-emergent values are defined below in Table 7.

Number (%) of patients with any post-baseline PCS vital sign values was summarized by treatment group. A listing of patients who meet the threshold criteria was provided.

Physical Examination: A physical examination included source documentation of general appearance, skin, and specific head and neck, heart, lung, abdomen, extremities, and neuromuscular assessments.

Height, Weight and Body Mass Index: Height and weight were measured.

Measurement of weight was performed with the patient dressed in indoor clothing, with shoes removed, and bladder empty.

Waist Circumference: Waist circumference was measured with a tape measure, as follows: Start at the top of the hip bone then bring the tape measure all the way around—level with the navel. Make sure the tape measure is snug, but without compressing the skin, and that it is parallel with the floor. Patients should not have held their breath while measuring waist circumference.

12-Lead Electrocardiogram (ECG): ECGs (standard 12-lead) were obtained annually. Site personnel made every attempt to perform a patient's ECG using the same equipment at each visit. ECGs were reviewed by the site for the detection of silent MI. Silent MIs were sent for event adjudication. All post-randomization ECGs (protocol-specified and other) were sent to the CEC for evaluation of silent MI. The 12-lead ECG parameters included Heart Rate (bpm), PR Interval (msec), QRS Interval (msec), QT Interval (msec), and QTc Interval (msec) were measured, and Overall Interpretation and Silent MI (Yes/No) were summarized for all patients at Screening (Visit 1), Randomization visit (Visit 2; Day 0) and all other follow-up visits including the last visit of the study.

A treatment-emergent PCS high value at any time was defined as a change from a value less than or equal to the defined PCS value at baseline to a PCS high value at any post-baseline measurement. A treatment-emergent PCS low value at any time was defined as a change from a value greater than or equal to the lower PCS value at baseline to a PCS low value at any post-baseline measurement. Table 8 provides the PCS ECG values.

TABLE 8

Potentially Clinically Significant ECG Value Definitions

| ECG Parameter | PCS Low | PCS High |
|---|---|---|
| PR Interval | <120 msec | >120 msec and increase of >20 msec from baseline |
| QRS Interval | N/A | >110 msec |
| QTc | N/A | >500 msec |

Number (%) of patients with post-baseline PCS ECG values were presented by treatment group. A listing of subjects with potentially clinically significant changes in ECG values was included.

Treatment and Procedures

Treatment Regimen, Dosage, and Duration: Eligible study patients were randomly assigned on Day 0 to one of the 2 treatment groups. Patients in each group received either 4 g/day AMR101 or placebo for up to 6.5 years, depending on individual date of randomization and overall study stop date according to Table 9. The daily dose of study drug was 4 capsules per day taken as two capsules taken on two occasions per day (2 capsules were given twice daily).

TABLE 9

Dosing Schedule during the Treatment Period

| Treatment Group | Daily Dose | Number of Capsules per Day |
|---|---|---|
| 1 | 4 g | 4 capsules of 1000 mg AMR101 |
| 2 | Placebo | 4 capsules of matching placebo |

Patients were instructed to take study drug with food (i.e., with or at the end of their morning and evening meals). On days that patients were scheduled for study visits, the daily dose of study drug was administered by site personnel with food provided by the site following collection of all fasting blood samples. For the purposes of this study, fasting was defined as nothing by mouth except water (and any essential medications) for at least 10 hours. Treatment Assignment Identification Number: A unique patient identification number (patient number) was established for each patient at each site. The patient number was used to identify the patient throughout the study and was entered on all documentation. If a patient was not eligible to receive treatment, or if a patient discontinued from the study, the patient number could not be reassigned to another patient. The patient number was used to assign patients to one of the 2 treatment groups according to the randomization schedule.

Drug Randomization: Only qualified patients who meet all of the inclusion criteria and none of the exclusion criteria were randomized and received study medication starting at Visit 2 (Day 0). Eligible patients were randomly assigned to one of the 2 treatment groups. Randomization was stratified by CV risk category, use of ezetimibe and by geographical region (Westernized, Eastern European, and Asia Pacific countries). Approximately 70% of randomized patients were in the CV Risk Category 1, including patients with established CVD, and approximately 30% of randomized patients were in the CV Risk Category 2, including patients with diabetes and at least one additional risk factor but no established CVD. Enrollment with patients of a CV risk category was stopped when the planned number of patients in that risk category was reached.

Emergency Unblinding: In an emergency, when knowledge of the patient's treatment assignment was essential for the clinical management or welfare of the patient, the investigator could request the patient's treatment assignment for unblinding. Prior to unblinding the patient's individual treatment assignment, the investigator assessed the relationship of an adverse event to the administration of the study drug (Yes or No). If the blind was broken for any reason, the investigator recorded the date and reason for breaking the blind on the appropriate Case Report Form (CRF) and source documents.

Compliance Control: Unless clear contraindications arise, patients were strongly encouraged to adhere to their treatment regimen with the study drug for the duration of the trial. Any interruptions of therapy were, if possible, brief (e.g., <4 weeks) and only for clinically indicated reasons, such as adverse events. Discontinuations were discouraged as much as possible. Any discontinuations were based on compelling clinical reasons. For every patient, an assessment of compliance to the study drug treatment regimen was obtained at each scheduled visit. Study medication was dispensed in amounts exceeding the amount required for the study. Patients were instructed to return all unused study medication at the next visit. Compliance to the study drug regimen was evaluated at each visit by counting unused capsules. Discrepancies were evaluated and discussed with each patient to assess compliance. If compliance was unsatisfactory, the patient was counseled about the importance of compliance to the dosing regimen. At the end of the study, the final study medication compliance was determined by unused capsule count.

Study Restrictions

Concomitant Medications during Treatment/Follow-Up Period: Any medications administered during the study period were documented on the Concomitant Medication CRF. Patients had not taken any investigational agent within 90 days prior to screening. Patients could not participate in any other investigational medication trial while participating in this study. The following non-study drug related, non-statin, lipid-altering medications and supplements, and foods were prohibited during the study (from Visit 1 until after the Last Visit-End of Study), except for compelling medical reasons in ODIS patients:

niacin >200 mg/day;
fibrates;
prescription omega-3 fatty acid medications;
dietary supplements containing omega-3 fatty acids (e.g., flaxseed, fish, krill, or algal oils);
bile acid sequestrants;
PCSK9 inhibitors;
cyclophosphamide; and
systemic retinoids.

If any of these products were used during the treatment/follow-up period of the study, it was for compelling medical reasons in ODIS patients, and documented in the Concomitant Medication CRF. If the ODIS patient agreed to restart study medication, the use of excluded medication was discontinued. Foods enriched with omega-3 fatty acids were strongly discouraged after Visit 1 for the duration of the study (does not apply to The Netherlands or Canada only. Therefore, all centers in The Netherlands and Canada ignored this request). The following products were allowed: statins, ezetimibe, and herbal products & dietary supplements not containing omega-3 fatty acids.

Statins:

The same statin at the same dose was continued until the end of the study, unless deemed medically necessary to change because of an adverse event or lack of efficacy (LOE). It was preferred that if LOE was the determining factor that ezetimibe was added to the present dose;

Switching between a brand name statin and the generic version of the same statin was allowed at any time during the study;

Statins were administered with or without ezetimibe;

Based on the FDA recommendation, simvastatin 80 mg was used only in patients who had been taking this dose for 12 months or more and had not experienced any muscle toxicity. (See reference: FDA Drug Safety Communication: Ongoing safety review of high-dose Zocor (simvastatin) and increased risk of muscle injury. (http://www.fda.gov/Drugs/DrugSafety/Postmarket-DrugSafetyInformationforPatie ntsandProviders/ ucm204882.htm); and Changing of the type of statin or the statin dose during the treatment/follow-up period of the study was only done for compelling medical reasons and was documented in the CRF. Maintaining statin therapy throughout the study was important and, in the rare circumstance that it became medically compelling to discontinue statin use, the patient could remain in the study and on study medication with approval from the Medical Monitor. Under such conditions, resumption of statin therapy was attempted when/if medically appropriate.

If the level of LDL-C exceeded 130 mg/dL (3.37 mmol/L) during the study (initial measurement and confirmed by a second determination at least 1 week later), the investigator either increased the dose of the present statin therapy or added ezetimibe to lower LDL-C. The investigator used the best clinical judgment for each patient.

LDL-C Rescue: If the level of LDL-C exceeded 130 mg/dL (3.37 mmol/L) during the study (initial measurement and confirmed by a second determination at least 1 week later), the investigator either increased the dose of the present statin therapy or added ezetimibe to lower LDL-C. The investigator used the best clinical judgment for each patient.

No data were available with regard to potential interactions between ethyl-EPA and oral contraceptives. There were no reports suggesting that omega-3 fatty acids, including ethyl-EPA, would decrease the efficacy of oral contraceptives.

Medications that were excluded if not at a stable dose for 28 days prior to screening, could be initiated post-randomization if medically warranted (i.e., tamoxifen, estrogens, progestins, thyroid hormone therapy, systemic corticosteroids and HIV-protease inhibitors).

Patient Restrictions: Beginning at the screening visit, all patients were instructed to refrain from excessive alcohol consumption, to follow a physician recommended diet and to maintain it through the duration of the study. Excessive alcohol consumption is on average 2 units of alcohol per day or drinking 5 units or more for men or 4 units or more for women in any one hour (episodic excessive drinking or binge drinking). A unit of alcohol is defined as a 12-ounce (350 mL) beer, 5-ounce (150 mL) wine, or 1.5-ounce (45 mL) of 80-proof alcohol for drinks.

Investigational Product

Clinical Trial Material: The following clinical materials were supplied by the Sponsor:

AMR101 1000 mg capsules

Placebo capsules (to match AMR 101 1 g Capsules)

The Sponsor supplied sufficient quantities of AMR101 1000 mg capsules and placebo capsules to allow for completion of the study. The lot numbers of the drugs supplied were recorded in the final study report. Records were maintained indicating the receipt and dispensation of all drug supplies. At the conclusion of the study, any unused study drug was destroyed.

Pharmaceutical Formulations: AMR101 1000 mg and placebo capsules (paraffin) were provided in liquid-filled, oblong, gelatin capsules. Each capsule was filled with a clear liquid (colorless to pale yellow in color). The capsules were approximately 25.5 mm in length with a diameter of approximately 9.5 mm.

Labeling and Packaging: Study medication was packaged in high-density polyethylene bottles. Labeling and packaging were performed according to GMP guidelines and all applicable country-specific requirements. The bottles were numbered for each patient based on the randomization schedule. The patient randomization number assigned by IWR or a designee of the Sponsor for the study (if no IWR system was used), corresponds to the number on the bottles. The bottle number for each patient was recorded in the Electronic Data Capture (EDC) system for the study.

Dispensing Procedures and Storage Conditions

Dispensing Procedures: At Visit 2 (Day 0), patients were assigned a study drug according to their treatment group determined by the randomization schedule. Once assigned to a treatment group, patients received study drug supplies. At each visit, patients brought unused drug supplies dispensed to them earlier. From the drug supplies assigned to each patient, site personnel administered the drug while the patients were at the Research Site. The investigator or designee contacted the IWR system or a designee of the Sponsor for the study (if no IWR system is used) when any unscheduled replacements of study medication were needed. During the last visit of the treatment period, patients brought the unused drug supplies for site personnel to calculate the final study medication compliance by unused capsule count.

Storage Conditions: At the Research Sites, study drugs were stored at room temperature, 68° F. to 77° F. (20° C. to 25° C.). Storage temperature did not go below 59° F. (15° C.) or above 86° F. (30° C.) and the drug was stored in the original package. Study drugs were stored in a pharmacy or locked and secure storage facility, accessible only to those individuals authorized by the investigator to dispense the drug. The investigator or designee kept accurate dispensing records. At the conclusion of the study, study site personnel accounted for all used and unused study drug. Any unused study drug was destroyed. The investigator agreed not to distribute study drug to any patient, except those patients participating in the study.

Efficacy Assessments

Specification of Variables and Procedures: The primary endpoint and the majority of the secondary and tertiary endpoints were based on clinical events related to CVD and mortality. All events occurring between randomization and the study end date (inclusive) were recorded. Only adjudicated events were included in the final analyses.

Primary Efficacy Endpoint: The primary efficacy endpoint was time from randomization to the first occurrence of the composite of the following clinical events: CV death; non-fatal MI (including silent MI; ECGs were performed annually for the detection of silent MIs); nonfatal stroke; coronary revascularization; and unstable angina determined to be caused by myocardial ischemia by invasive/non-invasive testing and requiring emergent hospitalization. The first occurrence of any of these major adverse vascular events during the follow-up period of the study were included in the incidence.

Secondary Efficacy Endpoints: The key secondary efficacy endpoint was the time from randomization to the first occurrence of the composite of CV death, nonfatal MI (including silent MI), or nonfatal stroke. Other secondary efficacy endpoints were time from randomization to the first occurrence of the individual or composite endpoints as follows (tested in the order listed):

The composite of CV death or nonfatal MI (including silent MI);
Fatal or nonfatal MI (including silent MI);
Non-elective coronary revascularization represented as the composite of emergent or urgent classifications;
CV death;
Unstable angina determined to be caused by myocardial ischemia by invasive/non-invasive testing and requiring emergent hospitalization;
Fatal and nonfatal stroke;
The composite of total mortality, nonfatal MI (including silent MI), or nonfatal stroke; and/or
Total mortality.

For the secondary endpoints that count a single event, the time from randomization to the first occurrence of this type of event was counted for each patient. For secondary efficacy endpoints that were composites of two or more types of events, the time from randomization to the first occurrence of any of the event types included in the composite were counted for each patient.

Tertiary Efficacy Endpoints: The following tertiary endpoints were evaluated as supporting efficacy and safety analyses. Where applicable and unless specified otherwise, endpoint analyses were conducted as time from randomization to the first occurrence of the individual or composite endpoint as follows:

Total CV events analysis defined as the time from randomization to occurrence of the first and all recurrent major CV events defined as CV death, nonfatal MI (including silent MI), nonfatal stroke, coronary revascularization, or unstable angina determined to be caused by myocardial ischemia by invasive/non-invasive testing and requiring emergent hospitalization;
Primary composite endpoint in subset of patients with diabetes mellitus at baseline;
Primary composite endpoint in the subset of patients with metabolic syndrome at baseline with waist circumference cut points specifically set at 35 inches (88 cm) for all women and Asian, Hispanic, or Latino men, and 40 inches (102 cm) for all other men;
Primary composite endpoint in the subset of patients with impaired glucose metabolism at baseline (Visit 2 FBG of 100-125 mg/dL);
Key secondary composite endpoint in the subset of patients with impaired glucose metabolism at baseline (Visit 2 FBG 100-125 mg/dL);
The composite of CV death, nonfatal MI (including silent MI), nonfatal stroke, cardiac arrhythmia requiring hospitalization of 24 hours, or cardiac arrest;
The composite of CV death, nonfatal MI (including silent MI), non-elective coronary revascularizations (defined as emergent or urgent classifications), or unstable angina determined caused by myocardial ischemia by invasive/non-invasive testing and requiring emergent hospitalization;
The composite of CV death, nonfatal MI (including silent MI), non-elective coronary revascularizations (defined as emergent or urgent classifications), unstable angina determined caused by myocardial ischemia by invasive/non-invasive testing and requiring emergent hospitalization, nonfatal stroke, or PVD requiring intervention, such as angioplasty, bypass surgery, or aneurism repair;
The composite of CV death, nonfatal MI (including silent MI), non-elective coronary revascularizations (defined as emergent or urgent classifications), unstable angina determined caused by myocardial ischemia by invasive/non-invasive testing and requiring emergent hospitalization, PVD requiring intervention, or cardiac arrhythmia requiring hospitalization of 24 hours;
New CHF;
New CHF as the primary cause of hospitalization;
Transient ischemic attack (TIA);
Amputation for PVD;
Carotid revascularization;
All coronary revascularizations defined as the composite of emergent, urgent, elective, or salvage;
Emergent coronary revascularizations;
Urgent coronary revascularizations;
Elective coronary revascularizations;
Salvage coronary revascularizations;
Cardiac arrhythmias requiring hospitalization of 24 hours;
Cardiac arrest;
Ischemic stroke;
Hemorrhagic stroke;
Fatal or nonfatal stroke in the subset of patients with a history of stroke prior to baseline;
New onset diabetes, defined as Type 2 diabetes newly diagnosed during the treatment/follow-up period;
New onset hypertension, defined as blood pressure 140 mmHg systolic OR 90 mm Hg diastolic newly diagnosed during the treatment/follow-up period;
Fasting TG, TC, LDL-C, HDL-C, non-HDL-C, VLDL-C, apo B, hsCRP (hsCRP and log[hsCRP]), hsTnT, and RLP-C (to be estimated from standard lipid panel, RLP-C=TC−HDL-C−LDL-C [Varbo 2014]), (based on ITT estimands):
Assessment of the relationship between baseline biomarker values and treatment effects within the primary and key secondary composite endpoints;
Assessment of the effect of AMR101 on each marker; and
Assessment of the relationship between post-baseline biomarker values and treatment effects within the primary and key secondary composite endpoints by including post-baseline biomarker values (for example, at 4 months, or at 1 year) as a covariate.
Change in body weight; and
Change in waist circumference.

Where applicable and unless specified otherwise, for the tertiary endpoints that count a single event, the time from randomization to the first occurrence of this type of event was counted in each patient. Similarly, where applicable and unless specified otherwise, for tertiary endpoints that were composites of two or more types of events, the time from randomization to the first occurrence of any of the event types included in the composite was counted in each patient.

Other sensitivity, supportive, and exploratory analyses for the primary efficacy endpoint were carried out, namely, an on-treatment analysis which included primary event onset up to 0 and 30-days after the permanent discontinuation of the drug.

The following clinical events that were positively adjudicated by the Clinical Endpoint Committee were analyzed as tertiary endpoints for the ITT intent-to-treat (ITT) population:

Composition of total mortality, or congestive heart failure (CHF);
Composite of CV death, or new CHF;
Sudden cardiac death;
Peripheral artery disease (PAD); and
Atrial fibrillation, or atrial flutter.

The above tertiary endpoints were analyzed similarly as the primary endpoint.

In addition, the following were analyzed as tertiary endpoints for the ITT population:

Relationship between on-treatment high-sensitivity C-reactive protein (hsCRP) and the primary key secondary endpoints; and
Relationship between on-treatment serum eicosapentaenoic acid (EPA) and the primary and key secondary endpoints.

To assess the relationship between on-treatment hsCRP and the primary and key secondary endpoints, subgroup analyses were carried out as done for the ITT population for patients grouped according to values greater or equal to or less than 2 mg/dL at baseline and at 2 years. To assess the relationship between on-treatment serum EPA and the primary and key secondary endpoints, Kaplan-Meier (KM) curves were produced for AMR101 treated patients grouped into tertiles based on their values at year 1 and were compared with the placebo-treated patients.

Safety Assessments

Specification of Variables and Procedures: Safety assessments included adverse events, clinical laboratory measurements (chemistry, hematology), 12-lead ECGs, vital signs (systolic and diastolic blood pressure, heart rate, respiratory rate, and body temperature), weight, waist circumference, and physical examinations as per Study Procedures in Table 1. A complete medical, surgical and family history was completed at Visit 1. All laboratory test results were evaluated by the investigator as to their clinical significance. Any observations at physical examinations or laboratory values considered by the investigator to be clinically significant were considered an adverse event.

Adverse Events: An adverse event is defined as any untoward medical occurrence, which does not necessarily have a causal relationship with the medication under investigation. An adverse event can therefore be any unfavorable and/or unintended sign (including an abnormal laboratory finding), symptom, or disease temporally associated with the use of an investigational medication product, whether or not related to the investigational medication product. All adverse events, including observed or volunteered problems, complaints, or symptoms, were recorded on the appropriate CRF. Each adverse event was evaluated for duration, intensity, and causal relationship with the study medication or other factors.

Adverse events, which included clinical laboratory test variables, were monitored from the time of informed consent until study participation was complete. Patients were instructed to report any adverse event that they experienced to the investigator. Beginning with Visit 2, investigators assessed for adverse events at each visit and recorded the event on the appropriate adverse event CRF.

Wherever possible, a specific disease or syndrome rather than individual associated signs and symptoms was identified by the investigator and recorded on the CRF. However, if an observed or reported sign or symptom was not considered a component of a specific disease or syndrome by the investigator, it was recorded as a separate adverse event on the CRF.

Any medical condition that was present when a patient was screened or present at baseline that did not deteriorate were not reported as an adverse event. However, medical conditions or signs or symptoms present at baseline and that changed in severity or seriousness at any time during the study were reported as an adverse event.

Clinically significant abnormal laboratory findings or other abnormal assessments that were detected during the study or were present at baseline and significantly worsened were reported as adverse events or SAEs. The investigator exercised his or her medical and scientific judgment in deciding whether an abnormal laboratory finding, or other abnormal assessment was clinically significant.

The investigator rated the severity (intensity) of each adverse event as mild, moderate, or severe, and also categorized each adverse event as to its potential relationship to study drug using the categories of Yes or No. The severity was defined as:

Mild—An event that is usually transient in nature and generally not interfering with normal activities.
Moderate—An event that is sufficiently discomforting to interfere with normal activities.
Severe—An event that is incapacitating with inability to work or do usual activity or inability to work or perform normal daily activity.

Causality Assessment: The relationship of an adverse event to the administration of the study drug was assessed according to the following definitions:

No (unrelated, not related, no relation)—The time course between the administration of study drug and the occurrence or worsening of the adverse event rules out a causal relationship and another cause (concomitant drugs, therapies, complications, etc.) is suspected.
Yes (related, probably related, possibly related)—The time course between the administration of study drug and the occurrence or worsening of the adverse event is consistent with a causal relationship and no other cause (concomitant drugs, therapies, complications, etc.) can be identified.

The following factors were also considered:
The temporal sequence from study medication administration;
The event occurred after the study medication was given. The length of time from study medication exposure to event was evaluated in the clinical context of the event;
Underlying, concomitant, intercurrent diseases;
Each report was evaluated in the context of the natural history and course of the disease being treated and any other disease the patient may have had;
Concomitant medication;
The other medications the patient was taking or the treatment the patient received were examined to determine whether any of them might have caused the event in question;
Known response pattern for this class of study medication;
Clinical and/or preclinical data may have indicated whether a particular response was likely to be a class effect;

Exposure to physical and/or mental stresses;
The exposure to stress might induce adverse changes in the patient and provide a logical and better explanation for the event;
The pharmacology and pharmacokinetics of the study medication; and
The known pharmacologic properties (absorption, distribution, metabolism, and excretion) of the study medication were considered.

Unexpected Adverse Events: An unexpected adverse event is an adverse event either not previously reported or where the nature, seriousness, severity, or outcome is not consistent with the current Investigator's Brochure.

Serious Adverse Events: A serious adverse event (SAE) is defined as an adverse event that meets any of the following criteria:
Results in death;
Is life-threatening—The term "life-threatening" in the definition of "serious" refers to an event in which the patient was at risk of death at the time of the event. It does not refer to an event, which hypothetically might have caused death, if it were more severe;
Requires hospitalization or prolongation of existing hospitalization. In general, hospitalization for treatment of a pre-existing condition(s) that did not worsen from baseline was not considered adverse events and was not reported as SAEs;
Results in disability/incapacity;
Is a congenital anomaly/birth defect; and
Is an important medical event. Important medical events that may not result in death, be life threatening, or require hospitalization were considered an SAE when, based upon appropriate medical judgment, they may have jeopardized the patient and may have required medical or surgical intervention to prevent one of the outcomes listed above. Examples of such medical events included allergic bronchospasm requiring intensive treatment in an emergency room or at home, blood dyscrasias or convulsions that did not result in inpatient hospitalizations, or the development of drug dependency.

By design of this study SAEs that were endpoint events were only recorded for the endpoint determination and not captured as SAEs. The intention was that the endpoint events were not reported to IRBs as SAEs, unless the IRB required that these were reported. Investigators specifically informed their institution/IRB of this plan and confirm whether or not they wanted the endpoint events reported. By agreement with the US FDA, these endpoints were also not reported to the US FDA as SAEs; rather they were reported as endpoint events. Following adjudication if the event was determined to not meet the criteria for an event, the event was evaluated as an SAE beginning with that day as Day 0.

Adverse Events of Special Interest: Bleeding-related adverse events, glucose control (fasting blood glucose and HbA1c), and indicators of hepatic disorders (e.g., ALT or AST increases >3×ULN, total bilirubin increases of ≥2×ULN) were summarized separately and compared between treatment groups.

Serious Adverse Event Reporting—Procedure for Investigators

Initial Reports: All SAEs occurring from the time of informed consent until 28 days following the last administration of study medication were reported to the Sponsor or designee within 24 hours of the knowledge of the occurrence (this refers to any adverse event that meets any of the aforementioned serious criteria). SAEs that the investigator considered related to study medication occurring after the 28-day follow-up period were also reported to the Sponsor or designee. The investigator was required to submit SAE reports to the Institutional Review Board (IRB) or Independent Ethics Committee (IEC) in accordance with local requirements. All investigators involved in studies using the same investigational medicinal product (IMP) received any Suspected Unexpected Serious Adverse Reaction (SUSAR) reports for onward submission to their local IRB as required. All reports sent to investigators were blinded. In addition, regulatory agencies were notified of SAEs per the requirements of the specific regulatory jurisdiction regulations and laws.

Follow-Up Reports: The investigator followed the patient until the SAE subsided, or until the condition became chronic in nature, stabilized (in the case of persistent impairment), or the patient died. Within 24 hours of receipt of follow-up information, the investigator updated the SAE form electronically in the EDC system for the study and submitted any supporting documentation (e.g., laboratory test reports, patient discharge summary, or autopsy reports) to the Sponsor or designee via fax or email.

Reporting by the Sponsor: IRBs and IECs were informed of SUSARs according to local requirements. Cases were unblinded for reporting purposes as required.

Exposure In Utero During Clinical Trials: If a patient became pregnant during the study, the investigator reported the pregnancy to the Sponsor or designee within 24 hours of being notified. The Sponsor or designee then forwarded the Exposure In Utero form to the investigator for completion. The patient was followed by the investigator until completion of the pregnancy. If the pregnancy ended for any reason before the anticipated date, the investigator notified the Sponsor or designee. At the completion of the pregnancy, the investigator documented the outcome of the pregnancy. If the outcome of the pregnancy met the criteria for immediate classification as an SAE (i.e., postpartum complication, spontaneous abortion, stillbirth, neonatal death, or congenital anomaly), the investigator followed the procedures for reporting an SAE.

Treatment Discontinuation/Patient Withdrawal

Patients could withdraw from the study at any time and for any reason. Study drug administration could also be discontinued at any time, at the discretion of the investigator. In any case, follow-up for efficacy and safety was continued in subjects that discontinued therapy, but remained in the study (i.e., ODIS patients).

Reasons for Early Study Drug Discontinuation: Study drug discontinuation was avoided as much as possible, but could have been done for any of the following reasons:
Patient withdrew consent or requested early discontinuation from the study for any reason. Patients were encouraged to continue to participate in the study for the entire duration of the study even if they choose not to take study medication any longer;
Occurrence of a clinical or laboratory adverse event, either serious or non-serious, at the discretion of the investigator. The Sponsor or designee was notified if a patient was discontinued because of an adverse event or laboratory abnormality. It was recommended that, unless clear contraindications arise, patients were strongly encouraged to adhere to their treatment regimen with the study drug for the duration of the trial. Any interruptions of therapy were, if possible, brief (e.g., <4 weeks) and only for clinically indicated reasons, such as adverse events. The following were considered a reason for discontinuation:

ALT>3×ULN and bilirubin >1.5×ULN;
ALT>5×ULN;
ALT>3×ULN and appearance or worsening of hepatitis;
ALT>3×ULN persisting for >4 weeks; and/or
ALT>3×ULN and cannot be monitored weekly for 4 weeks Any medical condition or personal circumstance that, in the opinion of the investigator, exposed the patient to risk by continuing in the study or precluded adherence to the protocol;

Sponsor discontinued the study;

Investigative site closure, in the event that:
Another investigative site cannot accommodate the patient, or
The patient was unable or unwilling to travel to another investigative site; and/or A TG value was flagged as critically high, i.e., >1000 mg/dL (11.29 mmol/L), and confirmed as critically high by a repeat measurement (new fasting blood sample) within 7 days. In this case, a patient could be discontinued from study drug (with the option to remain ODIS) and other lipid-altering medications may be (re)initiated. If the TG value was flagged as >2000 mg/dL (22.58 mmol/L) then appropriate medical action was taken by the investigator as soon as possible.

Occurrence of an outcome event according to the judgment of the investigator was not considered a valid reason for study drug discontinuation. Patients whose treatment with study medication was discontinued early, and had not withdrawn consent, stayed in the study and were monitored until the end of the study. Patients that continued in the study after 30 days cessation of therapy were characterized as Off Drug In Study (ODIS). ODIS patients were asked to return to the study site for an interim visit once the patient had been off study drug for >30 days. Procedures at this visit were consistent with those at Visit 5. If not contraindicated, patients also had the option to restart study medication at any point once characterized as ODIS. For patients who discontinued study medication (e.g., for an AE that may or may not have been drug-related), a brief therapy interruption could have been followed with a re-challenge (re-initiating study medication) as soon as clinically appropriate; thereby allowing a causative role for study medication to be confirmed or ruled out and continuing a patient in the study and on study drug if appropriate. The reason for study drug discontinuation or interruption was recorded on the CRF.

Follow-Up after Early Study Drug Discontinuation/Lost to Follow-Up

Patients who prematurely discontinued study drug were not replaced. All randomized patients were followed up until the study end date or death, regardless of whether they discontinued study drug prematurely or not. Any event occurring after early study drug discontinuation was recorded up through the study end date. In order to follow the medical status of the patients, especially when they discontinued the study, investigators were encouraged to obtain information from the patient's primary care practitioner (physician or any other medical care provider). Investigators were also requested to try as much as possible to re-contact those patients at the end of the trial to obtain at least their vital status as well as their status with respect to the primary endpoint, and thus avoided lost to follow-up for the efficacy assessment. If patients were lost to follow-up, the CRF was completed up to the last visit or contact.

Statistics

Randomized Population: The randomized population included all patients who sign the informed consent form and are assigned a randomization number at Visit 2 (Day 0).

Intent-to-Treat Population: The ITT population included all patients who were randomized via the IRWS (Interactive Web Response System). All efficacy analyses were performed on the ITT population. Patients were analyzed according to the randomized treatment.

Modified Intent-to-Treat Population: The Modified Intent-to-Treat (mITT) population included all randomized patients who had the study drug dispensed after randomization. Groups were defined based on the randomized treatment.

Per-Protocol Population: The per-protocol (PP) population included all mITT patients without any major protocol deviations, and who had ≥80% compliance while on treatment. To be included in the PP population the minimum time on therapy was 90 days.

Safety Population: All safety analyses were conducted based on the safety population, which is defined as all randomized patients. This was the same as the ITT population.

Statistical Methods: Safety and efficacy variables were analyzed using appropriate statistical methods that were described in detail in a separate Statistical Analysis Plan (SAP). The SAP was finalized before study unblinding.

Patient Disposition and Demographic/Baseline Characteristics: The number and percentage of patients was tabulated for each of the following categories for each treatment group:

Screened (total only);
Re-screened and reasons for re-screening (total only);
ITT overall and by stratification factors (CV risk, ezetimibe use, and geographical region);
mITT population; overall and by stratification factors (CV risk, ezetimibe use, and geographical region);
PP population; overall and by stratification factors (CV risk, ezetimibe use, and geographical region);
Safety population;
Patients who completed the study;
Patients who terminated from the trial early and the primary reason for early termination;
Patients who terminated the trial early prior to having a confirmed primary endpoint event;
Patients with complete follow-up, defined as those for whom all components of the primary endpoint have been ascertained during the entire observation period (or until death); and
Patients who, at the time of study completion, were discontinued from study drug prematurely, but continued within the study (i.e. ODIS patients), along with the primary reason.

For randomized patients who discontinued treatment with study drug, the primary reason for discontinuation was listed and summarized by treatment group. Demographic and baseline characteristics, including age, gender, ethnicity, race, height, body weight, BMI, diabetes, hypertension, metabolic syndrome, overweight/obese/normal according to BMI, and diabetes plus obesity were summarized using descriptive statistics by treatment group in the ITT population.

Demographic data and baseline characteristics were compared among treatment groups for the ITT and PP population. Differences in demographic and baseline characteristics were tested using a chi-square test (for categorical variables) or t-test (for continuous variables). The p-values used were considered descriptive, primarily as an assessment of the balance between the two groups. Age in years was calculated using the date of randomization (Visit 2) and the date of birth.

Study Medication Exposure and Compliance: Study drug exposure was summarized by treatment group using descriptive statistics for each time point and overall. Overall study drug compliance was calculated as the number of doses assumed to be taken relative to scheduled dosing period as follows:

$$\text{Compliance}(\%) = \frac{(\text{\# Capsules of total dispensed} - \text{\# Capsules of total returned})}{(\text{last dose date} - \text{first dose date} + 1) \times 4 \text{ capsules/day}} \times 100$$

Overall percent compliance was calculated per patient in the ITT and Modified ITT populations and summarized by treatment group using descriptive statistics.

Concomitant Therapies: Concomitant medication/therapy verbatim terms were coded using the latest available version, prior to data base lock, of the World Health Organization Drug Dictionary and the Anatomical Therapeutic Chemical classification system. The numbers and percentages of patients in each treatment group taking concomitant medications were summarized. All verbatim descriptions and coded terms were listed for all non-study medications.

Analysis of Efficacy: For efficacy endpoints including CV events, only adjudicated events were included in the final statistical analyses.

Summary Statistics: Summary statistics (n, mean, standard deviation, median, minimum, and maximum) for the baseline and post-baseline measurements, the percent changes, or changes from baseline were presented by treatment group and by visit for all efficacy variables analyzed. The summary statistics included changes in body weight and body mass index from baseline by treatment group and by visit.

Primary Endpoint Analyses: The analysis of the primary efficacy endpoint was performed using the log-rank test comparing the 2 treatment groups (AMR101 and placebo) and including the stratification factor "CV risk category", use of ezetimibe and geographical region (Westernized, Eastern European, and Asia Pacific countries) (each as recorded in the IWR at the time of enrollment) as covariates. The two-sided alpha level for the primary analysis was reduced from 0.05 to account for the interim analyses based on a group sequential design with O'Brien-Fleming boundaries generated using the Lan-DeMets alpha-spending function. The hazard ratio (HR) for treatment group (AMR101 vs. placebo) from a Cox proportional hazard model that included the stratification factor was also reported, along with the associated 95% confidence interval (CI). Kaplan-Meier estimates from randomization to the time to the primary efficacy endpoint were plotted.

The size and direction of the treatment effects of the individual components of the composite endpoint and their relative contribution to the composite endpoint were determined as well. All observed data that were positively adjudicated by the CEC, including data after discontinuation of study treatment for patients who discontinued study drug prematurely, were included in the primary analysis. Patients who did not experience a primary efficacy event prior to the end of the study or who withdraw from the study early without a preceding primary efficacy event were censored at the date of their last visit/phone contact. The longest pre-specified interval between visits (onsite or phone) was 90 days. In view of the up to 90-day monitoring period for CV events, the primary endpoint for patients who had a non-CV death within 90 days of last contact without having had an earlier CV event was censored at the time of death. The primary endpoint for patients who had a non-CV death more than 90 days after last contact without having had an earlier CV event were censored at the time of last contact.

The primary analysis assumed that all silent MIs occurred on the date of the first tracing indicative of a silent MI; a second (sensitivity) analysis assumed that all silent MIs occurred on the day after the last prior normal ECG; and a third (sensitivity) analysis assumed that all silent MIs occurred at the mid-point between the last normal ECG and the ECG with the new MI. All deaths causally adjudicated as "undetermined" were combined with those adjudicated as "CV deaths" for the primary analysis. A sensitivity analysis of the CV death category was performed that excluded the "undetermined cause of death" cohort.

The primary efficacy analysis was performed on the ITT population. A sensitivity analysis was performed using the mITT and PP populations. As a sensitivity analysis, patients who discontinued study drug prematurely were censored for the primary composite endpoint analysis on the date of drug discontinuation. The primary analysis was repeated using this censoring rule for the mITT population. As a supportive analysis, a multivariable, stratified Cox proportional hazards model was constructed for the primary endpoint to evaluate the treatment effect adjusting for important covariates.

Secondary Endpoint Analyses: The key secondary hypothesis was tested as part of the confirmatory process only if the primary analysis was statistically significant. For the analysis of secondary efficacy endpoints, the Type 1 error was controlled by testing each endpoint sequentially, starting with the key endpoint. Testing was done at a significance level consistent with that used for the primary endpoint and ceased when a secondary endpoint was found for which treatments did not significantly differ. P-values were presented for all analyses, but they were considered descriptive after the first non-significant result was obtained. Each of the secondary endpoints were analyzed by the same methods described for the primary efficacy endpoint. Kaplan-Meier estimated, the log-rank test stratified by stratification factors used at randomization, and the Cox proportional hazards model including the stratification factors as specified above for the primary efficacy endpoint, were summarized by treatment group. In view of the 90-day monitoring period for CV events, the key secondary endpoint for patients who had a non-CV death within 90 days of last contact without having had an earlier CV event was censored at the time of death. The key secondary endpoint for patients who had a non-CV death more than 90 days after last contact without having had an earlier CV event was censored at the time of last contact. Kaplan-Meier curves stratified by each stratification factor were presented. These analyses were conducted for the ITT population.

Tertiary Endpoints Analyses: Time-to-event tertiary endpoints were analyzed by the same methods as described for the primary efficacy endpoint. Kaplan-Meier estimates, the log-rank test stratified by stratification factors used at randomization, and the Cox proportional hazards model as specified for the primary efficacy endpoint, were summarized by treatment group. In view of the 90-day monitoring period for CV events, if applicable, tertiary endpoints for patients who had a non-CV death within 90 days of last contact without having had an earlier CV event were censored at the time of death. If applicable, tertiary endpoints for patients who gad a non-CV death more than 90 days after last contact without having had an earlier CV event were censored at the time of last contact. Kaplan-Meier curves stratified by each of the stratification factors were presented.

The fasting lipid panel was tested at Screening (Visit 1 or Visit 1.1), Randomization visit (Visit 2; Day 0), Visit 3 (Day 120; ~4 Months) and all other follow-up visits including the last visit. For change from baseline to 1 year preparative ultracentrifugation measurements for LDL-C were analyzed, unless this value was missing. If the LDL-C preparative ultracentrifugation values were missing, then another LDL-C value was used, with prioritization of values obtained from LDL-C Direct measurements, followed by LDL-C derived by the Friedewald calculation (only for subjects with TG<400 mg/dL), and finally LDL-C derived using the calculation published by Hopkins University investigators (Martin S S, Blaha M J, Elshazly M B, et al. Comparison of a novel method vs the Friedewald equation for estimating low-density lipoprotein cholesterol levels from the standard lipid profile. JAMA. 2013; 310:2061-8.). In addition, change from baseline to day 120 in LDL-C utilizing Friedewald's and Hopkins methods was analyzed, using the arithmetic mean of LDL-C obtained at Visit 2 (Day 0) and the preceding Visit 1 (or Visit 1.1). If one of these values was missing, the single available LDL-C value was used. LDL-C according to Hopkins was calculated at each visit.

The randomization visit was considered Baseline. If a baseline value was not available from the randomization visit, then the latest screening value was used. For measurements of lipids, lipoproteins and inflammatory markers, the change and the percent change were summarized at each visit. Since these biomarkers are typically not normally distributed, the Wilcoxon rank-sum test was used for treatment comparisons of the percent change from baseline, and medians and quartiles were provided for each treatment group. The medians of the differences between the treatment groups and 95% CIs were estimated with the Hodges-Lehmann method. In addition, shift-tables were generated as appropriate.

As an additional exploratory analysis, the relationship between post-baseline biomarker values and treatment effects with the primary and key secondary endpoints were assessed by adding biomarker values (for example, at 4 months, or at 1 year, etc.) as time-dependent covariates in the Cox proportional hazards model. Diagnostic plots for the proportional hazards assumption were evaluated. Weight was measured at the screening visit and at all follow-up visits, including the last visit of the study. Waist circumference was measured at the randomization visit (Visit 2; Day 0), Visit 5 (Day 720) and the last visit of the study. Descriptive statistics were presented by visit and treatment group for baseline, post-treatment change from baseline, and the percent change from baseline. Analysis methods for repeated measurements were used to compare percent change from baseline between treatments.

Additional prespecified efficacy endpoints and analyses of this study are listed below. These endpoints and analyses were exploratory in nature and were not included in the original testing scheme:
- Time-to-event analyses as done for the primary analysis were carried out at 1-year and 2-year landmarks for the ITT Population;
- For the recurrent CV events analyses based on the 5-component MACE (CV death, non-fatal MI, non-fatal stroke, unstable angina requiring hospitalization, or coronary revascularization), a total CV event was performed using a Negative Binomial Model analysis;
- An on treatment sensitivity analysis was performed including primary events with onset up to 0 and 30 days after permanent discontinuation of study drug;
- As done for the primary analysis, time-to-event analyses at 1-year and 2-year landmarks for the key secondary endpoints for the ITT Population;
- An analysis of the following clinical events that are positively adjudicated as tertiary endpoints for the ITT Population:
  - Composite of total mortality, or new CHF;
  - Composite of CV death, or new CHF;
  - Sudden cardiac death;
  - Peripheral artery disease (PAD); and
  - Atrial fibrillation, or atrial flutter.
- An analysis of the following as tertiary endpoints for the ITT Population:
  - Relationship between on-treatment hsCRP and primary and key secondary endpoints; and
  - Relationship between on-treatment serum EPA and primary and key secondary endpoints.
- To assess relationships between on-treatment hsCRP and primary and key secondary endpoints, subgroup analyses as done for the ITT population for patients grouped according to (1) values greater or equal to or (2) less than 2 mg/dL at baseline and at 2 years;
- To assess relationships between on-treatment serum EPA and primary and key secondary endpoints, Kaplan Meier curves for AMR101 patients grouped into tertiles based on values at year 1 compared with placebo patients;
- The following were added to the subgroup analyses:
  - Baseline HbA1c value (<6.5%, ≥6.5%);
  - Baseline PAD; and
  - Baseline TG≥150 mg/dL with HDL-C≤40 mg/dL for males and ≤50 mg/dL for females.

The following list presents additional pre-specified exploratory efficacy analyses that are of particular interest to the general clinical and scientific community that were also explored in this study:
- Non-fatal myocardial infarction (MI) (including both clinical manifestation and silent MI categorizations) for the ITT Population;
- Evaluation of effect of time-weighted (or area under the curve [AUC]) EPA data on the primary and key secondary composite endpoints for the ITT Population;
- Sensitivity analyses on primary and key secondary composite endpoints by excluding elective coronary artery revascularizations if onset is <3 months post randomization; and also excluding peri-procedural MIs for the ITT Population;
- Two silent MI (SMI) sensitivity analyses on primary and key secondary composite endpoints—ITT Population:
  - Counting all potential SMIs identified by CEC ECG reviewer, whether confirmed at final ECG or not; and
  - Counting only potential SMIs that have at least one confirmatory ECG showing persistence of Q-waves (even if not present at final ECG).
- Non-alcoholic fatty liver disease (NAFLD) analyses using NAFLD Fibrosis Score (NFS), assessing—ITT Population:
  - Effect on primary and key secondary composite endpoints by baseline NFS category; and
  - Treatment effect on change from baseline in NFS at 1 and 5 years.

Individual and combined on-treatment goal achievement of triglyceride (TG) 150 mg/dL and hsCRP 2 mg/L at 2 years, and end of study for the ITT Population;
Additional renal function (eGFR) analyses—ITT Population:
  Primary and key secondary composite endpoints for patients with baseline renal dysfunction [eGFR]≥60 and <90 mL/min/1.73 m$^2$; and
  Treatment effect on change from baseline in renal function (eGFR) at 1 and 5 years.
Sensitivity analyses on primary and key secondary composite endpoints by excluding patients with post-randomization LDL-C values >100 mg/dL; and another for >70 mg/dL for the ITT Population;
Analyses of hospitalization data (pooled positively adjudicated unstable angina requiring hospitalization, congestive heart failure [CHF] requiring hospitalization, and cardiac arrhythmia requiring hospitalization) for the ITT Population;
  Time from randomization to first hospitalization; and
  Recurrent event analysis on hospitalizations.
Additional subgroup analyses (US versus Non-US) on the primary and key secondary composite endpoints; also potentially other endpoints for the ITT Population;
Additional subgroup analyses for patients with very high-risk cardiovascular disease (CVD) (defined as recurrent cardiovascular [CV] events or CV events in more than one vascular bed, i.e., polyvascular disease) on the primary and key secondary composite endpoints; also potentially other endpoints for the ITT Population;
Sensitivity analyses for apo B to assess whether subgroup(s) with apo B reductions from baseline beyond certain threshold(s) have corresponding incremental reductions in clinical endpoint events;
Sensitivity analyses for myocardial infarctions excluding peri-procedural MIs (Type 4a);
  Additional analyses factoring for recency and number of prior MIs
Sensitivity analyses for stroke, factoring for patients with history of stroke
Sensitivity analyses for heart failure, factoring for patients with history of heart failure
Sensitivity analyses for endpoints comprised of coronary revascularizations which exclude early elective revascularizations (e.g., within 30-90 days post-randomization)
Subgroup analyses of primary (and potentially key secondary) endpoint(s) among the following cohorts:
  High risk patients with "the hypertriglyceridemic waist" (obese patients at high CV risk);
  High risk subgroup defined by baseline hsTNT level (and potentially by NT-proBNP from archived frozen samples); and
  High TG/low LDL-C phenotypes;
  High-risk patients as defined by their atherothrombotic risk score.
Treatment effect on:
  Peripheral arterial events (e.g., major adverse limb events [MALE]); and
  Hypertension, using BP as a continuous variable.
Using archived frozen serum biosamples, additional analyses of fatty-acid levels (and ratios), including baseline and on-treatment effects on EPA, DHA, DPA, AA (and associated ratios) and relationships between fatty-acid levels and cardiovascular outcomes;
  Relationship between on-treatment fatty-acid levels;
  Baseline fatty-acid levels; and
  Study medication compliance.
Using archived frozen biosamples (e.g., serum and whole blood); potential analyses of treatment effects on biomarkers and genetic markers and associations with outcomes, including but not limited to the following:
  LDL-P;
  RLP-C (measured);
  LDL-TG;
  Ox-LDL;
  Galectin-3;
  Lp(a) at baseline, as a predictor of CVD benefit;
  LpPLA2;
  HDL2, HDL3, apo A-I, apo A-II, HDL-P, apo C-III (and apo C-III in apo-B containing proteins), apo A-V, Apo E subtypes (2, 3, 4), IL-6, lipoprotein lipase (LPL); and
  Analyses may include change (and percent change) from baseline, on-treatment comparisons between treatment groups with testing as predictors of CV risk.
Exploratory analyses of differential treatment effects for potential benefit (from adverse event reports) of:
  Ophthalmologic changes (e.g., incidence of age-related macular degeneration, progression of diabetic retinopathy);
  Cognitive impairment;
  Erectile dysfunction; and
  Ischemic cardiomyopathy (as indicated by hospitalization for CHF, ICD placement etc.).
Additional genetic bioassays including genes which may relate to triglyceride, lipid metabolism, and CVD; and
Effects of potential mediators identified post hoc on primary/key secondary outcome measures.

In this study, new onset diabetes was defined as Type 2 diabetes newly diagnosed during the treatment/follow-up period (i.e. patients with no history of diabetes at randomization). For purposes of this study, a diagnosis of diabetes was made based on the observation of:
  HbA$_{1c}$≥6.5%. The test was performed in a laboratory using a method that is National Glycohemoglobin Standardization Program (NGSP) certified and standardized to the Diabetes Control and Complications Trial (DCCT) assay. In the absence of unequivocal hyperglycemia, HbA$_{1c}$≥6.5 c/c) was confirmed by repeat testing;
  Fasting plasma glucose (FPG)≥126 mg/dL (7.0 mmol/L). Fasting was defined as no caloric intake for at least 8 hr. In the absence of unequivocal hyperglycemia, FPG≥126 mg/dL (7.0 mmol/L) was confirmed by repeat testing;
  2-hr plasma glucose ≥200 mg/dL (11.1 mmol/L) during an Oral Glucose Tolerance Test (OGTT). The test was performed as described by the World Health Organization, using a glucose load containing the equivalent of 75 g anhydrous glucose dissolved in water. In the absence of unequivocal hyperglycemia, 2-hr plasma glucose ≥200 mg/dL (11.1 mmol/L) during an Oral Glucose Tolerance Test (OGTT) were confirmed by repeat testing; and/or
  In a patient with classic symptoms of hyperglycemia or hyperglycemic crisis, a random plasma glucose ≥200 mg/dL (11.1 mmol/L).

In the absence of unequivocal hyperglycemia, the first three criteria were confirmed by repeat testing.

Exploratory Subgroup Analyses: Analyses of the effects that patients off study drug and withdrawn from study have on the primary endpoint were performed. Subgroup analyses of the primary and key secondary endpoints were performed as described for the primary endpoint. For each subgroup, Kaplan-Meier estimates, the log-rank test stratified by stratification factors used at randomization (except where the subgroup was a stratification factor), and HRs and CIs from the Cox proportional hazards model as specified for the primary efficacy endpoint, were summarized by treatment group. Demographic, disease, treatment, and baseline lipid and lipoproteins parameters were explored.

Demographic parameters included: Gender; age at baseline (<65 years and ≥65 years); race (white and nonwhite, or any other subset with at least 10% of the total number of patients); geographical region (Westernized, Eastern European, and Asia Pacific countries); and baseline ezetimibe use (yes/no).

Disease parameters included: CV risk category; the presence/absence of diabetes at baseline; and renal dysfunction at baseline (estimated glomerular filtration rate [eGFR]<60 mL/min/1.73 m$^2$) using the Chronic Kidney Disease Epidemiology Collaboration (CKD-EPI) equation as follows:

$$eGFR = 141 \times \min(S_{cr}/\kappa, 1)^\alpha \times \max(S_{cr}/\kappa, 1)^{-1.209} \times 0.993^{Age} \times 1.018 \text{ [if female]} \times 1.159 \text{ [if black]}$$

Where:
$S_{cr}$ is serum creatinine in mg/dL,
$\kappa$ is 0.7 for females and 0.9 for males,
$\alpha$ is −0.329 for females and −0.411 for males,
min indicates the minimum of $S_{cr}/\kappa$ or 1, and
max indicates the maximum of $S_{cr}/\kappa$ or 1.

Treatment Parameters included: Statin intensity at baseline (statin type and regimen); and statin intensity categories as defined in ACC/AHA Cholesterol Guidelines (Stone 2013) and patient's 10-year CV Risk Score (Goff 2013).

Baseline Lipid and Lipoprotein Parameter included: LDL-C (by tertile); HDL-C (by tertile, and tertile by gender); TG (by tertile, and tertile by gender); RLP-C (by tertile); TG≥150 mg/dL and TG<150 mg/dL; TG≥200 mg/dL and TG<200 mg/dL; TG≥median, TG<median; combined highest tertile for TG and lowest tertile for HDL-C; gender-specific highest tertile for TG and lowest tertile for HDL-C; TG≥200 mg/dL with HDL-C≤35 mg/dL; hsCRP (≤3 mg/L and >3 mg/L) and by gender; hsCRP (≤2 mg/L and >2 mg/L) and by gender; Apo B (by tertile); non-HDL-C (by tertile); baseline hemoglobin A1c (Hb1c) value (<6.5%, ≥6.5%); baseline PAD; and baseline TG levels ≥150 mg/dL with high-density lipoprotein cholesterol (HDL-C) levels ≤40 mg/dL for males and ≤50 mg/dL for females.

A Cox proportional hazard (PH) model as mentioned above but additionally with baseline TG as a covariate were fitted to the data at each interim. Diagnostic plots for the PH assumption were evaluated. The consistency of the treatment effects in subgroups was assessed for the primary and key secondary efficacy endpoints. For each subgroup variable, a Cox PH model with terms for treatment, stratification factors (with the exception of those subgroup variables related to the stratification factors, i.e., CV risk category), subgroup, and treatment-by-subgroup interaction were performed. The main treatment effect was tested with this model. P-values for testing the interaction terms <0.15 were considered significant. Results were presented in a Forest plot.

Subgroup analyses of the primary and key secondary endpoints were performed as described for the primary endpoint. For each subgroup, Kaplan-Meier estimates, the log-rank test stratified by stratification factors used at randomization (except where the subgroup was a stratification factor), and HRs and CIs from the Cox proportional hazards model as specified for the primary efficacy endpoint, were summarized by treatment group. All subgroup analyses were conducted for the ITT, mITT and PP populations.

Interim Efficacy Analysis: Two interim analyses were planned for the primary efficacy endpoint using adjudicated events when approximately 60% (967 events) and approximately 80% (1290 events) of the total number of primary endpoint events planned (1612) was reached. The planned interim analyses were based on a group-sequential design.

The interim results of the study were monitored by an independent Data Monitoring Committee (DMC). The analyses were performed by the independent statistical team who was unblinded to the treatment assignment and reported only to the DMC. If the study was terminated early following interim analysis, patients were notified promptly and brought in for their final close-out visit, and the final analyses of efficacy and safety included all data through their final visit. All suspected events were adjudicated in a blinded manner by the CEC. The time to event was calculated as the time from randomization to the onset date of the event (as determined by the CEC). Patients who do not experience any of the above events at the time of data cutoff for the interim but were still in the trial were considered censored at the time of their last regular contact before the interim data cutoff.

The alpha-levels for the two protocol prespecified interim analyses and the final analysis are based on a group sequential design (GSD) with O'Brien-Fleming boundaries generated using the Lan-DeMets alpha spending function. The one-sided alpha-levels and boundaries based on a Z-test and the achieved p-values for each of the two interim analyses and the final analysis are given in Table 10.

TABLE 10

Group Sequential P-Values Boundaries According to Two Actual Interim Analyses Information Fractions

| Look | Analysis | No. of Events | Information Fraction | Efficacy Boundary (1-sided) α-level) | Efficacy Boundary (2-sided α-level) | Achieved P-value (2-sided) |
|---|---|---|---|---|---|---|
| 1 | IA#1 | 953 | 59.3% | 0.00356 | 0.0071 | 0.0000463 |
| 2 | IA#2 | 1218 | 75.8% | 0.00885 | 0.0177 | 0.00000082 |
| 3 | Final | 1606 | 100% | 0.02186 | 0.0437 | 0.00000001 |

Analysis of Safety: All analyses of safety were conducted on the safety population, which was defined as all randomized patients. The safety assessment was based on the frequency of adverse events, physical exams, vital signs and safety laboratory tests. AEs with new onset during the study between the initiation of study drug and 30 days after the last dose of study drug for each patient was considered treatment-emergent (TEAEs). This included any AE with onset prior to initiation of study drug and increased severity after the treatment initiation.

Treatment-emergent adverse events were summarized by system organ class and preferred term, and by treatment. This included overall incidence rates (regardless of severity and relationship to study drug), and incidence rates for moderate or severe adverse events. A summary of SAEs and adverse events leading to early discontinuation (for ≥30 days) were presented through data listings. Patients who restarted study drug were included in the summary of AEs leading to discontinuation. Safety laboratory tests and vital signs were summarized by post-treatment change from baseline for each of the parameters using descriptive statistics by treatment group. Those patients with significant laboratory abnormalities were identified in data listings. Additional safety parameters were summarized in data listings.

In addition to the treatment-emergent adverse events analyses, analyses on all AEs (serious and non-serious) and all serious AEs were performed.

All AEs included: treatment-emergent adverse event (TEAE) by high level group term (HLGT); TEAE by high level term (HLT); and TEAE by system organ class (SOC), HLGT, HLT, and preferred term (PT) (4-level table).

All SAEs included: treatment emergent SAE by HLGT; treatment emergent SAE by HLT; and treatment emergent SAE by SOC, HLGT, HLT, and PT (4-level table).

Clinical Laboratory Evaluation

The criteria for potentially clinically significant (PCS) laboratory values are provided in Table 11 and Table 12. A treatment-emergent PCS high value at any time was defined as a change from a value less than or equal to the upper reference limit at baseline to a PCS high value at any post-baseline measurement. A treatment-emergent PCS low value at any time was defined as a change from a value greater than or equal to the lower reference limit at baseline to a PCS low value at any post-baseline measurement. Number (%) of patients with any post-baseline PCS laboratory values was summarized by treatment group. A listing of patients with PCS laboratory values at any time, i.e., baseline or at any post-baseline visit, were included.

TABLE 11

Potentially Clinically Significant Chemistry Values

| Parameter | PCS Low | PCS High |
|---|---|---|
| Albumin | ≤3.3 g/dL | ≥5.8 g/dL |
| Alkaline Phosphate | Not Applicable (N/A) | >1x ULN to 2x ULN<br>>2x ULN to 3x ULN<br>>3x ULN |
| ALT | N/A | >1x ULN to 2x ULN<br>>2x ULN to 3x ULN<br>>3x ULN |
| AST | N/A | >1x ULN to 2x ULN<br>>2x ULN to 3x ULN<br>>3x ULN |
| Bilirubin | N/A | >1x ULN to 2x ULN<br>>2x ULN to 3x ULN<br>>3x ULN |
| ALT + Bilirubin | N/A | >3x ULN + 2x ULN (Bilirubin) |
| AST + Bilirubin | N/A | >3x ULN + 2x ULN (Bilirubin) |
| Calcium | ≤7 mg/dL | ≥11 g/dL<br>≤12 mg/dL |
| Chloride | <70 mmol/L | >120 mmol/L |
| Creatinine | <0.5 mg/dL (Female)<br><0.65 mg/dL (Male) | >1.6 mg/dL (Female)<br>>2.0 mg/dL (Male);<br>≥50% increase from baseline |
| Creatine Kinase | <30 U/L (Female)<br><0.55 U/L (Male) | >1x ULN to 5x ULN<br>>5x ULN to 10x ULN<br>>10x ULN |
| Glucose (fasting) | ≤36 mg/dL;<br>≤70 mg/dL | ≥126 mg/dL;<br>≥130 mg/dL |
| Potassium (K) | ≤3.0 mEq/L | ≥150 mEq/L |
| Total Protein | <5.0 g/dL | ≥9.5 g/dL |
| Urea Nitrogen (BUN) | N/A | ≥31 mg/dL |
| Uric Acid | <1.9 mg/dL (Female)<br><2.5 mg/dL (Male) | >7.5 mg/dL (Female)<br>>8 mg/dL (Male) |

TABLE 12

Potentially Clinically Significant Hematology Values

| Parameter | PCS Low | PCS High |
|---|---|---|
| Red Blood Cell (RBC) | <3.5 × $10^6$/μL (Female)<br><3.8 × $10^6$/μL (Male) | >3.5 × $10^6$/μL (Female)<br>>3.8 × $10^6$/μL (Male) |
| Hemoglobin (Hgb) | <10.0 g/dL (Female)<br><10.0 g/dL (Male) | ><br>> |
| Hematocrit (Hct) | <37% (Female)<br><42% (Male) | ><br>> |
| White Blood Cells (WBC) | <1.5 × $10^3$/μL | N/A |
| White Cell Differential | Segmented neutrophils <50%<br>Lymphocytes <30%<br>Monocytes N/A<br>Basophils N/A<br>Eosinophils N/A | Segmented neutrophils >70%<br>Lymphocytes >45%<br>Monocytes >6%<br>Basophils >1%<br>Eosinophils >3% |
| Platelet Count | <100 × $10^3$/μL | >500 × $10^3$/μL |

Drug-Induced Liver Injury (DILI)

DILI cases were investigated through the following analyses:

A graph of distribution of peak values of alanine aminotransferase (ALT) versus peak values of total bilirubin (TBL) during the treatment period was prepared, using a logarithmic scale. In the graph, for each patient, the peak TBL times the Upper Limit of Normal (ULN) were plotted against the peak ALT times the ULN, where the peak TBL and peak ALT may or may not have happened on the same day of liver testing. The graph was divided into 4 quadrants with a vertical line corresponding to 3×ULN for ALT and a horizontal line corresponding to 2×ULN for TBL. The upper right quadrant was referred to as the potential Hy's Law quadrant, including potentially DILI cases.

A similar graph was plotted with respect to aspartate aminotransferase (AST).

The individual patient profile of liver function tests (ALT, AST, alkaline phosphatase [ALP] and TBL) over time was provided through a graph for all patients with peak value of ALT>3×ULN and peak value of TBL>2×ULN during the treatment period.

Number (%) of patients was provided for the following:
ALT or AST>3×ULN;
ALT or AST>3×ULN and TBL>2×ULN; and
ALT or AST>3×ULN and TBL>2×ULN, and ALP<2× ULN.

Study Design

This was a Phase 3b, multi-center, multi-national, prospective, randomized, double-blind, placebo-controlled, parallel-group study. This was also an event-driven trial comparing the effect of AMR101 vs. placebo in terms of the composite endpoint listed above as the primary endpoint. The placebo contained mineral oil to mimic the color and consistency of icosapent ethyl in AMR101 and was administered in the same capsule fill volume and count as the AMR101. The study accrued a total of 1612 efficacy endpoint events with two planned interim analyses when approximately 967 (60%) and 1290 (80%) of the events had been adjudicated. The study included patients with established CVD (CV Risk Category 1) and patients 50 years old with diabetes and at least one additional risk factor for CVD but with CVD not established (CV Risk Category 2). Randomization was stratified by cardiovascular risk stratum which included the secondary-prevention cohort (i.e., CV Risk Category 1) or primary-prevention cohort (i.e., CV Risk Category 2), with the primary prevention cohort capped at 30% of enrolment, use or no use of ezetimibe, and by geographical region. Details of the study design are shown in FIG. 1.

Sample size calculation was based on the assumption of constant hazard, asymmetric recruitment rate over time and without factoring for dropouts. A risk reduction corresponding to a HR of 0.85 (AMR101 vs. placebo) was assumed. 1612 events were required to detect this HR with approximately 90% power with one-sided alpha-level at 2.5% and with two interim analyses. The operating characteristics of this design were identical to those of a corresponding group sequential design with a two-sided alpha level of 0.05.

The recruitment period was assumed to be 4.2 years with 20% recruitment in the first year, 40% in the second year, 20% in the third year, 19% in the fourth year and the remaining 1% in the last 0.2 years. The estimated maximum study duration was 6.5 years unless the trial was terminated early for efficacy or safety issues. A one-year event rate of 5.2% (hazard=0.053) in the control arm was also assumed. Under these assumptions the number of patients enrolled was N=7990.

Since this was an events-driven trial, the 'sample size' was the number of events rather than the number of patients. The number of events that occurred depends primarily on three factors: how many patients were enrolled; the combined group event rate; and how long the patients were followed. Because of the difficulty in predicting the combined event rate, the Sponsor monitored the event rate as the trial progressed. If the combined event rate was less than anticipated, either increasing the number of patients, extending the length of follow-up, or a balance of adjusting both factors was necessary to achieve the sample size of 1612 events.

At completion of study enrollment, the actual number of patients randomized may have varied from the target number (either original or revised) as a result of the inherent lag between the date the last patient started screening and the date the last patient was randomized.

Completion of Study

The end of the study was at the time the last patient-last visited of the follow-up period of the study. The IRB and IEC were notified about the end of the study according to country-specific regulatory requirements.

Standardized Definitions for the Cardiovascular Trial Endpoint Events

In assessing patients in this clinical trial, the follow definitions were used:

Definition of Cardiovascular Death: Cardiovascular death includes death resulting from an acute myocardial infarction, sudden cardiac death, death due to congestive heart failure (CHF), death due to stroke, death due to cardiovascular (CV) procedures, death due to CV hemorrhage, and death due to other cardiovascular causes.

Death due to acute myocardial infarction: refers to a death by any mechanism (e.g., arrhythmia, CHF) within 30 days after a MI related to the immediate consequences of the MI, such as progressive CHF or recalcitrant arrhythmia. Mortal events that occur after a "break" (e.g., a CHF and arrhythmia-free period of at least a week) should be classified as CV or non-CV death, and if classified as a CV death, should be attributed to the immediate cause, even though the MI may have increased the risk of that event (e.g., the risk of arrhythmic death is increased for many months after an acute MI). Acute MI should be verified to the extent possible by the diagnostic criteria outlined for acute MI (see Definition of MI) or by autopsy findings showing recent MI or recent coronary thrombosis. Death resulting from a procedure to treat a MI (percutaneous coronary intervention (PCI), coronary artery bypass graft surgery (CABG)), or to treat a complication resulting from MI, should also be considered death due to acute MI. Death resulting from an elective coronary procedure to treat myocardial ischemia (i.e., chronic stable angina) or death due to a MI that occurs as a direct consequence of a CV investigation/procedure/operation should be considered as a death due to a CV procedure.

Sudden Cardiac Death: refers to a death that occurs unexpectedly, not within 30 days of an acute MI, and includes the following deaths: death witnessed and instantaneous without new or worsening symptoms; death witnessed within 60 minutes of the onset of new or worsening cardiac symptoms, unless the symptoms suggest an acute MI; death witnessed and attributed to an identified arrhythmia (e.g., captured on an electrocardiographic (ECG) recording, witnessed on a monitor, or unwitnessed but found on implantable cardioverter-defibrillator review); death after unsuccessful resuscitation from cardiac arrest; death after successful resuscitation from cardiac arrest and without identification of a non-cardiac etiology; and/or unwitnessed death without other cause of death (information regarding the patient's clinical status preceding death should be provided, if available)

General Considerations for Sudden Cardiac Death: A subject seen alive and clinically stable 12-24 hours prior to being found dead without any evidence or information of a specific cause of death should be classified as "sudden cardiac death." Deaths for which there is no information beyond "patient found dead at home" are classified as "death due to other cardiovascular causes". (See Definition of Undetermined Cause of Death, for full details below).

Death due to Congestive Heart Failure: refers to a death in association with clinically worsening symptoms and/or signs of heart failure (See Definition of Heart Failure Event, for full details below). Deaths due to heart failure can have various etiologies, including single or recurrent myocardial infarctions, ischemic or non-ischemic cardiomyopathy, hypertension, or valvular disease.

Death due to Stroke: refers to death after a stroke that is either a direct consequence of the stroke or a complication of the stroke. Acute stroke should be verified to the extent possible by the diagnostic criteria outlined for stroke (See Definition of Transient Ischemic Attack and Stroke, for full details below).

Death due to Cardiovascular Procedures: refers to death caused by the immediate complications of a cardiac procedure.

Death due to Cardiovascular Hemorrhage: refers to death related to hemorrhage such as a non-stroke intracranial hemorrhage (see Definition of Transient Ischemic Attack and Stroke, for full details below), non-procedural or non-traumatic vascular rupture (e.g., aortic aneurysm), or hemorrhage causing cardiac tamponade.

Death due to Other Cardiovascular Causes: refers to a CV death not included in the above categories (e.g., pulmonary embolism or peripheral arterial disease).

Definition of Non-Cardiovascular Death: Non-cardiovascular death is defined as any death that is not thought to be due to a cardiovascular cause. The following is a suggested list of non-cardiovascular causes of death for this trial.

Non-malignant, Non-cardiovascular Death:
Pulmonary;
Renal;
Gastrointestinal;
Hepatobiliary;
Pancreatic;
Infection (includes sepsis)
Non-infectious (e.g., systemic inflammatory response syndrome (SIRS));
Hemorrhage that is neither cardiovascular bleeding nor a stroke;
Accidental (e.g., physical accidents or drug overdoses) or trauma;
Suicide; and/or
Prescription Drug Error (e.g., prescribed drug overdose, use of inappropriate drug, or drug-drug interaction); and
Neurological process that is not a stroke or hemorrhage.
Malignancy: Malignancy is coded as cause of death, if:
Death results directly from the cancer; or
Death results from a concurrent illness that could be a consequence of a cancer; or
Death results from withdrawal of other therapies because of concerns relating to the poor prognosis associated with the cancer; and
Death results from an illness that is not a consequence of a cancer.

Cancer deaths may arise from cancers that were present prior to randomization or which developed subsequently. It may be helpful to distinguish these two scenarios (i.e. worsening of prior malignancy; new malignancy). Suggested categorization includes the following organ systems; Lung/larynx, breast, leukemia/lymphoma, upper GI, melanoma, central nervous system, colon/rectum, renal, bladder, prostate, other/unspecified, or unknown.

Definition of Undetermined Cause of Death: refers to a death not attributable to one of the above categories of cardiovascular death or to a non-cardiovascular cause. The inability to classify the cause of death is generally due to lack of information (e.g., the only available information is "patient died") or when there is insufficient supporting information or detail to assign the cause of death. In this trial, when a cause of death was not readily apparent (e.g., found dead at home), the cause was assumed to be cardiovascular in origin, unless one of the following two scenarios occur: there is no information or data available regarding the circumstances of death other than that a death has occurred; or the available data are conflicting regarding whether the death was cardiovascular or non-cardiovascular.

Definition of Myocardial Infarction: The term myocardial infarction (MI) is used when there is evidence of myocardial necrosis in a clinical setting consistent with myocardial ischemia. In general, the diagnosis of MI requires the combination of: evidence of myocardial necrosis (either changes in cardiac biomarkers or postmortem pathological findings); and supporting information derived from the clinical presentation, electrocardiographic changes, or the results of myocardial or coronary artery imaging.

The totality of the clinical, electrocardiographic, and cardiac biomarker information should be considered to determine whether or not a MI has occurred. Specifically, timing and trends in cardiac biomarkers and electrocardiographic information require careful analysis. The adjudication of MI should also take into account the clinical setting in which the event occurs. MI may be adjudicated for an event that has characteristics of a MI, but which does not meet the strict definition because biomarker or electrocardiographic results are not available.

The Criteria for myocardial infarction include clinical presentation, biomarker evaluation, and ECG changes.

Clinical Presentation: The clinical presentation is consistent with diagnosis of myocardial ischemia and infarction. Other findings that might support the diagnosis of MI should be take into account because a number of conditions are associated with elevations in cardiac biomarkers (e.g., trauma, surgery, pacing, ablation, congestive heart failure, hypertrophic cardiomyopathy, pulmonary embolism, severe pulmonary hypertension, stroke or subarachnoid hemorrhage, infiltrative and inflammatory disorders of cardiac muscle, drug toxicity, burns, critical illness, extreme exertion, and chronic kidney disease). Supporting information can also be considered from myocardial imaging and coronary imaging. The totality of the data may help differentiate acute MI from the background disease process.

Biomarker Evaluation: For cardiac biomarkers, laboratories should report an upper reference limit (URL). If the 99th percentile of the upper reference limit (URL) from the respective laboratory performing the assay is not available, then the URL for myocardial necrosis from the laboratory should be used. If the 99th percentile of the URL or the URL for myocardial necrosis is not available, the MI decision limit for the particular laboratory should be used as the URL. Laboratories can also report both the 99th percentile of the upper reference limit and the MI decision limit. Reference limits from the laboratory performing the assay are preferred over the manufacturer's listed reference limits in an assay's instructions for use. CK-MB and troponin are preferred, but CK may be used in the absence of CK-MB and troponin. For MI subtypes, different biomarker elevations for CK, CK-MB, or troponin were required. The specific criteria were referenced to the URL. In this study, patients may present acutely to hospitals which are not participating sites, it is not practical to stipulate the use of a single biomarker or assay, and the locally available results are to be used as the basis for adjudication. Since the prognostic significance of different types of myocardial infarctions (e.g., periprocedural myocardial infarction versus spontaneous myocardial infarction) may be different, considerations evaluating outcomes for these subsets of patients separately were made.

ECG Changes: ECG changes can be used to support or confirm a MI. Supporting evidence may be ischemic changes and confirmatory information may be new Q waves.

Criteria for acute myocardial ischemia (in absence of left ventricular hypertrophy (LVH) and left bundle branch block (LBBB)) include:
  ST elevation: New ST elevation at the J point in two anatomically contiguous leads with the cut-off points: ≥0.2 mV in men (>0.25 mV in men <40 years) or ≥0.15 mV in women in leads V2-V3 and/or ≥0.1 mV in other leads.
  ST depression and T-wave changes new horizontal or down-sloping ST depression ≥0.05 mV in two contiguous leads; and/or new T inversion ≥0.1 mV in two contiguous leads.

The above ECG criteria illustrate patterns consistent with myocardial ischemia. In patients with abnormal biomarkers, it is recognized that lesser ECG abnormalities may represent an ischemic response and may be accepted under the category of abnormal ECG findings.

Criteria for pathological Q-wave include: any Q-wave in leads V2-V3≥0.02 seconds or QS complex in leads V2 and V3; Q-wave≥0.03 seconds and ≥0.1 mV deep or QS complex in leads I, II, aVL, aVF, or V4-V6 in any two leads of a contiguous lead grouping (I, aVL, V6; V4-V6; II, III, and aVF); and R-wave 0.04 s in V1-V2 and R/S ratio >1 with a concordant positive T-wave in the absence of a conduction defect.

The same criteria are used for supplemental leads V7-V9, and for the Cabrera frontal plane lead grouping.

Criteria for Prior Myocardial Infarction include: pathological Q-waves, as defined above; and R-wave ≥0.04 seconds in V1-V2 and R/S≥1 with a concordant positive T-wave in the absence of a conduction defect.

Myocardial Infarction Subtypes: Several MI subtypes are commonly reported in clinical investigations and each is defined below:
1. Spontaneous MI:
  Detection of rise and/or fall of cardiac biomarkers with at least one value above the URL with at least one of the following:
    Clinical presentation consistent with ischemia;
    ECG evidence of acute myocardial ischemia;
    New pathological Q waves;
    Imaging evidence of new loss of viable myocardium or new regional wall motion abnormality; and/or
    Autopsy evidence of acute MI
  If biomarkers are elevated from a prior infarction, then a spontaneous myocardial infarction is defined as one of the following:
    Clinical presentation consistent with ischemia;
    ECG evidence of acute myocardial ischemia;
    New pathological Q waves;
    Imaging evidence of new loss of viable myocardium or new regional wall motion abnormality; and/or
    Autopsy evidence of acute MI; and
  Both of the Following:
    Evidence that cardiac biomarker values were decreasing (e.g., two samples 3-6 hours apart) prior to the suspected MI (note: If biomarkers are increasing or peak is not reached, then a definite diagnosis of recurrent MI is generally not possible); and
    ≥20% increase (and >URL) in troponin or CK-MB between a measurement made at the time of the initial presentation and a further sample taken 3-6 hours later.
2. Percutaneous Coronary Intervention-Related Myocardial Infarction: is defined by any of the following criteria. MI associated with and occurring within 48 hours of PCI, with elevation of cardiac biomarker values to >5×99$^{th}$ percentile of the URL in patients with normal baseline values (≤99$^{th}$ percentile URL), or a rise of [cardiac biomarker] values ≥20% if baseline values are elevated and are stable or falling. This classification also requires at least 1 of the following:
  Symptoms suggestive of myocardial ischemia (i.e., prolonged ischemia 20 min);
  New ischemic changes on ECG or new LBBB;
  Angiographic loss of patency of a major coronary artery or a side branch or persistent slow flow or no flow or embolization; and/or
  Imaging evidence of new loss of viable myocardium or new regional wall motion abnormality.
3. Coronary Artery Bypass Grafting-Related (CABG) Myocardial Infarction: is defined by the following criteria. Symptoms of cardiac ischemia were not required and data was collected in such a way that analyses using ≥20% or ≥50% could both be performed.
  Biomarker elevations within 48 hours of CABG:
    Troponin or CK-MB (preferred)>10×99$^{th}$ percentile of the URL; and
    No evidence that cardiac biomarkers were elevated prior to the procedure; or
    Both of the following are true:
      ≥50% increase in the cardiac biomarker result; and
      Evidence that cardiac biomarker values were decreasing (e.g., two samples 3-6 hours apart) prior to the suspected MI; and
  One of the following are true:
    New pathological Q-waves persistent through 30 days;
    New persistent non-rate-related LBBB;
    Angiographically documented new graft or native coronary artery occlusion Other complication in the operating room resulting in loss of myocardium; or
    Imaging evidence of new loss of viable myocardium.
  Autopsy evidence of acute MI.
4. Silent Myocardial Infarction: is defined by the following:
  No evidence of acute myocardial infarction; and
  Any one of the following criteria:
    New pathological Q-waves. A confirmatory ECG is recommended if there have been no clinical symptoms or history of myocardial infarction;

Imaging evidence of a region of loss of viable myocardium that is thinned and fails to contract, in the absence of a non-ischemic cause; and/or Autopsy evidence of a healed or healing MI.

In the case of evanescent Q waves, the last ECG determines whether a silent infarction has occurred.

Sub-classification of Myocardial Infarction: The universal MI definition includes clinical classification of different types of MI, electrocardiographic features, and by biomarker evaluation, with the definition of each provided below.

Clinical Classification of Different Types of Myocardial Infarction include the following:

Type 1: Spontaneous myocardial infarction related to ischemia due to a primary coronary event such as plaque erosion and/or rupture, fissuring, or dissection;

Type 2: Myocardial infarction secondary to ischemia due to either increased oxygen demand or decreased supply, e.g., coronary artery spasm, coronary embolism, anemia, arrhythmias, hypertension, or hypotension;

Type 3: Sudden unexpected cardiac death, including cardiac arrest, often with symptoms suggestive of myocardial ischemia, accompanied by presumably new ST elevation, or new LBBB, or evidence of fresh thrombus in a coronary artery by angiography and/or at autopsy, but death occurring before blood samples could be obtained, or at a time before the appearance of cardiac biomarkers in the blood;

Type 4a: Myocardial infarction associated with Percutaneous Coronary Intervention (PCI);

Type 4b: Myocardial infarction associated with stent thrombosis as documented by angiography or at autopsy;

Type 4c: Myocardial infarction associated with stent restenosis as detected by angiography or at autopsy; and Type 5: Myocardial infarction associated with CABG.

By Electrocardiographic Features include:

ST-Elevation MI (STEMI). The additional categories of STEMI include: Q wave, non-Q-wave, or unknown (no ECG or ECG non-interpretable);

Non-ST-Elevation MI (NSTEMI). The additional categories NSTEMI may include: Q wave, non-Q-wave, or unknown (no ECG or ECG non-interpretable); and Unknown (no ECG or ECG not interpretable).

All events adjudicated as MI were classified as STEMI, NSTEMI, or Unknown; however, it is acknowledged that a significant proportion of periprocedural (PCI or CABG) events may have missing, inadequate or uninterpretable ECG documentation.

By Biomarker Elevation (per Universal MI Definition): The magnitude of cardiac biomarker elevation can be calculated as a ratio of the peak biomarker value divided by the 99th percentile URL. The biomarker elevation can be provided for various MI subtypes.

Definition of Hospitalize of Unstable Angina: Unstable angina requiring hospitalization is defined as:

Ischemic discomfort (angina, or symptoms thought to be equivalent) 10 minutes in duration occurring at rest or in an accelerating pattern with frequent episodes associated with progressively decreased exercise capacity;

Prompting an unscheduled hospitalization within 24 hours of the most recent symptoms. Hospitalization is defined as an admission to an inpatient unit or a visit to an emergency department that results in at least a 24-hour stay (or a date change if the time of admission/discharge is not available); and At least one of the following:

New or worsening ST or T wave changes on resting ECG (in absence of confounders, such as LBBB or LVH);

Transient ST elevation (duration <20 minutes): New ST elevation at the J point in two anatomically contiguous leads with the cut-off points: 0.2 mV in men (>0.25 mV in men <40 years) or ≥0.15 mV in women in leads V2-V3 and/or 0.1 mV in other leads ST depression and T-wave changes: New horizontal or down-sloping ST depression ≥0.05 mV in two contiguous leads; and/or new T inversion 0.1 mV in two contiguous leads.

Definite evidence of inducible myocardial ischemia as demonstrated by:

An early positive exercise stress test, defined as ST elevation or ≥2 mm ST depression prior to 5 mets; or at least one of the following: stress echocardiography (reversible wall motion abnormality); myocardial scintigraphy (reversible perfusion defect); or MRI (myocardial perfusion deficit under pharmacologic stress.

Angiographic evidence of new or worse ≥70% lesion and/or thrombus in an epicardial coronary artery that is believed to be responsible for the myocardial ischemic symptoms/signs; and Need for coronary revascularization procedure (PCI or CABG) for the presumed culprit lesion(s). This criterion would be fulfilled if revascularization was undertaken during the unscheduled hospitalization, or subsequent to transfer to another institution without interceding home discharge;

Negative cardiac biomarkers and no evidence of acute MI.

General Considerations include:

Escalation of pharmacotherapy for ischemia, such as intravenous nitrates or increasing dosages of β-blockers, should be considered supportive of the diagnosis of unstable angina. However, a typical presentation and admission to the hospital with escalation of pharmacotherapy, without any of the additional findings listed under category 3, would be insufficient alone to support classification as hospitalization for unstable angina.

If subjects were admitted with suspected unstable angina, and subsequent testing revealed a noncardiac or non-ischemic etiology, this event should not have been recorded as hospitalization for unstable angina. Potential ischemic events meeting the criteria for myocardial infarction should not have been adjudicated as unstable angina.

Planned hospitalization or re-hospitalization for performance of an elective revascularization in patients who did not fulfill the criteria for unstable angina should not have been considered a hospitalization for unstable angina. For example: hospitalization of a patient with stable exertional angina for coronary angiography and PCI that is prompted by a positive outpatient stress test should not be considered hospitalization for unstable angina; or re-hospitalization of a patient meeting the criteria for unstable angina who was stabilized, discharged, and subsequently readmitted for revascularization, does not constitute a second hospitalization for unstable angina.

A patient who underwent an elective catheterization where incidental coronary artery disease was found and who subsequently underwent coronary revascularization was not be considered as meeting the hospitalization for unstable angina endpoint.

Transient Ischemic Attack: Transient ischemic attack (TIA) is defined as a transient episode (<24 hours) of neurological dysfunction caused by focal brain, spinal cord, or retinal ischemia, without acute infarction.

Stroke: Stroke is defined as an acute episode of neurological dysfunction caused by focal or global brain, spinal cord, or retinal vascular injury.

Ischemic Stroke: Ischemic stroke is defined as an acute episode of focal cerebral, spinal, or retinal dysfunction caused by an infarction of central nervous system tissue. Hemorrhage may be a consequence of ischemic stroke. In this situation, the stroke is an ischemic stroke with hemorrhagic transformation and not a hemorrhagic stroke.

Hemorrhagic Stroke: Hemorrhagic stroke is defined as an acute episode of focal or global cerebral or spinal dysfunction caused by a nontraumatic intraparenchymal, intraventricular, or subarachnoid hemorrhage. However, microhemorrhages seen on T2-weighted MRI imaging, subdural and epidural hemorrhages are not considered hemorrhagic strokes.

Undetermined Stroke: Undetermined stroke is defined as an acute episode of focal or global neurological dysfunction caused by presumed brain, spinal cord, or retinal vascular injury as a result of hemorrhage or infarction but with insufficient information to allow categorization as ischemic or hemorrhagic.

Stroke Disability: Stroke disability should be measured by a reliable and valid scale in all cases, typically at each visit and 90 days after the event. For example, the modified Rankin Scale show below in Table 13 may be used to address this requirement:

TABLE 13

Rankin Scaled Used to Assess Stroke Disability in Patients

| Scale | Disability |
|---|---|
| 0 | No symptoms at all. |
| 1 | No significant disability despite symptoms; able to carry out all usual duties and activities. |
| 2 | Slight disability, unable to perform all previous activities but able to look after own affairs without assistance. |
| 3 | Moderate disability; requiring some help but able to walk without assistance. |
| 4 | Moderately severe disability, unable to walk without assistance and unable to attend to own bodily needs without assistance. |
| 5 | Severe disability, bedridden, incontinent, and requiring constant nursing and attention. |
| 6 | Dead |

Additional Considerations: Evidence of vascular central nervous system injury without recognized neurological dysfunction may be observed. Examples include micro-hemorrhage, silent infarction, and silent hemorrhage. Subdural hematomas are intracranial hemorrhagic events and not strokes. The distinction between a Transient Ischemic Attack and an Ischemic Stroke is the presence of Infarction. Persistence of symptoms is an acceptable indicator of acute infarction.

Definition of Heart Failure Event: is defined as an event that meets all of the following criteria:

The patient is admitted to the hospital with a primary diagnosis of HF;

The patient's length-of-stay in hospital extends for at least 24 hours (or a change in calendar date if the hospital admission and discharge times are unavailable);

The patient exhibits documented new or worsening symptoms due to HF on presentation, including at least one of the following: dyspnea (dyspnea with exertion, dyspnea at rest, orthopnea, paroxysmal nocturnal dyspnea), decreased exercise tolerance, fatigue, or other symptoms of worsened end-organ perfusion or volume overload (must be specified and described by the protocol);

The patient has objective evidence of new or worsening HF, consisting of at least two physical examination findings or one physical examination finding and at least one laboratory criterion), including:

Physical examination findings considered to be due to heart failure, including new or worsened: Peripheral edema, increasing abdominal distention or ascites (in the absence of primary hepatic disease), $S_3$ gallop, clinically significant or rapid weight gain thought to be related to fluid retention; or Laboratory evidence of new or worsening HF, if obtained within 24 hours of presentation, including: increased B-type natriuretic peptide (BNP)/N-terminal pro-BNP (NT-proBNP) concentrations consistent with decompensation of heart failure (such as BNP>500 pg/mL or NT-proBNP>2,000 pg/mL). In patients with chronically elevated natriuretic peptides, a significant increase should be noted above baseline, radiological evidence of pulmonary congestion, or non-invasive or invasive diagnostic evidence of clinically significant elevated left- or right-sided ventricular filling pressure or low cardiac output. For example, echocardiographic criteria could include: E/e'>15 or D-dominant pulmonary venous inflow pattern, plethoric inferior vena cava with minimal collapse on inspiration, or decreased left ventricular outflow tract (LVOT) minute stroke distance (time velocity integral [TVI]) OR right heart catheterization showing a pulmonary capillary wedge pressure (pulmonary artery occlusion pressure) ≥18 mmHg, central venous pressure ≥12 mmHg, or a cardiac index <2.2 L/min/m².

The patient receives initiation or intensification of treatment specifically for HF, including at least one of the following: significant augmentation in oral diuretic therapy, intravenous diuretic, inotrope, or vasodilator therapy, or Mechanical or surgical intervention. The mechanical or surgical intervention including mechanical circulatory support (e.g., intra-aortic balloon pump, ventricular assist device) and/or mechanical fluid removal (e.g., ultrafiltration, hemofiltration, dialysis).

New Heart Failure/Heart Failure Not Requiring Hospitalization: is defined as an event that meets all of the following: the patient has an urgent, unscheduled office/practice or emergency department visit for a primary diagnosis of HF, but not meeting the criteria for a HF hospitalization; all signs and symptoms for HF hospitalization must be met as defined in A Heart Failure Hospitalization above; and the patient receives initiation or intensification of treatment specifically for HF, as detailed in the above section with the exception of oral diuretic therapy, which was not sufficient.

Interventional Cardiology Definitions

Clinical Definitions:

Clinically-Driven Target Lesion Revascularization: Revascularization is clinically-driven if the target lesion diameter stenosis is >50% by quantitative coronary angiography (QCA) and the subject has clinical or functional ischemia which cannot be explained by another native coronary or bypass graft lesion. Clinical or functional ischemia includes any of the following: a history of angina pectoris, presumably related to the target vessel; objective signs of ischemia at rest (electrocardiographic changes) or during exercise test (or equivalent), presumably related to the target vessel; and abnormal results of any invasive functional diagnostic test (e.g., coronary flow reserve [CFR] or fractional flow reserve [FFR]).

Non-Target Lesion and Non-Target Lesion Revascularization: A lesion for which revascularization is not attempted or one in which revascularization is performed using a non-study device, respectively.

Non-Target Vessel and Non-Target Vessel Revascularization: A vessel for which revascularization is not attempted or one in which revascularization is performed using a non-study device, respectively.

Percutaneous Coronary Intervention (PCI) Status includes:

Elective: The procedure can be performed on an outpatient basis or during a subsequent hospitalization without significant risk of myocardial infarction (MI) or death. For stable in-patients, the procedure is being performed during this hospitalization for convenience and ease of scheduling and NOT because the patient's clinical situation demands the procedure prior to discharge.

Urgent: The procedure should be performed on an inpatient basis and prior to discharge because of significant concerns that there is risk of myocardial ischemia, MI, and/or death. Patients who are outpatients or in the emergency department at the time that the cardiac catheterization is requested would warrant hospital admission based on their clinical presentation.

Emergency: The procedure should be performed as soon as possible because of substantial concerns that ongoing myocardial ischemia and/or MI could lead to death. "As soon as possible" refers to a patient who is of sufficient acuity that one would cancel a scheduled case to perform this procedure immediately in the next available room during business hours, or one would activate the on-call team were this to occur during off-hours.

Salvage: The procedure is a last resort. The patient is in cardiogenic shock when the PCI begins (i.e., the time at which the first guide wire or intracoronary device is introduced into a coronary artery or bypass graft for the purpose of mechanical revascularization) or within the last ten minutes prior to the start of the case or during the diagnostic portion of the case, the patient has also received chest compressions or has been on unanticipated circulatory support (e.g., intra-aortic balloon pump, extracorporeal mechanical oxygenation, or cardiopulmonary support).

Percutaneous Coronary Intervention (PCI): Placement of an angioplasty guide wire, balloon, or other device (e.g., stent, atherectomy catheter, brachytherapy delivery device, or thrombectomy catheter) into a native coronary artery or coronary artery bypass graft for the purpose of mechanical coronary revascularization. In the assessment of the severity of coronary lesions with the use of intravascular ultrasound, CFR, or FFR, insertion of a guide wire was not considered PCI.

Peripheral Vascular Intervention Definitions:

Peripheral Vascular Intervention Definition: Peripheral vascular intervention is a catheter-based or open surgical procedure designed to improve peripheral arterial or venous blood flow or otherwise modify or revise vascular conduits. Procedures may include, but are not limited to, balloon angioplasty, stent placement, thrombectomy, embolectomy, atherectomy, dissection repair, aneurysm exclusion, treatment of dialysis conduits, placement of various devices, intravascular thrombolysis or other pharmacotherapies, and open surgical bypass or revision. In general, the intention to perform percutaneous peripheral vascular intervention is denoted by the insertion of a guide wire into a peripheral artery or vein. The target vessel(s) and the type of revascularization procedure (e.g., surgical bypass, thrombectomy, endarterectomy, percutaneous angioplasty, stent placement, thromboembolectomy, and thrombolysis) should be specified and recorded. For the sake of simplicity, this definition applies to the extracranial carotid artery and other non-cardiac arteries and veins and excludes the intracranial vessels and lymphatics.

Procedural Status includes:

Non-Elective: Non-elective procedures include emergent and urgent procedures. A non-elective procedure is a procedure that is performed without delay, because there is clinical consensus that the procedure should occur imminently. Non-elective procedures imply a degree of instability of the patient, urgency of the medical condition, or instability of the threatening lesion.

Emergent: A procedure that is performed immediately because of the acute nature of the medical condition (e.g., acute limb ischemia, acute aortic dissection), and the increased morbidity or mortality associated with a temporal delay in treatment.

Urgent: An urgent procedure is one that is not emergent but required to be performed on a timely basis (≤24 hrs) (e.g., a patient who has been stabilized following initial treatment of acute limb ischemia, and there is clinical consensus that a definitive procedure should occur within the next 24 hours).

Elective: An elective procedure is one that is scheduled and is performed on a patient with stable disease, or in whom there is no urgency and/or increased morbidity or mortality associated with a planned procedure.

Definition of Any Revascularization Procedure: Any revascularization includes any arterial vascular intervention done to treat ischemia or prevent major ischemic events, including percutaneous or surgical intervention of the coronary, peripheral, or carotid arteries. Aneurysm repairs, dissection repairs, arterial-venous fistula or graft placement or repairs, or renal arterial intervention for hypertension or renal dysfunction are not included.

Definition of Cardiac Arrhythmia Requiring Hospitalization: An arrhythmia that either results in hospitalization (24 hours) during or within 24 hours of the termination of the last episode for treatment or requires continued hospitalization for treatment, including any one of the following:

Atrial arrhythmia—atrial fibrillation, atrial flutter, supraventricular tachycardia that requires cardio-version, drug therapy, or is sustained for greater than 1 minute;

Ventricular arrhythmia—Ventricular tachycardia or ventricular fibrillation requiring cardio-version and/or intravenous antiarrhythmics; and/or Bradyarrhythmia—High-level AV block (defined as third-degree AV block or second-degree AV block), junctional or ventricular escape rhythm, or severe sinus bradycardia (typically with heart rate <30 bpm). The bradycardia must require temporary or permanent pacing.

Definition of Cardiac Arrest (Sudden Cardiac Death): A sudden, unexpected death due to the cessation of cardiac mechanical activity, confirmed by the absence of a detectable pulse, unresponsiveness, and apnea (or agonal, gasping respirations) of presumed cardiac etiology. An arrest is presumed to be cardiac (i.e., related to heart disease) if this is likely, based on the available information, including hospital records and autopsy data. The cardiac arrest is further sub-classified into either: witnessed, occurring within 60 min from the onset of new symptoms, in the absence of a clear cause other than cardiovascular; or unwitnessed, within 24 hours of being observed alive, in the absence of pre-existing other non-cardiovascular causes of death;

Non-cardiac causes of cardiac arrest, such as drug overdose, suicide, drowning, hypoxia, exsanguination, cerebrovascular accident, subarachnoid hemorrhage, or trauma must not be present.

Definition of Resuscitated Cardiac Arrest: Resuscitated Cardiac Arrest is present when there is restoration of both: organized electrical activity and organized mechanical activity resulting in restoration of spontaneous circulation (defined as the documented presence of a measurable pulse and blood pressure at any time after initiation of resuscitative efforts).

Criteria for the Diagnosis of Metabolic Syndrome: The diagnosis of metabolic syndrome requires the presence of three out of the following five specific components using the following criteria with cut points of parameters as defined in Table 1 and listed below, and waist circumference cut points further guided by the Table 14.

A waist circumference ≥35 inches (88 cm) for all women, and Asian, Hispanic, or Latino men, and waist circumference ≥40 inches (102 cm) for all other men;

Elevated TG (TG≥150 mg/dL);

Reduced HDL-C (HDL-C<40 mg/dL if male; HDL-C<50 mg/dL if female);

Elevated blood pressure (systolic ≥130 mmHg and/or diastolic ≥85 mmHg, or an antihypertensive therapy with medical history of hypertension; and Elevated fasting glucose (fasting glucose ≥100 mg/dL, or on drug therapy for elevated glucose.

TABLE 14

Current Recommended Waist Circumference Thresholds for Abdominal Obesity by Organization and Population.

| Organization | Population (Reference) | Waist Circumference Threshold | |
|---|---|---|---|
| | | Men(cm) | Women (cm) |
| IDF (4) | Europid | ≥94 | ≥80 |
| WHO (7) | Caucasian | ≥94 (increased risk) | ≥80 |
| | | ≥102 (still higher risk) | ≥88 |
| AHA/NHLBI (ATP III)* | US | ≥102 | ≥88 |
| Health Canada | Canada | ≥102 | ≥88 |
| European Cardiovascular Societies | European | ≥102 | ≥88 |
| IDF | Asian (including Japanese) | ≥90 | ≥80 |
| WHO | Asian | ≥90 | ≥80 |
| Japanese Obesity Society | Japanese | ≥85 | ≥90 |
| Cooperative Task Force | China | ≥85 | ≥80 |
| IDF | Middle East, Mediterranean | ≥94 | ≥80 |
| IDF | Sub-Saharan African | ≥94 | ≥80 |
| IDF | Ethnic Central & South American | ≥90 | ≥80 |

IDF = International Diabetes Federation; WHO = World Health Organization; AHA/NHLBI (ATP III) = American Heart Association/National Heart, Lung, and Blood Institute Adult Treatment Panel III;

*Recent AHA/NHLBI guidelines for metabolic syndrome recognize an increased risk for cardiovascular disease and diabetes at waist-circumference thresholds of ≥94 cm in men and ≥80 cm in women and identify these as optional cut points for individuals or populations with increased insulin resistance.

Statistical Analysis

In this event-driven trial, it was estimated that approximately 1612 adjudicated primary endpoint events would be necessary to provide 90% power to detect a 15% lower risk of the primary composite endpoint in the AMR101 group than in the placebo group. This resulted in an estimated sample size of approximately 7990 patients to reach the number of primary endpoints. The primary efficacy analysis was based on the time from randomization to the first occurrence of any component of the primary composite endpoint. If the relative risk reduction with administration of AMR101 in the primary endpoint was significant (final two-sided alpha level=0.0437; determined from O'Brien-Fleming boundaries generated using the Lan-DeMets alpha-spending function after accounting for two protocol pre-specified interim efficacy analyses), in a hierarchical fashion, the key secondary endpoint and other prespecified secondary endpoints were to be tested at the same final alpha level of 0.0437. All primary efficacy analyses followed the intent-to-treat principle. HRs and 95% CI were generated using a Cox proportional hazard model with treatment as covariate, and stratified by cardiovascular risk category, geographic region, and use of ezetimibe. Log-rank P values were reported from a Kaplan-Meier analysis, stratified by the three randomization factors, to evaluate the timing of events in the two treatment groups.

Results

Figure 2:
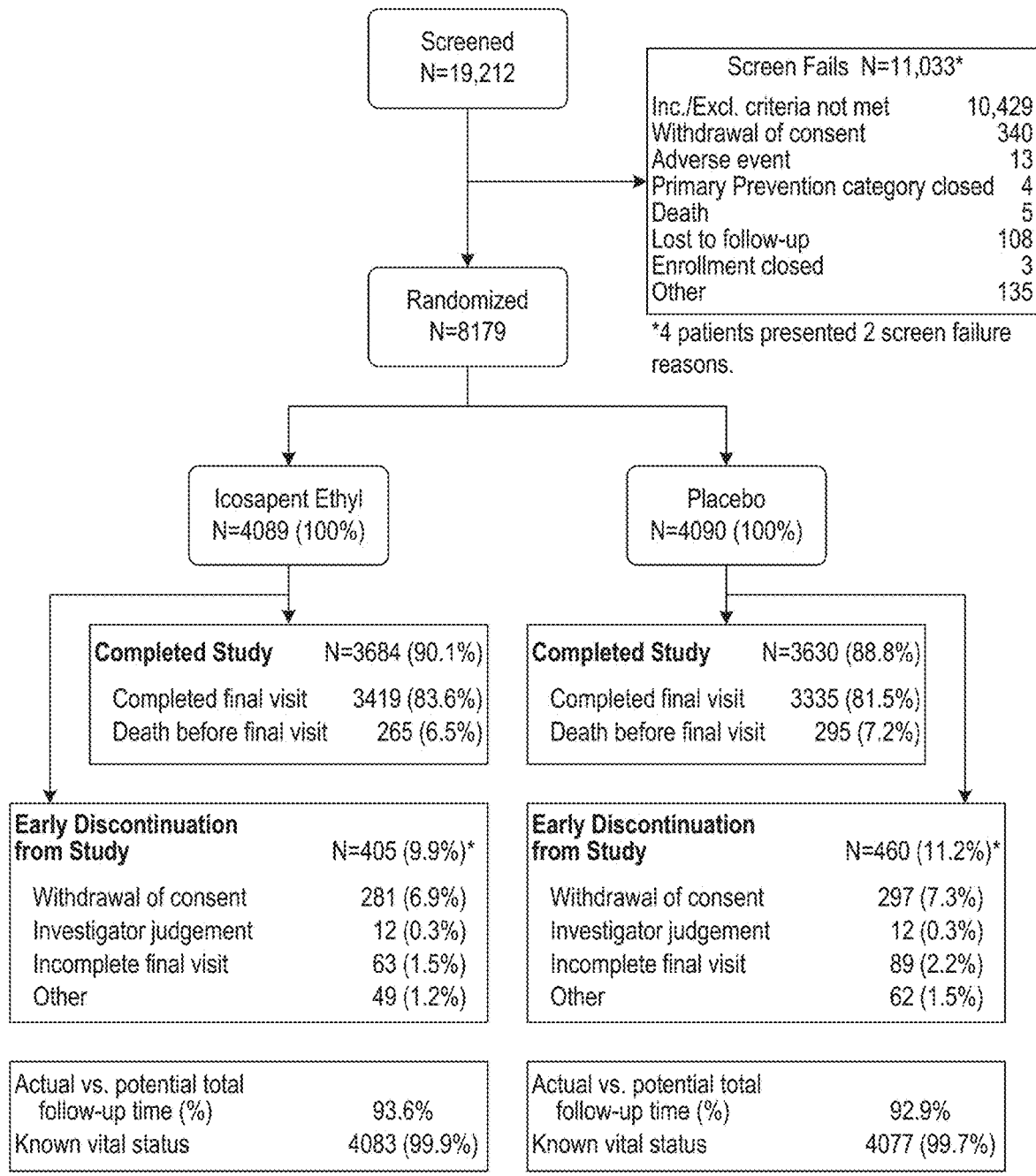
FIG. 2 is a schematic showing disposition of patients according to an embodiment of the present disclosure.

Subject Disposition: The subject disposition by treatment group is depicted in FIG. 2. A total of 19,212 patients were screened of whom 8,179 (43%) were randomized. At the time of database lock, vital status was available in 99.8%; 152 (1.9%) patients did not complete final study visits and 578 (7.1%) patients withdrew consent.

Demographic and Baseline Disease Characteristics: Among the patients who underwent randomization, 70.7% were enrolled on the basis of secondary prevention (i.e., patients had established cardiovascular disease) and 29.3% for primary prevention (i.e., patients had diabetes mellitus and at least one additional risk factor). The median age was 64 years, 28.8% were female, and 38.5% were from the United States. At baseline, the median LDL-cholesterol was 75.0 mg/dL, HDL-cholesterol was 40.0 mg/dL, and triglycerides were 216.0 mg/dL. The baseline characteristics of the patients are provided below in Table 16.

TABLE 16

| Demographic and Randomization Stratification Information of the ITT Population | | |
|---|---|---|
| | Icosapent ethyl (N = 4089) | Placebo (N = 4090) |
| Age (years), Median (Q1-Q3) | 64.0 (57.0-69.0) | 64.0 (57.0-69.0) |
| Female, (n %) | 1162 (28.4%) | 1195 (29.2%) |
| Non-White, (n %) | 398 (9.7%) | 401 (9.8%) |
| Age ≥65 years, n (%) | 1857 (45.4%) | 1906 (46.6%) |
| Male, n (%) | 2927 (71.6%) | 2895 (70.8%) |
| White, n (%)[1] | 3691 (90.3%) | 3688 (90.2%) |
| BMI (kg/m$^2$), Median (Q1-Q3) | 30.8 (27.8-34.5) | 30.8 (27.9-34.7) |
| BMI ≥30 (kg/M$^2$), n (%) | 2331 (57.0%) | 2362 (57.8%) |
| Geographic Region, n (%) | | |
| Westernized [2] | 2906 (71.1%) | 2905 (71.0%) |
| Eastern Europe [3] | 1053 (25.8%) | 1053 (25.7%) |
| Asia Pacific [4] | 130 (3.2%) | 132 (3.2%) |
| CV Risk Category, n (%) | | |
| Secondary Prevention | 2892 (70.7%) | 2893 (70.7%) |
| Primary Prevention | 1197 (29.3%) | 1197 (29.3%) |
| Ezetimibe Use, n (%) | 262 (6.4%) | 262 (6.4%) |
| Statin Intensity, n (%) | | |
| Low | 254 (6.2%) | 267 (6.5%) |
| Moderate | 2533 (61.9%) | 2575 (63.0%) |
| High | 1290 (31.5%) | 1226 (30.0%) |
| Missing | 12 (0.3%) | 22 (0.5%) |
| Diabetes, n (%) | | |
| Type I Diabetes | 27 (0.7%) | 30 (0.7%) |
| Type II Diabetes | 2367 (57.9%) | 2363 (57.8%) |
| No Diabetes at Baseline | 1695 (41.5%) | 1694 (41.4%) |
| Data Missing | 0 | 3 (0.1%) |
| hsCRP (mg/L), Median (Q1-Q3) | 2.2 (1.1-4.5) | 2.1 (1.1-4.5) |
| Triglycerides (mg/dL), Median (Q1-Q3) | 216.5 (176.5-272.0) | 216.0 (175.5-274.0) |
| HDL-C (mg/dL), Median (Q1-Q3) | 40.0 (34.5-46.0) | 40.0 (35.0-46.0) |
| LDL-C (mg/dL), Median (Q1-Q3) | 74.0 (61.5-88.0) | 76.0 (63.0-89.0) |
| Triglycerides Category | | |
| <150 mg/dL | 412 (10.1%) | 429 (10.5%) |
| 150 to <200 mg/dL | 1193 (29.2%) | 1191 (29.1%) |
| ≥200 mg/dL | 2481 (60.7%) | 2469 (60.4%) |
| Triglycerides ≥200 mg/dL and HDL-C ≤35 mg/dL | 823 (20.1%) | 794 (19.4%) |
| EPA (μg/mL), Median (Q1-Q3) | 26.1 (17.1-40.1) | 26.1 (17.1-39.9) |

In general, the baseline value is defined as the last non-missing measurement obtained prior to the randomization. The baseline LDL-C value obtained via Preparative Ultracentrifugation was used, unless this value was missing. If the LDL-C Preparative Ultracentrifugation value was missing, then another LDL-C value was be used, with prioritization of values obtained from LDL-C Direct measurements, followed by LDL-C derived by the Friedewald calculation (only for patients with TG <400 mg/dL), and finally LDL-C derived using the calculation published by Johns Hopkins University investigators. 22 At Visit 1 and Visit 1.1 Direct LDL-C was used if at the same visit TG >400 mg/dL At all l remaining visits LDL-C was measured by Direct LDL-C or by Preparative Ultracentrifugation if at the same visit TG >400 mg/dL. For all other lipid and lipoprotein marker parameters, wherever possible, baseline was derived as the arithmetic mean of the Visit 2 (Day 0) value and the preceding Visit 1 (or Visit 1.1) value. If only one of these values was available, the single available value was used as baseline. The only significant baseline between group difference with p < 0.05 was LDL-C (p = 0.03).

[1] Race as reported by the investigators.

[2] Westernized region includes Australia, Canada, Netherlands, New Zealand, United States, and South Africa.

[3] Eastern European region includes Poland, Romania, Russian Federation, and Ukraine.

[4] Asia Pacific region includes India.

The median trial follow-up duration was 4.9 years with a maximum of 6.2 years. The median change in triglycerides from baseline to one year was −18.3% (−39.0 mg/dL) in the AMR101 group and +2.2% (4.5 mg/dL) in the placebo group; the median reduction from baseline (as estimated with the use of the Hodges-Lehmann approach) was 19.7% greater in the AMR101 group than in the placebo group (a 44.5 mg/dL [0.50 mmol/L] greater reduction; P<0.001). The median change in LDL cholesterol level from baseline was an increase of 3.1% (2.0 mg/dL [0.05 mmol/L]) in the AMR101 group and an increase of 10.2% (7.0 mg/dL [0.18 mmol/L]) in the placebo group—a 6.6% (5.0 mg/dL [0.13 mmol/L]) lower increase with AMR101 than with placebo (P<0.001).

Figure 3A:
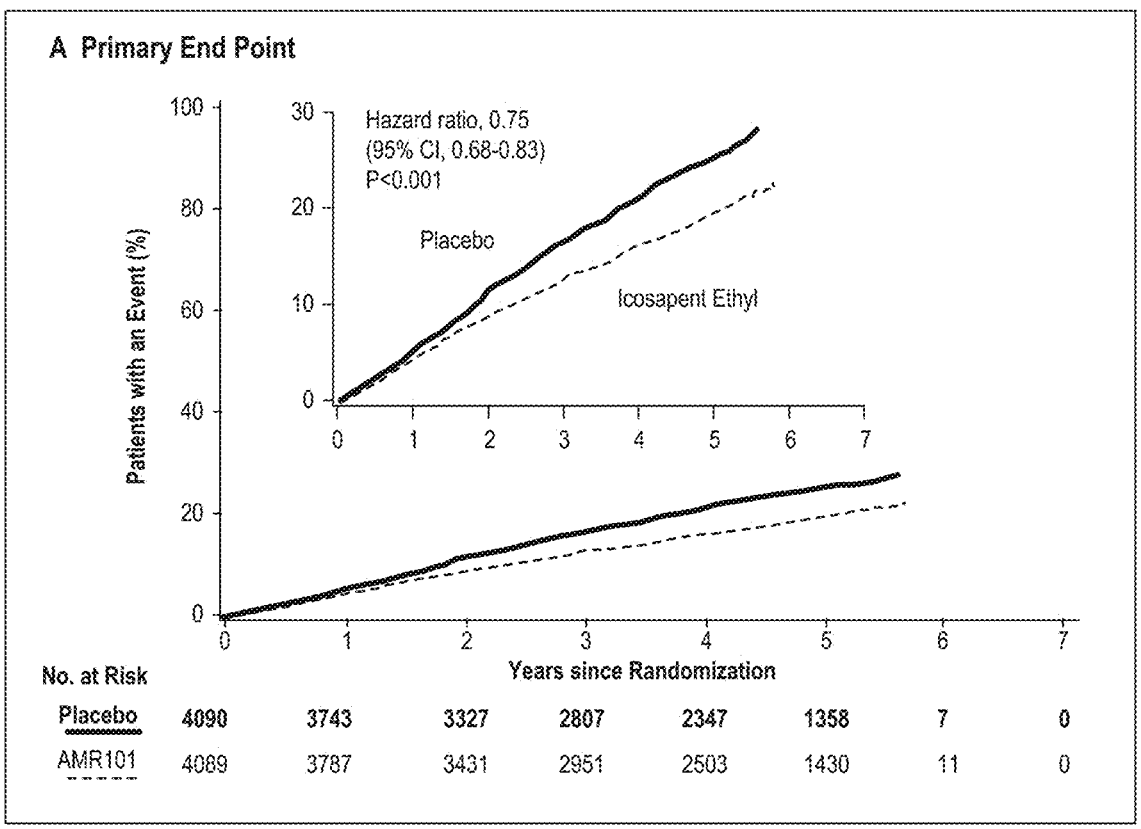
FIGS. 3A and 3B are representative Kaplan-Meier event curves for the cumulative incidence of the primary composite endpoints.
Figure 3B:
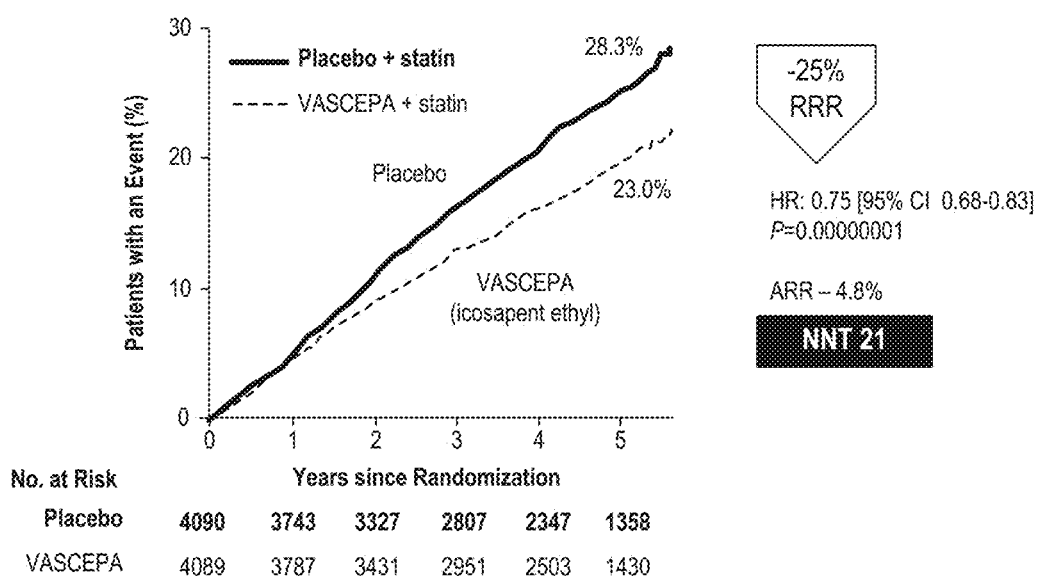

Analyses of Primary Composite Endpoint:

There was a total of 1606 adjudicated primary endpoint first events. FIG. 3A shows the Kaplan-Meier event curves for the primary efficacy endpoint of time to first occurrence of cardiovascular death, nonfatal myocardial infarction, nonfatal stroke, coronary revascularization, or unstable angina in the AMR101 and placebo groups with the inset showing the data on an expanded y axis. All patients were included in the analysis and patients experiencing more than one type of endpoint event were counted for their first occurrence in each event type. The primary endpoint as shown in FIG. 3A occurred in 17.2% of AMR101 patients versus in 22.0% of placebo patients (HR, 0.75; 95% CI, 0.68-0.83; P<0.001) for an absolute risk reduction (AAR) of 4.8% (95% CI, 3.1-6.5%) and number needed to treat (NNT) of 21 (95% CI, 15-33) over median follow up 4.9 years. Similarly, FIG. 3B shows the Kaplan-Meier estimates of the cumulative incidence of the primary composition endpoints over time. Significantly, FIG. 3B indicates a 25% relative risk reduction for the primary composite endpoint over the course of 5 years.

Figure 4:
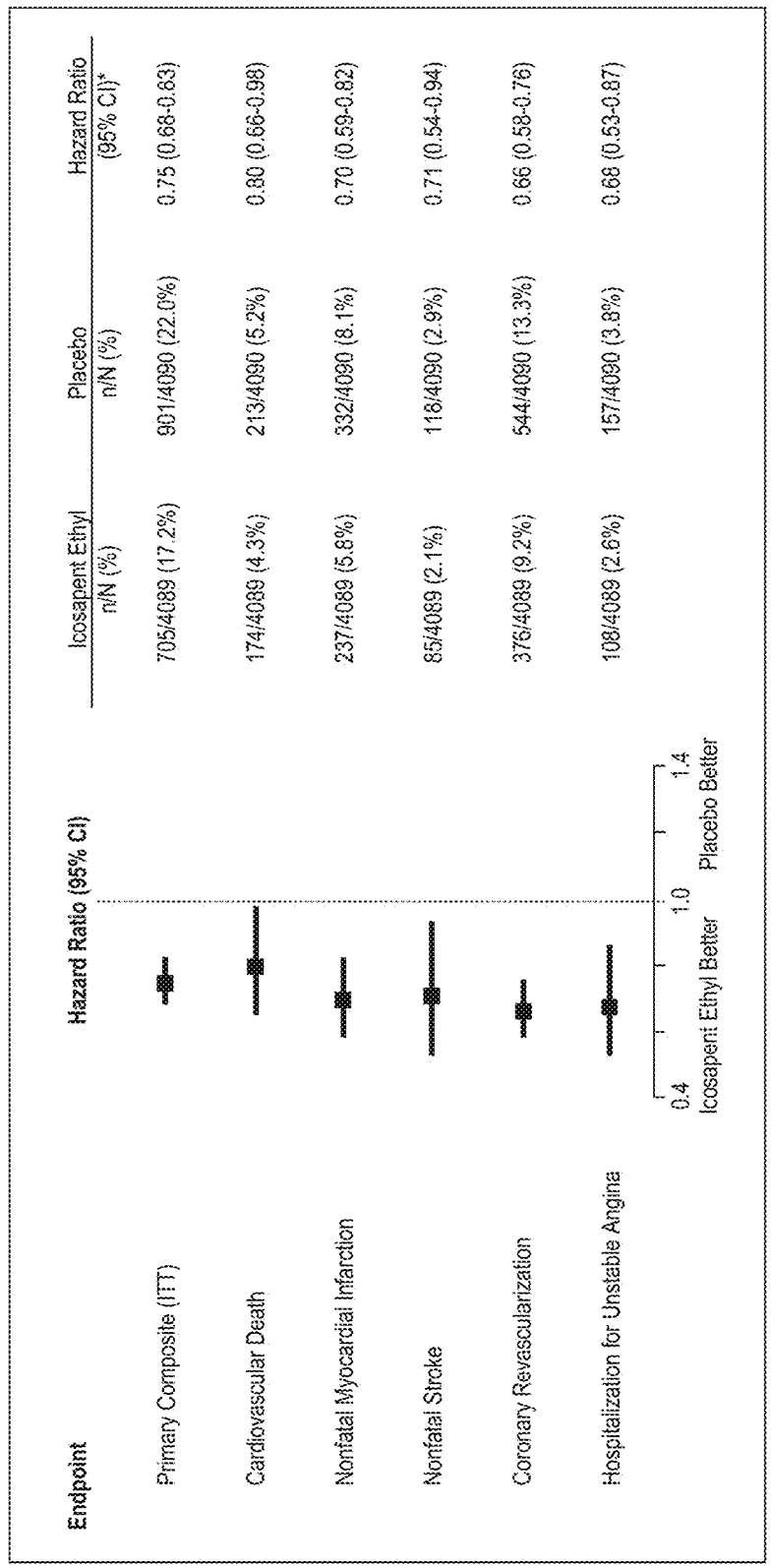
FIG. 4 is a representative forest plot of individual components of primary endpoints analyzed as time to first event of each individual endpoint and indicates that each component, individually, was reduced.

FIG. 4 lists the individual components of the primary endpoint analyzed as time to first event of each individual endpoint. Shown first in FIG. 4 is the HR and 95% CI for the primary composite endpoint event (time to first occurrence of either cardiovascular death, nonfatal myocardial infarction, nonfatal stroke, coronary revascularization, or unstable angina). Shown separately beneath FIG. 4 are HRs and 95% CIs for time to first occurrence of each type of individual primary endpoint component event, irrespective of whether contributing to the primary composite endpoint event or not.

Figure 5A:
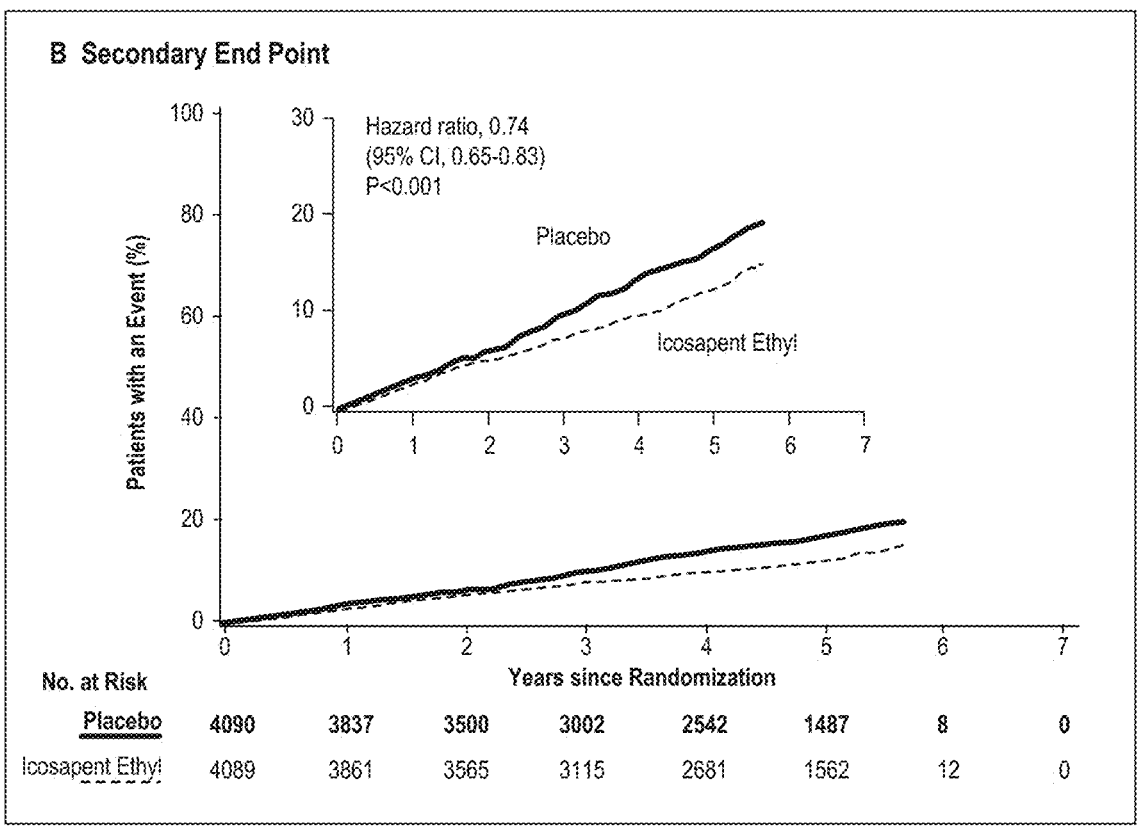
FIGS. 5A and 5B are representative Kaplan-Meier event curves for the cumulative incidence of the key secondary composite endpoints.
Figure 5B:
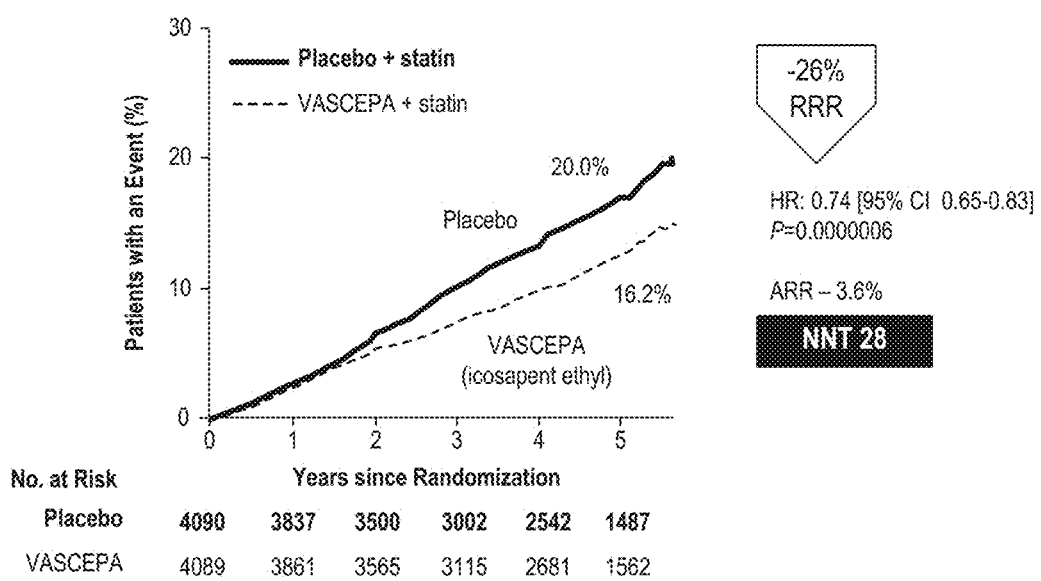

Analyses of Key Secondary Endpoints:

FIG. 5A shows the Kaplan-Meier event curves for the key secondary efficacy endpoint of time to first occurrence of cardiovascular death, nonfatal myocardial infarction, or nonfatal stroke in the AMR101 and placebo groups with the inset showing the data on an expanded y axis. All patients were included in the analysis and patients experiencing more than one type of endpoint event were counted for their first occurrence in each event type. The key secondary efficacy endpoint as shown in FIG. 5A occurred in 11.2% of AMR101 patients versus 14.8% of placebo patients (HR, 0.74, 95% CI 0.65-0.83, P<0.001) for an absolute risk reduction of 3.6% (95% CI, 2.1-5.0%) and a number needed to treat of 28 (95% CI, 20-47) over median follow up 4.9 years. Similarly, FIG. 5B shows the Kaplan-Meier estimates of the cumulative incidence of the key secondary composition endpoints over time. Significantly, FIG. 5B indicates a 26% relative risk reduction for the key secondary composite endpoint over the course of 5 years.

Analysis of Prespecified Subgroups

Figure 6:
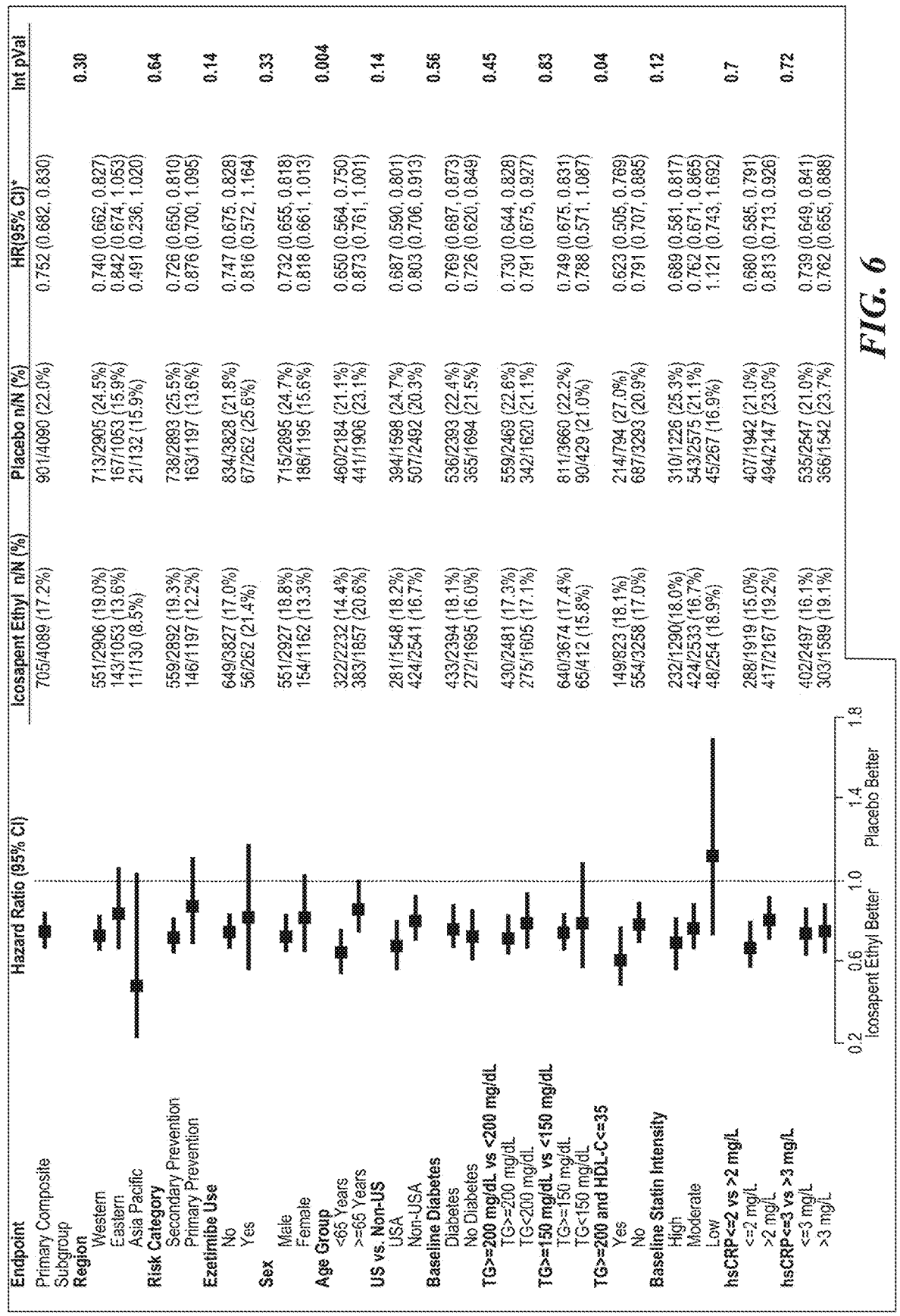
FIGS. 6 and 7 are representative forest plots of primary efficacy outcomes in select prespecified subgroups.
Figure 7:
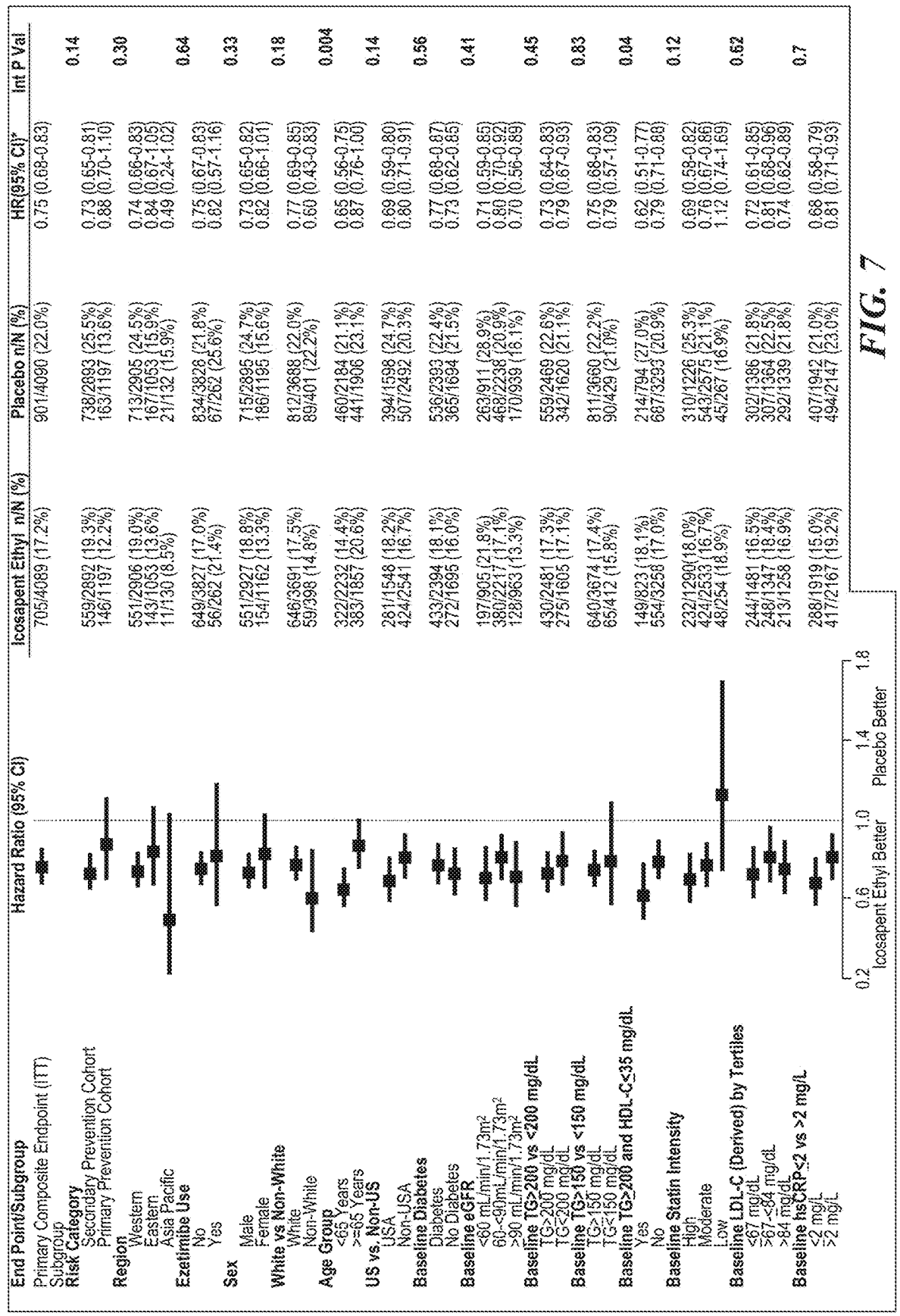
Figure 8:
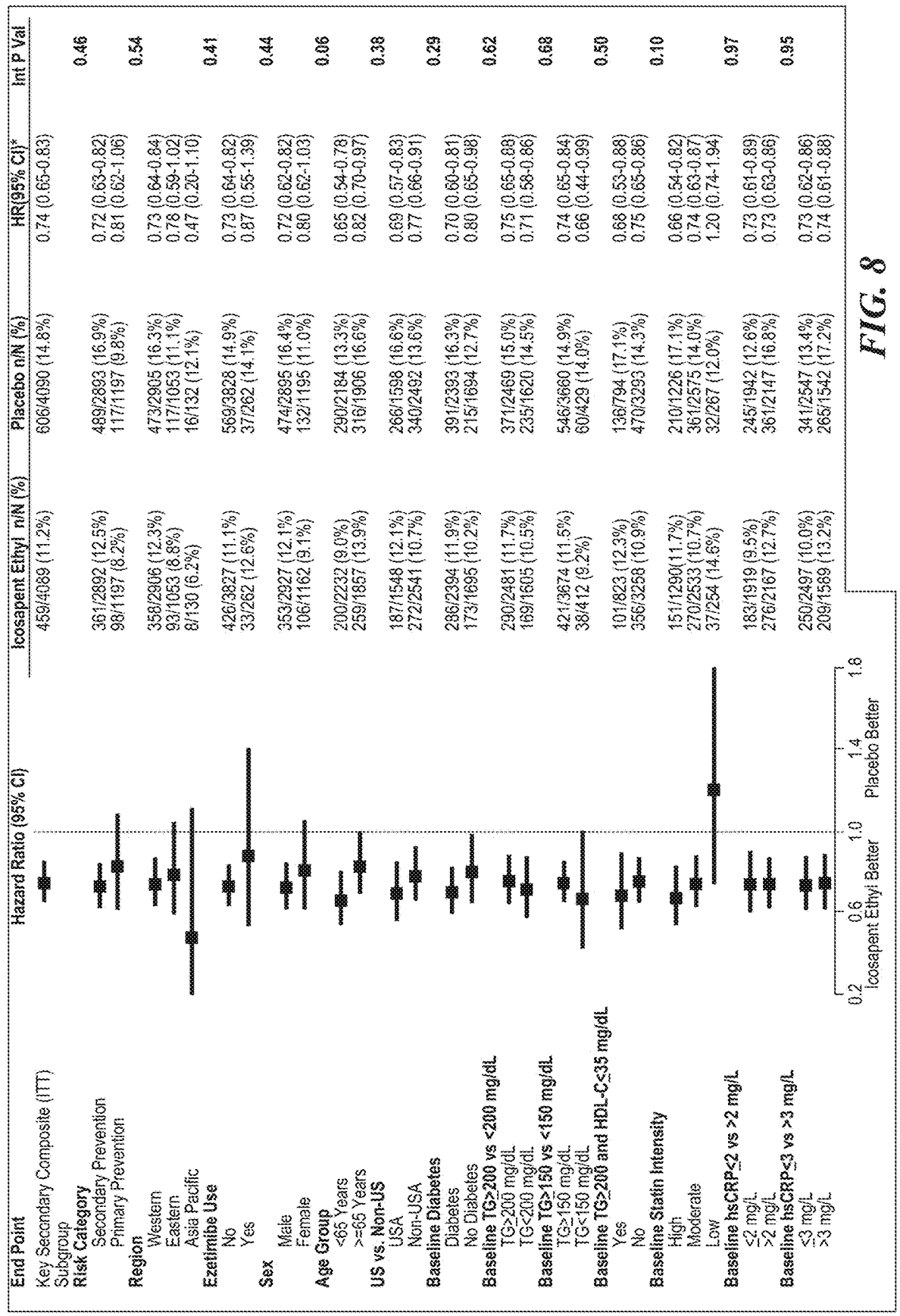
FIGS. 8 and 9 are representative forest plots of secondary efficacy outcomes in select prespecified subgroups.
Figure 9:
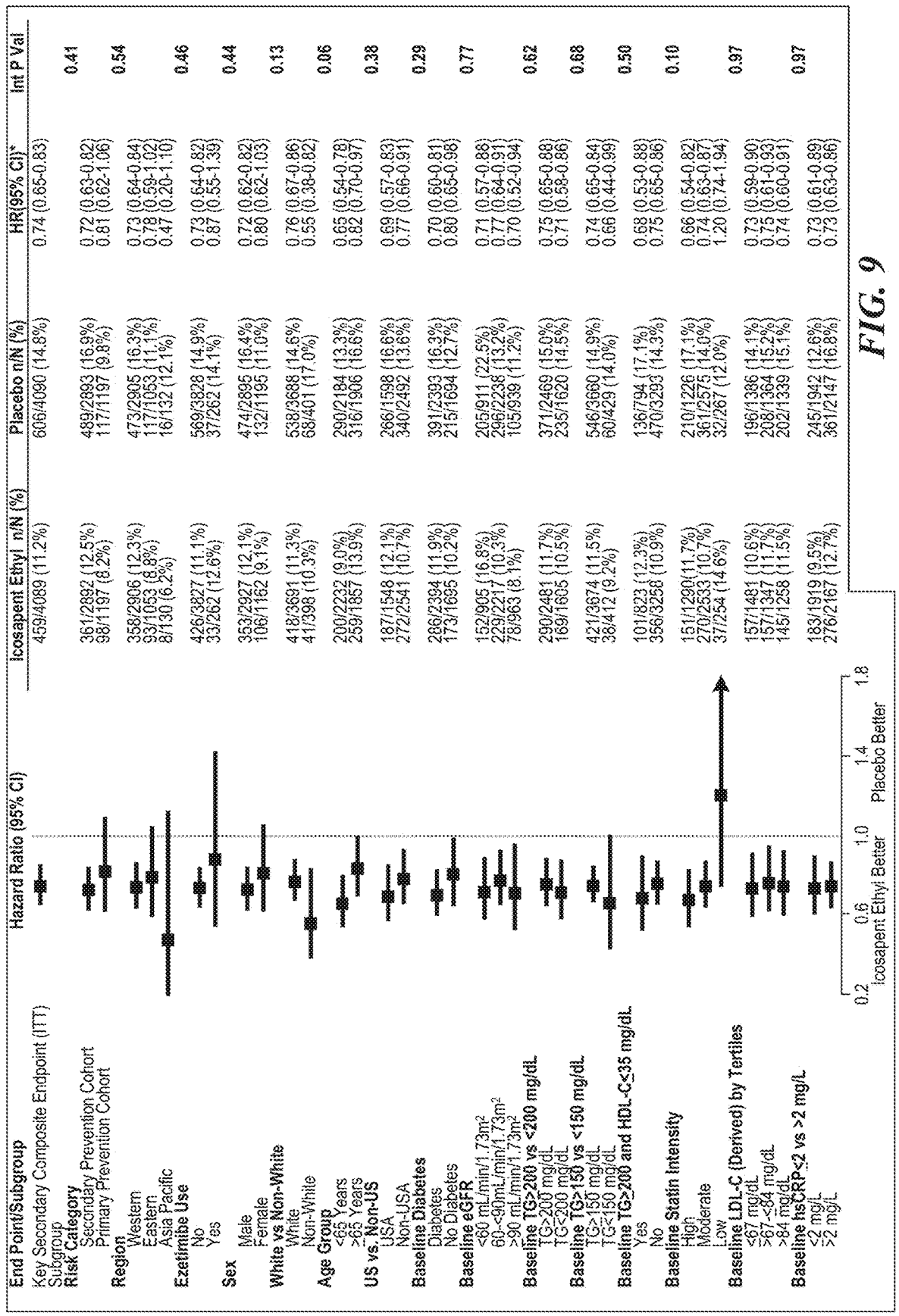

The primary efficacy outcomes in select prespecified subgroups are shown in FIGS. 6 and 7 with corresponding HRs and 95% CIs for the primary efficacy endpoint of time to first occurrence of cardiovascular death, nonfatal myocardial infarction, nonfatal stroke, coronary revascularization, or unstable angina from select prespecified subgroups in the AMR101 and placebo groups. The key secondary efficacy outcomes in select prespecified subgroups are shown in FIGS. 8 and 9 with corresponding HRs and 95% CIs for the key secondary efficacy endpoint of time to first occurrence of cardiovascular death, nonfatal myocardial infarction, nonfatal stroke, coronary revascularization, or unstable angina from select prespecified subgroups in the AMR101 and placebo groups. Significantly, FIGS. 6-9 indicate that a subject's baseline triglyceride levels (e.g., ≥150 vs. <150 mg/dL or ≥200 or <200 mg/dL) had no influence on the primary or key secondary efficacy endpoints.

Figure 10A:
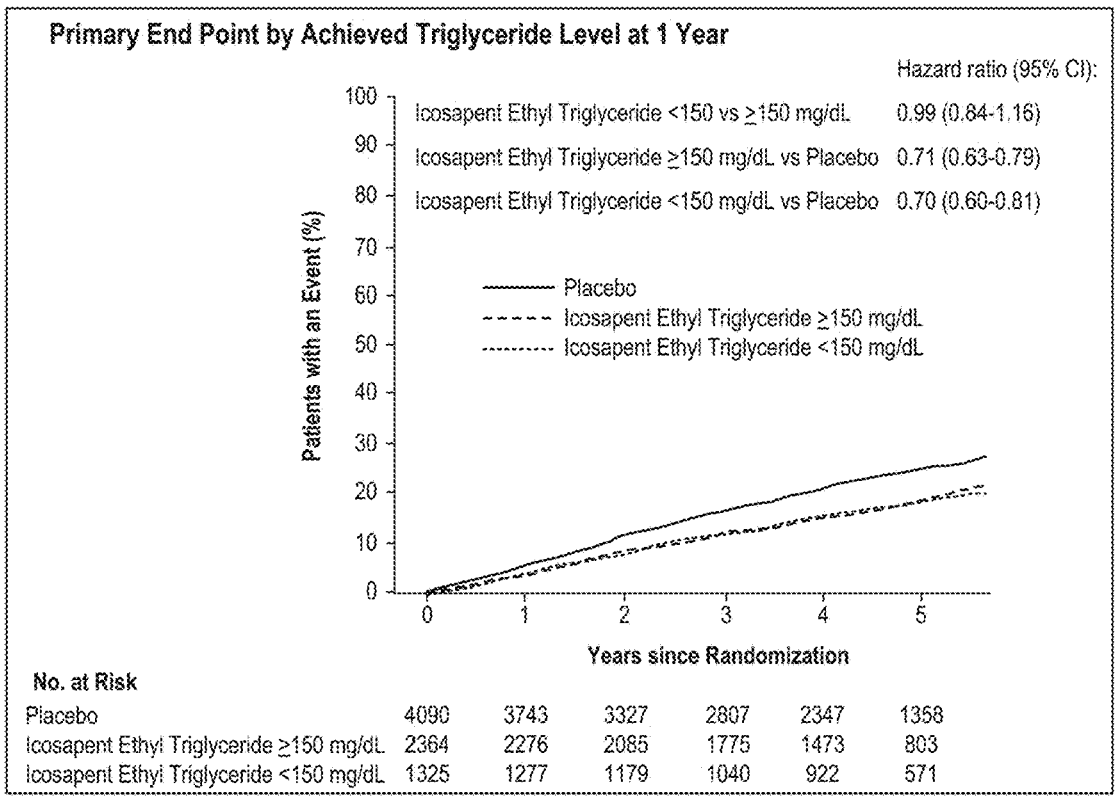
FIGS. 10A and 10B are representative Kaplan-Meier curves of primary and key secondary endpoints by achieved triglyceride level at 1 year.
Figure 10B:
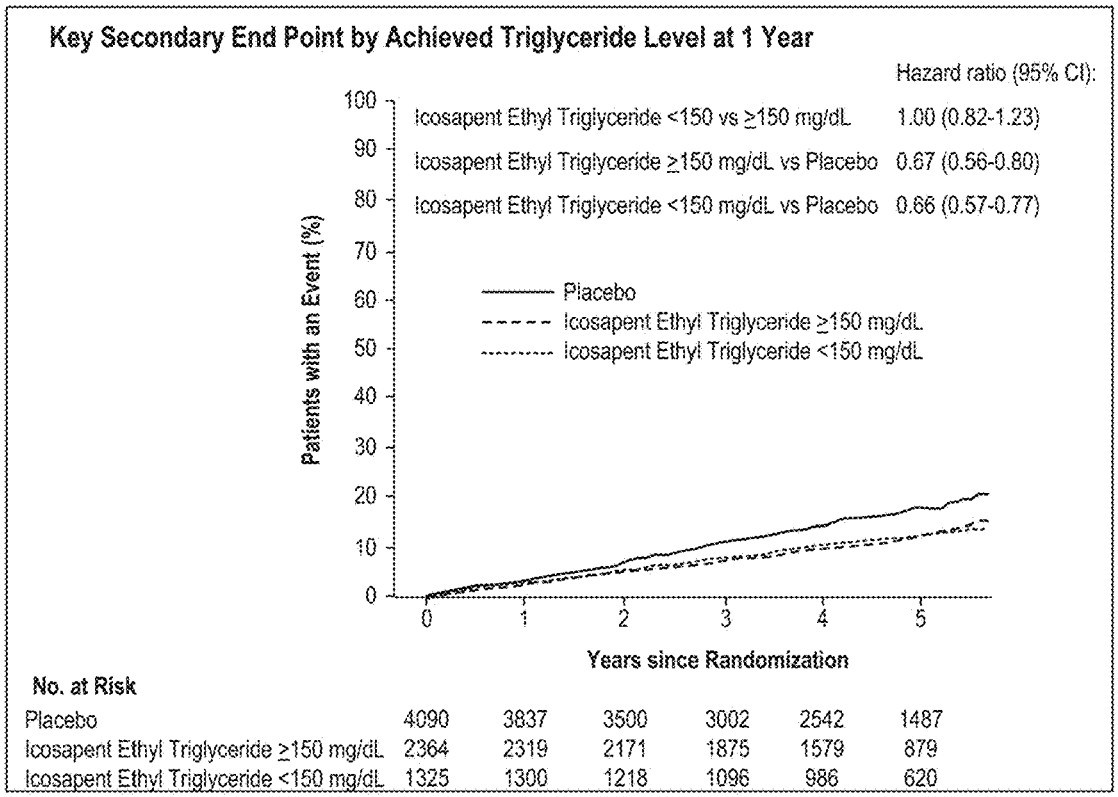

This conclusion is further substantiated by the combination of FIGS. 10A and 10B which show that achievement of on-treatment triglyceride levels above or below 150 mg/dL at one year did not influence the efficacy of AMR101 versus placebo. In particular, FIGS. 10A and 10B show the primary and key secondary endpoints by achieved triglyceride level (e.g., above or below 150 mg/dL) at 1 year (e.g., patients with a triglyceride level above or below 150 mg/dL after 1 year of having received the AMR101). FIG. 10A are the Kaplan-Meier curves for the primary endpoint of time to first occurrence of cardiovascular death, nonfatal myocardial infarction, nonfatal stroke, coronary revascularization, or unstable angina in the AMR101 treatment group for patients with achieved triglycerides, and the placebo group at year 1. Conversely, FIG. 10B are the Kaplan-Meier event curves for the key secondary endpoint of time to first occurrence of cardiovascular death, nonfatal myocardial infarction, or nonfatal stroke in the AMR101 treatment group for patients with achieved triglycerides, and the placebo group at year 1. Importantly, FIGS. 10A and 10B indicate that regardless of the subject's triglyceride levels at year 1, the subject experienced a statistically significant reduction in time to first occurrence of cardiovascular death, nonfatal myocardial infarction, nonfatal stroke, coronary revascularization, or unstable angina. The attainment of triglyceride levels of 150 mg/dL or higher or below 150 mg/dL at 1 year after randomization also had no influence on the efficacy of AMR101 as compared with placebo with respect to the primary or key secondary efficacy endpoint. In a post hoc analysis, no substantial difference in the benefit of AMR101 as compared with placebo was observed with respect to the primary endpoint according to whether the patients who received placebo had an increase in LDL cholesterol levels at 1 year or had no change or a decrease in LDL cholesterol levels.

Figure 11:
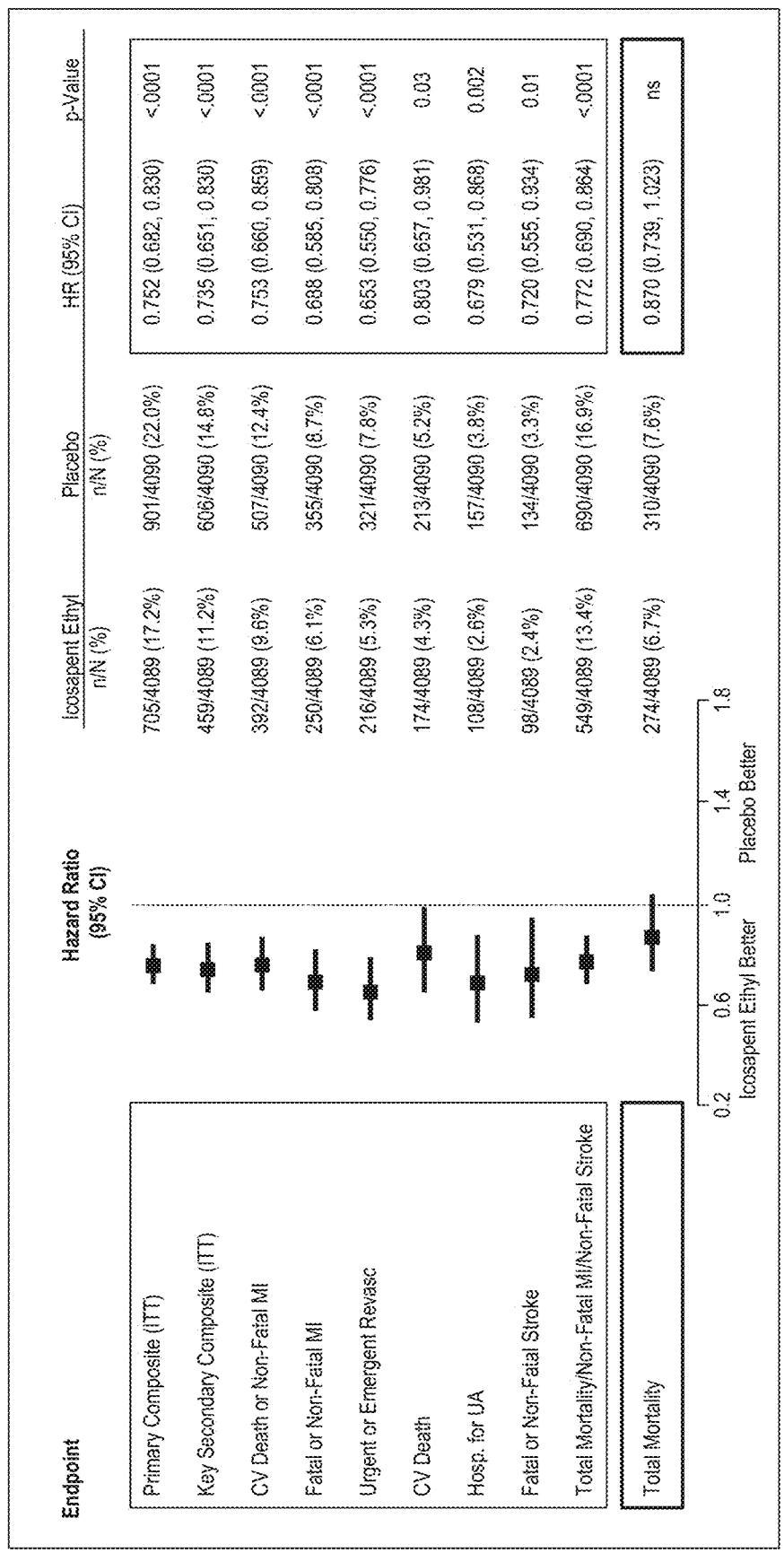
FIG. 11 is a representative forest plot of prespecified hierarchical testing of endpoints and indicates that all individual and composite ischemic endpoints were significantly reduced by icosapent ethyl (AMR101).

FIG. 11 depicts the prespecified hierarchical testing of the endpoints; except for the last hierarchical secondary endpoint of death from any cause (also referred to as total mortality), all other individual and composite ischemic endpoints were significantly reduced by AMR101, including cardiovascular death (4.3% versus 5.2%; HR, 0.80; 95% CI, 0.66-0.98; P=0.03). Total mortality was 6.7% versus 7.6% (HR, 0.87; 95% CI, 0.74-1.02; P=0.09) in the AMR101 and placebo groups, respectively. For each of the prespecified endpoints in FIG. 11, icosapent ethyl 4 g per day provide a RRR of 25% for the primary composite endpoint, 26% for the secondary composite endpoint, 25% for the composite of cardiovascular death or nonfatal myocardial infarction, 31% for fatal or nonfatal myocardial infarction, 35% for urgent or emergent revascularization, 20% for cardiovascular death, 32% for hospitalization for unstable angina, 28% for fatal or nonfatal stroke, 23% reduction in the composite of total mortality, nonfatal myocardial infarction, or nonfatal stroke, and lastly, a 13% reduction in total mortality.

Results for selected tertiary outcomes are shown in Table 17. A tertiary endpoint, adjudicated sudden cardiac death was 2.1% versus 1.5% (HR, 0.69; 95% CI, 0.50-0.96).

TABLE 17

Selected Prespecified Adjudicated Tertiary Endpoints

| Tertiary Endpoint | Icosapent Ethyl n/N (%) | Placebo n/N (%) | HR (95% CI) |
|---|---|---|---|
| Primary Endpoint in Patients with Diabetes at Baseline | 433/2394 (18.1%) | 536/2393 (22.4%) | 0.77 (0.68, 0.87) |
| New Heart Failure | 169/4089 (4.1%) | 176/4090 (4.3%) | 0.95 (0.77, 1.17) |
| New Heart Failure Requiring Hospitalization | 141/4089 (3.4%) | 144/4090 (3.5%) | 0.97 (0.77, 1.22) |
| Transient Ischemic Attack | 64/4089 (1.6%) | 48/4090 (1.2%) | 1.32 (0.91, 1.92) |
| Amputation for PVD | 22/4089 (0.5%) | 21/4090 (0.5%) | 1.04 (0.57, 1.89) |
| Carotid Revascularization | 31/4089 (0.8%) | 26/4090 (0.6%) | 1.18 (0.70, 1.98) |
| Coronary Revascularization | 376/4089 (9.2%) | 544/4090 (13.3%) | 0.66 (0.58, 0.76) |
| Emergent Revascularization | 41/4089 (1.0%) | 65/4090 (1.6%) | 0.62 (0.42, 0.92) |
| Urgent Revascularization | 181/4089 (4.4%) | 268/4090 (6.6%) | 0.66 (0.54, 0.79) |
| Elective Revascularization | 194/4089 (4.7%) | 278/4090 (6.8%) | 0.68 (0.57, 0.82) |
| Salvage Revascularization | 0/4089 (0.0%) | 2/4090 (0.0%) | 0.00 (0.00, —) |
| Cardiac Arrhythmias Requiring Hospitalization of ≥24 Hours | 188/4089 (4.6%) | 154/4090 (3.8%) | 1.21 (0.97, 1.49) |
| Cardiac Arrest | 22/4089 (0.5%) | 42/4090 (1.0%) | 0.52 (0.31, 0.86) |
| Sudden Cardiac Death | 61/4089 (1.5%) | 87/4090 (2.1%) | 0.69 (0.50, 0.96) |
| Ischemic Stroke | 80/4089 (2.0%) | 122/4090 (3.0%) | 0.64 (0.49, 0.85) |
| Hemorrhagic Stroke | 13/4089 (0.3%) | 10/4090 (0.2%) | 1.28 (0.56, 2.93) |
| New Onset of Diabetes[1] | 65/1695 (3.8%) | 63/1697 (3.7%) | 1.04 (0.73, 1.47) |

[1]Patents with diabetes at baseline are excluded from this endpoint analysis.

Analysis of Additional Biomarker from Baseline:
The effects on additional biomarkers to year 1 are shown in Table 18.

TABLE 18

Effect on Biomarkers from Baseline to Year 1

| | Icosapent Ethyl (N = 4089) Median | | Placebo (N = 4090) Median | | Median Between Group Difference at Year 1 | | |
|---|---|---|---|---|---|---|---|
| Biomarker | Baseline | Year 1 | Baseline | Year 1 | Absolute Change from Baseline | % Change from Baseline | % Change P-value |
| Triglycerides (mg/dL) | 216.5 | 175.0 | 216.0 | 221.0 | −44.5 | −19.7 | <0.0001 |
| Non-HDL-C (mg/dL) | 118.0 | 113.0 | 118.5 | 130.0 | −15.5 | −13.1 | <0.0001 |
| LDL-C (mg/dL) | 74.5 | 77.0 | 76.0 | 84.0 | −5.0 | −6.6 | <0.0001 |
| HDL-C (mg/dL) | 40.0 | 39.0 | 40.0 | 42.0 | −2.5 | −6.3 | <0.0001 |
| Apo B (mg/dL) | 82.0 | 80.0 | 83.0 | 89.0 | −8.0 | −9.7 | <0.0001 |
| hsCRP (mg/L) | 2.2 | 1.8 | 2.1 | 2.8 | −0.9 | −39.9 | <0.0001 |
| EPA (µg/mL) | 26.1 | 144.0 | 26.1 | 23.3 | 114.9 | 358.8 | <0.0001 |

The effects on lipid, lipoprotein, and inflammatory marker over time for the ITT population are shown in Table 19.

TABLE 19

Lipid, Lipoprotein, and Inflammatory Marker Data Over Time for the ITT Population

| | | Icosapent Ethyl (N = 4089) | | | | Placebo (N = 4090) | |
|---|---|---|---|---|---|---|---|
| Biomarker | Visit | Median Observed Value | Median Absolute Change from Baseline | Median % Change from Baseline | Median % Change P-value[1] | Median Observed Value | Median Absolute Change from Baseline |
| Triglycerides (mg/dL) | Baseline | 216.5 | | | | 216.0 | |
| | Month 4 | 177.0 | −37.5 | −18.6 | <0.001 | 221.0 | 5.5 |
| | Year 1 | 175.0 | −39.0 | −18.3 | <0.001 | 221.0 | 4.5 |
| | Year 2 | 173.0 | 85 | −18.9 | <0.001 | 220.0 | 4.3 |

TABLE 19-continued

Lipid, Lipoprotein, and Inflammatory Marker Data Over Time for the ITT Population

|  |  |  |  |  |  |  |  |
|---|---|---|---|---|---|---|---|
|  | Year 3 | 167.0 | −44.0 | −21.7 | <0.001 | 212.0 | 1.0 |
|  | Year 4 | 163.0 | −42.5 | −21.7 | <0.001 | 200.0 | −7.0 |
|  | Year 5 | 158.0 | −38.0 | −20.0 | <0.001 | 193.0 | −3.0 |
|  | Last Visit | 170.0 | −45.0 | −21.6 | <0.001 | 202.0 | −13.0 |
| Non-HDL-C | Baseline | 118.0 |  |  |  | 118.5 |  |
| (mg/dL) | Month 4 | 113.0 | −4.5 | −4.0 | <0.001 | 128.0 | 9.5 |
|  | Year 1 | 113.0 | −4.0 | −3.6 | <0.001 | 130.0 | 12.0 |
|  | Year 2 | 113.0 | −3.5 | −3.1 | 0.002 | 129.0 | 11.5 |
|  | Year 3 | 112.0 | −4.8 | −4.2 | <0.001 | 128.0 | 10.5 |
|  | Year 4 | 110.5 | −5.0 | −4.2 | <0.001 | 126.0 | 9.5 |
|  | Year 5 | 109.0 | −5.0 | −4.4 | 0.004 | 123.0 | 7.0 |
|  | Last Visit | 112.0 | −5.0 | −4.4 | <0.001 | 124.0 | 6.0 |
| LDL-C derived | Baseline | 74.0 |  |  |  | 76.0 |  |
| (mg/dL)[4] | Year 1 | 77.0 | 2.0 | 3.1 | <0.001 | 84.0 | 7.0 |
|  | Last Visit | 77.0 | 2.0 | 3.1 | <0.001 | 84.0 | 7.0 |
| LDL-C Hopkins | Baseline | 85.8 |  |  |  | 86.7 |  |
| (mg/dL) | Month 4 | 83.6 | −1.6 | −2.0 | 0.01 | 93.7 | 7.3 |
|  | Year 1 | 85.3 | −1.1 | −1.2 | 0.06 | 95.8 | 9.3 |
|  | Year 2 | 85.5 | −0.1 | −0.2 | <0.001 | 96.1 | 9.5 |
|  | Year 3 | 84.6 | −1.0 | −1.2 | 0.01 | 95.7 | 9.0 |
|  | Year 4 | 83.6 | −0.5 | −0.6 | 0.07 | 94.7 | 8.8 |
|  | Year 5 | 82.2 | −0.8 | −0.7 | 0.23 | 91.6 | 6.2 |
|  | Last Visit | 84.0 | −1.0 | −1.2 | 0.14 | 92.1 | 5.7 |
| HDL-C | Baseline | 40.0 |  |  |  | 40.0 |  |
| (mg/dL) | Month 4 | 39.0 | −1.0 | −2.8 | <0.001 | 42.0 | 2.0 |
|  | Year 1 | 39.0 | −1.0 | −2.6 | <0.001 | 42.0 | 1.5 |
|  | Year 2 | 40.0 | 0.0 | 0.0 | 0.21 | 42.0 | 1.5 |
|  | Year 3 | 40.0 | 0.0 | 0.0 | 0.006 | 42.0 | 1.5 |
|  | Year 4 | 40.5 | 0.5 | 1.0 | <0.001 | 43.0 | 2.0 |
|  | Year 5 | 41.0 | 0.0 | 0.0 | 0.02 | 43.0 | 1.5 |
|  | Last Visit | 41.0 | 1.0 | 2.5 | <0.001 | 42.0 | 2.0 |
| Apo B | Baseline | 82.0 |  |  |  | 83.0 |  |
| (mg/dL) | Year 2 | 80.0 | −2.0 |  | 0.05 | 89.0 | 6.0 |
|  | Last Visit | 80.0 | −2.0 |  | 0.06 | 86.0 | 4.0 |
| hsCRP | Baseline | 2.2 |  |  |  | 2.1 |  |
| (mg/L) | Year 2 | 1.8 | −0.2 | −13.9 | 0.04 | 2.8 | 0.5 |
|  | Last Visit | 1.8 | −0.2 | −12.6 | 0.75 | 2.8 | 0.4 |
| Log hsCRP | Baseline | 0.8 |  |  |  | 0.8 |  |
| (mg/L) | Year 2 | 0.6 | −0.1 | −21.8 | <.0001 | 1.0 | 0.3 |
|  | Last Visit | 0.6 | −0.1 | −23.1 | <.0001 | 1.0 | 0.3 |
| EPA | Baseline | 26.1 |  |  |  | 26.1 |  |
| (µg/mL)[5] | Year 1 | 144.0 | 112.6 | 393.5 | <0.001 | 23.3 | −2.9 |

| | | Placebo (N = 4090) | | Between Group Difference Median | | |
|---|---|---|---|---|---|---|
| Biomarker | Visit | Median % Change from Baseline | Median % Change P-value[1] | Absolute Change from Baseline[2] | Median % Change from Baseline[2] | Median % Change P value[3] |
| Triglycerides | Baseline |  |  |  |  |  |
| (mg/dL) | Month 4 | 2.7 | <0.001 | −45.5 | −20.1 | <0.001 |
|  | Year 1 | 2.2 | <0.001 | −44.5 | −19.7 | <0.001 |
|  | Year 2 | 2.1 | <0.001 | −43.8 | −19.7 | <0.001 |
|  | Year 3 | 0.4 | <0.001 | −45.5 | −20.3 | <0.001 |
|  | Year 4 | −3.7 | >0.99 | −38.0 | −17.4 | <0.001 |
|  | Year 5 | −1.5 | 0.23 | −33.5 | −16.7 | <0.001 |
|  | Last Visit | −6.5 | <0.001 | −32.0 | −14.1 | <0.001 |
| Non-HDL-C | Baseline |  |  |  |  |  |
| (mg/dL) | Month 4 | 8.2 | <0.001 | −14.3 | −12.2 | <0.001 |
|  | Year 1 | 10.4 | <0.001 | −15.5 | −13.1 | <0.001 |
|  | Year 2 | 9.8 | <0.001 | −14.5 | −12.5 | <0.001 |
|  | Year 3 | 9.2 | <0.001 | −14.5 | −12.4 | <0.001 |
|  | Year 4 | 8.1 | <0.001 | −14.0 | −12.0 | <0.001 |
|  | Year 5 | 6.1 | <0.001 | −11.0 | −9.9 | <0.001 |
|  | Last Visit | 5.1 | <0.001 | −10.0 | −8.6 | <0.001 |
| LDL-C derived | Baseline |  |  |  |  |  |
| (mg/dL)[4] | Year 1 | 10.2 | <0.001 | −5.0 | −6.6 | <0.001 |
|  | Last Visit | 10.2 | <0.001 | −5.0 | −6.6 | <0.001 |
| LDL-C Hopkins | Baseline |  |  |  |  |  |
| (mg/dL) | Month 4 | 8.7 | <0.001 | −8.7 | −10.3 | <0.001 |
|  | Year 1 | 10.9 | <0.001 | −9.6 | −11.4 | <0.001 |
|  | Year 2 | 11.4 | <0.001 | −9.4 | −11.1 | <0.001 |

TABLE 19-continued

Lipid, Lipoprotein, and Inflammatory Marker Data Over Time for the ITT Population

|  |  |  |  |  |  |  |
|---|---|---|---|---|---|---|
|  | Year 3 | 10.5 | <0.001 | −8.7 | −10.4 | <0.001 |
|  | Year 4 | 10.1 | <0.001 | −8.9 | −10.6 | <0.001 |
|  | Year 5 | 6.9 | <0.001 | −6.6 | −8.0 | <0.001 |
|  | Last Visit | 6.5 | <0.001 | −6.2 | −7.4 | <0.001 |
| HDL-C | Baseline |  |  |  |  |  |
| (mg/dL) | Month 4 | 4.7 | <0.001 | −3.0 | −7.2 | <0.001 |
|  | Year 1 | 3.8 | <0.001 | −2.5 | −6.3 | <0.001 |
|  | Year 2 | 4.2 | <0.001 | −2.0 | −4.6 | <0.001 |
|  | Year 3 | 4.0 | <0.001 | −1.5 | −3.8 | <0.001 |
|  | Year 4 | 4.8 | <0.001 | −1.5 | −3.9 | <0.001 |
|  | Year 5 | 3.0 | <0.001 | −1.5 | −3.0 | <0.001 |
|  | Last Visit | 5.7 | <0.001 | −1.0 | −3.0 | <0.001 |
| Apo B | Baseline |  |  |  |  |  |
| (mg/dL) | Year 2 | 7.8 | <0.001 | −8.0 | −9.7 | <0.001 |
|  | Last Visit | 4.5 | <0.001 | −5.0 | −6.7 | <0.001 |
| hsCRP | Baseline |  |  |  |  |  |
| (mg/L) | Year 2 | 32.3 | <0.001 | −0.9 | −39.9 | <0.001 |
|  | Last Visit | 29.9 | <0.001 | −0.8 | −37.6 | <0.001 |
| Log hsCRP | Baseline |  |  |  |  |  |
| (mg/L) | Year 2 | 0.0 | 0.9203 | −0.4 | −22.5 | <0.001 |
|  | Last Visit | −4.0 | 0.0481 | −0.4 | −21.2 | <0.001 |
| EPA | Baseline |  |  |  |  |  |
| (μg/mL)[5] | Year 1 | −12.8 | <0.001 | 114.9 | 358.8 | <0.001 |

Safety Results

The results from this study showed no new or unexpected important adverse effects were observed in the safety population for this study as shown below in Tables 20 and 21. These conclusions are consistent with the independent DMC review conclusions and with quarterly safety review conclusions.

TABLE 20

Overview of Treatment-Emergent Adverse Events of the Safety Population

|  | AMR101 (N = 4089) | Placebo (N = 4090) | p-value[1] |
|---|---|---|---|
| Subjects with at Least One TEAE [2], n(%) | 3343 (81.8%) | 3326 (81.3%) | 0.63 |
| Serious TEAE | 1252 (30.6%) | 1254 (30.7%) | 0.98 |
| TEAE Leading to Withdrawal of Study Drug [3] | 321 (7.9%) | 335 (8.2%) | 0.60 |
| Serious TEAE Leading to Withdrawal of Study Drug [3] | 88 (2.2%) | 88 (2.2%) | 1.00 |
| Serious TEAE Leading to Death[4] | 94 (2.3%) | 102 (2.5%) | 0.61 |

Note:

A treatment-emergent adverse event (TEAE) is defined as an event that first occurs or worsens in severity on or after the date of dispensing study drug and within 30 days after the completion or withdrawal from study. Percentages are based on the number of patients randomized to each treatment group in the Safety population (N). Events that were positively adjudicated as clinical endpoints are not included.

[1] p-value from Fisher's Exact test.

[2] All adverse events are coded using the Medical Dictionary for Regulatory Activities (MedDRA Version 20.1).

[3] Withdrawal of study drug excludes patients who were off drug in study (ODIS) for 30 days or more, and restarted study drug.

[4] The most common serious TEAEs leading to death by system organ class were neoplasms (1.1%); infections and infestations (0.4%); respiratory, thoracic, and mediastinal disorders (0.2%); cardiac disorders (0.2%); and vascular disorders (0.1%). No serious TEAEs leading to death by system organ class were statistically significant across treatment groups except for cardiac disorders, which occurred in 3 (0.1%) of VASCEPA ® patients and 15 (0.4%) of placebo patents (p = 0.008).

TABLE 21

Serious Bleeding Treatment-Emergent Adverse Events by Preferred term.

| Preferred Term | Icosapent Ethyl (N = 4089) | Placebo (N = 4090) | p-value [1] |
|---|---|---|---|
| Bleeding related disorders | 111 (2.7%) | 85 (2.1%) | 0.06 |
| Gastrointestinal bleeding | 62 (1.5%) | 47 (1.1%) | 0.15 |
| Central nervous system bleeding | 14 (0.3%) | 10 (0.2%) | 0.42 |
| Other bleeding | 41 (1.0%) | 30 (0.7%) | 0.19 |

Note:
A treatment-emergent adverse event (TEAE) is defined as an event that first occurs or worsens in severity on or after the date of dispensing study drug and within 30 days after the completion or withdrawal from study. Percentages are based on the number of subjects randomized to each treatment group in the Safety population (N). Events that were positively adjudicated as clinical endpoints are not included.
All adverse events are coded using the Medical Dictionary for Regulatory Activities (MedDRA Version 20.1).
[1] Fishers Exact test.

Adverse events occurring in ≥5% are reported in Table 22. Compared with placebo, AMR101 was associated with a significantly higher rate of atrial fibrillation (5.3% versus 3.9%), and peripheral edema (6.5% vs 5%), but a lower rate of diarrhea (9% vs 11.1%), anemia (4.7% vs 5.8%), and gastrointestinal adverse events (33.0% to 35.1%). There was no significant difference in the prespecified adjudicated tertiary endpoint of heart failure (4.1% vs 4.3%). The prespecified adjudicated tertiary endpoint of atrial fibrillation or flutter requiring hospitalization was more common with the AMR101 group than the placebo group (3.1% vs 2.1%; P=0.004).

TABLE 22

Number (%) Patients with Most Frequent Treatment-Emergent Adverse Events (≥5%) in Either Treatment Group By Preferred Term for the Safety Population

| Preferred Term | Icosapent Ethyl (N = 4089) | Placebo (N = 4090) | P-value [1] |
|---|---|---|---|
| Diarrhea | 367 (9.0%) | 453 (11.1%) | 0.002 |
| Back pain | 335 (8.2%) | 309 (7.6%) | 0.29 |
| Hypertension | 320 (7.8%) | 344 (8.4%) | 0.35 |
| Nasopharyngitis | 314 (7.7%) | 300 (7.3%) | 0.56 |
| Arthralgia | 313 (7.7%) | 310 (7.6%) | 0.90 |
| Upper respiratory tract infection | 312 (7.6%) | 320 (7.8%) | 0.77 |
| Bronchitis | 306 (7.5%) | 300 (7.3%) | 0.80 |
| Chest pain | 273 (6.7%) | 290 (7.1%) | 0.48 |
| Peripheral edema | 267 (6.5%) | 203 (5.0%) | 0.002 |
| Pneumonia | 263 (6.4%) | 277 (6.8%) | 0.56 |
| Influenza | 263 (6.4%) | 271 (6.6%) | 0.75 |
| Dyspnea | 254 (6.2%) | 240 (5.9%) | 0.52 |
| Urinary tract infection | 253 (6.2%) | 261 (6.4%) | 0.75 |
| Cough | 241 (5.9%) | 241 (5.9%) | 1.00 |
| Osteoarthritis | 241 (5.9%) | 218 (5.3%) | 0.27 |
| Dizziness | 235 (5.7%) | 246 (6.0%) | 0.64 |
| Pain in extremity | 235 (5.7%) | 241 (5.9%) | 0.81 |
| Cataract | 233 (5.7%) | 208 (5.1%) | 0.22 |
| Fatigue | 228 (5.6%) | 196 (4.8%) | 0.11 |
| Constipation | 221 (5.4%) | 149 (3.6%) | <0.001 |
| Atrial fibrillation | 215 (5.3%) | 159 (3.9%) | 0.003 |
| Angina pectoris | 200 (4.9%) | 205 (5.0%) | 0.84 |
| Anemia | 191 (4.7%) | 236 (5.8%) | 0.03 |

Note:
A treatment-emergent adverse event (TEAE) is defined as an event that first occurs or worsens in severity on or after the date of dispensing study drug and within 30 days after the completion or withdrawal from study. Percentages are based on the number of patients randomized to each treatment group in the Safety population (N). Events that were positively adjudicated as clinical endpoints are not included.
All adverse events are coded using the Medical Dictionary for Regulatory Activities (MedDRA Version 20.1).
[1] P-value from Fishers Exact test.

Serious treatment-emergent events occurring in ≥2% are reported in Table 23.

TABLE 23

Number (%) Patients with Serious Treatment-Emergent Adverse Events (≥2%) in Either Treatment Group by Preferred Term

| Preferred Term | Icosapent Ethyl (N = 4089) | Placebo (N = 4090) | P-value [1] |
|---|---|---|---|
| Pneumonia | 105 (2.6%) | 118 (2.9%) | 0.42 |

Note:
A treatment-emergent adverse event (TEAE) is defined as an event that first occurs or worsens in severity on or after the date of dispensing study drug and within 30 days after the completion or withdrawal from study. Percentages are based on the number of subjects randomized to each treatment group in the Safety population (N). Events that were positively adjudicated as clinical endpoints are not included. All adverse events are coded using the Medical Dictionary for Regulatory Activities (MedDRA Version 20.1).
[1] Fishers Exact test.

Adjudicated events from hospitalization for arterial fibrillation or atrial flutter are reported in Table 24.

TABLE 24

Number (%) Patients with Serious Treatment-Emergent Adverse Events (≥2%) in Either Treatment Group by Preferred Term

| Preferred Term | Icosapent Ethyl (N = 4089) | Placebo (N = 4090) | P-value [1] |
|---|---|---|---|
| Positively Adjudicated Atrial Fibrillation/Flutter [1] | 127 (3.1%) | 84 (2.1%) | 0.0037 |

Note:
A treatment-emergent adverse event (TEAE) is defined as an event that first occurs or worsens in severity on or after the date of dispensing study drug and within 30 days after the completion or withdrawal from study. Percentages are based on the number of subjects randomized to each treatment group in the Safety population (N). Events that were positively adjudicated as clinical endpoints are not included.
All adverse events are coded using the Medical Dictionary for Regulatory Activities (MedDRA Version 20.1).
[1] Fishers Exact test.

Tolerability of gastrointestinal TEAS in either treatment group are reported are reported in Table 25.

TABLE 25

Tolerability of gastrointestinal TEAEs

| Primary System Organ Class Preferred Term | Icosapent Ethyl (N = 4089) | Placebo (N = 4090) | P-value [1] |
|---|---|---|---|
| Gastrointestinal disorders | 1350 (33.0%) | 1437 (35.1%) | 0.04 |
| Diarrhea | 367 (9.0%) | 453 (11.1%) | 0.002 |
| Constipation | 221 (5.4%) | 149 (3.6%) | <0.001 |
| Nausea | 190 (4.6%) | 197 (4.8%) | 0.75 |
| Gastroesophageal Reflux Disease | 124 (3.0%) | 118 (2.9%) | 0.70 |

Note:
A treatment-emergent adverse event (TEAE) is defined as an event that first occurs or worsens in severity on or after the date of dispensing study drug and within 30 days after the completion or withdrawal from study. Percentages are based on the number of patients randomized to each treatment group in the Safety population (N). Events that were positively adjudicated as clinical endpoints are not included.
All adverse events are coded using the Medical Dictionary for Regulatory Activities (MedDRA Version 20.1).
[1] P value from Fisher's Exact test.

When grouping treatment-emergent serious adverse events for bleeding, the rate was 2.7% in the AMR101 group versus 2.1% in the placebo group (P=0.06), although there were no fatal bleeding events in either group, and no significant increases in adjudicated hemorrhagic stroke (0.3% vs 0.2%; P=0.55), serious central nervous system bleeding (0.3% versus 0.2%; P=0.42), or gastrointestinal bleeding (1.5% versus 1.1%; P=0.15). Table 26 enumerates the serious bleeding treatment-emergent adverse events by preferred term.

TABLE 26

Assessment of Serious Bleeding Treatment-Emergent
Adverse Events by Category and by Preferred Term.

|  | Icosapent Ethyl (N = 4089) | Placebo (N = 4090) | P-value[1] |
|---|---|---|---|
| Patients with Bleeding-Related Disorders[2] | 111 (2.7%) | 85 (2.1%) | 0.06 |
| By Category | | | |
| Gastrointestinal Bleeding[3] | 62 (1.5%) | 47 (1.1%) | 0.15 |
| Central Nervous System Bleeding[4] | 14 (0.3%) | 10 (0.2%) | 0.42 |
| Other Bleeding[5] | 41 (1.0%) | 30 (0.7%) | 0.19 |
| By Preferred Term | | | |
| Gastrointestinal Hemorrhage | 26 (0.6%) | 20 (0.5%) | 0.38 |
| Rectal Hemorrhage | 10 (0.2%) | 6 (0.1%) | 0.33 |
| Subdural Hematoma | 9 (0.2%) | 5 (0.1%) | 0.30 |
| Hematuria | 8 (0.2%) | 4 (0.1%) | 0.27 |
| Epistaxis | 7 (0.2%) | 4 (0.1%) | 0.39 |
| Lower Gastrointestinal Hemorrhage | 5 (0.1%) | 4 (0.1%) | 0.75 |
| Post Procedural Hemorrhage | 5 (0.1%) | 3 (0.1%) | 0.51 |
| Hemorrhagic Anemia | 4 (0.1%) | 1 (0.0%) | 0.22 |
| Gastric Ulcer Hemorrhage | 3 (0.1%) | 1 (0.0%) | 0.37 |
| Hematemesis | 3 (0.1%) | 0 (0.0%) | 0.12 |
| Hemorrhoidal Hemorrhage | 3 (0.1%) | 1 (0.0%) | 0.37 |
| Melaena | 3 (0.1%) | 4 (0.1%) | >0.99 |
| Upper Gastrointestinal Hemorrhage | 3 (0.1%) | 3 (0.1%) | >0.99 |
| Diverticulum Intestinal Hemorrhagic | 3 (0.1%) | 3 (0.1%) | >0.99 |
| Shock Hemorrhagic | 2 (0.0%) | 0 (0.0%) | 0.25 |
| Cystitis Hemorrhagic | 2 (0.0%) | 0 (0.0%) | 0.25 |
| Subarachnoid Hemorrhage | 2 (0.0%) | 1 (0.0%) | 0.62 |
| Subdural Hemorrhage | 2 (0.0%) | 1 (0.0%) | 0.62 |
| Traumatic Hematoma | 2 (0.0%) | 1 (0.0%) | 0.62 |
| Duodenal Ulcer Hemorrhage | 2 (0.0%) | 0 (0.0%) | 0.25 |
| Aortic Aneurysm Rupture | 1 (0.0%) | 1 (0.0%) | >0.99 |
| Ecchymosis | 1 (0.0%) | 0 (0.0%) | 0.50 |
| Extravasation Blood | 1 (0.0%) | 0 (0.0%) | 0.50 |
| Gastric Hemorrhage | 1 (0.0%) | 3 (0.1%) | 0.62 |
| Gastrointestinal Angiodysplasia Hemorrhagic | 1 (0.0%) | 0 (0.0%) | 0.50 |
| Genital Hemorrhage | 1 (0.0%) | 0 (0.0%) | 0.50 |
| Hematochezia | 1 (0.0%) | 2 (0.0%) | >0.99 |
| Hematoma | 1 (0.0%) | 1 (0.0%) | >0.99 |
| Hemoptysis | 1 (0.0%) | 0 (0.0%) | 0.50 |
| Hemorrhagic Transformation Stroke | 1 (0.0%) | 0 (0.0%) | 0.50 |
| Hemothorax | 1 (0.0%) | 1 (0.0%) | >0.99 |
| Intra-Abdominal Hemorrhage | 1 (0.0%) | 0 (0.0%) | 0.50 |
| Large Intestinal Hemorrhage | 1 (0.0%) | 1 (0.0%) | >0.99 |
| Mallory-Weiss Syndrome | 1 (0.0%) | 0 (0.0%) | 0.50 |
| Menorrhagia | 1 (0.0%) | 0 (0.0%) | 0.50 |
| Pancreatitis Hemorrhagic | 1 (0.0%) | 0 (0.0%) | 0.50 |
| Peptic Ulcer Hemorrhage | 1 (0.0%) | 0 (0.0%) | 0.50 |
| Post Procedural Hematoma | 1 (0.0%) | 1 (0.0%) | >0.99 |
| Retinal Hemorrhage | 1 (0.0%) | 1 (0.0%) | >0.99 |
| Retroperitoneal Hemorrhage | 1 (0.0%) | 0 (0.0%) | 0.50 |
| Ulcer Hemorrhage | 1 (0.0%) | 0 (0.0%) | 0.50 |
| Urinary Bladder Hemorrhage | 1 (0.0%) | 1 (0.0%) | >0.99 |
| Hemarthrosis | 0 (0.0%) | 1 (0.0%) | >0.99 |
| Brain Contusion | 0 (0.0%) | 2 (0.0%) | 0.50 |
| Intracranial Hemorrhage | 0 (0.0%) | 1 (0.0%) | >0.99 |
| Immune Thrombocytopenic Purpura | 0 (0.0%) | 1 (0.0%) | >0.99 |
| Catheter Site Hemorrhage | 0 (0.0%) | 1 (0.0%) | >0.99 |
| Mouth Hemorrhage | 0 (0.0%) | 1 (0.0%) | >0.99 |
| Esophageal Hemorrhage | 0 (0.0%) | 1 (0.0%) | >0.99 |
| Cerebral Hemorrhage | 0 (0.0%) | 2 (0.0%) | 0.50 |
| Pericardial Hemorrhage | 0 (0.0%) | 1 (0.0%) | >0.99 |
| Post Procedural Hematuria | 0 (0.0%) | 1 (0.0%) | >0.99 |
| Renal Hemorrhage | 0 (0.0%) | 1 (0.0%) | >0.99 |
| Retroperitoneal Hematoma | 0 (0.0%) | 1 (0.0%) | >0.99 |
| Traumatic Intracranial Hemorrhage | 0 (0.0%) | 1 (0.0%) | >0.99 |

TABLE 26-continued

Assessment of Serious Bleeding Treatment-Emergent
Adverse Events by Category and by Preferred Term.

| | Icosapent Ethyl (N = 4089) | Placebo (N = 4090) | P-value[1] |
|---|---|---|---|
| Diverticulitis Intestinal Hemorrhagic | 0 (0.0%) | 1 (0.0%) | >0.99 |
| Hemorrhagic Duodenitis | 0 (0.0%) | 1 (0.0%) | >0.99 |

Note:
A treatment-emergent adverse event (TEAE) is defined as an event that first occurs or worsens in severity on or after the date of dispensing study drug and within 30 days after the completion or withdrawal from study. Percentages are based on the number of patients randomized to each treatment group in the Safety population (N). Events that were positively adjudicated as clinical endpoints are not included.
All adverse events are coded using the Medical Dictionary for Regulatory Activities (MedDRA Version 20.1).
[1]P value from Fisher's Exact test.
[2]Bleeding related events are identified using the Hemorrhage terms (excl laboratory terms), a Standard MedDRA Query (SMQ).
[3]Gastrointestinal (GI) related bleeding events are identified using the Gastrointestinal hemorrhage SMQ.
[4]Central nervous system (CNS) related bleeding events are identified using the Central Nervous System hemorrhages and cerebrovascular conditions SMQs.
[5]Other bleeding events are identified from the Hemorrhage terms (excluding laboratory terms) SMQ excluding GI bleeding and CNS bleeding.

Among the 8,179 patients (70.7% secondary prevention) followed for a median 4.9 years, the primary endpoint occurred in 17.2% of AMR101 patients versus 22.0% of placebo (HR, 0.75; 95% CI, 0.68-0.83; P<0.001) and the key secondary endpoint in 11.2% versus 14.8% (HR, 0.74; 95% CI, 0.65-0.83; P<0.001). Additional ischemic endpoints, assessed according to a prespecified hierarchical schema, were significantly reduced, including cardiovascular death (4.3% versus 5.2%; HR, 0.80; 95% CI, 0.66-0.98; P=0.03). Atrial fibrillation or flutter hospitalization was more common with the AMR101 patients than the placebo patients (3.1% versus 2.1%; P=0.004); serious bleeding occurred in 2.7% of the AMR101 patients versus 2.1% in the placebo patients (P=0.06). There were no significant differences between treatments in the overall rate of treatment emergent adverse events or serious adverse events leading to withdrawal of study drug as shown in Table 20. The only serious adverse event occurring at a frequency ≥2% was pneumonia at 2.6% in the AMR101 group versus 2.9% in the placebo group (P=0.42).

Conclusion

In this study, the risk of the primary composite endpoint of cardiovascular death, nonfatal myocardial infarction, nonfatal stroke, coronary revascularization, or unstable angina, assessed in a time-to-event analysis, was significantly lower, by 25%, among the patients who received 2 g of icosapent ethyl twice daily than among those who received placebo, corresponding to an absolute between-group difference of 4.8 percentage points in the rate of the endpoint and a number needed to treat of 21. The risk of the key secondary composite endpoint of cardiovascular death, nonfatal myocardial infarction, or nonfatal stroke in a time-to-event analysis was also significantly lower, by 26%, in patients who received 2 g of icosapent ethyl twice daily than among those who received placebo, corresponding to an absolute between-group difference of 3.6 percentage points in the rate of the endpoint and a number needed to treat of 28. Prespecified hierarchical testing of other secondary endpoints revealed that the risks of a variety of fatal and nonfatal ischemic events were lower in the AMR101 group than in the placebo group, including a 20% lower risk of cardiovascular death. The benefits were observed against a background of appropriate statin use among patients who had a median LDL cholesterol level of 75.0 mg/dL at baseline.

Overall adverse event rates were similar across treatment groups. There were numerically more serious adverse events related to bleeding, though overall rates were low, with no fatal bleeding observed in either group and no significant increase in adjudicated hemorrhagic stroke or serious central nervous system or gastrointestinal bleeding. There was a significantly higher rate of hospitalization for atrial fibrillation or flutter, though rates were low in those patients who received 2 g of icosapent ethyl twice daily. Adverse event and serious adverse event rates leading to study drug discontinuation were similar to placebo. The rates of adverse events and serious adverse events leading to discontinuation of trial drug were similar in the two groups.

The results from this study stand apart from the negative findings of several recent trials of other agents that also lower triglyceride levels, such as other omega-3 fatty acids, extended-release niacin, fenofibrate, and cholesteryl ester transfer protein-inhibitors. It is not known whether the lack of benefit of omega-3 fatty acids in previous trials might be attributable to the low dose or the low ratio of EPA to DHA. Both the formulation (a highly purified and stable EPA acid ethyl ester) and dose (4 grams daily) used in this study are different from all prior omega-3 outcome trials. Despite utilizing a standard PROBE design limitation of those previous trials included an open label design without placebo, use of a low-intensity statin, and conducted in a single country; in contrast to the present report, patients in those trials had higher baseline LDL-C levels (182 mg/dL prior to statin initiation) and lower triglyceride values (151 mg/dL). In contrast, the present study provides robust, multinational data showing significant reductions in ischemic events with administration of icosapent ethyl in patients with well-controlled LDL-C. Metabolic data support that icosapent ethyl does not raise LDL cholesterol levels, which DHA containing formulations do.

A triglyceride level ≥150 mg/dL was required for inclusion in this study however, owing to initial allowance for variability in these levels and differences between qualifying and randomization measurements, 10.3% of enrolled patients had triglycerides less than 150 mg/dL on study entry. Cardiovascular benefits appeared similar across baseline levels of triglycerides (e.g., 135-149, 150 to 199, and 200 mg/dL or greater). Additionally, the robust reduction in major adverse cardiovascular events with administration of icosapent ethyl appeared to occur irrespective of an achieved triglyceride level above or below 150 mg/dL at one year, suggesting that the cardiovascular risk reduction was not tied to achieving a more normal (i.e., <150 mg/dL) triglyceride level. These observations suggest that at least some of the impact of icosapent ethyl on the reduction in ischemic events may be explained by metabolic effects other than triglyceride lowering.

Mechanisms responsible for the benefit in the present study are currently not known. The timing of divergence of the Kaplan-Meier event curves suggests a delayed onset to benefit, which may reflect the time to benefit from triglyceride reduction or other mechanisms. The modestly higher rate of bleeding suggests that there might be an anti-thrombotic mechanism of action. However, it is unlikely that an anti-thrombotic effect would reduce elective revascularization. Also, if the full explanation were an antiplatelet or anticoagulant effect, one might expect a large increase in major bleeding, which was not seen. Potentially, membrane-stabilizing effects could explain part of the benefit. Stabilization and/or regression of coronary plaque may also play a part. The observation in the present study of a lower rate of sudden cardiac death might support that mechanism, though this finding should be viewed as exploratory. It is also possible that the 40% reduction in hsCRP observed in patients from this trial may contribute to benefit. Samples (e.g., serum and plasma) from patients who participated in this trial have been banked for biomarker and genetic analyses, which may provide more information regarding mechanisms of action.

Regarding higher rates of diarrhea in the mineral oil placebo group, a post hoc analysis excluding patients with diarrhea still resulted in a significant risk reduction of 25% in the primary endpoint. Also, there were no differences in the primary or key secondary endpoints for placebo patients with an increase in LDL-C compared to those with no change or a decrease in LDL-C.

In conclusion, AMR101 4 grams daily demonstrated similar overall adverse event rates as placebo, and reduced important ischemic events, including cardiovascular death, in statin-treated patients with elevated triglycerides. Compared with placebo, icosapent ethyl 4 g per day significantly reduced cardiovascular events by 25% including: a 31% reduction in heart attack, 28% reduction in stroke, 31% reduction in myocardial infarction, and a 20% reduction in death due to cardiovascular events.

The following are key conclusions obtained from this trial that indicate a very favorable risk-benefit profile (1) significant reduction in primary endpoint with a RRR of 24.8%, ARR of 4.8%, NNT of 21, and a p-value of 0.00000001, (2) significant reduction in key secondary endpoint with a RRR of 26.5%, ARR of 3.6%, NNT of 28, and a p-value of 0.0000062, (3) consistent results across subgroups to include triglycerides and secondary and primary prevention, (4) consistent results across hierarchical secondary endpoints to include cardiovascular death, (5) consistent results across recurrent events, and (6) safety with a small but insignificant increase in atrial fibrillation/flutter with low event rates and non-significant increase in serious bleeding with low event rates.

Example 2: The Impact of Icosapent Ethyl on Recurrent Events and Total Ischemic Events in Statin-Treated Patients Despite statin therapy, patients with established cardiovascular disease or diabetes remain at high risk for, not only first but also, recurrent ischemic events. The study results described in Example 1 demonstrated that icosapent ethyl reduces the first occurrence of the composite of cardiovascular death, nonfatal myocardial infarction, nonfatal stroke, coronary revascularization, or unstable angina, with a 25% relative risk reduction and a 4.8% absolute risk reduction. The time to first occurrence of the composite of cardiovascular death, nonfatal myocardial infarction, and nonfatal stroke was also reduced with icosapent ethyl, with a 26% relative risk reduction and a 3.6% absolute risk reduction.

The objective of the following study was to assess the impact of icosapent ethyl on recurrent events and total ischemic events. With a greater number of events, it was contemplated that there might be sufficient statistical power to examine the effect of icosapent ethyl in the two separate cardiovascular risk strata in the trial: patients with established atherosclerosis or patients with diabetes plus at least one other cardiovascular risk factor. Accordingly, the goal of the following study was to determine if icosapent ethyl administered at 4 g per day (e.g., 2 g twice daily) reduces total major adverse cardiovascular events in patients with fasting triglycerides ≥150 and <500 mg/dL and LDL-cholesterol >40 and ≤100 mg/dL who are at increased cardiovascular risk despite statin therapy.

Study Design

Figure 12:
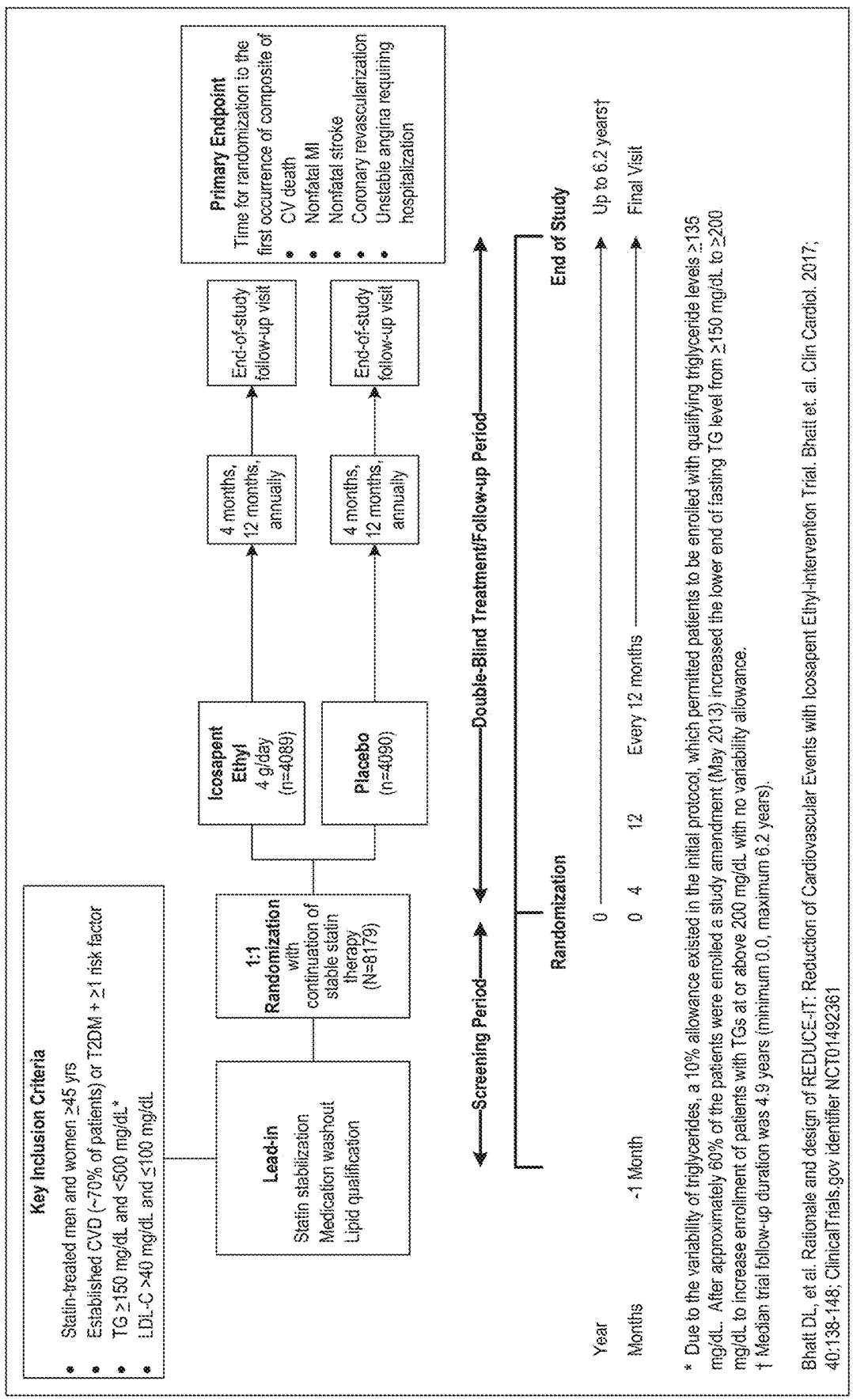
FIG. 12 is a schematic of the study design according to an embodiment of the present disclosure.

The following study was a multi-center, placebo-controlled clinical trial the details of which are described above in Example 1, the REDUCE-IT design. As shown in FIG. 12, patients were randomized in a double-blind manner to icosapent ethyl 4 g/day (2 grams twice daily with food) versus placebo. Randomization was stratified by cardiovascular risk cohort (i.e., secondary or primary prevention), use of ezetimibe, and by geographic region.

Study Population

The study participants included patients with a history of atherosclerosis or diabetes who were on statins and had fasting triglycerides ≥150 and <500 mg/dL and LDL-cholesterol >40 and ≤100 mg/dL. Of the study participants, 71% of the patients had a history of atherosclerosis and 29% had a history of diabetes. In order to be eligible for the trial, patients had to be ≥45 years of age with either established cardiovascular disease (i.e., secondary prevention stratum) or ≥50 years old with type 2 or type 1 diabetes mellitus requiring treatment with medication and at least one additional risk factor (i.e., primary prevention stratum).

The secondary prevention stratum consisted of patients with documented coronary artery disease (≥50% stenosis in at least two major epicardial coronary arteries with or without prior revascularization; prior MI; hospitalization for non-ST-segment elevation acute coronary syndrome with ST-segment deviation or positive biomarkers); documented cerebrovascular disease (prior ischemic stroke; symptomatic ≥50% carotid stenosis; asymptomatic carotid disease with ≥70% stenosis; history of carotid revascularization); or documented peripheral artery disease (ankle-brachial index <0.9 with symptoms of intermittent claudication; history of aorto-iliac or peripheral surgery or intervention).

The primary prevention stratum consisted of patients with no documented cardiovascular disease as defined above, with diabetes, and with at least one of the following cardiovascular risk factors: men ≥55 years of age or women ≥65 years of age; cigarette smoker or stopped smoking within 3 months before first visit; blood pressure ≥140 mmHg systolic or ≥90 mmHg diastolic or on antihypertensive medication; HDL-cholesterol ≤40 mg/dL for men or ≤50 mg/dL for women; hsCRP>3 mg/L; creatinine clearance >30 and <60 mL/min; non-proliferative retinopathy, pre-proliferative retinopathy, proliferative retinopathy, maculopathy, advanced diabetic eye disease or a history of photocoagulation; micro- or macro-albuminuria; or asymptomatic ankle-brachial index <0.9.

The participants were required to have fasting triglycerides between ≥150 mg/dL and <500 mg/dL and LDL-cholesterol >40 mg/dL and ≤100 mg/dL. In the initial version of the clinical trial protocol, a 10% allowance in qualifying triglyceride levels was allowed, and therefore patients with triglycerides ≥135 mg/dL were randomized. The study included 841 (10.3%) patients with baseline triglyceride levels <150 mg/dL. After approximately 60% of the patients were enrolled, an amendment changed the lower limit of allowed triglyceride levels to 200 mg/dL with no variability allowance. Patients were required to be on stable statin therapy for at least four weeks.

Exclusion criteria for the study participants included severe heart failure or liver disease, hemoglobin A1c levels >10.0%, planned coronary intervention, familial lipoprotein lipase deficiency, intolerance or hypersensitivity to statins, history of acute or chronic pancreatitis, and hypersensitivity to fish, shellfish, or ingredients of icosapent ethyl or placebo.

Main Outcomes and Measures

The primary outcome for the study was total recurrent events consisting of the composite of cardiovascular death, nonfatal myocardial infarction, nonfatal stroke, coronary revascularization, or hospitalization for unstable angina. Recurrent event analyses were also performed for the key secondary endpoint, a composite of cardiovascular death, non-fatal myocardial infarction, or non-fatal stroke. For each of these composite endpoints, the effects of icosapent ethyl in the secondary and primary prevention strata were examined separately.

Statistical Considerations

Demographic and baseline disease characteristics are presented using frequencies and percentages for categorical variables and medians with interquartile ranges for continuous variables. Between treatment group comparisons were derived using the chi-square test for categorical variables and Wilcoxon rank test for continuous variables. All clinical endpoint events used in the efficacy analyses were adjudicated by an independent Clinical Endpoint Committee (CEC) who were blinded to the treatment assignment. Since the primary efficacy endpoint was the time from randomization to the first occurrence of any component of the composite endpoint, and recurrence of such events within each patient is possible, a pre-specified analysis using a Cox proportional-hazard with the counting-process formulation of Andersen and Gill was performed to model the first and all recurrent cardiovascular events. Hazard ratios (HR) and corresponding 95% confidence intervals (CI) are reported from this model. In addition, as a marginal model and an extension of survival models based on the Cox proportional hazard model, the modified Wei-Lin-Weissfeld (WLW) method for analysis of recurrent events in the presence of deaths was carried out as a supportive analysis. In addition, as pre-specified, a recurrent event analysis using the Andersen-Gill and Wei-Lin-Weissfeld methods were carried out for the individual primary event components other than CV death. Though not pre-specified, additional recurrent event analyses were performed for the key secondary endpoint, which is a composite of CV death, non-fatal MI, or non-fatal stroke, and for the primary endpoint and the key secondary endpoint in the primary and secondary prevention strata to explore further the consistency of clinical benefit of icosapent ethyl. In subgroup analyses of the two cardiovascular risk strata (i.e., primary and secondary prevention), site-level discrepancies in cardiovascular risk group assignment occurring at entry and detected during the study (1.8%) were adjusted to conform with documented medical history data prior to randomization. All efficacy analyses were performed according to the intention-to-treat principle. All tests were based on a 2-sided nominal significance level of 5% with no adjustments for multiple comparisons.

Results

Baseline Characteristics

A total of 8,179 patients were randomized and followed for a median of 4.9 years. The patients were well matched in the icosapent ethyl and placebo groups as shown in Table 16 (See Example 1). The secondary and primary prevention according to the adjusted stratification for this study are shown in Table 26.

TABLE 26

Secondary and Primary Prevent Per Adjusted Stratification for Patients Randomized to Placebo or Icosapent Ethyl.

| Stratification Factors | Icosapent ethyl (N = 4089) | Placebo (N = 4090) | p-value [1] |
|---|---|---|---|
| Secondary Prevention per Adjusted Stratification | 2933 (71.7%) | 2920 (71.4%) | 0.7367 |
| Primary Prevention per Adjusted Stratification | 1156 (28.3%) | 1170 (28.6%) | |

[1] P-value is from a Wilcoxon rank-sum test for continuous variables and a chi-square test for categorical variables.

At baseline, the patient's median triglyceride levels were 216 mg/dL and median LDL-C levels were 75 mg/dL. Additional baseline characteristics of the patients with no events, a single event, and multiple recurrent events are shown in Table 27.

TABLE 27

Baseline Characteristics of Patients with No Events, a Single Event, or Multiple Events.
Baseline Characteristics in Patients with No Events, a Single Event, or Multiple Events

| | No Events (N = 6573) | 1 Event (N = 844) | Multiple Events (N = 762) | p-value [1] |
|---|---|---|---|---|
| Demographics | | | | |
| Age (years), Median (Q1-Q3) | 63.0 (57.0-69.0) | 65.0 (59.0-71.0) | 64.0 (58.0-70.0) | <.0001 |
| Age ≥65 years, n(%) | 2939 (44.7%) | 456 (54.0%) | 368 (48.3%) | <.0001 |
| Male, n(%) | 4556 (69.3%) | 661 (78.3%) | 605 (79.4%) | <.0001 |
| White, n(%)[2] | 5921 (90.1%) | 765 (90.6%) | 693 (90.9%) | 0.6908 |

TABLE 27-continued

Baseline Characteristics of Patients with No Events, a Single Event, or Multiple Events.
Baseline Characteristics in Patients with No Events, a Single Event, or Multiple Events

|  | No Events (N = 6573) | 1 Event (N = 844) | Multiple Events (N = 762) | p-value [1] |
|---|---|---|---|---|
| BMI (kg/m$^2$), Median (Q1-Q3) | 30.8 (27.8-34.6) | 31.1 (27.8-34.7) | 30.8 (28.0-34.2) | 0.5124 |
| BMI ≥30, n(%)[3] | 3762 (57.2%) | 499 (59.1%) | 432 (56.7%) | 0.7771 |
| *Stratification Factors* | | | | |
| Geographic Region, n(%) | | | | <.0001 |
| Westernized [4] | 4547 (69.2%) | 639 (75.7%) | 625 (82.0%) | |
| Eastern Europe [5] | 1796 (27.3%) | 185 (21.9%) | 125 (16.4%) | |
| Asia Pacific [6] | 230 (3.5%) | 20 (2.4%) | 12 (1.6%) | |
| CV Risk Category as Randomized, n(%) | | | | <.0001 |
| Secondary Prevention per Randomization | 4488 (68.3%) | 640 (75.8%) | 657 (86.2%) | |
| Primary Prevention per Randomization | 2085 (31.7%) | 204 (24.2%) | 105 (13.8%) | |
| CV Risk Category Actual, n(%) | | | | <.0001 |
| Secondary Prevention per Adjusted Stratification | 4537 (69.0%) | 652 (77.3%) | 664 (87.1%) | |
| Primary Prevention per Adjusted Stratification | 2036 (31.0%) | 192 (22.7%) | 98 (12.9%) | |
| Ezetimibe Use, n(%) | 401 (6.1%) | 59 (7.0%) | 64 (8.4%) | 0.0378 |
| *Statin Intensity and Diabetes Status* | | | | |
| Statin Intensity, n(%) | | | | 0.0819 |
| Low | 428 (6.5%) | 49 (5.8%) | 44 (5.8%) | |
| Moderate | 4141 (63.0%) | 519 (61.5%) | 448 (58.8%) | |
| High | 1974 (30.0%) | 274 (32.5%) | 268 (35.2%) | |
| Missing | 30 (0.5%) | 2 (0.2%) | 2 (0.3%) | |
| Diabetes, n(%) | | | | 0.5535 |
| Type I Diabetes | 44 (0.7%) | 5 (0.6%) | 8 (1.0%) | |
| Type II Diabetes | 3773 (57.4%) | 511 (60.5%) | 445 (58.4%) | |
| Both Type I and Type II Diabetes | 1 (0.0%) | 0 | 0 | |
| No Diabetes at Baseline | 2752 (41.9%) | 328 (38.9%) | 309 (40.6%) | |
| Missing | 3 (0.0%) | 0 | 0 | |
| *Laboratory Measurements* | | | | |
| hsCRP (mg/L), Median (Q1-Q3) | 2.1 (1.1-4.4) | 2.4 (1.2-5.3) | 2.4 (1.2-4.6) | 0.0004 |
| Triglycerides (mg/dL), Median (Q1-Q3) | 215.5 (176.0-272.0) | 215.5 (175.0-270.3) | 223.0 (178.5-285.5) | 0.0539 |
| HDL-C (mg/dL), Median (Q1-Q3) | 40.0 (35.0-46.0) | 39.5 (34.4-45.5) | 38.8 (33.5-44.5) | <.0001 |
| LDL-C (mg/dL), Median (Q1-Q3) | 75.0 (62.0-89.0) | 75.0 (63.0-88.0) | 75.0 (63.0-89.0) | 0.9903 |
| Triglycerides Category | | | | 0.3523 |
| <150 mg/dL | 686 (10.4%) | 79 (9.4%) | 76 (10.0%) | |
| 150 to <200 mg/dL | 1922 (29.2%) | 259 (30.7%) | 203 (26.6%) | |
| ≥200 mg/dL | 3961 (60.3%) | 506 (60.0%) | 483 (63.4%) | |
| Triglycerides ≥200 mg/dL and HDL-C ≤35 mg/dL | 1254 (19.1%) | 173 (20.5%) | 190 (24.9%) | 0.0005 |
| EPA (μg/mL), Median (Q1-Q3) | 26.2 (17.2-40.3) | 24.6 (15.9-36.7) | 26.9 (17.7-40.2) | 0.0141 |

In general, the baseline value is defined as the last non-missing measurement obtained prior to the randomization.

The baseline LDL-C value obtained via preparative ultracentrifugation was used, unless this value was missing. If the LDL-C preparative ultracentrifugation value was missing, then another LDL-C value was be used, with prioritization of values obtained from LDL-C Direct measurements, followed by LDL-C derived by the Friedewald calculation (only for subjects with TG <400 mg/dL), and finally LDL-C derived using the calculation published by Johns Hopkins University investigators.

For all other lipid and lipoprotein marker parameters, wherever possible, baseline was derived as the arithmetic mean of the Visit 2 (Day 0) value and the preceding Visit 1 (or Visit 1.1) value. If only one of these values was available, the single available value was used as baseline.

[1] P-value is from a Wilcoxon rank-sum test for continuous variables and a chi-square test for categorical variables.
[2] Race as reported by the investigators.
[3] Percentages are based on the number of randomized subjects.
[4] Westernized region includes Australia, Canada, Netherlands, New Zealand, United States, and South Africa.
[5] Eastern European region includes Poland, Romania, Russian Federation, and Ukraine.
[6] Asia Pacific region includes India.

Figure 13:
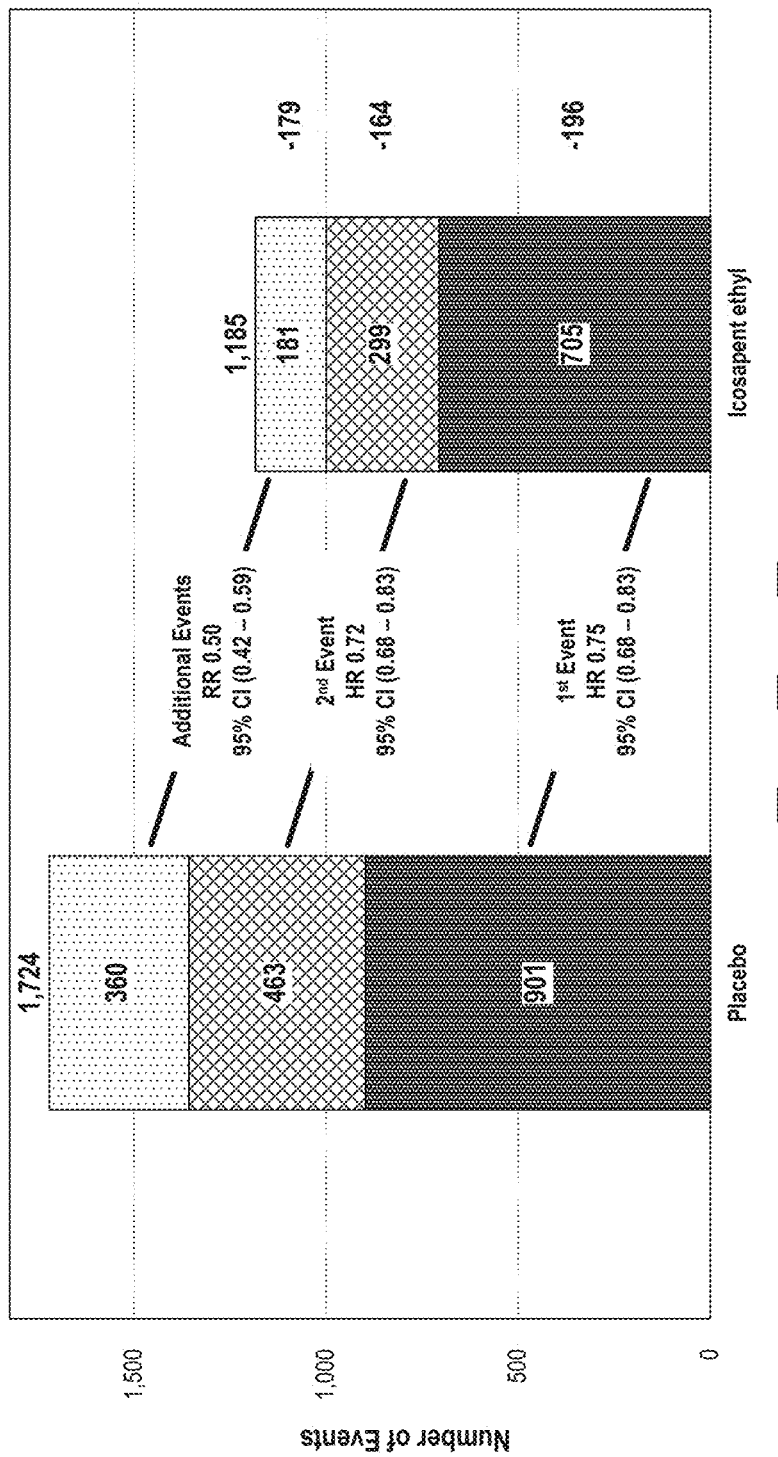
FIG. 13 is a representative bar graph depicting the distribution of first, second, and recurrent ischemic events in patients.
Figure 14:
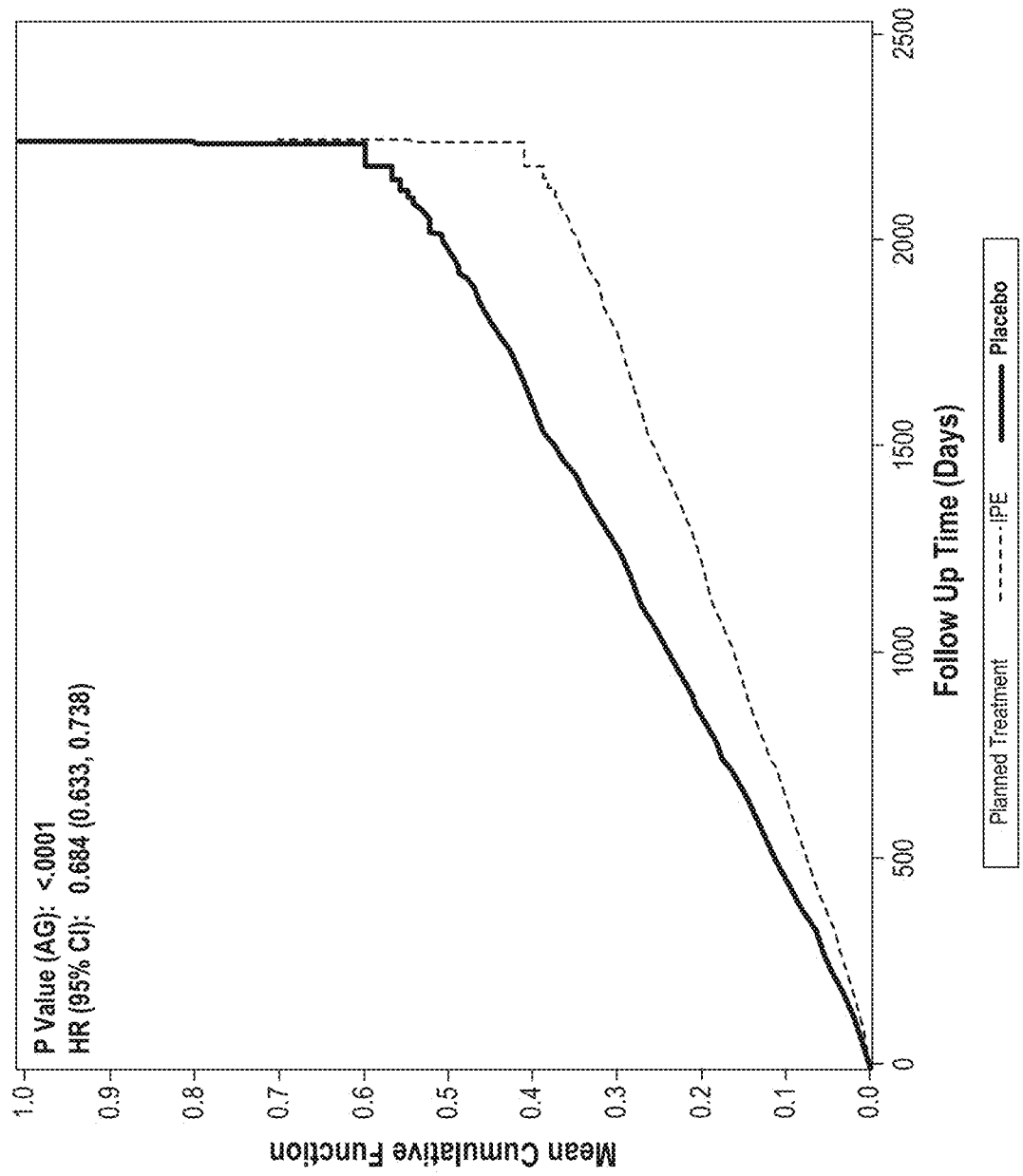
FIG. 14 is a representative overall cumulative event Kaplan-Meier event curve for the primary endpoint indicating that overall cumulative primary endpoints were reduced in patients randomized to icosapent ethyl.
Figure 15:
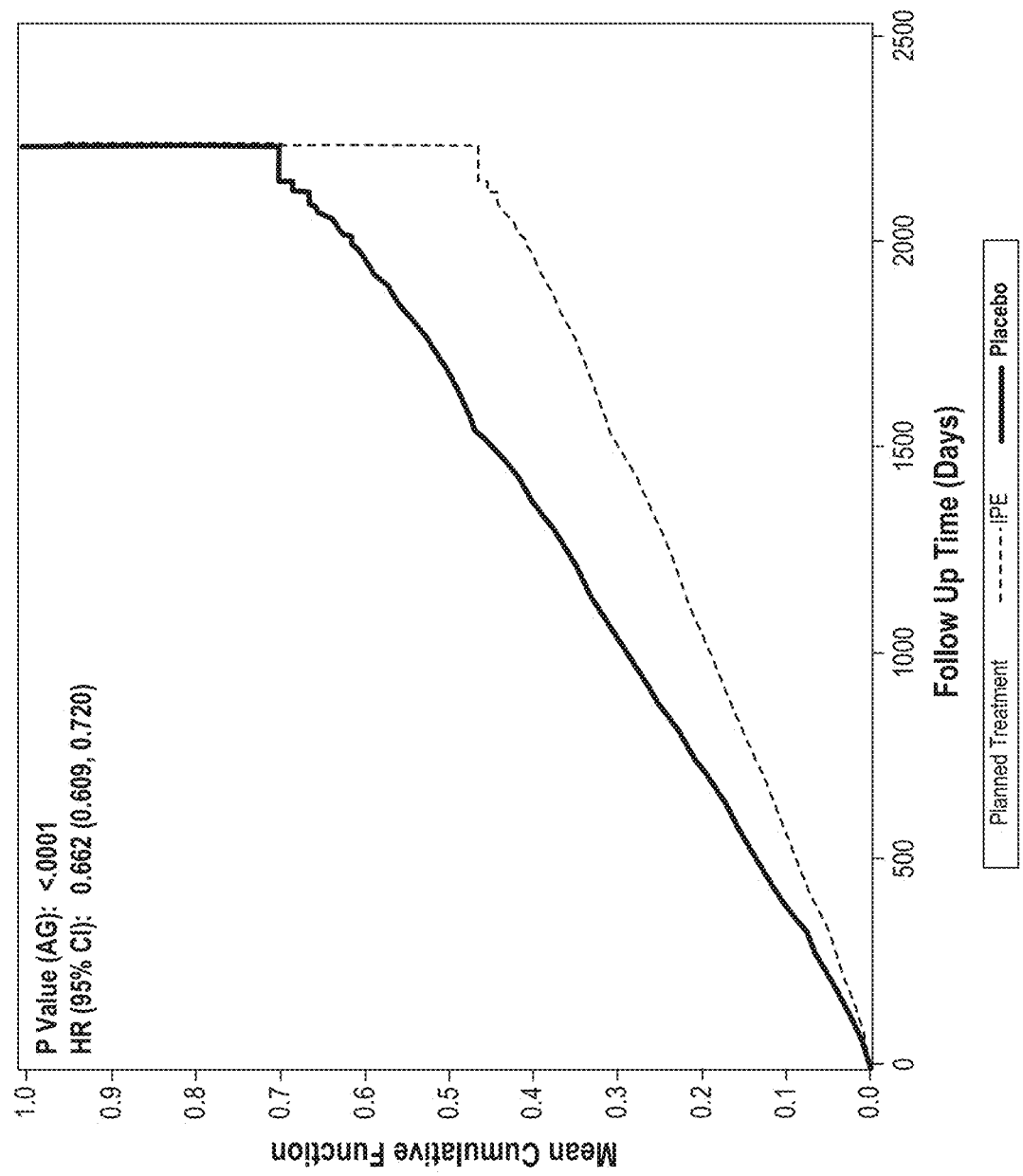
FIG. 15 is a representative cumulative event Kaplan-Meier event curve for the primary endpoint for patients in the secondary prevention cohort, which, similar to FIG. 14, indicates that cumulative primary endpoints were also reduced in patients in the secondary prevention cohort randomized to icosapent ethyl.
Figure 16:
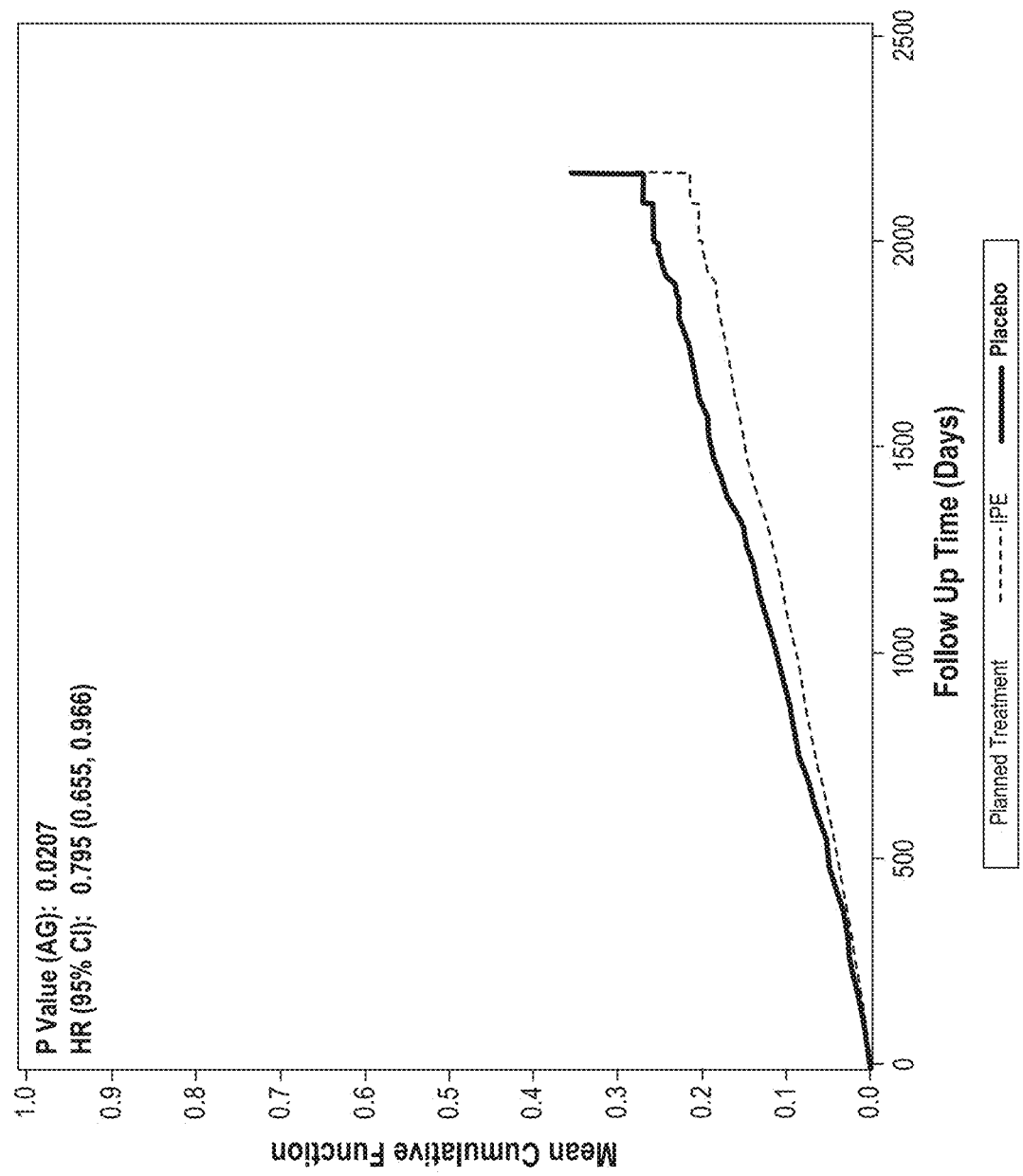
FIG. 16 is a representative cumulative event Kaplan-Meier event curve for the primary endpoint for patients in the primary prevention cohort, which, similar to FIGS. 14 and 15, indicates that cumulative primary endpoints were also reduced in patients in the primary prevention cohort randomized to icosapent ethyl.

Total Events for Primary Efficacy Endpoint: The total events for the primary efficacy endpoint showed that of 8,179 patients, there were 1,606 (i.e., 55.2% of the endpoints) first primary endpoints and 1,303 (i.e., 44.8% of the endpoints) additional primary endpoints, for a total of 2,909 endpoint events among the 1,606 patients. There were 762 second events, 272 third events, and 269 fourth or more events. FIG. 13 shows a distribution of first and recurrent events in the patients randomized to icosapent ethyl or placebo before and after the trial. In the overall trial, total primary endpoints were reduced from 1,724 to 1,185 (HR 0.68, 95% CI 0.63-0.74, P<0.0001) with icosapent ethyl as shown in FIG. 13. Within the primary endpoint reductions, first events were reduced from 901 to 705 (i.e., a total reduction of 196), second events were reduced from 463 to 299 (i.e., a total reduction of 164), and additional endpoints were reduced from 360 to 131 (i.e., a total reduction of 179) with icosapent ethyl (See FIG. 13). Using the Wei-Lin-Weissfeld model, the first occurrence of a primary composite endpoint was reduced with icosapent ethyl versus placebo (HR 0.75, 95% CI 0.68-0.83, P<0.0001) as was the second occurrence (HR 0.72, 95% CI 0.62-0.83, P<0.0001). FIGS. 14-16 depict the overall cumulative event curves from the primary endpoint of cardiovascular death, nonfatal myocardial infarction, nonfatal stroke, coronary revascularization, and unstable angina. The overall cumulative events are shown in FIG. 14, the secondary prevention stratum events are shown in FIG. 15, and the primary prevention stratum events are shown in FIG. 16.

Figure 17:
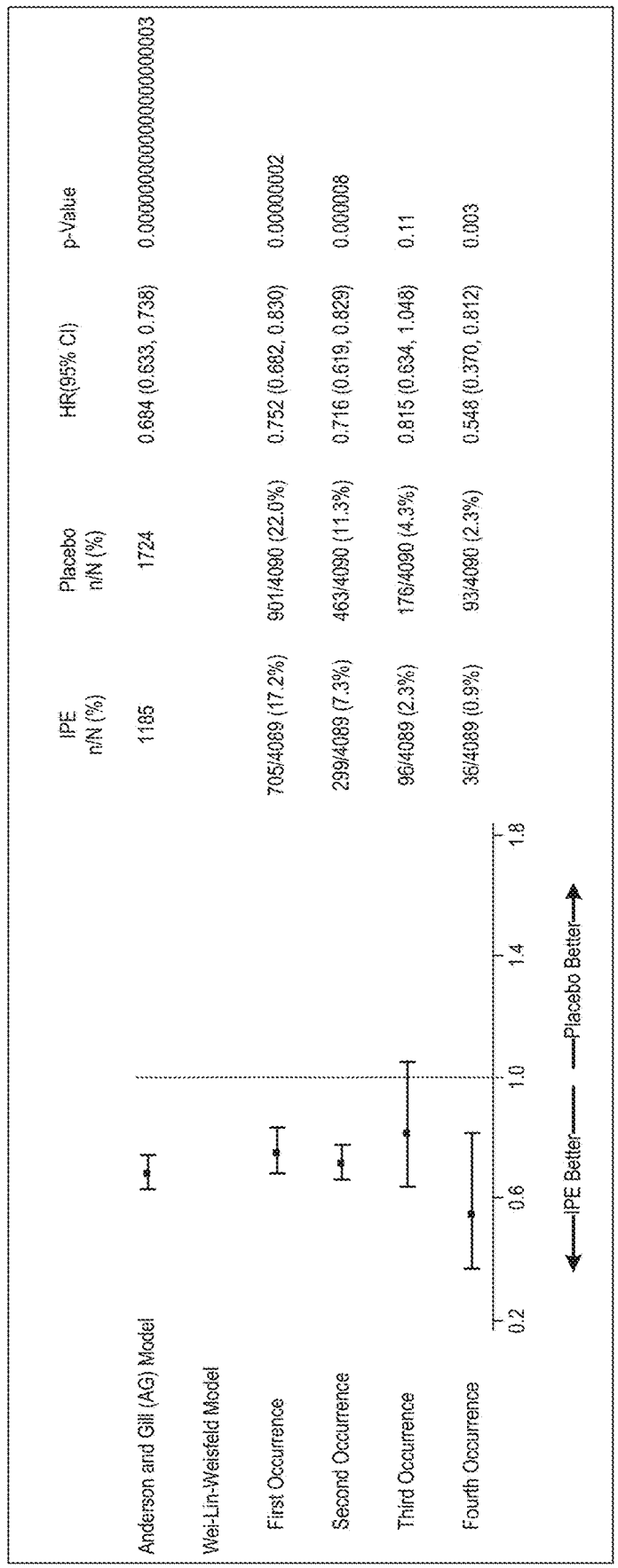
FIG. 17 is a representative forest plot of the total event for each occurrence of the primary endpoint.
Figure 18:
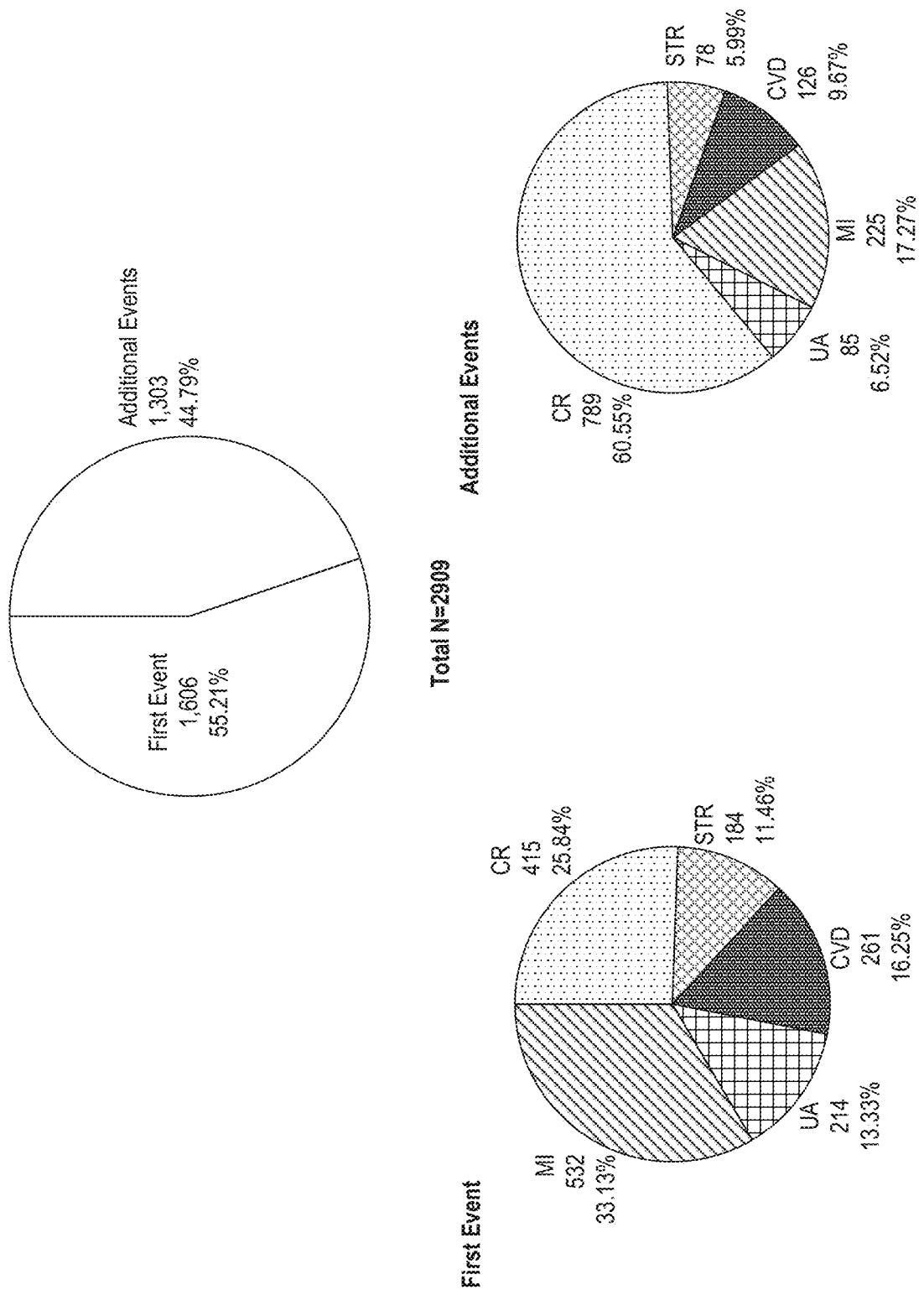
FIG. 18 includes representative pie charts for the proportion of first and subsequent primary endpoint events, overall and by component.
Figure 19:
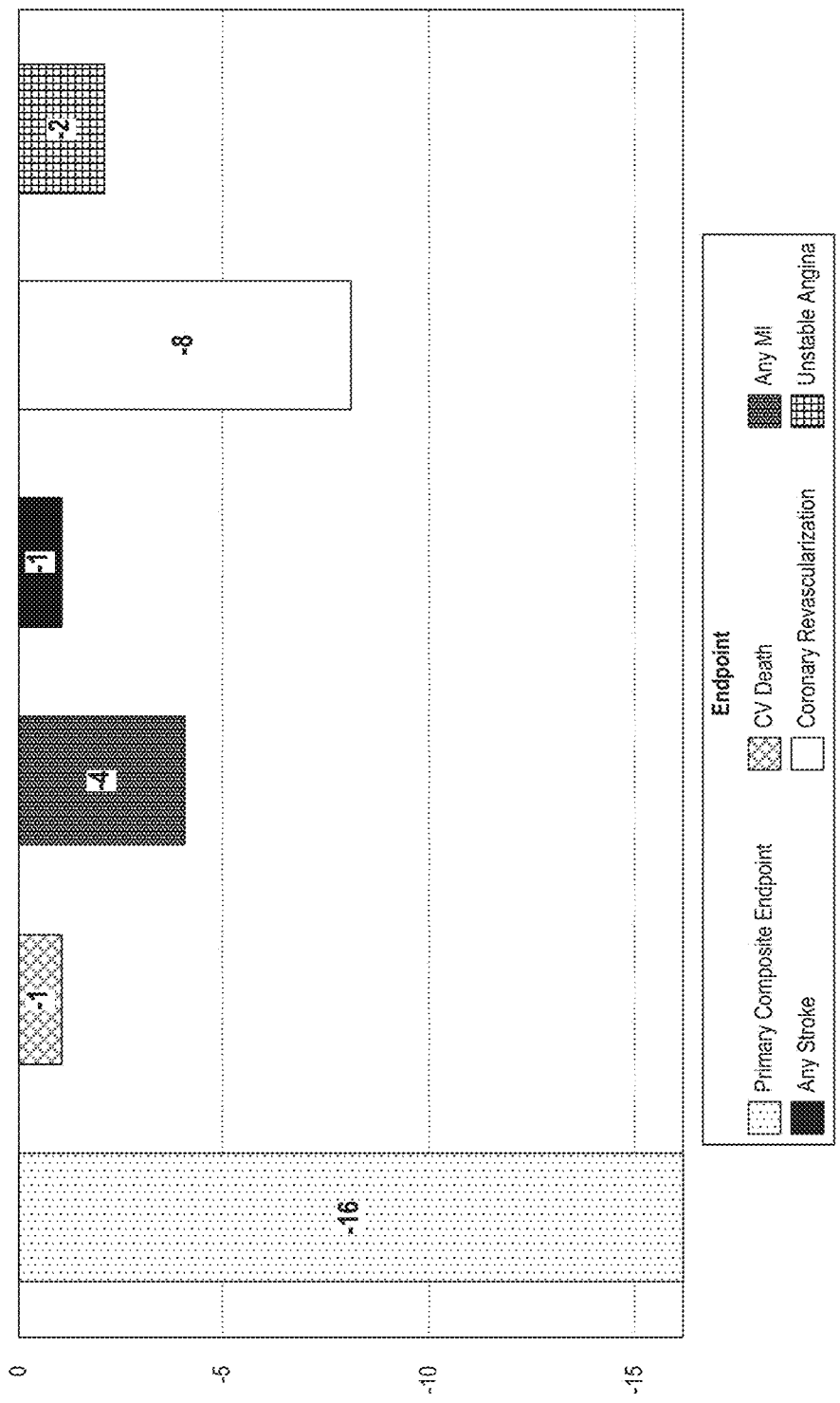
FIG. 19 is a representative graph depicting the risk difference in 100 patients treated for five years with icosapent ethyl versus placebo of the composite primary endpoint.

The total events for each occurrence of the primary endpoint, inclusive of the first and all subsequent occurrences of primary endpoints components (i.e., cardiovascular death, nonfatal myocardial in fraction, nonfatal stroke, coronary revascularization, and unstable angina) are shown in FIG. 17. Importantly, FIG. 17 shows that the times to first occurrence, second occurrence, third occurrence or fourth occurrence of the primary composite endpoint were consistently reduced in the icosapent ethyl group as compared to the placebo control group. The proportions of first and subsequent primary endpoint events, overall and by component, are depicted in FIG. 18. The risk differences for every 100 patients treated for five years with icosapent ethyl vs placebo control for the components of the composite primary endpoint are shown in FIG. 19.

Figure 20:
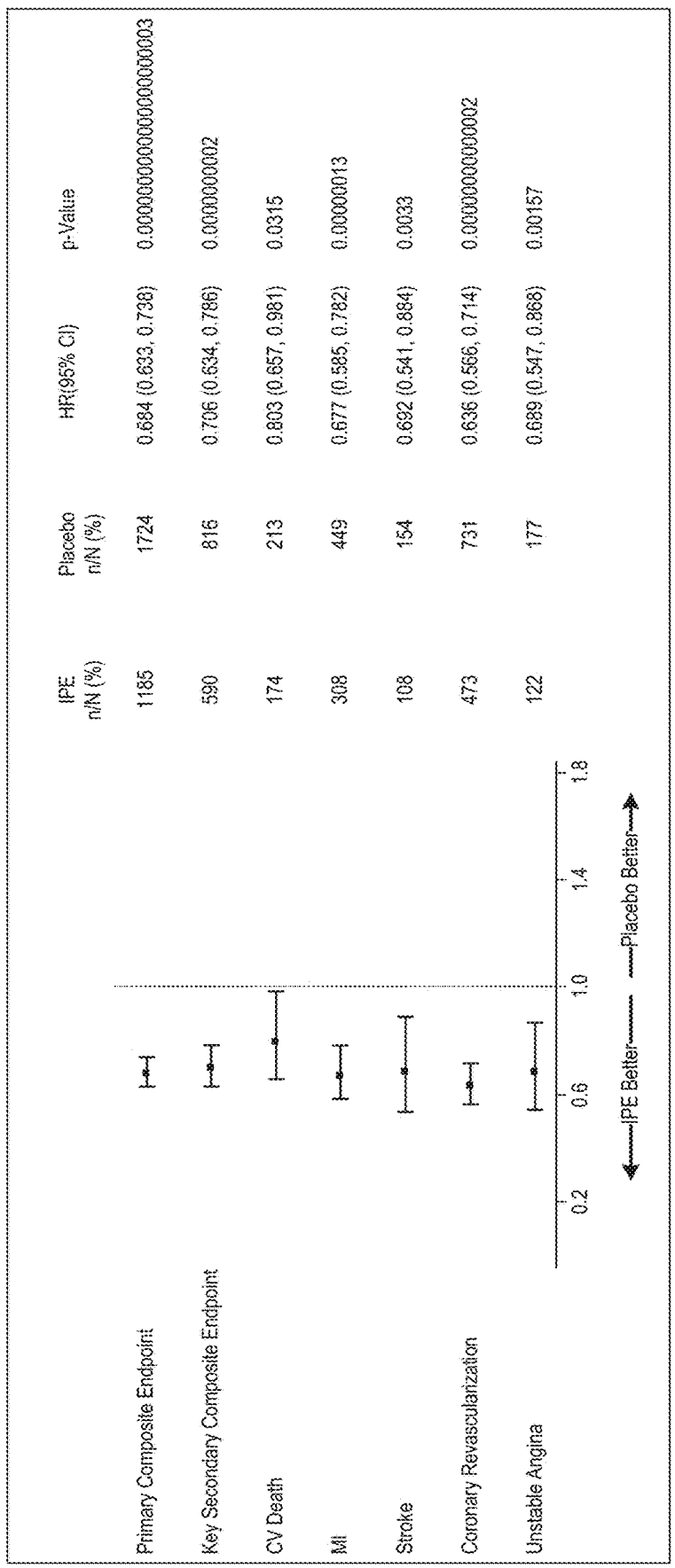
FIG. 20 is a representative forest plot of the total event for each occurrence of the primary and key secondary efficacy endpoints.

The total events for each component of the primary and key secondary efficacy endpoints inclusive of the first and all subsequent occurrences of the primary and key secondary endpoints components (i.e., cardiovascular death, nonfatal myocardial in fraction, nonfatal stroke, coronary revascularization, and unstable angina) and key secondary endpoint components (i.e., nonfatal myocardial infarction, nonfatal stroke, and cardiovascular death) are shown in FIG. 20. Importantly, FIG. 20 shows that total events for each component of the primary endpoint were also significantly reduced. In the secondary prevention stratum, total primary endpoint events were reduced from 1,468 to 988 (HR 0.66, 95% CI 0.61-0.72, P<0.0001), and in the primary prevention stratum, from 256 to 197 (HR 0.79, 95% CI 0.65-0.96, P=0.018; $P_{interaction}$=0.098). Without adjusting for stratification differences, total primary endpoint events in the secondary prevention stratum were reduced from 1,461 to 964 (HR 0.65, 95% CI 0.60-0.71, P<0.0001) and from 263 to 221 (HR 0.86, 95% CI 0.71-1.03, P=0.105) in the primary prevention stratum; $P_{interaction}$=0.009.

Figure 21:
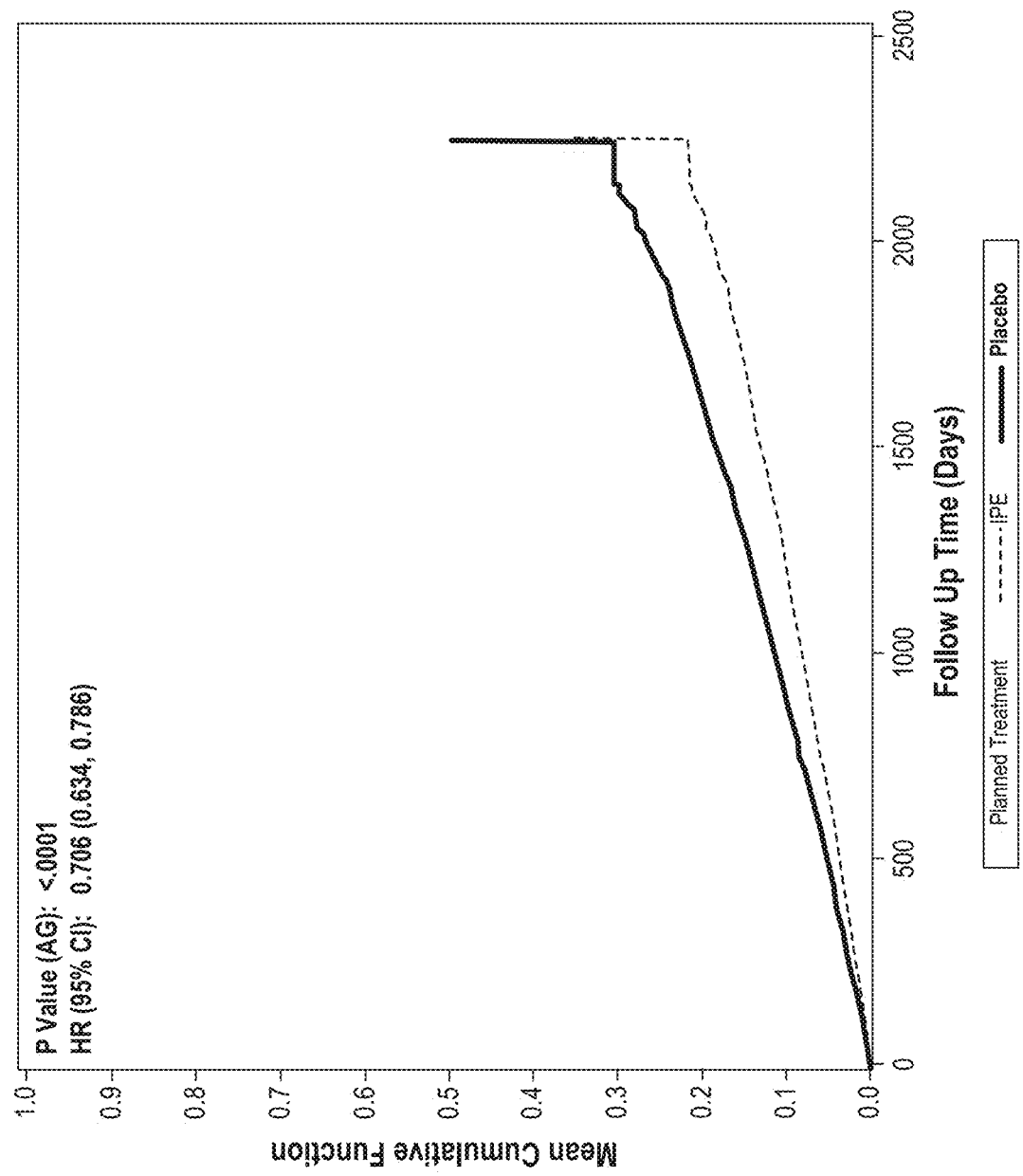
FIG. 21 is a representative overall cumulative event Kaplan-Meier curve for the key secondary endpoint indicating that overall cumulative key secondary endpoints were reduced in patients randomized to icosapent ethyl.
Figure 22:
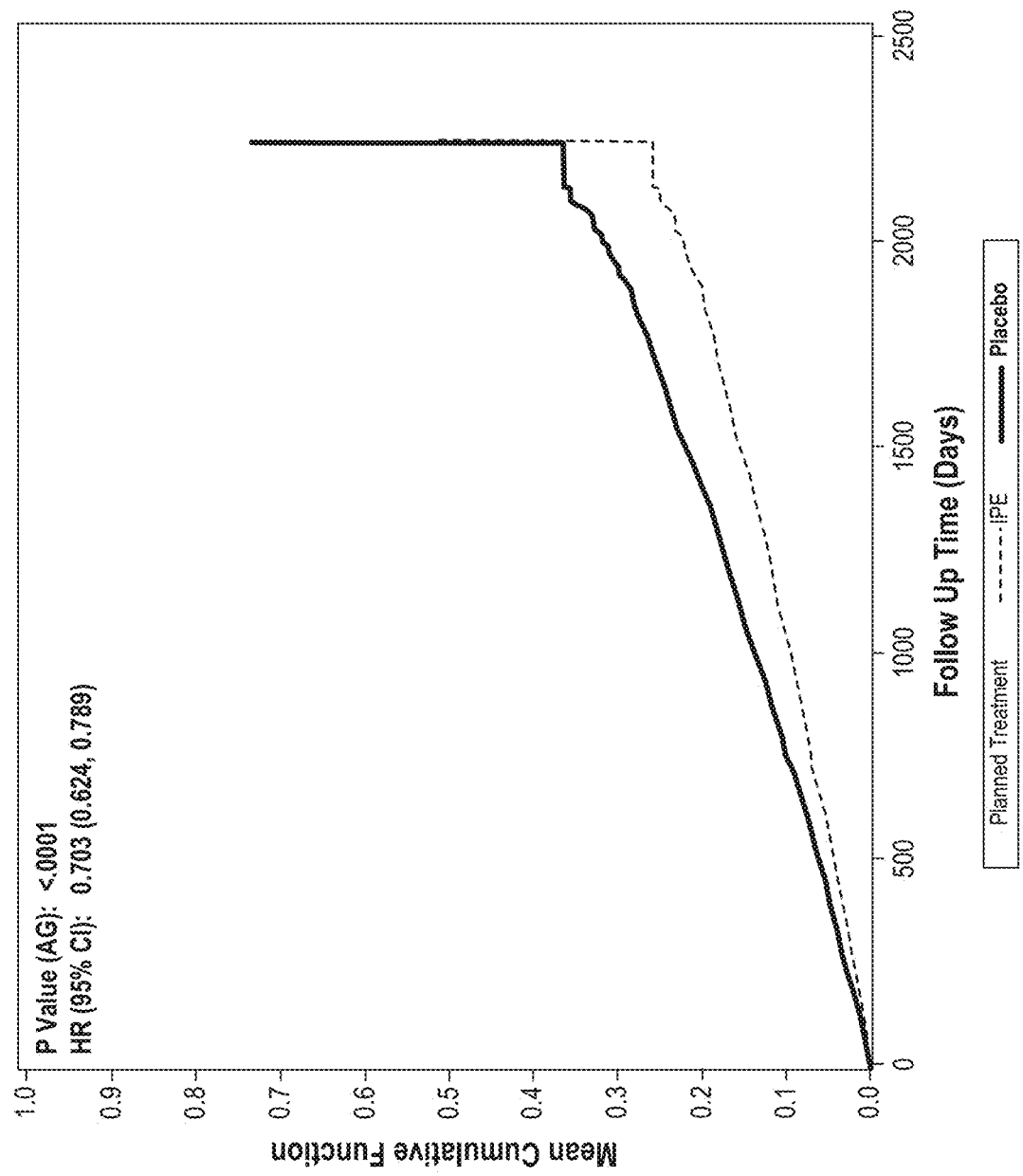
FIG. 22 is a representative cumulative event Kaplan-Meier event curve for the key secondary endpoint for patients in the secondary prevention cohort, which similar to FIG. 21 indicates that cumulative key secondary endpoints were also reduced in patients in the secondary prevention cohort randomized to icosapent ethyl.
Figure 23:
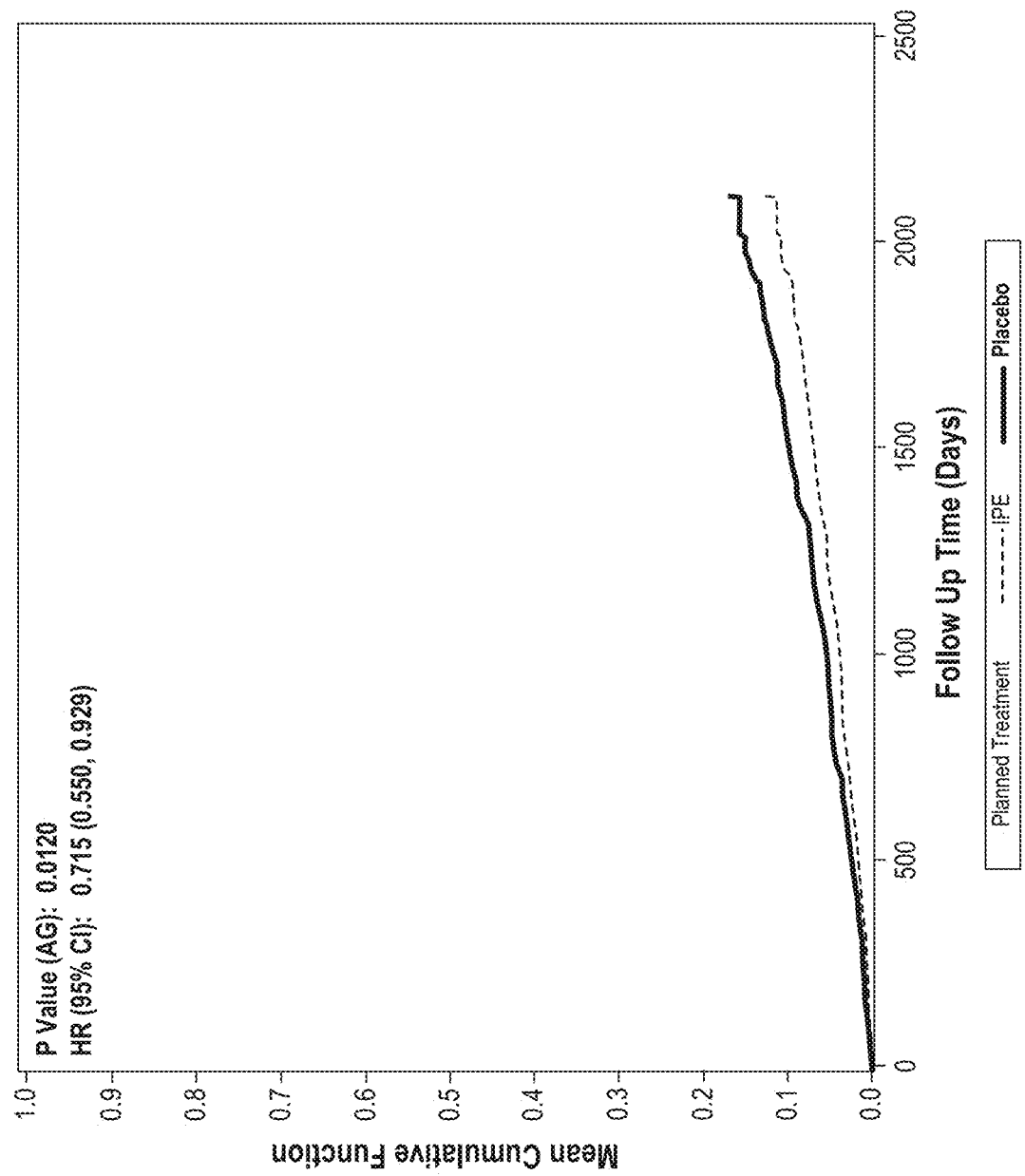
FIG. 23 is representative cumulative event Kaplan-Meier curve for the key secondary endpoint for patients in the primary prevention cohort, which, similar to FIGS. 21 and 22, indicates that cumulative secondary endpoints were also reduced in patients in the primary prevention cohort randomized to icosapent ethyl.

Total Events for the Key Secondary Efficacy Endpoint: FIGS. 21-23 depict the cumulative event curves from the key secondary endpoint of cardiovascular death, nonfatal myocardial infarction, and nonfatal stroke. The overall cumulative events are shown in FIG. 21, the secondary prevention stratum events are shown in FIG. 22, and the primary prevention stratum events are shown in FIG. 23. Total key secondary endpoints were significantly reduced from 861 to 590 (HR 0.71, 95% CI 0.63-0.79, P<0.0001) with icosapent ethyl versus placebo as shown in FIG. 21. Similar patterns were seen for the key secondary endpoint, both in the secondary prevention (HR 0.70, 95% CI 0.63-0.79, P<0.0001) and primary prevention (HR 0.71, 95% CI 0.55-0.93, P=0.011) strata as shown in FIGS. 22 and 23, respectively, $P_{interaction}$=0.90. Without adjustment for stratification differences, total key secondary endpoint events in the secondary prevention stratum were reduced from 671 to 478 (HR 0.69, 95% CI 0.61-0.78, P<0.0001) and from 142 to 112 (HR 0.78, 95% CI 0.60-1.00, P=0.047) in primary prevention; $P_{interaction}$=0.39.

Figure 24:
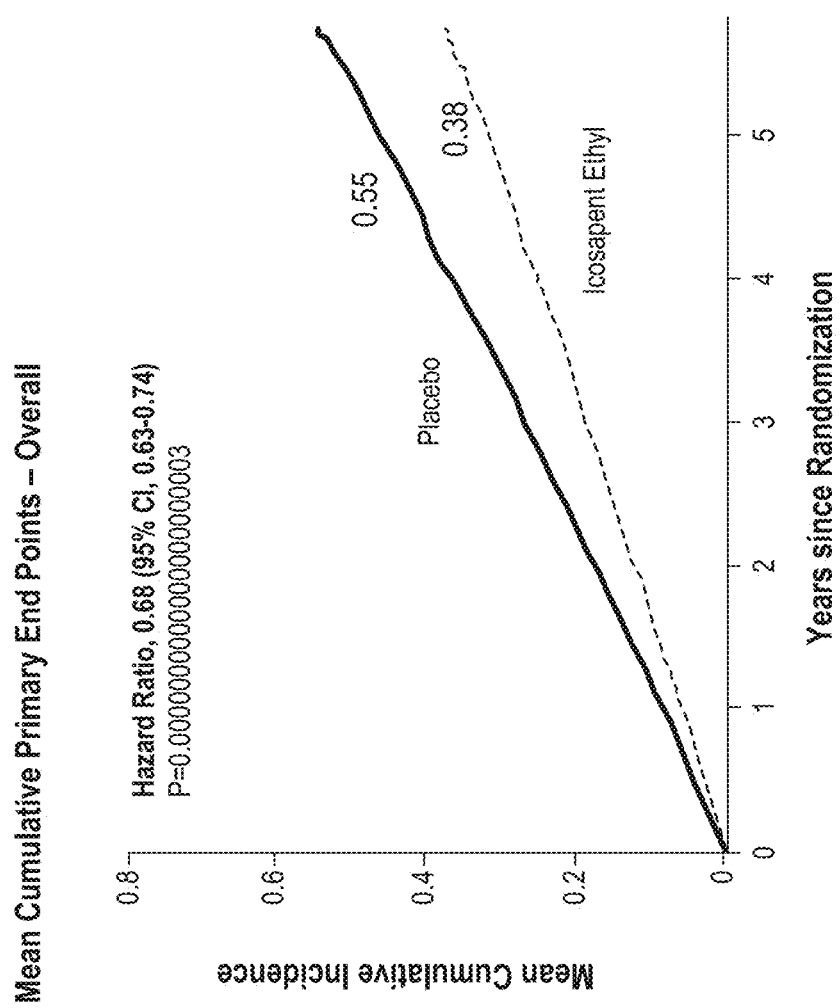
FIG. 24 is a representative overall cumulative Kaplan-Meier event curve as a function of years since randomization for the primary endpoint indicating that overall cumulative primary endpoints were reduced in patients randomized to icosapent ethyl.
Figure 25:
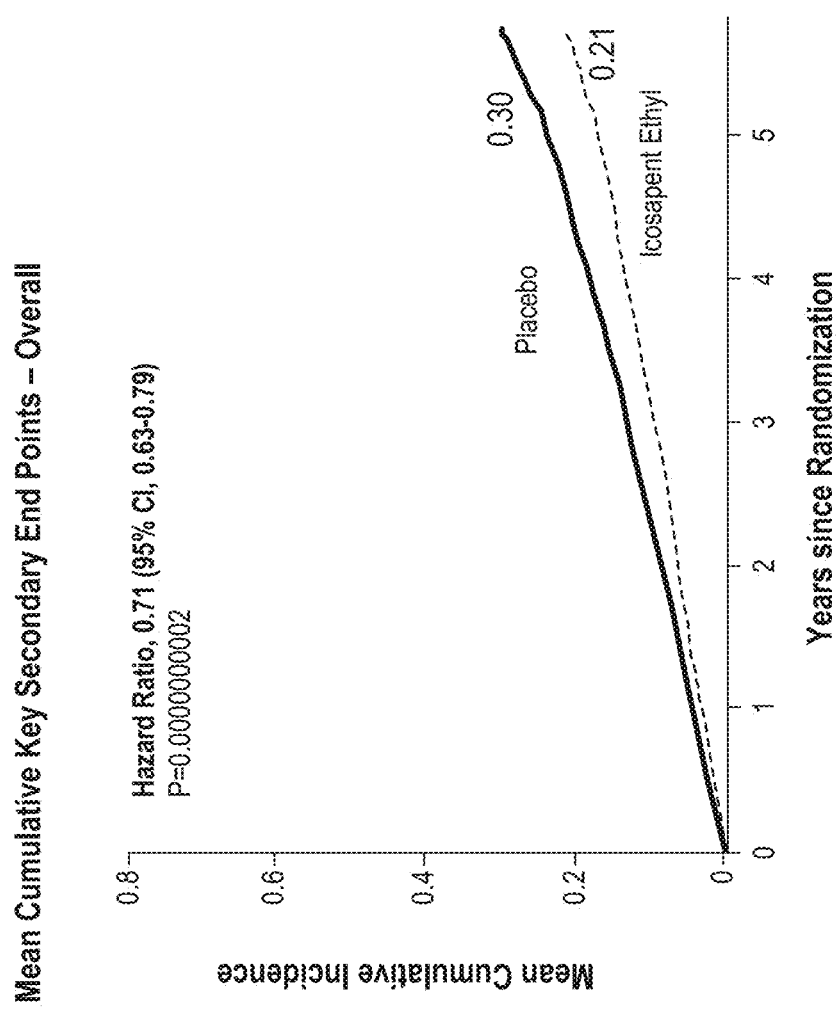
FIG. 25 is a representative overall cumulative event Kaplan-Meier curve as a function of years since randomization for the key secondary endpoint indicating that overall cumulative key secondary endpoints were reduced in patients randomized to icosapent ethyl.
Figure 26:
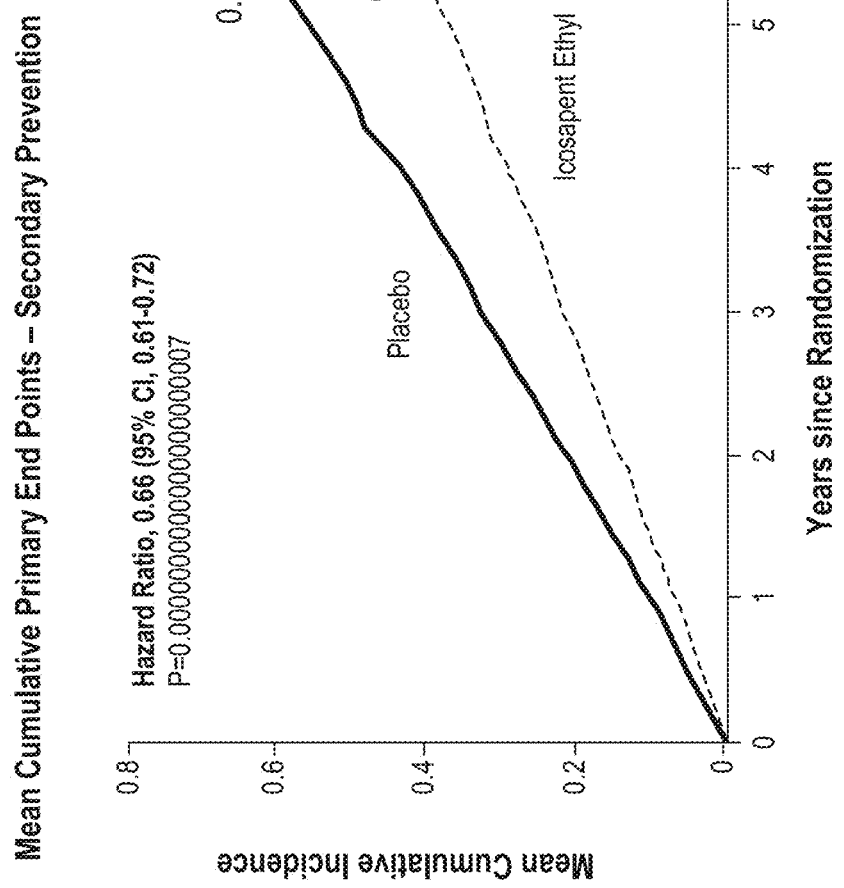
FIG. 26 is a representative Kaplan-Meier curve for recurrent events as a function of years since randomization of the primary endpoint for patients in the secondary prevention cohort indicating that cumulative primary endpoints were reduced in patients in the secondary prevention cohort randomized to icosapent ethyl.
Figure 27:
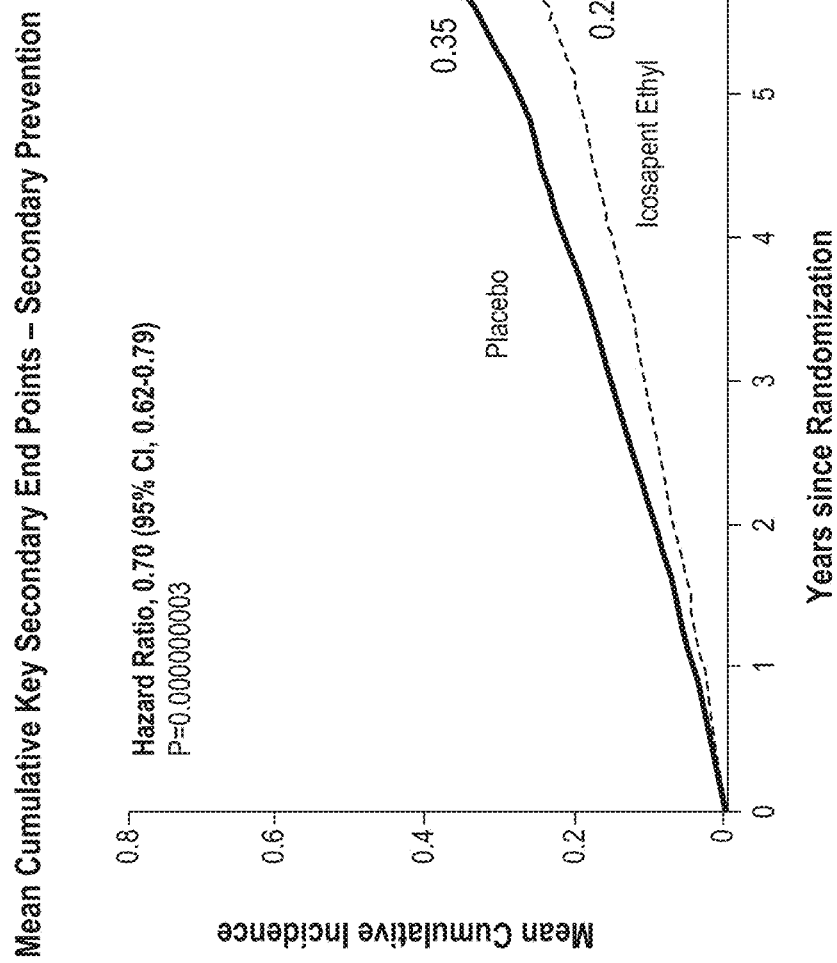
FIG. 27 is a representative Kaplan-Meier curve as a function of years since randomization for recurrent events of the key secondary endpoint for patients in the secondary prevention cohort indicating that cumulative key secondary endpoints were also reduced in patients in the secondary prevention cohort randomized to icosapent ethyl.
Figure 28:
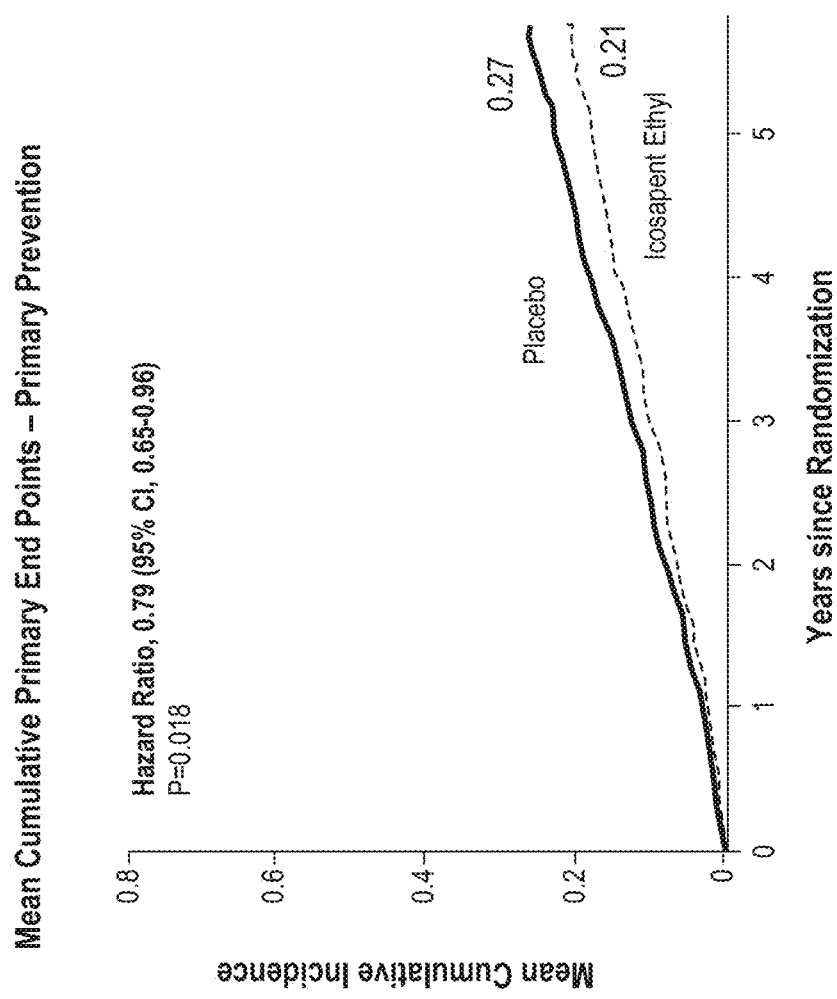
FIG. 28 is a representative Kaplan-Meier curve as a function of years since randomization for recurrent events of the primary endpoint for patients in the primary prevention cohort indicating that cumulative primary endpoints were also reduced in patients in the primary prevention cohort randomized to icosapent ethyl.
Figure 29:
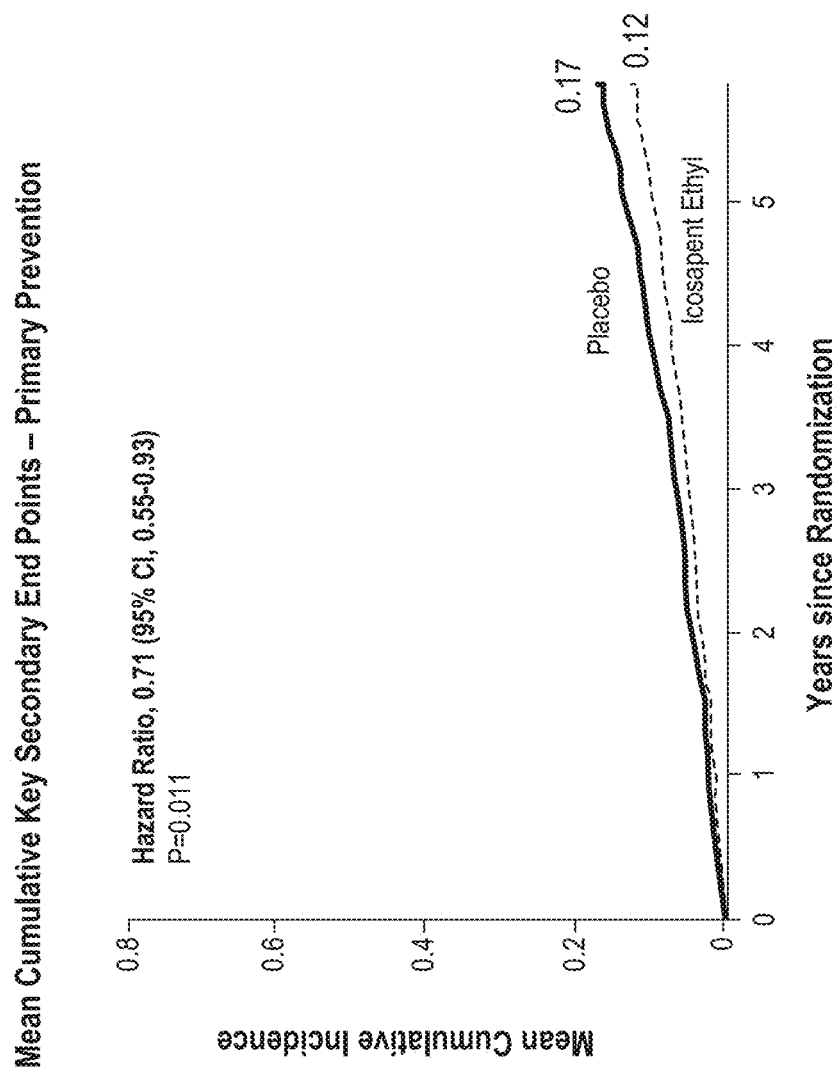
FIG. 29 is a representative Kaplan-Meier curve as a function of years since randomization for recurrent events of the key secondary endpoint for patients in the primary prevention cohort indicating that cumulative key secondary endpoints were reduced in patients in the primary prevention cohort randomized to icosapent ethyl.

Similarly, the total events for the primary and key secondary efficacy endpoints are further depicted in FIGS. 24-29 as a function of the total cumulative incidence vs years since randomization. This contrasts FIGS. 14-16 and FIGS. 21-23 which report the total events for the primary and key secondary efficacy endpoints as a function of the mean cumulative function vs follow up time in days from randomization. FIGS. 24 and 25 show the overall mean cumulative recurrent events of the primary composite endpoint and key secondary endpoint, respectively. FIGS. 26 and 27 depict the recurrent events of primary and key secondary endpoints for the secondary prevention stratum, respectively. Lastly, FIGS. 28 and 29 further depict the recurrent events of primary and key secondary endpoints for the primary prevention stratum, respectively.

Overall, the results of this study indicated that the use icosapent ethyl was superior as compared to a placebo in reducing total ischemic events, with a consistent benefit in secondary as well as primary prevention.

Conclusion

This study, an analysis of the total events in the REDUCE-IT trial as outlined above in Example 1, indicated a significant reduction in ischemic events with icosapent ethyl versus placebo. More specifically, the results from this study show that there was a 32% relative risk reduction and in total events for the primary composite efficacy outcome. In addition, first events were reduced by 25%, second events were reduced by 28%, and third or more events were reduced by 50%. For every 100 patients treated with icosapent ethyl for five years, approximately 16 total primary endpoint events could be prevented: 1 cardiovascular death, 4 myocardial infarctions, 1 stroke, 8 coronary revascularizations, and 2 episodes of unstable angina. An examination of total events for the key secondary endpoint corroborated the significant reduction in important ischemic events seen with the primary endpoint. There was a consistent benefit in both the secondary prevention and primary prevention strata.

There were significant reductions in the number of total events for each individual component of the composite primary endpoint. This benefit of icosapent ethyl across a variety of different endpoints (i.e., coronary, cerebral, fatal, non-fatal, ischemic events, revascularizations) suggests that the drug benefit is not likely to be explained by triglyceride lowering alone but rather, strongly suggests that there are multiple mechanisms of action of the drug beyond triglyceride lowering that work together to achieve the observed benefits. Basic investigations support this contention. Icosapent ethyl was well tolerated with no significant difference in rates of serious adverse events versus placebo. Although overall rates were low in both treatment groups, and none of the events were fatal, there was a trend towards increased serious bleeding with no significant increases in adjudicated hemorrhagic stroke, serious central nervous system bleeding, or gastrointestinal bleeding. There was a small, but statistically significant increase in hospitalization for atrial fibrillation or flutter noted in the REDUCE-IT study as described in Example 1. Nevertheless, the large number of important ischemic events averted, including a significant reduction in cardiovascular death, provides a very favorable risk-benefit profile. Given the broad inclusion criteria and relatively few exclusion criteria, these results are likely generalizable to a large proportion of statin-treated patients with atherosclerosis or diabetes.

In conclusion, icosapent ethyl 4 g per day (i.e., 2 g per day) significantly reduces total ischemic events in patients with established atherosclerosis or with diabetes and additional cardiovascular risk factors already being treated with statin therapy, with consistent benefits across a variety of individual ischemic endpoints. In patients with elevated triglycerides with cardiovascular disease or diabetes, icosapent ethyl reduces total ischemic events in both secondary and primary prevention. In such patients with fasting triglycerides 135 mg/dL and above, icosapent ethyl should be considered in order to reduce the total burden of atherosclerotic events.

Example 3: The Impact of Icosapent Ethyl on Total Ischemic Events in Statin-Treated Patients As described above in Example 1, in time-to-first-event analyses, icosapent ethyl significantly reduced the risk of ischemic events, including cardiovascular death, among patients with elevated triglycerides receiving statins. However, these patients remain at risk for first and subsequent ischemic events. Results from Example 2 indicated that the use icosapent ethyl was superior as compared to a placebo in reducing total ischemic events, with a consistent benefit in secondary as well as primary prevention. The objective of the study described in this example was to use pre-specified analyses to determine the extent to which icosapent ethyl reduced total ischemic events in patients from the REDUCE-IT trial.

Methods

The following study was a multi-center, placebo-controlled clinical trial the details of which are described above in Example 1, the REDUCE-IT design. Briefly, the REDUCE-IT trial randomized 8,179 statin-treated patients with triglycerides ≥135 and <500 mg/dL (median baseline of 216 mg/dL) and LDL-cholesterol >40 and ≤100 mg/dL (median baseline of 75 mg/dL), and a history of atherosclerosis (i.e., 71% patients) or diabetes (i.e., 29% patients) to icosapent ethyl 4 g per day or placebo. The main outcomes were total primary composite endpoint events defined as cardiovascular death, nonfatal myocardial infarction, nonfatal stroke, coronary revascularization, or hospitalization for unstable angina and total key secondary composite endpoint events defined as cardiovascular death, nonfatal myocardial infarction, or nonfatal stroke. In the context of this study, total events refer to any first event as well as any subsequent event. Differences in total events were determined using other statistical models, including Andersen-Gill, Wei-Lin-Weissfeld (Li and Lagakos), both pre-specified, and a post hoc and joint-frailty analysis.

For the present prespecified analysis, the primary outcome was the total of first plus subsequent ischemic events consisting of the composite of cardiovascular death, nonfatal myocardial infarction, nonfatal stroke, coronary revascularization, or hospitalization for unstable angina. The composite of hard major adverse cardiovascular events (i.e., cardiovascular death, non-fatal myocardial infarction, non-fatal stroke) are designated as the "key secondary endpoint" per suggestions from the Food and Drug Administration. Exploratory analyses of the total of first and subsequent events were also performed for the key secondary composite endpoint.

Baseline characteristics were compared between treatment groups using the chi-squared test for categorical variables and the Wilcoxon rank sum test for continuous variables. There are several methods for analyzing first and subsequent (recurrent) event data. As a pre-specified statistical method, a negative binomial regression was used to calculate rates and rate ratios for total cardiovascular events, which accounts for the variability in each patient's risk of events. As pre-specified supportive analyses, the modified Wei-Lin-Weissfeld method (Li and Lagakos modification) was used to calculate hazard ratios (HRs) for the time to the first event, second event, or third event. An additional pre-specified analysis, the Andersen-Gill model using a Cox proportional-hazard with the counting-process formulation was performed to model the total events. In addition, in order to account for informative censoring due to cardiovascular death, the HR for total non-fatal events was calculated using a joint frailty model (See Rondeau V. Joint frailty models for recurring events and death using maximum penalized likelihood estimation: application on cancer events. Biostatistics. 2007; 8:708-21). The joint frailty model simultaneously estimates hazard functions for non-fatal and fatal CV events and takes into account the fact that patients who are prone to have nonfatal events have an elevated risk of a cardiovascular death. The application of the joint frailty model used a gamma distribution for the frailty term.

To improve the performance and validity of the statistical models, a bundling approach was employed, whereby non-fatal events occurring on the same day as a CV death were excluded, and at most, one non-fatal event was counted on any given day (e.g., for coronary revascularization occurring after a myocardial infarction which eventually resulted in the patient's death, only the death would be included). Statistical analyses using the full adjudicated endpoint events dataset without exclusions using this bundling approach were also determined.

All efficacy analyses were conducted in accordance with the intention-to-treat principle. All tests were based on a 2-sided nominal significance level of 5% with no adjustments for multiple comparisons, consistent with prespecified plans for such endpoints.

Results

A total of 8,179 patients were randomized and followed for a median of 4.9 years. The baseline characteristics were well matched across the icosapent ethyl and placebo groups as shown in Table 28. At baseline, the median triglyceride levels were 216 mg/dL with median LDL-C levels of 75 mg/dL. Additional baseline characteristics across treatment groups and for patients with no events, a single event, and multiple subsequent events are shown in Tables 28 and 29, respectively.

TABLE 28

Baseline Characteristics of Patients in Icosapent Ethyl and Placebo Treatment Groups

| | Icosapent Ethyl (N = 4089) | Placebo (N = 4090) | P Value [1] |
|---|---|---|---|
| Demographics | | | |
| Age (years), Median (Q1-Q3) | 64.0 (57.0-69.0) | 64.0 (57.0-69.0) | 0.7446 |
| Age ≥65 years, n (%) | 1857 (45.4%) | 1906 (46.6%) | 0.2815 |
| Male, n (%) | 2927 (71.6%) | 2895 (70.8%) | 0.4245 |
| White, n (%)[2] | 3691 (90.3%) | 3688 (90.2%) | 0.9110 |
| BMI (kg/m$^2$), Median (Q1-Q3) | 30.8 (27.8-34.5) | 30.8 (27.9-34.7) | 0.3247 |
| BMI ≥30, n (%)[3] | 2331 (57.0%) | 2362 (57.8%) | 0.5287 |
| Stratification Factors | | | |
| Geographic Region, n (%) | | | 0.9924 |
| Westernized [4] | 2906 (71.1%) | 2905 (71.0%) | |
| Eastern Europe [5] | 1053 (25.8%) | 1053 (25.7%) | |
| Asia Pacific [6] | 130 (3.2%) | 132 (3.2%) | |
| CV Risk Category, n (%) | | | 0.9943 |
| Secondary Prevention | 2892 (70.7%) | 2893 (70.7%) | |
| Primary Prevention | 1197 (29.3%) | 1197 (29.3%) | |
| Ezetimibe Use, n (%) | 262 (6.4%) | 262 (6.4%) | 0.9977 |
| Statin Intensity and Diabetes Status | | | |
| Statin Intensity, n (%) | | | 0.1551 |
| Low | 254 (6.2%) | 267 (6.5%) | |
| Moderate | 2533 (61.9%) | 2575 (63.0%) | |
| High | 1290 (31.5%) | 1226 (30.0%) | |
| Missing | 12 (0.3%) | 22 (0.5%) | |
| Diabetes, n (%) | | | 0.9926 |
| Type I Diabetes | 27 (0.7%) | 30 (0.7%) | |
| Type II Diabetes | 2367 (57.9%) | 2363 (57.8%) | |
| No Diabetes at Baseline | 1695 (41.5%) | 1694 (41.4%) | |
| Missing | 0 | 3 (0.1%) | |
| Laboratory Measurements | | | |
| hsCRP (mg/L), Median (Q1-Q3) | 2.2 (1.1-4.5) | 2.1 (1.1-4.5) | 0.7197 |
| Triglycerides (mg/dL), Median (Q1-Q3) | 216.5 (176.5-272.0) | 216.0 (175.5-274.0) | 0.9120 |
| HDL-C (mg/dL), Median (Q1-Q3) | 40.0 (34.5-46.0) | 40.0 (35.0-46.0) | 0.1370 |
| LDL-C (mg/dL), Median (Q1-Q3) | 74.5 (62.0-88.0) | 76.0 (63.0-89.0) | 0.0284 |
| LDL-C Tertiles, n(%) | | | 0.0556 |
| Lowest (≤67 mg/dL) | 14831 (36.2%) | 1386 (33.9%) | |
| Middle (>67-≤84 mg/dL) | 1347 (32.9%) | 1364 (33.3%) | |
| Upper (>84 mg/dL) | 1258 (30.8%) | 1339 (32.7%) | |
| Missing | 3 (0.1%) | 1 | |
| Triglycerides Category, n (%) | | | 0.8297 |
| <150 mg/dL | 412 (10.1%) | 429 (10.5%) | |
| 150 to <200 mg/dL | 1193 (29.2%) | 1191 (29.1%) | |
| ≥200 mg/dL | 2481 (60.7%) | 2469 (60.4%) | |
| Triglyceride Tertiles, n (%) | | | 0.4887 |
| Lowest (≤190 mg/dL) | 1378 (33.7%) | 1381 (33.8%) | |
| Middle (>190-≤250 mg/dL) | 1370 (33.5%) | 1326 (32.4%) | |
| Upper (>250 mg/dL) | 1338 (32.7%) | 1382 (33.8%) | |
| Missing | 3 (0.1%) | 1 | |
| Triglycerides ≥200 mg/dL and HDL-C ≤35 mg/dL, n (%) | 823 (20.1%) | 794 (19.4%) | 0.4019 |
| EPA (µg/mL), Median (Q1-Q3) | 26.1 (17.1-40.1) | 26.1 (17.1-39.9) | 0.8867 |
| Cardiovascular Disease History[7] | | | |
| Prior Atherosclerotic Cardiovascular Disease (ASCVD), n (%) | 2816 (68.9%) | 2835 (69.3%) | 0.6667 |
| Prior Atherosclerotic Coronary Artery Disease and Related Morbidities | 2387 (58.4%) | 2393 (58.5%) | 0.9107 |
| Ischemic Dilated Cardiomyopathy | 137 (3.4%) | 109 (2.7%) | 0.0702 |
| Myocardial Infarction | 1938 (47.4%) | 1881 (46.0%) | 0.2065 |
| Unstable Angina | 1017 (24.9%) | 1015 (24.8%) | 0.9592 |

TABLE 28-continued

Baseline Characteristics of Patients in Icosapent Ethyl and Placebo Treatment Groups

|  | Icosapent Ethyl (N = 4089) | Placebo (N = 4090) | P Value [1] |
|---|---|---|---|
| Prior Atherosclerotic Cerebrovascular Disease and Related Morbidities, n (%) | 641 (15.7%) | 662 (16.2%) | 0.5457 |
| Carotid Disease | 343 (8.4%) | 372 (9.1%) | 0.2730 |
| Ischemic Stroke | 267 (6.5%) | 242 (5.9%) | 0.2529 |
| Transient Ischemic Attack | 194 (4.7%) | 181 (4.4%) | 0.4925 |
| Prior Atherosclerotic Peripheral Arterial Disease, n (%) | 387 (9.5%) | 388 (9.5%) | 1.0000 |
| ABI <0.9 Without Symptoms of Intermittent Claudication | 97 (2.4%) | 76 (1.9%) | 0.1073 |
| Peripheral Artery Disease | 377 (9.2%) | 377 (9.2%) | 1.0000 |
| Prior Non-Atherosclerotic Cardiovascular Disease, n (%) | 3649 (89.2%) | 3645 (89.1%) | 0.8868 |
| Prior Structural Cardiac Disorders | 827 (20.2%) | 866 (21.2%) | 0.2997 |
| Congestive Heart Failure | 703 (17.2%) | 743 (18.2%) | 0.2583 |
| Hypertrophic Cardiomyopathy | 23 (0.6%) | 20 (0.5%) | 0.6507 |
| Non-Ischemic Dilated Cardiomyopathy | 35 (0.9%) | 29 (0.7%) | 0.4552 |
| Non-Rheumatic Valvular Heart Disease | 150 (3.7%) | 163 (4.0%) | 0.4892 |
| Rheumatic Valvular Heart Disease | 17 (0.4%) | 9 (0.2%) | 0.1215 |
| Prior Cardiac Arrhythmias | 229 (5.6%) | 243 (5.9%) | 0.5377 |
| Atrio-Ventricular Block Above First Degree | 51 (1.2%) | 54 (1.3%) | 0.8444 |
| Sick Sinus Syndrome | 30 (0.7%) | 32 (0.8%) | 0.8987 |
| Supra-Ventricular Tachycardia Other Than Atrial Fibrillation /Atrial flutter | 74 (1.8%) | 77 (1.9%) | 0.8696 |
| Sustained Ventricular Tachycardia | 34 (0.8%) | 34 (0.8%) | 1.0000 |
| Torsades De Pointes | 1 (0.0%) | 3 (0.1%) | 0.6249 |
| Ventricular Fibrillation | 61 (1.5%) | 65 (1.6%) | 0.7877 |
| Prior Non-Cardiac/ Non-Atherosclerotic Vascular Disorders, n (%) | 3568 (87.3%) | 3566 (87.2%) | 0.9472 |
| Arterial Embolism | 12 (0.3%) | 9 (0.2%) | 0.5229 |
| Deep Vein Thrombosis | 70 (1.7%) | 60 (1.5%) | 0.3785 |
| Hypertension | 3541 (86.6%) | 3543 (86.6%) | 0.9741 |
| Hypotension | 45 (1.1%) | 33 (0.8%) | 0.1745 |
| Pulmonary Embolism | 31 (0.8%) | 42 (1.0%) | 0.2396 |
| Non-Ischemic Stroke | 79 (1.9%) | 84 (2.1%) | 0.7518 |
| Hemorrhagic Stroke | 18 (0.4%) | 22 (0.5%) | 0.6350 |
| Stroke of Unknown Origin | 63 (1.5%) | 62 (1.5%) | 0.9285 |
| Other Prior Conditions | | | |
| Metabolic Syndrome | 507 (12.4%) | 540 (13.2%) | 0.2896 |
| Baseline Laboratory Abnormalities, n (%) | 1783 (43.6%) | 1707 (41.7%) | 0.0893 |
| Renal Disorders | 470 (11.5%) | 429 (10.5%) | 0.1474 |
| Creatinine Clearance (CRCL) >30 and <60 ML/Min | 309 (7.6%) | 286 (7.0%) | 0.3279 |
| Macroalbuminuria | 34 (0.8%) | 24 (0.6%) | 0.1909 |
| Microalbuminuria | 146 (3.6%) | 134 (3.3%) | 0.4664 |
| Proteinuria | 75 (1.8%) | 63 (1.5%) | 0.3046 |
| Other Morbidities | 173 (4.2%) | 173 (4.2%) | 1.0000 |
| Pancreatitis | 14 (0.3%) | 9 (0.2%) | 0.3067 |
| Retinopathy | 161 (3.9%) | 167 (4.1%) | 0.7782 |
| Carotid Stenosis [8] | | | |
| n | 316 | 346 | |
| Mean (%) (SD) | 59.0 (21.04) | 56.9 (22.99) | 0.4101 |
| Medication Taken at Baseline | | | |
| Anti-Diabetic, n (%) | 2190 (53.6%) | 2196 (53.7%) | 0.9036 |
| Anti-Hypertensive | 3895 (95.3%) | 3895 (95.2%) | 0.9605 |
| Anti-Platelet[9] | 3257 (79.7%) | 3236 (79.1%) | 0.5514 |
| One Anti-platelet | 2416 (59.09%) | 2408 (58.88%) | 0.8469 |
| Two or more Anti-platelets | 841 (20.57%) | 828 (20.4%) | 0.7171 |
| Anticoagulant | 385 (9.4%) | 390 (9.5%) | 0.8531 |
| Anticoagulant plus Anti-platelet | 137 (3.4%) | 137 (3.4%) | 0.9984 |

TABLE 28-continued

Baseline Characteristics of Patients in Icosapent Ethyl and Placebo Treatment Groups

|  | Icosapent Ethyl (N = 4089) | Placebo (N = 4090) | P Value [1] |
|---|---|---|---|
| No Antithrombotic | 584 (14.3%) | 601 (14.7%) | 0.5965 |
| ACE | 2112 (51.7%) | 2131 (52.1%) | 0.6825 |
| ARB | 1108 (27.1%) | 1096 (26.8%) | 0.7598 |
| ACE or ARB | 3164 (77.4%) | 3176 (77.7%) | 0.7662 |
| Beta Blockers | 2902 (71.0%) | 2880 (70.4%) | 0.5812 |

Abbreviations: ABI = ankle brachial index; ACE = angiotensin-converting enzyme; ARB = angiotensin receptor blockers.

Percentages are based on the number of subjects randomized to each treatment group in the ITT population (N). In general, the baseline value is defined as the last non-missing measurement obtained prior to the randomization.

The baseline LDL-C value obtained via Preparative Ultracentrifugation was used, unless this value was missing. If the LDL-C Preparative Ultracentrifugation value was missing, then another LDL-C value was be used, with prioritization of values obtained from LDL-C Direct measurements, followed by LDL-C derived by the Friedewald calculation (only for subjects with TG < 400 mg/dL), and finally LDL-C derived using the calculation published by Johns Hopkins University investigators.[1]

For all other lipid and lipoprotein marker parameters, wherever possible, baseline was derived as the arithmetic mean of the Visit 2 (Day 0) value and the preceding Visit 1 (or Visit 1.1) value. If only one of these values was available, the single available value was used as baseline.

[1] P Values from Wilcoxon rank-sum test for continuous variables and chi-square test for categorical variables.

[2] Race as reported by the investigators.

[3] Body-mass index is the weight in kilograms divided by the square of the height in meters.

[4] Westernized region includes Australia, Canada, Netherlands, New Zealand, United States, and South Africa.

[5] Eastern European region includes Poland, Romania, Russian Federation, and Ukraine.

[6] Asia Pacific region includes India.

[7] The summary is based on the data collected from CV history Case Report Form (CRF).

[8] Two outliers of Carotid Stenosis (%) with a value over 100% are excluded from the analysis. Carotid Stenosis (%) data reported in categorical format of >x % and <y % is analysed as x % and y %, respectively; and data reported as x % to y % is analysed as an average of x % and y %.

[9] Dual anti-platelets were classified as such if both components have a robust history of regulatory approval affirming anti-platelet effects, thus excluding combinations where one element lacks robust regulatory approval (e.g. Aspirin + Magnesium Oxide is classified as a single agent because the latter component lacks robust regulatory support as an anti-platelet agent).

TABLE 29

Baseline Characteristics of Patients with No Primary Endpoint Events, a Single Event, or Multiple Events

|  | No Events (N = 6573) | 1 Event (N = 844) | Multiple Events (N = 762) | P Value [1] |
|---|---|---|---|---|
| Demographics | | | | |
| Age (years), Median (Q1-Q3) | 63.0 (57.0-69.0) | 65.0 (59.0-71.0) | 64.0 (58.0-70.0) | 0.0400 |
| Age ≥65 years, n (%) | 2939 (44.7%) | 456 (54.0%) | 368 (48.3%) | 0.0217 |
| Male, n (%) | 4556 (69.3%) | 661 (78.3%) | 605 (79.4%) | 0.5972 |
| White, n (%)[2] | 5921 (90.1%) | 765 (90.6%) | 693 (90.9%) | 0.8328 |
| BMI (kg/m²), Median (Q1-Q3) | 30.8 (27.8-34.6) | 31.1 (27.8-34.7) | 30.8 (28.0-34.2) | 0.2609 |
| BMI ≥30, n (%)[3] | 3762 (57.2%) | 499 (59.1%) | 432 (56.7%) | 0.4656 |
| Stratification Factors | | | | |
| Geographic Region | | | | 0.0082 |
| Westernized [4] | 4547 (69.2%) | 639 (75.7%) | 625 (82.0%) | |
| Eastern Europe [5] | 1796 (27.3%) | 185 (21.9%) | 125 (16.4%) | |
| Asia Pacific [6] | 230 (3.5%) | 20 (2.4%) | 12 (1.6%) | |
| CV Risk Category as Randomized, n (%) | | | | <.0001 |
| Secondary Prevention | 4488 (68.3%) | 640 (75.8%) | 657 (86.2%) | |
| Primary Prevention | 2085 (31.7%) | 204 (24.2%) | 105 (13.8%) | |
| Ezetimibe Use, n (%) | 401 (6.1%) | 59 (7.0%) | 64 (8.4%) | 0.2892 |
| Statin Intensity and Diabetes Status | | | | |
| Statin Intensity, n (%) | | | | 0.7138 |
| Low | 436 (6.6%) | 52 (6.2%) | 44 (5.8%) | |
| Moderate | 4153 (63.2%) | 520 (61.6%) | 451 (59.2%) | |
| High | 1953 (29.7%) | 270 (32.0%) | 265 (34.8%) | |
| Missing | 31 (0.5%) | 2 (0.2%) | 2 (0.3%) | |
| Diabetes, n (%) | | | | 0.4420 |
| Type I | 44 (0.7%) | 5 (0.6%) | 8 (1.0%) | |
| Type II | 3773 (57.4%) | 511 (60.5%) | 445 (58.4%) | |

TABLE 29-continued

Baseline Characteristics of Patients with No Primary Endpoint Events, a Single Event, or Multiple Events

| | No Events (N = 6573) | 1 Event (N = 844) | Multiple Events (N = 762) | P Value [1] |
|---|---|---|---|---|
| No Diabetes at Baseline | 2752 (41.9%) | 328 (38.9%) | 309 (40.6%) | |
| Missing | 3 (0.0%) | 0 | 0 | |
| Laboratory Measurements | | | | |
| hsCRP (mg/L), Median (Q1-Q3) | 2.1 (1.1-4.4) | 2.4 (1.2-5.3) | 2.4 (1.2-4.6) | 0.3325 |
| Triglycerides (mg/dL), Median (Q1-Q3) | 215.5 (176.0-272.0) | 215.5 (175.0-270.3) | 223.0 (178.5-285.5) | 0.0701 |
| HDL-C (mg/dL), Median (Q1-Q3) | 40.0 (35.0-46.0) | 39.5 (34.4-45.5) | 38.8 (33.5-44.5) | 0.0631 |
| LDL-C (mg/dL), Median (Q1-Q3) | 75.0 (62.0-89.0) | 75.0 (63.0-88.0) | 75.0 (63.0-89.0) | 0.7384 |
| LDL-C Tertiles, n (%) | | | | 0.5416 |
| Lowest (≤67 mg/dL) | 2321 (35.3%) | 283 (33.5%) | 263 (34.5%) | |
| Middle (>67-≤84 mg/dL) | 2156 (32.8%) | 302 (35.8%) | 253 (33.2%) | |
| Upper (>84 mg/dL) | 2092 (31.8%) | 259 (30.7%) | 246 (32.3%) | |
| Triglyceride Category | | | | |
| <150 mg/dL | 686 (10.4%) | 79 (9.4%) | 76 (10.0%) | |
| 150 to ≤200 mg/dL | 1922 (29.2%) | 259 (30.7%) | 203 (26.6%) | |
| ≥200 mg/dL | 3961 (60.3%) | 506 (60.0%) | 483 (63.4%) | |
| Triglyceride Tertiles, n (%) | | | | 0.1993 |
| Lowest (≤190 mg/dL) | 2235 (34.0%) | 287 (34.0%) | 237 (31.1%) | |
| Middle (>190-≤250 mg/dL) | 2167 (33.0%) | 283 (33.5%) | 246 (32.3%) | |
| Upper (>250 mg/dL) | 2167 (33.0%) | 274 (32.5%) | 279 (36.6%) | |
| Lowest | | | | |
| Triglycerides ≥200 mg/dL and HDL-C ≤35 mg/dL | 1254 (19.1%) | 173 (20.5%) | 190 (24.9%) | 0.0336 |
| EPA (µg/mL), Median (Q1-Q3) | 26.2 (17.2-40.4) | 24.6 (15.9-36.7) | 26.9 (17.7-40.2) | 0.0120 |
| Cardiovascular Disease History [7] | | | | |
| Prior Atherosclerotic Cardiovascular Disease | 4370 (66.5%) | 633 (75.0%) | 648 (85.0%) | <.0001 |
| Prior Atherosclerotic Coronary Artery Disease and Related Morbidities | 3662 (55.7%) | 542 (64.2%) | 576 (75.6%) | <.0001 |
| Myocardial Infarction | 2931 (44.6%) | 430 (50.9%) | 458 (60.1%) | <.0002 |
| Unstable Angina | 1497 (22.8%) | 236 (28.0%) | 299 (39.2%) | <.0001 |
| Ischemic Dilated Cardiomyopathy | 164 (2.5%) | 46 (5.5%) | 36 (4.7%) | 0.5707 |
| Prior Atherosclerotic Cerebrovascular Disease and | 965 (14.7%) | 173 (20.5%) | 165 (21.7%) | 0.5816 |
| Carotid Disease | 543 (8.3%) | 90 (10.7%) | 82 (10.8%) | 1.0000 |
| Ischemic Stroke | 380 (5.8%) | 64 (7.6%) | 65 (8.5%) | 0.5203 |
| Transient Ischemic Attack | 254 (3.9%) | 61 (7.2%) | 60 (7.9%) | 0.6371 |
| Prior Atherosclerotic Peripheral Arterial Disease | 548 (8.3%) | 109 (12.9%) | 118 (15.5%) | 0.115 |
| Peripheral Artery Disease | 534 (8.1%) | 106 (12.6%) | 114 (15.0%) | 0.1679 |
| ABI <0.9 Without Symptoms of Intermittent Claudication | 132 (2.0%) | 24 (2.8%) | 17 (2.2%) | 0.5269 |
| Prior Non-Atherosclerotic Cardiovascular Disease | 5836 (88.8%) | 775 (91.8%) | 683 (89.6%) | 0.1420 |
| Prior Structural Cardiac Disorders | 1289 (19.6%) | 234 (27.7%) | 170 (22.3%) | 0.0133 |
| Congestive Heart Failure | 1099 (16.7%) | 200 (23.7%) | 147 (19.3%) | 0.0337 |
| Hypertrophic Cardiomyopathy | 32 (0.5%) | 6 (0.7%) | 5 (0.7%) | 1.0000 |
| Non-Ischemic Dilated Cardiomyopathy | 49 (0.7%) | 11 (1.3%) | 4 (0.5%) | 0.1239 |
| Non-Rheumatic Valvular Heart Disease | 225 (3.4%) | 54 (6.4%) | 34 (4.5%) | 0.0996 |
| Rheumatic Valvular Heart Disease | 22 (0.3%) | 3 (0.4%) | 1 (0.1%) | 0.6265 |
| Prior Cardiac Arrhythmias | 354 (5.4%) | 65 (7.7%) | 53 (7.0%) | 0.6323 |
| Atrio-Ventricular Block Above First Degree | 77 (1.2%) | 15 (1.8%) | 13 (1.7%) | 1.0000 |
| Sick Sinus Syndrome | 49 (0.7%) | 5 (0.6%) | 8 (1.0%) | 0.4056 |
| Supra-Ventricular Tachycardia Other Than Atrial fibrillation/Atrial flutter | 115 (1.7%) | 24 (2.8%) | 12 (1.6%) | 0.0934 |
| Sustained Ventricular Tachycardia | 50 (0.8%) | 10 (1.2%) | 8 (1.0%) | 0.8179 |

TABLE 29-continued

Baseline Characteristics of Patients with No Primary Endpoint Events, a Single Event, or Multiple Events

| | No Events (N = 6573) | 1 Event (N = 844) | Multiple Events (N = 762) | P Value [1] |
|---|---|---|---|---|
| Torsades De Pointes | 3 (0.0%) | 0 (0.0%) | 1 (0.1%) | 0.4744 |
| Ventricular Fibrillation | 95 (1.4%) | 16 (1.9%) | 15 (2.0%) | 1.0000 |
| Prior Non-Cardiac/Non-Atherosclerotic Vascular Disorders | 5716 (87.0%) | 752 (89.1%) | 666 (87.4%) | 0.3125 |
| Hypotension | 52 (0.8%) | 9 (1.1%) | 17 (2.2%) | 0.0754 |
| Hypertension | 5669 (86.2%) | 750 (88.9%) | 665 (87.3%) | 0.3544 |
| Non-Ischemic Stroke | 123 (1.9%) | 24 (2.8%) | 16 (2.1%) | 0.4231 |
| Hemorrhagic Stroke | 32 (0.5%) | 4 (0.5%) | 4 (0.5%) | 1.0000 |
| Stroke of Unknown Origin | 92 (1.4%) | 20 (2.4%) | 13 (1.7%) | 0.3826 |
| Arterial Embolism | 9 (0.1%) | 11 (1.3%) | 1 (0.1%) | 0.0069 |
| Deep Vein Thrombosis | 90 (1.4%) | 20 (2.4%) | 20 (2.6%) | 0.7514 |
| Pulmonary Embolism | 49 (0.7%) | 12 (1.4%) | 12 (1.6%) | 0.8391 |
| Other Prior Conditions or Investigations Influencing Cardiovascular Risk | 4870 (74.1%) | 642 (76.1%) | 587 (77.0%) | 0.6799 |
| Prior Metabolic Disorders | 3988 (60.7%) | 530 (62.8%) | 477 (62.6%) | 0.9588 |
| Diabetes Type I | 45 (0.7%) | 5 (0.6%) | 8 (1.0%) | 0.4056 |
| Diabetes Type II | 3774 (57.4%) | 511 (60.5%) | 445 (58.4%) | 0.3872 |
| Metabolic Syndrome | 843 (12.8%) | 108 (12.8%) | 96 (12.6%) | 0.9402 |
| Baseline Laboratory Abnormalities | 2725 (41.5%) | 395 (46.8%) | 370 (48.6%) | 0.4842 |
| Renal Disorders | 660 (10.0%) | 129 (15.3%) | 110 (14.4%) | 0.6737 |
| Creatinine Clearance >30 And <60 mL/Min | 430 (6.5%) | 83 (9.8%) | 82 (10.8%) | 0.5651 |
| Proteinuria | 100 (1.5%) | 20 (2.4%) | 18 (2.4%) | 1.0000 |
| Macroalbuminuria | 43 (0.7%) | 7 (0.8%) | 8 (1.0%) | 0.7964 |
| Microalbuminuria | 217 (3.3%) | 38 (4.5%) | 25 (3.3%) | 0.2468 |
| Other Morbidities | 275 (4.2%) | 42 (5.0%) | 29 (3.8%) | 0.2754 |
| Pancreatitis | 19 (0.3%) | 2 (0.2%) | 2 (0.3%) | 1.0000 |
| Retinopathy | 259 (3.9%) | 42 (5.0%) | 27 (3.5%) | 0.1758 |
| Carotid Stenosis[8] | | | | |
| n | 503 | 86 | 73 | |
| Mean (%) (SD) | 57.0 (21.94) | 58.2 (22.85) | 63.5 (21.67) | 0.1582 |
| Medication Taken at Baseline | | | | |
| Anti-Diabetic | 3498 (53.2%) | 478 (56.6%) | 410 (53.8%) | 0.2548 |
| Anti-Hypertensive | 6239 (94.9%) | 817 (96.8%) | 734 (96.3%) | 0.6008 |
| Anti-Platelet | 5138 (78.2%) | 691 (81.9%) | 664 (87.1%) | 0.0037 |
| One Anti-platelet | 3912 (59.52%) | 486 (57.58%) | 426 (55.91%) | 0.4980 |
| Two or more Anti-platelets | 1226 (18.65%) | 205 (24.29%) | 238 (31.23%) | 0.0019 |
| Anticoagulant | 560 (8.5%) | 125 (14.8%) | 90 (11.8%) | 0.0780 |
| Anticoagulant plus Anti-platelet | 185 (2.8%) | 46 (5.5%) | 43 (5.6%) | 0.8661 |
| No Antithrombotic | 1060 (16.1%) | 74 (8.8%) | 51 (6.7%) | 0.1212 |
| ACE | 3424 (52.1%) | 429 (50.8%) | 390 (51.2%) | 0.8880 |
| ARB | 1743 (26.5%) | 235 (27.8%) | 226 (29.7%) | 0.4220 |
| ACE or ARB | 5090 (77.4%) | 645 (76.4%) | 605 (79.4%) | 0.1518 |
| Beta Blockers | 4541 (69.1%) | 655 (77.6%) | 586 (76.9%) | 0.7368 |

Abbreviations: ABI = ankle brachial index; ACE = angiotensin-converting enzyme; ARB = angiotensin receptor blockers.

In general, the baseline value is defined as the last non-missing measurement obtained prior to the randomization.

The baseline LDL-C value obtained via Preparative Ultracentrifugation was used, unless this value was missing. If the LDL-C preparative ultracentrifugation value was missing, then another LDL-C value was used, with prioritization of values obtained from LDL-C Direct measurements, followed by LDL-C derived by the Friedewald calculation (only for subjects with TG <400 mg/dL), and finally LDL-C derived using the calculation published by Johns Hopkins University investigators.

For all other lipid and lipoprotein marker parameters, wherever possible, baseline was derived as the arithmetic mean of the Visit 2 (Day 0) value and the preceding Visit 1 (or Visit 1.1) value. If only one of these values was available, the single available value was used as baseline.

[1] P-value comparing Single Event group with Multiple Events group is from a Wilcoxon test for continuous variables and a Fishers Exact test for categorical variables.

[2] Race as reported by the investigators.

[3] Body-mass index is the weight in kilograms divided by the square of the height in meters.

[4] Westernized region includes Australia, Canada, Netherlands, New Zealand, United States, and South Africa.

[5] Eastern European region includes Poland, Romania, Russian Federation, and Ukraine.

[6] Asia Pacific region includes India.

[7] The summary is based on the data collected from CV history Case Report Form (CRF).

[8] Two outliers of Carotid Stenosis (%) with a value over 100% are excluded from the analysis. Carotid Stenosis (%) data reported in categorical format of >x % and <y % is analysed as x % and y %, respectively; and data reported as x % to y % is analysed as an average of x % and y %.

[9] Dual anti-platelets were classified as such if both components have a robust history of regulatory approval affirming anti-platelet effects, thus excluding combinations where one element lacks robust regulatory approval (e.g. Aspirin + Magnesium Oxide is classified as a single agent because the latter component lacks robust regulatory support as an anti-platelet agent).

At baseline the percentage of patients taking at least one other cardiovascular medication including antiplatelet agents was (79.7 and 79.1%), beta blockers (71.0% and 70.4%), angiotensin converting enzyme (ACE) inhibitors (51.7% and 52.1%), or angiotensin receptor blockers (27.1% and 26.8%) in the icosapent ethyl and placebo treatment arms, respectively.

Total Events for the Primary Efficacy Endpoint: Across 8,179 randomized patients, there were 1,606 (i.e., 55.2%) first primary endpoint events and 1,303 (i.e., 44.8%) additional primary endpoint events, for a total of 2,909 endpoint events as shown in Table 30 and FIGS. 30, 31A and 31B.

TABLE 30

Total Primary and Key Secondary Composite Endpoints Accounting for Statistical Handling of Multiple Endpoints Occurring in a Single Calendar Day as a Single Event

|  | Primary endpoint | | | Key secondary endpoint | | |
|---|---|---|---|---|---|---|
| n (%) | Icosapent ethyl (N = 4089) | Placebo (N = 4090) | Overall (N = 8179) | Icosapent ethyl (N = 4089) | Placebo (N = 4090) | Overall (N = 8179) |
| Total events before reduction | 1185 (40.7) | 1724 (59.3) | 2909* (100) | 590 (42.0) | 816 (58.0) | 1406 (100) |
| Total events after reduction‡ | 1076 (41.0) | 1546 (59.0) | 2622 (100) | 558 (42.1) | 767 (57.9) | 1325 (100) |
| Fatal events | 174 (45.0) | 213 (55.0) | 387 (100) | 174 (45.0) | 213 (55.0) | 387 (100) |
| Non-fatal events | 902 (40.4) | 1333 (59.6) | 2235 (100) | 384 (40.9) | 554 (59.1) | 938 (100) |

Percentages are based on the total number of randomized patients within each category.
*A single event was experienced by 844 patients (844 events) and 2 or more events were experienced by 762 patients (2065) events, for a total of 1606 patients experiencing a total of 2909 events.
‡Reduction means 1) any nonfatal events on the same day as death are removed and 2) if 2 nonfatal events occur on the same day only the first one is counted.

Figure 32:
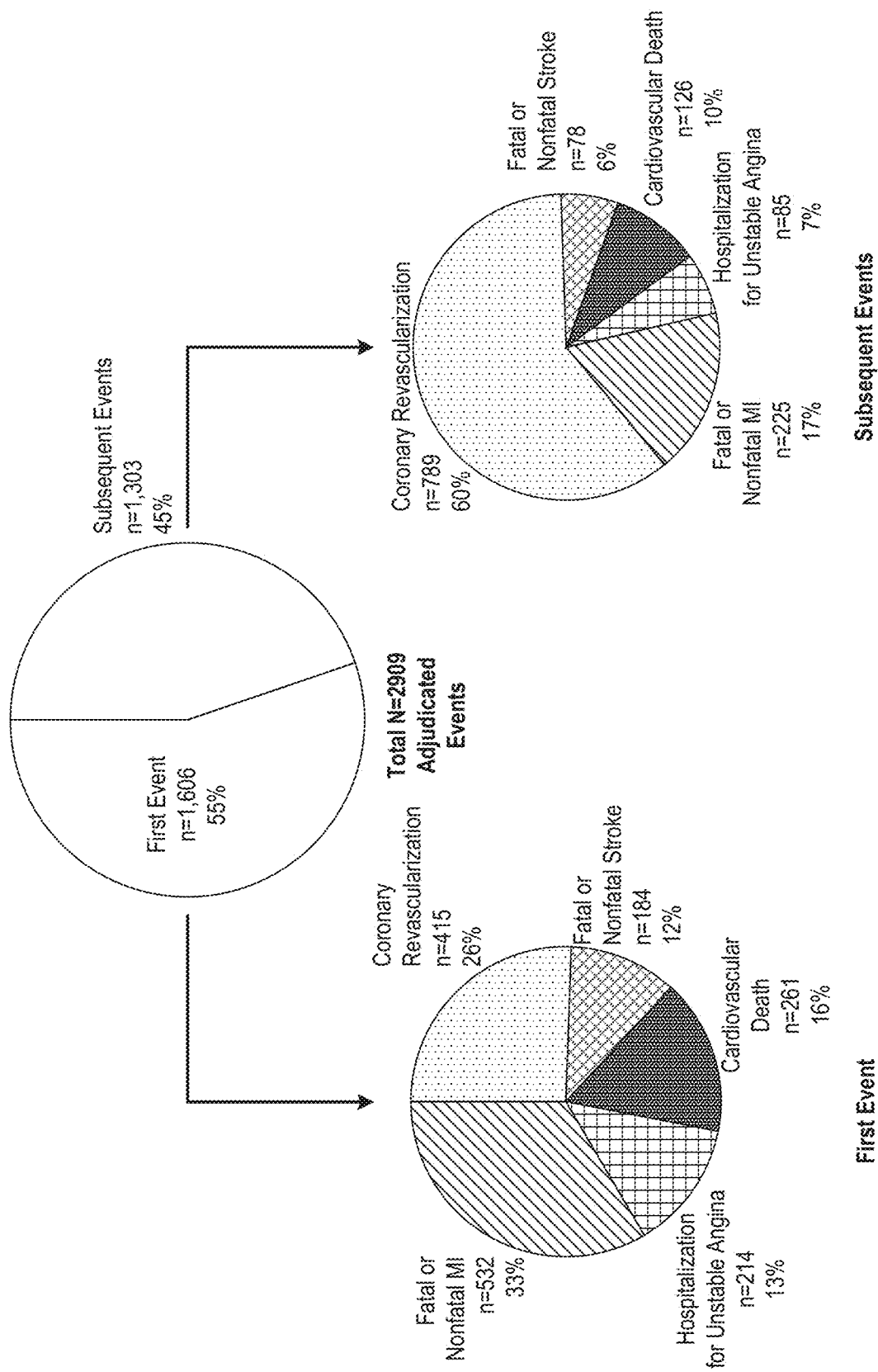
FIG. 32 includes representative pie charts for a proportion of first and subsequent primary endpoint events, overall and by component.
Figure 33:
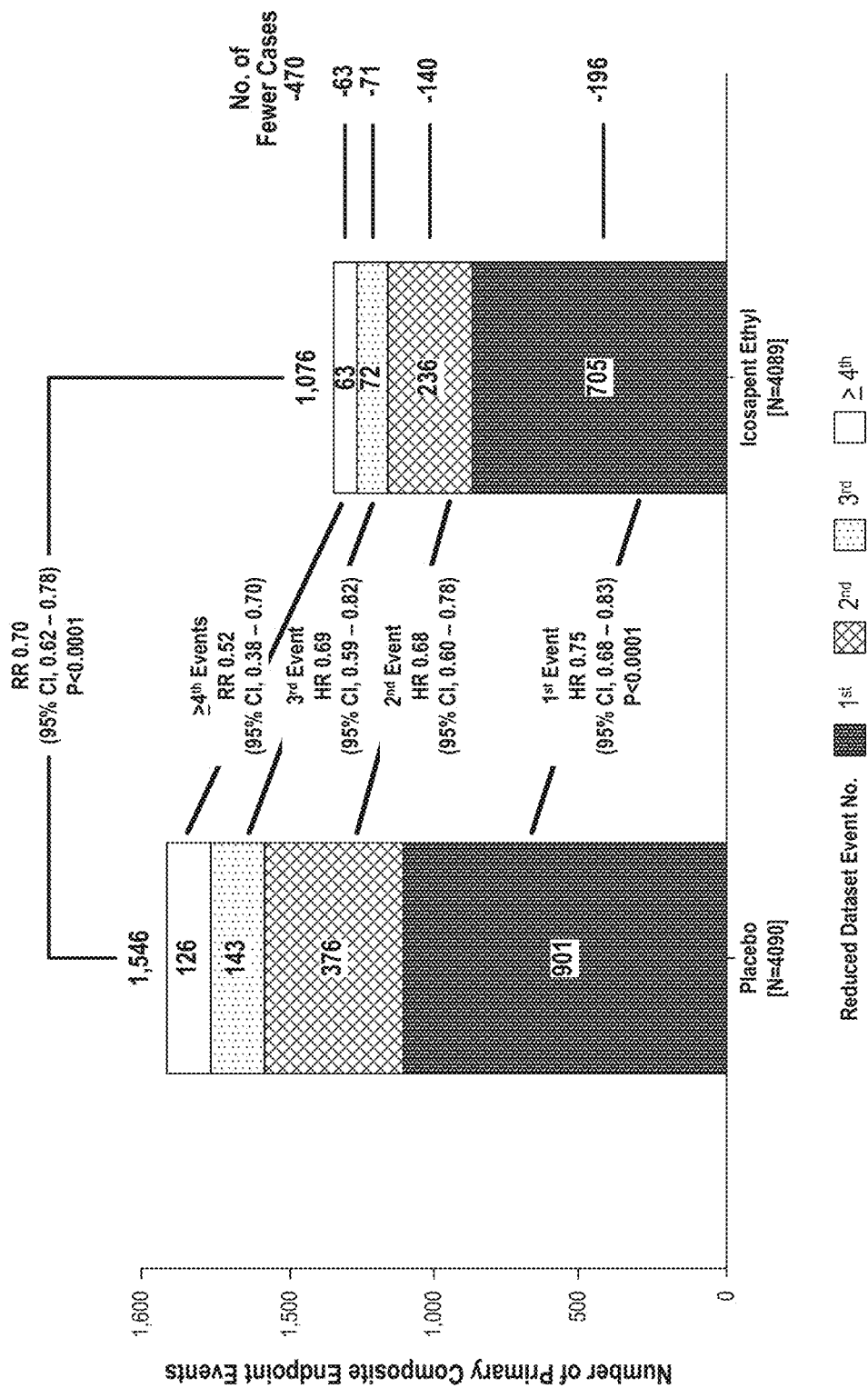
FIG. 33 is a representative bar graph depicting a distribution of total (i.e., first and subsequent) primary composite endpoint events in patients.

The proportions of first and subsequent primary endpoint events, overall and by component type, are depicted in FIG. 32. There were 762 second events, 272 third events, and 269 fourth or more events. Overall, total (i.e., first and subsequent) primary endpoint event rates were reduced to 61 from 89 to per 1000 patient years (i.e., rate ratio (RR) 0.70, 95% CI 0.62-0.78, P<0.0001) with icosapent ethyl as shown in the central illustration in FIG. 33. Using the Wei-Lin-Weissfeld model, the first occurrence of a primary composite endpoint was reduced with icosapent ethyl versus placebo (i.e., HR 0.75, 95% CI 0.68-0.83, P<0.0001) as was the second occurrence (i.e., HR 0.68, 95% CI 0.60-0.78, P<0.0001). There was a 30% relative risk reduction in the total (first and subsequent) ischemic events for the primary composite endpoint with icosapent ethyl. First events were reduced by 25%, second events by 32%, third events by 31%, and fourth or more events by 48%.

Figure 34A:
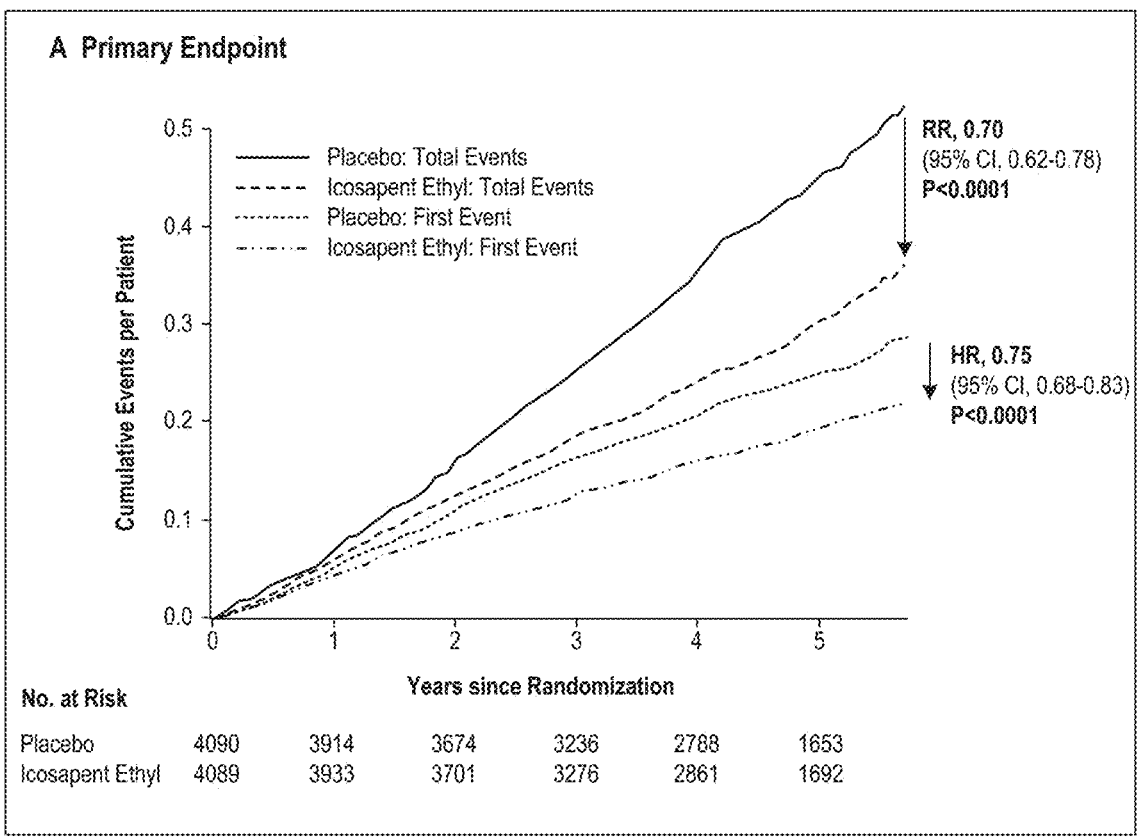
FIGS. 34A and 34B are representative Kaplan-Meier curves over time for total (i.e., first and subsequent) and time to first primary composite events and secondary composite endpoint events, respectively.
Figure 34B:
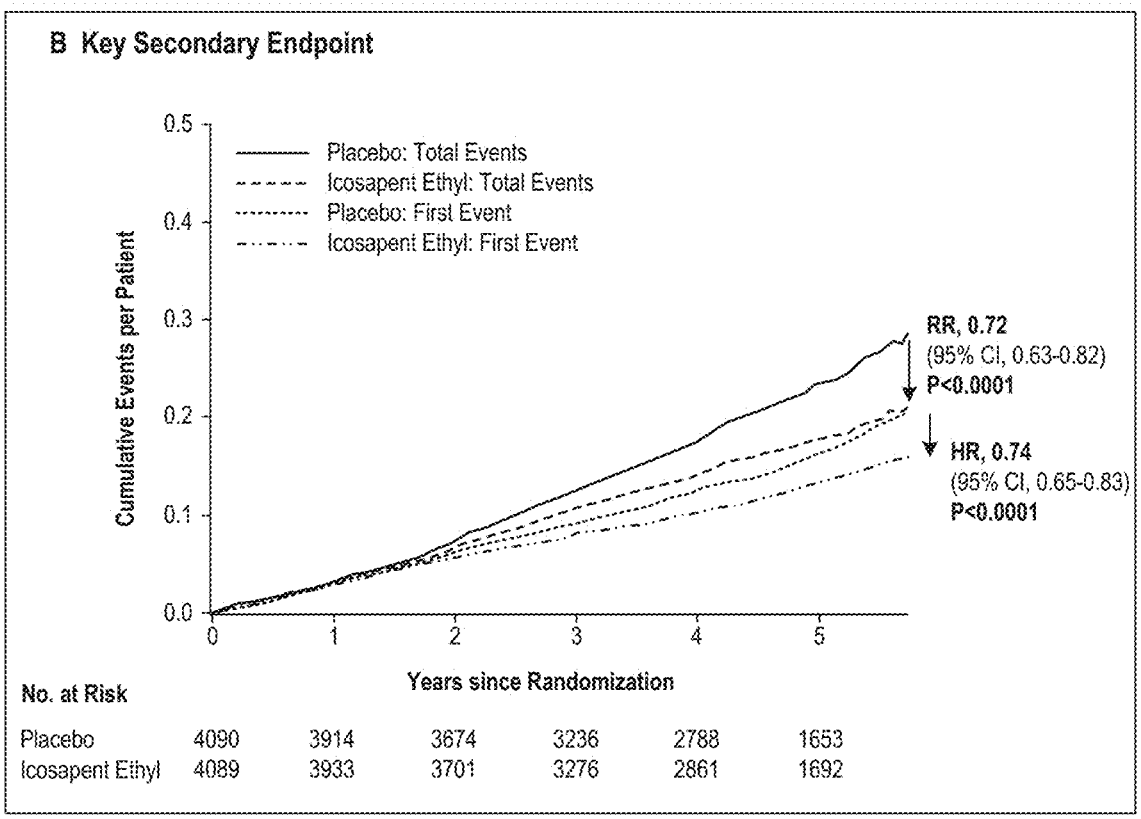
Figure 35:
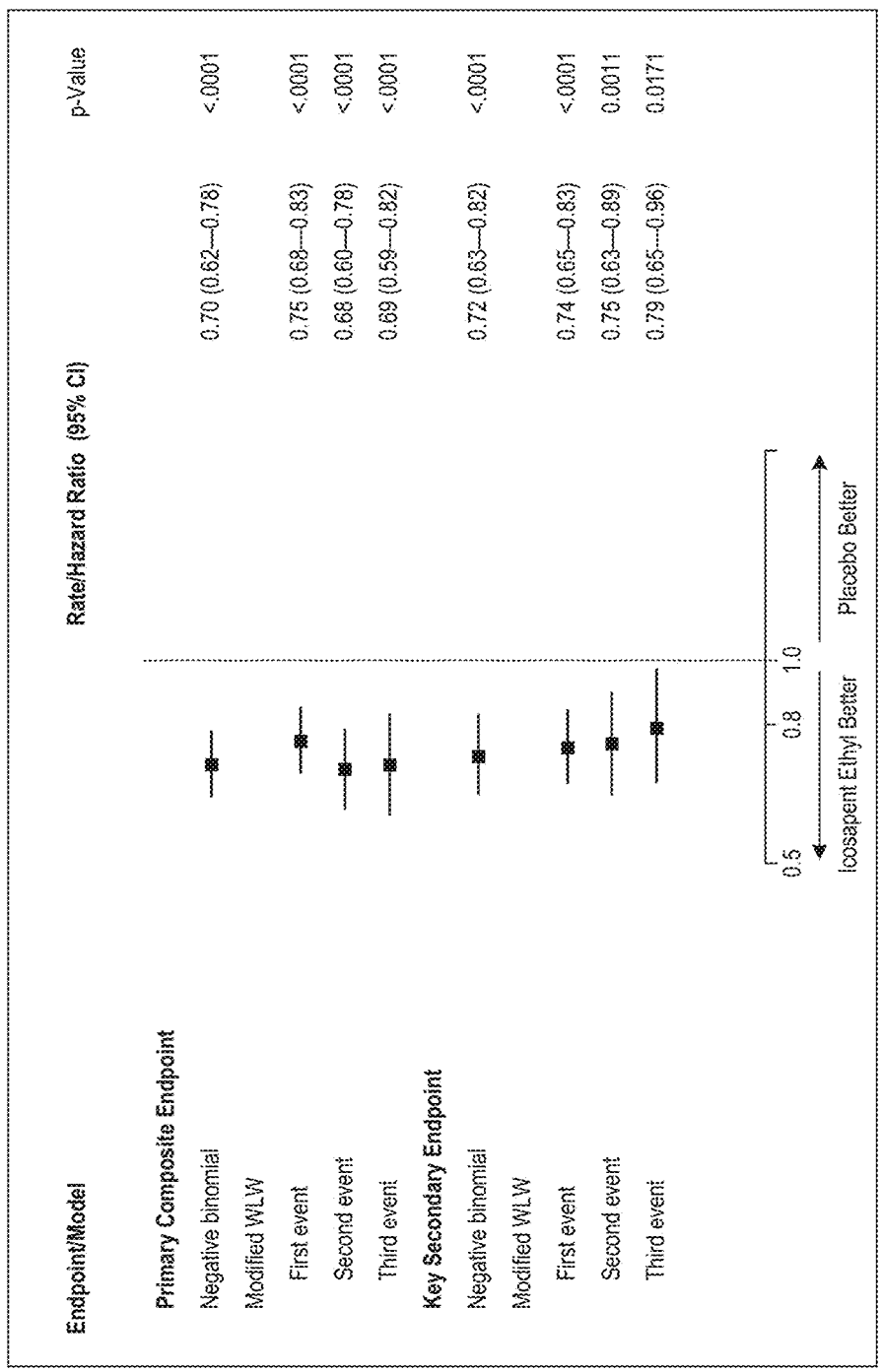
FIG. 35 is a representative forest plot of total primary and key secondary composite endpoint events and indicates that times to first, second, and third occurrence of the primary and secondary endpoints were significantly reduced in patients randomized to icosapent ethyl compared placebo.

The cumulative events over time are shown in FIGS. 34A and 34B. Specifically, FIG. 34A depicts the total (i.e., first and subsequent) and time to first primary composition endpoint events and FIG. 34B shows the key secondary endpoint events. Total key secondary endpoint event rates were significantly reduced to 32 from 44 per 1000 patient years for icosapent ethyl versus placebo, respectively (i.e., RR 0.72, 95% CI 0.63-0.82, P<0.0001) with icosapent ethyl versus placebo as shown in FIG. 34B. The times to first occurrence, second occurrence, third occurrence or fourth occurrence of the primary composite endpoint were consistently reduced as shown FIG. 35 with icosapent ethyl. There were similar results for the models irrespective of whether bundling and/or single accounting was employed as shown in Tables-31-33.

TABLE 31

HRs for Pre-Specified Analyses of Total for Primary and Key Secondary Composite Endpoint Events Using the Reduced Dataset

| | | Primary composite endpoint | | | | Key secondary composite endpoint | | | |
|---|---|---|---|---|---|---|---|---|---|
| | | Unadjusted RR/HR (95% CI) | Unadjusted p-value | Adjusted RR/HR (95% CI) | Adjusted p-value | Unadjusted RR/HR (95% CI) | Unadjusted p-value | Adjusted RR/HR (95% CI) | Adjusted p-value |
| Negative binomial | | 0.68 (0.61, 0.77) | $1.5 \times 10^{-10}$ | 0.70 (0.62, 0.78) | $3.6 \times 10^{-10}$ | 0.71 (0.62, 0.82) | $8.9 \times 10^{-7}$ | 0.72 (0.63, 0.82) | $7.1 \times 10^{-7}$ |
| Andersen-Gill (I) | | 0.69 (0.64, 0.74) | $3.5 \times 10^{-21}$ | 0.69 (0.64, 0.74) | $3.3 \times 10^{-21}$ | 0.72 (0.64, 0.80) | $2.4 \times 10^{-9}$ | 0.72 (0.64, 0.80) | $2.4 \times 10^{-9}$ |
| Andersen-Gill (II) | | 0.69 (0.61, 0.77) | $9.1 \times 10^{-11}$ | 0.69 (0.61, 0.77) | $5.2 \times 10^{-11}$ | 0.72 (0.63, 0.82) | $1.2 \times 10^{-8}$ | 0.72 (0.63, 0.82) | $1.0 \times 10^{-8}$ |
| Modified WLW | First event | 0.76 (0.69, 0.83) | $2.7 \times 10^{-8}$ | 0.75 (0.68, 0.83) | $1.6 \times 10^{-8}$ | 0.74 (0.65, 0.83) | $7.4 \times 10^{-7}$ | 0.74 (0.65, 0.83) | $7.0 \times 10^{-7}$ |
| | Second event | 0.69 (0.60, 0.79) | $2.7 \times 10^{-8}$ | 0.68 (0.60, 0.78) | $1.8 \times 10^{-8}$ | 0.75 (0.63, 0.89) | $1.1 \times 10^{-3}$ | 0.75 (0.63, 0.89) | $1.1 \times 10^{-3}$ |

TABLE 31-continued

HRs for Pre-Specified Analyses of Total for Primary and Key Secondary Composite Endpoint Events Using the Reduced Dataset

| | | Primary composite endpoint | | | | Key secondary composite endpoint | | | |
|---|---|---|---|---|---|---|---|---|---|
| | | Unadjusted RR/HR (95% CI) | Unadjusted p-value | Adjusted RR/HR (95% CI) | Adjusted p-value | Unadjusted RR/HR (95% CI) | Unadjusted p-value | Adjusted RR/HR (95% CI) | Adjusted p-value |
| | Third event | 0.69 (0.59, 0.82) | $2.1 \times 10^{-5}$ | 0.69 (0.59, 0.82) | $2.0 \times 10^{-5}$ | 0.79 (0.65, 0.96) | .0170 | 0.79 (0.65, 0.96) | .0171 |

Rate ratios (RR) are presented for results from negative binomial model; Hazard ratios (HR) are presented for results from Andersen Gill (I) model, Andersen Gill (II) model, and modified Wei-Lin-Weisfeld model.
Unadjusted analyses only included treatment group in the model; Adjusted analyses also included stratification factors (cardiovascular risk category, geographic region, and use of ezetimibe) as covariate, in addition to treatment group in the model.
Andersen Gill (I) model is based on an intensity model with model-based variance estimate and was a pre-specified methodology.
Andersen Gill (II) model is based on a proportional means model with cluster-robust standard errors, with the cluster set to the patient ID.
This is a an updated methodology than the prespecified method. Wei-Lin-Weisfeld model is based on Li-Lagarkos modification. Analyses are based on reduced dataset accounting for statistical handling of multiple endpoints occurring in a single calendar day as a single event.

TABLE 32

Results from Joint Frailty Model for Primary and Key Secondary Endpoints Using the Reduced Dataset

| | | Non-fatal Cardiovascular Event | | Cardiovascular Death | |
|---|---|---|---|---|---|
| | | HR (95% CI) | P-value | HR (95% CI) | P-value |
| Primary endpoint | Unadjusted | 0.66 (0.60, 0.73) | $7.40 \times 10^{-17}$ | 0.80 (0.65, 0.98) | 0.0282 |
| | Adjusted | 0.67 (0.61, 0.74) | $7.20 \times 10^{-16}$ | 0.80 (0.65, 0.98) | 0.0306 |
| Key secondary endpoint | Unadjusted | 0.68 (0.59, 0.78) | $3.30 \times 10^{-8}$ | 0.79 (0.63, 0.99) | 0.0366 |
| | Adjusted | 0.68 (0.59, 0.78) | $4.30 \times 10^{-8}$ | 0.79 (0.63, 0.99) | 0.0380 |

Joint frailty model is based on Rondeau (See Rondeau V. Joint frailty models for recurring events and death using maximum penalized likelihood estimation: application on cancer events. Biostatistics. 2007; 8: 708-21) implemented in the frailty pack R package. Default settings were used, except that 3 knots were used to model the baseline hazard function (to improve speed given that we know from the mean cumulative plots that the shape of the baseline hazard function is unlikely to be complex) and recurrent AG == TRUE (i.e., thereby assuming independence between events conditional on the frailty term).
Unadjusted analyses only included treatment group in the model; Adjusted analyses also included stratification factors (cardiovascular risk category, geographic region, and use of ezetimibe) as covariate, in addition to treatment group in the model.
Analyses are based on reduced dataset accounting for statistical handling of multiple endpoints occurring in a single calendar day as a single event.

TABLE 33

Hazard and Rate Ratios for Pre-Specified Analyses for Primary and Key Secondary Endpoints Using the Full Dataset

| | Primary Composite Endpoint | | | | Key Secondary Composite Endpoint | | | |
|---|---|---|---|---|---|---|---|---|
| | Unadjusted | | Adjusted | | Unadjusted | | Adjusted | |
| | RR/HR (95% CI) | p-value | RR/HR (95% CI) | p-value | RR/HR (95% CI) | p-value | RR/HR (95% CI) | p-value |
| Negative binomial | 0.67 (0.60, 0.76) | $1.6 \times 10^{-10}$ | 0.69 (0.61, 0.77) | $4.4 \times 10^{-10}$ | 0.71 (0.62, 0.81) | 1.4e-06 | 0.71 (0.62, 0.82) | $1.2 \times 10^{-06}$ |
| Andersen-Gill (I) | 0.68 (0.63, 0.74) | 3.4e-22 | 0.68 (0.63, 0.74) | 3.0e-22 | 0.71 (0.64, 0.79) | $1.8 \times 10^{-10}$ | 0.71 (0.63, 0.79) | $1.7 \times 10^{-10}$ |
| Andersen-Gill (II) | 0.68 (0.61, 0.77) | $4.5 \times 10^{-11}$ | 0.68 (0.61, 0.76) | $3.4 \times 10^{-11}$ | 0.71 (0.62, 0.81) | $4.1 \times 10^{-7}$ | 0.71 (0.62, 0.81) | $3.4 \times 10^{-07}$ |
| Modified WLW | | | | | | | | |
| First event | 0.76 (0.69, 0.83) | $2.7 \times 10^{-8}$ | 0.75 (0.68, 0.83) | $1.7 \times 10^{-8}$ | 0.74 (0.65, 0.83) | $7.4 \times 10^{-7}$ | 0.74 (0.65, 0.83) | $7.1 \times 10^{-07}$ |
| Second event | 0.69 (0.61, 0.78) | $4.6 \times 10^{-9}$ | 0.68 (0.60, 0.78) | $3.1 \times 10^{-9}$ | 0.75 (0.63, 0.89) | 0.0011 | 0.75 (0.63, 0.89) | 0.0011 |

TABLE 33-continued

Hazard and Rate Ratios for Pre-Specified Analyses for Primary and Key Secondary Endpoints Using the Full Dataset

| | Primary Composite Endpoint | | | | Key Secondary Composite Endpoint | | | |
|---|---|---|---|---|---|---|---|---|
| | Unadjusted | | Adjusted | | Unadjusted | | Adjusted | |
| | RR/HR (95% CI) | p-value | RR/HR (95% CI) | p-value | RR/HR (95% CI) | p-value | RR/HR (95% CI) | p-value |
| Third event | 0.70 (0.60, 0.83) | $2.2 \times 10^{-5}$ | 0.70 (0.60, 0.83) | $2.1 \times 10^{-5}$ | 0.79 (0.65, 0.96) | 0.0170 | 0.79 (0.65, 0.96) | 0.0171 |

Rate ratios (RR) are presented for results from negative binomial model; Hazard ratios (HR) are presented for results from Andersen Gill (I) model, Andersen Gill (II) model, and modified Wei-Lin-Weisfeld model.
Unadjusted analyses only included treatment group in the model; Adjusted analyses also included stratification factors (cardiovascular risk category, geographic region, and use of ezetimibe) as covariate, in addition to treatment group in the model.
Negative Binomial model. (add references)
Andersen Gill (I) model is based on an intensity model with model-based variance estimate and was a pre-specified methodology.
Andersen Gill (II) model is based on a proportional means model with cluster-robust standard errors, with the cluster set to the patient ID.
This is a more standard methodology than the prespecified method.

Figure 30:
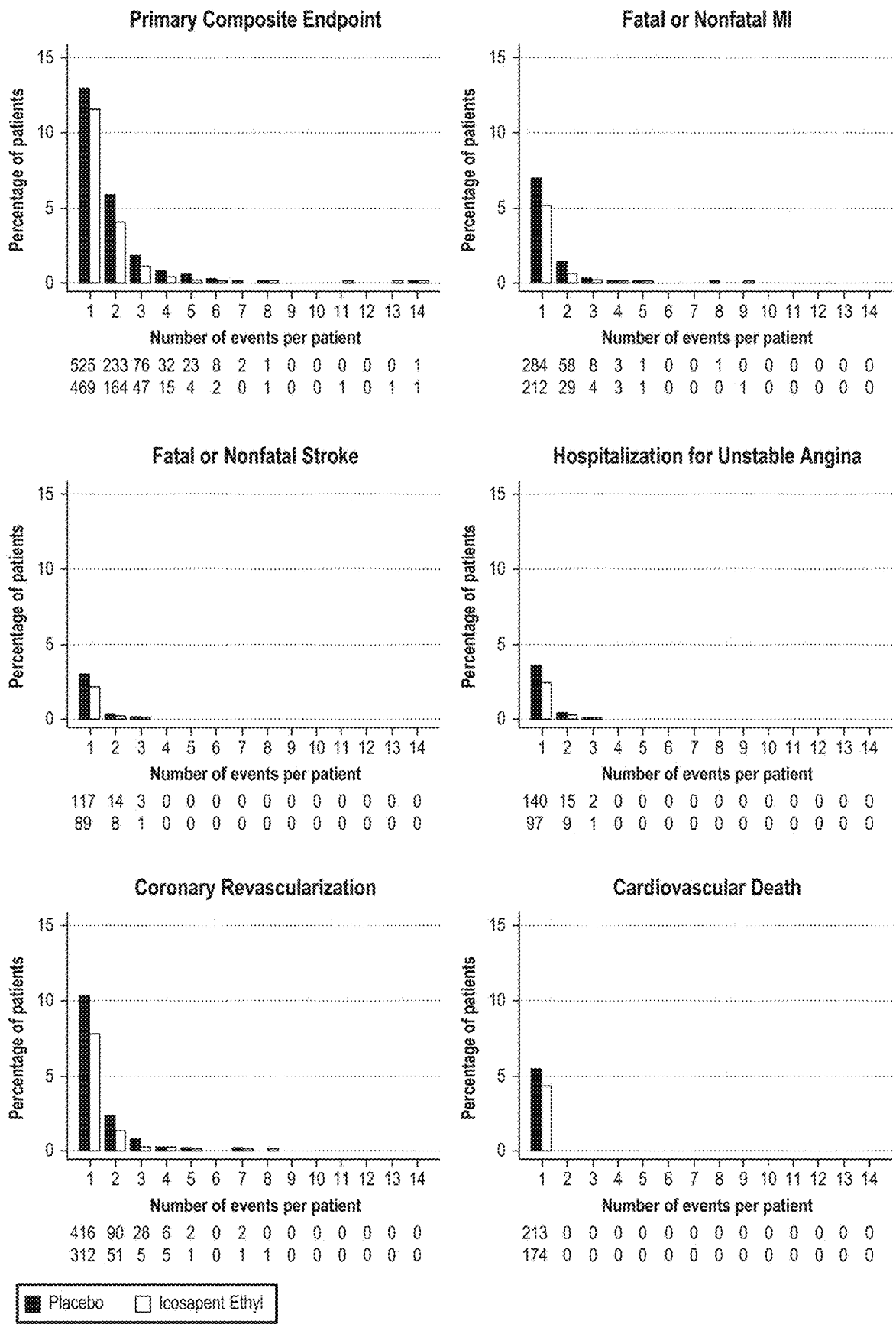
FIG. 30 are representative plots of the total events by number of events per patient for the primary composite endpoints and for each individual component for patients randomized to icosapent ethyl and placebo.
Figure 31A:
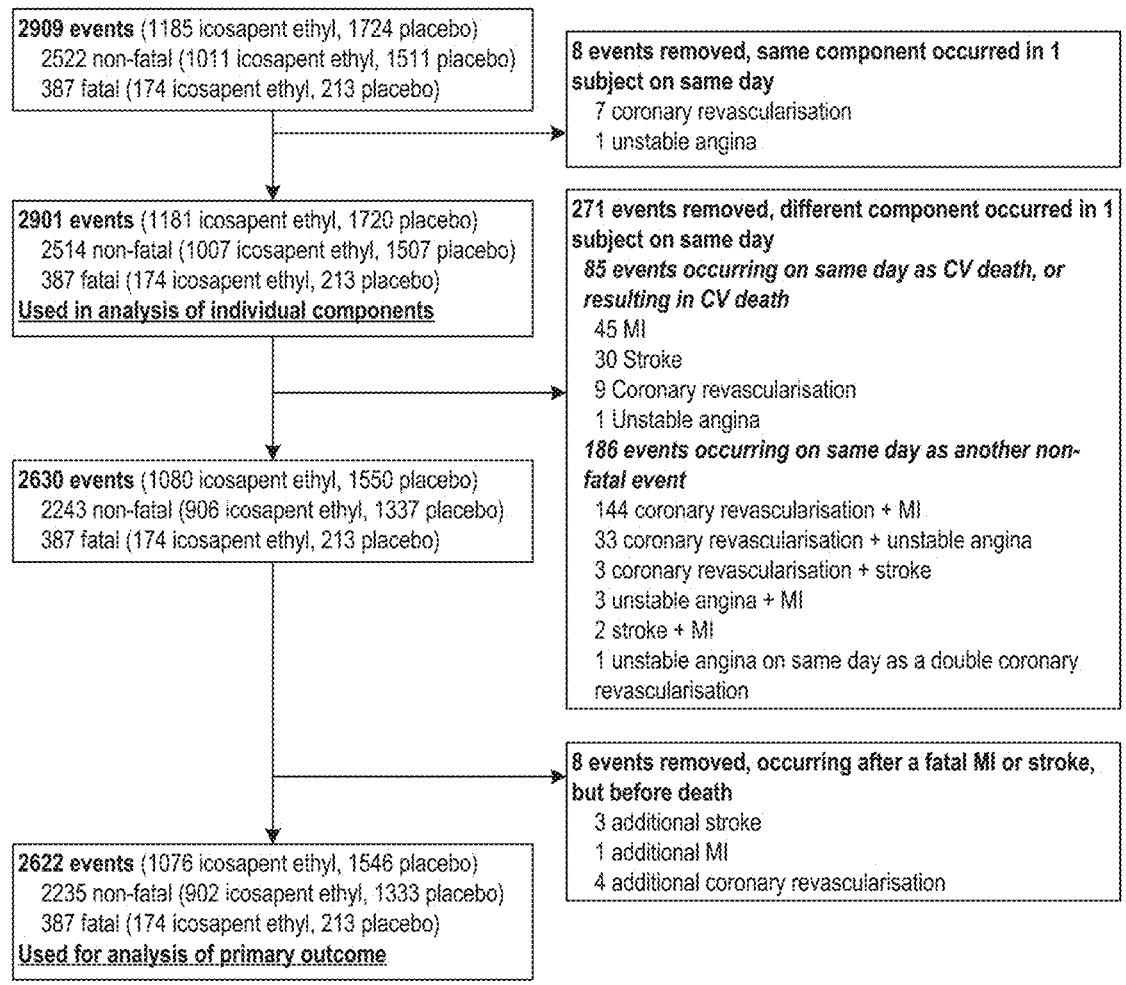
FIGS. 31A and 31B are representative flow charts of the total primary and secondary composite endpoint events for patients randomized to AMR101 and placebo, respectively.
Figure 31B:
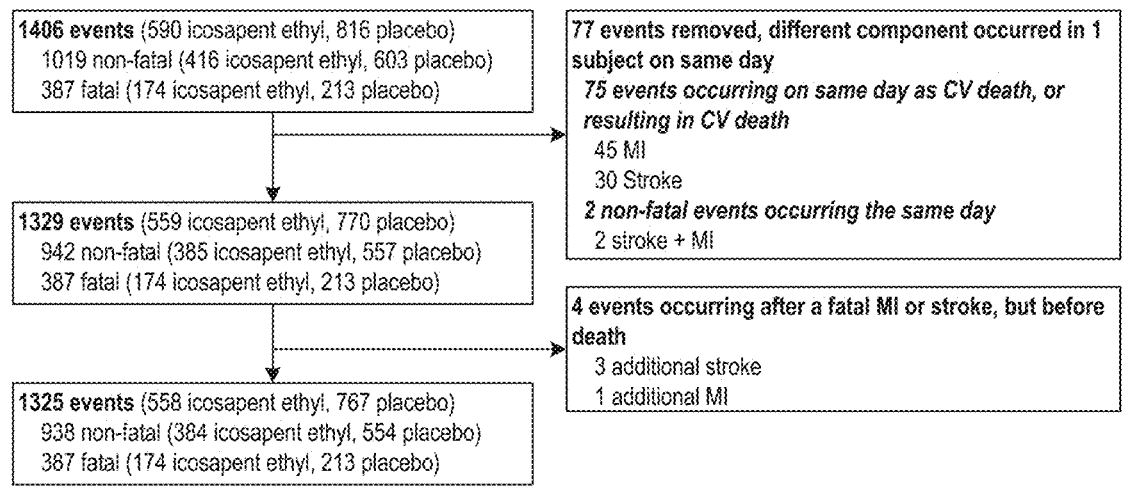
Figure 36:
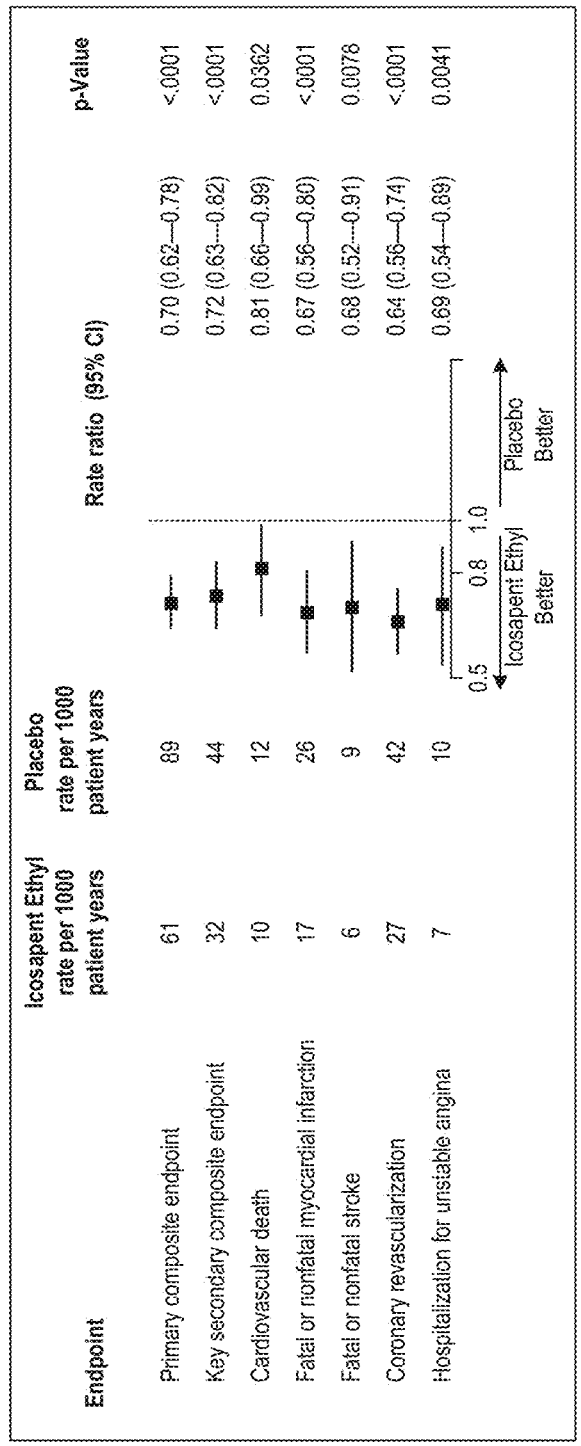
FIG. 36 is a representative forest plot of total primary and key secondary composite endpoints and each individual component or endpoint for patients randomized to icosapent ethyl and placebo indicating that not only was there a significant reduction in the composite of the primary and key secondary endpoints, but also, each individual component was also significantly reduced.

Total events for each component of the primary endpoint were also significantly reduced as shown in FIG. 36, FIG. 30, and Table 34.

Figure 37A:
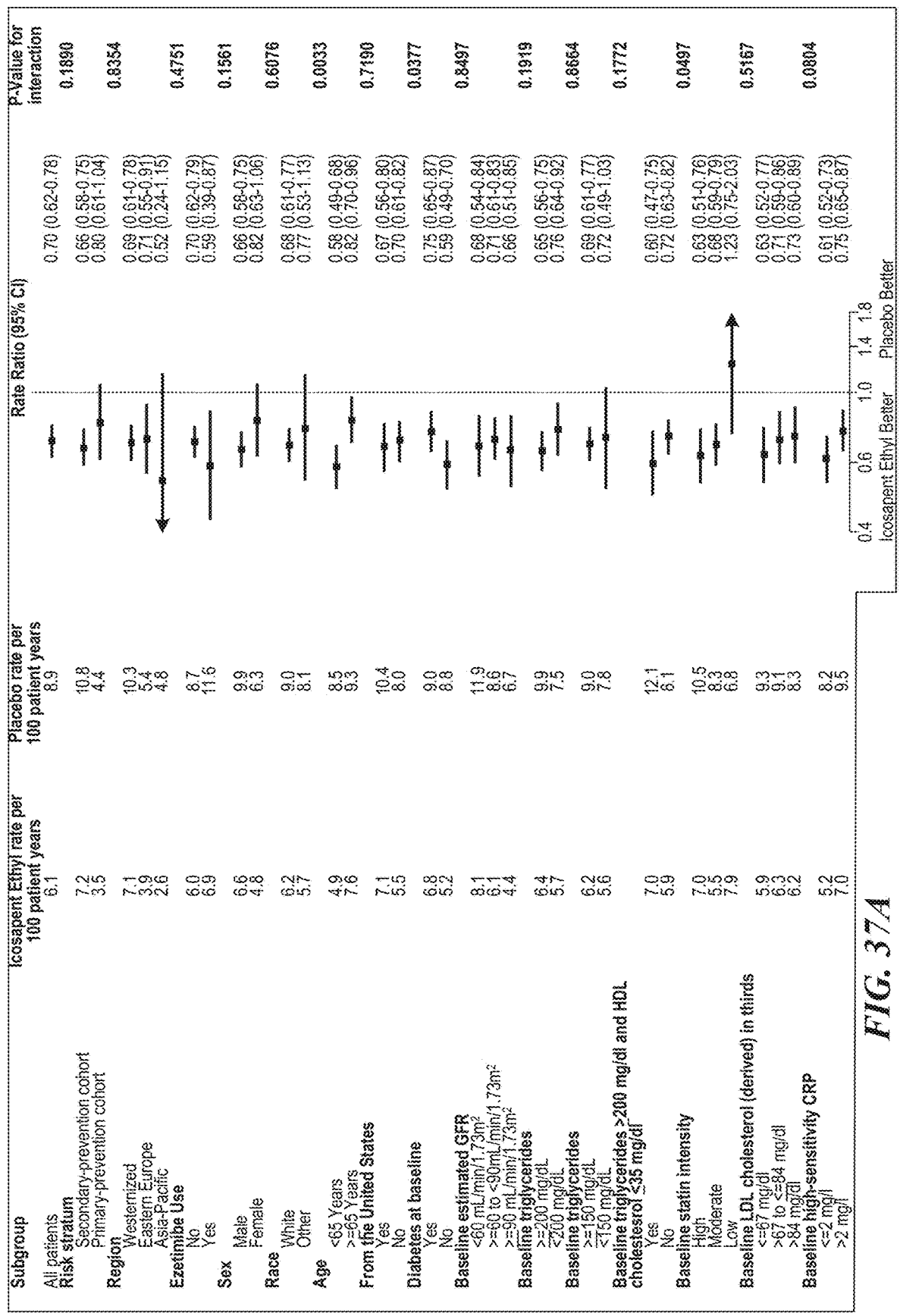
FIGS. 37A and 37B are representative forest plots of total primary and secondary composite endpoints in selected subgroups by the negative binomial model, respectively, for patients randomized to icosapent ethyl and placebo.
Figure 37B:
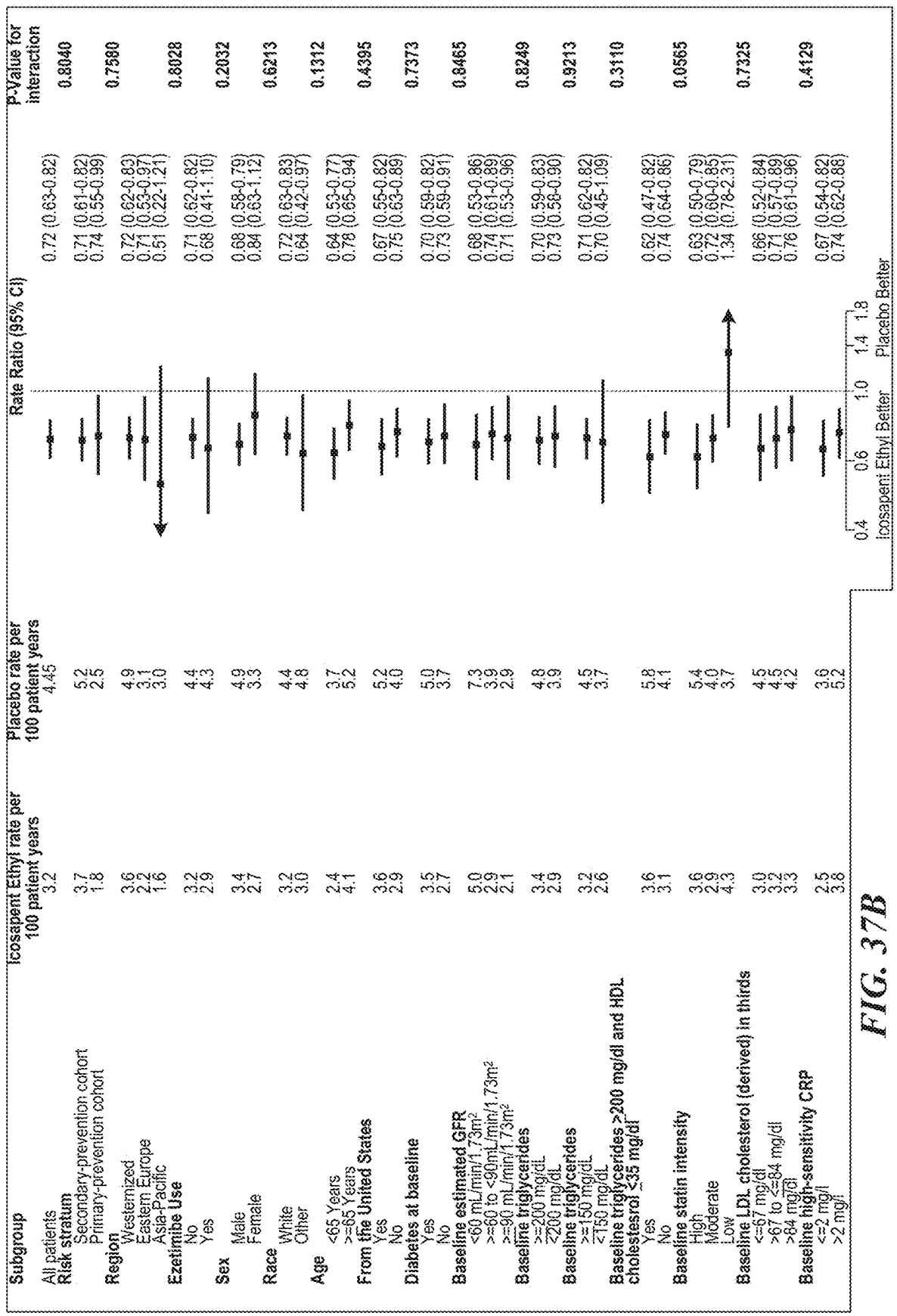
Figure 38:
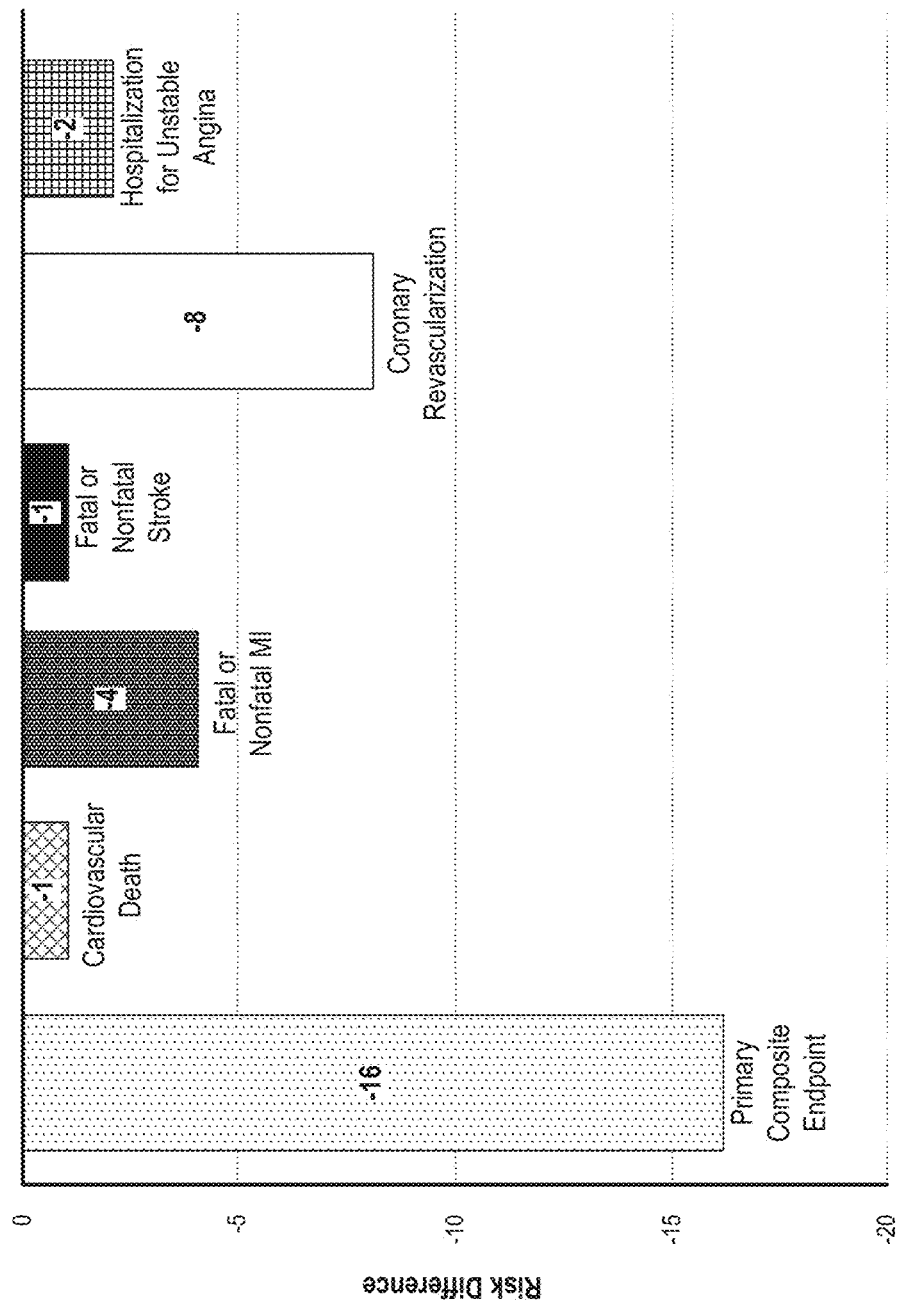
FIG. 38 is a representative graph depicting the risk difference in patients treated for five years with icosapent ethyl versus placebo for total components of the composite primary endpoint and indicates that approximately 159 total primary endpoint events could be prevented within that time frame to include 12 cardiovascular deaths, 42 myocardial infarctions, 14 strokes, 76 coronary revascularizations, and 16 episodes of hospitalization for unstable angina.
Figure 39:
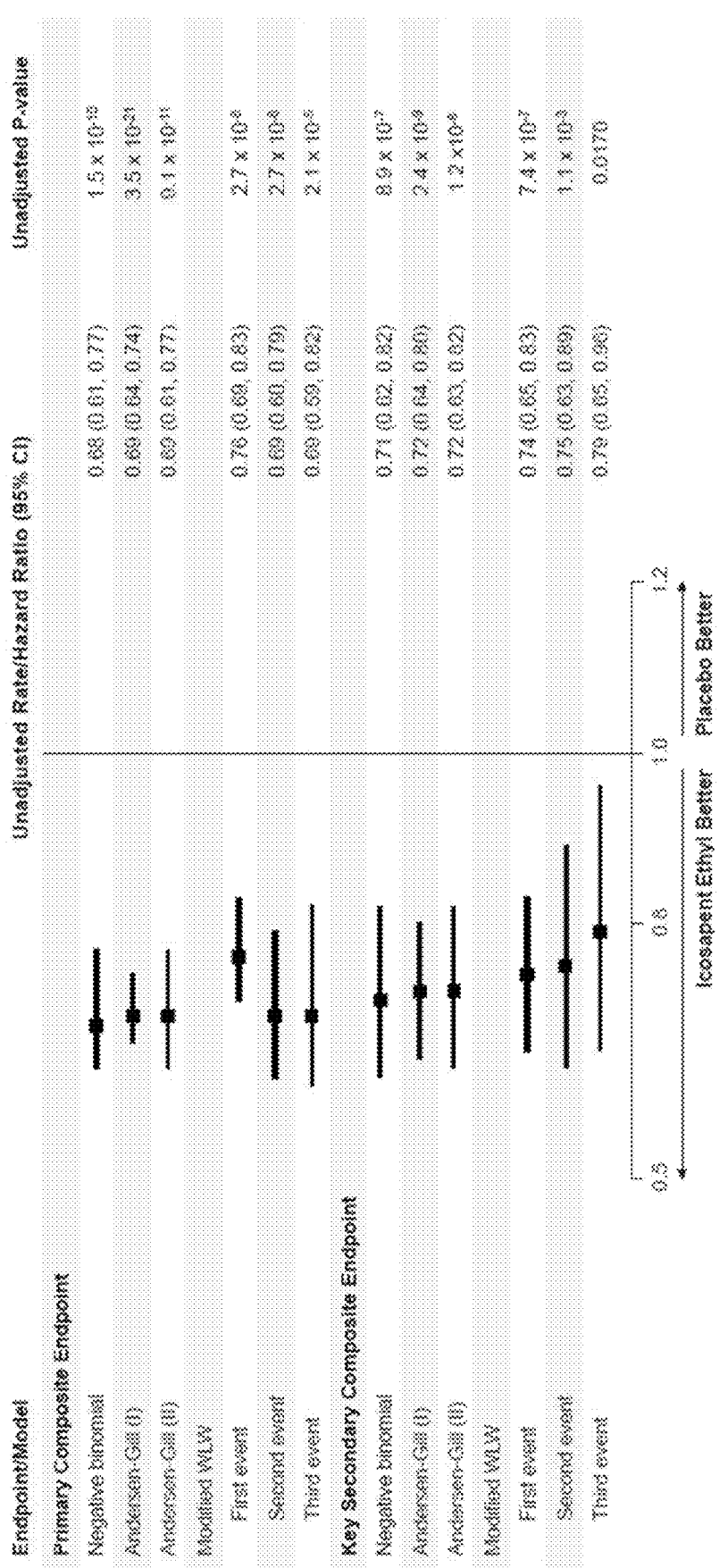
FIGS. 39 and 40 show the forest plot for total primary and key secondary composite endpoint events and first second, and third occurrences for the reduced dataset with unadjusted and adjusted values, respectively.
Figure 40:
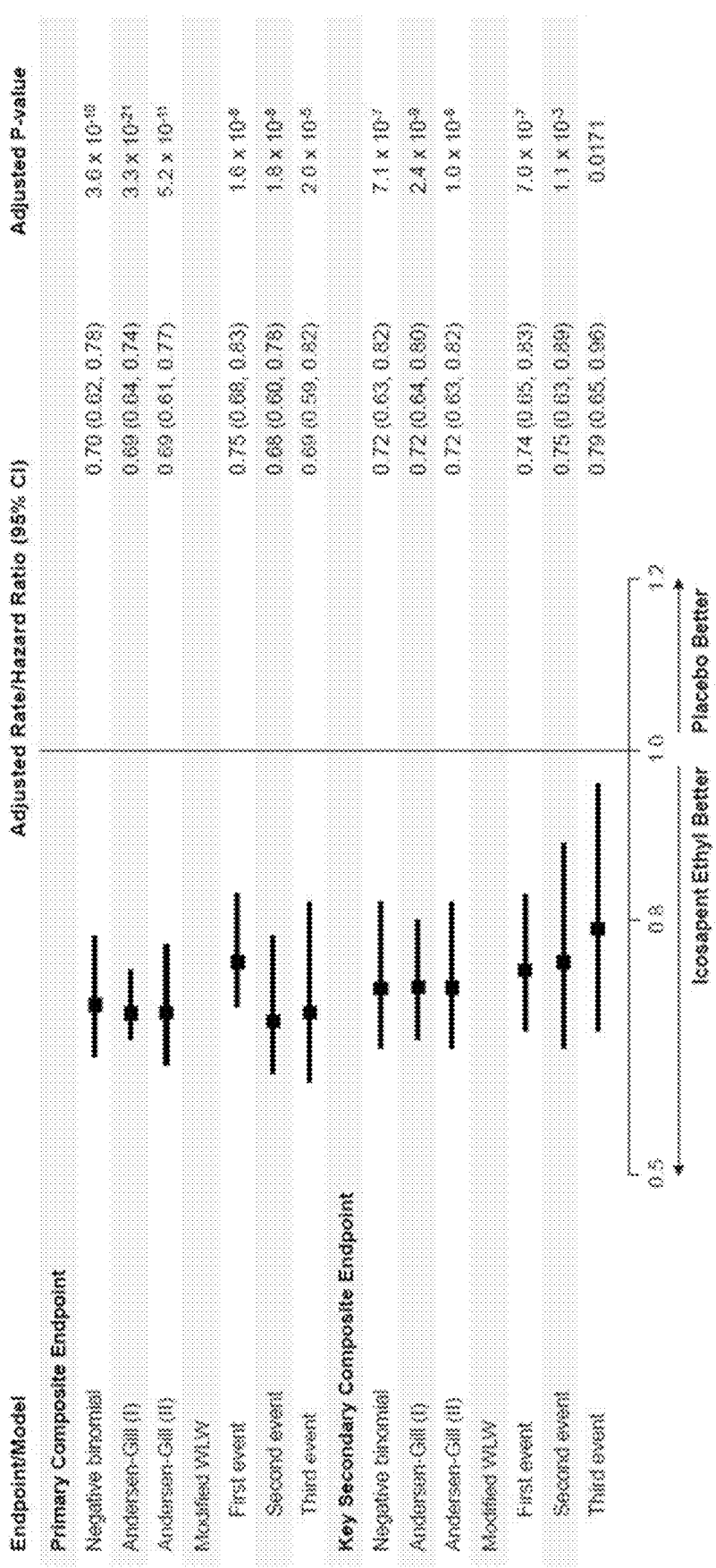
Figure 41:
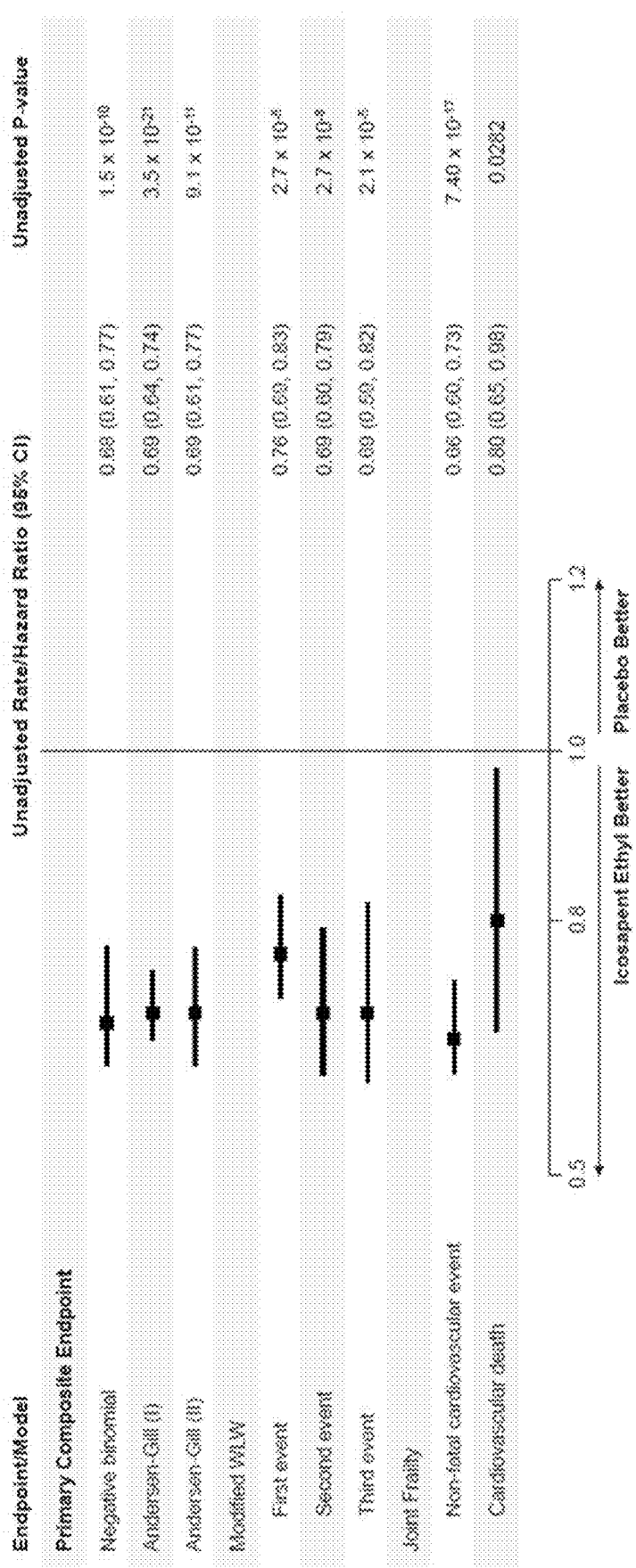
FIGS. 41 and 42 show the forest plots for the total primary composite endpoint events and total key secondary composite endpoint events and first, second, and third occurrences for the reduced data with unadjusted values, respectively.
Figure 42:
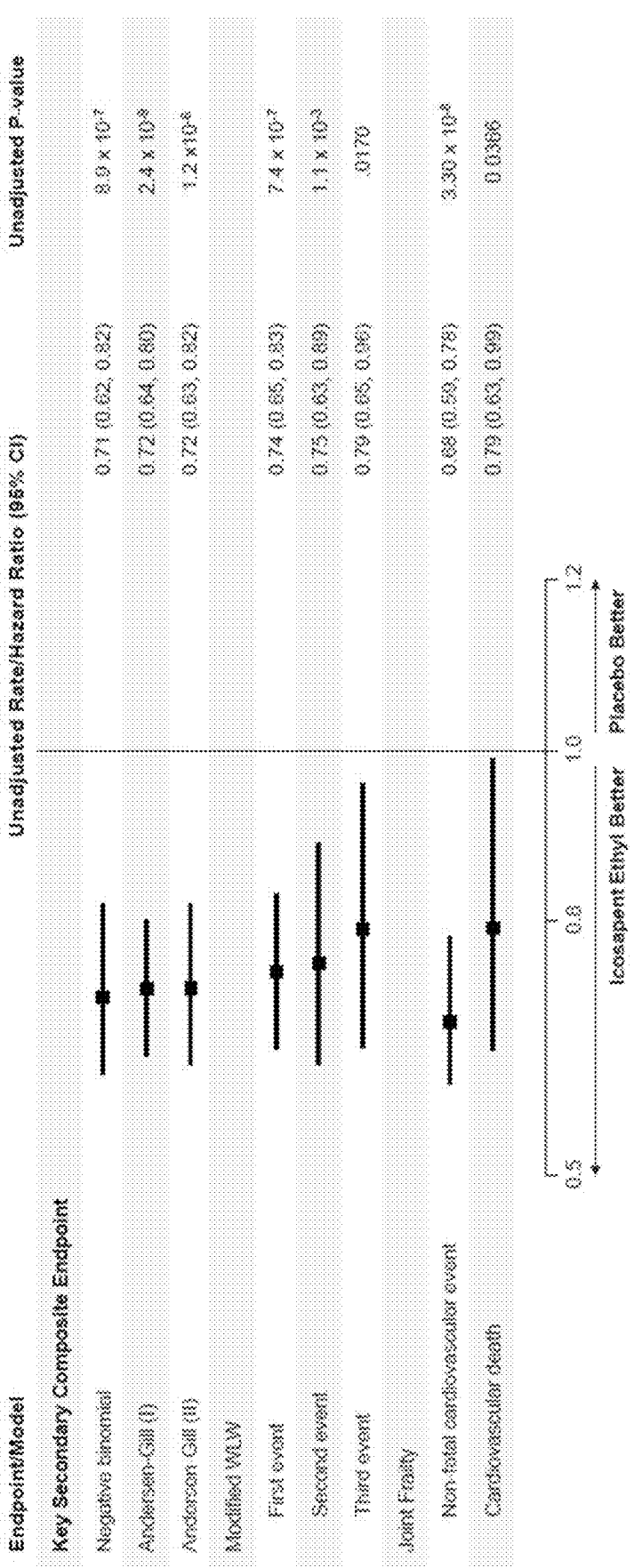
Figure 43:
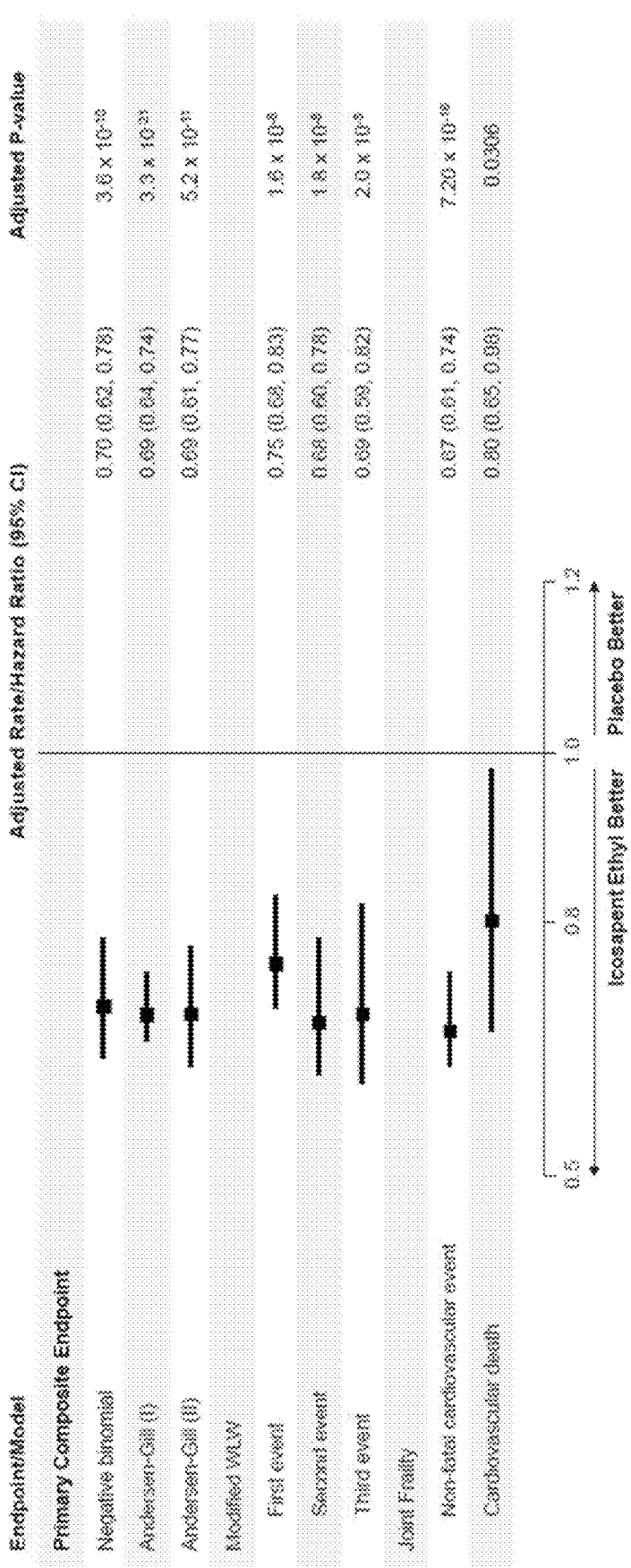
FIGS. 43 and 44 show the total primary composite endpoint events and key secondary composite endpoint events and first, second, and third occurrences for the reduced data set with adjusted values, respectively.
Figure 44:
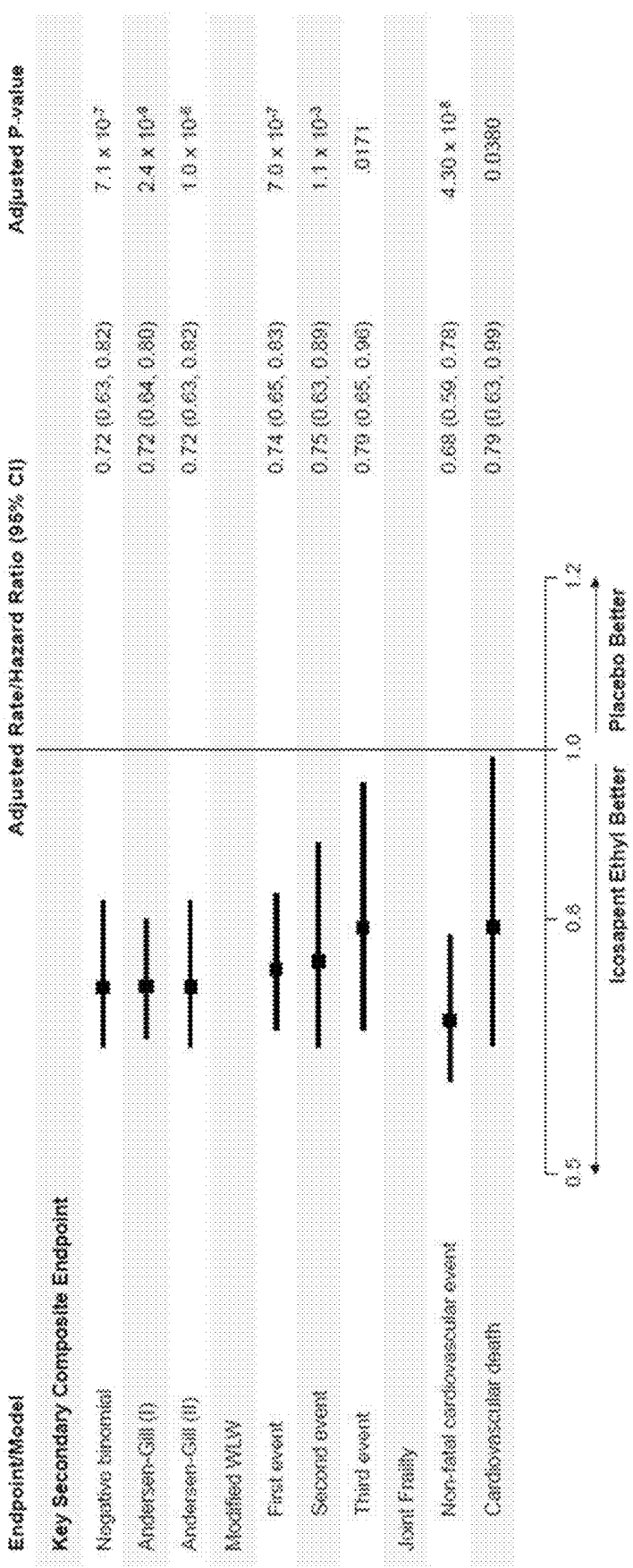
Figure 45:
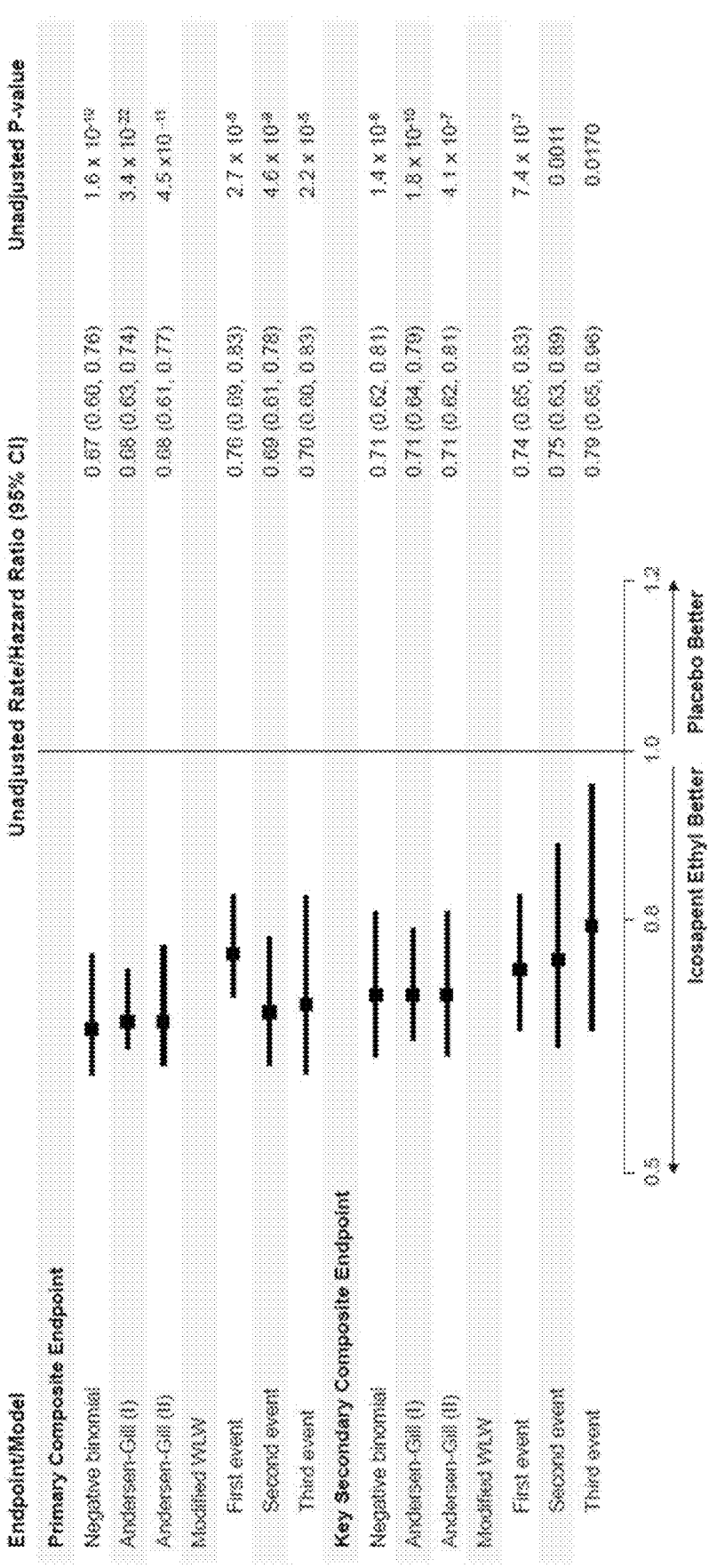
FIGS. 45 and 46 show the total primary and key secondary composite endpoint events and first, second, and third occurrences for the full data set for the unadjusted and adjusted values, respectively.
Figure 46:
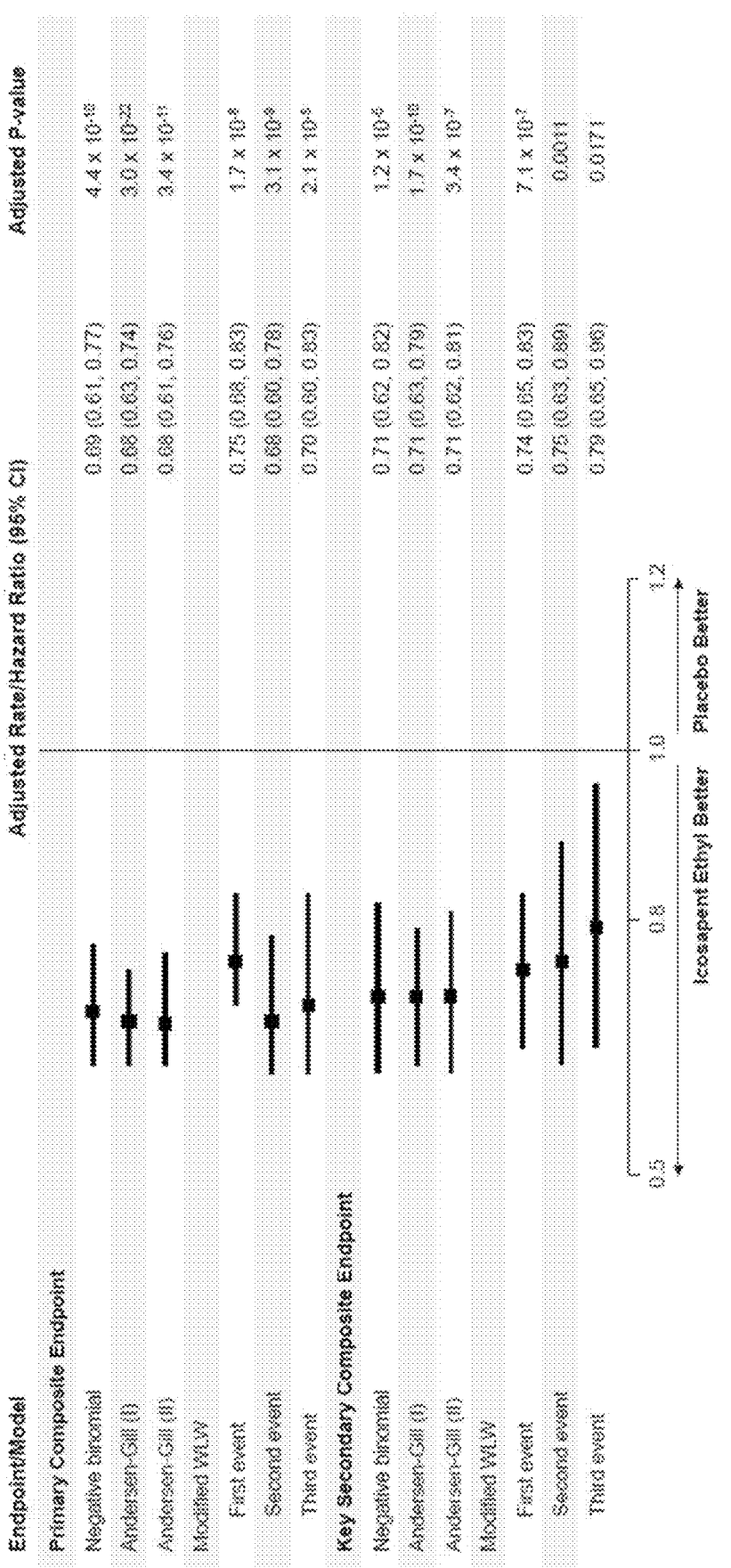

FIGS. 37A and 37B show the total primary and key secondary composite endpoints in selected subgroup analyses by the negative binomial model. The risk differences for every 1000 patients treated for five years with icosapent ethyl for the five components of the composite primary endpoint are shown in FIG. 38; approximately 159 total primary endpoint events could be prevented within that time frame: 12 cardiovascular deaths, 42 myocardial infarctions, 14 strokes, 76 coronary revascularizations, and 16 episodes of hospitalization for unstable angina. FIGS. 39 and 40 show the forest plot for total primary and key secondary composite endpoint events and first second, and third occurrences for the reduced dataset with unadjusted and adjusted values, respectively. FIGS. 41 and 42 show the forest plots for the total primary composite endpoint events and total key secondary composite endpoint events and first, second, and third occurrences for the reduced data with unadjusted values, respectively. FIGS. 43 and 44 show the total primary composite endpoint events and key secondary composite endpoint events and first, second, and third occurrences for the reduced data set with adjusted values, respectively. FIGS. 45 and 46 show the total primary and key secondary composite endpoint events and first, second, and third occurrences for the full data set for the unadjusted and adjusted values, respectively.

The study drug adherence in patients with recurrent events was also explored. At the time of a first primary endpoint event (fatal or nonfatal), 81.3% (573/705) of icosapent ethyl and 81.8% (737/901) of placebo patients with a first primary endpoint event were receiving randomized study drug. At the time of subsequent primary endpoint events (fatal or nonfatal), 79.7% (188/236) and 79.5% (299/376) of patients with a second event, 68.1% (49/72) and 74.1% (106/143) of patients with a third event, and 68.0% (17/25) and 71.6% (48/67) of patients with a fourth event were receiving randomized study drug in the icosapent ethyl and placebo groups, respectively. Therefore, the majority of the first, second, third, and fourth events occurred while patients were on randomized study treatment. Numerical differences in study drug adherence among patients with recurrent events were not statistically significant between treatment groups.

Conclusion

In these total event analyses of the REDUCE-IT clinical trial as described in Example 1, large and significant reductions in total ischemic events with icosapent ethyl versus placebo were found in the total event analyses. Three prespecified and one post hoc analyses with various statistical methodologies demonstrated consistent effects on total ischemic events, with substantial relative and absolute risk reductions. There was a 30% relative risk reduction in the total (i.e., first and subsequent) ischemic events for the primary composite endpoint with icosapent ethyl. For every 1000 patients treated with icosapent ethyl for five years, approximately 159 total primary endpoint events could be prevented. Total events for the hard MACE key secondary endpoint also demonstrated large and clinically meaningful reductions, which further corroborated the significant reduction in important ischemic events seen with the primary endpoint.

There were significant reductions in the first, subsequent and total ischemic events for each individual component of the composite primary endpoint. This benefit of icosapent ethyl across a variety of different ischemic endpoints (e.g., coronary, cerebral, fatal and non-fatal events, and revascularizations) suggests that the drug benefit is not likely to be explained by triglyceride lowering alone and suggests strongly that there are multiple mechanisms of action of the drug beyond triglyceride lowering that may work together to achieve the observed benefits.

Icosapent ethyl was well tolerated with no significant differences in rates of serious adverse events versus placebo. Although overall rates were low in both treatment groups, and none of the events were fatal, with icosapent ethyl there was a trend towards increased serious bleeding albeit with no significant increases in adjudicated hemorrhagic stroke, serious central nervous system bleeding, or gastrointestinal bleeding. There was a small, but statistically significant increase in hospitalization for atrial fibrillation or flutter endpoints observed in patients from the clinical trial. Nevertheless, the large number of important ischemic events averted with the drug, including a significant reduction in fatal and nonfatal stroke (28%), cardiac arrest (48%), sudden death (31%) and cardiovascular death (20%), in indicative of a very favorable risk-benefit profile.

The patients for the REDUCE-IT clinical trial represent a population at high risk for ischemic events, as suggested by the annualized placebo event rate (5.74%), which was expected per study design and is consistent with historical data for similar high-risk statin-treated patient populations. It is therefore not surprising that the total atherosclerotic event burden was also high for REDUCE-IT patients. Substantial and consistent risk reduction with icosapent ethyl was observed in total event analyses for the primary endpoint, each contributing component, and the key secondary endpoint. Time-to-first-event results provide low number needed to treat (NNT) values (i.e., 21 for the primary endpoint; 28 for the key secondary endpoint); the total event analyses results provide incremental evidence of substantial reduction of the total atherosclerotic burden with icosapent ethyl in these patients, with 16 total primary events prevented for every 100 patients treated with icosapent ethyl for 5 years. Without intending to be bound by any particular theory, given the broad inclusion criteria and relatively few exclusion criteria, these results may be generalizable to a large proportion of at-risk statin-treated patients with atherosclerosis or diabetes.

Study drug adherence in patients with recurrent events was strong in both treatment groups at the time of their first primary endpoint event, decreasing somewhat across both treatment groups from the occurrence of the first to the fourth event. For example, at the time of a first occurrence of a fatal or nonfatal primary endpoint event, 81.3% of icosapent ethyl and 81.8% of placebo patients with a first primary endpoint event were on study drug; these rates decreased to 68.0% and 71.6% for patients with a fourth primary endpoint event.

The primary study results for the REDUCE-IT trial and the recurrent and total endpoint event findings discussed herein stand in stark contrast to cardiovascular outcome studies with other agents that lower triglyceride levels and with low-dose omega-3 fatty acid mixtures, where cardiovascular outcome benefit has not been consistently observed in statin-treated patients. EPA has unique lipid and lipoprotein, anti-inflammatory, anti-platelet, anti-thrombotic, and cellular modifying effects, all of which may contribute to benefits in atherosclerotic processes such as reduced development, slowed progression, and increased stabilization of atherosclerotic plaque. The aggregate contribution of these EPA-related effects may contribute to the large observed reductions in total ischemic events with icosapent ethyl.

Each total event analysis model employed in this study provides statistical handling of subsequent events, with some distinct and some overlapping strengths. Despite differences in statistical methodologies, the consistency of findings across the models speaks to the robustness of the study conclusions and the underlying outcomes data.

In conclusion, icosapent ethyl four grams daily (i.e., administered two grams twice daily) significantly reduces total ischemic events in statin-treated patients with well-controlled LDL-C and cardiovascular risk factors including elevated triglycerides with consistent benefits observed across a variety of individual ischemic endpoints. In such patients, icosapent ethyl presents an important treatment option to further reduce the total burden of atherosclerotic events beyond that provided by statin therapy alone.

Example 4: The Impact of Icosapent Ethyl on Ischemic Events in Statin-Treated Patients as a Function of Baseline Triglyceride Tertile The objective of the following example was to determine the extent to which icosapent ethyl reduced ischemic events in patients from the REDUCE-IT trial, as described in Example 1 as a function of triglyceride level.

In the REDUCE-IT trial as described in Example 1, patients underwent a screening visit to determine eligibility, including testing of statin-stabilized triglyceride levels. If patients met inclusion and exclusion criteria, including triglyceride levels, they could then be entered into the study at a subsequent randomization visit. Triglyceride levels were also measured from blood drawn at the randomization visit, but randomization values were not utilized for study qualification. Randomization values did not always fall within the inclusion criteria that were previously met within qualifying visits. In total, the baseline triglyceride levels of the patients ranged from 81 mg/dL to 1401 mg/dL.

The patients were then categorized into three tertiles based on their triglyceride levels. The lowest tertile range included those patients with triglyceride levels of ≥81 to ≤190 mg/dL with a median triglyceride level of 163 mg/dL, the middle tertile range included those patients with triglycerides of >190 to ≤250 mg/dL with a median triglyceride level of 217 mg/dL, and the uppermost tertile range included patients with triglyceride levels of >250 to ≤1401 mg/dL with a median triglyceride level 304 mg/dL. The baseline characteristics of the patients to include the triglyceride category by tertile are shown below in Table 34.

TABLE 34

Baseline Characteristics of Patients

|  | Icosapent Ethyl (N = 4089) | Placebo (N = 4090) |
| --- | --- | --- |
| Age (Years) | 64 | 64 |
| Female, % | 28.4% | 29.2% |
| CV Risk Category, % | | |
| Secondary Prevention Cohort | 70.7% | 70.7% |
| Primary Prevention Cohort | 29.3% | 29.3% |
| Prior Atherosclerotic Cardiovascular Disease, % | 68.9% | 69.3% |
| Prior Atherosclerotic Cerebrovascular Disease, % | 15.7% | 662 (16.2%) |
| Prior Atherosclerotic Peripheral Artery Disease, % | 9.5% | 388 (9.5%) |
| LDL-C (mg/dL), Median (Q1-Q3) | 74.0 (61.5-88.0) | 76.0 (63.0-89.0) |
| Triglycerides (mg/dL), Median (Q1-Q3) | 216.5 (176.5-272.0) | 216.0 (175.5-274.0) |
| Triglycerides Category (by Tertiles)* | | |
| ≥81 to ≤190 mg/dL | Median 163 mg/dL | |
| >190 to ≤250 mg/dL | Median 217 mg/dL | |
| >250 to ≤1401 mg/dL | Median 304 mg/dL | |

Figure 47:
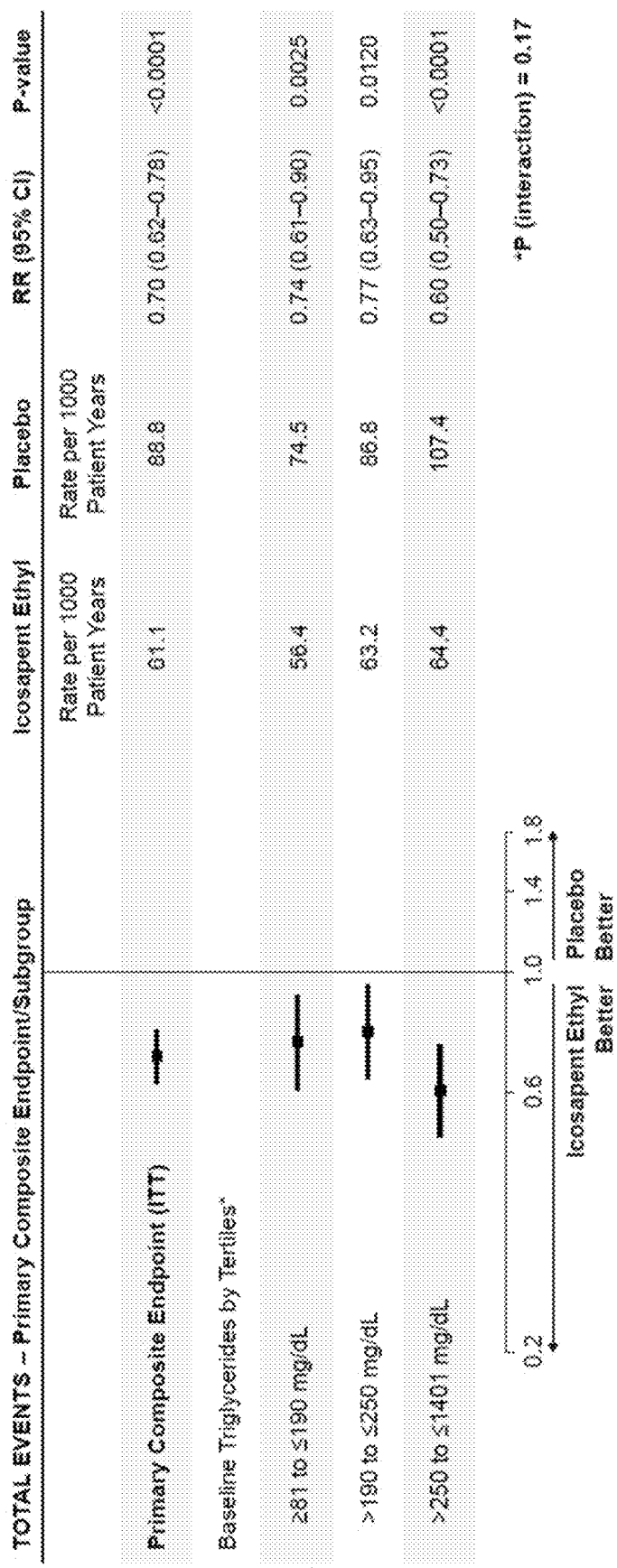
FIG. 47 is a representative forest plot depicting the reduction of total primary composite endpoint events in subjects as a function of triglyceride level.
Figure 48:
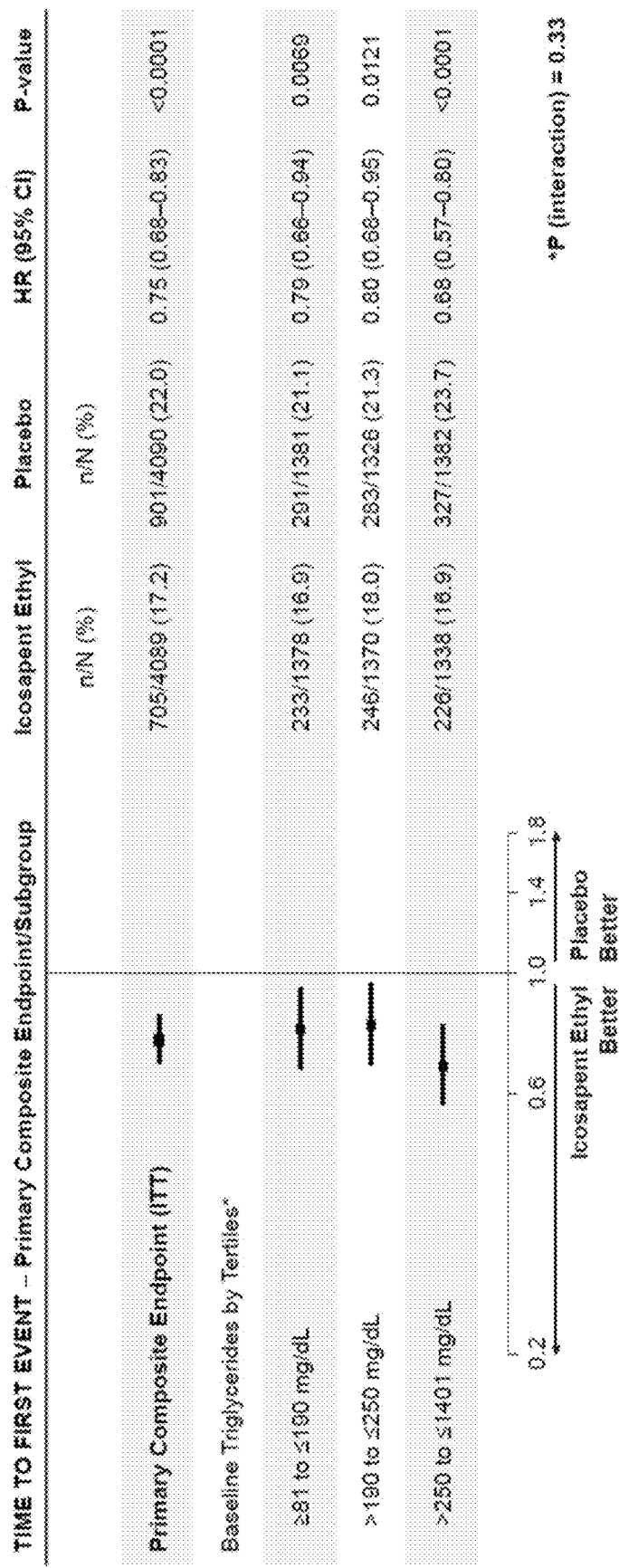
FIG. 48 is a representative forest plot depicting time to first event of primary composite endpoint events in subjects as a function of triglyceride level.

FIG. 47 is a forest plot demonstrating that the total events (i.e., first and subsequent) for the primary composite endpoint of CV death, non-fatal stroke, non-fatal myocardial infarction, coronary revascularizations, or unstable angina requiring hospitalization was reduced in all patients across the entire triglyceride range and within each of the defined triglyceride tertiles. Similarly, FIG. 48 demonstrates that the time to first event of the primary composition endpoint was reduced across the entire triglyceride range.

In conclusion, patients from the REDUCE-IT clinical trial with baseline triglyceride levels across all tertiles (e.g., between 81 mg/dl to 1410 mg/dl), regardless of their specific triglyceride baseline level, benefited from the administration of 4 g of icosapent ethyl per day and experienced statistically significant reductions in not only the time to first cardiovascular event, but also, total cardiovascular events in both the primary and key secondary composite endpoints.

Figure 49:
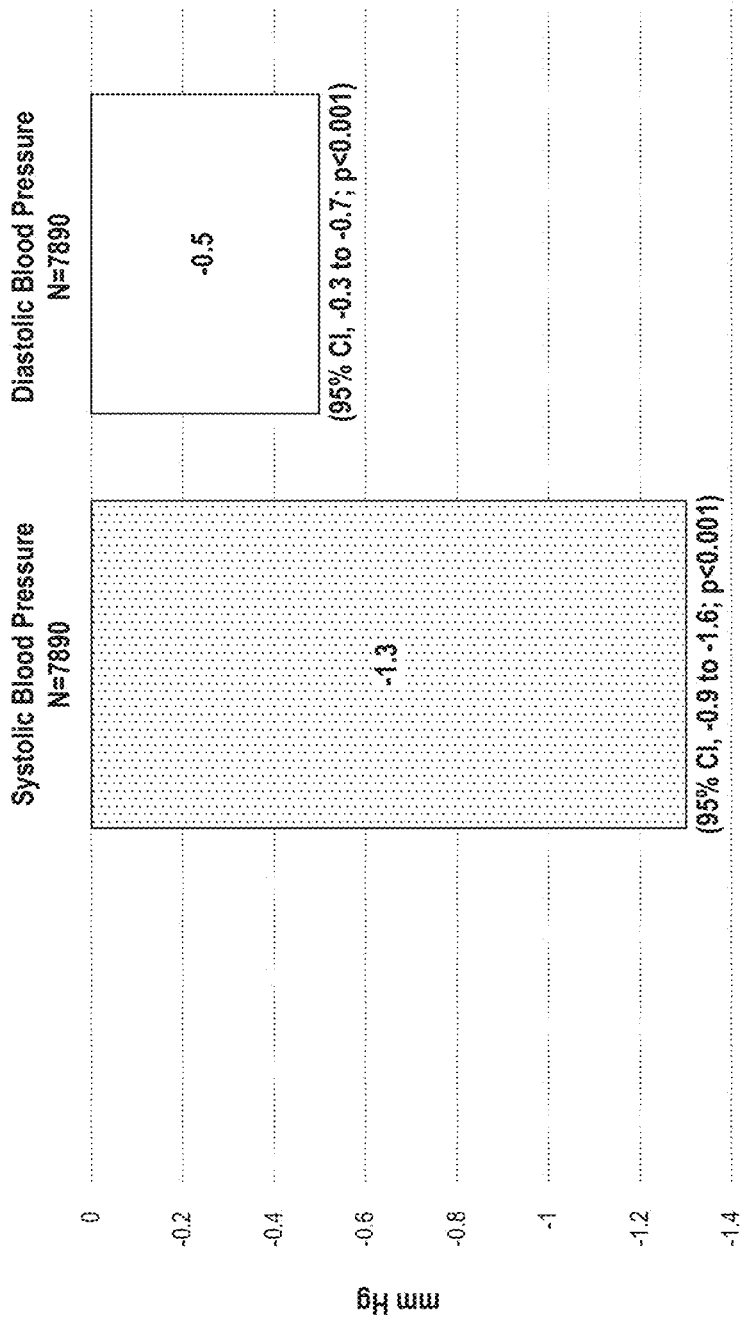
FIG. 49 is a representative bar graph for a placebo-corrected reduction in blood pressure in patients administered icosapent ethyl 4 g per day.
Figure 50:
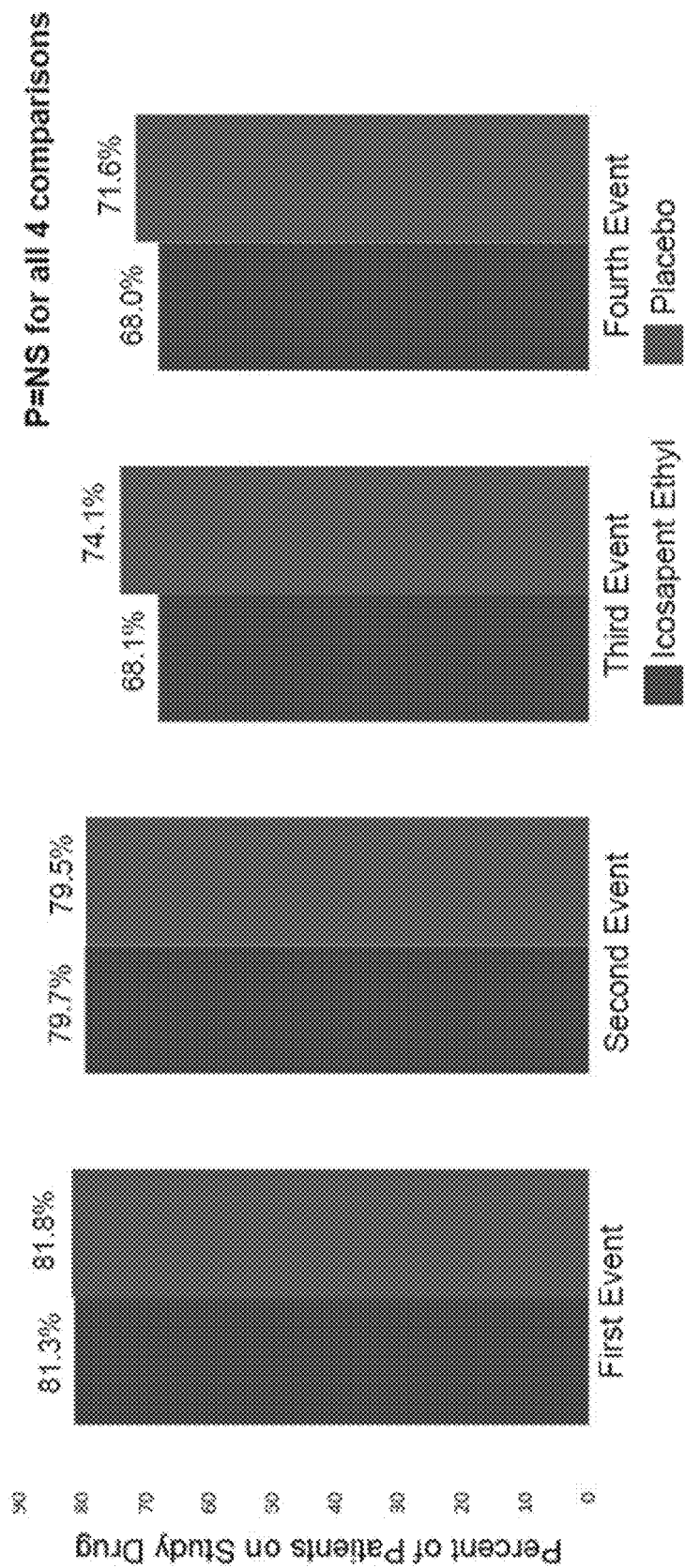
FIG. 50 is a representative bar graph for the study drug adherence over time for each of the first, second, third, and fourth events.

The results from the REDUCE-IT clinical trial showed a significant cardiovascular benefit associated with the administration of icosapent ethyl. It is contemplated that a number of factors contribute to the significant reduction in the cardiovascular risk. Without intending to be bound by any particular theory, one of the contributing factors might relate to the dose and formulation of the icosapent ethyl administered to the patients, in marked contrast to previous studies of omega-3 fatty acid studies. An additional contributing factor could relate to the patients' blood pressure. For example, prespecified exploratory analyses of icosapent ethyl with no adjustment for multiple comparisons showed average placebo-corrected reductions from baseline in systolic blood pressure of 1.3 mm Hg (95% CI, 0.9 to 1.6) and in diastolic blood pressure of 0.5 mm Hg (95% CI, 0.3 to 0.7) as shown in FIG. 49. FIG. 49 shows repeated-measurements analysis of change from baseline blood pressure over time by a mixed effects model for the ITT population (icosapent ethyl: n=4089, placebo: n=4091, maximum number of observations per patient=6). These differences appear to be modest, but it is contemplated, that they might contribute to the benefits of icosapent ethyl. It is further contemplated that biomarkers (e.g., the ratio of EPA to arachidonic acid) and blood pressure, may also provide an understanding of the effects of icosapent ethyl and potential mechanistic insight for the observed reduction in cardiovascular risk. Further, as common in long-term clinical trials, study drug adherence waned over time. However, despite the waning there was a long-sustained treatment effect on total events as shown in FIG. 50.

Example 5: Reduction in Heart Failure with Icosapent Ethyl

The study results described in Example 1 demonstrated that icosapent ethyl reduces the first occurrence of the composite of cardiovascular death, nonfatal myocardial infarction, nonfatal stroke, coronary revascularization, or unstable angina, with a 25% relative risk reduction and a 4.8% absolute risk reduction. The objective of the following study was to assess the impact of icosapent ethyl on reducing new heart failure (NHF).

Methods

The study design was the same as that described above in Example 1 related to the REDUCE-IT clinical trial. In brief, REDUCE-IT was a multicenter, double-blind, placebo-controlled trial, randomized 8,179 statin-treated patients with established CV disease or risk factors, and well-controlled LDL-C (41-100 mg/dL), but elevated triglycerides (135-499 mg/dL), to icosapent ethyl 4 g daily or placebo; median follow-up was 4.9 years.

Results

Figure 51:
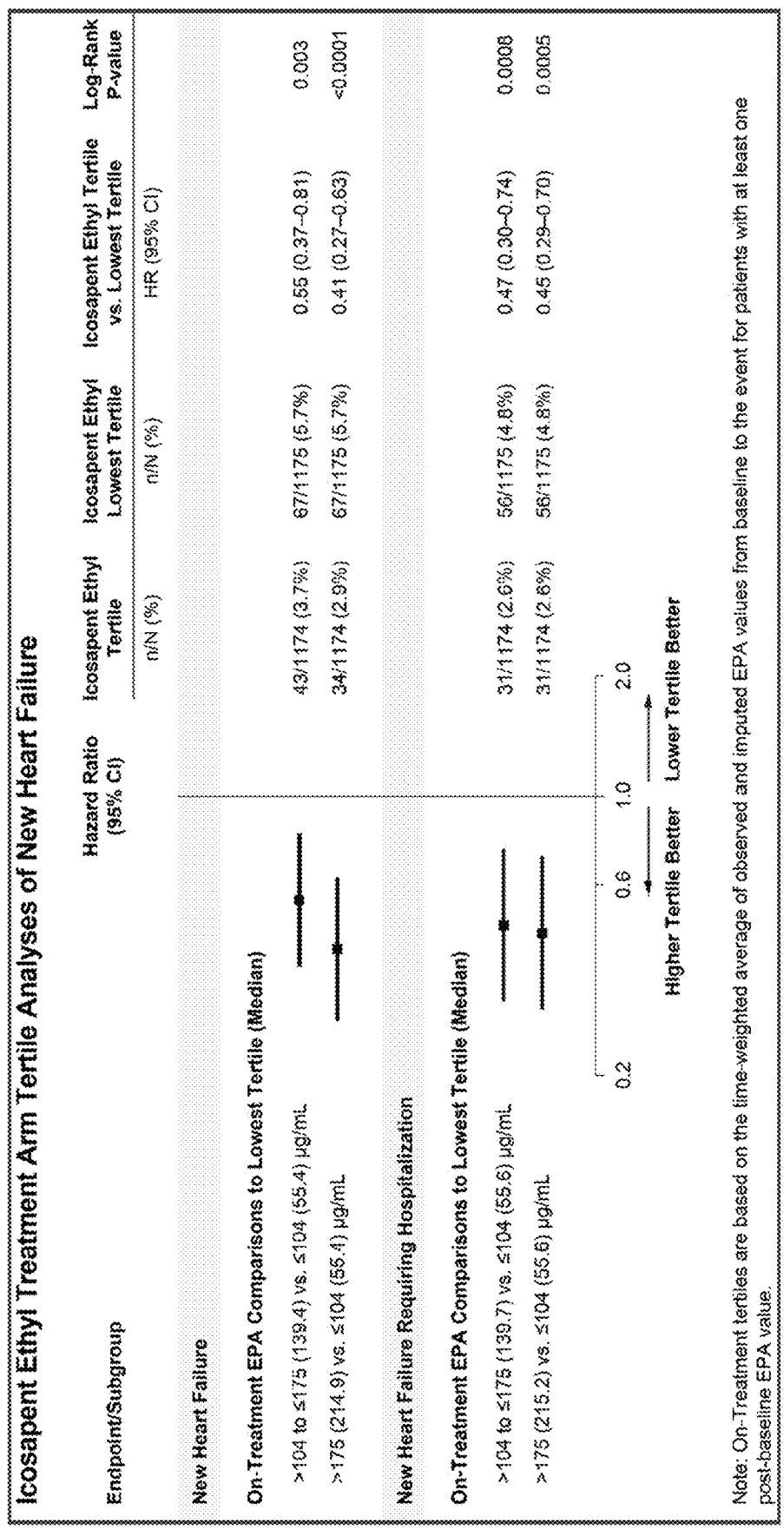
FIG. 51 is a representative forest plot indicating that new heart failure (NHF) is reduced in a subjects administered icosapent ethyl 4 g per day as a function of EPA tertile.

Prespecified tertiary endpoints of NHF (HR=0.95; 95% CI, 0.77-1.17; p=0.63) and NHF requiring hospitalization (HR=0.97; 0.77-1.22; p=0.78) from the REDUCE-IT clinical trial were not significant. However, in post hoc analyses of patients in the icosapent ethyl group only, compared with the lowest on treatment EPA tertile (median 55 µg/mL), patients in the middle (139 µg/mL) and upper (215 µg/mL) tertiles observed substantial benefit in new heart failure (HR=0.55; 95% CI 0.37-0.81, p=0.003; HR=0.41, 0.27-0.63, p<0.0001, respectively) and new heart failure requiring hospitalization (HR=0.47, 0.30-0.74, p=0.0008; HR=0.45, 0.29-0.70, p=0.0005) (FIG. 51).

Conclusion

Within the icosapent ethyl group, without placebo, EPA tertile analyses demonstrate statistically and clinically meaningful risk reductions in NHF with achievement of EPA levels above 104 µg/mL. Without intending to be bound by any particular theory, it is contemplated that the observed benefit may necessitate achieving EPA, which may differ across CV endpoints.

The invention claimed is:

1. A method of reducing risk of heart failure in a subject having a baseline triglyceride level of at least 135 mg/dL and a baseline serum and/or plasma eicosapentaenoic acid (EPA) level of about 26 µg/mL, the method comprising administering to said subject about 4 g of ethyl icosapentate per day for a period effective to increase said subject's EPA level to at least about 104 µg/mL.

2. A method of reducing risk of heart failure in a subject having a baseline serum and/or plasma eicosapentaenoic acid (EPA) level of about 26 µg/mL, the method comprising administering to said subject about 4 g of ethyl icosapentate per day for a period effective to increase said subject's baseline serum and/or plasma EPA level to at least about 104 µg/mL.

3. The method of claim 1, wherein the subject is administered ethyl icosapentate for a period of time effective to increase said subject's baseline serum and/or plasma EPA level to about 104 µg/mL to about 175 µg/mL.

4. The method of claim 3, wherein the subject is administered ethyl icosapentate for a period of time effective to increase said subject's baseline serum and/or plasma EPA level to at least about 175 µg/mL.

5. The method of claim 1, wherein the heart failure is new heart failure.

6. The method of claim 2, wherein the heart failure is new heart failure requiring hospitalization.

7. The method of claim 1, further comprising reducing a risk of one or more of cardiovascular death, myocardial infarction, stroke, coronary revascularization, and unstable angina.

8. The method of claim 7, wherein the subject is on statin therapy.

9. The method of claim 1, wherein the ethyl icosapentate is present in a pharmaceutical composition and the ethyl icosapentate comprises at least about 90 wt. % of all omega-3 fatty acids in the pharmaceutical composition.

10. The method of claim 1, wherein the ethyl icosapentate is present in a pharmaceutical composition and the ethyl icosapentate comprises at least about 96 wt. % of all omega-3 fatty acids in the pharmaceutical composition.

11. The method of claim 10, wherein about 1 g of the pharmaceutical composition is present in each of 4 capsules.

12. The method of claim 1, wherein the subject has established cardiovascular disease.

13. The method of claim 1, wherein the subject has a high risk for cardiovascular disease and at least one risk factor for cardiovascular disease.

14. The method of claim 2, wherein the subject is administered ethyl icosapentate for a period of time effective to increase said subject's baseline serum and/or plasma EPA level to about 104 μg/mL to about 175 μg/mL.

15. The method of claim 14, wherein the subject is administered ethyl icosapentate for a period of time effective to increase said subject's baseline serum and/or plasma EPA level to at least about 175 μg/mL.

16. The method of claim 2, further comprising reducing a risk of one or more of cardiovascular death, myocardial infarction, stroke, coronary revascularization, and unstable angina, and wherein the subject is on statin therapy.

17. The method of claim 2, wherein the ethyl icosapentate is present in a pharmaceutical composition and the ethyl icosapentate comprises at least about 90 wt. % of all omega-3 fatty acids in the pharmaceutical composition.

18. The method of claim 2, wherein the subject has established cardiovascular disease or has a high risk for cardiovascular disease and at least one risk factor for cardiovascular disease.

\* \* \* \* \*